(12) United States Patent
Lang

(10) Patent No.: US 11,311,341 B2
(45) Date of Patent: *Apr. 26, 2022

(54) AUGMENTED REALITY GUIDED FITTING, SIZING, TRIALING AND BALANCING OF VIRTUAL IMPLANTS ON THE PHYSICAL JOINT OF A PATIENT FOR MANUAL AND ROBOT ASSISTED JOINT REPLACEMENT

(71) Applicant: Philipp K. Lang, Franconia, NH (US)

(72) Inventor: Philipp K. Lang, Franconia, NH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/454,546

(22) Filed: Nov. 11, 2021

(65) Prior Publication Data
US 2022/0087746 A1 Mar. 24, 2022

Related U.S. Application Data

(63) Continuation of application No. 17/323,080, filed on May 18, 2021, now Pat. No. 11,172,990, which is a
(Continued)

(51) Int. Cl.
A61B 34/10 (2016.01)
A61B 34/00 (2016.01)
(Continued)

(52) U.S. Cl.
CPC ............ A61B 34/10 (2016.02); A61B 17/155 (2013.01); A61B 17/157 (2013.01); A61B 17/1703 (2013.01); A61B 17/1742 (2013.01); A61B 17/1764 (2013.01); A61B 17/1775 (2016.11); A61B 17/1778 (2016.11); A61B 34/74 (2016.02); A61B 90/36 (2016.02); A61B 90/37 (2016.02); A61F 2/32 (2013.01); A61F 2/389 (2013.01); A61F 2/3859 (2013.01); H05K 999/99 (2013.01); A61B 17/15 (2013.01);
(Continued)

(58) Field of Classification Search
CPC .. A61B 17/1775; A61B 17/1778; A61B 34/10
See application file for complete search history.

(56) References Cited

U.S. PATENT DOCUMENTS 5,526,812 A 6/1996 Dumoulin et al.
5,676,673 A 10/1997 Ferre et al.
(Continued)

FOREIGN PATENT DOCUMENTS

EP 1028659 B1 2/2004
GB 2498833 B 12/2016
(Continued)

OTHER PUBLICATIONS

Sauer et al., "An Augmented Reality Navigation System with a Single-Camera Tracker System Design and Needle Biopsy Phantom Trial", Proceedings of the 5th International Conference on Medical Image Computing and Computer-Assisted Intervention—Part II, pp. 116-124, Sep. 2002.
(Continued)

Primary Examiner — Andrew Yang
(74) Attorney, Agent, or Firm — Greenberg Traurig, LLP; Natalie Salem; Barry Schindler

(57) ABSTRACT

Devices and methods for performing a surgical step or surgical procedure with visual guidance using an optical head mounted display are disclosed.

30 Claims, 41 Drawing Sheets

Related U.S. Application Data continuation of application No. 17/111,643, filed on Dec. 4, 2020, now Pat. No. 11,013,560, which is a continuation of application No. 17/036,631, filed on Sep. 29, 2020, which is a continuation of application No. 16/668,360, filed on Oct. 30, 2019, now Pat. No. 10,799,296, which is a continuation of application No. 16/524,436, filed on Jul. 29, 2019, now Pat. No. 10,603,113, which is a continuation of application No. 16/406,392, filed on May 8, 2019, now Pat. No. 10,405,927, which is a continuation of application No. 15/988,455, filed on May 24, 2018, now Pat. No. 10,292,768, which is a continuation of application No. 15/843,239, filed on Dec. 15, 2017, now Pat. No. 9,980,780, which is a continuation of application No. 15/456,084, filed on Mar. 10, 2017, now Pat. No. 9,861,446.

(60) Provisional application No. 62/453,484, filed on Feb. 1, 2017, provisional application No. 62/445,691, filed on Jan. 12, 2017, provisional application No. 62/425,019, filed on Nov. 21, 2016, provisional application No. 62/406,379, filed on Oct. 10, 2016, provisional application No. 62/393,054, filed on Sep. 11, 2016, provisional application No. 62/378,242, filed on Aug. 23, 2016, provisional application No. 62/354,780, filed on Jun. 26, 2016, provisional application No. 62/331,995, filed on May 5, 2016, provisional application No. 62/323,716, filed on Apr. 17, 2016, provisional application No. 62/318,157, filed on Apr. 4, 2016, provisional application No. 62/307,476, filed on Mar. 12, 2016.

(51) Int. Cl.

| | | |
|---|---|---|
| *A61B 90/00* | (2016.01) | |
| *A61B 17/17* | (2006.01) | |
| *A61B 17/15* | (2006.01) | |
| *A61F 2/32* | (2006.01) | |
| *A61F 2/38* | (2006.01) | |
| *A61B 17/00* | (2006.01) | |
| *A61B 34/20* | (2016.01) | |
| *A61B 17/16* | (2006.01) | |
| *A61B 17/56* | (2006.01) | |
| *A61B 90/50* | (2016.01) | |
| *A61F 2/40* | (2006.01) | |
| *A61F 2/42* | (2006.01) | |

(52) U.S. Cl.
CPC ........... *A61B 17/1666* (2013.01); *A61B 17/17* (2013.01); *A61B 2017/00216* (2013.01); *A61B 2017/568* (2013.01); *A61B 2034/104* (2016.02); *A61B 2034/107* (2016.02); *A61B 2034/2048* (2016.02); *A61B 2034/2055* (2016.02); *A61B 2034/2059* (2016.02); *A61B 2090/365* (2016.02); *A61B 2090/368* (2016.02); *A61B 2090/372* (2016.02); *A61B 2090/373* (2016.02); *A61B 2090/374* (2016.02); *A61B 2090/376* (2016.02); *A61B 2090/3762* (2016.02); *A61B 2090/502* (2016.02); *A61F 2002/4018* (2013.01); *A61F 2002/4205* (2013.01); *A61F 2002/4207* (2013.01)

(56) References Cited

U.S. PATENT DOCUMENTS

| | | |
|---|---|---|
| 5,800,352 A | 9/1998 | Ferre et al. |
| 5,803,089 A | 9/1998 | Ferre et al. |
| 5,829,444 A | 11/1998 | Ferre et al. |
| 5,873,822 A | 2/1999 | Ferre et al. |
| D415,146 S | 10/1999 | Hori |
| 5,967,980 A | 10/1999 | Ferre et al. |
| 6,175,756 B1 | 1/2001 | Ferre et al. |
| 6,341,231 B1 | 1/2002 | Ferre et al. |
| 6,396,497 B1 | 5/2002 | Reichlen |
| 6,445,943 B1 | 9/2002 | Ferre et al. |
| 6,599,247 B1 | 7/2003 | Stetten |
| 6,714,810 B2 | 3/2004 | Grzeszczuk et al. |
| 7,130,676 B2 | 10/2006 | Barrick |
| 7,774,044 B2 | 8/2010 | Sauer et al. |
| 7,812,815 B2 | 10/2010 | Banerjee et al. |
| 8,320,612 B2 | 11/2012 | Knobel et al. |
| 8,730,266 B2 | 5/2014 | Brown et al. |
| 8,989,843 B2 | 3/2015 | Chien |
| 9,068,820 B2 | 6/2015 | Kosmecki et al. |
| 9,068,824 B2 | 6/2015 | Findeisen et al. |
| 9,123,155 B2 | 9/2015 | Cunningham et al. |
| 9,183,560 B2 | 11/2015 | Abelow |
| 9,215,293 B2 | 12/2015 | Miller |
| 9,299,138 B2 | 3/2016 | Zellner et al. |
| 9,310,559 B2 | 4/2016 | Macnamara |
| 9,311,284 B2 | 4/2016 | Warila et al. |
| 9,389,424 B1 | 7/2016 | Schowengerdt |
| 9,417,452 B2 | 8/2016 | Schowengerdt et al. |
| 9,429,752 B2 | 8/2016 | Schowengerdt et al. |
| 9,503,681 B1 | 11/2016 | Popescu et al. |
| 9,547,940 B1 | 1/2017 | Sun et al. |
| 9,582,717 B2 | 2/2017 | Lee et al. |
| 9,792,721 B2 | 10/2017 | Kosmecki et al. |
| 9,861,446 B2 | 1/2018 | Lang |
| 9,980,780 B2 | 5/2018 | Lang |
| 10,078,221 B2 | 9/2018 | Pilkinton et al. |
| 10,136,952 B2 | 11/2018 | Couture et al. |
| 10,154,239 B2 | 12/2018 | Gasas |
| 10,159,530 B2 | 12/2018 | Lang |
| 10,278,777 B1 | 5/2019 | Lang |
| 10,292,768 B2 | 5/2019 | Lang |
| 10,368,947 B2 | 8/2019 | Lang |
| 10,405,927 B1 | 9/2019 | Lang |
| 10,603,113 B2 | 3/2020 | Lang |
| 10,743,939 B1 | 8/2020 | Lang |
| 10,799,296 B2 | 10/2020 | Lang |
| 10,849,693 B2 | 12/2020 | Lang |
| 11,013,560 B2 | 5/2021 | Lang |
| 11,172,990 B2 | 11/2021 | Lang |
| 2001/0041838 A1 | 11/2001 | Holupka et al. |
| 2002/0082498 A1 | 6/2002 | Wendt et al. |
| 2002/0016349 A1 | 11/2002 | Sauer |
| 2005/0113846 A1 | 5/2005 | Carson |
| 2005/0215879 A1 | 9/2005 | Chuanggui |
| 2005/0028146 A1 | 12/2005 | Marquart et al. |
| 2005/0267353 A1 | 12/2005 | Marquart et al. |
| 2005/0281465 A1 | 12/2005 | Marquart et al. |
| 2006/0142739 A1 | 6/2006 | Disilestro et al. |
| 2007/0015999 A1 | 1/2007 | Heldreth et al. |
| 2007/0035511 A1 | 2/2007 | Banerjee et al. |
| 2007/0038944 A1 | 2/2007 | Carignano et al. |
| 2007/0236514 A1 | 10/2007 | Agusanto et al. |
| 2007/0276234 A1 | 11/2007 | Shahidi |
| 2009/0068620 A1 | 3/2009 | Knobel et al. |
| 2009/0089081 A1 | 4/2009 | Haddad |
| 2009/0138019 A1 | 5/2009 | Wasielewski |
| 2009/0267805 A1 | 10/2009 | Jin et al. |
| 2011/0190637 A1 | 8/2011 | Knobel et al. |
| 2013/0093829 A1 | 4/2013 | Rosenblatt et al. |
| 2013/0096373 A1 | 4/2013 | Chabanas et al. |
| 2013/0116574 A1 | 5/2013 | Knobel et al. |
| 2013/0169683 A1 | 7/2013 | Perez et al. |
| 2013/0261503 A1 | 10/2013 | Sherman et al. |
| 2013/0261504 A1 | 10/2013 | Claypool et al. |
| 2013/0261633 A1 | 10/2013 | Thornberry |

(56) References Cited

U.S. PATENT DOCUMENTS

| | | |
|---|---|---|
| 2013/0296682 A1 | 11/2013 | Clavin et al. |
| 2013/0326364 A1 | 12/2013 | Latta et al. |
| 2014/0081659 A1 | 3/2014 | Nawana et al. |
| 2014/0085203 A1 | 3/2014 | Kobayashi |
| 2014/0088941 A1 | 3/2014 | Banerjee et al. |
| 2014/0118335 A1 | 5/2014 | Gurman |
| 2014/0135746 A1 | 5/2014 | Schoepp |
| 2014/0198190 A1 | 7/2014 | Okumu |
| 2014/0218366 A1 | 8/2014 | Kosmecki et al. |
| 2014/0275760 A1 | 9/2014 | Lee et al. |
| 2014/0303491 A1 | 10/2014 | Shekhar et al. |
| 2014/0334670 A1 | 11/2014 | Guigues et al. |
| 2015/0100067 A1 | 4/2015 | Cavanagh et al. |
| 2015/0206218 A1 | 7/2015 | Banerjee et al. |
| 2015/0366628 A1 | 12/2015 | Ingmanson |
| 2016/0163105 A1 | 6/2016 | Hong et al. |
| 2016/0182877 A1 | 6/2016 | DeLuca |
| 2016/0191887 A1 | 6/2016 | Casas |
| 2016/0206379 A1 | 7/2016 | Flett et al. |
| 2016/0220105 A1 | 8/2016 | Duret |
| 2016/0225192 A1 | 8/2016 | Jones et al. |
| 2016/0228193 A1 | 8/2016 | Moctezuma de la Barrera et al. |
| 2016/0287337 A1 | 10/2016 | Aram et al. |
| 2016/0324580 A1 | 11/2016 | Esterberg |
| 2016/0381256 A1 | 12/2016 | Aguirre-Valencia |
| 2017/0027651 A1 | 2/2017 | Esterberg |
| 2017/0035517 A1 | 2/2017 | Geri et al. |
| 2017/0071673 A1 | 3/2017 | Ferro et al. |
| 2017/0108930 A1 | 4/2017 | Banerjee et al. |
| 2017/0160549 A1 | 6/2017 | Badiali et al. |
| 2017/0178375 A1 | 6/2017 | Benishti et al. |
| 2017/0202633 A1 | 7/2017 | Liu |
| 2017/0231714 A1 | 8/2017 | Kosmecki et al. |
| 2017/0258526 A1 | 9/2017 | Lang |
| 2018/0049622 A1 | 2/2018 | Ryan et al. |
| 2018/0116728 A1 | 5/2018 | Lang |
| 2018/0125584 A1 | 5/2018 | Lang |
| 2018/0256256 A1 | 9/2018 | May et al. |
| 2018/0263704 A1 | 9/2018 | Lang |
| 2019/0000564 A1 | 1/2019 | Navab et al. |
| 2019/0110842 A1 | 4/2019 | Lang |
| 2019/0192226 A1 | 6/2019 | Lang |
| 2019/0216452 A1 | 7/2019 | Nawana et al. |
| 2019/0262078 A1 | 8/2019 | Lang |
| 2019/0380784 A1 | 12/2019 | Lang |
| 2020/0060767 A1 | 2/2020 | Lang |
| 2020/0246074 A1 | 8/2020 | Lang |
| 2020/0305980 A1 | 10/2020 | Lang |
| 2021/0022808 A1 | 1/2021 | Lang |
| 2021/0106386 A1 | 4/2021 | Lang |
| 2021/0267691 A1 | 9/2021 | Lang |

FOREIGN PATENT DOCUMENTS

| | | |
|---|---|---|
| WO | 9325157 | 12/1993 |
| WO | 2005088539 | 9/2005 |
| WO | 2010/034117 A1 | 4/2010 |
| WO | 2014057352 A1 | 4/2014 |
| WO | 2015/110859 A1 | 7/2015 |
| WO | 2015145395 | 10/2015 |
| WO | 2015145395 A1 | 10/2015 |
| WO | 2016028828 | 2/2016 |
| WO | 2016162789 | 10/2016 |
| WO | 2016195401 | 12/2016 |
| WO | 2016207628 | 12/2016 |
| WO | 2016207628 A1 | 12/2016 |
| WO | 2018/085417 A1 | 5/2018 |
| WO | 2018/085691 A1 | 5/2018 |
| WO | 2018/052966 A1 | 10/2018 |

OTHER PUBLICATIONS

Sauer et al., "Augmented Workspace: Designing an AR Testbed", Proceedings IEEE and ACM International Symposium on Augmented Reality, pp. 47-53, Munich 2000.

Scuderi et al., "Total Knee Arthroplasty with a Novel Navigation System Within the Surgical Field", Orthopedic Clinics, vol. 45, Issue 2, pp. 167-173, Apr. 2014.

Shen et al., "3D Augmented Reality with Integral Imaging Display", Proceedings of SPIE—The International Society for Optical Engineering, vol. 9867, Article No. 98670Y, Apr. 2016.

Sherstyuk et al., "Dynamic Eye Convergence for Head-Mounted Displays Improves User Performance in Virtual Environments", Proceedings of the ACM SIGGRAPH Symposium on Interactive 3D Graphics and Games, pp. 23-30, Mar. 2012.

Tong et al., "Scanning 3D Full Human Bodies Using Kinects", IEEE Transactions on Visualization and Computer Graphics, vol. 18, Issue 4, pp. 643-650, Apr. 1, 2012.

Trevisan et al., "Towards Markerless Augmented Medical Visualization", AMI-ARCS, pp. 57-66, 2004.

Vagvolgyi et al., "Video to CT Registration for Image Overlay on Solid Organs", Procedural Augmented Reality in Medical Imaging and Augmented Reality in Computer-Aided Surgery (AMIARCS) pp. 78-86, 2008.

Vercauteren et al., "Real Time Autonomous Video Image Registration for Endomicroscopy: Fighting the Compromises", Three-Dimensional and Multidimensional Microscopy: Image Acquisition and Processing XV., vol. 6861, pp. 68610C. International Society for Optics and Photonics, Feb. 12, 2008.

Vogt et al., "Reality Augmentation for Medical Procedures: System Architecture, Single Camera Marker Tracking, and System Evaluation", International Journal of Computer Vision, vol. 70, No. 2, pp. 179-190, 2006.

Vogt, Sebastian, "Real-Time Augmented Reality for Image-Guided Interventions", PhD Thesis, Nürnberg: Der Technischen Fakultät der Universität Erlangen, 2009.

Wang et al., "3D Modeling from Wide Baseline Range Scans Using Contour Coherence", Proceedings of the IEEE Conference on Computer Vision and Pattern Recognition, pp. 4018-4025, 2014.

Wang et al., "Augmented Reality Navigation with Automatic Marker-Free Image Registration Using 3-D Image Overlay tor Dental Surgery", IEEE Transactions on Biomedical Engineering, vol. 61, No. 4, pp. 1295-1304, Apr. 2014.

Xiaojun et al., "Development of a Surgical Navigation System Based on Augmented Reality Using an Optical See-Through Head-Mounted Display", Journal of Biomedical Informatics, vol. 55, pp. 124-131, 2015.

Ye et al., "Accurate 3D Pose Estimation From a Single Depth Image", IEEE International Conference on Computer Mision (ICCV), pp. 731-738, Nov. 2011.

Yoon et al., "Technical Feasibility and Safety of an Intraoperative Head-Up Display Device During Spine Instrumentation", The International Journal of Medical Robotics and Computer Assisted Surgery, vol. 13, No. 3, pp. 1-9, Sep. 2017.

Bauer, Sebastian, Doctoral Thesis, "Rigid and Non-Rigid Surface Registration for Range Imaging Applications in Medicine", urn:nbn:de:bvb:29-opus4-54665, Nov. 27, 2014.

Bauer et al., "Joint ToF Image Denoising and Registration with a CT Surface in Radiation Therapy", Scale Space and Variational Methods in Computer Vision, Lecture Notes in Computer Science, Springer, vol. 6667, pp. 98-109.

Bauer et al., "Multi-Modal Surface Registration for Markerless Initial Patient Setup in Radiation Therapy Using Microsoft's Kinect Sensor", 2011 IEEE International Conference on Computer Vision Workshops (ICCV Workshops), Barcelona, Nov. 2011, pp. 1175-1181, Jan. 16, 2012.

Bauer et al., "Real-Time Range Imaging in Health Care: A Survey", Time-of-Flight and Depth Imaging. Sensors, Algorithms, and Applications. Lecture Notes in Computer Science, vol. 8200, pp. 228-254, 2017.

(56) References Cited

OTHER PUBLICATIONS

Birkfellner et al., "Computer-enhanced stereoscopic vision in a head-mounted operating binocular", Physics in Medicine & Biology, vol. 48, No. 3, pp. 49-57, Feb. 7, 2003.
Birkfellner et al., "In-Vitro Aassessment of a Registration Protocol for Image Guided Implant Dentistry", Clinical Oral Implants Research, vol. 12, Issue 1, pp. 69-78, Feb. 2001.
Birkfellner et al., "A Head-Mounted Operating Binocular for Augmented Reality Visualization in Medicine—Design and Initial Evaluation", IEEE Transactions on Medical Imaging, vol. 21, No. 8, pp. 991-997, Aug. 2002.
Blackwell et al., "An Image Overlay System for Medical Data Visualization", Medical Image Analysis vol. 4, pp. 67-72, 2000.
Blackwell et al., "Augmented Reality and Its Future in Orthopaedics", Clinical Orthopaedics & Related Research, vol. 354, pp. 111-122, Sep. 1998.
Abe et al., "A Novel 3D Guidance System Using Augmented Reality for Percutaneous Vertebroplasty", Journal of Neurological Spine, vol. 19, pp. 492-501, Oct. 2013.
Castillo et al., "Augmented Reality for Assistance of Total Knee Replacement", Journal of Electrical and Computer Engineering, vol. 2016, Article 9358369, pp. 1-6, 2016.
Catani et al., "Knee Surgery Using Computer Assisted Surgery and Robotics", Springer Heidelberg Publishing, Book, pp. 1-221, 2013.
Cui et al., "KinectAvatar: Fully Automatic Body Capture Using a Single Kinect", ACCV'12 Proceedings of the 11th International Conference on Computer Vision—vol. 2, pp. 133-147, Nov. 2012.
DeLambert et al., "Electromagnetic Tracking for Registration and Navigation in Endovascular Aneurysm Repair: A Phantom Study" European Journal of Vascular and Endovascular Surgery, vol. 43, pp. 684-689, 2012.
Draelos, Mark, "The Kinect Up Close: Modifications for Short-Range Depth Imaging", NC State Theses and Dissertations, pp. 1-88, Mar. 26, 2012.
Ferrari et al., "Video See-Through in the Clinical Practice", 1st International Workshop on Engineering Interactive Computing Systems for Medicine and Health Care, EICS4Med. vol. 727, pp. 19-24, 2011.
Fischer et al., "Medical Augmented Reality Based on Commercial Image Guided Surgery", European Association for Computer Graphics, Proceedings of the 10th Eurographics Symposium on Virtual Environments, pp. 83-86, Jun. 2004.
Flusser et al., "Image Fusion: Principles, Methods and Applications", Tutorial EISIPCO 2007 Lecture Notes.
Germano et al., Advanced Techniques in Image-Guided Brain and Spine Surgery, Thieme Medical Publishers, Incorporated, 2002.
Hayashibe et al., "Surgical Navigation Display System Using Volume Rendering of Intraoperatively Scanned CT Images", Computer Aided Surgery, vol. 11, No. 5, pp. 240-246, Sep. 2006.
Hu et al., "A Convenient Method of Video See-through Augmented Reality Based on Image-Guided Surgery System", Internet Computing for Engineering and Science, 2013 Seventh International Conference on Internet Computing for Engineering and Science, Shanghai, pp. 100-103, Dec. 12, 2013.
Hua et al., "A 3D Integral Imaging Optical See-Through Head-Mounted Display", Optical Society of America, vol. 22, No. 11, pp. 1-8, Jun. 2, 2014.
Jiang et al., "A Robust Automated Markerless Registration Framework for Neurosurgery Navigation", The International Journal of Medical Robotics and Computer Assisted Surgery, vol. 11, pp. 436-447, Oct. 19, 2014.
Jolesz, Ferenc A., "Intraoperative Imaging and Image-Guided Therapy", Springer Science & Business Media, 893 pages, Jan. 14, 2014.
Kanade et al., "Simulation, Planning, and Execution of Computer-Assisted Surgery", Proceedings of the NSF Grand Challenges Workshop, 1996.
Kersten-Oertel et al., "The State of the Art of Visualization in Mixed Reality Image Guided Surgery", Computerized Medical Imaging and Graphics, vol. 37, pp. 98-112, Jan. 2013.

Kim et al., "Registration Accuracy Enhancement of a Surgical Navigation System for Anterior Cruciate Ligament Reconstruction: A Phantom and Cadaveric Study", The Knee, vol. 24, pp. 329-339, 2017.
Kutter et al., "Real-time Volume Rendering for High Quality Visualization in Augmented Reality", International Workshop on Augmented Environments for Medical Imaging including Augmented Reality in Computer-aided Surgery (AMI-ARCS 2008), New York, MICCAI Society, Sep. 2008.
Liao et al., "Surgical Navigation by Autostereoscopic Image Overlay of Integral Videography", IEEE Transactions on Information Technology in Biomedicine, vol. 8, No. 2, pp. 114-121, Jun. 2004.
Liao et al., "3-D Augmented Reality for MRI-Guided Surgery Using Integral Videography Autostereoscopic Image Overlay", IEEE Transactions on Biomedical Engineering, vol. 57, No. 6, pp. 1476-1486, Jun. 2010.
Lievin et al., "Stereoscopic Augmented Reality System for Computer-Assisted Surgery", International Congress Series, vol. 1230, pp. 107-111, Jun. 2001.
Liu et al., "An Optical See-Through Head Mounted Display with Addressable Focal Planes" IEEE International Symposium on Mixed and Augmented Reality, Cambridge, UK, pp. 33-42, Oct. 3, 2008.
Masamune et al., "An Image Overlay System with Enhanced Reality for Percutaneous Therapy Performed Inside CT Scanner", Medical Image Computing and Computer-Assisted Intervention, Lecture Notes in Computer Science, vol. 2489, pp. 77-84, Oct. 2002.
Maurer et al., "Augmented-Reality Visualization of Brain Structures with Stereo and Kinetic Depth Cues: System Description and Initial Evaluation with Head Phantom", Proceedings, vol. 4319, Medical Imaging 2001 Visualization, Display, and Image-Guided Procedures, pp. 445-456, May 28, 2001.
Maier-Hein et al., "Optical Techniques for 3D Surface Reconstruction in Computer-Assisted Laparoscopic Surgery", Medical Image Analysis, vol. 17, pp. 974-996, May 3, 2013.
Menozzi et al., "Development of Vision-Aided Navigation for a Wearable Outdoor Augmented Reality System", IEEE Plans, Position Location and Navigation Symposium, Article No. 6851442, pp. 760-772, 2014.
Muller et al., "Automatic Multi-Modal ToF/CT Organ Surface Registration", Bildverarbeitung für die Medizin, pp. 154-158, Mar. 2011.
Noonan et al., "The Design and Initial Calibration of an Optical Tracking System Using the Microsoft Kinect", IEEE Nuclear Science Symposium Conference Record, pp. 3614-3617, Oct. 2011.
Okamura, Allison, "Tracking and Surgical Navigation, Registration", Stanford Lecture 8: ME 328: Medical Robotics, pp. 1-19, Spring 2013.
Pauly et al., "Machine Learning-Based Augmented Reality for Improved Surgical Scene Understanding", Computerized Medical Imaging and Graphics, vol. 1280, pp. 1-6, Jun. 2014.
Peters et al., "Image-Guided Interventions, Technology and Applications", Springer Science and Business Media, 576 pages, 2018.
Ren et al., "Marker-Based Surgical Instrument Tracking Using Dual Kinect Sensors", IEEE Transactions on Automation Science and Engineering, vol. 11, No. 3, pp. 921-924, Jul. 2014.
Rinaldi et al., "Computer-Guided Applications for Dental Implants, Bone Grafting, and Reconstructive Surgery", Elsevier Inc., 556 pages, 2016.
Robinett et al., "A Computational Model for the Stereoscopic Optics of a Head-Mounted Display", Proceedings vol. 1457, Stereoscopic Displays and Applications II, pp. 140-160, 1991.
Rolland et al., "A Comparison of Optical and Video See-through Head-mounted Displays", Proceedings vol. 2351, Telemanipulator and Telepresence Technologies, pp. 293-307, Dec. 21, 1995.
Rolland et al., "Optical Versus Video See-Through Head-Mounted Displays in Medical Visualization", Presence: Teleoperators and Virtual Environments, vol. 9, Issue 3, pp. 287-309, Jun. 2000.
Rosman et al., "Articulated Motion Segmentation of Point Clouds by Group-Valued Regularization", Eurographics Workshop on 3D Object Retrieval, EG 3DOR, pp. 77-84, May 2012.

(56) References Cited

OTHER PUBLICATIONS

Daniel and Ramos, "Augmented Reality for Assistance of Total Knee Replacement", Journal of Electrical and Computer Engineering, vol. 2016, Article ID 9358369, Hindawi Publishing Corporation.
Davies et al., "Computer Assisted Orthopaedic Surgery", 8th Annual Meeting of CAOS-International Proceedings, Apr. 2008.
Fritz et al., "Augmented Reality Visualization with Image Overlay for MRI-Guided Intervention: Accuracy for Lumbar Spinal Procedures with a 1 5-T MRI System", Vascular and Interventional Radiology, AJR: 198, Mar. 2012.
George et al., "Low Cost Augmented Reality for Training of MRI-Guided Needle Biopsy of the Spine", Medicine Meets Virtual Reality 16, pp. 138-140, IOS Press, 2008.
Linte et al., "On Mixed Reality Environments for Minimally Invasive Therapy Guidance: Systems Architecture, Successes and Challenges in their Implementation from Laboratory to Clinic", Comput Med Imaging Graph, Mar. 2013;37(2): 83-97, DOI: 10.1016/j.compmedimag.2012.12.002.
Moore et al., "Image Guidance for Spinal Facet Injections Using Tracked Ultrasound", MICCAI 2009, Part I, LNCS 5761, pp. 516-523 2009.
Weiss et al., "Augmented Reality Visualization Using Image-Overlay for MR-Guided Interventions: System Description, Feasibility, and Initial Evaluation in a Spine Phantom", Musculoskeletal Imaging, AJR:196, Mar. 2011, DOI:10.2214/AJR.10.5038.
Blackwell et al., "An Image Overlay System for Medical Data Visualization", In: Wells W.M., Colchester A., Delp S. (eds) Medical Image Computing and Computer-Assisted Intervention—MICCAI'98. MICCAI 1998. Lecture Notes in Computer Science, vol. 1496. Springer, Berlin, Heidelberg; pp. 232-240.
"3D Optical Microscopy for Orthopedic Implants"; Brunker Nano Surfaces, Jun. 17, 2016.
"A Look into the Body—Augmented Reality in Computer Aided Surgery", Department of Informatics, Research—Highlights; Technische Universitat Munchen.
Armstrong et al., "A Heads-Up Display for Diabetic Limb Salvage Surgery: A View Through the Google Looking Glass"; Journal of Diabetes Science and Technology 2014, vol. 8(5) 951-956.
Besl PJ, McKay ND. 2, 1992. A method for registration of 3-D shapes. IEEE Trans PAMI, vol. 14, pp. 239-256.
Bichlmeier et al., "Virtually Extended Surgical Drilling Device: Virtual Mirror for Navigated Spine Surgery"; MICCAI 2007, Part I, LNCS 4791, pp. 434-441.
Chandak, "MEMS Based Wireless Controlled Robot with Voice and Video Camera"; International Journal of Scientific & Engineering Research, vol. 5, Issue 4, Apr. 2014.
Charbonnier et al., "Real Virtuality: Perspectives offered by the combination of Virtual Reality headsets and Motion Capture", Artanim, Real Virtuality White Paper, Aug. 23, 2015.
Chen et al., "Development of a surgical navigation system based on augmented reality using an optical see-through head-mounted display"; Journal of Biomedical Informatics 55 (2015) 124-131.
Elmi-Terander et al., "Surgical Navigation Technology Based on Augmented Reality and Integrated 3D Intraoperative Imaging"; Spine Surgery, vol. 41, No. 21, pp. E1303-1311, 2016.
Fischer et al., "Medical Augmented Reality based on Commercial Image Guided Surgery"; Eurographics Symposium Virtual Environments (2004).
Fritz et al., "Augmented Reality Visualization with Use of Image Overlay Technology for MR Imaging—guided Interventions: Assessment of Performance in Cadaceric Shoulder and Hip Arthrography at 1.5T"; Radiology: vol. 265, No. 1, Oct. 2012, pp. 254-259.
Garon, Mathieu; Boulet, Pierre-Olivier; Doiron, Jean-Philippe; Beaulieu, Luc; Lalonde, Jean-François (2016): Real-time High Resolution 3D Data on the HoloLens. In: International Symposium on Mixed and Augmented Reality (ISMAR).
Garrido-Jurado, S.; Muñoz-Salinas, R.; Madrid-Cuevas, F. J.; Marín-Jiménez, M. J. (2014): Automatic generation and detection of highly reliable fiducial markers under occlusion. In: Pattern Recognition 47 (6), S. 2280-2292. DOI:10.1016/j.patcog.2014.01.005.
Gavaghan et al., "Augmented Reality Image Overlay Projection for Image Guided Open Liver Ablation of Metastatic Liver Cancer"; C.A. Linte et al. (Eds ): AE-CAI 2011, LNCS, pp. 36-46, 2012.
Gromov et al., "What is the optimal alignment of the tibial and femoral components in knee arthroplasty?: An overview of the literature"; Acta Orthopaedica 2014; 85(5): 480-487.
Hinterstoisser, S. Holzer S.; Cagniart, C.; Ilic, S.; Konolige, K.; Navab, N.; Lepetit, V. (2011b): Multimodal Templates for Real-Time Detection of Texture-less Objects in Heavily Cluttered Scenes.
Hinterstoisser, S.; Cagniart, C.; Ilic, S.; Sturm, P.; Navab, N.; Fua, P.; Lepetit, V. (2012a): Gradient Response Maps for Real-Time Detection of Texture-Less Objects. In: IEEE Transactions on Pattern Analysis and Machine Intelligence.
Hinterstoisser, S.; Lepetit, V.; Benhimane, S.; Fua, P.; Navab, N. (2011a): Learning Real-Time Perspective Patch Rectification In: International Journal of Computer Vision (IJCV), Springer. DOI: 10.1007/s11263-010-0379-x.
Hinterstoisser, S.; Lepetit, V.; Ilic, S.; Holzer, S.; Bradski, G.; Konolige, K.; Navab, N. (2012b): Model Based Training, Detection and Pose Estimation of Texture-Less 3D Objects in Heavily Cluttered Scenes.
Hoff, "Fusion of Data from Head-Mounted and Fixed Sensors"; First International Workshop on Augmented Reality, 1, 1998, pp. 1-15.
Holographic weapon sight—Wikipedia https://en.wikipedia.org/wiki/Holographic_weapon_sight retrieved on Nov. 22, 2016.
Hu et al., "A Convenient Method of Video See-Through Augmented Reality Based on Image-Guided Surgery System" Internet Computing for Engineering and Science, Sep. 20-22, 2013.
International Search Report and Written Opinion from International Application No. PCT/US2017/021859 dated May 24, 2017.
Ji et al., "Real-Time Eye, Gaze, and Face Pose Tracking for Monitoring Driver Vigilance"; Real-Time Imaging 8, pp. 357-377, 2002.
Kato, H.; Billinghurst, M. (1999): Marker tracking and HMD calibration for a video-based augmented reality conferencing system. In: Augmented Reality, 1999. (IWAR '99) Proceedings. 2nd IEEE and ACM International Workshop on, S. 85-94.
Kim, Y., Lee, B.H., Mekuria, K., Cho, H., Park, S., Wang, J.H., Lee, D. Registration accuracy enhancement of a surgical navigation system for anterior cruciate ligament reconstruction: A phantom and cadaveric study. Knee. Mar. 2017;24(2):329-339. doi: 10.1016/j.knee.2016.12.007. Epub Feb. 9, 2017.
Kolodzey et al., "Wearable technology in the operating room: a systematic review"; GMJ Innov 2017; 3:55-63.
Kumar et al., "A Portable Wireless Head Movement Controlled Human-Computer Interface for People with Disabilities", International Journal of Advanced Research in Electrical, Electronics and Instrumentation Engineering, vol. 3, Issue 7, Jul. 2014.
Lamata et al., "Augmented Reality for Minimally Invasive Surgery: Overview and Some Recent Advances"; Augmented Reality, Jan. 2010.
Lindert et al., "The use of a head-mounted display for visualization in neuroendoscopy", Computer Aided Surgery, 2004; 9(6): 251-256.
Lorensen WE, Cline HE. [ed.], in M.C. Stone. 1987. Marching cubes: A high resolution 3d surface construction algorithm. Proceedings of SIGGRAPH 87. pp. 163-169.
Melzer, "Head-Mounted Displays", The Avionics Handbook, 2001.
MicroVision 2015 Annual Report and Proxy Statement for 2016 Annual Meeting of Shareholders.
Newcombe, R. A.; Izadi, S.; Hilliges, O.; Molyneaux, D.; Kim, D.; Davison, A. J. et al. (2011): KinectFusion. Real-time dense surface mapping and tracking. In: 2011 10th IEEE International Symposium on Mixed and Augmented Reality, S. 127-136.
Nikou et al., "Augmented Reality Imaging Technology for Orthopaedic Surgery", Operative Techniques in Orthopaedics, vol. 10, No. 1 Jan. 2000: pp. 82-86.
Ortega et al., "Usefulness of a head mounted monitor device for viewing intraoperative fluoroscopy during orthopaedic procedures", Arch Orthop Trauma Surg (2008) 128:1123-1126.

(56) References Cited

OTHER PUBLICATIONS

Paprosky et al., "Intellijoint HIP: a 3D mini-optical navigation tool for improving intraoperative accuracy during total hip arthroplasty"; Med Devices (Auckl). 2016; 9:401-408.

Ponce et al., "Emerging Technology in Surgical Education: Combining Real-Time Augmented Reality and Wearable Computing Devices", The Cutting Edge, Nov. 2014, vol. 37, No. 11.

Qian, Long; Azimi, Ehsan; Kazanzides, Peter; Navab, Nassir (2017): Comprehensive Tracker Based Display Calibration for Holographic Optical See-Through Head-Mounted Display.

Rhodes, "A brief history of wearable computing", MIT Wearable Computing Project.

Rosenthal et al., "Augmented Reality Guidance for Needle Biopsies: A Randomized, Controlled Trial in Phantoms" MICCAI 2001, LNCS 2208: 240-248.

Sanko, "Microvision's Nomad Augmented Vision System: The How and the Why"; SID Pacific Northwest Chapter Meeting, Jun. 11, 2003.

State et al., "Stereo Imagery from the UNC Augmented Reality System for Breast Biopsy Guidance", MMVR 2003.

Tan, D. J.; Tombari, F.; Ilic, S.; Navab, N. (2015): A Versatile Learning-Based 3D Temporal Tracker. Scalable, Robust, Online. In: 2015 IEEE International Conference on Computer Vision (ICCV), S. 693-701.

Traub, J., Stefan, P., Heining, S.M., Sielhorst, T., Riquarts, C., Eulerz, E., Navab, N. (2006): Hybrid Navigation Interface for Orthopedic and Trauma Surgery. R. Larsen, M. Nielsen, and J. Sporring (Eds.): MICCAI 2006, LNCS 1190, pp. 373-380.

Wang et al., "Augmented Reality 3D Displays with Micro Integral Imaging"; Journal of Display Technology, Oct. 2014.

Wilson et al., "Validation of Three-Dimensional Models of the Distal Femur Created from Surgical Navigation Point Cloud Data"; CAOS 2015.

Aichert et al., "Image-Based Tracking of the Teeth for Orthodontic Augmented Reality", Medical Image Computing and Computer-Assisted Intervention, Lecture Notes in Computer Science, vol. 7511, Springer, pp. 601-608, 2012.

Anderson et al., "Virtual annotations of the surgical field through an augmented reality transparent display", The Visual Computer, vol. 32, Issue 11, pp. 1481-1498, Nov. 2016.

Baker et al., "The Emergence of Augmented Reality in Orthopaedic Surgery and Education", The Orthopaedic Journal at Harvard Medical School, vol. 16, pp. 8-16, Jun. 2015.

Aguerreche L. et al., "Reconfigurable Tangible Devices for 3D Virtual Object Manipulation by Single or Multiple Users." VRST 2010, Nov. 2010, Hong Kong, Hong Kong SAR China, inria-00534095.

Azura, R., "A survey of augmented reality." Teleoperators and Virtual Environments, vol. 6, Issue 4, Aug. 1997, pp. 355-385.

Bajura, M., et al., "Merging Virtual Objects with the Real World: Seeing Ultrasound Imagery Within the Patient.", In Proceedings of SIGGRAPH '92,1992, New York: ACM Press, pp. 203-210.

Benford, S. et al., "User embodiment in collaborative virtual environments", Proceedings of the SIGCHI conference on uman factors in computing systems, CHI '95, pp. 242-249, 1995.

Bichlmeier C., et al. "Contextual Anatomic Mimesis Hybrid In-Situ Visualization Method for Improving Multi-Sensory Depth Perception in Medical Augmented Reality.", IEEE 2007, 2007 6th IEEE and ACM International Symposium on Mixed and Augmented Reality.

Billinghurst, et al., "The MagicBook: A Transitional AR Interface.", Computers and Graphics, Nov. 2001, pp. 745-753.

Billinghurst, M., et al., "Experiments with Face to Face Collaborative AR Interfaces.", Virtual Reality Journal, vol. 4, No. 2, (2002).

Billinghurst, M., et al., "Collaborative Mixed Reality.", Communications of the ACM 2002, vol. 45 Issue 7, pp. 64-70 (2002).

Billinghurst, M., et al., "Collaborative Mixed Reality", First International Symposium on Mixed Reality (ISMR '99). Mixed Reality—Merging Real and Virtual Worlds, pp. 261-284. Berlin: Springer Verlag.

Cruz-Neira C. et al., "The cave: audio visual experience automatic virtual environment.", Commun. ACM, vol. 35, No. 6. pp. 64-72, Jun. 1992.

Fitzmaurice, G., et al., "Bricks: Laying the Foundations for Graspable User Interfaces.", Proceedings of Conference on Human Factors in Computing Systems (CHI '95), Denver, Colorado, ACM Press, 442-449, (1995).

Gee A, et al., "Processing and visualizing three-dimensional ultrasound data.", The British Journal of Radiology, vol. 17, S186-S193, (2004).

Gonzalez, Smart Multi-Level Tool for Remote Patient Monitoring Based on a Wireless Sensor Network and Mobile Augmented Reality, Sensors, Sep. 2014; 14(9): 17212-17234.

Gorbert, M... et al., "Triangles: Tangible Interface for Manipulation and Exploration of Digital Information Topography.", Proceedings of CHI '98, Apr. 18-23, 1998, © 1998 ACM.

Ishii, H., et al., "Iterative Design of Seamless Collaboration Media.", Communications of the ACM, vol. 37, No. 8, Aug. 1994, pp. 83-97.

Maier-Hein, L. et al., "Towards Mobile Augmented Reality for On-Patient Visualization of Medical Images.", Bildverarbeitung für die Medizin 2011: Algorithmen—Systeme—Anwendungen Proceedings des Workshops vom 20.—Mar. 22, 2011 in Lübeck (pp. 389-393).

Medeiros D. et al., "Proposal and evaluation of a tablet-based tool for 3D virtual environments.", SBC Journal on 3D Interactive Systems, vol. 4, No. 2, pp. 30-40, (2013).

Nicolau, "Augmented Reality in Laparoscopic Surgical Oncology.", Surgical Oncology, vol. 20, pp. 89-201 (2011).

Salmi Jamali, S. et al., "Utilising Mobile-Augmented Reality for Learning Human Anatomy.", 7th World Conference on Educational Sciences, (WCES-2015), Feb. 5-7, 2015, Novotel Athens Convention Center, Athens, Greece.

Schramm, Kinect: The Company Behind the Tech Explains How it Works, Jun. 19, 2010, https://www.engadget.com/2010/06/19/kinect-how-it-works-from-the-company-behind-the-tech/?guccounter=1&guce_referrer=aHR0cHM6Ly93d3cuZ29vZ2xILmNvbS8&guce_referrer_sig=AQAAAKHcnRaFMexHHXiRrcGjKYjWQ2VJGsMA556eCVncvte7f0VM4aN3GpWj1WqU3RfCnTwHcTbxmibv1Iz_TUFgILvsRhShqXDrSM63OcvvjSzpUpBvsC2LsOmHqf-zifqdYe1ctf0D0MDM78YhH-u7w9JUfxuLDGVUxUi9hDQLZo.

Watsen, K., et al., "A Handheld Computer as an Interaction Device to a Virtual Environment.", Proceedings of the International Projection Technologies Workshop, Stuttgart, Germany, May 10-11, 1999.

Wellner, P., "Interacting with Paper on the DigitalDesk.", Communications of the ACM. 36, 7, 87-96, (1993).

Yamazaki, K. et al., "Gesture Laser and Gesture Laser Car—Development of an Embodied Space to Support Remote Instruction.", In Bodker, S., Kyng, M. and Schmidt, K. (eds.), Proceedings of the Sixth European Conference on Computer Supported Cooperative Work—ECSC W'99, Sep. 12-16, Copenhagen, Denmark. Kluwer Academic Publishers, Dordrecht.

Yang H. et al., "Exploring collaborative navigation.", Proceedings of the 4th international conference on Collaborative virtual environments, CVE, pp. 135-142, (2002).

Wang H. et al., "Precision insertion of percutaneous sacroiliac screws using a novel augmented reality-based avigation system: a pilot study"., Inti. Orthop. (SICOT) 2016, 40:1941-1947.

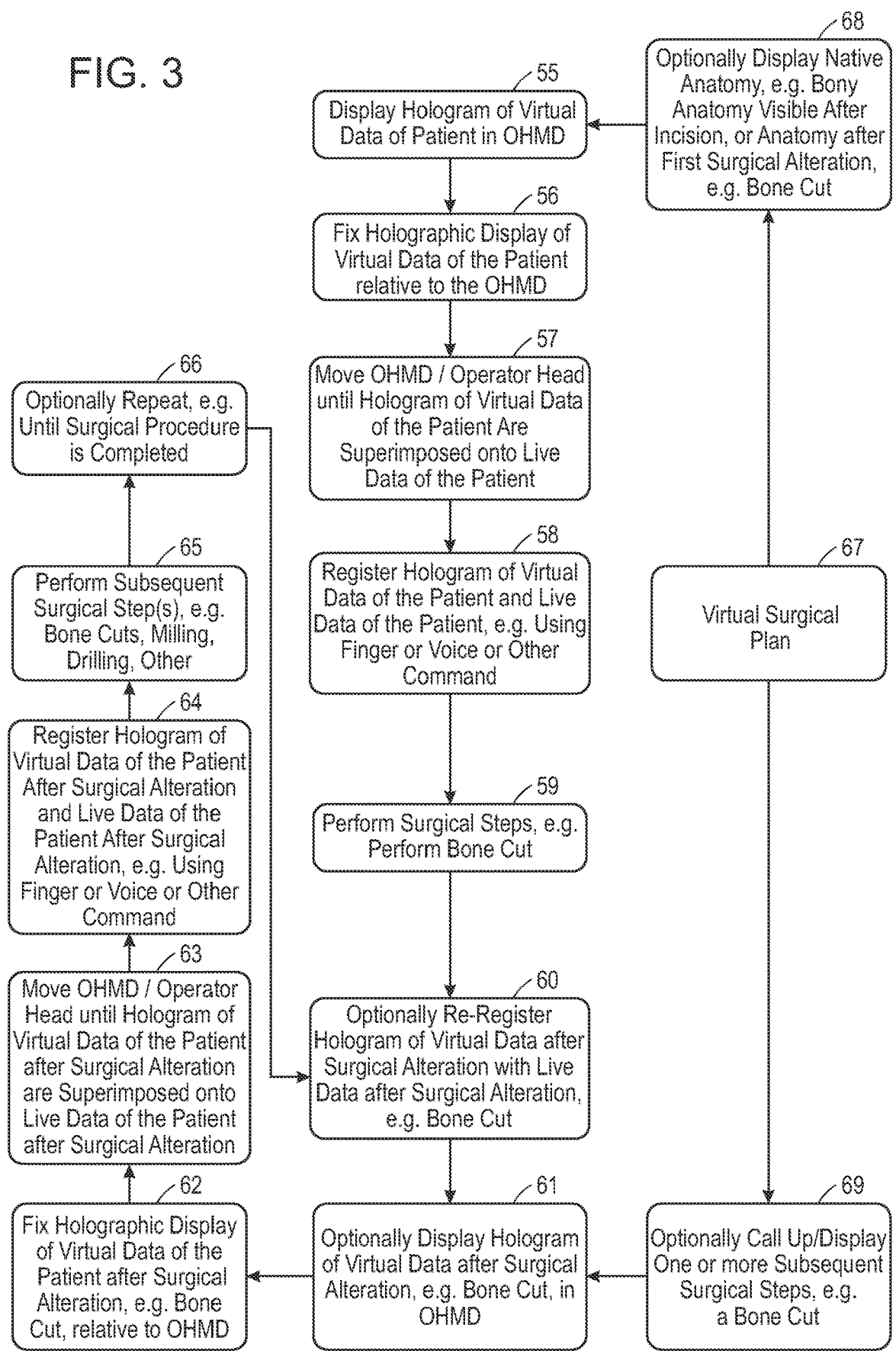

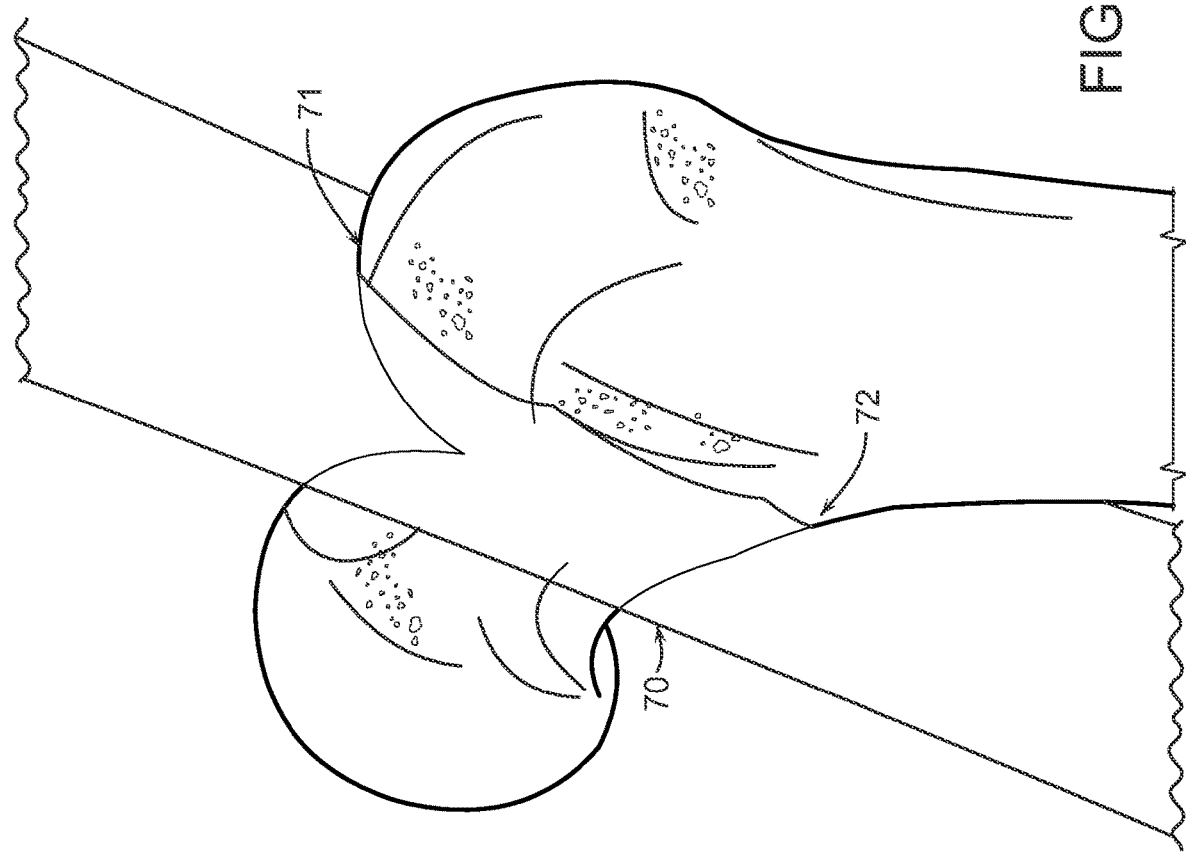

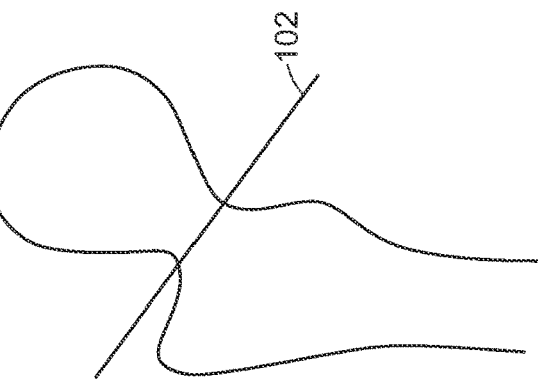
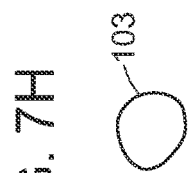
FIG. 7A  FIG. 7B
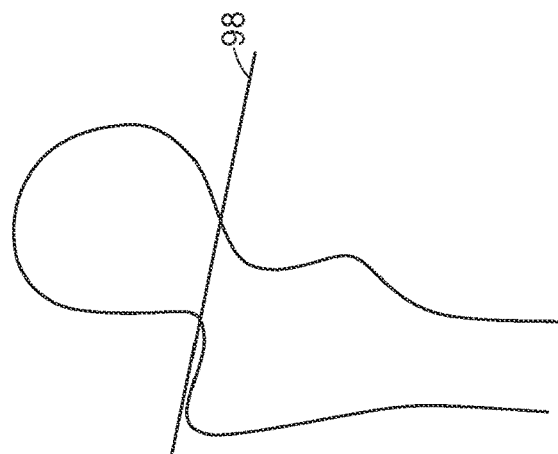
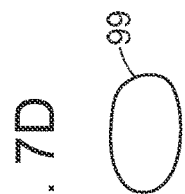
FIG. 7C  FIG. 7D
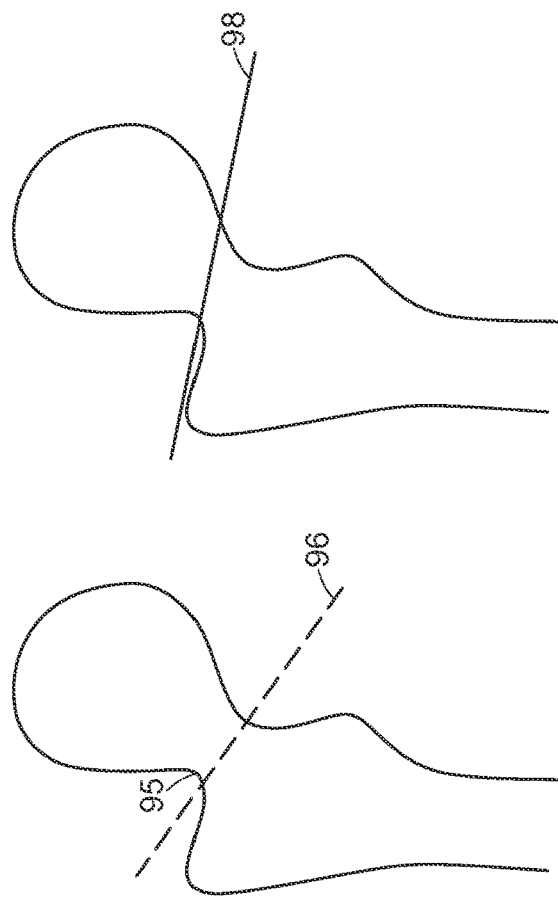
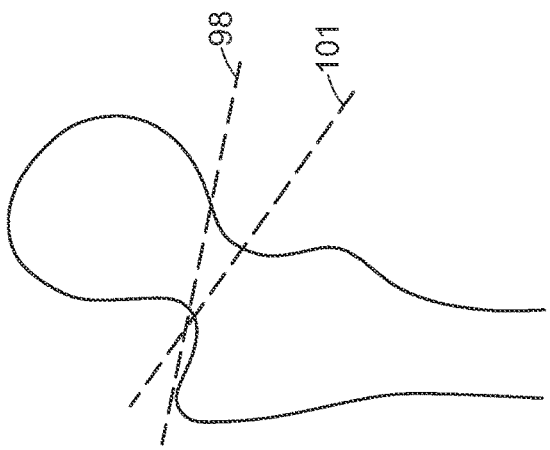
FIG. 7E  FIG. 7F
FIG. 7G  FIG. 7H
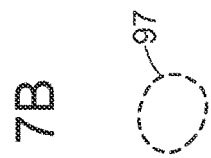

AUGMENTED REALITY GUIDED FITTING, SIZING, TRIALING AND BALANCING OF VIRTUAL IMPLANTS ON THE PHYSICAL JOINT OF A PATIENT FOR MANUAL AND ROBOT ASSISTED JOINT REPLACEMENT

RELATED APPLICATIONS

This application is a continuation application of U.S. application Ser. No. 17/323,080, filed May 18, 2020, which is a continuation of U.S. application Ser. No. 17/111,643, filed Dec. 4, 2020, now U.S. Pat. No. 11,013,560, which is a continuation application of Ser. No. 17/036,631, filed Sep. 29, 2020, which is a continuation application of U.S. application Ser. No. 16/668,360, filed Oct. 30, 2019, now U.S. Pat. No. 10,799,296, which is a continuation application of U.S. application Ser. No. 16/524,436, filed Jul. 29, 2019, now U.S. Pat. No. 10,603,113, which is a continuation application of U.S. application Ser. No. 16/406,392, filed May 8, 2019, now U.S. Pat. No. 10,405,927, which is a continuation application of U.S. application Ser. No. 15/988,455, filed May 24, 2018, now U.S. Pat. No. 10,292,768, which is a continuation of U.S. application Ser. No. 15/843,239, filed Dec. 15, 2017, now U.S. Pat. No. 9,980,780, which is a continuation of U.S. application Ser. No. 15/456,084, filed Mar. 10, 2017, now U.S. Pat. No. 9,861,446, which claims the benefit of and priority to U.S. Provisional Application Ser. No. 62/307,476, filed Mar. 12, 2016, U.S. Provisional Application Ser. No. 62/318,157, filed Apr. 4, 2016, U.S. Provisional Application Ser. No. 62/323,716, filed Apr. 17, 2016, U.S. Provisional Application Ser. No. 62/331,995, filed May 5, 2016, U.S. Provisional Application Ser. No. 62/354,780, filed Jun. 26, 2016, U.S. Provisional Application Ser. No. 62/378,242, filed Aug. 23, 2016, U.S. Provisional Application Ser. No. 62/393,054, filed Sep. 11, 2016, U.S. Provisional Application Ser. No. 62/406,379, filed Oct. 10, 2016, U.S. Provisional Application Ser. No. 62/425,019, filed Nov. 21, 2016, U.S. Provisional Application Ser. No. 62/445,691, filed Jan. 12, 2017, and U.S. Provisional Application Ser. No. 62/453,484, filed Feb. 1, 2017, the entire contents of each of which are hereby incorporated by reference in their entireties.

TECHNICAL FIELD

Aspects of the invention relate to devices and methods for performing a surgical step or surgical procedure with visual guidance using an optical head mounted display.

BACKGROUND

With computer assisted surgery, e.g. surgical navigation or robotics, pre-operative imaging studies of the patient can be used. The imaging studies can be displayed in the OR on an external computer monitor and the patient's anatomy, e.g. landmarks, can be registered in relationship to the information displayed on the monitor. Since the surgical field is in a different location and has a different view coordinate system for the surgeon's eyes than the external computer monitor, hand-eye coordination can be challenging for the surgeon.

SUMMARY OF THE INVENTION

Aspects of the invention provides, among other things, for a simultaneous visualization of live data of the patient, e.g. a patient's spine or joint, and digital representations of virtual data such as virtual cuts and/or virtual surgical guides including cut blocks or drilling guides through an optical head mounted display (OHMD). In some embodiments, the surgical site including live data of the patient, the OHMD, and the virtual data are registered in a common coordinate system. In some embodiments, the virtual data are superimposed onto and aligned with the live data of the patient. Unlike virtual reality head systems that blend out live data, the OHMD allows the surgeon to see the live data of the patient, e.g. the surgical field, while at the same time observing virtual data of the patient and/or virtual surgical instruments or implants with a predetermined position and/or orientation using the display of the OHMD unit.

Aspects of the invention describe novel devices for performing a surgical step or surgical procedure with visual guidance using an optical head mounted display, e.g. by displaying virtual representations of one or more of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

Aspects of the invention relate to a device comprising at least one optical head mounted display, the device being configured to generate a virtual surgical guide. In some embodiments, the virtual surgical guide is a three-dimensional representation in digital format which corresponds to at least one of a portion of a physical surgical guide, a placement indicator of a physical surgical guide, or a combination thereof. In some embodiments, the at least one optical head mounted display is configured to display the virtual surgical guide superimposed onto a physical joint based at least in part on coordinates of a predetermined position of the virtual surgical guide, and the virtual surgical guide is configured to align the physical surgical guide or a physical saw blade with the virtual surgical guide to guide a bone cut of the joint.

In some embodiments, the device comprises one, two, three or more optical head mounted displays.

In some embodiments, the virtual surgical guide is configured to guide a bone cut in a knee replacement, hip replacement, shoulder joint replacement or ankle joint replacement.

In some embodiments, the virtual surgical guide includes a virtual slot for a virtual or a physical saw blade.

In some embodiments, the virtual surgical guide includes a planar area for aligning a virtual or a physical saw blade.

In some embodiments, the virtual surgical guide includes two or more virtual guide holes or paths for aligning two or more physical drills or pins.

In some embodiments, the predetermined position of the virtual surgical guide includes anatomical information, and/or alignment information of the joint. For example, the anatomic and/or alignment information of the joint can be based on at least one of coordinates of the joint, an anatomical axis of the joint, a biomechanical axis of the joint, a mechanical axis, or combinations thereof.

In some embodiments, the at least one optical head mounted display is configured to align the virtual surgical guide based on a predetermined limb alignment. For example, the predetermined limb alignment can be a normal mechanical axis alignment of a leg.

In some embodiments, the at least one optical head mounted display is configured to align the virtual surgical guide based on a predetermined femoral or tibial component rotation. In some embodiments, the at least one optical head mounted display is configured to align the virtual surgical guide based on a predetermined flexion of a femoral component or a predetermined slope of a tibial component.

In some embodiments, the virtual surgical guide is configured to guide a proximal femoral bone cut based on a predetermined leg length.

In some embodiments, the virtual surgical guide is configured to guide a bone cut of a distal tibia or a talus in an ankle joint replacement and the at least one optical head mounted display is configured to align the virtual surgical guide based on a predetermined ankle alignment, wherein the predetermined ankle alignment includes a coronal plane implant component alignment, a sagittal plane implant component alignment, an axial plane component alignment, an implant component rotation or combinations thereof.

In some embodiments, the virtual surgical guide is configured to guide a bone cut of a proximal humerus in a shoulder joint replacement and the at least one optical head mounted display is configured to align the virtual surgical guide based on a predetermined humeral implant component alignment, wherein the humeral implant component alignment includes a coronal plane implant component alignment, a sagittal plane implant component alignment, an axial plane component alignment, an implant component, or combinations thereof.

In some embodiments, the predetermined position of the surgical guide is based on a pre-operative or intra-operative imaging study, one or more intra-operative measurements, intra-operative data or combinations thereof.

Aspects of the invention relate to a device comprising two or more optical head mounted displays for two or more users, wherein the device is configured to generate a virtual surgical guide, wherein the virtual surgical guide is a three-dimensional representation in digital format which corresponds to at least one of a portion of a physical surgical guide, a placement indicator of a physical surgical guide, or a combination thereof, wherein the optical head mounted display is configured to display the virtual surgical guide superimposed onto a physical joint based at least in part on coordinates of a predetermined position of the virtual surgical guide, and wherein the virtual surgical guide is configured for aligning the physical surgical guide or a saw blade to guide a bone cut of the joint.

Aspects of the invention relate to a device comprising at least one optical head mounted display and a virtual bone cut plane, wherein the virtual bone cut plane is configured to guide a bone cut of a joint, wherein the virtual bone cut plane corresponds to at least one portion of a bone cut plane, and wherein the optical head mounted display is configured to display the virtual bone cut plane superimposed onto a physical joint based at least in part on coordinates of a predetermined position of the virtual bone cut plane. In some embodiments, the virtual bone cut plane is configured to guide a bone cut in a predetermined varus or valgus orientation or in a predetermined tibial slope or in a predetermined femoral flexion of an implant component or in a predetermined leg length.

Aspects of the invention relates to a method of preparing a joint for a prosthesis in a patient. In some embodiments, the method comprises registering one or more optical head mounted displays worn by a surgeon or surgical assistant in a coordinate system, obtaining one or more intra-operative measurements from the patient's physical joint to determine one or more intra-operative coordinates, registering the one or more intra-operative coordinates from the patient's physical joint in the coordinate system, generating a virtual surgical guide, determining a predetermined position and/or orientation of the virtual surgical guide based on the one or more intra-operative measurements, displaying and superimposing the virtual surgical guide, using the one or more optical head mounted displays, onto the physical joint based at least in part on coordinates of the predetermined position of the virtual surgical guide, and aligning the physical surgical guide or a physical saw blade with the virtual surgical guide to guide a bone cut of the joint.

In some embodiments, the one or more optical head mounted displays are registered in a common coordinate system. In some embodiments, the common coordinate system is a shared coordinate system.

In some embodiments, the virtual surgical guide is used to guide a bone cut in a knee replacement, hip replacement, shoulder joint replacement or ankle joint replacement.

In some embodiments, the predetermined position of the virtual surgical guide determines a tibial slope for implantation of one or more tibial implant components in a knee replacement. In some embodiments, the predetermined position of the virtual surgical guide determines an angle of varus or valgus correction for a femoral and/or a tibial component in a knee replacement.

In some embodiments, the virtual surgical guide corresponds to a physical distal femoral guide or cut block and the predetermined position of the virtual surgical guide determines a femoral component flexion.

In some embodiments, the virtual surgical guide corresponds to a physical anterior or posterior femoral surgical guide or cut block and the predetermined position of the virtual surgical guide determines a femoral component rotation.

In some embodiments, the virtual surgical guide corresponds to a physical chamfer femoral guide or cut block.

In some embodiments, the virtual surgical guide corresponds to a physical multi-cut femoral guide or cut block and the predetermined position of the virtual surgical guide determines one or more of an anterior cut, posterior cut, chamfer cuts and a femoral component rotation.

In some embodiments, the virtual surgical guide is used in a hip replacement and the predetermined position of the virtual surgical guide determines a leg length after implantation. In some embodiments, the virtual surgical guide is a virtual plane for aligning the physical saw blade to guide the bone cut of the joint.

In some embodiments, the one or more intraoperative measurements include detecting one or more optical markers attached to the patient's joint, the operating room table, fixed structures in the operating room or combinations thereof. In some embodiments, one or more cameras or image capture or video capture systems included in the optical head mounted display detect one or more optical markers including their coordinates (x, y, z) and at least one or more of a position, orientation, alignment, direction of movement or speed of movement of the one or more optical markers.

In some embodiments, registration of one or more of optical head mounted displays, surgical site, joint, spine, surgical instruments or implant components can be performed with use of spatial mapping techniques.

In some embodiments, registration of one or more of optical head mounted displays, surgical site, joint, spine, surgical instruments or implant components can be performed with use of depth sensors.

In some embodiments, the virtual surgical guide is used to guide a bone cut of a distal tibia or a talus in an ankle joint replacement and the one or more optical head mounted display is used to align the virtual surgical guide based on a predetermined tibial or talar implant component alignment, wherein the predetermined tibial or talar implant component alignment includes a coronal plane implant component alignment, a sagittal plane implant component alignment, an axial plane component alignment, an implant component rotation of an implant component or combinations thereof.

In some embodiments, the virtual surgical guide is used to guide a bone cut of a proximal humerus in a shoulder joint replacement and wherein the one or more optical head mounted display is used to align the virtual surgical guide based on a predetermined humeral implant component alignment, wherein the humeral implant component alignment includes a coronal plane implant component alignment, a sagittal plane implant component alignment, an axial plane component alignment, a humeral implant component rotation, or combinations thereof. Aspects of the invention relate to a system comprising at least one optical head mounted display and a virtual library of implants, wherein the virtual library of implants comprises at least one virtual implant component, wherein the virtual implant component has at least one dimension that corresponds to a dimension of the implant component or has a dimension that is substantially identical to the dimension of the implant component, wherein the at least one optical head mounted display is configured to display the virtual implant component in substantial alignment with a tissue intended for placement of the implant component, wherein the placement of the virtual implant component is intended to achieve a predetermined implant component position and/or orientation.

BRIEF DESCRIPTION OF THE DRAWINGS

Illustrative, non-limiting example embodiments will be more clearly understood from the following detailed description taken in conjunction with the accompanying drawings.

FIG. 3 illustrates an example of registering a digital hologram for an initial surgical step, performing the surgical step and re-registering one or more digital holograms for subsequent surgical steps according to some embodiments of the present disclosure.

FIGS. 4A, 4B and 4C are illustrative examples of arbitrary virtual planes in the hip and a femoral neck cut plane according to some embodiments of the present disclosure.

FIGS. 7A-7H depict illustrative examples of a femoral neck cut and techniques to correct a femoral neck cut according to some embodiments of the present disclosure.

DETAILED DESCRIPTION OF THE INVENTION

Figure 1:
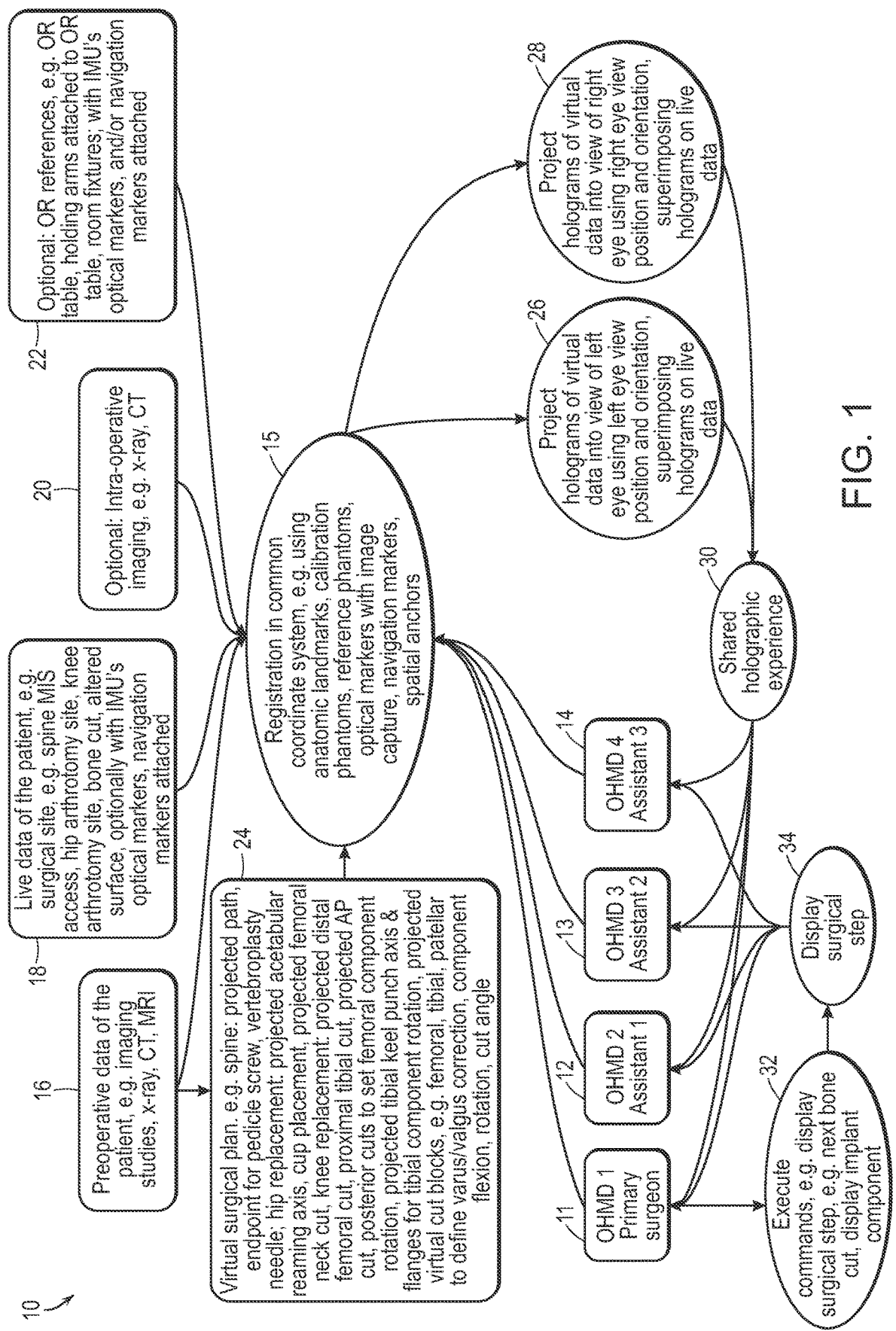
FIG. 1 shows the use of multiple OHMDs for multiple viewer's, e.g. a primary surgeon, second surgeon, surgical assistant(s) and/or nurses(s) according to some embodiments of the present disclosure.

Various exemplary embodiments will be described more fully hereinafter with reference to the accompanying drawings, in which some example embodiments are shown. The present inventive concept may, however, be embodied in many different forms and should not be construed as limited to the example embodiments set forth herein. Rather, these example embodiments are provided so that this disclosure will be thorough and complete, and will fully convey the scope of the present inventive concept to those skilled in the art. In the drawings, the sizes and relative sizes of layers and regions may be exaggerated for clarity. Like numerals refer to like elements throughout.

The term live data of the patient, as used herein, includes the surgical site, anatomy, anatomic structures or tissues and/or pathology, pathologic structures or tissues of the patient as seen by the surgeon's or viewer's eyes without information from virtual data, stereoscopic views of virtual data, or imaging studies. The term live data of the patient does not include internal or subsurface tissues or structures or hidden tissues or structures that can only be seen with assistance of a computer monitor or OHMD.

The terms real surgical instrument, actual surgical instrument, physical surgical instrument and surgical instrument are used interchangeably throughout the application; the terms real surgical instrument, actual surgical instrument, physical surgical instrument and surgical instrument do not include virtual surgical instruments. For example, the physical surgical instruments can be surgical instruments provided by manufacturers or vendors for spinal surgery, pedicle screw instrumentation, anterior spinal fusion, knee replacement, hip replacement, ankle replacement and/or shoulder replacement; physical surgical instruments can be, for example, cut blocks, pin guides, awls, reamers, impactors, broaches. Physical surgical instruments can be re-useable or disposable or combinations thereof. Physical surgical instruments can be patient specific. The term virtual surgical instrument does not include real surgical instrument, actual surgical instrument, physical surgical instrument and surgical instrument.

The terms real surgical tool, actual surgical tool, physical surgical tool and surgical tool are used interchangeably throughout the application; the terms real surgical tool, actual surgical tool, physical surgical tool and surgical tool do not include virtual surgical tools. The physical surgical tools can be surgical tools provided by manufacturers or vendors. For example, the physical surgical tools can be pins, drills, saw blades, retractors, frames for tissue distraction and other tools used for orthopedic, neurologic, urologic or cardiovascular surgery. The term virtual surgical tool does not include real surgical tool, actual surgical tool, physical surgical tool and surgical tool.

The terms real implant or implant component, actual implant or implant component, physical implant or implant component and implant or implant component are used interchangeably throughout the application; the terms real implant or implant component, actual implant or implant component, physical implant or implant component and implant or implant component do not include virtual implant or implant components. The physical implants or implant components can be implants or implant components provided by manufacturers or vendors. For example, the physical surgical implants can be a pedicle screw, a spinal rod, a spinal cage, a femoral or tibial component in a knee replacement, an acetabular cup or a femoral stem and head in hip replacement. The term virtual implant or implant component does not include real implant or implant component, actual implant or implant component, physical implant or implant component and implant or implant component.

With surgical navigation, a first virtual instrument can be displayed on a computer monitor which is a representation of a physical instrument tracked with navigation markers, e.g. infrared or RF markers, and the position and/or orientation of the first virtual instrument can be compared with the position and/or orientation of a corresponding second virtual instrument generated in a virtual surgical plan. Thus, with surgical navigation the positions and/or orientations of the first and the second virtual instruments are compared.

Aspects of the invention relates to devices, systems and methods for positioning a virtual path, virtual plane, virtual tool, virtual surgical instrument or virtual implant component in a mixed reality environment using a head mounted display device, optionally coupled to one or more processing units.

With guidance in mixed reality environment, a virtual surgical guide, tool, instrument or implant can be superimposed onto the physical joint, spine or surgical site. Further, the physical guide, tool, instrument or implant can be aligned with the virtual surgical guide, tool, instrument or implant displayed or projected by the OHMD. Thus, guidance in mixed reality environment does not need to use a plurality of virtual representations of the guide, tool, instrument or implant and does not need to compare the positions and/or orientations of the plurality of virtual representations of the virtual guide, tool, instrument or implant.

In various embodiments, the OHMD can display one or more of a virtual surgical tool, virtual surgical instrument including a virtual surgical guide or virtual cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated or predetermined non-visualized portions for one or more devices or implants or implant components or surgical instruments or surgical tools, and/or one or more of a predetermined tissue change or alteration.

Any of a position, location, orientation, alignment, direction, speed of movement, force applied of a surgical instrument or tool, virtual and/or physical, can be predetermined using, for example, pre-operative imaging studies, pre-operative data, pre-operative measurements, intra-operative imaging studies, intra-operative data, and/or intra-operative measurements.

Any of a position, location, orientation, alignment, sagittal plane alignment, coronal plane alignment, axial plane alignment, rotation, slope of implantation, angle of implantation, flexion of implant component, offset, anteversion, retroversion, and position, location, orientation, alignment relative to one or more anatomic landmarks, position, location, orientation, alignment relative to one or more anatomic planes, position, location, orientation, alignment relative to one or more anatomic axes, position, location, orientation, alignment relative to one or more biomechanical axes, position, location, orientation, alignment relative to a mechanical axis of a trial implant, an implant component or implant, virtual and/or physical, can be predetermined using, for example, pre-operative imaging studies, pre-operative data, pre-operative measurements, intra-operative imaging studies, intra-operative data, and/or intra-operative measurements. Intra-operative measurements can include measurements for purposes of registration, e.g. of a joint, a spine, a surgical site, a bone, a cartilage, an OHMD, a surgical tool or instrument, a trial implant, an implant component or an implant.

In some embodiments, multiple coordinate systems can be used instead of a common or shared coordinate system. In this case, coordinate transfers can be applied from one coordinate system to another coordinate system, for example for registering the OHMD, live data of the patient including the surgical site, virtual instruments and/or virtual implants and physical instruments and physical implants.

Optical Head Mounted Displays

In some embodiments of the invention, a pair of glasses is utilized. The glasses can include an optical head-mounted display. An optical head-mounted display (OHMD) can be a wearable display that has the capability of reflecting projected images as well as allowing the user to see through it. Various types of OHMDs can be used in order to practice the invention. These include curved mirror or curved combiner OHMDs as well as wave-guide or light-guide OHMDs. The OHMDs can optionally utilize diffraction optics, holographic optics, polarized optics, and reflective optics.

Traditional input devices that can be used with the OHMDs include, but are not limited to touchpad or buttons, smartphone controllers, speech recognition, and gesture recognition. Advanced interfaces are possible, e.g. a brain-computer interface.

Optionally, a computer or server or a workstation can transmit data to the OHMD. The data transmission can occur via cable, Bluetooth, WiFi, optical signals and any other method or mode of data transmission known in the art. The OHMD can display virtual data, e.g. virtual data of the patient, in uncompressed form or in compressed form. Virtual data of a patient can optionally be reduced in resolution when transmitted to the OHMD or when displayed by the OHMD.

When virtual data are transmitted to the OHMD, they can be in compressed form during the transmission. The OHMD can then optionally decompress them so that uncompressed virtual data are being displayed by the OHMD.

Alternatively, when virtual data are transmitted to the OHMD, they can be of reduced resolution during the transmission, for example by increasing the slice thickness of image data prior to the transmission. The OHMD can then optionally increase the resolution, for example by re-interpolating to the original slice thickness of the image data or even thinner slices so that virtual data with resolution equal to or greater than the original virtual data or at least greater in resolution than the transmitted data are being displayed by the OHMD.

In some embodiments, the OHMD can transmit data back to a computer, a server or a workstation. Such data can include, but are not limited to:
Positional, orientational or directional information about the OHMD or the operator or surgeon wearing the OHMD
Changes in position, orientation or direction of the OHMD
Data generated by one or more IMUs
Data generated by markers (radiofrequency, optical, light, other) attached to, integrated with or coupled to the OHMD
Data generated by a surgical navigation system attached to, integrated with or coupled to the OHMD
Data generated by an image and/or video capture system attached to, integrated with or coupled to the OHMD
Parallax data, e.g. using two or more image and/or video capture systems attached to, integrated with or coupled to the OHMD, for example one positioned over or under or near the left eye and a second positioned over or under or near the right eye
Distance data, e.g. parallax data generated by two or more image and/or video capture systems evaluating changes in distance between the OHMD and a surgical field or an object
Motion parallax data
Data related to calibration or registration phantoms (see other sections of this specification)
Any type of live data of the patient captured by the OHMD including image and/or video capture systems attached to, integrated with or coupled to the OHMD
For example, alterations to a live surgical site
For example, use of certain surgical instruments detected by the image and/or video capture system
For example, use of certain medical devices or trial implants detected by the image and/or video capture system Any type of modification to a surgical plan
  Portions or aspects of a live surgical plan
  Portions or aspects of a virtual surgical plan Radiofrequency tags used throughout the embodiments can be of active or passive kind with or without a battery.

Exemplary optical head mounted displays include the ODG R-7, R-8 and R-8 smart glasses from ODG (Osterhout Group, San Francisco, Calif.), the NVIDIA 942 3-D vision wireless glasses (NVIDIA, Santa Clara, Calif.) and the Microsoft HoloLens (Microsoft, Redmond, Wis.).

The Microsoft HoloLens is manufactured by Microsoft. It is a pair of augmented reality smart glasses. Hololens can use the Windows 10 operating system. The front portion of the Hololens includes, among others, sensors, related hardware, several cameras and processors. The visor includes a pair of transparent combiner lenses, in which the projected images are displayed. The HoloLens can be adjusted for the interpupillary distance (IPD) using an integrated program that recognizes gestures. A pair of speakers is also integrated. The speakers do not exclude external sounds and allow the user to hear virtual sounds. A USB 2.0 micro-B receptacle is integrated. A 3.5 mm audio jack is also present.

The HoloLens has an inertial measurement unit (IMU) with an accelerometer, gyroscope, and a magnetometer, four environment mapping sensors/cameras (two on each side), a depth camera with a 120°×120° angle of view, a 2.4-megapixel photographic video camera, a four-microphone array, and an ambient light sensor.

Hololens has an Intel Cherry Trail SoC containing the CPU and GPU. HoloLens includes also a custom-made Microsoft Holographic Processing Unit (HPU). The SoC and the HPU each have 1 GB LPDDR3 and share 8 MB SRAM, with the SoC also controlling 64 GB eMMC and running the Windows 10 operating system. The HPU processes and integrates data from the sensors, as well as handling tasks such as spatial mapping, gesture recognition, and voice and speech recognition. HoloLens includes a IEEE 802.11ac Wi-Fi and Bluetooth 4.1 Low Energy (LE) wireless connectivity. The headset uses Bluetooth LE and can connect to a Clicker, a finger-operating input device that can be used for selecting menus and functions.

A number of applications are available for Microsoft Hololens, for example a catalogue of holograms, HoloStudio, a 3D modelling application by Microsoft with 3D print capability, Autodesk Maya 3D creation application Free-Form, integrating HoloLens with the Autodesk Fusion 360 cloud-based 3D development application, and others.

HoloLens utilizing the HPU can employ sensual and natural interface commands—voice, gesture, and gesture. Gaze commands, e.g. head-tracking, allows the user to bring application focus to whatever the user is perceiving. Any virtual application or button can be are selected using an air tap method, similar to clicking a virtual computer mouse. The tap can be held for a drag simulation to move an display. Voice commands can also be utilized.

The HoloLens shell utilizes many components or concepts from the Windows desktop environment. A bloom gesture for opening the main menu is performed by opening one's hand, with the palm facing up and the fingers spread. Windows can be dragged to a particular position, locked and/or resized. Virtual windows or menus can be fixed at locations or physical objects. Virtual windows or menus can move with the user or can be fixed in relationship to the user. Or they can follow the user as he or she moves around.

The Microsoft HoloLens App for Windows 10 PC's and Windows 10 Mobile devices can be used by developers to run apps and to view live stream from the HoloLens user's point of view, and to capture augmented reality photos and videos.

Almost all Universal Windows Platform apps can run on Hololens. These apps can be projected in 2D. Select Windows 10 APIs are currently supported by HoloLens. Hololens apps can also be developed on Windows 10 PC's. Holographic applications can use Windows Holographic APIs. Unity and Vuforia are some apps that can be utilized. Applications can also be developed using DirectX and Windows API's.

Computer Graphics Viewing Pipeline

Figure 16A:
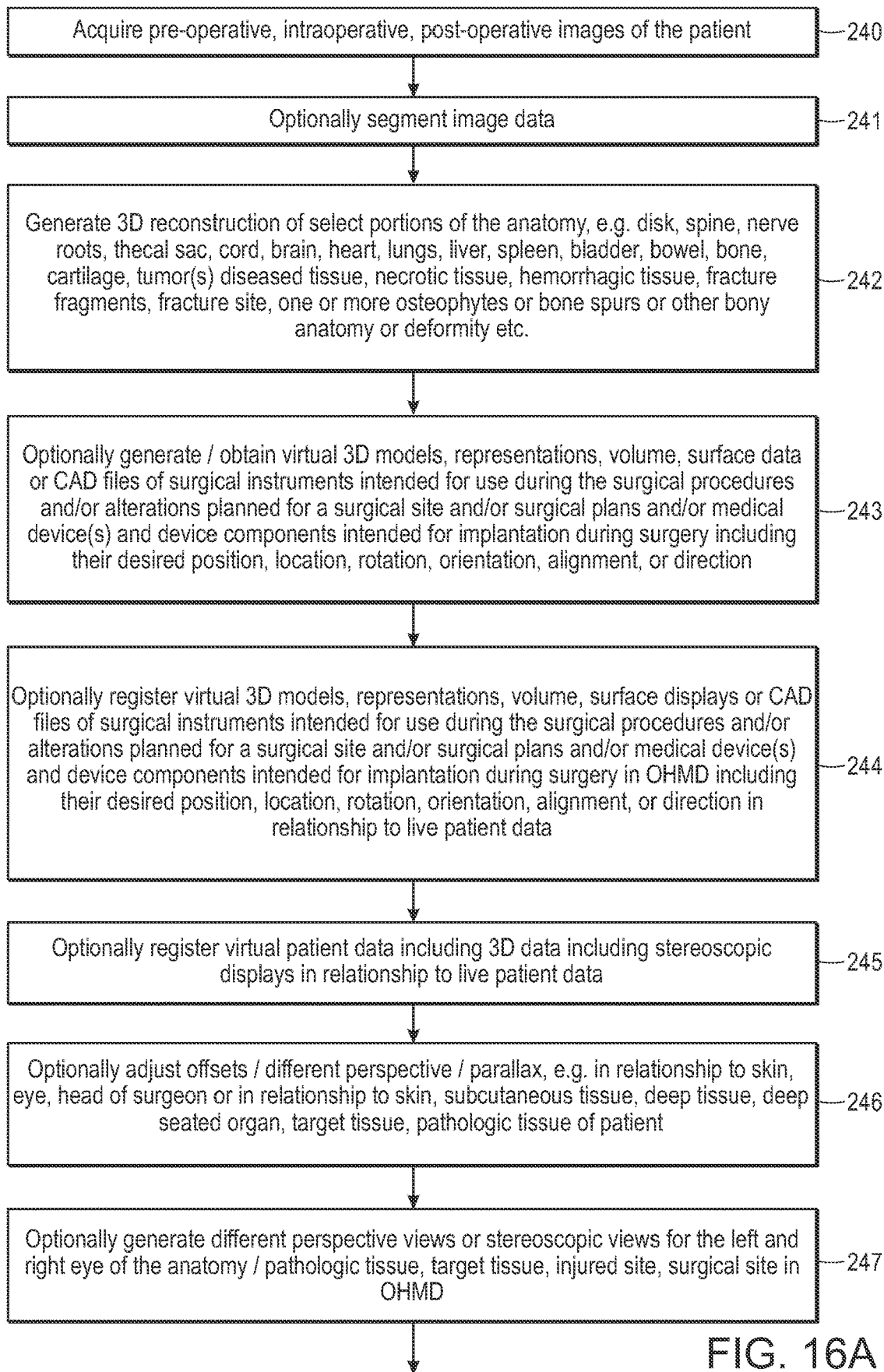
FIGS. 16A and 16B are flow charts summarizing model generation, registration and view projection for one or more OHMDs, e.g. by a primary surgeon, second surgeon, surgical assistant nurse, or others according to some embodiments of the present disclosure.
Figure 16A:
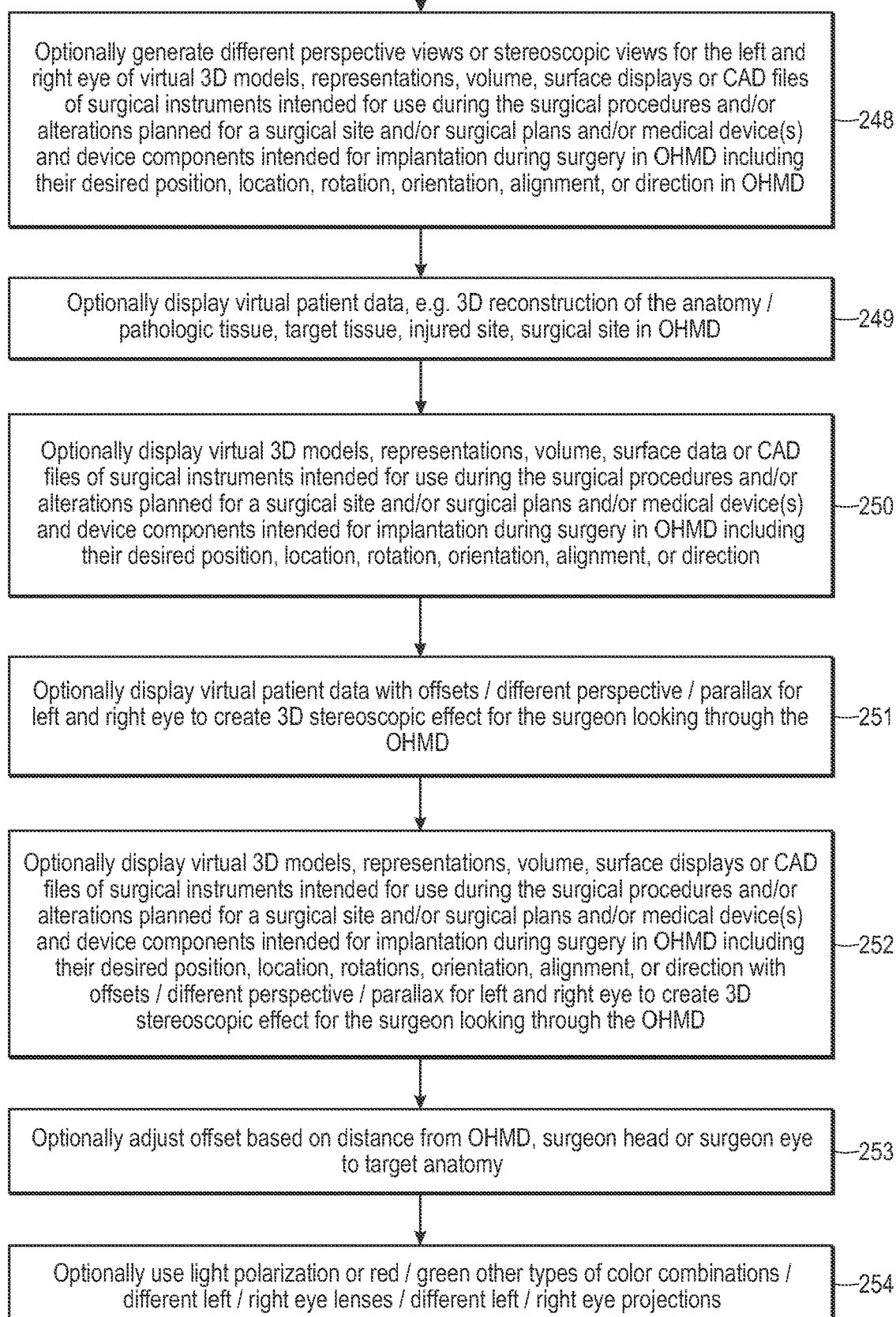
Figure 16B:
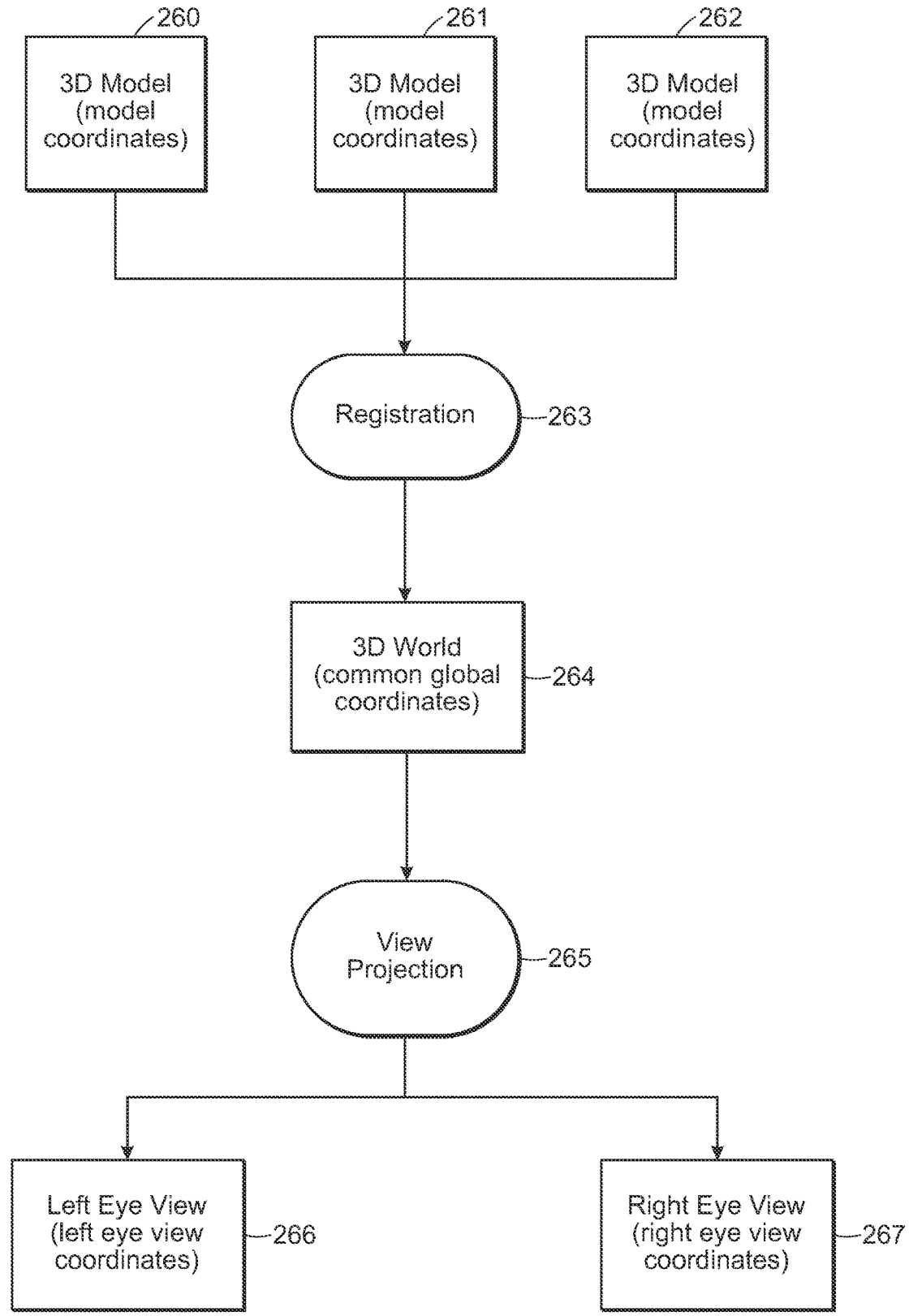

In some embodiments of the invention, the optical head mount display uses a computer graphics viewing pipeline that consists of the following steps to display 3D objects or 2D objects positioned in 3D space or other computer generated objects and models FIG. 16B:

1. Registration
2. View projection

Registration:

The different objects to be displayed by the OHMD computer graphics system (for instance virtual anatomical models, virtual models of instruments, geometric and surgical references and guides) are initially all defined in their own independent model coordinate system. During the registration process, spatial relationships between the different objects are defined, and each object is transformed from its own model coordinate system into a common global coordinate system. Different techniques that are described below can be applied for the registration process.

For augmented reality OHMDs that superimpose computer-generated objects with live views of the physical environment, the global coordinate system is defined by the environment. A process called spatial mapping, described below, creates a computer representation of the environment that allows for merging and registration with the computer-generated objects, thus defining a spatial relationship between the computer-generated objects and the physical environment.

View Projection:

Once all objects to be displayed have been registered and transformed into the common global coordinate system, they are prepared for viewing on a display by transforming their coordinates from the global coordinate system into the view coordinate system and subsequently projecting them onto the display plane. This view projection step uses the viewpoint and view direction to define the transformations applied in this step. For stereoscopic displays, such as an OHMD, two different view projections can be used, one for the left eye and the other one for the right eye. For augmented reality OHMDs the position of the viewpoint and view direction relative to the physical environment can be known in order to correctly superimpose the computer-generated objects with the physical environment. As the viewpoint and view direction change, for example due to head movement, the view projections are updated so that the computer-generated display follows the new view.

Eye Tracking Systems

The present invention provides for methods of using the human eye including eye movements and lid movements as well as movements induced by the peri-orbital muscles for executing computer commands. The invention provides also for methods of executing computer commands by way of facial movements and movements of the head.

Command execution induced by eye movements and lid movements as well as movements induced by the peri-orbital muscles, facial movements and head movements can be advantageous in environments where an operator does not have his hands available to type on a keyboard or to execute commands on a touchpad or other hand-computer interface. Such situations include, but are not limited, to industrial applications including automotive and airplane manufacturing, chip manufacturing, medical or surgical procedures and many other potential applications.

In some embodiments, the optical head mount display can include an eye tracking system. Different types of eye tracking systems can be utilized. The examples provided below are in no way thought to be limiting to the invention. Any eye tracking system known in the art now can be utilized.

Eye movement can be divided into fixations and saccades—when the eye gaze pauses in a certain position, and when it moves to another position, respectively. The resulting series of fixations and saccades can be defined as a scan path. The central one or two degrees of the visual angle provide most of the visual information; the input from the periphery is less informative. Thus, the locations of fixations along a scan path show what information locations were processed during an eye tracking session, for example during a surgical procedure.

Eye trackers can measure rotation or movement of the eye in several ways, for example via measurement of the movement of an object (for example, a form of contact lens) attached to the eye, optical tracking without direct contact to the eye, and measurement of electric potentials using electrodes placed around the eyes.

If an attachment to the eye is used, it can, for example, be a special contact lens with an embedded mirror or magnetic field sensor. The movement of the attachment can be measured with the assumption that it does not slip significantly as the eye rotates. Measurements with tight fitting contact lenses can provide very accurate measurements of eye movement. Additionally, magnetic search coils can be utilized which allow measurement of eye movement in horizontal, vertical and torsion direction.

Alternatively, non-contact, optical methods for measuring eye motion can be used. With this technology, light, optionally infrared, can be reflected from the eye and can be sensed by an optical sensor or a video camera. The information can then be measured to extract eye rotation and/or movement from changes in reflections. Optical sensor or video-based eye trackers can use the corneal reflection (the so-called first Purkinje image) and the center of the pupil as features to track, optionally over time. A more sensitive type of eye tracker, the dual-Purkinje eye tracker, uses reflections from the front of the cornea (first Purkinje image) and the back of the lens (fourth Purkinje image) as features to track. An even more sensitive method of tracking is to image features from inside the eye, such as the retinal blood vessels, and follow these features as the eye rotates and or moves. Optical methods, particularly those based on optical sensors or video recording, can be used for gaze tracking.

In some embodiments, optical or video-based eye trackers can be used. A camera focuses on one or both eyes and tracks their movement as the viewer performs a function such as a surgical procedure. The eye-tracker can use the center of the pupil for tracking. Infrared or near-infrared non-collimated light can be utilized to create corneal reflections. The vector between the pupil center and the corneal reflections can be used to compute the point of regard on a surface or the gaze direction. Optionally, a calibration procedure can be performed at the beginning of the eye tracking.

Bright-pupil and dark-pupil eye tracking can be employed. Their difference is based on the location of the illumination source with respect to the optics. If the illumination is co-axial relative to the optical path, then the eye acts is retroreflective as the light reflects off the retina creating a bright pupil effect similar to a red eye. If the illumination source is offset from the optical path, then the pupil appears dark because the retroreflection from the retina is directed away from the optical sensor or camera.

Bright-pupil tracking can have the benefit of greater iris/pupil contrast, allowing more robust eye tracking with all iris pigmentation. It can also reduce interference caused by eyelashes. It can allow for tracking in lighting conditions that include darkness and very bright lighting situations.

The optical tracking method can include tracking movement of the eye including the pupil as described above. The optical tracking method can also include tracking of the movement of the eye lids and also periorbital and facial muscles.

In some embodiments, the eye-tracking apparatus is integrated in an optical head mounted display. In some embodiments, head motion can be simultaneously tracked, for example using a combination of accelerometers and gyroscopes forming an inertial measurement unit (see below).

In some embodiments, electric potentials can be measured with electrodes placed around the eyes. The eyes generate an electric potential field, which can also be detected if the eyes are closed. The electric potential field can be modelled to be generated by a dipole with the positive pole at the cornea and the negative pole at the retina. It can be measured by placing two electrodes on the skin around the eye. The electric potentials measured in this manner are called an electro-oculogram.

If the eyes move from the center position towards the periphery, the retina approaches one electrode while the cornea approaches the opposing one. This change in the orientation of the dipole and consequently the electric potential field results in a change in the measured electro-oculogram signal. By analyzing such changes eye movement can be assessed. Two separate movement directions, a horizontal and a vertical, can be identified. If a posterior skull electrode is used, a EOG component in radial direction can be measured. This is typically the average of the EOG channels referenced to the posterior skull electrode. The radial EOG channel can measure saccadic spike potentials originating from extra-ocular muscles at the onset of saccades.

EOG can be limited for measuring slow eye movement and detecting gaze direction. EOG is, however, well suited for measuring rapid or saccadic eye movement associated with gaze shifts and for detecting blinks. Unlike optical or video-based eye-trackers, EOG allows recording of eye movements even with eyes closed. The major disadvantage of EOG is its relatively poor gaze direction accuracy compared to an optical or video tracker. Optionally, both methods, optical or video tracking and EOG, can be combined in select embodiments of the invention.

A sampling rate of 15, 20, 25, 30, 50, 60, 100, 120, 240, 250, 500, 1000 Hz or greater can be used. Any sampling frequency is possibly. In many embodiments, sampling rates greater than 30 Hz will be preferred.

Measuring Location, Orientation, Acceleration

The location, orientation, and acceleration of the human head, portions of the human body, e.g. hands, arms, legs or feet, as well as portions of the patient's body, e.g. the patient's head or extremities, including the hip, knee, ankle, foot, shoulder, elbow, hand or wrist and any other body part, can, for example, be measured with a combination of gyroscopes and accelerometers. In select applications, magnetometers may also be used. Such measurement systems using any of these components can be defined as inertial measurement units (IMU).

As used herein, the term IMU relates to an electronic device that can measure and transmit information on a body's specific force, angular rate, and, optionally, the magnetic field surrounding the body, using a combination of accelerometers and gyroscopes, and, optionally, magnetometers. An IMU or components thereof can be coupled with or registered with a navigation system or a robot, for example by registering a body or portions of a body within a shared coordinate system. Optionally, an IMU can be wireless, for example using WiFi networks or Bluetooth networks.

Pairs of accelerometers extended over a region of space can be used to detect differences (gradients) in the proper accelerations of frames of references associated with those points. Single- and multi-axis models of accelerometer are available to detect magnitude and direction of the acceleration, as a vector quantity, and can be used to sense orientation (because direction of weight changes), coordinate acceleration (so long as it produces g-force or a change in g-force), vibration, shock. Micromachined accelerometers can be utilized in some embodiments to detect the position of the device or the operator's head.

Piezoelectric, piezoresistive and capacitive devices can be used to convert the mechanical motion into an electrical signal. Piezoelectric accelerometers rely on piezoceramics or single crystals Piezoresistive accelerometers can also be utilized. Capacitive accelerometers typically use a silicon micro-machined sensing element.

Accelerometers used in some of the embodiments can include small micro electro-mechanical systems (MEMS), consisting, for example, of little more than a cantilever beam with a proof mass.

Optionally, the accelerometer can be integrated in the optical head mounted devices and both the outputs from the eye tracking system and the accelerometer(s) can be utilized for command execution.

With an IMU, the following exemplary information can be captured about the operator and the patient and respective body parts: Speed, Velocity, Acceleration, Position in space, Positional change, Alignment, Orientation, and/or Direction of movement (e.g. through sequential measurements)

Operator and/or patient body parts about which such information can be transmitted by the IMU include, but are not limited to: Head, Chest, Trunk, Shoulder, Elbow, Wrist, Hand, Fingers, Arm, Hip, Knee, Ankle, Foot, Toes, Leg, Inner organs, e.g. brain, heart, lungs, liver, spleen, bowel, bladder etc.

Any number of IMUs can be placed on the OHMD, the operator and/or the patient and, optionally, these IMUs can be cross-referenced to each other within a single or multiple coordinate systems or, optionally, they can be cross-referenced in relationship to an OHMD, a second and third or more OHMDs, a navigation system or a robot and one or more coordinate systems used by such navigation system and/or robot. A navigation system can be used in conjunction with an OHMD without the use of an IMU. For example, navigation markers including infrared markers, retroreflective markers, RF markers can be attached to an OHMD and, optionally, portions or segments of the patient or the patient's anatomy. The OHMD and the patient or the patient's anatomy can be cross-referenced in this manner or registered in one or more coordinate systems used by the navigation system and movements of the OHMD or the operator wearing the OHMD can be registered in relationship to the patient within these one or more coordinate systems. Once the virtual data and the live data of the patient and the OHMD are registered in the same coordinate system, e.g. using IMUs, optical markers, navigation markers including infrared markers, retroreflective markers, RF markers, and any other registration method described in the specification or known in the art, any change in position of any of the OHMD in relationship to the patient measured in this fashion can be used to move virtual data of the patient in relationship to live data of the patient, so that the visual image of the virtual data of the patient and the live data of the patient seen through the OHMD are always aligned, irrespective of movement of the OHMD and/or the operator's head and/or the operator wearing the OHMD. Similarly, when multiple OHMDs are used, e.g. one for the primary surgeon and additional ones, e.g. two, three, four or more, for other surgeons, assistants, residents, fellows, nurses and/or visitors, the OHMDs worn by the other staff, not the primary surgeon, will also display the virtual representation(s) of the virtual data of the patient aligned with the corresponding live data of the patient seen through the OHMD, wherein the perspective of the virtual data that is with the patient and/or the surgical site for the location, position, and/or orientation of the viewer's eyes for each of the OHMDs used and each viewer. The foregoing embodiments can be achieved since the IMUs, optical markers, RF markers, infrared markers and/or navigation markers placed on the operator and/or the patient as well as any spatial anchors can be registered in the same coordinate system as the primary OHMD and any additional OHMDs. The position, orientation, alignment, and change in position, orientation and alignment in relationship to the patient and/or the surgical site of each additional OHMD can be individually monitored thereby maintaining alignment and/or superimposition of corresponding structures in the live data of the patient and the virtual data of the patient for each additional OHMD irrespective of their position, orientation, and/or alignment in relationship to the patient and/or the surgical site.

Referring to FIG. 1, a system 10 for using multiple OHMDs 11, 12, 13, 14 for multiple viewer's, e.g. a primary surgeon, second surgeon, surgical assistant(s) and/or nurses(s) is shown. The multiple OHMDs can be registered in a common coordinate system 15 using anatomic structures, anatomic landmarks, calibration phantoms, reference phantoms, optical markers, navigation markers, and/or spatial anchors, for example like the spatial anchors used by the Microsoft Hololens. Pre-operative data 16 of the patient can also be registered in the common coordinate system 15. Live data 18 of the patient, for example from the surgical site, e.g. a spine, optionally with minimally invasive access, a hip arthrotomy site, a knee arthrotomy site, a bone cut, an altered surface can be measured, for example using one or more IMUs, optical markers, navigation markers, image or video capture systems and/or spatial anchors. The live data 18 of the patient can be registered in the common coordinate system 15. Intra-operative imaging studies 20 can be registered in the common coordinate system 15. OR references, e.g. an OR table or room fixtures can be registered in the common coordinate system 15 using, for example, optical markers IMUs, navigation markers or spatial mapping 22. The pre-operative data 16 or live data 18 including intra-operative measurements or combinations thereof can be used to develop, generate or modify a virtual surgical plan 24. The virtual surgical plan 24 can be registered in the common coordinate system 15. The OHMDs 11, 12, 13, 14 can project digital holograms of the virtual data or virtual data into the view of the left eye using the view position and orientation of the left eye 26 and can project digital holograms of the virtual data or virtual data into the view of the right eye using the view position and orientation of the right eye 28 of each user, resulting in a shared digital holographic experience 30. Using a virtual or other interface, the surgeon wearing OHMD 1 11 can execute commands 32, e.g. to display the next predetermined bone cut, e.g. from a virtual surgical plan or an imaging study or intra-operative measurements, which can trigger the OHMDs 11, 12, 13, 14 to project digital holograms of the next surgical step 34 superimposed onto and aligned with the surgical site in a predetermined position and/or orientation.

Virtual data of the patient can be projected superimposed onto live data of the patient for each individual viewer by each individual OHMD for their respective view angle or perspective by registering live data of the patient, e.g. the surgical field, and virtual data of the patient as well as each OHMD in a common, shared coordinate system. Thus, virtual data of the patient including aspects of a virtual surgical plan can remain superimposed and/or aligned with live data of the patient irrespective of the view angle or perspective of the viewer and alignment and/or superimposition can be maintained as the viewer moves his or her head or body.

Novel User Interfaces

One subject of the present invention is to provide a novel user interface where the human eye including eye movements and lid movements including movements induced by the orbital and peri-orbital and select skull muscles are detected by the eye tracking system and are processed to execute predefined, actionable computer commands.

An exemplary list of eye movements and lid movements that can be detected by the system is provided in Table 1.

Table 1: Exemplary list of eye movements and lid movements detected by the eye tracking software
  1 blink
  2 blinks
  3 blinks
  Fast blink, for example less than 0.5 seconds
  Slow blink, for example more than 1.0 seconds
  2 or more blinks with fast time interval, e.g. less than 1 second
  2 or more blinks with long time interval, e.g. more than 2 seconds (typically chosen to be less than the natural time interval between eye blinks)
  Blink left eye only
  Blink right eye only
  Blink left eye and right eye simultaneously
  Blink left eye first, then within short time interval (e.g. less than 1 second), blink right eye
  Blink right eye first, then within short time interval (e.g. less than 1 second), blink left eye
  Blink left eye first, then within long time interval (e.g. more than 2 seconds), blink right eye
  Blink right eye first, then within long time interval (e.g. more than 2 seconds), blink left eye
  Rapid eye movement to left
  Rapid eye movement to right
  Rapid eye movement up
  Rapid eye movement down
  Widen eyes, hold for short time interval, e.g. less than 1 second
  Widen eyes, hold for long time interval, e.g. more than 2 seconds
  Close both eyes for 1 second etc.
  Close both eyes for 2 seconds or more etc.
  Close both eyes, hold, then open and follow by fast blink
  Close left eye only 1 second, 2 seconds etc.
  Close right eye only 1 second, 2 seconds etc.
  Close left eye, then right eye
  Close right eye, then left eye
  Blink left eye, then right eye
  Blink right eye, then left eye
  Stare at field, virtual button for 1, 2, 3 or more seconds; activate function, e.g. Zoom in or Zoom out Any combination of blinks, eye movements, sequences, and time intervals is possible for encoding various types of commands. These commands can be computer commands that can direct or steer, for example, a surgical instrument or a robot.

The invention provides also for methods of executing commands by way of facial movements and movements of the head.

An exemplary list of facial movements and head movements that can be detected by the system is provided in Table 2. (This list is only an example and by no way meant to be exhaustive; any number or combination of movements is possible).

Table 2: Exemplary list of facial movements and head movements detected:
  Move head fast to right and hold
  Move head fast to left and hold
  Move head fast down and hold
  Move head fast down and hold
  Move head fast to right and back
  Move head fast to left and back
  Move head fast down and back
  Move head fast down and back
  Tilt head to left and hold
  Tilt head to right and hold
  Tilt head to left and back
  Tilt head to right and back
  Open mouth and hold
  Open mouth and close
  Twitch nose once
  Twitch nose twice etc.

Exemplary commands executed using eye movements, lid movements, facial movements and head movements are listed in Table 3.

Table 3: Exemplary list of commands that can be executed by tracking eye movement, lid movement, facial movement and head movement (this list is only an example and by no way meant to be exhaustive; any number or combination of commands is possible; application specific commands can be executed in this manner as well).
  Click
  Point
  Move pointer
    Slow
    Fast
  Scroll, e.g. through images
    Fast scroll
    Slow scroll
  Scroll up
  Scroll down
  Scroll left
  Scroll right
  Drag
  Swoosh Register
Toggle 2D vs. 3D
Switch imaging study
Overlay images
Fuse images
Register images
Cut
Paste
Copy
Undo
Redo
Delete
Purchase
Provide credit card information
Authorize
Go to shopping card
OHMD on
OHMD off
Eye tracking on
Eye tracking off
Eye command execution on
Eye command execution off
Facial command execution on
Facial command execution off
Turn surgical instrument on (e.g. oscillating saw, laser etc.)
Turn surgical instrument off
Increase intensity, speed, energy deposed of surgical instrument
Reduce intensity, speed, energy deposed of surgical instrument
Change direction of surgical instrument
Change orientation of surgical instrument
Change any type of setting surgical instrument In some embodiments of the invention, eye movements, lid movements, facial movement, head movements alone or in combination can be used to signal numerical codes or sequences of numbers or sequences of machine operations. Such sequences of numbers can, for example, be used to execute certain machine operating sequences.

Head Movement to Control Movement of a Surgical Instrument

In some embodiments of the invention, head movement can be used to control a surgical instrument. For example, in a robot assisted procedure with haptic feedback from the robot, the surgeon can use his or her hands in controlling the direction of a surgical instrument. The surgeon can move the head forward. This forward motion is captured by an IMU and translated into a forward movement of a robotic arm holding a surgical instrument along the direction of the surgical instrument. A backward movement of the head can be captured by the IMU and can be translated into a backward movement of the robotic arm holding a surgical instrument along the direction of the surgical instrument.

In some embodiments of the invention, eye movements, lid movements, facial movement, head movements alone or in combination can be used to signal Morse codes. The International Morse Code encodes the Latin alphabet using a small set of punctuation and procedural signals as standardized sequences of short and long signals called dots and dashes. Each character (letter or numeral) is represented by a unique sequence of dots and dashes. The duration of a dash is three times the duration of a dot. Each dot or dash is followed by a short silence, equal to the dot duration. The letters of a word are separated by a space equal to three dots (one dash), and the words are separated by a space equal to seven dots.

An example how Morse code can be executed using eye commands is provided as follows; this is in no way meant to be limiting. Many different implementations are possible. A dot can be executed, for example, using a fast blink of both eyes (typically less than 1 sec), while a dash can be executed by closing the right eye only, for example for one second. The letter A in Morse code is a dot followed by a dash. With this encoding of Morse code, the letter A can be executed with a fast blink of both eyes (dot), followed by closing the right eye only for one second (dash). The letter B (dash, three dots), can be executed by closing the right eye only for one second (dash) followed by three fast blinks of both eyes (three dots) and so forth. Letters can be separated, for example, by maintaining a two second or longer break between eye commands. Alternatively, in another example, letters can be separate by closing only the left eye for about one second.

Binary codes can optionally also be executed using eye commands. For example, a fast blink of both eyes can represent the number 0, while closing the right eye only for about one second can represent the number 1. Alternatively, closing the right eye only for about one second can represent the number 0, while closing the left eye only for about one second can represent the number 1. Many different types of encoding are possible. Other numericals can also be executed using, for example, some of the eye, lid, facial and/or head movements shown in Tables 1 and 2.

Many different languages can be executed in this fashion. These include, optionally, also computer languages, e.g. Fortran, Pascal, C, C++, C−−, Basic and many others known in the art. In some embodiments of the invention, eye, lid, facial and head movement commands can be paired or used in conjunction with voice commands, hand commands, gesture commands, keyboard commands, track pad commands, mouse commands, graphical user interface commands and any other command input device known in the art. The OHMD can optionally also include one or more touch sensitive sensors.

In select environments, eye commands add benefit of being able to navigate a screen or execute commands while maintaining privacy or confidentiality related to the commands. For example, in a hospital environment, with other patients or visitors nearby, eye commands can be utilized to access a patient's medical records or to order lab tests or other diagnostic tests without bystanders being aware that these records are being reviewed or that these tests are being ordered.

At a conference, the wearer of an optical head mounted display can utilize eye commands to turn on a video or audio recording function or transmission to a remote site or remote conference room without disclosing that the recording function has been activated. This is quite different from manual activation of a recording function, where the user would, for example, push a button or a touch sensitive sensor on the optical head mounted display in order to activate the recording function.

In some embodiments, a user can utilize eye movements, facial movements or head movements to direct digital camera for taking photographs or videos. Commands can include but are not limited to zoom in, zoom out, move region of interest left, right up, down, take photo, take sequence of photos, turn on/off flash start video recording, stop video recording, change resolution, increase resolution, decrease resolution.

Any other camera command known in the art can be executed in this manner using eye movement, facial movement or head movement based commands. By utilizing one or more commands of this type, the user can maintain privacy while obtaining image information about the surrounding environment.

Eye commands can be useful to surgeons or operating room personnel to execute commands without use of the hands and thereby maintaining sterility.

Fusing Physical World with Imaging and Other Data of a Patient

In some embodiments of the invention, an operator such as a surgeon may look through an OHMD observing physical data or information on a patient, e.g. a surgical site or changes induced on a surgical site, while pre-existing data of the patient are superimposed onto the physical visual representation of the live patient.

The pre-existing data of the patient can be an imaging test or imaging data or other types of data including metabolic information or functional information.

The pre-existing data of the patient including one or more imaging tests or other types of data including metabolic or functional information can be obtained at a time different from the time of the surgical procedure. For example, the pre-existing data of the patient can be obtained one, two, three or more days or weeks prior to the surgical procedure.

The pre-existing data of the patient including one or more imaging tests or other types of data including metabolic or functional information are typically obtained with the patient or the surgical site being located in a different location or a different object coordinate system in the pre-existing data when compared to the location or the object coordinate system of the live patient or the surgical site in the live patient. Thus, pre-existing data of the patient or the surgical site are typically located in a first object coordinate system and live data of the patient or the surgical site are typically located in a second object coordinate systems; the first and the second object coordinate system are typically different from each other. The first object coordinate system with the pre-existing data needs to be registered with the second object coordinate system with the live data of the patient including, for example, the live surgical site.

Scan Technology

The following is an exemplary list of scanning and imaging techniques that can be used or applied for various aspects of the invention; this list is not exhaustive, but only exemplary. Anyone skilled in the art can identify other scanning or imaging techniques that can be used in practicing the invention.

For a detailed description of these different scanning and imaging techniques, see for example, Bushberg et al. The Essential Physics of Medical Imaging, 3$^{rd}$ edition, Wolters, Kluwer, Lippincott, 2012.

X-ray imaging, 2D, 3D, supine, upright or in other body positions and poses, including analog and digital x-ray imaging Digital tomosynthesis Cone beam CT Ultrasound Doppler ultrasound Elastography, e.g. using ultrasound or MRI

CT

MRI including, for example, fMRI, diffusion imaging, stroke imaging, MRI with contrast media Functional MRI (fMRI), e.g. for brain imaging and functional brain mapping Magnetic resonance spectroscopy

PET

SPECT-CT

PET-CT

PET-MRI

Upright scanning, optionally in multiple planes or in 3D using any of the foregoing modalities, including x-ray imaging, ultrasound etc.

Contrast media e.g. iodinated contrast agents for x-ray and CT scanning, or MRI contrast agents.

contrast agents can include antigens or antibodies for cell or tissue specific targeting other targeting techniques, e.g. using liposomes, can also be applied molecular imaging To highlight metabolic abnormalities in the brain and target surgical instruments towards area of metabolic abnormality any contrast agent known in the art can be used in conjunction with the invention.

Multi-Dimensional Imaging, Reconstruction and Visualization

Various embodiments of this invention can be practiced in one, two, three or more dimensions. The following is an exemplary list of potential dimensions, views, projections, angles, or reconstructions that can be applied; this list is not exhaustive, but only exemplary. Anyone skilled in the art can identify additional dimensions, views, projections, angles or reconstructions that can be used in practicing the invention. Exemplary dimensions are listed in Table 4.

TABLE 4: Exemplary list of potential dimensions, views, projections, angles, or reconstructions that can be displayed using virtual representations with optical head mounted display(s), optionally stereoscopic $1^{st}$ dimension: superoinferior, e.g. patient physical data $2^{nd}$ dimension: mediolateral, e.g. patient physical data $3^{rd}$ dimension: anteroposterior, e.g. patient physical data $4^{th}$-$6^{th}$ dimension: head motion (and with it motion of glasses/OHMD) in 1, 2 or 3 dimensions $7^{th}$-$9^{th}$ dimension: instrument motion in 1, 2 or 3 dimensions, e.g. in relationship to surgical field, organ or head including head motion $10^{th}$-$13^{th}$ dimension: arm or hand motion in 1, 2 or 3 dimensions, e.g. in relationship to surgical field, organ or head including head motion $14^{th}$-$16^{th}$ dimension: virtual 3D data of patient, obtained, for example from a scan or intraoperative measurements $17^{th}$-$19^{th}$ dimension: vascular flow; in 1, 2 or 3 dimensions, e.g. in relationship to surgical field, organ or head including head motion $20^{th}$-$22^{nd}$ dimension: temperature map (including changes induced by cryo- or hyperthermia), thermal imaging, in 1, 2 or 3 dimensions, e.g. in relationship to surgical field $25^{th}$-$28^{th}$ dimension: metabolic map (e.g. using MRS, PET-CT, SPECT-CT), in 1, 2 or 3 dimensions, e.g. in relationship to surgical field $29^{th}$-$32^{nd}$ dimension: functional map (e.g. using fMRI, PET-CT, SPECT-CT, PET, kinematic imaging), in 1, 2 or 3 dimensions, e.g. in relationship to surgical field or patient Any oblique planes are possible. Any perspective projections are possible. Any oblique angles are possible. Any curved planes are possible. Any curved perspective projections are possible. Any combination of 1D, 2D, and 3D data between the different types of data is possible.

Registering Virtual Data with Live Data Seen Through Optical Head Mounted Display In some embodiments, virtual data of a patient can be superimposed onto live data seen through the optical head mounted display. The virtual data can be raw data in unprocessed form, e.g. preoperative images of a patient, or they can be processed data, e.g. filtered data or segmented data.

Data Segmentation

Figure 2:
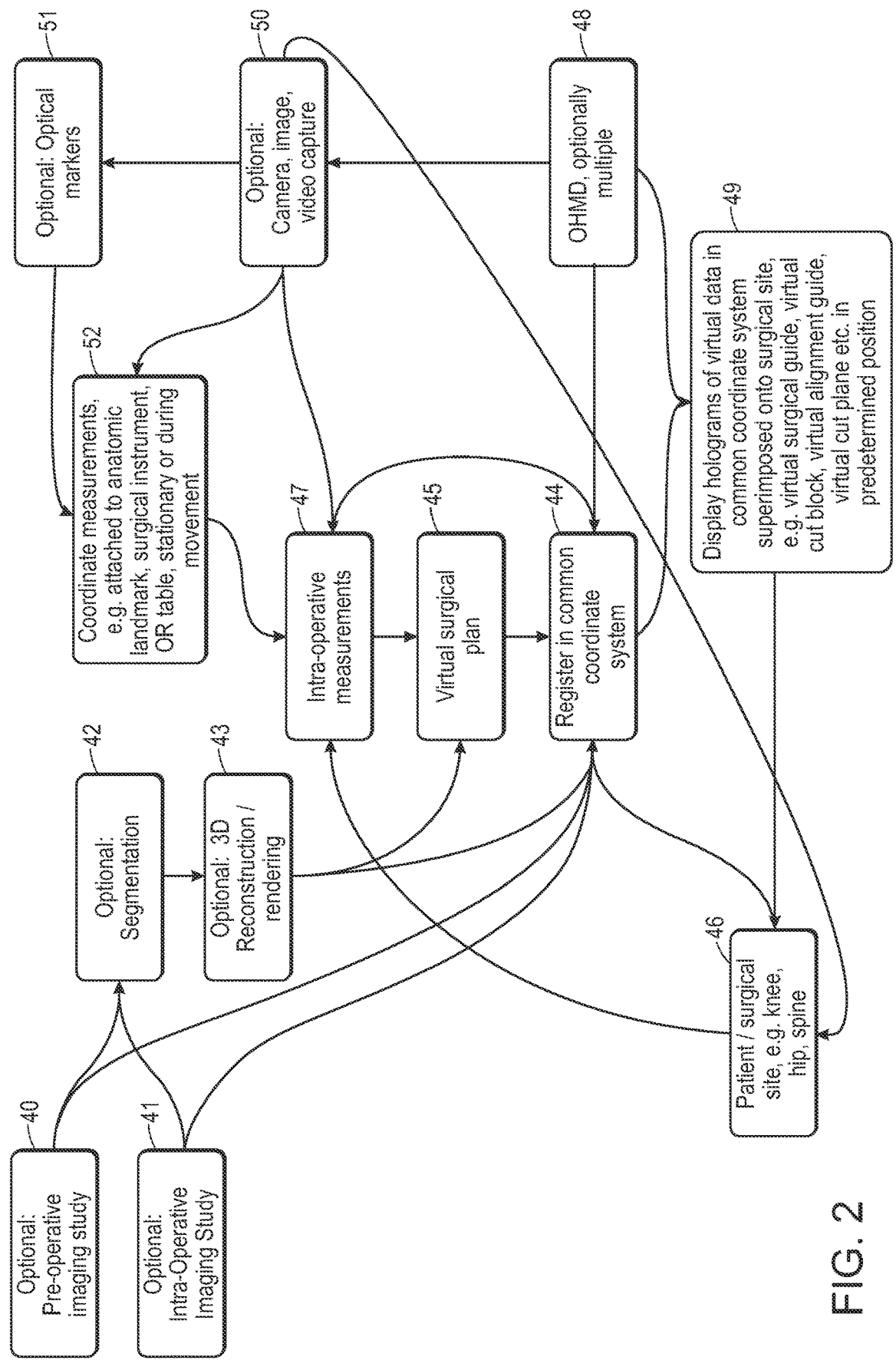
FIG. 2 shows a workflow for segmentation and select subsequent steps according to some embodiments of the present disclosure.

When images of the patient are superimposed onto live data seen through the optical head mounted display, in many embodiments image segmentation can be desirable. Any known algorithm in the art can be used for this purpose, for example thresholding, seed point techniques, live wire, deformable models, statistical models, active shape models, level set methods, marching cubes algorithms, artificial neural networks, deep learning techniques, or combinations thereof and the like. Many of these algorithms are available is part of open-source or commercial libraries, for instance the Insight Segmentation and Registration Toolkit (ITK), the Open Source Computer Vision Library OpenCV, G'MIC (GREYC's Magic for Image Computing), Caffe, or MATLAB (MathWorks, Natick, Mass.). A representative workflow for segmentation and subsequent is provided in FIG. 2. An optional pre-operative imaging study 40 can be obtained. An optional intra-operative imaging study 41 can be obtained. The pre-operative 40 or intra-operative 41 imaging study can be segmented 42, extracting, for example, surfaces, volumes or key features. An optional 3D reconstruction or 3D rendering 43 can be generated. The pre-operative 40 or intra-operative 41 imaging study and any 3D reconstruction or 3D rendering 43 can be registered in a common coordinate system 44. The pre-operative 40 or intra-operative 41 imaging study and any 3D reconstruction or 3D rendering 43 can be used for generating a virtual surgical plan 45. The virtual surgical plan 45 can be registered in the common coordinate system 44. The surgical site 46 can be registered in the common coordinate system 44. Intra-operative measurements 47 can be obtained and can be used for generating a virtual surgical plan 45. An optical head mounted display 48 can project or display digital holograms of virtual data or virtual data 49 superimposed onto and aligned with the surgical site. The OHMD 48 is configured to use a built in camera or image capture or video capture system 50 to optionally detect and/or measure the position and/or orientation and/or alignment of one or more optical markers 51, which can be used for the coordinate measurements 52, which can be part of the intra-operative measurements 47.

Software and Algorithms for Registration

Registration of virtual data with live data can be performed using a variety of techniques know in the art. These include, but are not limited to, surface registration algorithms such as the Iterative Closest Point algorithm, statistical models, Active Shape Models, mutual information-based or other volume registration algorithms, object recognition, pattern recognition or computer vision techniques, deep learning or other artificial intelligence methods. The processed data can, for example, consist of mesh data, parametric surface data, point cloud data, volume data or a combination thereof. These methods are known in the art and have been implemented in publicly and/or commercially available code libraries and application programming interfaces (API's), such as the Insight Segmentation and Registration Toolkit (ITK), the open-source computer vision library OpenCV, Elastix, Plastimatch, or the Medical Image Registration Toolkit (MIRTK).

Superimposition of Virtual Data and Live Data by the OHMD

In some embodiments, segmented data or raw data can be superimposed on the patient's live data seen through the optical head mounted display. This superimposition can occur in unregistered form, i.e. the patient's virtual data may not be aligned with the live data seen through the optical head mounted display. In this case, the operator who is wearing the OHMD may move his/her head in a direction of orientation that will superimpose corresponding features of virtual data and live patient data. The surgeon or operator can also move and re-orient the virtual data using other means, e.g. a trackball or a virtual display interface displayed in the OHMD, unrelated to the surgeon/operator head movement. The operator can adjust the magnification of the live data so that the size, shape, length, thickness of certain features of the virtual data matches that of the live data for a given distance to the object/patient.

For example, during brain surgery, the surgeon may visually in live data look at the exposed gyri and sulci of the patient's brain. The OHMD can display a virtual 3D model of the gyri and sulci of the patient. The surgeon can optionally adjust the magnification of the 3D model so that the model will match the size or width or the length of the corresponding gyri and sulci in the live data. The surgeon can optionally adjust the transparency or opacity of the virtual data displayed in the OHMD. The ratio of virtual vs. live data transmitted through the OHMD can be 1:10, 1:9, 1:8, 1:5, 1:2, 1:1, 2:1, 3:1, 5:1, 8:1, 10:1, as well as fractions or multiples thereof. Any combination of transparency or opacity of virtual data and live data is possible. The surgeon can move his/her head in a direction or orientation that will superimpose virtual features, e.g. the patient's gyri and sulci, with the live patient data.

Once the data have been superimposed, the surgeon can optionally register the virtual data with the live data. This registration can be as simple as described here, e.g. a visual confirmation from the surgeon that virtual and live data are substantially matching or substantially superimposed. At this time, the surgeon can optionally reference the virtual data and/or the coordinate system of the virtual data in 2, 3 or more dimensions with the live data and/or the coordinate system of the live data. Once the data are registered, the surgeon can move his/her head into any desired position or orientation, for example for viewing the patient's brain or a lesion and adjacent, e.g. sensitive, anatomy from different view angles. The IMU of the OHMD will register the head movement, the direction of the head movement, the new head position and head orientation. The change in location and orientation of the surgeon's head can be simultaneously or, if desired, non-simultaneously applied to the virtual data which can now be superimposed with the resultant new position and orientation in relationship to the live data. In addition, when the surgeon moves his/her head or body further away from the target anatomy, the change in position and the increase in distance from the target anatomy can be measured by the IMU. Depending on the distance from the IMU, a magnification or minification factor can be applied to the virtual data so that the size, shape and dimensions of the virtual data will, in some embodiments, be close to or match the size, shape and dimensions of the live data, irrespective of the distance, location and orientation of the surgeon's head.

For purposes of registration of virtual data and live data, the OHMD can be optionally placed in a fixed position, e.g.

mounted on a stand or on a tripod. While the OHMD is placed in the fixed position, live data can be viewed by the surgeon and they can be, optionally recorded with a camera and/or displayed on a monitor. Virtual data can then be superimposed and the matching and registration of virtual data and live data can be performed. At this point, the surgeon or an operator can remove OHMD from the fixed position and the surgeon can wear the OHMD during the surgical procedure.

The virtual data can optionally be displayed using a different color, e.g. red, green, yellow etc. Optionally, only the outline of select features of the virtual data may be displayed. For example, these features can be the sulci of the patient's brain (e.g. with a black line or black or lines with other colors), with no visualization of the gyri that these sulci border. Or, for example, only a lesion, e.g. a tumor such as, in the example of the brain, glioblastoma, can be displayed. Or combinations of virtual data of normal tissue and pathologic tissue can be displayed.

The virtual data can be registered with the live data seen through the optical head mounted display. The registration can occur using any method known in the art for registering or cross-referencing virtual and live data, in 2, 3, or more dimensions.

In some embodiments, the registration of the virtual data and the live data will be maintained through the surgical procedure. In some embodiments, the registration of the virtual data and the live data will be maintained during select portions of the surgical procedure or the surgical plan, which can be or can include a virtual, e.g. a preoperatively generated, surgical plan.

In some embodiments of the invention, the superimposition of the virtual data and the live data by the OHMD occurs simultaneously. In some embodiments, the superimposition of the virtual data and the live data by the OHMD is not simultaneous. For example, the virtual data can be superimposed intermittently.

Virtual data can be transparent, translucent or opaque. If virtual data are opaque, they may be displayed intermittently so that the operator or surgeon can see how they project in relationship to the live data of the patient.

If combinations of virtual data are displayed simultaneously with the live data, the different types of virtual data can be displayed with different colors. Representative combinations of virtual and live data are provided below. The following is only illustrative in nature and by no means meant to be limiting of the invention:

Live data: the patient's brain; surgically exposed gyri and sulci.

Live data: surgical instrument, e.g. biopsy needle or cutting tool

Virtual data: the patient's brain with gyri and sulci derived and optionally segmented from an imaging modality, e.g. a CT scan or an MRI scan Virtual data: a brain tumor, deep seated inside the brain Virtual data: the same surgical instrument currently used by the surgeon, in a virtual representation of the instrument, the virtual data indicating the desired orientation, location or direction of the surgical instrument.

Any of the foregoing virtual data can be displayed in two dimensions or three dimensions. Multi-dimensional displays as outlined in other sections of the specification are possible.

For example, the patient's normal tissue, e.g. normal brain tissue, can optionally be displayed in two dimensions, e.g. using grey level images, while the patient's abnormal tissue, e.g. a stroke, a hemorrhage or a tumor, can be displayed in three dimensions. Any combination of 2D, 3D, and multi-dimensional images is possible for display by the OHMD; any combination of 2D, 3D, and multi-dimensional images can be superimposed on live patient data by the OHMD.

The virtual 2D, 3D, and multi-dimensional data can be generated or acquired by different data acquisition technologies, e.g. different imaging tests etc.

Locking or Moving of Virtual Data

In some embodiments of the invention, virtual data can be locked in relationship to the surgeon or operator or in relationship to the patient or a certain target anatomy within a patient. This means even if the surgeon moves his or her head or the body or parts of the patient's anatomy are being moved, the virtual data will not move in the OHMD display. For example, once registration has occurred, the OHMD can display a virtual image of a target tissue or adjacent tissue. The virtual image of the target tissue or adjacent tissue can be, for example, an image through a tumor or other type of pathologic tissue. As the surgeon or operator moves his or her head or body during the surgical procedure, the virtual data will not move, but are being displayed within the same location.

In some embodiments of the invention, virtual data can move in relationship to the surgeon or operator or in relationship to the patient or a certain target anatomy within a patient. This means if the surgeon moves his or her head or the body or parts of the patient's anatomy are being moved, the virtual data will move in the OHMD display. For example, once registration has occurred, the OHMD can display a virtual image of a target tissue or adjacent tissue. The virtual image of the target tissue or adjacent tissue can be, for example, an image through a tumor or other type of pathologic tissue. As the surgeon or operator moves his or her head or body during the surgical procedure, the virtual data will move and change location and orientation the same way how the surgeon moves his/her head or body, typically reflecting the change in perspective or view angle that the surgeon obtained by moving his or her head or body.

Optionally the moving of the virtual data can be at greater virtual distance or greater angle or lesser virtual distance or lesser angle than the movement of the surgeon's head or body.

Improving the Accuracy of Moving or Re-Orienting Virtual Data

Once registration between virtual data and physical data has occurred, the moving or re-orienting of virtual data to follow, for example, the surgeon's head movements or body movements or operating arm or hand movements, or the movements of the patient or certain body parts of the patient can be accomplished, for example, by monitoring the movement and change in location and/or orientation of the surgeon's head using the IMU of the OHMD.

In some embodiments, optical or RF tracker's or other tracking devices known in the art can be applied to the OHMD and/or the patient including select body parts or target tissues of the patient, e.g. the patient's knee. Using standard surgical navigation techniques known in the art, the spatial location of the optical or RF trackers can be recorded, for example for a starting pose or position or location. Movement of the trackers, e.g. induced by movement of the surgeon's head or body or by movement of at least a part of the patient, can then be tracked using the navigation system. The information on positional change, orientational change or movement direction of the surgeon's head or the patient or both can then be used to update the virtual data, or the display of the virtual data in the OHMD, or both correspondingly. In this manner, the virtual data and the live data can be superimposed by the OHMD, typically in an accurate manner.

Optionally, positional, orientational, directional data and the like generated by the IMU can be used in conjunction with such data generated by a surgical navigation system. A combination of data can be beneficial for more accurate measurement of changes in position or orientation of the surgeon's head, body, operating arm, hand, or the patient.

Use of Virtual Data in 2 or More Dimensions

In some embodiments of the invention, the OHMD can display a 2D virtual image of the patient. The image can be a transmission type image, e.g. an x-ray or CT scout scan. The image can be a cross-sectional image of select anatomy of the patient. The image can be an original image or a reformatted, reconstructed or segmented or partially segmented image of the patient.

In some embodiments of the invention, a surgeon will look through the OHMD at the patient's live data, e.g. the exposed brain surface with the patient's gyri and sulci. The surgeon can register virtual data of the patient, e.g. an MRI scan of the patient's brain, relative to the patient's live data. Registration can occur in 2, 3 or more dimensions. Registration of virtual data in relationship to live data can include registration of different types of virtual data, e.g. different types of normal or diseased tissue, different imaging modalities used, different dimensions used for different types of normal or diseased tissue etc. More than one 2D scan plane can be displayed simultaneously. These 2D scan planes can be parallel or non-parallel, orthogonal or non-orthogonal at variable angles.

Scrolling Through, Moving of Virtual Data Superimposed onto Live Data

In some embodiments of the invention, a surgeon or operator may optionally scroll through a set of consecutive or non-consecutive virtual 2D image data as well as 3D image data which are being superimposed onto the patient's live data, typically live data from the same anatomic region, e.g. a brain, a spine, a hip, a knee etc. The scrolling can be directed through any type of user interface, known in the art. For example, a surgeon can use a virtual interface projected by the OHMD where he or she can move a virtual arrow up or down or left or right to scroll the images backward or forward or, for example, to rotate the images or to display them in different multiplanar angles or to change the view angle or projection angle.

Optionally, the surgeon can scroll through the virtual image data or move virtual image data by moving his head back and forth, e.g. for scrolling backward or forward in a virtual image volume. The surgeon can move his or her head left or right for example, to rotate the images or to display them in different multiplanar angles or to change the view angle or projection angle of a 3D image.

Optionally, the surgeon can scroll through the virtual image data by moving his or her hand or finger or any other body part back and forth, e.g. for scrolling backward or forward in a virtual image volume. The surgeon can move his or her hand or finger or any other body part back and forth left or right for example, to rotate the images or to display them in different multiplanar angles or to change the view angle or projection angle. The surgeon can move his or her hand or finger in a spinning or rotating movement to spin or rotate the virtual data. Any combination of head or hand or eye and other body signals can be used for changing the display of the virtual data.

Optionally, these display changes of the virtual data can be executed in the OHMD using the same location, position, orientation, angular, direction and movement related changes that are made by the surgeon's body part used to trigger the change in display. Alternatively, any one of location, position, orientation, angular, direction and movement related changes of the virtual data can be executed using a magnification factor or a minification factor in relationship to the changes in location, position, orientation, angular, direction and movement of the surgeon's body part. These magnification or minification factors can be linear or non-linear, e.g. exponential or logarithmic. In some embodiments, the further the surgeon's body part controlling the movement of the virtual data in the OHMD display moves away from its original position, the greater the induced change on the movement of the virtual data in the OHMD. In some embodiments, the further the surgeon's body part controlling the movement of the virtual data in the OHMD display moves away from its original position, the smaller the induced change on the movement of the virtual data in the OHMD.

Use of Virtual Data in 3 or More Dimensions

In some embodiments of the invention, the OHMD can display a 3D virtual image of the patient. A 3D representation of the patient can include a 3D display of different types of anatomy, for example in an area of intended surgery or a surgical site.

A 3D reconstruction of image data or other data of the patient can be generated preoperatively, intraoperatively and/or postoperatively. A virtual 3D representation can include an entire anatomic area or select tissues or select tissues of an anatomic area. Different tissues can be virtually displayed by the OHMD in 3D using, for example, different colors. Normal tissue(s) and pathologic tissue(s) can be displayed in this manner.

Normal tissue can, for example, include brain tissue, heart tissue, lung tissue, liver tissue, vascular structures, bone, cartilage, spinal tissue, intervertebral disks, nerve roots. Any tissue can be visualized virtually by the OHMD.

Registration of Virtual Data and Live Data of a Patient, for Example Over a Surgical Site In some embodiments of the invention virtual data of a patient displayed by an OHMD and live data of a patient seen through an OHMD are spatially registered in relationship to each other, for example in a common coordinate system, for example with one or more optical OHMDs in the same common coordinate system. Virtual and physical surgical instruments and implant components can also be registered in the common coordinate system. Spatial co-registration can have the benefit that the simultaneous display of virtual and live data of the patient is not affected or less affected when the surgeon moves his or her head or body, when the OHMD moves or when the patient moves. Thus, the view perspective of the live data of the patient seen by the surgeon's eyes through the OHMD, e.g. the live surgical field, can stay the same as the view perspective of the virtual data of the patient seen by the surgeon's eyes through the display of the OHMD unit, e.g. the virtual surgical field, virtual surgical plane, virtual paths, virtual cut paths or planes, projected into the surgeon's eyes, even as the surgeon moves his or her head or body. In this manner, the surgeon does not need to re-think or adjust his hand eye coordination since live data of the patient seen through the surgeon's eye and virtual data of the patient seen through the OHMD display are superimposed, which is fundamentally different from other approaches such as surgical navigation which employ a separate computer monitor in the OR with a view angle for the surgeon that is different than his or her view angle for the live data of the patient and the surgical field. Also, with surgical navigation, a first virtual instrument can be displayed on a computer monitor which is a representation of a physical instrument tracked with navigation markers, e.g. infrared or RF markers, and the position and/or orientation of the first virtual instrument can be compared with the position and/or orientation of a corresponding second virtual instrument generated in a virtual surgical plan. Thus, with surgical navigation the positions and/or orientations the first and the second virtual instruments are compared.

With guidance in mixed reality environment, e.g. with stereoscopic display like an electronic holographic environment, a virtual surgical guide, tool, instrument or implant can be superimposed onto the joint, spine or surgical site. Further, the physical guide, tool, instrument or implant can be aligned with the 2D or 3D representation of the virtual surgical guide, tool, instrument or implant. Thus, guidance in mixed reality environment does not need to use a plurality of virtual representations of the guide, tool, instrument or implant and does not need to compare the positions and/or orientations of the plurality of virtual representations of the virtual guide, tool, instrument or implant.

In some embodiments, virtual data can move in relationship to the surgeon or operator or in relationship to the patient or a certain target anatomy within a patient. This means if the surgeon moves his or her head or the body or parts of the patient's anatomy are being moved, the virtual data will move in the OHMD display. For example, once registration of the OHMD, the virtual data of the patient and the live data of the patient in a common coordinate system has occurred, the OHMD can display a virtual image of a target tissue or adjacent tissue. The virtual image of the target tissue or adjacent tissue can be, for example, an image of or through a tumor or other type of pathologic tissue or a spine or a spinal pedicle. As the surgeon or operator moves his or her head or body during the surgical procedure, the virtual data will move and change location and orientation the same way how the surgeon moves his/her head or body, typically reflecting the change in perspective or view angle that the surgeon obtained by moving his or her head or body. The virtual data can include a 3D representation of a surgical tool or instrument such as a needle for kyphoplasty or vertebroplasty, where the virtual representation of the needle shows its intended location, orientation or path in relationship to the spine and/or a pedicle. The virtual data can also include a medical device, such as a pedicle screw, wherein the virtual data of the pedicle screw shows its intended location, orientation or path in relationship to the spine, and/or a pedicle, and/or a vertebral body.

In some embodiments, registration is performed with at least three or more points that can be superimposed or fused into a common object coordinate system for virtual data and live data. Registration can also be performed using a surface or a 3D shape of an anatomic structure present in both virtual data and live data of the patient. In this case the virtual surface can be moved until it substantially matches the live surface of the patient or the virtual shape can be moved until it substantially matches the live shape of the patient.

Registration of virtual data of a patient and live data of a patient can be achieved using different means. The following is by no means meant to by limiting of the invention, but is only exemplary in nature.

Registration of Virtual Patient Data and Live Patient Data Using Directly or Indirectly Connected Object Coordinate Systems Registration of virtual and live data of the patient can be performed if the virtual data, e.g. imaging data of the patient, are acquired with the patient located in a first object coordinate system and the live data, e.g. during surgery, are observed or acquired with the patient located in a second object coordinate system, wherein the first and the second object coordinate system can be connected by direct, e.g. physical, or indirect, e.g. non-physical, means. A direct connection of the first and second object coordinate system can be, for example, a physical connection between the first and second object coordinate system. For example, the patient can be moved from the first to the second object coordinate system along the length of a tape measure. Or the patient can be scanned inside a scanner, e.g. a CT scanner or MRI scanner, and the scanner table can be subsequently moved out of the scanner for performing a surgical procedure with the patient still located on the scanner table. In this case, the scanner table can be a form of physical connection between the first and the second object coordinate system and the length of the table movement between the scan position and the outside the scanner position (for the live data, e.g. the surgical procedure) can define the coordinate transformation from the first to the second object coordinate system.

An indirect connection between the first (virtual data) and second (live data) object can be established if the patient is moved between the acquiring the virtual data, e.g. using an imaging test, and the live data, e.g. while performing a surgical procedure, along a defined path, wherein the direction(s) and angle(s) of the path are known so that the first and the second object coordinate system can be cross-referenced and an object coordinate transfer can be applied using the known information of the defined path and virtual data of the patient, live data of the patient and the OHMD can be registered in a common coordinate system. Virtual and physical surgical instruments and implant components can also be registered in the common coordinate system.

Registration of virtual patient data and live patient data is also possible without directly or indirectly connected object coordinate systems using other means and methods as will be explained in the following paragraphs and columns, for example when the patient performed one or more movements of unknown direction, length or magnitude. Combinations of all different registration methods described in the specification are possible, e.g. for switching registration methods during a procedure or for simultaneously using multiple registration methods, e.g. for enhancing the accuracy of the registration.

Registration Using Spatial Mapping

Live data, e.g. live data of the patient, the position and/or orientation of a physical instrument, the position and/or orientation of an implant component, the position and/or orientation of one or more OHMDs, can be acquired or registered, for example, using a spatial mapping process. This process creates a three-dimensional mesh describing the surfaces of one or more objects or environmental structures using, for example and without limitation, a depth sensor, laser scanner, structured light sensor, time of flight sensor, infrared sensor, or tracked probe. These devices can generate 3D surface data by collecting, for example, 3D coordinate information or information on the distance from the sensor of one or more surface points on the one or more objects or environmental structures. The 3D surface points can then be connected to 3D surface meshes, resulting in a three-dimensional surface representation of the live data. The surface mesh can then be merged with the virtual data using any of the registration techniques described in the specification.

The live data can be static, or preferably, it can be continuously updated with additional information to incorporate changes in the position or surface of the one or more objects or environmental structures. The additional information can, for example be acquired by a depth sensor, laser scanner, structured light sensor, time of flight sensor, infrared sensor, or tracked probe.

For initial spatial mapping and updating of mapping data, commonly available software code libraries can be used. For example, this functionality can be provided by the Microsoft HoloToolkit or the Google Project Tango platform. Various techniques have been described for spatial mapping and tracking including those described in U.S. Pat. No. 9,582,717, which is expressly incorporated by reference herein.

Registration of Virtual Patient Data and Live Patient Data Using Visual Anatomic Features a) Visual registration of virtual patient data in relationship to live patient data by the surgeon or operator In some embodiments, a surgeon or operator can visually align or match virtual patient data with live patient data. Such visually aligning or matching of virtual patient data and live patient data can, for example, be performed by moving the OHMD, for example via movement of the head of the operator who is wearing the OHMD. In this example, the virtual patient data can be displayed in a fixed manner, not changing perspective as the operator moves the OHMD. The operator will move the OHMD until the live patient data are aligned or superimposed onto the fixed projection of the virtual patient data. Once satisfactory alignment, matching or superimposition of the live patient data with the virtual patient data has been achieved, the surgeon can execute a registration command, for example via a voice command or a keyboard command. The virtual patient data and the live patient data are now registered. At this point, upon completion of the registration, the virtual patient data will move corresponding to the movement of the OHMD, for example as measured via the movement of an integrated IMU, image and field of view tracking, e.g. using anchor points in an image or field of view using an image and/or video capture system, and/or an attached navigation system with optical or RF or other trackers, which can be attached to the patient, the surgical site, a bone or any other tissue of the patient, the surgeon, the surgeon's arm, the surgeon's head or an OHMD worn by the surgeon.

Thus, once a satisfactory alignment or match has been achieved the surgeon can execute a command indicating successful registration. The registration can include changes in at least one of position, orientation, and magnification of the virtual data and the live data in order to achieve the alignment or match. Magnification applied to the virtual data can be an indication of the distance from the OHMD or the surgeon's head to the matched tissue. As a means of maximizing the accuracy of the registration, the estimated distance between the OHMD and the target tissue or the skin surface or other reference tissue can be confirmed with an optional physical measurement of the distance, in particular if the OHMD is, for example, in a fixed position, e.g. on a stand or tripod, which may be used optionally during the initial registration. Upon successful alignment or matching, the surgeon command can register, for example, the virtual patient data and the live patient data or images and the OHMD in the same common coordinate system. Virtual and physical surgical instruments and implant components can also be registered in the common coordinate system.

In some embodiments of the invention, the visual anatomic data can be, for example, gyri of the brain or osteophytes or bone spurs or pathologic bone deformations or tumor nodes or nodules, e.g. on the surface of a liver or a brain.

In some embodiments of the invention, the registration of virtual patient data and live patient data using the methods described herein can be repeated after one or more surgical steps have been performed. In this case, the surgically altered tissue or tissue surface or tissue contour or shape, e.g. shape of a bone after milling or reaming, or tissue perimeter, e.g. perimeter of a bone cut, or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient, with substantially identical view angle of the virtual data of the patient seen by the surgeon's eyes through the display of the OHMD unit and the live data of the patient seen by the surgeon's eyes through the OHMD unit. The matching, superimposing and/or registering of the live data of the patient and the virtual data of the patient after the surgical tissue alteration can be performed using the same methods described in the foregoing or any of the other registration methods described in the specification or any other registration method known in the art. Referring to FIG. 3, FIG. 3 illustrates an example of registering a digital hologram or virtual data for an initial surgical step, performing the surgical step and re-registering one or more holograms for subsequent surgical steps. An optical head mounted display can project or display a digital hologram of virtual data or virtual data of the patient 55. The digital hologram can optionally be fixed to the OHMD so that it will move with the movement of the OHMD 56. The operator can move the OHMD until digital hologram of the virtual data or virtual data of the patient is superimposed and aligned with the live data of the patient, e.g. the surgical site 57. The digital hologram of the virtual data or virtual data can then be registered using the same or similar coordinates as those of the live data with which the digital hologram is superimposed 58. The surgeon can then perform one or more predetermined surgical steps, e.g. bone cuts 59. A digital hologram of the virtual data or virtual data can optionally be registered or re-registered after the surgical alteration with the live data 60. The digital hologram of the virtual data or virtual data after the surgical alteration can optionally be displayed by the OHMD 61. The digital hologram of the virtual data or virtual data after the surgical alteration can optionally be fixed relative to the OHMD so that it will move with the movement of the OHMD 62. The operator can move the OHMD until digital hologram of the virtual data or virtual data of the patient after the surgical alteration is superimposed and aligned with the live data of the patient after the surgical alteration 63. The digital hologram of the virtual data or virtual data can then be registered using the same or similar coordinates as those of the live data after the surgical alteration with which the digital hologram is superimposed 64. The surgeon can then perform one or more predetermined subsequent surgical steps, e.g. bone cuts, milling or drilling 65. The preceding steps can optionally be repeated until the surgical procedures is completed 66. A virtual surgical plan 67 can be utilized. Optionally, the native anatomy of the patient including after a first surgical alteration can be displayed by the OHMD 68. The OHMD can optionally display digital holograms of subsequent surgical steps 69.

b) Automatic or semi-automatic registration of virtual patient data in relationship to live patient data using image processing and/or pattern recognition and matching techniques c) In some embodiments of the invention, image processing techniques, pattern recognition techniques or deep learning/artificial neural-network based techniques can be used to match virtual patient data and live patient data. Optionally, image processing and/or pattern recognition algorithms can be used to identify certain features, e.g. gyri or sulci on the brain surface of virtual data of a patient. An ear including its unique shape can also be used for the purpose of matching virtual patient data and live patient data.

For example, with brain surgery, the patient can be placed on the operating table. Optionally, cleaning or sterilization fluid can be applied to the shaved skull, for example using betadine. The OHMD can be placed over the patient, either on a tripod or worn by the operator, for example with the head of the patient turned sideways over the live patient's ear and lateral skull. The OHMD will be placed over an area of the live patient that includes the virtual data of the patient to be displayed.

Virtual data of the patient can be displayed in the OHMD. The virtual data of the patient can include, for example, a visualization of the patient's skin or other data, e.g. the patient's ear or nose, for example derived from preoperative MRI data. The virtual data of the patient's skin or other structures, e.g. the patient's ear or nose, can be displayed simultaneous with the live patient data. The virtual data of the patient can then be moved, re-oriented, re-aligned and, optionally, magnified or minified until a satisfactory alignment, match or superimposition has been achieved. Optionally, the OHMD can be moved also during this process, e.g. to achieve a satisfactory size match between virtual data and live data of the patient, optionally without magnification or minification of the virtual data of the patient.

Once a satisfactory alignment, match or superimposition has been achieved between virtual data and live data of the patient, the operator can execute a command indicating successful registration. Changes in position, orientation, or direction of the OHMD, for example as measured via an integrated IMU, image and field of view tracking, e.g. using anchor points in an image or field of view using an image and/or video capture system, and/or a navigation system attached to the OHMD, can be used to move the virtual patient data with the view of the live patient data through the OHMD, with substantially identical object coordinates of the virtual data of the patient and the live data of the patient, thereby maintaining registration during the course of the surgery irrespective of any movements of the OHMD, e.g. head movement by the operator wearing the OHMD, and ensuring that the virtual data of the patient is correctly superimposed with the live data of the patient when projected into the surgeon's view.

After successful registration of the virtual patient data to the patient's skin or other structures, e.g. an ear or a nose, the operator or an assistant can apply a marker or calibration or registration phantom or device on the patient, for example close to the intended site of a craniotomy. The marker or calibration or registration phantom or device will not be covered by any drapes or surgical covers that will be placed subsequently. A secondary registration of the virtual patient data to the live patient data can then occur, by registering the virtual patient data to the live patient data, using the live marker or calibration or registration phantom or device placed on the patient and by cross-referencing these to the live data of the patient's skin or other structures, e.g. an ear or a nose. This can be achieved, for example, by registering the patient's skin or other structures, e.g. an ear or a nose, in the same coordinate system as the marker or calibration or registration phantom or device placed on the patient, e.g. by co-registering the virtual patient data of the patient's skin or other structures, e.g. an ear or a nose or an osteophyte or bone spur or other bony anatomy or deformity, with the live data of the marker or calibration or registration phantom or device. The distance, offset, angular offset or overall difference in coordinates between the patient's skin or other structures, e.g. an ear or nose or an osteophyte or bone spur or other bony anatomy or deformity, to the marker or calibration or registration phantom or device attached to the patient can be measured and can be used to switch the registration of the virtual patient data to the live patient data from the live data of the patient's skin or other structures, e.g. an ear or a nose, to the live data of the marker or calibration or registration phantom or device. Optionally, registration can be maintained to both the live data of the patient's skin or other structures, e.g. an ear or a nose, and the live data of the marker or calibration or registration phantom or device. Optionally, the system can evaluate if registration to the live data of the patient's skin or other structures, e.g. an ear or a nose, or to the live data of the marker or calibration or registration phantom or device is more accurate and the system can switch back and forth between either. For example, if the distance increases or decreases from the OHMD to the patient's skin or other structure, e.g. an ear or a nose, beyond a certain level, e.g. a threshold, which can be optionally predefined, or if some of them is partially covered by a drape, the system can switch the registration to the live data of the marker or calibration or registration phantom or device. The reverse is possible. Or, if the angle from the OHMD increases or decreases beyond a certain level, e.g. a threshold, which can be optionally predefined, to the patient's skin or other structure, e.g. an ear or a nose or an osteophyte or bone spur or other bony anatomy or deformity, the system can switch the registration to the live data of the marker or calibration or registration phantom or device. The reverse is possible.

The operator or the assistants can then place sterile drapes or surgical covers over the site, however preferably not covering the marker or calibration or registration phantom or device. Registration can be maintained via the live data of the marker or calibration or registration phantom or device attached to the patient, e.g. adjacent to or inside a craniotomy site.

Image processing and/or pattern recognition of the live data of the patient can then be performed through the OHMD, e.g. using a built in image capture apparatus for capturing the live data of the patient or image and/or video capture systems attached to, integrated with or coupled to the OHMD.

Virtual and live data features or patterns can then be matched. The matching can include a moving and/or reorienting and/or magnification and/or minification of virtual data for successful registration with the live data of the patient and superimposition of both. Virtual and live data can include an osteophyte or bone spur or other bony anatomy or deformity. Combination of (a) and (b), e.g. automatic registration with manual adjustment option, e.g. by moving the virtual image data in relation to the live image data after image processing software and/or pattern recognition software and/or matching software have identified a potential match or performed an initial matching, which can then be followed by manual/operator based adjustments.

Alternatively, manual/operator based matching and registration can be performed first, followed then by fine-tuning via software or algorithm (image processing, pattern recognition, etc.) based matching and registration. Virtual and live data can include an osteophyte or bone spur or other bony anatomy or deformity.

In some embodiments of the invention, the registration of virtual patient data and live patient data using the methods described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the specification or any other registration method known in the art.

Registration of Virtual Patient Data and Live Patient Data Using Anatomic Landmarks In some embodiments, a surgeon can identify select anatomic landmarks on virtual data of the patient, e.g. on an electronic preoperative plan of the patient, and on live data of the patient. For example, the surgeon can identify a landmark by placing a cursor or a marker on it on an electronic image of the virtual data of the patient and by clicking on the landmark once the cursor or marker is in the desired location. In a spine, such a landmark can be, for example, the posterior tip of a spinous process, a spinal lamina, an inferior facet on the patient's left side, a superior facet on the patient's left side, an inferior facet on the patient's right side, a superior facet on the patient's right side, a tip of a facet joint, a bone spur, an osteophyte etc. In a hip, such landmarks can be the most anterior point of the acetabulum, an osteophyte, e.g. on the acetabular rim, in the acetabulum, adjacent to the acetabulum, on the femoral head, on the femoral neck or the neck shaft junction, the center of the femoral head in a 2D or 3D image, the most anterior point of the femoral head, an anterosuperior iliac spine, an anteroinferior iliac spine, a symphysis pubis, a greater trochanter, a lesser trochanter etc. In a knee, such landmarks can be a femoral condyle, a femoral notch, an intercondylar space, a medial or lateral epicondyle, a femoral axis, an epicondylar axis, a trochlear axis, a mechanical axis, a trochlear groove, a femoral osteophyte, a marginal femoral osteophyte, a central femoral osteophyte, a dome of the patella, a superior, medial, lateral, inferior edge of the patella or the femur or femoral articular surface, a patellar osteophyte, an anterior tibia, a tibial spine, a medial, lateral, anterior, posterior edge of the tibia, a tibial osteophyte, a marginal tibial osteophyte, a central tibial osteophyte. The surgeon can then identify the same landmarks live in the patient. For example, as the surgeon looks through the OHMD, the surgeon can point with the finger or with a pointing device at the corresponding anatomic landmark in the live data. The tip of the pointer or the tip of the finger can, optionally, include a tracker which locates the tip of the pointer or the finger in space. Such locating can also be done visually using image capture, e.g. in a stereoscopic manner through the OHMD for more accurate determination of the distance and location of the pointer or finger in relationship to the OHMD. An image and/or video capture systems can also be attached to, integrated with or coupled to the OHMD. Virtual and live data can include an osteophyte or bone spur or other bony anatomy or deformity.

Representative anatomic landmarks that can be used for registration of virtual and live data of the patient can include (but are not limited to):

In Spine:
A portion or an entire spinous process
A portion or an entire spinal lamina
A portion or an entire spinal articular process
A portion of or an entire facet joint
A portion of or an entire transverse process
A portion of or an entire pedicle
A portion of or an entire vertebral body
A portion of or an entire intervertebral disk
A portion of or an entire spinal osteophyte
A portion of or an entire spinal bone spur
A portion of or an entire spinal fracture
A portion of or an entire vertebral body fracture
Combinations of any of the foregoing Hip:
A portion of or an entire acetabulum
A portion of or an entire edge of an acetabulum
Multiple portions of an edge of an acetabulum
A portion of an iliac wall
A portion of a pubic bone
A portion of an ischial bone
An anterior superior iliac spine
An anterior inferior iliac spine
A symphysis pubis
A portion of or an entire greater trochanter
A portion of or an entire lesser trochanter
A portion of or an entire femoral shaft
A portion of or an entire femoral neck
A portion of or an entire femoral head
A fovea capitis
A transverse acetabular ligament
A pulvinar
A ligamentum teres
A labrum
One or more osteophytes, femoral and/or acetabular
Combinations of any of the foregoing Knee:
A portion or an entire medial femoral condyle
A portion or an entire lateral femoral condyle
A portion or an entire femoral notch
A portion or an entire trochlea
A portion of an anterior cortex of the femur
A portion of an anterior cortex of the femur with adjacent portions of the trochlea
A portion of an anterior cortex of the femur with adjacent portions of the trochlea and osteophytes when present
One or more osteophytes femoral and/or tibial
One or more bone spurs femoral and/or tibial
An epicondylar eminence
A portion or an entire medial tibial plateau
A portion or an entire lateral tibial plateau
A portion or an entire medial tibial spine
A portion or an entire lateral tibial spine
A portion of an anterior cortex of the tibia
A portion of an anterior cortex of the tibia and a portion of a tibial plateau, medially or laterally or both
A portion of an anterior cortex of the tibia and a portion of a tibial plateau, medially or laterally or both and osteophytes when present
A portion or an entire patella
A medial edge of a patella A lateral edge of a patella
A superior pole of a patella
An inferior pole of a patella
A patellar osteophyte
An anterior cruciate ligament
A posterior cruciate ligament
A medial collateral ligament
A lateral collateral ligament
A portion or an entire medial meniscus
A portion or an entire lateral meniscus
Combinations of any of the foregoing
Shoulder:
A portion or an entire glenoid
A portion or an entire coracoid process
A portion or an entire acromion
A portion of a clavicle
A portion or an entire humeral head
A portion or an entire humeral neck
A portion of a humeral shaft
One or more humeral osteophytes
One or more glenoid osteophytes
A portion or an entire glenoid labrum
A portion or an entire shoulder ligament, e.g. a coracoacromial ligament, a superior, middle, or inferior glenohumeral ligament
A portion of a shoulder capsule
Combinations of any of the foregoing
Skull and Brain:
A portion of a calvarium
A portion of an occiput
A portion of a temporal bone
A portion of a occipital bone
A portion of a parietal bone
A portion of a frontal bone
A portion of a facial bone
A portion of a facial structure
A portion or an entire bony structure inside the skull
Portions or all of select gyri
Portions or all of select sulci
A portion of a sinus
A portion of a venous sinus
A portion of a vessel
A portion of an ear
A portion of an outer auditory canal
Organs:
A portion of an organ, e.g. a superior pole or inferior pole of a kidney
An edge or a margin of a liver, a spleen, a lung
A portion of a hepatic lobe
A portion of a vessel
A portion of a hiatus, e.g. in the liver or spleen
A portion of a uterus Someone skilled in the art can identify other anatomic landmarks of hard tissues, soft-tissues and or organs including brain that can be used for registration of virtual data (including optionally including virtual surgical plans) and live data of the patient and the OHMD in a common coordinate system. Virtual and physical surgical instruments and implant components can also be registered in the common coordinate system.

In some embodiments of the invention, the OHMD can display an arbitrary virtual plane over the surgical field. The arbitrary virtual plane can be moveable using a virtual or other interface. For example, the arbitrary virtual plane can include a "touch area", wherein gesture recognition software, for example the one provided by Microsoft with the Microsoft Hololens including, for example, the integrated virtual "drag function" for holograms can be used to move the arbitrary virtual plane. For example, one or more cameras integrated or attached to the OHMD can capture the movement of the surgeon's finger(s) in relationship to the touch area; using gesture tracking software, the virtual plane can then be moved by advancing the finger towards the touch area in a desired direction.

The OHMD can display the arbitrary virtual plane in any location initially, e.g. projected onto or outside the surgical field, e.g. a hip joint, knee joint, shoulder joint, ankle joint, or a spine. The OHMD can optionally display the arbitrary virtual plane at a defined angle, e.g. orthogonal or parallel, relative to a fixed structure in the operating room, which can, for example, be recognized using one or more cameras, image capture or video capture systems integrated into the OHMD and spatial recognition software such as the one provided by Microsoft with the Microsoft Hololens or which can be recognized using one or more attached optical markers or navigation markers including infrared or RF markers. For example, one or more optical markers can be attached to an extension of the operating table. The OHMD can detect these one or more optical markers and determine their coordinates and, with that, the horizontal plane of the operating room table. The arbitrary virtual plane can then be displayed perpendicular or at another angle relative to the operating room table.

For example, in a hip replacement, the OHMD can display a virtual arbitrary plane over the surgical site. The virtual arbitrary plane can be perpendicular to the operating table. Using a virtual interface, e.g. a touch area on the virtual surgical plane and gesture tracking, the OHMD can detect how the surgeon is moving the virtual arbitrary plane. Optionally, the virtual arbitrary plane can maintain its perpendicular (or of desired other angle) orientation relative to the OR table while the surgeon is moving and/or re-orienting the plane; a perpendicular orientation can be desirable when the surgeon intends to make a perpendicular femoral neck cut. A different angle can be desirable, when the surgeon intends to make the femoral neck cut with another orientation.

Using the touch area or other virtual interface, the surgeon can then move the arbitrary virtual plane into a desired position, orientation and/or alignment. The moving of the arbitrary virtual plane can include translation and rotation or combinations thereof in any desired direction using any desired angle or vector. The surgeon can move the arbitrary virtual plane to intersect with select anatomic landmarks or to intersect with select anatomic or biomechanical axes. The surgeon can move the arbitrary virtual plane to be tangent with select anatomic landmarks or select anatomic or biomechanical axes.

Figure 4B:
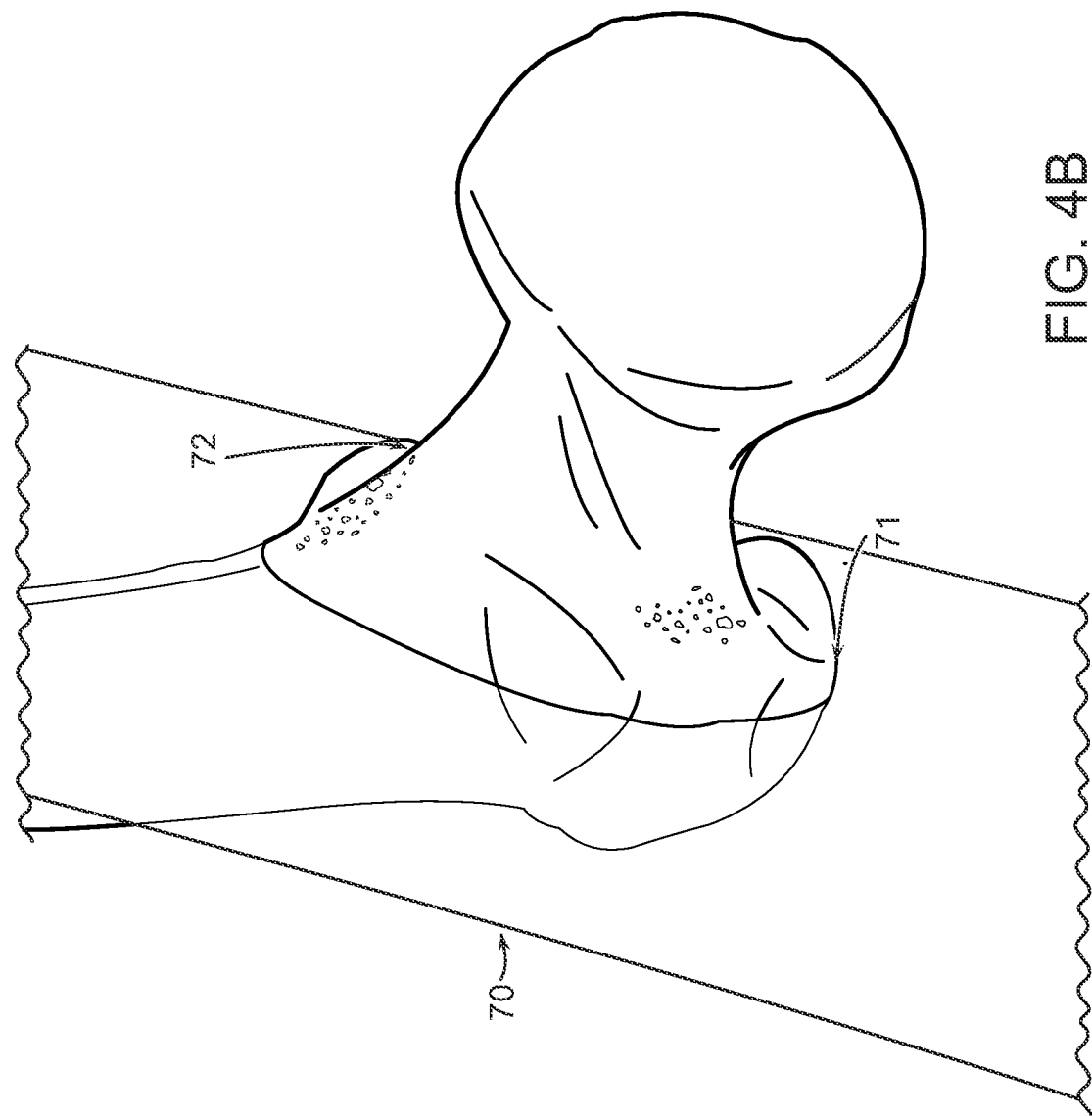

For example, in a hip replacement, the surgeon can move the arbitrary virtual plane to be tangent with the most superior aspect of the greater trochanter and the most superior aspect of the lesser trochanter. FIG. 4A shows an illustrative example of a virtual plane 70 that a primary surgeon has moved and aligned to be tangent with the most superior aspect of the greater trochanter 71 and the most superior aspect of the lesser trochanter 72. FIG. 4B shows an illustrative example of the same virtual plane 70 that the primary surgeon has moved and aligned to be tangent with the most superior aspect of the greater trochanter 71 and the most superior aspect of the lesser trochanter 72, now with the view from the optical head mounted display of a second surgeon or surgical assistant, e.g. on the other side of the OR table.

Figure 4C:
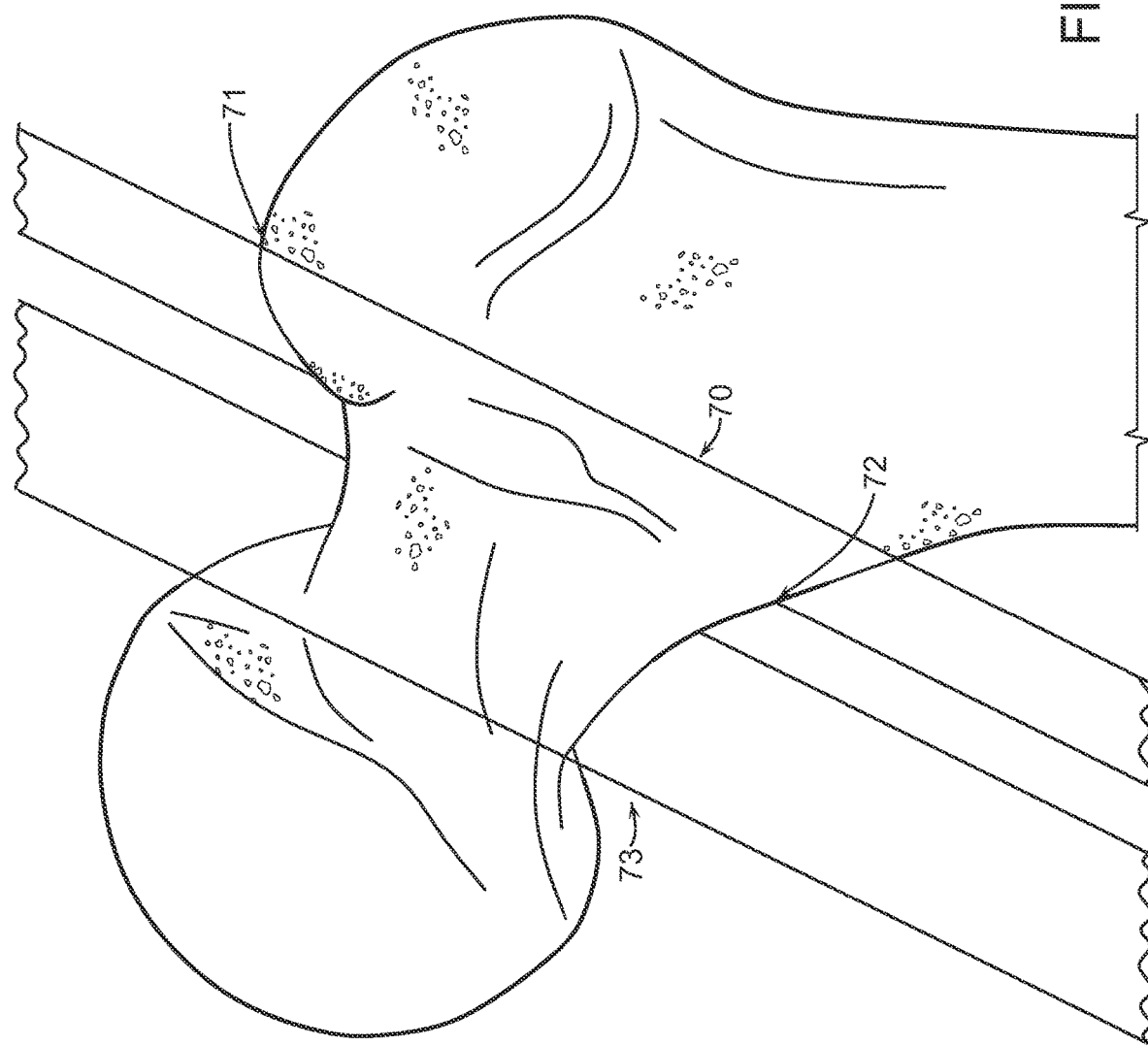

Optionally, for example with a pointer with an attached optical marker or an attached navigation marker, or with his finger detected using an image or video capture system integrated into the OHMD and gesture recognition software such as the one provided by Microsoft with the Hololens, or with his finger with an attached optical marker or navigation marker, the surgeon can point at and identify the sulcus point, e.g. the lowest point between the greater trochanter and the femoral neck, which can be an additional reference. The line connecting the most superior aspect of the greater trochanter and the most superior aspect of the lesser trochanter can then be determined on a pre-operative or intra-operative AP radiograph of the hip; optionally, the sulcus point can also be detected on the AP radiograph. The AP radiograph can include a template used by the surgeon for selecting and sizing, for example, the femoral and acetabular component, as well as the liner and/or femoral heads. The radiographic template can include an indication for the femoral neck cut. The angle between the line connecting the most superior aspect of the greater trochanter and the most superior aspect of the lesser trochanter and the indication for the femoral neck cut can be determined. FIG. 4C is an illustrative example that shows that a second virtual plane 73, the virtual femoral neck cut plane 73, can then be projected or displayed by the OHMD, also perpendicular to the OR table like the arbitrary virtual plane 70, the latter tangent with the most superior aspect of the greater trochanter 71 and the most superior aspect of the lesser trochanter 72, and the femoral neck cut plane 73 at the same angle and/or distance to the arbitrary virtual plane as the angle and distance between the line connecting the most superior aspect of the greater trochanter and the most superior aspect of the lesser trochanter and the indication for the femoral neck cut on the radiograph. In this manner, the femoral neck cut plane can be defined using a second virtual plane prescribed or predetermined based on the intra-operatively placed arbitrary virtual plane, moved by the operator to be tangent with the most superior aspect of the greater trochanter and the most superior aspect of the lesser trochanter. The virtual femoral neck cut plane prescribed and projected or displayed in this manner can also be a virtual guide, e.g. a virtual cut block that projects, for example, a virtual slot for guiding an physical saw. The virtual guide or virtual cut block can have one or more dimensions identical to an physical guide or cut block, so that the physical guide or cut block can be aligned with the virtual guide or cut block. The virtual guide or cut block can be an outline, 2D or 3D, partial or complete, of the physical guide or cut block, with one or more identical dimensions, so that the surgeon can align the physical guide or cut block with the virtual guide or cut block. The virtual guide or cut block can include placement indicia for the physical guide or cut block.

If radiographic magnification is a concern for prescribing a second virtual plane, e.g. a virtual cut plane, based on a first virtual plane, e.g. a plane tangent with or intersecting one or more anatomic landmarks or one or more anatomic or biomechanical axes, at an angle incorporated from or derived from a pre-operative radiograph, optionally, distance measurements can be incorporated and magnification correction can be applied. For example, the distance between one or more landmarks, e.g. the ones with which the virtual plane is tangent with or that the virtual plane intersects, can be measured in the live data of the patient and can be measured on the radiograph. If the radiographic distance is larger or smaller than the distance in the live patient, a magnification correction can be applied and, for example, the distance between the first virtual plane, e.g. a plane tangent with or intersecting one or more anatomic landmarks or one or more anatomic or biomechanical axes, and the second virtual plane, e.g. a virtual cut plane, can be corrected based on the radiographic magnification factor.

Figure 5:
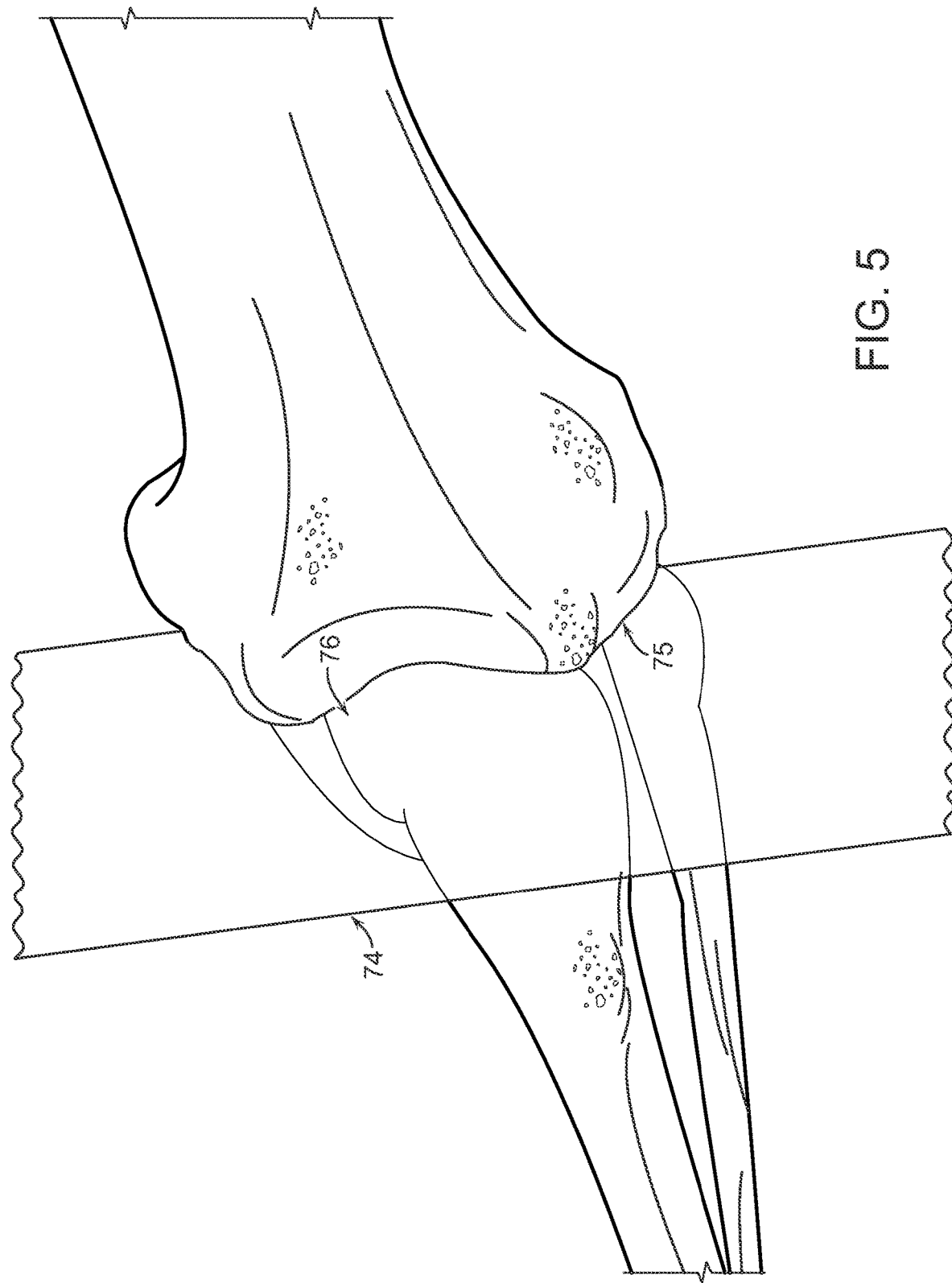
FIG. 5 is an illustrative example of an arbitrary virtual plane in the knee extending through the medial and lateral joint space according to some embodiments of the present disclosure.

In another example, an arbitrary virtual plane can be projected or displayed outside of or over the surgical field in a knee replacement. Optionally, the arbitrary virtual plane can be, at least initially, perpendicular to the OR table or at a defined angle to the OR table. If the mechanical axis of the leg has been determined in a preceding step, e.g. using an intra-operative measurement, for example with optical markers applied to the thigh and one or more optical markers applied to the ankle joint, for determining the center of rotation of the hip joint and the center of the ankle joint using an image capture or video capture system integrated into, attached to or separate from the OHMD, the arbitrary virtual plane can be configured to be perpendicular to the mechanical axis of the leg. Using a virtual interface, e.g. a touch area, and an image or video capture system integrated or attached to the OHMD and optional gesture tracking software, the surgeon can move and/or re-align the arbitrary virtual plane, for example to intersect with the medial and lateral joint space of the exposed knee joint, for example in extension or at 5, 10, 15, 20, 30, 45, or more degrees of flexion. FIG. 5 is an illustrative example of an arbitrary virtual plane 74 in the knee that intersects with the medial 76 and lateral 75 joint space in extension.

One or more additional arbitrary virtual planes can then optionally be projected, for example perpendicular or at another angle relative to the operating table or using a desired femoral component flexion angle or a desired tibial slope. The surgeon can optionally move these one or more arbitrary virtual planes to coincide with one or more anatomic axes, for example the anatomic femoral shaft axis or the anatomic tibial shaft axis in the live patient. The surgeon can also move a virtual arbitrary plane to be placed and oriented in the center of the femoral notch, parallel to the notch walls and extending centered between the medial and the lateral femoral shaft cortex as a means of estimating the anatomic femoral shaft axis.

Once the anatomic femoral and/or tibial axes have been determined or estimated, a virtual surgical plan with femoral and tibial resections designed to achieve a desired femoral mechanical axis correction, e.g. from the patient's mechanical axis alignment, e.g. 5, 10, 15 degrees of varus or valgus, to normal mechanical axis alignment or any desired residual, e.g. congenital varus or valgus, can be developed or generated. Implant size and desired polyethylene thickness can be factored into the virtual surgical plan. The OHMD can then, for example, project virtual surgical cut planes based on the virtual surgical plan and/or the intra-operative measurements, the desired varus and/or valgus correction, desired slope, and/or desired implant rotation. The surgeon can then align the physical saw blade with the projected or displayed virtual saw blade. Alternatively, the OHMD can display a virtual guide or virtual cut block with at least one or more dimensions identical to the physical guide or physical cut block and the surgeon can align the physical cut guide or cut block with the virtual guide or cut block, in the physical guide or cut block, insert the saw blade into the physical guide or cut block and execute the one or more blocks.

The foregoing concepts of projecting arbitrary virtual planes and aligning them with one or more anatomic landmarks, anatomic axes or biomechanical or mechanical axes can be applied to any joint and also the spine. Similarly, these concepts can be applied to brain surgery, where one or more virtual planes can be projected or displayed and moved to be tangent with or intercept one or more landmarks, e.g. gyri, pons, cerebellum etc. Similarly, these concepts can be applied to organ surgery, where one or more virtual planes can be projected or displayed and moved to be tangent with or intercept one or more landmarks, e.g. liver portal, anterior liver edge, one or more cardiac valves etc.

Other arbitrary 2D and/or 3D virtual shapes or outlines or surfaces, e.g. cubes, cuboids, prisms, cones, cylinders, spheres, ellipsoid derived 3D shapes, irregular shapes, can be virtually projected or displayed and automatically or using a virtual or other user interface moved, oriented or aligned to coincide, to be tangent with, to intersect, to be partially or completely superimposed with patient anatomy, pathology, anatomic axes, biomechanical including mechanical axes, anatomic planes, 3D shapes, 2D and/or 3D geometries, 3D surfaces, and/or 3D volumes of any internal organs, soft-tissues or hard tissues of the patient; after the moving, orienting or aligning, the coordinate information of the 2D and/or 3D virtual shapes or outlines or surfaces can then be measured. Optionally, based on the coordinate information, additional intraoperative measurements can be performed and/or, optionally, a virtual surgical plan can be developed or modified using the information.

In some embodiments of the invention, the registration of virtual patient data and live patient data using the methods described herein including anatomic landmarks can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the specification or any other registration method known in the art. Optionally, different anatomic landmarks can also be used for the first registration and any of the subsequent registrations. Or the same anatomic landmarks can be used for the first registration and any of the subsequent registrations.

Using Light Sources for Referencing Live Anatomic Landmarks

The tracker or pointing device can also be a light source, which can, for example, create a red point or green point created by a laser on the patient's tissue highlighting the anatomic landmark intended to be used for registration. A light source can be chosen that has an intensity and/or a color that will readily distinguish it from the live tissue of the patient.

The laser or other light source can optionally be integrated into or attached to the OHMD. For example, the laser or the light source can be integrated into or attached to a bridge connecting the frame pieces between the left and the right eye portion of the OHMD, for example over the nasal region.

Image capture, for example integrated into or attached to or coupled to the OHMD, can be used to identify the location of the light on the patient's tissue or the patient's anatomic landmark. Once the light has been directed to the desired location on the live data of the patient, specifically, the live landmark of the patient, registration can be performed by executing a registration command, registering the live data of the patient with the virtual data of the patient, e.g. the live landmark with the laser or other light being reflected of it and the corresponding virtual landmark of the patient. This process can be repeated for different anatomic landmarks, e.g. by pointing the light source at the next live anatomic landmark of the patient, confirming accurate placement or pointing, the light, e.g. a red or green laser point being reflected from the live patient landmark can be captured via the image capture device and software of the OHMD, and the next anatomic live landmark can be registered with the corresponding virtual anatomic landmark of the patient. Virtual and live data can include an osteophyte or bone spur or other bony anatomy or deformity. In this manner, the OHMD, live data of the patient and virtual data of the patient can be registered in a common coordinate system. Virtual and physical surgical instruments and implant components can also be registered in the common coordinate system.

In some embodiments, more than one live and virtual anatomic landmark of the patient will be used, e.g. two, three or more.

In some embodiments of the invention, ultrasound or a radiofrequency transmitter can be used to pinpoint certain live anatomic landmarks. For example, an ultrasonic transmitter or a radiofrequency transmitter can be integrated into a point device, for example the tip of a pointing device. When the tip touches the desired live anatomic landmark, the transmitter can transmit and ultrasonic or RF signal which can be captured at a receiving site, optionally integrated into the OHMD. Optionally, for example as a means of increasing the accuracy of live data registration, multiple receiving sites can be used in spatially different locations. Virtual and live data can include an osteophyte or bone spur or other bony anatomy or deformity.

In some embodiments of the invention, the dimensions of the pointer have been previously scanned and registered with the OHMD. The image and/or video capture system attached to, integrated with or coupled to the OHMD can recognize the pointer in the live data and can identify the tip of the pointer. When the tip of the pointer touches the live landmark on the patient that corresponds to the landmark in the virtual data, the surgeon can, for example, click to indicate successful cross-referencing. The two data points can then optionally be fused or superimposed in a common coordinate system. Virtual and live data and data points can include or can be generated from an osteophyte or bone spur or other bony anatomy or deformity. Virtual and physical surgical instruments and implant components can also be registered in the common coordinate system.

Anatomic landmarks can include an unaltered surface shape, e.g. skin, facial features, e.g. the tip of the nose, a distance between both eyes, the location of an ear, the shape of the ear. Anatomic landmarks can also be bony landmarks, e.g. a medial or lateral malleolus, a tibial tuberosity, a medial or lateral epicondyle, a trochlear notch, a spinous process etc. Virtual and live data and virtual and live anatomic landmarks can include an osteophyte or bone spur or other bony anatomy or deformity.

Optionally, a live anatomic surface can be used for registration purposes. In this embodiment, the live anatomic surface can be derived, for example, using a light scanning, infrared scanning or ultrasound technique, or ultrasonic scanning technique during the surgery. The live surfaces of the patient that are detected and generated in this manner can be matched or aligned with virtual surfaces of the patient, for example obtained preoperatively using an imaging test such as x-ray imaging, ultrasound, CT or MRI or any other technique known in the art. Virtual and live data and anatomic surfaces can include an osteophyte or bone spur or other bony anatomy or deformity.

In some embodiments of the invention, the registration of virtual patient data and live patient data using the methods described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same methods described in the foregoing or any of the other registration methods described in the specification or any other registration method known in the art.

Registration of Virtual Patient Data and Live Patient Data Using Implantable or Attachable Markers or Calibration or Registration Phantoms or Devices Including Optical Markers In some embodiments of the invention, a surgeon is optionally using implantable or attachable markers to register virtual data of the patient with live data of the patient. This embodiment can, for example, be useful if the surgery is very extensive and results in the removal of tissue in the surgical site, as can be the case during brain surgery, e.g. removal of a brain tumor, liver surgery, e.g. removal of a liver tumor, joint replacement surgery and many other types of surgery. Virtual and live data can include an osteophyte or bone spur or other bony anatomy or deformity.

The terms implantable markers, attachable markers, skin markers, soft-tissue markers, calibration or registration phantoms or devices, and image capture markers as used throughout the application can include optical markers, e.g. optical markers with different geometric shapes or patterns, with QR codes, with bar codes, with alphanumeric codes. Implantable or attachable markers or calibration or registration phantoms or devices can be implanted prior to the actual surgery and can be included in pre-, intra- and/or postoperative imaging. Implantable or attachable markers or calibration or registration phantoms or devices can be implanted on or attached to osteophytes or bone spurs or other bony anatomy or deformity.

If the implantable or attachable markers or calibration or registration phantoms or devices are present in the virtual image data, the surgeon can optionally identify the implantable or attachable markers or calibration or registration phantoms or devices after an incision as he or she gains access to the target tissue and the implantable markers placed next to the target tissue or inside the target tissue. Such implantable or attachable markers or calibration or registration phantoms or devices can, for example, include radiation beets or metallic beets, for example also used for stereographic imaging or registration.

Alternatively, implantable or attachable markers or calibration or registration phantoms or devices can be placed during the surgery and, for example using image capture through the OHMD or attached to, integrated with or coupled to the OHMD, the location of the implantable or attachable markers or calibration or registration phantoms or devices can be determined. The location of the implantable or attachable markers or calibration or registration phantoms or devices on the patient in the live data of the patient can then be matched with the location of the anatomic structure to which the implantable or attachable markers or calibration or registration phantoms or devices is attached in the virtual data of the patient. For example, the anatomic structure in the virtual and live data can include an osteophyte or bone spur or other bony anatomy or deformity. In some embodiments, a pointer or pointing device can optionally be placed on the implantable or attachable markers or calibration or registration phantoms or devices followed by image capture through the OHMD or other image capture device attached to, integrated with or coupled to the OHMD and registration of the tip of the pointer. In this manner, the OHMD, the implantable or attachable markers or calibration or registration phantoms or devices including optical markers and, through the use of the implantable or attachable markers or calibration or registration phantoms or devices including optical markers, the anatomic structures, pathologic structures, instruments, implant components and any other objects to which one or more implantable or attachable markers or calibration or registration phantoms or devices including optical markers can be attached, as well as the virtual data of the patient can be registered in a common coordinate system. Virtual and physical surgical instruments and implant components can also be registered in the common coordinate system. Implantable or attachable markers or calibration or registration phantoms or devices can include rigid or fixed registration markers. Such rigid or fixed registration markers can be used to maintain registration as surgical field is being altered. A rigid or fixed registration marker can, for example, be a screw or a pin. Virtual and live data can include an osteophyte or bone spur or other bony anatomy or deformity. The rigid or fixed registration marker can be attached to the osteophyte or bone spur or other bony anatomy or deformity. In some embodiments, the medical device that is being implanted or a component thereof that has been, for example, already temporarily or permanently attached to the patient's tissue, e.g. an osteophyte or bone spur or bony anatomy or deformity, or the anatomic site or the surgical site can be used as an implantable or attachable marker or calibration or registration phantom or device during the surgery, for example while subsequent steps of the surgery are being completed. Such subsequent steps can, for example, include the implantation of additional components of the medical device. For example, in spinal fusion surgery, a first pedicle screw can be implanted. Live data and virtual data of the first pedicle screw can be registered. Subsequent pedicle screws or other components can be virtually displayed in the OHMD including their intended path, position, location or orientation, by maintaining registration between live and virtual data using the registered first pedicle screw. Any other rigid or fixed registration marker or implantable device can be used in this manner for different types of surgeries of the human body.

The one or more implantable or attachable markers or calibration or registration phantoms or devices can be attached to bone, cartilage, soft-tissues, organs or pathologic tissues such as osteophytes or bone spur or other bony anatomy or deformity. etc.

The one or more implantable or attachable markers or calibration or registration phantoms or devices can optionally include optical markers, retroreflective markers, infrared markers, or RF markers or any other marker device described in the art.

Optical markers are markers that reflect light within the visible spectrum, i.e. the portion of the electromagnetic spectrum that is visible to the human eye, with wavelengths from about 390 to 700 nm or a frequency band from about 430-770 THz. Optical markers can also reflect light that includes a mix of different wavelengths within the visible spectrum. The light reflected by the optical markers can be detected by an image and/or video capture system integrated into, attached to or separate from the OHMD. Optical markers can be detected with regard to their location, position, orientation, alignment and/or direction of movement with use of an image and/or video capture system integrated into, attached to or separate from the OHMD with associated image processing and, optionally, pattern recognition software and systems. Optical markers can include markers with select geometric patterns and/or geometric shapes that an image and/or video capture system, for example integrated into, attached to or separate from the OHMD, can recognize, for example using image processing and/or pattern recognition techniques. Optical markers can include markers with select alphabetic codes or patterns and/or numeric codes or patterns and/or alphanumeric codes or patterns or other codes or patterns, e.g. bar codes or QR codes, that an image and/or video capture system, for example integrated into, attached to or separate from the OHMD, can recognize, for example using image processing and/or pattern recognition techniques. QR codes or quick response codes include any current or future generation matrix code including barcode. Barcodes and QR codes are machine readable optical labels that can include information, for example, about the patient including patient identifiers, patient condition, type of surgery, about the surgical site, the spinal level operated if spine surgery is contemplated, the patient's side operated, one or more surgical instruments, one or more trial implants, one or more implant components, including type of implant used and/or implant size, type of polyethylene, type of acetabular liner (e.g. standard, lipped, offset, other) if hip replacement is contemplated. A QR code can use different standardized encoding modes, e.g. numeric, alphanumeric, byte/binary, and/or kanji to store data. Other encoding modes can be used. Any current and/or future version of QR codes can be used. QR codes using single or multi-color encoding can be used. Other graphical markers, such as the ones supported by the Vuforia (PTC, Needham, Mass.) augmented reality platform, can be used as well.

A bar code, QR code or other graphical marker can be the optical marker. A bar code, QR code or other graphical marker can be part of an optical marker or can be integrated into an optical marker. The same QR code or bar code or other graphical marker can contain
  information related to the patient and/or the surgical site, e.g. patient identifiers, age, sex, BMI, medical history, risk factors, allergies, site and side (left, right), spinal level to be operated
  information related to inventory management, e.g. of surgical instruments and/or implants or implant components, e.g. left vs. right component, selected component size (match against virtual surgical plan and/or templating and/or sizing)

and can be used to obtain information about the location position, orientation, alignment and/or direction of movement, if applicable, of the surgical site, surgically altered tissue, one or more surgical instruments and one or more trial implants and/or implant components.

Geometric patterns, geometric shapes, alphabetic, numeric, alphanumeric, and other codes or patterns including bar codes and QR codes included in or part of one or more optical markers can be predefined and, optionally, stored in database accessible by an image and/or video capture system and associated image processing software and pattern recognition software. Geometric patterns, geometric shapes, alphabetic, numeric, alphanumeric, and other codes or patterns including bar codes and QR codes included in or part of one or more optical markers can be in 2D and some of it in 3D. For example, one or more planar or 2D patterns can be used in select embodiments. Alternatively, select 3D geometric shapes can be used, e.g. cubes, cuboids, prisms, cones, cylinders, spheres. Any 3D shape can be used including irregular shapes and/or asymmetric shapes. The 3D geometric shape can include 2D geometric patterns and/or alphabetic, numeric, alphanumeric, and other codes or patterns including bar codes and QR codes on one or more surfaces. For example, if a cuboid is used, the same or different geometric patterns and/or alphabetic, numeric, alphanumeric, and other codes or patterns including bar codes and QR codes can be included in, affixed to or integrated into one or more of its surfaces or faces, e.g. two opposing surfaces or two adjacent surfaces oriented, for example, perpendicularly. 2D geometric patterns and/or alphabetic, numeric, alphanumeric, and other codes or patterns including bar codes and QR codes included in, affixed to or integrated into one or more surfaces or faces of a 3D geometric shape can be used to determine the orientation of select surfaces or faces of the geometric shape including the optical marker and, with that, the orientation and/or alignment of the surface or face and with that the geometric shape, for example in relationship to a surgical site, a surgical alteration, e.g. a cut bone surface or a reamed bone surface, a surgical instrument and/or one or more implant components including trial implants.

Geometric patterns and/or geometric shapes, alphabetic, numeric, alphanumeric, and other codes or patterns including bar codes and QR codes can be in color or black and white. Geometric patterns and/or geometric shapes and/or alphabetic, numeric, alphanumeric, and other codes or patterns including bar codes and QR codes can include portions that include color and black and white sections, portions that include only color and portions that are only black and white. Geometric shapes can include faces or surfaces that include color and black and white, faces or surfaces that include only black and white, and faces or surfaces that include only color. Different colors and different color codes can be used for different faces or surfaces of a geometric shape part of an optical marker. Different colors and different color codes can be used for different geometric patterns and/or geometric shapes and/or alphabetic, numeric, alphanumeric, and other codes or patterns including bar codes and QR codes. Different colors and different color codes can be used for different optical markers. Different colors, e.g. red, blue, green, orange, cyan etc., can be used for different geometric patterns and/or geometric shapes and/or alphabetic, numeric, alphanumeric, and other codes or patterns including bar codes and QR codes. Different colors, e.g. red, blue, green, orange, yellow, pink, cyan can be used for different optical markers. Different optical markers can optionally be associated with different surgical steps and/or different surgical instruments and/or different implant components; the use of a particular marker can be recognized by an image and/or video capture system integrated into, attached to or separate from the OHMD using standard image processing and/or pattern recognition software, including, optionally a database of patterns, e.g. with their associations with a particular surgical step and/or surgical instruments. As the image and/or video capture system recognizes a particular optical marker in the field of view, for example based on a particular geometric patterns and/or geometric shape and/or alphabetic, numeric, alphanumeric, and other codes or patterns including bar codes and QR codes used, it can then optionally display the corresponding surgical step and/or surgical instrument and/or implant component associated with that optical marker.

2D geometric patterns, alphabetic, numeric, alphanumeric, and other codes or patterns including bar codes and QR codes or combinations thereof, optionally with color and/or black and white coding, included in, affixed to or integrated into one or more surfaces or faces of a 3D geometric shape can be used to determine the orientation and/or alignment of select surfaces or faces of the geometric shape and, with that, the orientation and/or alignment of the geometric shape and/or the optical marker, for example in relationship to an anatomic landmark, a surgical site, a surgical alternation, e.g. a cut bone surface or a reamed bone surface, a surgical instrument and/or one or more implant components including trial implants. One or more 2D geometric patterns, alphabetic, numeric, alphanumeric, and other codes or patterns including bar codes and QR codes, optionally with color and/or black and white coding, included in, affixed to or integrated into an optical marker can be used to determine the orientation and/or alignment of the optical marker, which can, for example, be affixed to or integrated into an anatomic landmark, a surgical site, a surgical alternation, e.g. a cut bone surface or a reamed bone surface, a surgical instrument and/or one or more implant components including trial implants. Optical markers can be affixed to an anatomic landmark, a surgical site, a surgical alteration, e.g. a cut bone surface or a reamed bone surface, or a drill hole of the patient and the corresponding anatomic landmark, surgical site, or surgical alternation can be identified in the virtual data of patient thereby enabling registration of the virtual data and the live data of the patient in the same coordinate system. Optical markers can also be attached to an OHMD including multiple OHMDs if multiple OHMDs are used during a surgery. Optionally, optical markers, e.g. with QR codes, can be used to differentiate a first from a second, third, fourth and/or more OHMDs. One or more optical markers can optionally be attached to the operating room table and they can be registered in a coordinate system, for example the same coordinate system in which the one or more OHMDs, the patient, and portions of the surgical site can be registered. One or more optical markers can optionally be attached to other structures in the operating room including fixed structures, e.g. walls, and movable structures, e.g. OR lights, and they can be registered in a coordinate system, for example the same coordinate system in which the one or more OHMDs, the patient, and portions of the surgical site can be registered. In this example, optical markers can also be mounted to fixed structures on holding arms or extenders, optionally moveable and, for example, of known dimensions, orientations, lengths and angles.

Optical markers attached to fixed structures such as OR walls can be used to enhance the accuracy of room recognition and spatial mapping, in particular when the coordinates and/or the angles and/or distances between different optical markers are known. Optical markers attached to fixed structures such as OR walls can also be used to enhance the determination of the location and pose and change in location or pose or the coordinates and change in coordinates of one or more optical head mounted displays, which can assist with increasing the accuracy of the display of virtual data and their superimposition on corresponding live data. Optical markers attached to movable structures can be used to track their location in the operating room. Optical markers attached to OR lights can be used to estimate the direction of light and the orientation and/or trajectory of shadows in the OR or a room. If the orientation and/or trajectory of shadows in the OR or the room is known, virtual shadowing or shading with the same or similar orientation or trajectory can be applied to virtual data display by the OHMD.

For example, one or more optical markers including one or more geometric shapes, geometric patterns, alphabetic, numeric, alphanumeric, and other codes or patterns including bar codes and QR codes or combinations thereof can be attached to a medial femoral epicondyle, for example using a pin or a screw or an adhesive. An image and/or video capture system integrated into, attached to or separate from the OHMD can be used to monitor the position, and/or orientation and/or alignment and/or direction of movement of the optical marker in relationship to the image and/or video capture system; as the distal femur moves, the image and/or video capture system can detect the marker, for example based on its pre-programmed geometric shape, geometric pattern, alphabetic, numeric, alphanumeric, and other codes or patterns including bar codes and QR codes, and can monitor and, optionally, record the movement. If a second optical marker, including one or more geometric shapes, geometric patterns, alphabetic, numeric, alphanumeric, and other codes or patterns including bar codes and QR codes or combinations thereof is attached to the lateral femoral condyle in the same example, the image and/or video capture system can also monitor and, optionally record the position, and/or orientation and/or alignment and/or direction of movement of the second optical marker in relationship to the image and/or video capture system; by monitoring the position, and/or orientation and/or alignment and/or direction of movement of the first optical marker on the medial femoral epicondyle and the position, and/or orientation and/or alignment and/or direction of movement of the second optical marker on the lateral femoral epicondyle, the image and/or video capture system and related image processing and pattern recognition software can also monitor and, optionally, record the movement of the femoral epicondylar axis, for example during flexion and extension of the knee. One or more optical markers including one or more geometric shapes, geometric patterns, alphabetic, numeric, alphanumeric, and other codes or patterns including bar codes and QR codes or combinations thereof can be attached to a proximal tibia, e.g. an anterior tibial rim, a medial and/or lateral tibial spine, a lowest point of a medial plateau and/or a highest point of a lateral tibial plateau, for example in the same example. The image and/or video capture system integrated into, attached to or separate from the OHMD can be used to monitor the position, and/or orientation and/or alignment and/or direction of movement of the optical marker(s) attached to the tibia in relationship to the image and/or video capture system and in relationship to one or more femoral optical markers, thereby monitoring and, optionally recording, tibiofemoral motion, e.g. during a surgery. One or more optical markers including one or more geometric shapes, geometric patterns, alphabetic, numeric, alphanumeric, and other codes or patterns including bar codes and QR codes or combinations thereof can be attached to a patella, e.g. a most superior aspect, a most inferior aspect, a most lateral aspect and/or a most medial aspect, for example in the same example. The image and/or video capture system integrated into, attached to or separate from the OHMD can be used to monitor the position, and/or orientation and/or alignment and/or direction of movement of the optical marker(s) attached to the patella in relationship to the image and/or video capture system and in relationship to one or more femoral optical markers, thereby monitoring and, optionally recording, patellofemoral motion, e.g. during a surgery. The image and/or video capture system integrated into, attached to or separate from the OHMD can be used to monitor the position, and/or orientation and/or alignment and/or direction of movement of the optical marker(s) attached to the patella in relationship to the one or more tibial optical markers, thereby monitoring and, optionally recording, patellar motion in relationship to the tibia, e.g. during tibial adduction or abduction.

In some embodiments of the invention, an optical marker, for example with one or more specific geometric shapes, geometric patterns, alphabetic, numeric, alphanumeric, and other codes or patterns including bar codes and QR codes or combinations thereof, can be assigned to a virtual surgical step. The marker can, for example, include written text defining the surgical step or corresponding to the surgical step, which can be the immediately preceding surgical step or the next surgical step, for example in a virtual surgical plan. In some embodiments, the text can be a number, for example a number corresponding to a particular surgical step, e.g. 1—for distal femoral cut, 2—for anterior femoral cut, 3—for posterior femoral cut, 4—for first chamfer cut, 5—for second chamfer cut. The number can be recognized by the image and/or video capture system, which can then display the virtual view for the corresponding surgical step, e.g. for 1—a cut plane for the distal femoral cut or a virtual outline of the corresponding physical distal femoral cut block. A combination of numbers and text can be used and the image and/or video capture system and associated software and optional pattern recognition software and systems can recognize the numbers and text and trigger a command to display the corresponding virtual view of the corresponding virtual surgical step, e.g. 1F—distal femoral cut, 2F—anterior femoral cut, 1T—proximal tibial cut, 2T—tibial keel punch etc.

In another example, an optical marker with one or more specific geometric shapes, geometric patterns, alphabetic, numeric, alphanumeric, and other codes or patterns including bar codes and QR codes or combinations thereof can be assigned to the step "distal femoral cut" in a virtual surgical plan for a total knee replacement in a patient; the optical marker can include the text "distal femoral cut". The surgeon can, for example, affix the marker to the cut bone surface of the distal femur or somewhere adjacent to it. An image and/or video capture system integrated into, attached to or separate from an OHMD can detect the optical marker with the one or more specific geometric patterns and/or specific geometric shapes assigned to "distal femoral cut", indicating that the distal femoral cut has been completed; the image capture signal can then initiate a command to the OHMD to display the next surgical step, e.g. an anterior cut plane or an outline of an anterior cut block or cut guide, as the surgeon prepares to perform the next cut, e.g. the anterior femoral cut in this example.

In some embodiments, an optical marker, for example with one or more specific geometric shapes, geometric patterns, alphabetic, numeric, alphanumeric, and other codes or patterns including bar codes and QR codes or combinations thereof, can be integrated into, included in, or attached to a surgical instrument used for a surgical step in a virtual surgical plan. For example, the optical marker can be included in, integrated into or attached to a surgical cut block or cutting tool, e.g. for a proximal tibial cut. Optionally, the marker can include written text defining the surgical step or corresponding to the surgical step, e.g. in a virtual surgical plan. In the immediately foregoing example, an optical marker with one or more specific geometric shapes, geometric patterns, alphabetic, numeric, alphanumeric, and other codes or patterns including bar codes and QR codes or combinations thereof can be assigned to the step "proximal tibial cut" in a virtual surgical plan for a total knee replacement in a patient; the optical marker can include the text "proximal tibial cut" which the surgeon can read and ensure that the correct marker is used for the next surgical step that he or she is contemplating, in this example a proximal tibial cut.

As the optical marker enters the surgeon's field of view, an image and/or video capture system integrated into or attached to the OHMD on the surgeon's head can detect the optical marker and display the next virtual surgical step, e.g. an outline of a virtual proximal tibial cut block corresponding to the physical proximal tibial cut block, so that the surgeon can align or superimpose the physical surgical cut block or instrument onto the outline of the virtual surgical cut block or instrument. Alternatively, as the optical marker enters the surgeon's field of view, an image and/or video capture system integrated into or attached to the OHMD on the surgeon's head can detect the optical marker and display the next virtual surgical step, e.g. a virtual cut plane with a predetermined resection level, varus or valgus angle and/or slope, so that the surgeon can align or superimpose the physical surgical cut block and/or the physical surgical saw with the virtual cut plane. Once the surgical step is completed, e.g. a proximal tibial cut, and the surgeon removes the physical surgical instrument with the integrated, included or attached optical markers from the surgical field and/or the field of view of the image and/or video capture system, the image and/or video capture system can detect that the optical marker is not present in the field of view anymore and software can generate a command to turn off the display of OHMD or the display of the completed virtual surgical step. Optionally, a command can be generated at this time, optionally automatically, to display the next surgical step, e.g. a tibial keel punch including, for example, setting tibial rotation. Alternatively, the display of the OHMD unit can display the next surgical step as the next surgical instrument with the corresponding optical marker for the next surgical step enters the field of view, e.g. in the surgeon's hand.

In a similar example, an optical marker can be attached to an acetabular reamer used for hip replacement. An image and/or video capture system integrated into or attached to an OHMD can detect the optical marker as it enters the surgeon's field of view triggering a command to display the reaming axis or a virtual display of the reamer with the intended alignment and/or direction for the reaming step; as the optical marker with the surgical instruments exits the surgeon's field of view, the image and/or video capture system can detect it triggering a command to stop the display of the reaming axis or virtual display of the reamer, optionally switching to the next surgical step.

In some embodiments, one or more optical markers can be included in, integrated into or attached to an insert for a cutting block or guide. The insert can be configured to fit into one or more slots or guides within the cutting block or guide for guiding a saw blade. Representative cutting blocks or guides are, for example, cutting blocks or guides used in knee replacement, shoulder replacement, hip replacement, and ankle replacement. These cutting blocks or guides are, for example, used to remove bone at the articular surface to fit the patient's bone to the bone facing side of an implant or implant component. The insert can be designed to partially or substantially fill the entire slot or guide, e.g. in x and y direction or x and z direction or y and z direction depending on the shape and/or design of the cutting block or guide. If the insert partially fills or substantially fills the slot or guide in x and y direction, the insert can be configured to extend beyond the slot or guide in z direction. If the insert partially fills or substantially fills the slot or guide in x and z direction, the insert can be configured to extend beyond the slot or guide in y direction. If the insert partially fills or substantially fills the slot or guide in y and z direction, the insert can be configured to extend beyond the slot or guide in x direction. Any direction is possible including oblique directions, orthogonal directions and non-orthogonal directions depending on the configuration of the cutting block or guide and the associated slots or guides. Oblique slots can, for example, be used for chamfer cuts in total knee replacement or oblique talar cuts in total ankle replacement.

The portion(s) of the insert that extend beyond the slot or guide can, for example, include one or more integrated or attached optical markers. If more than one optical marker are used, the optical markers can be arranged at predefined angles and locations, e.g. 90 degrees or less than 90 degrees or more than 90 degrees. The insert can have similar dimensions to a representative saw blade used with the cutting block or guide. The insert can indicate the position, location, orientation, alignment and direction of travel for a saw blade that will subsequently be inserted. The surgeon can place the insert inside the slot or guide of the physical cutting block or guide and align the insert, for example, with a virtual cut plane or a virtual outline of the insert or cutting block or guide projected by the OHMD onto the surgical site, e.g. a distal femur in total knee replacement or a proximal femur in total hip replacement. Once the insert is substantially aligned and/or superimposed with the virtual cut plane, the virtual outline of the insert or cutting block or guide, the surgeon can pin the physical cutting block or guide onto the bone, thereby affixing the cutting block or guide to the bone in a position where the virtual surgical plan, e.g. the virtual cut plane or virtual outline of the insert or cutting block or guide is substantially aligned with the physical cut plane and or the physical insert or cutting block or guide. The surgeon can then insert the physical saw blade and perform the physical cut. The insert can be configured to have a shape substantially similar to the physical saw blade, serving as a dummy saw blade.

Alternatively, the surgeon can place the physical saw blade inside the slot or guide of the physical cutting block or guide and the surgeon can align the physical saw blade, for example, with a virtual cut plane or a virtual outline of the saw blade or cutting block or guide projected by the OHMD onto the surgical site, e.g. a distal femur in total knee replacement or a proximal femur in total hip replacement. Once the physical saw blade is substantially aligned and/or superimposed with the virtual cut plane, the virtual outline of the saw blade or cutting block or guide, the surgeon can pin the physical cutting block or guide onto the bone, thereby affixing the cutting block or guide to the bone in a position where the virtual surgical plan, e.g. the virtual cut plane or virtual outline of the saw blade or cutting block or guide is substantially aligned with the physical cut plane and or the physical saw blade or cutting block or guide. The surgeon can then advance the physical saw blade and perform the physical cut.

Optical markers can be included in, integrated into or attached to the cutting block or guide or the insert, e.g. a dummy saw blade. Optical markers can also be attached or affixed the saw blade. The optical markers can include a text or alphanumeric code for the surgeon that designates, for example, a specific surgical step, e.g. 1F—distal femoral cut, 2F—anterior femoral cut, 1T—proximal tibial cut, 2T—tibial keel punch etc. The optical markers can also include one or more specific geometric shapes, geometric patterns, alphabetic, numeric, alphanumeric, and other codes or patterns including bar codes and QR codes or combinations thereof. The one or more specific geometric shapes, geometric patterns, alphabetic, numeric, alphanumeric, and other codes or patterns including bar codes and QR codes or combinations thereof can be specific for the surgical step, corresponding, for example, to the lettering or alphanumeric code that indicates the surgical step to the surgeon. An image and/or video capture system integrated into, attached to or separate from the OHMD can detect the one or more specific geometric shapes, geometric patterns, alphabetic, numeric, alphanumeric, and other codes or patterns including bar codes and QR codes or combinations thereof as the optical marker(s) enters the field of view; the specific geometric shapes, geometric patterns, alphabetic, numeric, alphanumeric, and other codes or patterns can be recognized using image processing and/or pattern recognition software triggering, for example, a command to display corresponding virtual surgical step in the OHMD superimposed onto the surgical field with the view angle for the surgeon aligned with the surgical field or target anatomy or bone cut. When the cutting block or guide, the insert, e.g. a dummy saw blade, or the physical saw blade with the optical marker is removed, the image and/or video capture system can detect that the optical marker is not present in the field of view any longer, triggering, for example a command to turn off the OHMD display or the display of the completed surgical step or to switch to the display of the next surgical step and corresponding virtual display.

In some embodiments of the invention, one or more optical markers, e.g. at select angles, e.g. 90 degrees or less or more or parallel or on one axis, can be included in, integrated into or attached to a cutting block or guide.

In some embodiments, one or more optical markers can be used in conjunction with a spinal surgery, e.g. a vertebroplasty, a kyphoplasty, a posterior spinal fusion, an anterior spinal fusion, a lateral spinal fusion and/or a disk replacement. For example one or more optical markers can be included in, integrated into, or attached to a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps and the like. The foregoing list is only exemplary and not to be construed limiting of the invention. The one or more optical markers can be used to designate the patient's left side and the patient's right side and/or they can be used to designate the patient's spinal level, using, for example, one or more geometric shapes, geometric patterns, alphabetic, numeric, alphanumeric, and other codes or patterns that can be detected with an image and/or video capture system integrated into, attached to or separate from the OHMD and that can be recognized using image processing and/or pattern recognition.

One or more optical markers can be used to determine the position, location, orientation, alignment and/or direction of a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach, an impactor, a cutting or drilling block, and/or other surgical instrument and/or trial implant and/or implant component with use of an image and/or video capture system integrated into, attached to or separate from the OHMD. For example, after the initial registration or any subsequent registration of the patient, the surgical site, the OHMD, optionally an image and/or video capture system integrated into, attached to or separate from the OHMD, the virtual data and/or the live data of the patient have been performed, the image and/or video capture system can detect an optical marker included in, integrated into, and/or attached to the surgical instrument. Since the location, position, alignment and/or orientation of the optical marker on the surgical instrument are known and the dimensions, e.g. at least one of them, or geometry of the surgical instrument are known, the image and/or video capture system can track the optical marker and the surgical instrument with regard to its location, position, orientation, alignment and/or direction of movement.

In another example, two or more optical markers can be integrated into or attached to different, optionally defined locations along the long axis of a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach, an impactor, a cutting or drilling block, and/or other surgical instrument and/or trial implant and/or implant component, for example instruments or trial implants or implant components in knee replacement or hip replacement. An image and/or video capture system can detect the two or more optical markers and their respective location can be determined. With the location of the two or more optical markers captured and defined by the image and/or video capture system, the long axis of the needle, pin, awl, probe, tap, mill, saw, reamer, broach, impactor, and/or other surgical instrument and/or trial implant and/or implant component can be determined; other axes can be determined in addition to the long axis or instead of the long axis. With the location of the optical markers on the needle, pin, awl, probe, tap, mill, saw, reamer, broach, impactor, and/or other surgical instrument and/or trial implant and/or implant component known, the long axis or other axis of the needle, pin, awl, probe, tap, mill, saw, reamer, broach, impactor, and/or other surgical instrument and/or trial implant and/or implant component known and the dimensions of the needle, pin, awl, probe, tap, mill, saw, reamer, broach, impactor, and/or other surgical instrument and/or trial implant and/or implant component known, any portions of the needle, pin, awl, probe, tap, mill, saw, reamer, broach, impactor, and/or other surgical instrument and/or trial implant and/or implant component hidden by the tissue, e.g. below the skin and/or inside or within muscle, can be estimated and can optionally be displayed by the OHMD in addition to the virtual or intended path or projected path or any other aspects of a virtual surgical plan. Rather than using two or more optical markers in the foregoing embodiment, an optical marker long enough or wide enough or deep enough to define one or more axes of a needle, pin, awl, probe, tap, mill, saw, reamer, broach, impactor, and/or other surgical instrument and/or trial implant and/or implant component can also be used.

Optionally, when two or more optical markers are used included in, integrated into or attached to a surgical instrument, the optical markers, can be arranged at the same angles, e.g. parallel or on the same axis, or at different angles, e.g. orthogonal angles or non-orthogonal angles. This can be particularly useful, when the optical markers include one or more of a geometric shape, geometric pattern, alphabetic, numeric, alphanumeric, and other codes or patterns including bar codes and QR codes or combinations thereof. By arranging the optical markers and any associated geometric shapes, geometric patterns, alphabetic, numeric, alphanumeric, and other codes or patterns including bar codes and QR codes or combinations thereof in this manner, the angular orientation of the surgical instrument can be determined in a more accurate manner. For example, at certain view angles from an image and/or video capture system integrated into or attached to an OHMD select geometric shapes, geometric patterns, alphabetic, numeric, alphanumeric, and other codes or patterns including bar codes and QR codes or combinations thereof of a first optical marker on a surgical instrument may be only partially visualized or not visualized at all due to the angular orientation; when a second optical marker is oriented at a different angle, location and/or orientation on the same surgical instrument, the view angle from the image and/or video capture system integrated into or attached to the OHMD to the second optical marker can allow for a complete or a more complete visualization of the one or more geometric shapes, geometric patterns, alphabetic, numeric, alphanumeric, and other codes or patterns including bar codes and QR codes or combinations thereof, thereby allowing a more accurate determination of the angular orientation of the second optical marker and, with that, the surgical instrument. In addition, the respective projections of the first optical marker and/or the second optical marker measured by the image and/or video capture system, optionally paired with any parallax information when two or more cameras are used, e.g. one positioned near the left eye and another positioned near the right eye, can be used to more accurately determine their relative position and the position of the surgical instrument.

An image and/or video capture system integrated into or attached to or separate from an OHMD can detect an optical marker included in, integrated into or attached to a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach an impactor, a cutting or drilling block, and/or other surgical instrument and/or trial implant and/or implant component as it enters the surgeon's field of view triggering a command to display the predetermined path or plane or a virtual display of the a needle, a pin, an awl, a feeler probe, a ball handle probe, a straight probe, a curved probe, a tap, a ratchet, a screw driver, a rod template, a rod inserter, a rod gripper, a bender, a plug starter, a compressor, a distractor, a break off driver, an obturator, a counter torque, a quick connector, a driver, a retractor, a retracting frame, an implant positioner, a caliper, a plate holder, a plate bender, a forceps, a mill, a saw, a reamer, a broach, an impactor, a cutting or drilling block, and/or other surgical instrument and/or trial implant and/or implant component or other display mode or type of the virtual surgical plan, for example with the intended position, location and/or alignment and/or direction for the intended surgical step; as the optical marker with the surgical instrument exits the surgeon's field of view, the image and/or video capture system can detect it triggering a command to stop the display of the predetermined path or the virtual display of the surgical instrument or other aspects of the virtual surgical plan, optionally switching to the next surgical step and corresponding virtual display. In a spinal procedure as well as select other procedures, the next surgical step can involve the same side of the patient or the opposite side of the patient at the same spinal level, where the corresponding virtual display for the next surgical step for a given level and side can be initiated by the OHMD display. The next surgical step can involve the same side of the patient or the opposite side of the patient at an adjoining or different spinal level, where the corresponding virtual display for the next surgical step for a given level and side can be initiated by the OHMD display.

Optical markers can include one or more QR codes. QR codes can be part of or can be embedded in a geometric pattern or geometric shape included in an optical marker. Optical markers can be a QR code.

If an optical marker is attached to a surgical instrument, the attachment can occur in a defined location and/or position and/or alignment, for example at an end of the surgical instrument. The attachment can include, for example, an opening with a stop thereby defining the location and/or position and/or alignment of the optical marker on the surgical instrument. For example, the optical marker can have an opening with a stop that is large enough to accommodate the surgeon facing end of a pin or drill, for example inserted into a spinous process or a facet joint or a portion of a pedicle. With this type of attachment and other attachments that secure the marker in a defined location, position and/or orientation on the surgical instrument, an image and/or video capture system can detect the optical marker and its location, position and/or orientation can be used to determine the location, position, and/or orientation of the surgical instrument, e.g. a pin, including its tip or frontal portion inside the patient due to their defined spatial relationship and due to the known geometry of the surgical instrument.

In some embodiments of the invention, an optical marker can be used to determine or identify the position, location, orientation, alignment, dimensions, axis or axes, plane or planes of a surgical alteration. For example, if a bone cut has been performed in a surgical step, one or more optical markers can be attached to the cut bone to determine one or more of its position, location, orientation, alignment, dimensions, shape, geometry, axis or axes, plane or planes. For example, one, two or more optical markers can be placed near or attached to the periphery or the edge of the cut bone or surgical alteration; an image and/or video capture system integrated into, attached to or separate from the OHMD can detect the location, position, and/or orientation of the optical markers and software can be used, for example, to analyze the location, position, and/or orientation information of the optical markers to derive information on the periphery and/or edge and/or shape of the cut bone or surgical alteration. One, two or more optical markers can be placed near or attached to the cut bone or surgical alteration; an image and/or video capture system integrated into, attached to or separate from the OHMD can detect the location, position, and/or orientation of the optical markers and software can be used, for example, to analyze the location, position, and/or orientation information of the optical markers to derive information on the shape or geometry of the cut bone or surgical alteration. If the bone cut is planar, one or more optical markers with a planar bone facing surface or one or more optical markers attached to a carrier or instrument, e.g. a plastic piece, with a planar bone facing surface can be held against, affixed to or attached to the cut bone surface; an image and/or video capture system integrated into, attached to or separate from an OHMD can then be used to detect the one or more optical markers and software can be used, for example, to analyze the location, position and/or orientation information of the one or more optical markers to derive information on the location and/or position and/or orientation and/or alignment of the plane of the bone cut, including for example in relationship to other anatomic landmarks and/or other optical markers. The carrier or instrument for the optical marker can be transparent or semi-transparent so that the surgeon can check or confirm that the carrier or instrument and the attached optical marker(s) are flush against the bone cut prior to determining or confirming, for example, the plane of the bone cut. Once the plane of the bone cut has been determined or confirmed in this manner, the optical marker(s) attached to the cut bone and/or the determined plane of the bone cut can be used to plan the next surgical alteration, e.g. the next bone cut or surgical alteration, e.g. an anterior or posterior femoral cut after the distal femoral cut in knee replacement, or a chamfer cut after the anterior and posterior femoral cuts in knee replacement, or a cut on an opposing articular surface. By determining, confirming and/or referencing a preceding surgical alteration, e.g. a bone cut, in this manner, the accuracy of subsequent surgical steps can be improved thereby ultimately improving the overall accuracy of the surgical procedure.

In some embodiments of the invention, one or more optical markers can be attached to or affixed to a patient's thigh or distal femur. The one or more optical markers can, for example, be attached to the skin of the distal thigh, e.g. above the knee joint space. The attachment can be performed using, for example, an adhesive that attaches the one or more optical markers to the patient's skin. The one or more optical markers can optionally be sterile. The one or more optical markers can optionally be magnetic. In this example, a magnetic base can optionally be attached to the patient's skin, for example using an adhesive. A surgical drape which can be transparent, semi-transparent or not transparent can then be placed over the magnetic base and the magnetic optical marker can then be attached to the magnetic base attached to the patient's skin. Alternatively, once a skin incision is made, one or more optical markers can be rigidly attached to one or more bones, e.g. the distal femur and/or the proximal tibia. The rigid attachment can be done using pins or screws or other attachment mechanisms.

An image and/or video capture system integrated into, attached to or separate from the OHMD can register the location and/or position and/or orientation and/or alignment of the one or more optical markers, for example while the leg is in neutral position and/or extension and/or any other position, including arbitrary positions or positions chosen by the surgeon and/or operator. The surgeon and/or operator can then move the leg and thigh into multiple different positions and/or orientations and/or alignments and/or the surgeon and/or operator can move the leg and thigh in circular fashion or semicircular fashion. An image and/or video capture system integrated into, attached to or separate from the OHMD can register the location and/or position and/or orientation and/or alignment of the one or more optical markers for these multiple different positions and/or orientations and/or alignments of the leg or thigh and/or during the different circular or semicircular movements. The resultant information can be used to determine the center of rotation, which, in this example, can be the center of the hip joint.

In some embodiments, an ankle clamp can be applied to the ankle of the patient's leg. The ankle clamp can include one or more optical markers including, for example, one or more QR codes. The ankle clamp and/or the optical markers can be disposable. The ankle clamp and the integrated or attached optical markers can be used to determine the position of the medial and lateral malleolus and with that, for example, the center or ⅓ or ⅔ distance points between the malleoli of the ankle joint using an image and/or video capture system integrated into, attached to or separate from the OHMD. Alternatively, one or more optical markers can be applied to medial and/or lateral malleolus. In some embodiments of the invention, a magnetic base can be affixed to the medial and lateral malleolus. The ankle can then be prepped and draped in sterile technique and one or more sterile, magnetic optical markers can be applied over the drape or surgical cover affixing the one or more optical markers to the magnetic base with the interposed drape or surgical cover. An image and/or video capture system integrated into, attached to or separate from the OHMD can then be used to identify the optical markers over the medial and lateral malleolus and the center, ⅓ or ⅔ distance points of the ankle joint.

With the center of the hip joint determined using the one or more optical markers on the thigh or distal femur and the center or ⅓ or ⅔ distance points of the ankle joint determined using the ankle clamp and/or one or more optical markers, the system can derive the patient's mechanical axis and any surgical interventions, e.g. correction of varus or valgus deformity with corresponding femoral and/or tibial and/or talar bone cuts can be planned and subsequently projected using the OHMD.

In some embodiments of the invention, one or more optical markers can be attached to or affixed to a patient's arm. The one or more optical markers can, for example, be attached to the skin of the upper arm thigh, e.g. above the elbow. The attachment can be performed using, for example, an adhesive that attaches the one or more optical markers to the patient's skin. The one or more optical markers can optionally be sterile. The one or more optical markers can optionally be magnetic. In this example, a magnetic base can optionally be attached to the patient's skin, for example using an adhesive. A surgical drape which can be transparent, semi-transparent or not transparent can then be placed over the magnetic base and the magnetic optical marker can then be attached to the magnetic base attached to the patient's skin. Alternatively, once a skin incision is made, one or more optical markers can be rigidly attached to one or more bones, e.g. the proximal humerus. The rigid attachment can be done using pins or screws or other attachment mechanisms.

An image and/or video capture system integrated into, attached to or separate from the OHMD can register the location and/or position and/or orientation and/or alignment of the one or more optical markers, for example while the arm is in neutral position and/or extension and/or abduction and/or any other position, including arbitrary positions or positions chosen by the surgeon and/or operator. The surgeon and/or operator can then move the arm into multiple different positions and/or orientations and/or alignments and/or the surgeon and/or operator can move the arm in circular fashion or semicircular fashion. An image and/or video capture system integrated into, attached to or separate from the OHMD can register the location and/or position and/or orientation and/or alignment of the one or more optical markers for these multiple different positions and/or orientations and/or alignments of the arm and/or during the different circular or semicircular movements. The resultant information can be used to determine the center of rotation, which, in this example, can be the center of rotation of the shoulder joint.

In some embodiments of the invention, one or more optical markers can be attached to an operating room (OR) table. If the optical marker is parallel to the OR table, a single marker can be sufficient to determine the principal plane of the OR table, e.g. the horizontal plane, which can be the plane on which the patient is resting, for example in supine, prone, lateral or oblique or other positions known in the art. This can be aided by using optical markers that include a surface or plane that is parallel or perpendicular or at a defined angle to the OR table and that is large enough to be detected by the camera, image or video capture system integrated into, attached to or separate from the OHMD. For example, such a plane of the optical marker can measure 1×1 cm, 2×2 cm, 2×3 cm, 4×4 cm, 4×6 cm and so forth. Alternatively, multiple, e.g. two, three or more, optical markers can be used to determine a plane through the markers corresponding to the principal plane of the OR table or a plane parallel to the principal plane of the OR table or, for example, a plane vertical to the OR table or, for example, a plane at a defined angle to the OR table. If the OR table is hidden by surgical drapes, one or more magnetic or otherwise attachable bases can be attached to the OR table prior to placing the drapes. After the drapes have been placed, one or more magnetic or otherwise attachable optical markers can be affixed to the magnetic bases or attachment mechanisms with the interposed surgical drapes. Alternatively, one or more holding arms or extenders of known geometry can be attached to the OR table and one or more optical markers can be attached to or can be integrated into the holding arms or extenders. An image and/or video capture system integrated into, attached to or separate from the OHMD can then identify the location, position, orientation and/or alignment of the one or more optical markers. The resultant information can be used to determine the principal plane of the OR table on which the patient is lying. One or more OHMDs can be referenced using, for example, an image and/or video capture system integrated into or attached to the OHMD relative to the OR table and/or the attached optical markers. Once the principal plane of the OR table is determined in the system, virtual surgical steps can be planned in the virtual surgical plan of the patient in relationship to the principal plane of the OR table. For example, one or more bone cuts can be planned and/or performed perpendicular to the principal plane of the OR table, for example with the patient in supine or prone position or any other desired position. One or more bone cuts can be planned and/or performed at defined angles other than 90 degrees relative to the horizontal plane of the OR table, for example with the patient in supine or prone position or any other desired position. One or more bone cuts can be planned and/or performed at a non-orthogonal plane or orientation relative to the principal plane or horizontal plane of the OR table, for example with the patient in supine or prone position or any other desired position, optionally referencing a plane vertical to the OR table, displayed by the OHMD. The principal plane of the OR table can be used as a reference in this manner including for comparing or referencing virtual data of the patient and live data of the patient and including for comparing or referencing a virtual surgical plan. Such bone cuts at orthogonal angles or non-orthogonal angles, e.g. relative to the OR table or relative to anatomy, anatomic landmarks, anatomic or biomechanical axes of the patient, can be executed using one or more virtual surgical guides or cut blocks and/or one or more physical surgical guides or cut blocks. Virtual surgical guides or cut blocks can include one or more dimensions corresponding to physical surgical guides or cut blocks.

One or more optical markers attached to or referencing the OR table can also serve as a fixed reference for the one or more OHMDs during a surgical procedure. This can be useful, for example, when the patient and/or the extremity and/or the surgical site moves during the procedure. A fixed reference to the OR table can aid in maintaining registration of the one or more OHMDs and the virtual surgical plan and the live data of the patient and/or OR.

In some embodiments of the invention, one or more optical markers can be placed on or attached to the patient in the area of the surgical field and/or in an area away from the surgical field. An image and/or video capture system integrated into, attached to or separate from the OHMD can be used to identify the one or more optical markers and to determine their location, position, orientation and/or alignment. The image and/or video capture system can also, optionally, determine the location, position, orientation and/or alignment of one or more optical markers attached to or referencing the OR table. The system can reference the coordinates and/or the spatial relationship of the one or more optical markers attached to the patient in the area of the surgical field and/or in an area away from the surgical field and the one or more optical markers attached to or referencing the OR table. In this manner, if the patient's body moves during the procedure, e.g. during a broaching of a proximal femur or an acetabular reaming during hip replacement, or a femoral or tibial component impacting during knee replacement, or during a pinning or cutting of a bone, or during a placement of a spinal device, e.g. a cage or a pedicle screw, the movement between the one or more optical markers attached to the patient in the area of the surgical field and/or in an area away from the surgical field and the one or more optical markers attached to or referencing the OR table and the change in coordinates of the one or more optical markers attached to the patient in the area of the surgical field and/or in an area away from the surgical field can be detected and the amount of movement, direction of movement and magnitude of movement can be determined; the resultant information can, for example, be used to update or adjust or modify a virtual surgical plan or to update or adjust or modify the display of the virtual surgical plan or virtual surgical steps or virtual displays for the movement of the patient, including for example by updating, moving or adjusting one or more aspects or components of the virtual surgical plan including one or more of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration using the new patient coordinates or the new coordinates of the surgical field.

In some embodiments of the invention, portions of the optical marker or the entire optical marker can be radiopaque, so that the optical marker can also be visible on a radiograph or other imaging studies that utilize ionizing radiation including, for example, fluoroscopy, digital tomosynthesis, cone beam CT, and/or computed tomography. Different levels or degrees of radiopacity can be present in different portions or areas of the optical marker. Different levels or degrees of radiopacity can be utilized to encode information. For example, different levels of radiopacity can be used to encode information also contained, for example, in an optically readable alphanumeric code, bar code or QR. The different levels of radiopacity can optionally be arranged in a bar like thickness distribution, which can optionally mirror portions or all of the information contained in a bar code. The different levels of radiopacity can optionally be arranged in a point or square like thickness distribution, which can optionally mirror portions of the information contained in a QR code. Different radiopacity can be obtained by varying the thickness of the metal, e.g. lead. Radiopaque optical markers with information encoded in such manner can, for example, be manufactured using 3D metal printers. They can also be CNC machined, e.g. from bar stock or cast blanks.

The radiopaque portions of the optical marker can include information on laterality, e.g. L for left and R for right, visible on the radiograph, for example through different material thicknesses, e.g. lead; the same information can be included in an attached alphanumeric code or text, bar code or QR code which can be read by a bar code or QR code reader or an image and/or video capture system integrated into, attached to or separate from the OHMD. The radiopaque portions of the optical marker can include information on anatomical site, e.g. L5 or L4, T1 or T2, C3 or C7, knee, hip, visible on the radiograph, for example through different material thicknesses, e.g. lead; the same information can be included in an attached alphanumeric code or text, bar code or QR code which can be read by a bar code or QR code reader or an image and/or video capture system integrated into, attached to or separate from the OHMD. Image processing techniques and/or software can be applied to the radiographic information including the optical marker and radiographically encoded information such as laterality and/or site and the information included in the radiograph can be compared against the information included on the optical scan. If any discrepancies are detected, an alert can be triggered, which can, for example, be displayed in the OHMD.

Multiple partially or completely radiopaque optical markers can be used. The radiopaque optical markers can be applied at different locations and in different planes around the surgical site. In spinal surgery, for example, one, two, three or more radiopaque optical markers can be applied to the skin around the spinal levels for the intended surgery; one, two, three or more radiopaque optical markers can be attached to a pin, drill or screw inserted into a spinous process and/or a pedicle or other spinal element; one, two, three or more radiopaque optical markers can be applied to the patient's flank or abdomen. In hip replacement surgery, one, two, three or more radiopaque optical markers can be applied to the anterior superior iliac spine on the patient's intended surgical side, e.g. with an adhesive to the skin or attached to a pin or drill to the bone; one, two, three or more radiopaque optical markers can be applied to the anterior superior iliac spine on the patient's contralateral side, e.g. with an adhesive to the skin or attached to a pin or drill to the bone; one, two, three or more radiopaque optical markers can be applied to the symphysis pubis, e.g. with an adhesive to the skin or attached to a pin or drill to the bone; one, two, three or more radiopaque optical markers can be applied to the acetabulum on the patient's intended surgical side, e.g. attached to a pin or drill to the bone; one, two, three or more radiopaque optical markers can be applied to the greater trochanter on the patient's intended surgical side, e.g. attached to a pin or drill to the bone. By using multiple radiopaque optical markers in multiple different locations and in different planes around the surgical site, the accuracy of any three-dimensional spatial registration and cross-reference of the optical markers in different modalities, e.g. radiographs, image capture, can be increased, for example by obtaining multiple x-rays at different angles, e.g. AP, lateral and/or oblique, and/or by imaging the radiopaque optical markers from multiple view angles using an image and/or video capture system integrated into, attached to or separate from the OHMD. By using multiple optical markers in multiple different locations and in different planes around the surgical site, the accuracy of any three-dimensional spatial registration of the optical markers can be increased, for example by imaging the optical markers from multiple view angles using an image and/or video capture system integrated into, attached to or separate from the OHMD. In addition, the accuracy of the registration can be better maintained as the view angle or radiographic angle changes, for example during the course of the surgical procedure or due to patient movement.

In some embodiments of the invention, the system performance can be tested. System performance tests can, for example, measure a phantom including two or more optical markers at known locations, positions, orientations and/or alignment. With the coordinates of the two or more optical markers known along with the distance(s) and angle(s) between the markers, the accuracy of performing distance measurements and/or angle measurements and/or area measurements and/or volume measurements using an image and/or video capture system integrated into, attached to or separate from the OHMD can be determined. In addition, by repeating the measurements, the reproducibility and/or precision of performing distance measurements and/or angle measurements and/or area measurements and/or volume measurements using an image and/or video capture system integrated into, attached to or separate from the OHMD can be determined. The accuracy and/or the reproducibility and/or the precision of performing distance measurements and/or angle measurements and/or area measurements and/or volume measurements using an image and/or video capture system integrated into, attached to or separate from the OHMD can be determined for static and dynamic conditions. Static conditions can be conditions where a patient, a spine, an extremity, a joint and/or a bone do not move. Dynamic conditions can be conditions where a patient, a spine, an extremity, a joint and/or a bone move during the image capture. Dynamic conditions can, for example, be useful in determining the center of rotation of a joint. Measurements for static conditions and for dynamic conditions can be performed for different view angles and distances of the image and/or video capture system integrated into, attached to or separate from the OHMD. Measurements for static conditions and for dynamic conditions can be performed with the OHMD at rest, not moving. Measurements for static conditions and for dynamic conditions can be performed with the OHMD not at rest, but moving, for example moving with the operators head.

TABLE 5 shows exemplary tests with various combinations of test conditions and test parameters for which the accuracy and the reproducibility and/or the precision of the measurements can be determined. Any combination is possible. Other parameters, e.g. reproducibility of color temperature (e.g. in Kelvin), can be measured. Other statistical tests can be applied. All measurements and all statistical determinations and parameters can be assessed for static, dynamic, OHMD at rest and OHMD moving conditions including at different angles and distances of the image and/or video capture system to the target anatomy and/or test apparatus and/or phantom.

| | Coordinates of optical markers | Distance between optical markers | Angle between optical markers | Area enclosed by optical markers | Volume of optical marker(s) | Volume enclosed by multiple optical markers |
|---|---|---|---|---|---|---|
| Accuracy | X | X | X | X | X | X |
| Reproducibility/ Precision | X | X | X | X | X | X |
| Static | X | X | X | X | X | X |
| Dynamic | X | X | X | X | X | X |
| OHMD at rest | X | X | X | X | X | X |
| OHMD moving | X | X | X | X | X | X |

Once the accuracy and/or the reproducibility and/or the precision of performing distance measurements and/or angle measurements and/or area measurements and/or volume measurements and/or coordinate measurements using an image and/or video capture system integrated into, attached to or separate from the OHMD has been determined, threshold values can, for example, be defined that can indicate when the system is operating outside a clinically acceptable performance range. The threshold values can be determined using standard statistical methods known in the art. For example, when a view angle and/or a distance or a movement speed of an image and/or video capture system integrated into an OHMD indicate that a measurement value can fall outside two standard deviations of the system performance including overall system performance, it can trigger an alert to the surgeon that the display of virtual data, e.g. portions of a virtual surgical plan, virtual projected paths or virtual planes, e.g. virtual cut planes, may not be accurate. A binary, e.g. yes, no, system can be used for triggering an alert that the image and/or video capture system and/or the OHMD display are operating outside a clinically acceptable performance range, e.g. exceeding certain view angles, exceeding or being below certain distances to the target anatomy, or exceeding an acceptable movement speed. Alternatively, a sliding scale can be used as the system enters progressively into a range outside the clinically acceptable performance range. The sliding scale can, for example, be a color scale from green to red with mixed colors in between. The sliding scale can be an acoustic signal that increases in intensity or frequency the further the system operates outside the clinically acceptable range. The sliding scale can be a vibration signal that increases in intensity or frequency the further the system operates outside the clinically acceptable range. In some embodiments of the invention, the OHMD can optionally turn off the display of any virtual data of the patient, e.g. virtual plan information, virtual surgical guides or cut blocks or virtual planes or intended paths, when one or more test data indicate that the system is operating outside its clinically acceptable performance range. When test data indicate that the system is operating again inside the clinically acceptable performance range, the OHMD display can turn back on. System tests including accuracy tests and reproducibility tests can be performed intermittently, e.g. every 3 seconds, 5 seconds, 10 seconds, 20 seconds, 30 seconds, 1 minutes, 2 minutes and so forth. System tests can be performed continuously. System tests can be performed intermittently or continuously but limited to times when virtual data are displayed by the OHMD. System tests can be performed intermittently or continuously but limited to times when surgical steps that require high accuracy or reproducibility are being performed. Such steps requiring high accuracy or high reproducibility can be identified for example by the surgeon through voice commands or other commands or they can be identified in the virtual surgical plan, e.g. automatically or by surgeon choice.

In some embodiments of the invention radiopaque and non-radiopaque optical markers can optionally be attached to or applied to extenders that increase the distance of the optical marker from the patient's skin. Such extenders can, for example, be anchored in a spinous process, a pedicle or other spinal element via a pin, drill or screw. The use of extenders with attached radiographic optical markers can increase the accuracy of registration between radiographic data and image capture data, for example when AP and lateral radiographs are used. The use of extenders with attached optical markers can help define anatomic or instrument axes and other information when image capture is used. When two or more markers are used with extenders and the markers are separated by a distance greater than the spatial resolution of the image and/or video capture system, the accuracy in determining, for example, an axis between the two markers can increase, for example as the length of the extender and the distance between the markers increases.

Optical markers can be visible with other imaging modalities, e.g. MRI, nuclear scintigraphy, SPECT or PET. Optical markers can, for example, be doped with an MRI contrast agent such as Gadolinium-DTPA so that they are MRI visible. Optical markers can, for example, be doped with an isotope or positron emitter so that they are SPECT or PET visible.

When an optical marker includes a QR code or when a QR code is used as an optical marker, it can also address inventory management issues and quality concerns before, during and after surgery. Operating the wrong side of a patient is a common quality problem related to surgery, which can have devastating consequences for the patient. Similarly, in spinal surgery, operating the wrong spinal level can result in serious injury of the patient. Optical markers used for determining the location, position, orientation, alignment and/or direction of travel, if applicable, of a patient, a limb, a joint, a surgical site, a surgical instrument, a trial implant and/or an implant component can also include information any of the following using, for example, bar codes or QR codes included in, integrated into or attached to the optical marker:

Patient identifiers
Patient demographics, e.g. age, sex, height, BMI
Patient medical history
Patient risk factors
Patient allergies
Side to be operated, e.g. left vs. right
Site to be operated, e.g. knee vs. hip, spinal level L1 vs. L2, etc.
Spinal level(s) to be operated
Portions of virtual surgical plan, e.g.
  resection amounts,
  resection levels for a given surgical step,
  position and/or orientation of bone cuts
  slope of a tibial cut,
  implant rotation, e.g. femoral component rotation, tibial component rotation
  implant flexion, e.g. femoral component flexion
  intended depth, location, position, orientation, direction, coordinates of burring
  intended depth, location, position, orientation, direction, coordinates of reaming
  intended depth, location, position, orientation, direction, coordinates of milling
  angle of a femoral neck cut,
  acetabular angle,
  acetabular anteversion,
  femoral anteversion,
  offset
  femoral shaft axis
  intended implant component axes/alignment
  intended polyethylene components, thickness (e.g. hip acetabular liner, knee tibial inserts, shoulder glenoid inserts)
Templating or sizing related information
  Size of selected implant component, e.g. knee femoral, tibial or patellar component, hip acetabular shell, acetabular liner, femoral stem, femoral head, with mobile bearing components femoral neck portion
  Side of implant component, left vs. right
Inventory management information, e.g.
  Version, type, model of instrument used
  Lot number of instrument used
  Place of manufacture of instrument used
  Date of manufacture of instrument used
  Date of first sterilization of instrument used
  Number of sterilization cycles applied to instrument used
  Date of last sterilization of instrument used
  Date instrument delivered to hospital or surgery center
  Version, type, model of implant component used
  Lot number of implant component used
  Place of manufacture of implant component used
  Date of manufacture of implant component used
  Date of sterilization of implant component used
  Date implant component delivered to hospital or surgery center
  Any other information relevant to inventory management Optionally, QR codes that include some of this information can also be separate from the optical marker. In some embodiments of the invention, separate bar code and/or QR code readers can be used prior to, during and/or after the surgery to read the information included on the bar codes and/or QR codes. In some embodiments of the invention, an image and/or video capture system integrated into or attached to or separate from the OHMD can be used to read the information included on the bar codes and/or QR codes. The information read from the bar code and/or QR code can then, for example, be compared against portions of the virtual surgical plan and/or, for example, the physical patient's side prepared for surgery, e.g. left vs. right, the physical patient site prepared for surgery, e.g. spinal level L4 vs. L5 (as seen, for example, on radiographs), the physical surgery executed, the physical instrument selected, the physical implant trial selected, the physical implant component selected.

When a pin or a screw is placed in a surgical site including a joint and/or a bone, for example also in a spinal level, e.g. a spinous process or pedicle, with an integrated or attached optical marker with a QR code or when an instrument, a trial implant, and/or an implant component with an integrated or attached optical marker with a QR code enters the field of view of a bar code and/or QR code reader and/or an image and/or video capture system integrated or attached to the OHMD, or enters the proximity of the surgical field or surgically altered tissue, the information on the bar code or QR code on the physical pin or screw, the physical instrument, the physical trial implant, and/or the physical implant component can be read and compared against the intended surgical site information and/or the intended laterality information and/or the virtual surgical plan and/or the intended sizing information and/or the intended templating information. In the example of a spinal level, the bar code and/or QR code reader and/or the image and/or video capture system integrated or attached to the OHMD, can read the QR code identifying the intended spinal level and side (left vs. right) for a pin or a pedicle screw or other device(s). The information can be compared to the virtual surgical plan of the patient and/or x-ray information. For example, intra-operative x-rays can be used by the system to automatically or semi-automatically or user-operated identify spinal levels, e.g. counting up from the sacrum, e.g. by detecting the sacral endplate and opposing endplates and/or pedicles. If the system detects a discrepancy in spinal level or laterality between the information read from the pin, screw or device and the integrated or attached optical marker and bar code or QR code, the virtual surgical plan and/or the radiographic information, it can trigger an alert to check the device, check the surgical plan, and/or to re-confirm the spinal level and/or side. The foregoing example is not limited to radiographic information; other imaging tests known in the art, e.g. CT, MRI, etc., can be used for determining or identifying the anatomic site and side, including for spinal levels.

If the reading of the QR code indicates a discrepancy in any of the information embedded in the QR code, e.g. site, laterality, level, portions or aspects of virtual surgical plan, sizing or templating information, vs. the physical live data during the surgery, e.g. the physical position or spinal level or laterality of the inserted pin or screw, the physical instrument used, the physical trial implant used, and/or the physical implant component used, an alert can be triggered, for example in the OHMD or on a computer monitor used for planning, display, or modifying the virtual surgical plan. The alert can be visual, e.g. red warning signs or stop signs or alert signs displayed, or acoustic, or a vibration, or combinations thereof. Any other alert known in the art can be used.

For example, when a surgeon is operating on a patient to replace the patient's left knee, one or more implant components or an attached holder or packaging label or sterile package can include an optical marker including a QR marker. The QR marker can indicate the laterality, e.g. left femoral component vs. right femoral component. If the scrub technician accidentally hands the surgeon a right femoral component for implantation into the patient's left knee, an image and/or video capture system integrated or attached to the OHMD that the surgeon is wearing can read the QR code as the surgeon takes the femoral component and as the femoral component with the attached optical marker and QR code enters the surgeon's field of view or enters the proximity of the surgical field. The image and/or video capture system and related system software can read the QR code identifying that the implant component is for a right knee; the system software can then compare the information to the virtual surgical plan of the patient or the templating and/or sizing information which can indicate that a left knee was planned, then triggering an alert that an incorrect femoral component has entered the field of view of the surgeon or has entered into the proximity of the surgical field, as for example demarcated by another optical marker. The alert can assist the surgeon in correcting the error by switching to the correct side component.

In another example, when a surgeon is operating on a patient to replace the patient's left knee, one or more implant components or an attached holder or packaging label or sterile package can include an optical marker including a QR marker. The QR marker can indicate the size of the implant component, e.g. size 5 or 6 or other femoral component or size 5 or 6 or other tibial component or size 2 or 3 or other patellar component. If the scrub technician accidentally hands the surgeon a size 4 femoral component for implantation into the patient's which has been templated for a size 6 femoral component, an image and/or video capture system integrated or attached to the OHMD that the surgeon is wearing can read the QR code as the surgeon takes the femoral component and as the femoral component with the attached optical marker and QR code enters the surgeon's field of view or enters the proximity of the surgical field. The image and/or video capture system and related system software can read the QR code identifying that the implant component is of a size 4; the system software can then compare the information to the virtual surgical plan of the patient or the templating and/or sizing information which can indicate that a size 6 femoral component was planned, then triggering an alert that an incorrect femoral component has entered the field of view of the surgeon or has entered into the proximity of the surgical field, as for example demarcated by another optical marker. The alert can assist the surgeon in correcting the error by switching to the correct size component.

An image and/or video capture system and/or a bar code and/or QR code reader integrated into, attached to or separate from the OHMD can also be used to read embedded information on the virtual surgical instruments and/or implant components for inventory management and billing and invoicing purposes. For example, the image and/or video capture system and/or a bar code and/or QR code reader can detect which instruments were used, monitor their frequency of use, and when a certain recommended frequency of used has been reached, the system can trigger an alert to send the instrument for servicing. In some embodiments, the image and/or video capture system and/or a bar code and/or QR code reader can detect which instruments were used and trigger an alert to send the instruments used for sterilization. In some embodiments, the image and/or video capture system and/or a bar code and/or QR code reader can detect which disposable instruments were used and trigger an alert in the system to replenish the supply and send new, additional disposable instruments to replace the ones used. In some embodiments, the image and/or video capture system and/or a bar code and/or QR code reader can detect which implant components and other chargeable components were used and trigger an alert in the system to replenish the supply and send new, additional implant to replace the ones used; the alert can also trigger a command to generate an invoice to the hospital and/or surgery center and to monitor payment.

Any of the foregoing embodiments can be applied to any surgical step and any surgical instrument or implant component during any type of surgery, e.g. knee replacement, hip replacement, shoulder replacement, ligament repair including ACL repair, spinal surgery, spinal fusion, e.g. anterior and posterior, vertebroplasty and/or kyphoplasty.

In some embodiments of the invention, pins or other implantable or attachable markers or calibration or registration phantoms or devices including optical markers can be placed initially, for example in a bone or an osteophyte or bone spur or other bony anatomy or deformity. Registration of virtual image data, for example using anatomic landmarks or locations or an osteophyte or bone spur or other bony anatomy or deformity, where the pins have been physically placed and optionally marking those on an electronic image, and live patient data can be performed. The pins can be optionally removed then, for example if they would interfere with a step of the surgical procedure. After the step of the surgical procedure has been performed, e.g. a bone cut, the pins can optionally be re-inserted into the pin holes remaining in the residual bone underneath the bone cut and the pins can be used for registered the virtual data of the patient with the live data of the patient even though the surgical site and anatomy has been altered by the surgical procedure.

In some embodiments of the invention, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using Patient Specific Markers or Templates Various techniques have been described for registering virtual patient data with live patient data using patient specific markers or templates including those described in WO9325157A1, which is expressly incorporated by reference herein.

In some embodiments of the invention, pre-operative imaging is performed to acquire 3D data of the patient. The pre-operative imaging can, for example, entail ultrasound, CT or MRI, any of the foregoing, optionally with administration of a contrast agent.

The pre-operative imaging can include a single area or region, such as a lumbar spine or portions of a lumbar spine or one or more spinal segments, or a single joint, such as a knee joint, hip joint, ankle joint, shoulder joint, elbow joint or wrist joint. Alternatively, the pre-operative imaging can include scanning through portions or all of one or more adjacent joints. This approach can be beneficial when information about a length of an extremity or axis alignment or rotational alignment is desirable. For example, in planning a hip replacement surgery, it can be beneficial to have image information through the distal femur and, optionally, the knee joint and/or the ankle joint available to determine, for example, leg length. In planning a knee replacement surgery, it can be beneficial to have image information through the hip joint and the ankle joint available. In this manner, the center of the hip and the ankle joint can be, for example, determined. This information can be used to determine the mechanical axis alignment of the patient and, optionally, to plan for any mechanical axis correction.

The pre-operative imaging can also entail imaging in one or more positions, e.g. prone, supine, upright, flexion, extension, lateral bending. Data obtained from scans with the patient in different positions can optionally be combined or fused. For example, an upright standing weight-bearing partial or full leg x-ray can be used to determine the mechanical axis alignment of the leg. 3D data of the knee, e.g. from CT or MRI can be used to obtain detailed anatomic information about the joint, for example to derive a surface shape and to design a patient specific marker or template. The information from the upright scan can be used to align the patient specific marker or template or aspects of it in relationship to the mechanical axis. The information from the 3D knee scan can be used to derive one or more patient specific surfaces that fit to the unique shape of the patient.

In a patient with spinal symptoms, 3D data of the spine can be obtained, for example, with a CT or MRI scan or a rotational fluoroscopy or C-arm scan. Upright imaging, for example in flexion and extension, can be used to determine the presence and degree of spinal instability, for example prior to an intended spinal fusion surgery with pedicle screws and/or cages. The degree of instability or slippage can be determined and used to decide on the degree of intended correction, if any, or the degree of a required foraminotomy, both of which can be optionally planned on the 3D data. Lateral bending views can optionally be used to determine the degree and angle of a partial vertebral corpectomy and the desired placement and/or height of intervertebral cages. Thus, data from upright imaging studies can be combined or optionally fused with data from supine or prone imaging studies. Data from 2D imaging studies can be combined or fused with data from 3D imaging studies. The 3D data can be used to derive one or more patient specific surfaces that fit to the unique shape of the patient, e.g. to the unique shape of one or more of the patient's spinous processes, one or more of the patient's transverse processes, one or more of the patient's laminae, one or more of the patient's articular processes, one or more of the patient's vertebral body.

The patient specific marker or template can include one or more surfaces that are designed and manufactured to fit the corresponding surface of the patient, typically like a negative or substantially a negative. Optional smoothing of the surface can be performed. Alternatively, the surface can be intentionally "roughened" to include more surface features than the segment 3D surface of the patient's target anatomy. Such surface features can, for example, include spike or pin-like structures to allow for enhanced fixation of the patient specific marker or template on the patient's tissue surface.

The patient specific marker or template can be developed from CT, MRI or ultrasound scans as well as x-ray imaging. Principally, any multi-planar 2D or 3D imaging modality is applicable, in particular when it provides information on surface shape or provides information to derive estimates of surface shape of an anatomic region. The patient specific marker or template can include one or more surfaces that are designed or manufactured to fit in any joint or in a spine or other anatomic locations a corresponding Cartilage surface of a patient
Subchondral bone surface of a patient
Cortical bone surface of a patient
Osteophyte or bone spur of a patient
Bone defect of a patient
Exuberant bone formation of a patient
Subchondral cyst of a patient
Soft-tissue shape, e.g. the shape of a thigh or calf or lower back, or thoracic region, or neck region, or foot or ankle region, or shoulder region
Soft-tissue shape in different body poses or positions, e.g. in prone position or in supine position or in lateral position
Ligament of a patient
Labrum of a patient
Meniscus of a patient
Organ shape of a patient
Organ rim or edge of a patient, e.g. a liver edge or spleen edge Different imaging tests can be particularly amenable for a given tissue. For example, if the patient specific marker or template is designed to fit the cartilage shape of the patient, MRI and ultrasound or CT arthrography are ideally suited to provide the surface information. If the patient specific marker or template is intended to fit the subchondral bone shape or cortical bone shape, CT can be used, although MRI and ultrasound can also provide information on bone shape.

Patient specific markers or templates can be manufactured using different materials, e.g. ABS or nylon or different types of plastics or metals. They can be machined, e.g. from a blank, wherein a CAD/CAM process transfers the patient specific shape information into the milling machines. They can also be produced using stereolithography or 3D printing techniques known in the art. If 3D printing is used, any residual powder can be removed using an air cleaning operation and/or a water bath. 3D printing can be performed using powder based or liquid resin based approaches, including, but not limited to continuous liquid interface production.

Patient specific markers or templates can include or incorporate optical markers, e.g. optical markers with different geometric shapes or patterns, with QR codes, with bar codes, with alphanumeric codes. Optionally, geometric shapes or patterns, QR codes, bar codes, alphanumeric codes can be printed, for example when 3D printing is used for manufacturing patient specific markers or templates. 3D printing can be performed with software, e.g. Materialise Magics (Materialise, Leuven, Belgium), and hardware known in the art, e.g. 3D printers from 3D Systems, Rock Hill, S.C., or Concept Laser, Lichtenfels, Germany.

Patient specific markers or templates can be made with different material properties. For example, they can be non-elastic, semi-elastic or elastic. They can be hard. They can be solid or include hollow spaces or openings. They can be opaque. Patient specific markers or templates can be semi-opaque. Patient specific markers can be transparent. In some embodiments, a patient specific marker or template can be semi-opaque or semi-transparent. However, when the patient specific marker or templates comes in contact with the patient and the patient specific surface(s) of the marker or template achieves a good fit with the corresponding surface of the patient, the patient specific marker or template becomes transparent due to the tissue moisture on the corresponding surface of the patient.

One or more patient specific markers or templates can be used on a first surface of a joint. One or more patient specific markers can be used on a second surface of a joint. The first and second surface can be on the same weight-bearing side of the joint. The first and second surface can be on opposite sides of the joint. The one or more patient specific markers or templates on the first surface of the joint cannot be connected to the one or more patient specific markers or templates on the second surface of the joint. In some embodiments, the one or more patient specific markers or templates on the first surface of the joint can, optionally, be connected or linked to the second surface of the joint. Thus, one or more patient specific markers or templates can optionally be cross-referenced.

Patient specific markers or templates can be designed for any joint, any portion of a spine, and any tissue of the human body. Patient specific markers or templates typically include one or more surfaces or shapes designed to fit a corresponding surface or shape of a patient. Representative, non-limiting examples of patient surfaces to which patient specific markers or templates can be designed and/or fitted include:

Spine:
A portion or an entire spinous process
A portion or an entire spinal lamina
A portion or an entire spinal articular process
A portion of or an entire facet joint
A portion of or an entire transverse process
A portion of or an entire pedicle
A portion of or an entire vertebral body
A portion of or an entire intervertebral disk
A portion of or an entire spinal osteophyte
A portion of or an entire spinal bone spur
A portion of or an entire spinal fracture
A portion of or an entire vertebral body fracture
Combinations of any of the foregoing Hip:
A portion of or an entire acetabulum
A portion of or an entire edge of an acetabulum
Multiple portions of an edge of an acetabulum
A portion of an iliac wall
A portion of a pubic bone
A portion of an ischial bone
A portion of or an entire greater trochanter
A portion of or an entire lesser trochanter
A portion of or an entire femoral shaft
A portion of or an entire femoral neck
A portion of or an entire femoral head
A fovea capitis
A transverse acetabular ligament
A pulvinar
A ligamentum teres
A labrum
One or more osteophytes, femoral and/or acetabular
Combinations of any of the foregoing Knee:
A portion or an entire medial femoral condyle
A portion or an entire lateral femoral condyle
A portion or an entire femoral notch
A portion or an entire trochlea
A portion of an anterior cortex of the femur
A portion of an anterior cortex of the femur with adjacent portions of the trochlea
A portion of an anterior cortex of the femur with adjacent portions of the trochlea and osteophytes when present
One or more osteophytes femoral and/or tibial
One or more bone spurs femoral and/or tibial
An epicondylar eminence
A portion or an entire medial tibial plateau A portion or an entire lateral tibial plateau
A portion or an entire medial tibial spine
A portion or an entire lateral tibial spine
A portion of an anterior cortex of the tibia
A portion of an anterior cortex of the tibia and a portion of a tibial plateau, medially or laterally or both
A portion of an anterior cortex of the tibia and a portion of a tibial plateau, medially or laterally or both and osteophytes when present
A portion or an entire patella
A medial edge of a patella
A lateral edge of a patella
A superior pole of a patella
An inferior pole of a patella
A patellar osteophyte
An anterior cruciate ligament
A posterior cruciate ligament
A medial collateral ligament
A lateral collateral ligament
A portion or an entire medial meniscus
A portion or an entire lateral meniscus
Combinations of any of the foregoing
Shoulder:
A portion or an entire glenoid
A portion or an entire coracoid process
A portion or an entire acromion
A portion of a clavicle
A portion or an entire humeral head
A portion or an entire humeral neck
A portion of a humeral shaft
One or more humeral osteophytes
One or more glenoid osteophytes
A portion or an entire glenoid labrum
A portion or an entire shoulder ligament, e.g. a coracoacromial ligament, a superior, middle, or inferior glenohumeral ligament
A portion of a shoulder capsule
Combinations of any of the foregoing
Skull and Brain:
A portion of a calvarium
A portion of an occiput
A portion of a temporal bone
A portion of an occipital bone
A portion of a parietal bone
A portion of a frontal bone
A portion of a facial bone
A portion or an entire bony structure inside the skull
Portions or all of select gyri
Portions or all of select sulci
A portion of a sinus
A portion of a venous sinus
A portion of a vessel
Organs:
A portion of an organ, e.g. a superior pole or inferior pole of a kidney
An edge or a margin of a liver, a spleen, a lung
A portion of a hepatic lobe
A portion of a vessel
A portion of a hiatus, e.g. in the liver or spleen
A portion of a uterus The patient specific marker or template can be designed or fitted to any of the previously mentioned tissues, if applicable for a particular anatomic region, e.g. cartilage, subchondral bone, cortical bone, osteophytes etc. The patient specific marker or template can be designed or fitted to normal tissue only. The patient specific marker or template can be designed or fitted to abnormal or diseased tissue only. The patient specific marker or template can be designed or fitted to combinations of normal and abnormal or diseased tissue. For example, the patient specific marker can be designed to normal cartilage, or to diseased cartilage, or to combinations of normal and diseased cartilage, e.g. on the same or opposing joint surfaces. Patient specific markers can be used to register one or more normal or pathologic tissues or structures in a common coordinate system, for example with one or more OHMDs and virtual data of the patient. Virtual and physical surgical instruments and implant components can also be registered in the common coordinate system.

The patient specific marker or template can be designed using virtual data of the patient, e.g. from a pre-operative imaging study such as a CT scan, MRI scan or ultrasound scan. The patient specific marker or template includes one or more surfaces that are designed and/or manufacture to achieve a close fit with a corresponding surface of the patient.

In some embodiments of the invention, a surgeon or an operator can apply the patient specific marker or template to the corresponding tissue of the patient. Once a satisfactory fit has been achieved and the two corresponding surfaces are substantially in contact, the patient specific marker or template can be used to register the virtual data of the patient and an optional virtual surgical plan with the live data of the patient. By applying the patient specific marker or template to its corresponding surface(s) on the patient, the surgeon is effectively identifying corresponding structures or surfaces in the virtual data and the live data of the patient.

The position, location and/or orientation of the patient specific marker or template can then be determined in relationship to the OHMD. Any of the embodiments described herein can be applied for determining the position, location and/or orientation of the patient specific marker or template in relationship to the OHMD. For example, the side of the patient specific marker or template that is opposite the patient specific surface can include certain standardized geometric features, e.g. rectangles, triangles, circles and the like, that can be readily recognized by an image and/or video capture system integrated into or attached to or coupled to the OHMD. In alternative embodiments, the patient specific marker or template can include one or more IMUs, including, for example, accelerometers, magnetometers, and gyroscopes, similar, for example, to the OHMD. In some embodiments, the patient specific marker or template can include one or more radiofrequency tags or markers or retroreflective markers and its position, location and/or orientation can be captured by a surgical navigation system. Radiofrequency tags can be active or passive. Optionally, the OHMD may also include one or more radiofrequency tags or markers or retroreflective markers and its position, location and/or orientation can also be captured by the surgical navigation system and cross-referenced to the patient specific marker or template. The patient specific marker or template can also include light sources, such as lasers or LEDs. A laser can be projected, for example, on a wall or a ceiling and the OHMD can be referenced in relationship to that. An LED attached to or integrated into the patient specific marker or template can be recognized, for example, by an image and/or video capture system integrated into or attached to r coupled to the OHMD.

In an additional embodiment, one or more of the surgical instruments and/or one or more of the implantable devices used during the surgery can include can include certain standardized geometric features, e.g. rectangles, triangles, circles and the like, that can be readily recognized by an image and/or video capture system integrated into or attached to or coupled to the OHMD. In alternative embodiments, one or more of the surgical instruments and/or one or more of the implantable devices used during the surgery can include one or more IMUs, including, for example, accelerometers, magnetometers, and gyroscopes, similar, for example, to the OHMD. In some embodiments, one or more of the surgical instruments and/or one or more of the implantable devices used during the surgery can include one or more radiofrequency tags or markers or retroreflective markers and its position, location and/or orientation can be captured by a surgical navigation system. Optionally, the OHMD may also include one or more radiofrequency tags or markers or retroreflective markers and its position, location and/or orientation can also be captured by the surgical navigation system and cross-referenced to the patient specific marker or template and/or the one or more of the surgical instruments and/or one or more of the implantable devices used during the surgery. One or more of the surgical instruments and/or one or more of the implantable devices used during the surgery can also include light sources, such as lasers or LEDs. A laser can be projected, for example, on a wall or a ceiling and the OHMD and the patient can be referenced in relationship to that. An LED attached to or integrated into the one or more of the surgical instruments and/or one or more of the implantable devices used during the surgery can be recognized, for example, by an image and/or video capture system integrated into or attached to or coupled to the OHMD. Optionally, multiple LEDs can be used. Optionally, two or more of the multiple LEDs emit light with different wavelength or color. The two or more LEDs can be located in spatially defined locations and orientations, e.g. at a pre-defined or fixed distance and at one or more pre-defined or fixed angles. In this manner, the two or more LEDs can be located by an image and/or video capture system integrated into, attached to or separate from the OHMD and their measured distance and/or angles as seen through the image and/or video capture system can, for example, be used to determine the distance and or orientation of the operator to the target anatomy, e.g. when the image and/or video capture system is close to the operator's eyes. By using LEDs with different wavelength or color, the image and/or video capture system can differentiate between different LEDs; when the LEDs are arranged in a known spatial orientation, this information can be helpful for increasing the accuracy of the registration and/or for obtaining accurate distance, angle, direction and/or velocity measurements. The use of two or more LEDs with different wavelength and color and measurements or registration as described above are applicable throughout the specification in all embodiments that incorporate the use of LEDs or that are amenable to using LEDs.

Optionally, the patient specific marker or template and, optionally, one or more of the surgical instruments and/or one or more of the implantable devices used during the surgery can also include color markings, optionally with different geometric shapes or located or oriented at different, known locations and different, known angles, that can be used, for example, by an image and/or video capture system integrated into or attached to or coupled to an OHMD to recognize such patterns and, for example, to estimate distances and angles, e.g. from the surgical site to the OHMD, or distances and angles between two markings, two surgical instruments or medical device components.

Optionally, the patient specific marker or template and, optionally, one or more of the surgical instruments and/or one or more of the implantable devices used during the surgery can also include scales, e.g. of metric distances, inches, or angles that can be used, for example, by an image and/or video capture system integrated into or attached to or coupled to an OHMD to recognize such scales or angles and, for example, to estimate distances and angles, e.g. from the surgical site to the OHMD, or distances and angles between two surgical instruments or medical device components.

In some embodiments of the invention, the patient specific marker or template can be attached to the corresponding surface of the patient or to an adjacent surface of the patient, for example using tissue glue such as fibrin glue or a pin or a staple.

In some embodiments, the patient specific marker or template can include openings or guides, for example for accepting a surgical instrument or tool such as a bur, a saw, a reamer, a pin, a screw and any other instrument or tool known in the art.

By cross-referencing virtual patient data and live patient data with use of a patient specific marker or template and, optionally, one or more of the surgical instruments and/or one or more of the implantable devices used during the surgery and an OHMD, any coordinate information, distance information, axis information, functional information contained in the virtual patient data can now be available and used during the surgery.

In some embodiments of the invention, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using Intraoperative Imaging In some embodiments of the invention, intraoperative imaging, for example using x-ray imaging or CT imaging and/or ultrasound imaging, can be performed. Virtual patient data obtained intraoperatively using intraoperative imaging can be used to register virtual patient data obtained preoperatively, for example using preoperative x-ray, ultrasound, CT or MRI imaging. The registration of preoperative and intraoperative virtual data of the patient and live data of the patient in a common coordinate system with one or more OHMDs can be performed, for example, by identifying and, optionally, marking corresponding landmarks, surfaces, object shapes, e.g. of a surgical site or target tissue, in the preoperative virtual data of the patient, the intraoperative virtual data of the patient, e.g. on electronic 2D or 3D images of one or more of the foregoing, and the live data of the patient. Virtual preoperative, virtual intraoperative and live data can include an osteophyte or bone spur or other bony anatomy or deformity. Virtual and physical surgical instruments and implant components can also be registered in the common coordinate system.

This embodiment can be advantageous when the amount of information obtained with intraoperative imaging is, for example, anatomically or in other ways more limited than the amount of information available with preoperative imaging or vice versa.

For example, intraoperative imaging may be performed using x-ray imaging, which is commonly only two-dimensional in nature. X-ray imaging can be augmented through image acquisition in more than one plane, e.g. orthogonal planes or one or more planes separated by a defined angle. Intraoperative x-ray images can be used to identify certain landmarks or shapes that can then be registered to preoperative imaging and/or live data of the patient during surgery. Preoperative imaging can, optionally, include 3D image data, for example obtained with CT or MRI. Acquisition of intraoperative images in multiple planes can be helpful to more accurately define the location of certain landmarks, contours or shapes intended for use in a registration of preoperative virtual data, intraoperative virtual data and live data of the patient. For purposes of clarification, intraoperative virtual data of the patient can be intraoperative images of the patient in 2D or 3D.

For example, in a spinal procedure such as vertebroplasty, kyphoplasty, pedicle screw placement, or placement of anterior spinal device including artificial disks or cages, intraoperative x-ray imaging can be used to identify, for example, the spinal level targeted for the surgery, in an AP projection certain landmarks or contours, e.g. the tip of a spinous process, a facet joint, the superior or inferior tip of a facet joint, the cortical edge of a lamina, a superior or inferior endplate or an osteophyte or bone spur or other bony anatomy or deformity. Optionally, the distance of the x-ray tube from the patient resulting in x-ray magnification can be factored into any registration in order to improve the accuracy of the registration of virtual preoperative data of the patient and virtual intraoperative data of the patient or live data of the patient. The intraoperative x-ray images can then be registered and, optionally, superimposed onto the preoperative data of the patient or the live data of the patient in the projection by the OHMD. The intraoperative virtual data of the patient, e.g. the tip of a spinous process, a facet joint, the superior or inferior tip of a facet joint, the cortical edge of a lamina, a superior or inferior endplate, can be registered to the live data of the patient, for example by touching the corresponding anatomic landmarks with a pointing device or a needle or a pin inserted through the skin and by cross-referencing the location of the tip of the live data pointing device with the intraoperative virtual data of the patient. In this manner, any one of preoperative virtual data of the patient, intraoperative virtual data of the patient, and live data of the patient and combinations thereof can be co-registered. Two or three of these data sets, preoperative virtual data of the patient, intraoperative virtual data of the patient, and live data of the patient, can optionally be seen in the OHMD. However, in many embodiments, intraoperative imaging may only be used for enhancing the accuracy of the registration of preoperative virtual data of the patient and live data of the patient and, for example, preoperative virtual data of the patient and/or a medical device intended for placement in a surgical site will be displayed by the OHMD together with the view of the live data of the patient or the surgical site.

In some embodiments of the invention, the registration of virtual patient data and live patient data using the techniques described herein can be repeated after one or more surgical steps have been performed and, optionally, intraoperative imaging can be repeated. In this case, the surgically altered tissue or tissue surface or tissue contour or tissue perimeter or tissue volume or other tissue features in the live patient or in the intraoperative repeat imaging data of the patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using Skin Markers or Soft-Tissue Markers In some embodiments of the invention, skin markers and soft-tissue markers, calibration or registration phantoms or devices can be used for registering preoperative virtual data, optionally intraoperative virtual data such as data obtained from intraoperative x-ray imaging, and live data seen through the OHMD in a common coordinate system with one or more OHMDs. Virtual and physical surgical instruments and implant components can also be registered in the common coordinate system. For example, an initial registration between preoperative virtual data and live data of the patient can happen at the beginning of the procedure. The initial registration can, for example, be performed using corresponding anatomic landmarks, surfaces or shapes, or using intraoperative imaging resulting in intraoperative virtual data or any of the other embodiments described in this invention. The registration can be used, for example, to place the virtual data and the live data and the optical head mounted display into a common coordinate system. Skin markers, calibration or registration phantoms or devices can then be applied. Virtual and physical surgical instruments and implant components can also be registered in the common coordinate system. Alternatively, or in addition, soft-tissue markers, calibration or registration phantoms or devices can be applied. Typically, more than one, such as two, three, four or more skin markers and soft-tissue markers, calibration or registration phantoms or devices will be applied. For clarity, the terms implantable markers, attachable markers, skin markers, soft-tissue markers, calibration or registration phantoms or devices as used through the application can include optical markers, e.g. optical markers with different geometric shapes or patterns, with QR codes, with bar codes, with alphanumeric codes. Skin markers and soft-tissue markers, calibration or registration phantoms or devices can, for example, be applied to the skin or the soft-tissue using a form of tissue compatible adhesive, including fibrin glue and the like. In some embodiments, one, two, three, four or more skin markers and soft-tissue markers, calibration or registration phantoms or devices can be included in a surgical drape or dressing or a transparent film applied to the skin prior to the procedure. The skin markers and soft-tissue markers, calibration or registration phantoms or devices can then be registered in the live data and cross-referenced to virtual data. The skin markers and soft-tissue markers, calibration or registration phantoms or devices can subsequently used, for example, when the surgical site is altered and the landmarks, surface or shape that was used for the initial registration of virtual and live data have been altered or removed and cannot be used or cannot be used reliably for maintaining registration between virtual data and live data. Virtual preoperative, virtual intraoperative and live data can include an osteophyte or bone spur or other bony anatomy or deformity.

In some embodiments of the invention, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

The same skin markers or soft-tissue markers or calibration phantoms or registration phantoms can be used after one or more surgical steps have been performed if the markers or phantoms are still in place. Alternatively, re-registration of the live data of the patient and virtual data of the patient can be performed after one or more surgical steps or surgical alterations. Following re-registration, one or more new skin markers or soft-tissue markers or calibration phantoms or registration phantoms can be applied and cross-referenced to the re-registered live and virtual data after the surgical step or alteration. The skin markers or soft-tissue markers or calibration phantoms or registration phantoms can then be used for subsequent matching, superimposition, movement and registration of live patient data and virtual patient data.

Registration of Virtual Patient Data and Live Patient Data Using Calibration or Registration Phantoms with Defined Dimensions or Shapes In some embodiments of the invention, calibration or registration phantoms with defined dimensions or shapes can be used to perform the registration of virtual data of the patient and live data of the patient. The calibration or registration phantoms can be of primarily two-dimensional or three-dimensional nature. For example, a calibration or registration phantom can be arranged or located primarily in a single plane. Other calibration phantoms can be located in multiple planes, thereby creating the opportunity for registration using more than one planes. For clarity, the terms calibration or registration phantoms, implantable markers, attachable markers, skin markers, soft-tissue markers, or devices as used through the application can include optical markers, e.g. optical markers with different geometric shapes or patterns, with QR codes, with bar codes, with alphanumeric codes.

Such calibration or registration phantoms can be, for example, attached to the patient's skin. The calibration or registration phantom can be integrated or attached to a surgical drape. The calibration or registration phantom can be attached to the patient's tissue. The calibration or registration phantom can be part of or a component of a medical device. The part or component of the medical device will typically have known dimensions. By using calibration or registration phantoms, as well as other markers, the live data of a patient and the virtual data of the patient can be registered in a common coordinate system, for example with one or more OHMDs. Virtual and physical surgical instruments and implant components can also be registered in the common coordinate system.

In some embodiments, the calibration or registration phantom includes known dimensions, angles or geometric 2D or 3D shapes. For example, the calibration or registration phantom can include structures such as circles, ovoids, ellipses, squares, rectangles, complex 2D geometries, 2D geometries with one or more defined distances, 2D geometries with one or more defined angles spheres, egg shaped structures, cylinders, cubes, cuboids, complex 3D geometries or shapes, 3D geometries with one or more defined distances, 3D geometries with one or more defined angles, 3D geometries with one or more defined surfaces Optionally, the calibration or registration phantoms can be radiopaque if pre-operative or intra-operative imaging is performed using an imaging modality with ionizing radiation, e.g. x-ray imaging, fluoroscopy in 2D or 3D, CT, cone beam CT etc.

In some embodiments, the calibration or registration phantom can be MRI visible or nuclear scintigraphy or SPECT visible or PET visible, for example by including portions or containers in the phantom containing Gadolinium-DTPA doped or radionuclide doped or PET isotope emitting water. Any contrast agent or MRI or nuclear scintigraphy or SPECT or PET visible agent known in the art can be used in this fashion.

In some embodiments, the calibration or registration phantom includes retroreflective markers or features which facilitate detection by an image and/or video capture system. The calibration or registration phantom can also be highlighted against the patient's tissue(s) including blood as well as surgical drapes through a choice of select colors, e.g. a bright green, bright blue, bright yellow, bright pink etc. Color combinations are possible. Any color or color combination known in the art can be used.

The calibration or registration phantom can optionally include LEDs, optionally battery powered. More than one LED can be used. The LEDs can emit a light of a known color, hue and intensity, preferably selected to be readily identifiable by the image and/or video capture system and any segmentation techniques or algorithms used for detecting the location, position and/or orientation of the LEDs.

The LEDs can be arranged in a spatially defined way, with two or more LEDs arranged at a defined distance or distances, at a defined angle or angles, in substantially the same plane or different planes. If LEDs are arranged in different planes, the spatial orientation of the planes is for example known and defined.

When two or more LEDs are used, the two or more LEDs can emit light utilizing different wavelengths, colors, intensity and, optionally also, blinking frequency. In this manner, an image and/or video capture system integrated into, attached to or separate from the OHMD can recognize each different LED based on one or more of their different wavelength, color, intensity and/or blinking frequency. When the LEDs are arrange in a spatially defined and known manner, e.g. using known distances or angles within the same plane or different planes, the identification of each individual LED and the change in distances and angles measured by the image and/or video capture system can be used to determine the position, location and/or orientation of the OHMD and/or the operator's head (e.g. if the image and/or video capture system is integrated into the OHMD or attached to the OHMD) or, in some applications, the movement of the patient or body part to which the calibration or registration phantom and LEDs are attached.

LEDs used throughout the specification can be re-useable. LEDs used throughout the specification can also be disposable, optionally with integrated, disposable battery cells/ batteries. LEDs can be operated utilizing wires, e.g. connected to a power supply and/or connected to a wired user interface or control unit. LEDs can be wireless, e.g. without attached power supply (e.g. battery operated) and/or connected to a wireless (e.g. WiFi, Bluetooth) control unit.

LEDs can be connected and/or organized in LIF networks. One or more LIF networks can be used, for example, to transmit or receive data or information back and forth from the one or more OHMDs to a control unit or computer, optionally with a user interface. In this example, LEDs participating or connected in the one or more LIF networks can be integrated into or attached to the OHMD. LEDs participating or connected in the one or more LIF networks can be attached to or, when applicable, integrated into any location or site on the surgeon, the OR staff, the patient, the surgical site, one or more OHMDs, one or more navigation systems, one or more navigation markers, e.g. retroreflective markers, infrared markers, RF markers; one or more optical markers, calibration or registration phantoms.

An LIF network can also be used to transmit or receive data or information about the spatial position, orientation, direction of movement, speed of movement etc. of individual LEDs. The same LEDs whose relative position, orientation, direction of movement, speed of movement, e.g. in relationship to the surgeon or the patient or the surgical site, is being measured, e.g. using an image and/or video capture system, can be used to transmit or receive information in the LIF network, optionally using different wavelengths, color, frequency, blinking patterns depending on the type of data being transmitted. The information can be about the position, orientation, direction of movement, speed of movement of individual LEDs. The information can also be data that are being transmitted or received by the OHMD. The information can be the information or data that are being displayed by the OHMD. The information can be information generated or received by navigation markers, RF markers. The information can be information captured by one or more image and/or video capture systems or cameras.

1, 2, 3, 4 or more LEDs can be connected to or attached to the patient, the target anatomy, the surgical site, the surgical site after a first, second or more surgical alterations, for example executed using a virtual surgical plan, the OHMD, a second, third and/or additional OHMDs, for example worn by a second surgeon, a scrub nurse, other OR personnel, the hand, forearm, upper arm and or other body parts of the surgeon/operator.

The relative position, orientation, movement, direction of movement, velocity of movement of each LED can be determined, for example using one or more image and/or video capture systems, e.g. integrated into, attached to or separate from the one or more OHMDs, e.g. when the one or more LEDs emit light utilizing different wavelengths, colors, intensity and, optionally also, blinking frequency.

The calibration or registration phantom can optionally include one or more lasers, optionally battery powered. More than one laser can be used. The laser can emit a light of a known color, hue and intensity, for example selected to be readily identifiable by the image and/or video capture system and any segmentation techniques or algorithms used for detecting the location, position and/or orientation of the laser.

The laser can be arranged in a spatially defined way, with two or more lasers arranged at a defined distance or distances, at a defined angle or angles, in substantially the same plane or different planes. If lasers are arranged in different planes, the spatial orientation of the planes can be known and defined.

The calibration or registration phantom can optionally include radiofrequency (RF) transmitters, optionally battery powered. More than one RF transmitter can be used. The RF transmitters can transmit a signal or signals selected to be readily identifiable by an RF receiver system used for detecting the location, position and/or orientation of the RF transmitters. One or more RF transmitters can transmit signals with different frequency and intensity, thereby permitting differentiation of the different RF transmitters by the RF receiver system.

The RF transmitters can be arranged in a spatially defined way, with two or more RF transmitters arranged at a defined distance or distances, at a defined angle or angles, in substantially the same plane or different planes. If RF transmitters are arranged in different planes, the spatial orientation of the planes is can be known and defined.

The calibration or registration phantom can optionally include ultrasound (US) transmitters, optionally battery powered. More than one US transmitter can be used. The US transmitters can transmit a signal or signals selected to be readily identifiable by an US receiver or transducer system used for detecting the location, position and/or orientation of the US transmitters. One or more US transmitters can transmit signal with different frequency and intensity, thereby permitting differentiation of the different US transmitters by the US receiver or transducer system.

The US transmitters can be arranged in a spatially defined way, with two or more US transmitters arranged at a defined distance or distances, at a defined angle or angles, in substantially the same plane or different planes. If US transmitters are arranged in different planes, the spatial orientation of the planes is can be known and defined.

Calibration phantoms or registration phantoms can be used for pre-operative imaging and/or for intraoperative imaging and/or image capture of live data, for example using an image and/or video capture system attached to or integrated into the OHMD or coupled to the OHMD or separate from the OHMD. Virtual preoperative, virtual intraoperative and live data can include an osteophyte or bone spur or other bony anatomy or deformity.

If the same calibration or registration phantom is used for pre-operative imaging and for intra-operative imaging, optionally, the imaging can be performed using the same imaging modality, e.g. x-ray imaging, and, for example, using the same orientation of the patient in relationship to the x-ray source and the detector system and, for example using the same distance of the patient in relationship to the x-ray source and the detector system. Using this approach, the anatomic structures visualized on the pre-operative imaging and intra-operative imaging can be superimposed and registered, optionally in the same coordinate system.

In the event, the calibration or registration phantom has been positioned differently on the patient for the pre-operative imaging and for the intraoperative imaging data acquisition, the difference in location or position or coordinates can be determined using the co-registration of the anatomic data visualized on the pre-operative imaging and intra-operative imaging. An adjustment for the difference in phantom location from the pre-operative to the intraoperative data can be performed; this adjustment can optionally be defined as a phantom offset between pre-operative and intra-operative data. Virtual preoperative, virtual intraoperative and live data can include an osteophyte or bone spur or other bony anatomy or deformity.

As an alternative to the anatomic registration from the anatomic structures visualized on the pre-operative imaging and intra-operative imaging, the registration between preoperative imaging data and intra-operative live data visualized through the OHMD or an attached, integrated or separate image and/or video capture system can be performed alternatively now using the calibration or registration phantom as visualized or as identified optically during the surgery, for example using the phantom offset between pre-operative and intra-operative data. In general, the initial registration of virtual data and live data is possible using any of the techniques described herein, e.g. using anatomic features, anatomic landmarks, intraoperative imaging etc. Then co-registration of the calibration or registration phantom, e.g. in the same coordinate system, can be performed. If initial registration fails during the surgical procedure, registration can be maintained using the calibration or registration phantom. For this purpose, the position, location, orientation and/or alignment of the calibration or registration phantom will be continuously or intermittently monitored using an image and/or video capture system, which can be integrated into or attached to the OHMD or coupled to the OHMD or separate from the OHMD.

In some embodiments of the invention, the preoperative imaging can entail a cross-sectional imaging modality, e.g. computed tomography, which can optionally generate 3D data of the patient, e.g. in the form of a spiral or a helical CT scan and, optionally, a 3D reconstruction. The 3D data of the patient, e.g. the spiral or helical CT scan or 3D reconstruction, can be re-projected into a 2D image, creating an x-ray like transmission image of the patient, e.g. of the bony structures of the patient including, but not limited to an osteophyte or bone spur or other bony anatomy or deformity. Optionally, this 2D re-projection of the 3D data, e.g. CT data, can be performed using the same plane or projection or view angle and, for example, the same or similar magnification as can be used subsequently during surgery with an intraoperative x-ray imaging test. The film-focus and, optionally, object distance of the x-ray system used for the intraoperative imaging part can be known at the time of the re-projection of the preoperative 3D data, so that the magnification of the patient or anatomic data resulting for a given intraoperative film-focus and optionally object distance will be matched or reflected in the re-projected pre-operative data. If the film-focus and, optionally, object distance of the x-ray system used for the intraoperative imaging part is not known at the time of the re-projection of the preoperative 3D data, the magnification of the re-projected data can be adjusted when they are visualized with and optionally superimposed onto the 2D intraoperative imaging data of the patient or anatomic data resulting for a given intraoperative film-focus and optionally object distance so that the magnification of both re-projected and intraoperative imaging data will be matched or substantially similar. Such matching in magnification can be achieved, for example, by aligning certain features or anatomic landmarks or pathologic tissues including an osteophyte or bone spur or other bony anatomy or deformity in the pre-operative re-projected data with the intraoperative data and adjusting the magnification until the feature or landmarks are substantially superimposed or substantially matching. With this approach, pre-operative imaging data can use the benefit of 3D data including, for example, more accurate three-dimensional placement of an implant component such as a spinal component or a component for joint replacement or fracture repair. Similarly, certain anatomic landmarks or features can be detected and utilized for surgical planning in the 3D data set. When the 3D data are then re-projected into a 2D re-projection or view, anatomic landmarks, features or data or pathologic data can be readily matched up or aligned with corresponding anatomic landmarks, features or data or pathologic data in the corresponding portions of the intra-operative 2D imaging study, e.g. intraoperative x-rays. Thus, while different 3D preoperative and 2D intraoperative imaging modalities can be used, 2D re-projection allows for cross-referencing and, optionally, co-registration of the 2D and 3D data sets. Any 2D and 3D imaging modality known in the art can be used in this manner.

In additional embodiments, the calibration/registration phantom can be used
1.) To estimate distance, position, orientation of OHMD from the patient, for primary or back-up registration, for example used in conjunction with an image and/or video capture system integrated into, attached to or coupled to or separate from the OHMD
2.) To estimate distance, position, orientation of target tissue or surgical site underneath the patient's skin, e.g. after cross-registration with pre-operative and/or intra-operative imaging data
3.) To estimate the path of a surgical instrument or to estimate the location of a desired implantation site for a medical device or implant or transplant
4.) To update a surgical plan The calibration or registration phantom can be used in physical time mode, using physical time registration, for example using an image and/or video capture system integrated into, attached to, coupled to, or separate from the OHMD, which can optionally operate in physical time mode. Physical time mode can, for example, mean that image capture is performed with more than 5 frames/second, 10 frames/second, 15 frames/second, 20 frames/second, 30 frames/second etc.

If images generated with the image and/or video capture system are segmented or, for example, image processing or pattern recognition is performed, this can optionally be performed on each frame generated with the image and/or video capture system. Alternatively, segmentation or image processing or pattern recognition can be performed on a subset of the image frames captured with the image and/or video capture system. Segmentation, image processing or pattern recognition data can be averaged between frames. The foregoing embodiments are applicable to all embodiments in this specification that utilize image capture.

Image processing can be performed to include data from one or more osteophytes or bone spurs or other bony anatomy or deformity. The one or more osteophytes or bone spurs or other bony anatomy or deformity can be used for purposes of registration of virtual and live data, including virtual preoperative and virtual intraoperative imaging or virtual functional data. Image processing can also be performed to exclude data from one or more osteophytes or bone spurs or other bony anatomy or deformity. The one or more osteophytes or bone spurs or other bony anatomy or deformity can be excluded or omitted from any data used for purposes of registration of virtual and live data, including virtual preoperative and virtual intraoperative imaging or virtual functional data. The inclusion or exclusion of one or more osteophytes or bone spurs or other bony anatomy or deformity can be selected based on the anatomic site, the surgical site, and/or the desired accuracy of the segmentation or the registration of virtual data and live data.

The calibration or registration phantom can be used in non-physical time mode, e.g. an intermittent mode, for example using an image and/or video capture system integrated into, attached to, coupled to, or separate from the OHMD, which can optionally operate in intermittent mode. Intermittent mode use of the calibration or registration phantom can be performed, for example, by using a timer or timing device, wherein image capture and registration is performed every 10 seconds, 8 seconds, 5 seconds, 3 seconds, 2 seconds, 1 second etc.

In some embodiments, physical-time and intermittent registration using the calibration or registration phantom will be selected or designed so that the data generated will for example not exceed the temporal resolution of the image and/or video capture system and/or the temporal resolution of the segmentation or image processing or pattern recognition used for the registration.

In any of the foregoing embodiments, the accuracy of registration can optionally be improved by using multiple registration points, patterns, planes or surfaces. In general, the accuracy of registration will improve with an increasing number of registration points, patterns, planes or surfaces. These may, in some embodiments, not exceed the spatial resolution of the image and/or video capture system. In some embodiments, these may exceed the spatial resolution of the image and/or video capture system. In that situation, optionally, down-sampling of data can be performed, e.g. by reducing the effective spatial resolution in one, two or three planes or by reducing the spatial resolution in select areas of the field of view seen through the OHMD or visualized in the virtual data. Virtual preoperative, virtual intraoperative and live data can include an osteophyte or bone spur or other bony anatomy or deformity.

In some embodiments of the invention, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

The same skin markers or soft-tissue markers or calibration phantoms or registration phantoms can be used after one or more surgical steps have been performed if the markers or phantoms are still in place. Alternatively, re-registration of the live data of the patient and virtual data of the patient can be performed after one or more surgical steps or surgical alterations. Following re-registration, one or more new skin markers or soft-tissue markers or calibration phantoms or registration phantoms can be applied and cross-referenced to the re-registered live and virtual data after the surgical step or alteration. The skin markers or soft-tissue markers or calibration phantoms or registration phantoms can then be used for subsequent matching, superimposition, movement and registration of live patient data and virtual patient data.

To Estimate Distance, Position, Orientation of OHMD from the Patient

If registration of virtual patient data and live patient data has occurred using any of the techniques or techniques described in this specification and if the calibration or registration phantom is also registered in relationship to the live patient data, the calibration or registration phantom can be used to maintain registration, for example on an intermittent or a physical-time basis, including while the surgeon or operator moves his or her head or body. The calibration or registration phantom can, for example, not be moved during the surgery. If the calibration or registration phantom needs to be moved, it may optionally be re-registered in relationship to any live patient data, virtual patient data, pre-operative data and intra-operative data.

In this and related embodiments, the calibration or registration phantom will be identified with regard to its location, position, orientation, alignment, surfaces or shape using an image and/or video capture system and, optionally, segmentation, image processing or pattern recognition and any other techniques known in the art for identifying an object in image data. The image and/or video capture system can be integrated into or attached to the OHMD. The image and/or video capture system can be coupled to or separate from the OHMD. The image and/or video capture system will be used to determine the location, position, orientation, alignment, surfaces or shape of the calibration or registration phantom in relationship to the patient, the operator and/or the OHMD.

Any other techniques known in the art, including as described in this specification, that can be used to determine the location, position, orientation, alignment, surfaces or shape of the calibration or registration phantom in relationship to the patient, the operator and/or the OHMD, can be used, including, but not limited to surgical navigation including optical or RF tracking, laser based distance measurements and the like.

The calibration or registration phantom can be used for primary or back-up registration. Optionally, synchronized registration can be used, wherein, for example, more than one technique of registration is used simultaneously to maintain registration between virtual patient data and live patient data, for example by simultaneously maintaining registration between virtual patient data and live patient data using one or more calibration or registration phantoms in conjunction with maintaining registration using corresponding anatomic landmarks or surfaces between virtual patient data and live patient data. If synchronized registration is used, optionally, rules can be applied to resolve potential conflicts between a first and a second registration technique for registering virtual and live patient data.

For example, with an image and/or video capture system integrated into or attached to the OHMD or coupled to the OHMD, any change in the position, location or orientation of the surgeon's or operator's head or body will result in a change in the perspective view and visualized size and/or shape of the calibration or registration phantom. The change in perspective view and visualized size and/or shape of the calibration or registration phantom can be measured and can be used to determine the change in position, location or orientation of the surgeon's or operator's head or body, which can then be used to maintain registration between the virtual patient data and the live patient data, by moving the virtual patient data into a position, location, orientation and/or alignment that ensures that even with the new position location or orientation of the surgeon's or operator's head or body the registration is maintained and the virtual and the live patient data are, for example, substantially superimposed or matched where desired. Similarly, when more than one OHMD is used, e.g. one for the primary surgeon, a second OHMD for an assistant, a third OHMD for a resident, a fourth OHMD for a scrub nurse and a fifth OHMD for a visitor, with an image and/or video capture system integrated into or attached to each of the different OHMDs or coupled to each of the different OHMDs, any change in the position, location or orientation of the user's or viewer's head or body will result in a change in the perspective view and visualized size and/or shape of the calibration or registration phantom. The change in perspective view and visualized size and/or shape of the calibration or registration phantom can be measured and can be used to determine the change in position, location or orientation of the user's or viewer's head or body, which can then be used to maintain registration between the virtual patient data and the live patient data, by moving the virtual patient data into a position, location, orientation and/or alignment that ensures that even with the new position location or orientation of the user's or viewer's head or body the registration is maintained and the virtual and the live patient data are, for example, substantially superimposed or aligned or matched where desired, with substantially identical view angle of the virtual data of the patient seen by the viewer's left eye through the display of the OHMD unit and the live data of the patient seen by the viewer's left eye through the OHMD unit and substantially identical view angle of the virtual data of the patient seen by the viewer's right eye through the display of the OHMD unit and the live data of the patient seen by the viewer's right eye through the OHMD unit for each of the OHMDs used. In some embodiments of the invention, the calibration or registration phantom can be used to check the accuracy of an integrated or attached or coupled or separate image and/or video capture system.

In a further embodiment of the invention, the calibration or registration phantom can be used to calibrate an integrated or attached or coupled or separate image and/or video capture system.

In some embodiments, the calibration or registration phantom can be used to calibrate the IMU, e.g. for distance measurements, movement, distance to object, since calibration or registration phantom includes known geometries, e.g. known distances or angles.

Registration of Virtual Patient Data and Live Patient Data Accounting for Tissue Deformation In some embodiments of the invention, tissue deformation, a shape change or removal of tissue caused by the surgery or surgical instruments can be simulated in the virtual data. The resultant simulated virtual data can then be registered related to the live patient data, either before and/or after deformation, alteration of shape or removal of tissue of the live patient. The tissue deformation, shape change or removal of tissue caused by the surgery or surgical instruments can include the shape alteration or removal of one or more osteophytes or bone spurs or other bony anatomy or deformity. The virtual data of the patient and the live data of the patient can be registered in a common coordinate system, for example with one or more OHMDs. Virtual and physical surgical instruments and implant components can also be registered in the common coordinate system.

In some embodiments of the invention, the registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art. Re-registration of live patient data and virtual patient data can be particularly helpful if the surgical alteration or surgical step has led to some tissue deformation. For example, the re-registration can be performed by matching, superimposing, and/or registering tissues that have not been performed by the surgical step or surgical alteration. Alternatively, the re-registration can be performed by matching, superimposing and/or registering deformed live patient data, e.g. from surgically deformed tissue, with virtual patient data that simulate the same tissue deformation after the virtual surgical step, e.g. an osteophyte or tissue removal.

Registration of Virtual Patient Data and Live Patient Data at Multiple Time Points, for Example at Different Stages of a Surgical Procedure In some embodiments of the invention, registration of virtual patient data and live patient data can occur at multiple time points, for example during different phases of tissue removal or implantation of a medical device. For select or each time point, e.g. for select or all stages of the surgical procedure, the live data of the patient and the virtual data of the patient can be registered in a common coordinate system, for example with one or more OHMDs. Virtual and physical surgical instruments can also be registered in the common coordinate system.

In knee replacement surgery or hip replacement surgery, for example, registration of virtual patient data and live patient data can be performed using, for example, the femoral or tibial or acetabular surface shape or using femoral or tibial or acetabular landmarks prior to the resection of any tissue. Optionally pins or other rigid fixation markers can be placed, for example in an area that will not be surgically resected during at least part of the surgical procedure. The registration of virtual and live patient data can be repeated using different registration sites, surfaces or landmarks after tissue has been removed, e.g. after a burring of the articular surface has occurred or after a bone cut has been performed or after reaming has been performed or after one or more osteophytes or bone spurs or other bony anatomy or deformity have been removed. The registration can now occur to a newly created landmark, created by the surgical procedure, or, for example, a newly created surface, e.g. created by the surgical procedure. Such a newly created surface can be, for example, a planar surface on the residual femur or tibia created by a bone cut. Optionally implanted pins or rigid fixation markers can be used to aid with the registration of the virtual data after surgical alteration and the live data of the patient altered by the surgery. Thus, the current invention allows for multiple time point registration of virtual patient data and live patient data, for example by registered virtual patient data to the live patient data prior to surgical alteration and after one or more surgical alterations. In this manner, it is possible to re-register multiple times as surgical field changes.

The registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data Using CAD Files or Data or 3D Files or Data, e.g. of a Medical Device In some embodiments of the invention, a CAD file or CAD data of a medical device can be displayed by the OHMD and superimposed on live data of the patient. The CAD file or CAD data can be a medical device intended for use or implantation during the surgical procedure. Any type of CAD file or CAD data or any type of 3D file or 3D data of a medical device, a surgical instrument or an implantable device can be superimposed and registered in relationship to the live data of the patient including normal anatomy or pathologic tissue, e.g. one or more osteophytes or bone spurs or other bony anatomy or deformity or soft-tissue or neoplastic tissue or abnormality in a common coordinate system, for example with one or more OHMDs.

Physical surgical instruments and implant components can also be registered in the common coordinate system.

Medical devices can include non-biologic as well as biologic devices, e.g. tissue scaffolds, cells, cell matrices etc. that can be implanted in a human body.

In some embodiments of the invention, multiple CAD files and/or 3D files of virtual data can be superimposed onto the live data of the patient. For example, CAD files can be CAD files of a medical device available in different sizes or shapes. Virtual 2D or 3D data of the patient, for example obtained from a preoperative imaging test, can be superimposed onto live data of the patient, e.g. a surgical site. The surgeon can then optionally introduce a 3D CAD file of a medical device into the display by the OHMD. The surgeon can check the size or shape of the medical device in relationship to the virtual 2D or 3D data of the patient and/or the live data of the patient. If the surgeon is not satisfied with the projected size or shape of the medical device in relationship to the virtual 2D or 3D data of the patient and/or the live data of the patient, the surgeon can select a different CAD file of a medical device with a different size and/or shape, project the CAD file optionally onto the virtual 2D or 3D data of the patient and the live data of the patient in the OHMD display and repeat the process as many times as needed until the surgeon is satisfied with the resultant size or shape of the selected medical device in relationship to the virtual 2D or 3D data of the patient and/or the live data of the patient.

The registration of virtual patient data and live patient data using the techniques described herein can be repeated after one or more surgical steps have been performed. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art. For example, CAD files simulating the virtual surgical step or surgical alteration in the virtual patient data can be matched, superimposed or registered with live patient data after the physical surgical step or surgical alteration in the live patient. In this manner, live and virtual data can be re-registered after the surgical step or surgical alteration.

Registration of Virtual Patient Data and Live Patient Data Using Non-Anatomic Data Registration of virtual data of the patient and live data of the patient can be performed using data other than anatomic or pathologic structures. Registration can be performed, for example, based on motion data, kinematic data (for example to determine the center of rotation of a joint in the live data which can then be registered to an estimate or simulated center of rotation in the virtual data of the patient). Registration can be performed using metabolic data, for example using an area of high 18 FDG-PET uptake in a PET scan or PET-MRI or PET CT, which can be, for example matched to an area of increased body temperature in a target surgical site. Registration can be performed using functional data, e.g. using functional MRI studies. Virtual data and live data of the patient can be registered in a common coordinate system, for example with one or more OHMDs. Virtual and physical surgical instruments and implant components can also be registered in the common coordinate system.

Optionally, different types of data, e.g. anatomic, motion, kinematic, metabolic, functional, temperature and/or vascular flow data can be used alone or in combination for registered virtual and live data of the patient.

The registration of virtual patient data and live patient data using the techniques described herein can be repeated after one or more surgical steps have been performed using non-anatomic data. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient, optionally using non-anatomic data. The matching, superimposing and/or registering of the live data of the patient and the virtual data of the patient after the surgical tissue alteration can be performed using the same techniques described in the foregoing or any of the other registration techniques described in the specification or any other registration technique known in the art.

Registration of Virtual Patient Data and Live Patient Data after Performing One or More Surgical Alterations to the Tissue or the Surgical Site In some embodiments of the invention, the registration of virtual patient data and live patient data using the techniques described herein can be repeated after one or more surgical steps have been performed and virtual data and live data of the patient can be registered in a common coordinate system after select steps or each surgical step or tissue alteration, for example with one or more OHMDs. Virtual and physical surgical instruments and implant components can also be registered in the common coordinate system after select steps or each surgical step or tissue alteration. The surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art.

The matching, superimposing and/or registering of the live data of the patient and the virtual data of the patient after the surgical tissue alteration can be manual, semi-automatic or automatic using information about the surgically altered tissue or tissue surface or tissue contour or tissue perimeter or tissue volume or other tissue features. Automated re-registration can, for example, be performed using an image and/or video capture system integrated into, attached to or separate from the OHMD which can capture information about the surgically altered tissue or tissue surface or tissue contour or tissue perimeter or tissue volume or other tissue features in the live patient data after the surgical alteration and compare the information to information in the virtual data of the patient, e.g. for the virtual data after performing the comparable step in a virtual surgical plan.

The surgical alteration or surgical steps can include, but are not limited to the procedures in Table 6:

TABLE 6: Exemplary surgical alterations or steps applied to various patient tissues, e.g. bone, cartilage, ligaments, tendons, joint capsule, skin, fat, organ tissue, e.g. liver, spleen, kidney, intestines, gallbladder, lung, heart, thyroid, brain etc.
Cutting, e.g. a bone cut
Sawing, e.g. sawing a bone with a saw
Milling, e.g. milling a bone with a mill
Reaming, e.g. reaming a bone with a reamer
Impacting, e.g. impacting a bone with an impactor
Drilling, e.g. drilling a bone with a drill
Pinning, e.g. pinning a bone with a pin
Radiofrequency ablation
Heat ablation
Cryoablation
Cauterization
Tissue resection
Tissue removal
Resection of a neoplasm
Fracture fixation
Trauma repair
Trauma reconstruction
Soft-tissue repair
Soft-tissue reconstruction
Tissue grafting
Placement of a registration marker or calibration phantom on the tissue surface or inside the tissue
Placement of a surgical instrument, e.g. a pin or a saw
Placement of a medical implant or a component thereof, e.g. a biopsy needle, pedicle needle, pedicle screw, a spinal rod, a component of a knee replacement system, a component of a hip replacement system, a component of a shoulder replacement system, a component of an ankle replacement system
Placement/injection of bone cement or other substances, hardening or non hardening
Placement of a trial implant
Placement of a tissue graft
Placement of a tissue matrix
Placement of a transplant
Placement of a catheter, e.g. an indwelling catheter
Placement or injection of cells, e.g. stem cells
Injection of a drug Optionally, the registration procedures described herein can be repeated after performing a surgical step. Optionally, the registration procedures described herein can be repeated after multiple surgical steps. Optionally, the registration procedures described herein can be repeated after each surgical step. Optionally, the registration procedures described herein can be repeated after major surgical steps. Optionally, the registration procedures described herein can be repeated when the surgeon wants to achieve high surgical accuracy. Optionally, the registration procedures described herein can be performed or repeated when the surgeon is concerned that the initial registration performed prior to the surgical step or surgical alteration was not accurate or is not accurate any longer or is affected by the surgical step or surgical alteration.

In some embodiments of the invention, the change on the patient's tissue induced by the surgical alteration or the surgical step can be known or estimated, for example as part of the virtual surgical plan using the virtual data of the patient. Surgical alterations and/or surgical steps applied to patient tissues can include any of the surgical alterations and/or surgical steps listed in the examples in Table 6, although any alteration to a patient's tissue known in the art can be included. The alteration and/or the change induced on the patient's tissue by the surgical alteration or surgical step can be estimated, for example in the virtual surgical plan and/or the virtual data of the patient. Exemplary changes induced on the patient's tissue by the surgical alteration or surgical step are tabulated in Table 7, which is only exemplary in nature and in no way meant to be limiting of the invention:

TABLE 7: Exemplary changes induced on the patient's tissue by a surgical alteration or surgical step. These changes can be induced in the live patient. These changes can also be planned/intended or simulated, e.g. for projection by one or more OHMDs, e.g. in a virtual surgical plan.
Change in tissue surface area
Change in tissue volume
Change in tissue surface shape
Change in tissue surface topography
Change in tissue perimeter (e.g. from uncut to cut surface, or from cut surface 1 to cut surface 2)
Change in tissue surface roughness
Change in tissue surface texture
Change in tissue surface color
Change in tissue surface reflexivity (e.g. reflected light or ultrasound)
Change in tissue surface area with different color (e.g. color change induced by surgical alteration)
Change in tissue surface perimeter, e.g. cut vs. uncut tissue surface
Change in tissue temperature
Change in tissue elasticity
Change in tissue composition, e.g. fat content (e.g. marrow fat on a cut bone surface)

Any of the foregoing changes can include all of the tissue or only a portion of the tissue. The embodiments of the invention can be directed towards all of the tissue or only partial tissue or portions of the tissue.

Following initial registration of the live data of the patient with the virtual data of the patient using any of the techniques described in the specification or known in the art, a first or any subsequent surgical alteration or surgical step can be performed inducing changes to the patient's tissue. The surgical alteration or surgical step can be performed with optional guidance through the OHMD display, e.g. by displaying one or more of virtual surgical tool, virtual surgical instrument including a virtual surgical guide or cut block, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

Once a surgical alteration or surgical step has been performed or induced on a patient's tissue in the live patient, the physical changes induced or the resultant tissue appearance and/or tissue properties/characteristics can be determined in the live data of the patient/the live patient. The physical changes induced or the resultant tissue appearance and/or tissue properties/characteristics can be determined in the live data of the patient/the live patient using any technique known in the art for assessing tissue appearance, tissue properties and/or characteristics including, for example, area, volume, shape, topography, roughness, texture, color, reflexivity, area with different color, perimeter, temperature, elasticity, and/or composition. For example, an image and/or video capture system integrated into, attached to or separate from an OHMD can be used to assess one or more of an area, shape, topography, roughness, texture, color, reflexivity, area with different color, perimeter, temperature, elasticity, and/or composition of a surgically altered tissue. Tissue probes, e.g. temperature probes, elasticity probes, can be used to assess characteristics and/or properties of the surgically altered tissue. Mechanical probes, e.g. with one or more attached optical markers, LEDs, infrared markers, retroreflective markers, RF markers, navigation markers and/or IMUs can be used to touch the tissue surface or perimeter and, for example, to circle a perimeter or to follow and assess a tissue topography of a surgically altered tissue.

Figure 6:
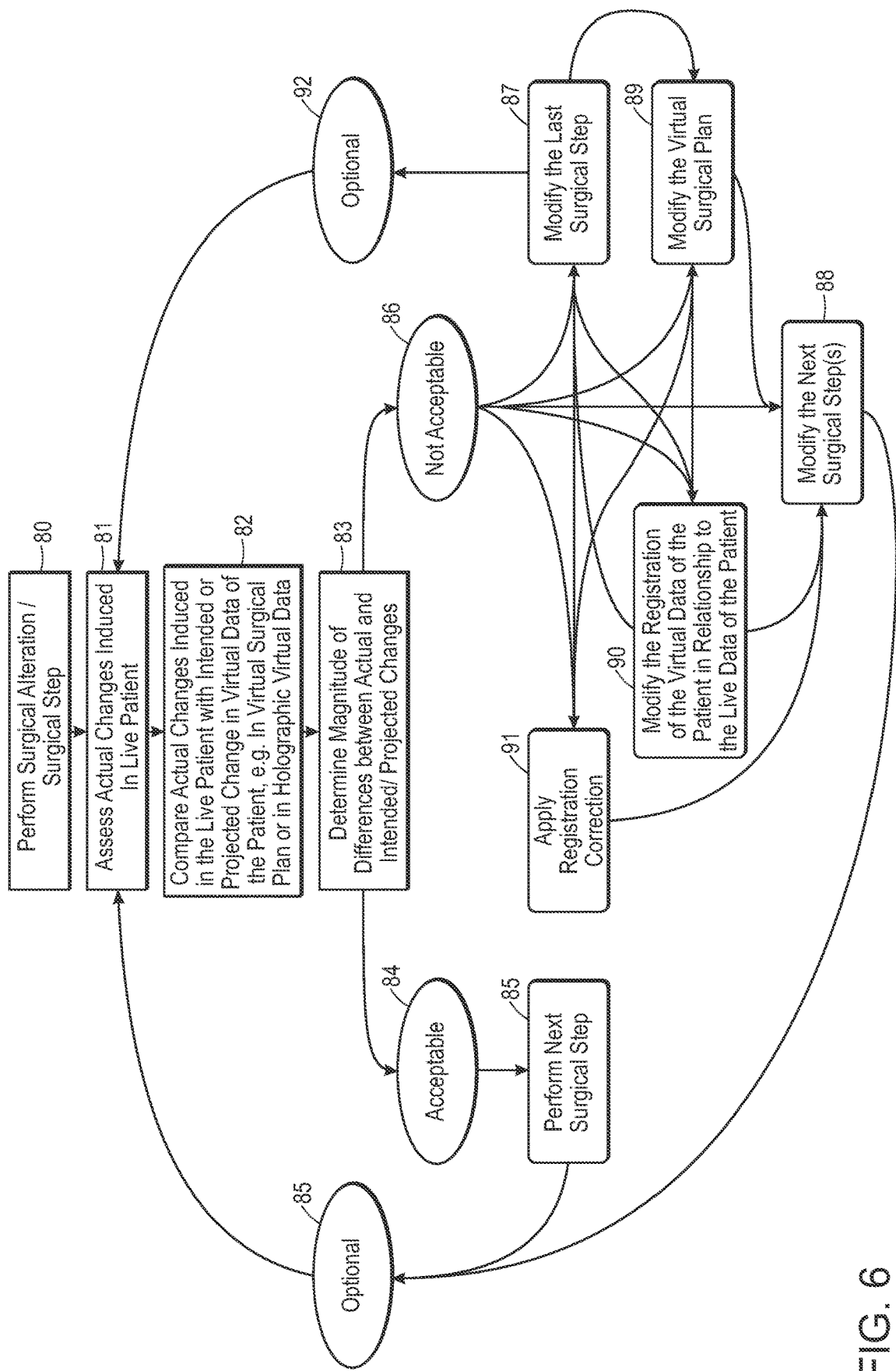
FIG. 6 is an illustrative flow chart that shows different methods of addressing inaccuracies between the changes induced by a surgical step and the intended, projected or predetermined changes in the virtual data of the patient according to some embodiments of the present disclosure.

The physical appearance, properties and/or characteristics of the surgically altered tissue can be assessed using any of the foregoing techniques or any of the techniques described in the specification or known in the art. The physical appearance, properties and/or characteristics of the surgically altered tissue can optionally be compared to the estimated or intended change or post-alteration appearance, e.g. surface area, volume, shape, topography, properties and/or characteristics of the tissue in the virtual data of the patient, for example the virtual surgical plan. If there are differences between the physical change in the physical surgically altered tissue and the virtually intended change in the virtually surgically altered tissue or if there are differences in the appearance, properties and/or characteristics of the physical surgically altered tissue and the virtually altered tissue, e.g. in the virtual data of the patient and/or the virtual surgical plan, the magnitude of the differences can be assessed: If the differences are deemed to be insignificant, for example, if they fall below an, optionally predefined, threshold in distance or angular deviation, the surgical procedure and subsequent surgical steps can continue as originally planned, e.g. in the virtual surgical plan. If the differences are deemed to be significant, for example, if they fall above an, optionally predefined, threshold in distance or angular deviation, the surgeon or the operator can have several options. The process and the options are also shown in illustrative form in FIG. 6: The surgeon can perform a surgical step 80. The surgeon can then assess the actual changes induced in the live patient 81. The surgeon can compare the actual changes induced in the live patient with the predetermined changes in the virtual data of the patient, e.g. in a virtual surgical plan or in a virtual 3D display 82. The magnitude of the difference(s) between the actual and the predetermined changes can be determined 83. If they are acceptable 84, the surgeon can perform the next surgical step 85. Optionally 85, the steps 81, 82, 83 can be repeated for the next surgical step. If the difference(s) between the actual and the predetermined changes are not acceptable 86, the surgeon has several means of addressing the difference(s), modify the last surgical step 87, modify the next surgical step 88, modify the virtual surgical plan 89, modify the registration of the virtual data of the patient in relationship to the live data of the patient 90, or apply registration correction 91. After the last surgical step has been modified 87, optionally 92, the steps 81, 82, 83 can be repeated for the next surgical step.

A). Modify the Last Surgical Step so that the physical appearance, physical properties and/or physical characteristics (including, for example, shape and dimensions, cut plane, perimeter of a cut plane/tissue plane, drill depth, angle, rotation, implant site etc.) of the surgically altered tissue in the live patient after the modification is more similar to and, optionally, more closely replicates the intended virtual appearance, virtual properties and/or virtual characteristics in the virtual data of the patient, e.g. a virtual surgical plan of the patient. This option can, for example, be chosen if the operator or surgeon is of the opinion that the last surgical step was subject to an inaccuracy, e.g. by a fluttering or deviating saw blade or a misaligned pin or a misaligned reamer or impactor or other problem, and should correct the inaccuracy. Once the modification has been completed, the surgeon or operator can again assess the physical change, physical appearance, physical properties and/or physical characteristics of the surgically altered tissue and compared it to the estimated or intended virtual change, virtual appearance, virtual properties and/or virtual characteristics of the tissue in the virtual data of the patient, for example the virtual surgical plan. Depending on the result of the assessment, the surgeon or operator can optionally repeat option A, or revert to options B or C.

B). Modify the Next Surgical Step(s) so that the physical appearance, physical properties and/or physical characteristics (including, for example, shape and dimensions, cut plane, perimeter of a cut plane/tissue plane, drill depth, angle, rotation, implant site etc.) of the surgically altered tissue in the live patient after the modification in the next surgical step(s) is more similar to and, optionally, more closely replicates the intended virtual appearance, virtual properties and/or virtual characteristics in the virtual data of the patient, e.g. a virtual surgical plan of the patient after the virtual modification in the next virtual surgical step(s). This option can, for example, be chosen if the operator or surgeon is of the opinion that the last surgical step was subject to an inaccuracy, e.g. by a fluttering or deviating saw blade or a misaligned pin or a misaligned reamer or impactor or other problem, and he or she should correct the inaccuracy in the next surgical step(s). Once the modification has been completed with the next surgical step(s), the surgeon or operator can again assess the physical change, physical appearance, physical properties and/or physical characteristics of the surgically altered tissue and compared it to the estimated or intended virtual change, virtual appearance, virtual properties and/or virtual characteristics of the tissue in the virtual data of the patient, for example the virtual surgical plan. Depending on the result of the assessment, the surgeon or operator can optionally repeat option A and/or B and/or revert to options C and/or D and/or E.

C). Modify the Virtual Surgical Plan of the patient so that the virtual appearance, virtual properties and/or virtual characteristics (including, for example, shape, volume and dimensions, cut plane, perimeter or surface/surface area of a cut plane/tissue plane, drill depth, angle, rotation, implant site etc.) of the surgically altered tissue in the virtual data of the patient after the modification is/are more similar to and, optionally, more closely replicates the physical appearance, physical properties and/or physical characteristics in the physical live data of the patient after the physical surgical alteration. This option can, for example, be chosen if the operator or surgeon is of the opinion that the last surgical step was accurate or accounted for unexpected variations in tissue conditions that were not accounted for in the virtual surgical plan. Such unexpected variations in tissue conditions can, for example, be ligament laxity or tightness as can be observed, for example, in knee replacement surgery or hip replacement or other joint replacement surgeries. If the modified surgical plan is modified in this manner, all subsequent virtual surgical steps can then be referenced off the last or preceding physical surgical step, thereby maintaining continuity of the procedure. The OHMD can then be used for projecting all or some of the subsequent virtual surgical steps, e.g. by projecting one or more of virtual surgical tool, virtual surgical instrument, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. The subsequent virtual surgical steps are thus modified to allow completion of the procedure and, optionally, placement of an implant or implant component or device or graft or transplant taking into account the one or more modified preceding physical surgical steps. Optionally, the modified subsequent virtual surgical steps can be further modified based on local tissue conditions/characteristics after the virtual or physical modification, for example, if subsequent surgical steps were to fall into a tissue void or would result in impairment of implant component placement.

D). Modify the Registration of the Virtual Data of the Patient in Relationship to the Live Data of the Patient. The operator or surgeon can optionally repeat the registration procedure using any of the techniques described in the specification or known in the art for registering the virtual data of the patient, including, for example the virtual surgical plan, in relationship to the live data of the patient after the physical surgical alteration. Once the virtual data of the patient and the live data of the patient after the surgical alteration have been re-registered, all subsequent virtual surgical steps displayed by the OHMD and any related virtual surgical plan can be referenced off the re-registration of the virtual and live data of the patient. For example, the OHMD can then be used after the re-registration for projecting all subsequent virtual surgical steps, e.g. by projecting one or more of virtual surgical tool, virtual surgical instrument, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

E). Apply Registration Correction. If there are differences between the physical change in the physical surgically altered tissue and the virtually intended change in the virtually surgically altered tissue or if there are differences in the appearance, properties and/or characteristics of the physical surgically altered tissue and the virtually altered tissue, e.g. in the virtual data of the patient and/or the virtual surgical plan, the magnitude of the differences can be assessed and can be used to apply a coordinate correction, coordinate adjustment or coordinate transfer of registration of the virtual data of the patient, including, optionally, the virtual surgical plan, and the live data of the patient, e.g. for any subsequent surgical steps or surgical procedures. For example, the OHMD can then project/display all subsequent virtual surgical steps using the coordinate correction or adjustment or transfer, e.g. by projecting one or more of virtual surgical tool, virtual surgical instrument including virtual surgical guide or cut block, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration using the coordinate correction, adjustment and/or transfer.

Any combinations of the foregoing Options A, B, C, D and/or E are possible.

If an image and/or video capture system is used to measure/capture the physical changes, e.g. change in surface/surface area, perimeter, perimeter shape, and/or shape of the cut surface or otherwise modified or altered surface, the data/images captured by the image and/or video capture system can be corrected for any angular distortion or projection, for example if the camera(s) is/are positioned at an angle other than 90 degrees relative to the cut surface or otherwise modified or altered surface. Similarly, the physical changes measured by the image and/or video capture system, e.g. the size of the surface/surface area, perimeter, perimeter shape, and/or shape of the cut surface or otherwise modified or altered surface, can be corrected or adjusted for the distance between the camera or image and/or video capture system and the changed surface/surface area, perimeter, perimeter shape, and/or shape of the cut surface or otherwise modified or altered surface. The angle and/or the distance of the image and/or video capture system to the physical changes, e.g. surface/surface area, perimeter, perimeter shape, and/or shape of the cut surface or otherwise modified or altered surface, can be assessed, for example, using one or more RF markers, optical markers, navigation markers including, but not limited to, infrared markers, retroreflective markers, RF markers, LEDs, and/or IMUs attached to the image and/or video capture system, and/or the OHMD, and/or the patient, and/or the cut, modified or altered surface.

For example, in a knee replacement, hip replacement or shoulder replacement procedure, a bone cut can be applied, optionally using virtual guidance of a bone saw by the OHMD, to a distal femur, proximal tibia, proximal femur or proximal humerus. The position, alignment and/or orientation of the bone cut, including, optionally, the surface/surface area, perimeter, perimeter shape, and/or shape of the cut surface can then be assessed in the live patient, for example using an image and/or video capture system integrated into, attached to or separate from the OHMD or using one or more probes, optionally with one or more attached optical markers, navigation markers including, but not limited to, infrared markers, retroreflective markers, RF markers, LEDs, or IMUs.

If the physical position, alignment, orientation, surface, surface area, perimeter, perimeter shape, and/or shape of the cut surface differ from the virtually intended/projected position, alignment, orientation, surface, surface area, perimeter, perimeter shape, and/or shape of the cut surface, the software can, optionally, determine a virtually modified position, alignment, orientation, surface, surface area, perimeter, perimeter shape, and/or shape of the cut surface that would more closely resemble the physical position, alignment, orientation, surface, surface area, perimeter, perimeter shape, and/or shape of the cut surface. The difference in coordinates between the virtually modified position, alignment, orientation, surface, surface area, perimeter, perimeter shape, and/or shape of the cut surface and the physical position, alignment, orientation, surface, surface area, perimeter, perimeter shape, and/or shape of the cut surface can then be used to determine any coordinate correction, adjustment or transfer for subsequent virtual surgical steps. The coordinate correction, adjustment or transfer can then by applied to the OHMD displays, for example when the OHMD displays in any subsequent surgical steps one or more of virtual surgical tool, virtual surgical instrument, virtual trial implant, virtual implant component, virtual implant or virtual device, all optionally selected from a virtual library, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration using the coordinate correction, adjustment and/or transfer.

The following is an exemplary description of a portion of a hip replacement procedure shown in the illustrative example in FIG. 7A-H, where the surgeon elects to make a correction to the proximal femoral cut prior to proceeding with the subsequent steps of the procedure. This example is in no way meant to be limiting, but only illustrative of certain aspects of the invention.

FIG. 7A shows a view of a predetermined femoral neck 95 cut or a virtual surgical plan, as optionally displayed by an OHMD in 2D or 3D, stereoscopic or non-stereoscopic, including using a digital holographic representation with a system such as a Microsoft Hololens (Microsoft, Redmond, Wash.). The OHMD can display a virtual predetermined path or plane (broken line) 96 for a saw blade selected to make the proximal femoral cut in this example. The OHMD can also display a digital hologram of the virtual femoral neck cut. The virtual projected path for a physical saw blade to make the proximal femoral neck cut and the virtual femoral neck cut can be the same; they can also be different, for example accounting for the thickness of the saw blade. For example, if a saw blade thickness is 2.0 mm, the predetermined path can be moved, e.g. in a proximal femur for hip replacement proximally, 1.00 mm or more to account for bone lost from the sawing so that the virtual femoral bone cut accounts for the bone lost by the sawing.

The display of the predetermined path can be in 2D or in 3D, stereoscopic or non-stereoscopic. The surgeon can align the physical saw blade with the predetermined path and the surgeon can then advance the saw blade while keeping the saw blade substantially aligned with the predetermined path as shown by the OHMD. Rather than display the predetermined path, the OHMD can also display a virtual bone saw aligned to make the virtual bone cut (optionally accounting for bone lost from the cutting or sawing) and the surgeon can align the physical bone saw with the virtual bone saw and make the cut.

FIG. 7B shows a cross-section or top view of the intended virtual femoral neck cut (broken outline) 97, for example as developed in the virtual surgical plan. The perimeter and/or cross-section and/or surface area and/or shape of the virtually cut femur, for example simulated using data from a pre-operative imaging study of the patient, e.g. CT or MRI, is relatively round in this example with slightly greater diameter in medial-lateral direction.

FIG. 7C shows the physical femoral neck cut 98 made in the live patient (straight solid line). The physical femoral neck cut is not aligned with the virtually projected or intended path for the saw blade and it is not aligned with the virtual femoral neck cut, for example in the virtual surgical plan, in this example. This can happen for various reasons in live surgery, for example unexpectedly sclerotic areas of bone that cause saw blade deviation. The difference in alignment between the virtually intended bone cut and the physical femoral bone cut can be difficult to detect for the surgeon intraoperatively, for example if the surgical field is small and deep seated, obscured or hidden or has limited lighting or if only a small portion of the cut bone is exposed.

FIG. 7D shows the top view or cross-section of the physical femoral neck cut (solid outline) 99. The perimeter and/or cross-section and/or surface area and/or shape of the physical femoral neck cut is different than the perimeter and/or cross-section and/or surface area and/or shape of the virtually planned cut femur. It is more elliptical or oblong in medial-lateral direction. The perimeter and/or cross-section and/or surface area and/or shape of the physical cut proximal femur can be detected, for example using an image and/or video capture system integrated into, attached to or separate from the OHMD or using a mechanical or optical probe, for example using RF, optical, navigation and other markers. It can then be compared to the perimeter and/or cross-section and/or surface area and/or shape of the virtual cut surface.

In FIG. 7E, once the perimeter and/or cross-section and/or surface area and/or shape of the physical cut proximal femur has been detected, for example using an image and/or video capture system integrated into, attached to or separate from the OHMD or using a mechanical or optical probe, for example using RF, optical, navigation and other markers, a corresponding perimeter and/or cross-section and/or surface area and/or shape of the physical cut proximal femur can be identified in the virtual data of the patient (broken outline) 100, for example using image processing algorithms known in the art.

In FIG. 7F, once the corresponding perimeter and/or cross-section and/or surface area and/or shape has been identified in the virtual data of the patient (FIG. 7E), a new, substitute virtual femur cut 101 which approximates the intended femoral cut can be identified in the virtual data of the patient. The difference in position, location, orientation, coronal, sagittal, axial angle/angulation between the originally planned or predetermined virtual femoral bone cut and the substitute, new virtual femoral bone cut can be determined. Depending on the severity and/or clinical significance of the difference between the originally planned or predetermined virtual femoral bone cut 96 and the substitute, new virtual femoral bone cut 101, corresponding to the physical femoral bone cut 98 executed in the patient, the surgeon can then decide or chose between or combine any of the preceding Options A-E, e.g. modify the last surgical step, modify the next surgical step(s), modify the virtual surgical plan of the patient, modify the registration of the virtual data of the patient in relationship to the live data of the patient, and/or apply registration correction or combinations thereof.

In FIG. 7G, the surgeon can elect to modify the last surgical step and correct the proximal femoral cut by applying a correction in the alignment and direction of the saw blade. The resultant corrected physical proximal femoral bone cut 102 can then closely approximate the originally intended, virtually planned, projected proximal femoral bone cut 97.

FIG. 7H shows that the perimeter and/or cross-section and/or surface area and/or shape of the corrected physical proximal femoral bone cut 103 approximates the perimeter and/or cross-section and/or surface area and/or shape of the original virtually planned proximal femoral bone cut.

In the example of a knee replacement, it is not uncommon that the distal femoral cut is not falling onto its intended location. For example, dense sclerotic bone underneath the arthritic area can cause a saw blade to deflect, thereby changing the angulation of the distal femoral cut. Once the distal femoral cut has been completed, the perimeter and/or cross-section and/or surface area and/or shape of the physical cut distal femoral bone can be assessed, for example using an image and/or video capture system integrated into, attached to or separate from the OHMD and/or using a laser scanner and/or 3D scanner and/or using one or more probes which can, for example, touch and/or follow the cut femoral bone optionally with one or more attached optical markers, LEDs, navigation markers including, but not limited to, infrared markers, retroreflective markers, RF markers, and/or IMUs. The perimeter and/or cross-section and/or surface area and/or shape of the of the physical cut distal femoral bone in the live patient can then be compared to the perimeter and/or cross-section and/or surface area and/or shape of the of the virtual cut distal femoral bone, for example in the virtual surgical plan of the patient. The perimeter and/or cross-section and/or surface area and/or shape of the physical cut distal femoral bone can be used to identify a corresponding perimeter and/or cross-section and/or surface area and/or shape of the virtual distal femoral bone or a corresponding virtual cut plane in the virtual data of the patient that can yield a similar perimeter and/or cross-section and/or surface area and/or shape of the virtual distal femoral bone.

If the difference between the physical cut distal femoral bone and the virtual cut distal femoral bone is below a certain threshold, e.g. 1, 2, 3 or more millimeter in cut depth from the distal femoral surface, and/or 1 degree, 2 degrees, 3 degrees or more in angulation, the surgery can proceed as originally planned. If the difference between the physical cut distal femoral bone and the virtual cut distal femoral bone is above a certain threshold, e.g. 1, 2, 3 or more millimeter in cut depth from the distal femoral surface, and/or 1 degree, 2 degrees, 3 degrees or more in angulation, the surgeon or operator can then decide or chose between the preceding Options A-E, e.g. modify the last surgical step, e.g. recut the distal femoral bone, optionally with use of thicker tibial inserts to compensate for the greater bone loss or a reduced tibial cut depth, modify one of the next surgical steps, e.g. cut the tibia to account for greater or lesser femoral bone loss and/or different femoral component angulation (e.g. in the sagittal plane or in the coronal plane (e.g. with different femoral mechanical axis alignment optionally corrected on the tibial side with different tibial mechanical axis alignment), modify the virtual surgical plan of the patient, modify the registration of the virtual data of the patient in relationship to the live data of the patient, and/or apply registration correction or combinations thereof.

Figure 8A:
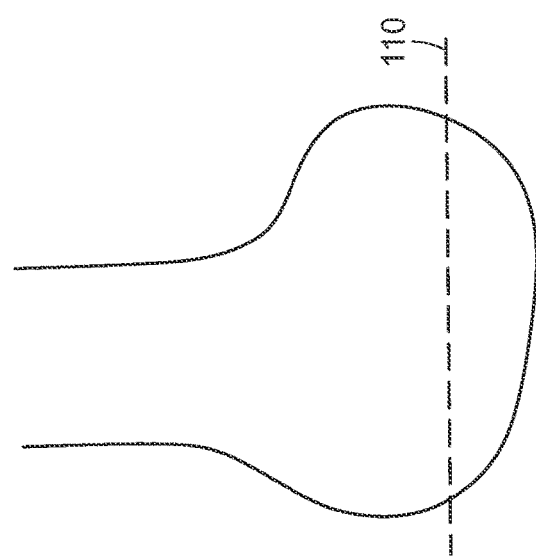
FIGS. 8A-8H depict illustrative examples of a distal femoral cut and techniques to correct a distal femoral cut according to some embodiments of the present disclosure.

FIG. 8A shows a predetermined distal femoral cut, for example as part of a view of virtual surgical plan, as optionally displayed by OHMD in 2D or 3D, non-stereoscopic or stereoscopic. The OHMD can display a virtual intended path or plane 110 for a physical saw blade selected to make the distal femoral cut in this example. The virtual/projected path or plane for the physical saw blade to make the distal femoral cut and the virtual distal femoral cut can coincide; they can also be different, for example accounting for the thickness of the saw blade. For example, if a saw blade thickness is 2.0 mm, the predetermined path can be moved, e.g. in a distal femur for knee replacement proximally, 1.00 mm or more to account for bone lost from the sawing so that the virtual femoral bone cut accounts for the bone lost by the sawing.

The display of the predetermined path can be in 2D or in 3D, stereoscopic or non-stereoscopic. The surgeon can align the physical saw blade with the predetermined path and the surgeon can then advance the saw blade while keeping the saw blade substantially aligned with the predetermined path or plane as shown by the OHMD. Rather than display the predetermined path or plane, the OHMD can also display a virtual bone saw aligned to make the virtual bone cut (optionally accounting for bone lost from the cutting or sawing) and the surgeon can align the physical bone saw with the virtual bone saw and make the cut.

Figure 8C:
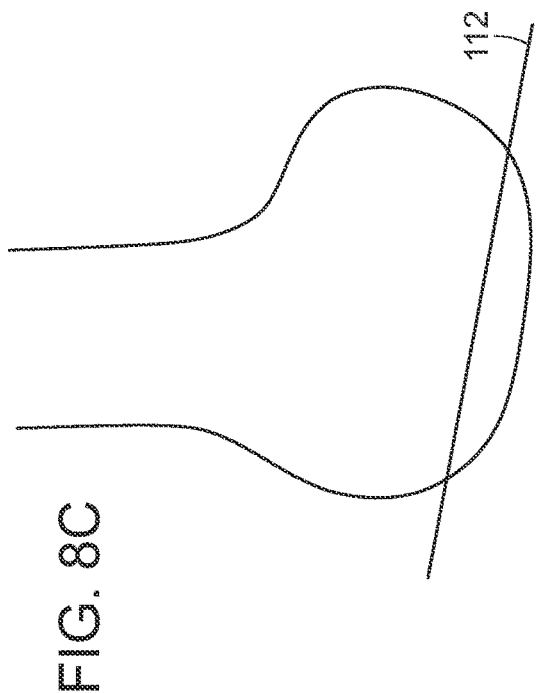
Figure 8B:
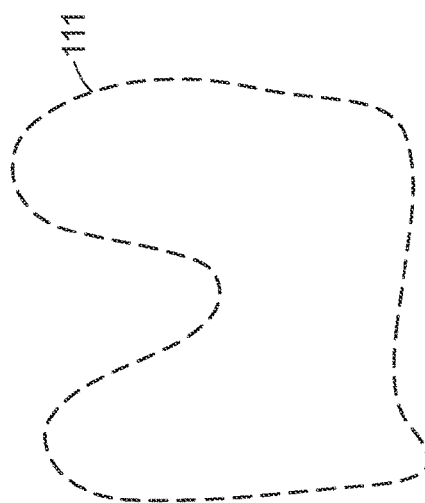

FIG. 8B shows a cross-section or view of the intended virtual distal femoral cut 111, for example as developed in the virtual surgical plan. The perimeter and/or cross-section and/or surface area and/or shape of the virtually cut femur, for example simulated using data from a pre-operative imaging study of the patient, e.g. CT or MRI or ultrasound or x-rays, is shown.

FIG. 8C shows the physical distal femoral cut made in the live patient 112. The physical distal femoral cut is not aligned with the virtually predetermined path for the saw blade and it is not aligned with the virtual distal femoral cut in the virtual surgical plan in this example. This can happen for various reasons in live surgery, for example unexpectedly sclerotic areas of bone that cause saw blade deviation. The difference in alignment between the virtually intended bone cut and the physical femoral bone cut can be difficult to detect for the surgeon intraoperatively.

Figure 8D:
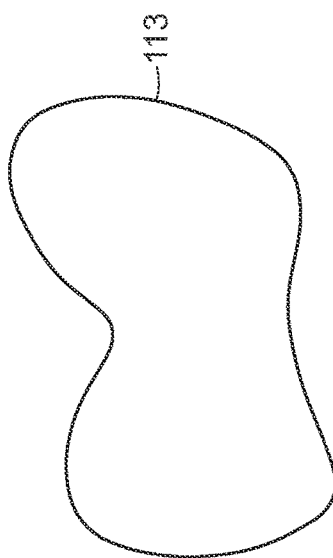

FIG. 8D shows the view or cross-section of the physical distal femoral cut 113. The perimeter and/or cross-section and/or surface area and/or shape of the physical distal femoral cut is different than the perimeter and/or cross-section and/or surface area and/or shape of the virtually planned cut femur. The perimeter and/or cross-section and/or surface area and/or shape of the physical cut distal femoral cut can be detected, for example using an image and/or video capture system integrated into, attached to or separate from the OHMD or using a mechanical or optical probe, for example using RF, optical, navigation and other markers. It can then be compared to the perimeter and/or cross-section and/or surface area and/or shape of the virtual cut surface.

Figure 8E:
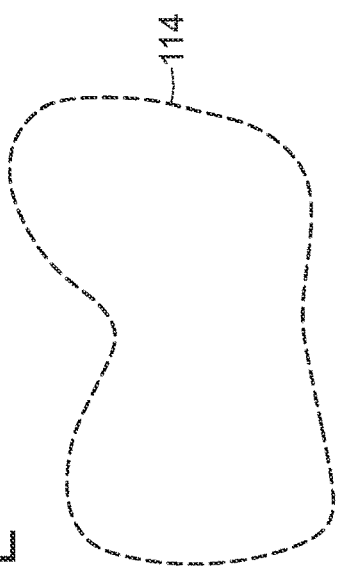

FIG. 8E. Once the perimeter and/or cross-section and/or surface area and/or shape of the physical cut distal femur has been detected, for example using an image and/or video capture system integrated into, attached to or separate from the OHMD or using a laser scanner and/or 3D scanner or using a mechanical or optical probe, for example using RF, optical, navigation and other markers, a corresponding perimeter and/or cross-section and/or surface area and/or shape of the physical cut distal femur can be identified in the virtual data of the patient 114, for example using image processing algorithms known in the art.

Figure 8G:
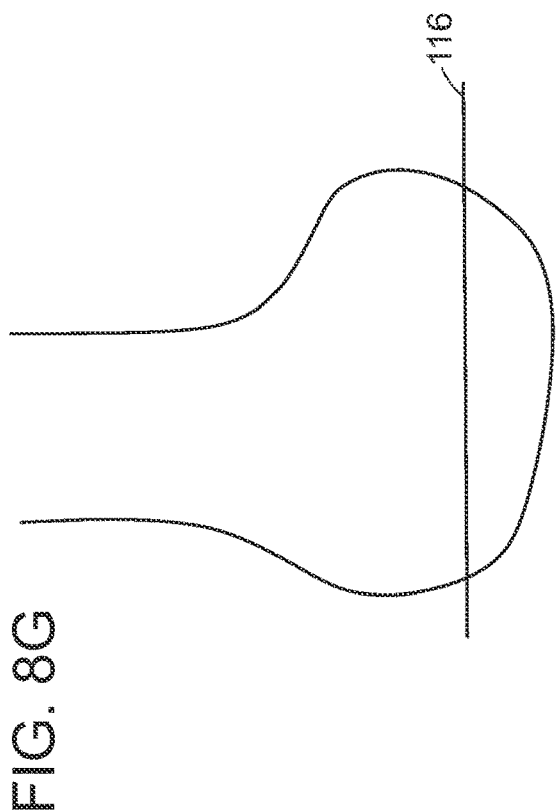
Figure 8F:
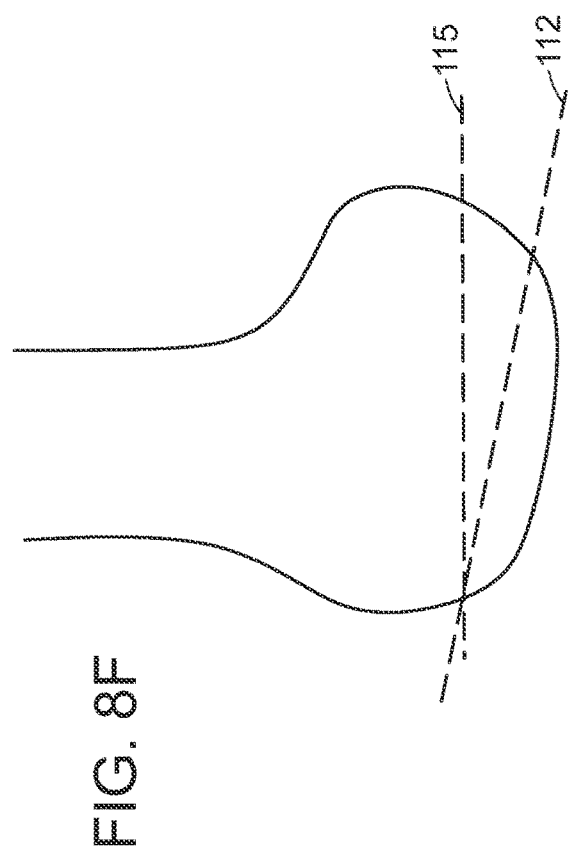

FIG. 8F. Once the corresponding perimeter and/or cross-section and/or surface area and/or shape has been identified in the virtual data of the patient (FIG. 8E), a new, substitute virtual femur cut which approximates the physical femoral cut can be identified 115 in the virtual data of the patient. The difference in position, location, orientation, coronal, sagittal, axial angle/angulation between the originally planned/predetermined virtual femoral bone cut and the substitute, new virtual femoral bone cut can be determined. Depending on the severity and/or clinical significance of the difference between the originally planned or predetermined virtual femoral bone cut and the physical femoral bone cut executed in the patient, the surgeon can then decide or chose between or combine any of the preceding options A-E, e.g. modify the last surgical step, modify the next surgical step(s), modify the virtual surgical plan of the patient, modify the registration of the virtual data of the patient in relationship to the live data of the patient, and/or apply registration correction or combinations thereof.

FIG. 8G The surgeon can elect to modify the last surgical step and correct the distal femoral cut by applying a correction in the alignment and direction of the saw blade, which can be, for example, in the sagittal plane (as shown in this example) or in the coronal plane if the physical cut was misaligned in the coronal plane. The resultant corrected physical distal femoral bone cut 116 can then closely approximate the originally intended, virtually planned, projected distal femoral bone cut.

Figure 8H:
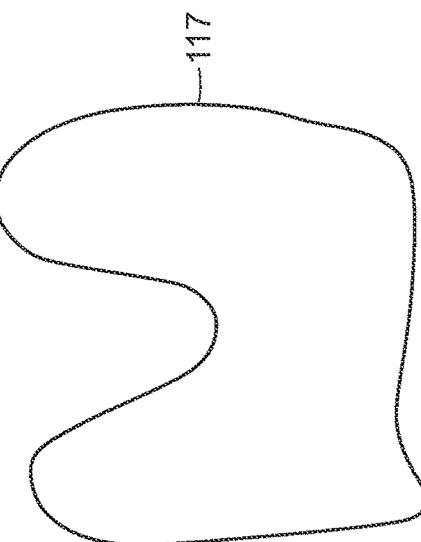

FIG. 8H shows that the perimeter and/or cross-section and/or surface area and/or shape of the corrected physical distal femoral bone cut 117 approximates the perimeter and/or cross-section and/or surface area and/or shape of the original virtually planned distal femoral bone cut.

For example, if the comparison of the perimeter and/or cross-section and/or surface area and/or shape of the physical cut distal femoral bone with the perimeter and/or cross-section and/or surface area and/or shape of the virtually planned cut distal femoral bone and, for example, the optional identification of a new virtual cut plane that corresponds in the virtual data to the physical distal femoral cut show that the difference in location, position, orientation and/or angulation between the virtual planned distal femoral cut and the physical femoral cut exceeds a threshold value, e.g. 3 degrees more angulation in flexion direction and/or 2 mm greater cut depth (i.e. more bone removal), then the surgeon can modify the registration of the live data of the patient (e.g. the perimeter and/or cross-section and/or surface area and/or shape of the physical distal cut distal femoral bone) with the virtual data of the patient by registering the corresponding virtual cut plane with the physical cut plane and the surgeon or the software can modify the virtual surgical plan. The modifications to the virtual surgical plan can, in this example, include that the angulation of the anterior femoral cut, posterior femoral cuts and the chamfer cuts will be changed to align with the distal femoral cut consistent with the dimensions and angulation of the planar surfaces of the femoral implant component in order to avoid a gap between the implant and the bone or an area where the remaining physical cut bone is too wide, which may result in the bone being too wide in select areas, wider than the implant dimensions thereby not accepting the implant. If a femur first technique is used, the modifications of the virtual surgical plan can also include that the cut height or depth of the proximal tibial cut and the cut angulation of the proximal tibial cut be adjusted, for example by cutting less tibia and by changing the slope of the cut to account for a more flexed femoral component and to maintain better soft-tissue/ligament balance accounting for the different physical distal femoral cut. These adjustments to the virtual surgical plan can optionally be displayed by the OHMD, e.g. by displaying one or more virtual corrected or adjusted anterior, posterior, chamfer cuts, and/or by displaying one or more corrected or adjusted proximal tibial cut(s) with a corrected or adjusted cut height/depth and/or corrected or adjusted tibial slope and/or corrected or adjusted tibial varus or valgus angle. The OHMD can display the virtually corrected or adjusted intended/projected path of the saw blade or surgical instrument, the virtually corrected or adjusted intended/projected cut planes, or the virtually corrected or adjusted intended/projected axes of the saw blade and/or power tools.

The following is another example, where the surgeon inadvertently mis-directs the femoral cut, with the assistance of the OHMD and an integrated or attached or separate image and/or video capture system detects the femoral miscut and then decides to perform the necessary correction(s) in a subsequent surgical step on the tibial side.

Figures 9C, 9D:
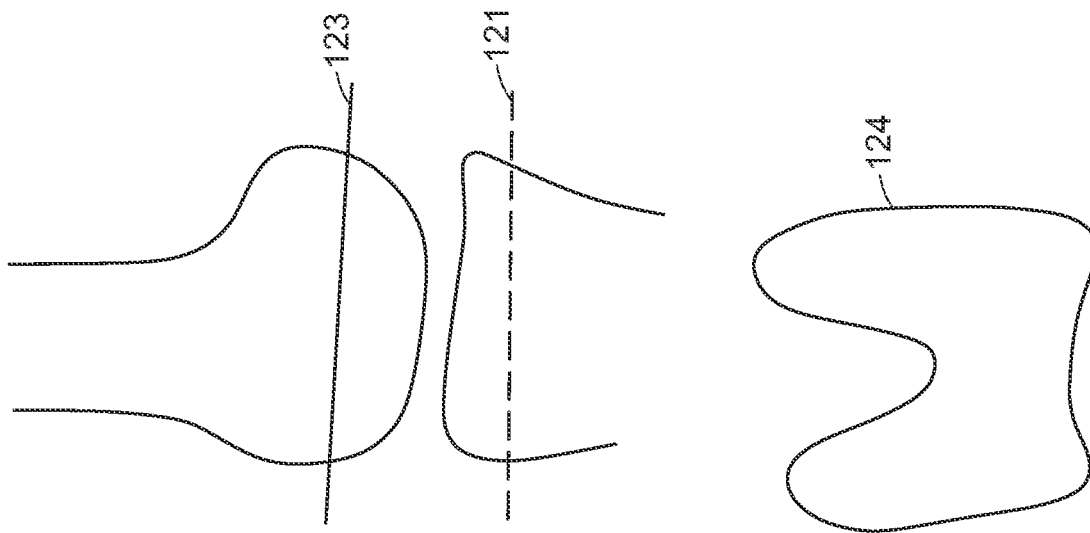
FIGS. 9A-9G depict illustrative examples of a distal femoral cut and techniques to correct a distal femoral cut according to some embodiments of the present disclosure.
Figures 9A, 9B:
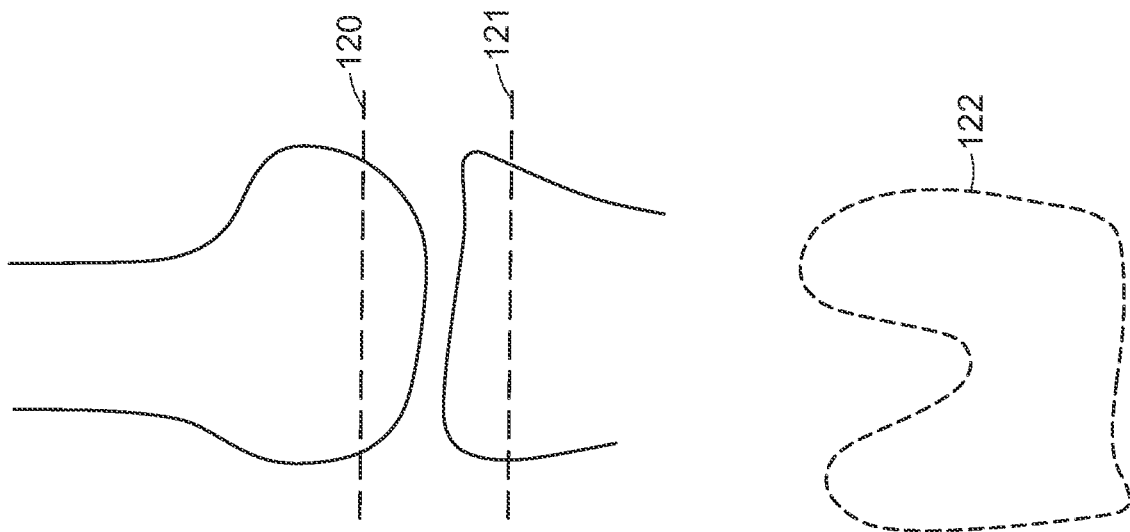

FIG. 9A shows a predetermined distal femoral cut and proximal tibial cut, for example as part of a view of a virtual surgical plan, as optionally displayed by OHMD in 2D or 3D, non-stereoscopic or stereoscopic. The OHMD can display a virtual predetermined path for a physical saw blade selected to make the distal femoral cut 120 and the proximal tibial cut 121 in this example. The OHMD can also display the virtual distal femoral and/or proximal tibial cut. The cut location can be adjusted for the thickness of the saw blade.

The display of the predetermined path can be in 2D or in 3D, non-stereoscopic or stereoscopic. The surgeon can align the physical saw blade with the predetermined path and the surgeon can then advance the saw blade while keeping the saw blade substantially aligned with the predetermined path as shown by the OHMD. Rather than display the predetermined path, the OHMD can also display a virtual bone saw aligned to make the virtual bone cut (optionally accounting for bone lost from the cutting or sawing) and the surgeon can align the physical bone saw with the virtual bone saw and make the cut.

FIG. 9B shows a cross-section or view of the intended virtual distal femoral cut 122, for example as developed in the virtual surgical plan. The perimeter and/or cross-section and/or surface area and/or shape of the virtually cut femur, for example simulated using data from a pre-operative imaging study of the patient, e.g. CT or MRI or ultrasound is visible.

FIG. 9C shows the physical distal femoral cut 123 made in the live patient. The physical distal femoral cut 123 is not aligned with the virtually predetermined path for the saw blade and it is not aligned with the virtual distal femoral cut 120 in the virtual surgical plan in this example. This can happen for various reasons in live surgery, for example unexpectedly sclerotic areas of bone that cause saw blade deviation. The difference in alignment between the virtually intended bone cut and the physical femoral bone cut can be difficult to detect for the surgeon intraoperatively. Broken line indicates predetermined tibial cut based on virtual surgical plan.

FIG. 9D shows the view or cross-section of the physical distal femoral cut 124. The perimeter and/or cross-section and/or surface area and/or shape of the physical distal femoral cut is different than the perimeter and/or cross-section and/or surface area and/or shape of the virtually planned cut femur 122. The perimeter and/or cross-section and/or surface area and/or shape of the physical cut distal femur can be detected, for example using an image and/or video capture system integrated into, attached to or separate from the OHMD or using a laser scanner and/or 3D scanner or using a mechanical or optical probe, for example using RF, optical, navigation and other markers. It can then be compared to the perimeter and/or cross-section and/or surface area and/or shape of the virtual cut surface.

Figure 9G:
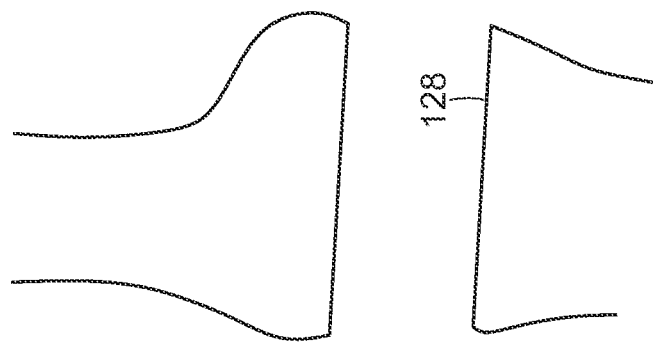
Figure 9E:
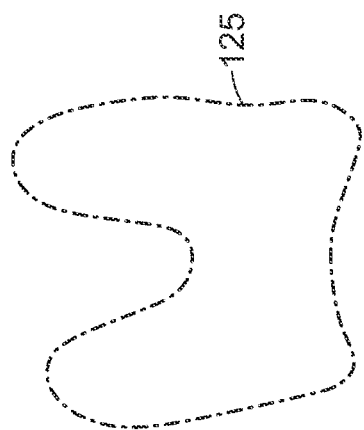

In FIG. 9E, once the perimeter and/or cross-section and/or surface area and/or shape of the physical cut distal femur has been detected, for example using an image and/or video capture system integrated into, attached to or separate from the OHMD or using a laser scanner and/or 3D scanner or using a mechanical or optical probe, for example using RF, optical, navigation and other markers, a corresponding perimeter and/or cross-section and/or surface area and/or shape of the physical cut distal femur can be identified in the virtual data of the patient 125, for example using image processing algorithms known in the art.

Figure 9F:
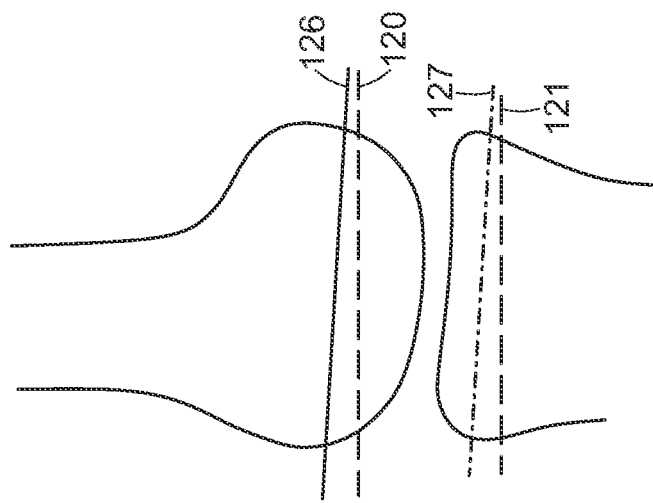

In FIG. 9F, once the corresponding perimeter and/or cross-section and/or surface area and/or shape has been identified in the virtual data of the patient (FIG. 9E), a new, substitute virtual femur cut can optionally be identified 126 in the virtual data of the patient. The difference in position, location, orientation, coronal, sagittal, axial angle/angulation between the originally planned or predetermined virtual femoral bone cut 120 and the new, substitute femoral bone cut 126 can be determined. Depending on the severity and/or clinical significance of the difference between the originally planned or predetermined virtual femoral bone cut and the physical femoral bone cut, the surgeon can decide or chose between or combine any of the preceding Options A-E, e.g. modify the last surgical step, modify the next surgical step(s), modify the virtual surgical plan of the patient, modify the registration of the virtual data of the patient in relationship to the live data of the patient, and/or apply registration correction or combinations thereof. In this example, the surgeon is electing to modify the next surgical step(s) by changing the angulation of the virtual tibial cut(s) from its original orientation 121 to a new orientation 127 that can optionally, at least partially, correct the overall alignment for the femoral mis-cut.

In FIG. 9G, the surgeon can elect to modify the next surgical step(s) and, in this example, change the proximal tibial cut by applying a correction in the alignment and direction of the saw blade to execute on the new, virtually modified tibial cut. The modified virtual and the resultant physical proximal tibial bone cut 128 can be placed to at least partially correct for the femoral mis-cut.

if the comparison of the perimeter and/or cross-section and/or surface area and/or shape of the physical cut distal femoral bone with the perimeter and/or cross-section and/or surface area and/or shape of the virtually planned cut distal femoral bone and, for example, the optional identification of a new virtual cut plane that corresponds in the virtual data to the physical distal femoral cut shows that the physical distal femoral cut surface is more angled, e.g. 3 degrees or more, in coronal direction than intended in the virtual surgical plan and/or the virtually cut distal femoral surface as displayed by the OHMD, then the surgeon can modify the last surgical step by re-cutting the distal femoral bone to correct the error in coronal plane angulation and to avoid any varus/valgus misalignment. The virtual predetermined cut plane or the virtual predetermined path for the saw blade or the virtual predetermined axis of the saw blade and/or power instrument and/or the virtual saw blade and/or power instrument aligned/oriented for the correction of the last surgical step can optionally be displayed by the OHMD. Alternatively, the surgeon can elect to correct one or more of the next surgical step(s), e.g. in this example by changing the intended cut for the tibial plateau to correct for the femoral cut coronal plane misangulation. The surgeon can align in either example the physical saw blade or surgical instrument with one or more of the virtual predetermined cut plane or the virtual predetermined path for the saw blade or the virtual predetermined axis of the saw blade and/or power instrument and/or the virtual saw blade and/or power instrument.

Figure 10C:
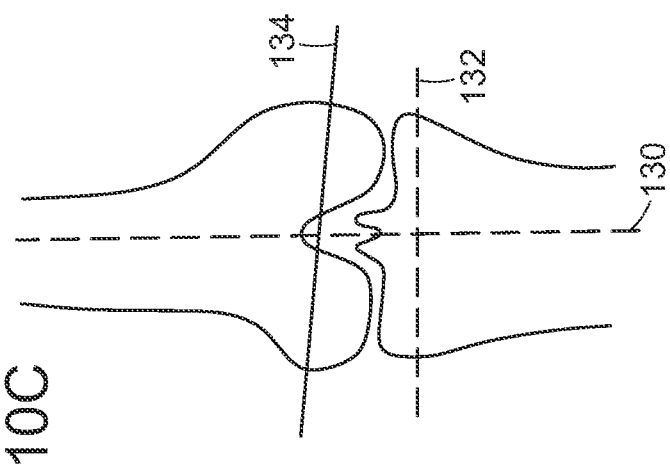
FIGS. 10A-10G depict illustrative examples of a distal femoral cut and proximal tibial cut and techniques to correct the cuts according to some embodiments of the present disclosure.
Figure 10D:
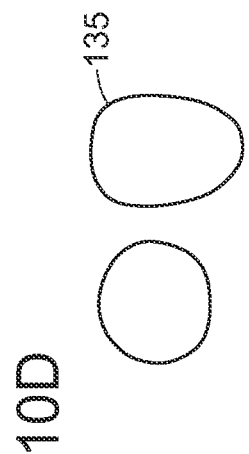
Figure 10A:
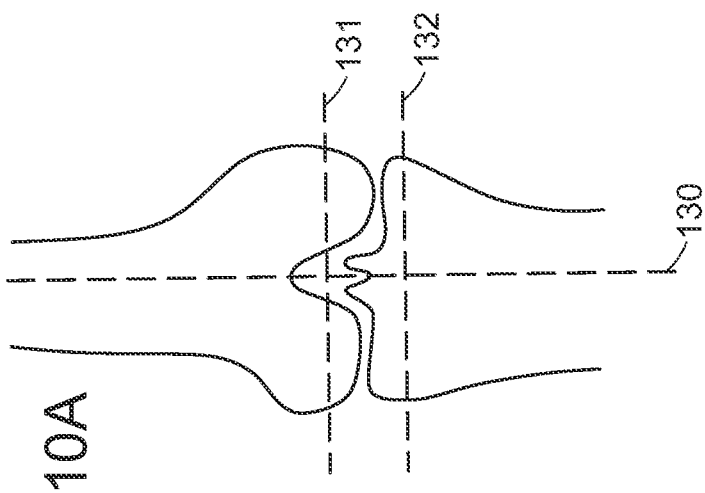

FIG. 10A shows a predetermined distal femoral cut and proximal tibial cut, for example as part of a view of a virtual surgical plan, as optionally displayed by OHMD in 2D or 3D, non-stereoscopic or stereoscopic. The OHMD can display a mechanical 130 or anatomic axis/axes of the knee, e.g. a femoral axis or a tibial axis, as well as various other kinematic or biomechanical axes, including a rotation axis of the knee. The virtual surgical plan can include the planning of femoral 131 and/or tibial 132 bone cuts that can be selected to correct any underlying mechanical axis deformity, e.g. varus or valgus deformity. For example, one or more of these bone cuts can be selected to be perpendicular to the patient's femoral or tibial mechanical axis. Alternatively, other alignments can be chosen and can be incorporated into the virtual surgical plan. For example, the medial femoral condyle surface, lateral femoral condyle surface and the medial tibial surface and lateral tibial surface can be optionally aligned with the patient's cartilage and/or subchondral bone or subchondral bone with an offset added to account for lost cartilage. The OHMD can display one or more virtual predetermined path (broken horizontal lines) for a physical saw blade selected to make the femoral cut and/or the tibial cut in this example. The OHMD can also display the virtual femoral and/or tibial cut. The virtual/projected path for a physical saw blade to make the femoral and/or tibial cut and the virtual femoral and/or tibial cut can be the same; they can also be different, for example accounting for the thickness of the saw blade. Rather than provide a virtual display of the predetermined path or plane, the OHMD can also display a virtual representation of a virtual bone saw or a 2D or 3D outline thereof aligned to make the virtual bone cuts (optionally accounting for bone lost from the cutting or sawing) and the surgeon can align the physical bone saw with the virtual bone saw or its 2D or 3D outline and make the cut.

Figure 10B:
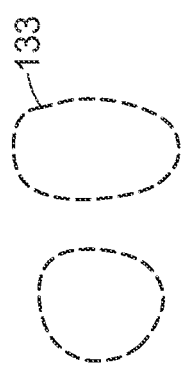

FIG. 10B shows a cross-section or view of the intended virtual femoral cut 133, for example as developed in the virtual surgical plan. The perimeter and/or cross-section and/or surface area and/or shape of the virtually cut femur, for example simulated using data from a pre-operative imaging study of the patient, e.g. CT or MRI or ultrasound, is relatively round in this example for the lateral condyle (left) and the medial condyle (right).

FIG. 10C shows the physical distal femoral cut made in the live patient 134. The physical femoral cut is not aligned with the virtually predetermined path for the saw blade and it is not aligned with the virtual femoral cut in the virtual surgical plan in this example. This can happen for various reasons in live surgery, for example unexpectedly sclerotic areas of bone or soft bone or osteoporotic bone that cause saw blade deviation.

FIG. 10D shows the view or cross-section of the physical femoral cut 135. The perimeter and/or cross-section and/or surface area and/or shape of the physical femoral cut is different than the perimeter and/or cross-section and/or surface area and/or shape of the virtually planned femoral cut. The perimeter and/or cross-section and/or surface area and/or shape of the physical cut distal femur can be detected, for example using an image and/or video capture system integrated into, attached to or separate from the OHMD or using a laser scanner and/or 3D scanner or using a mechanical or optical probe, for example using RF, optical, navigation and other markers. It can then be compared to the perimeter and/or cross-section and/or surface area and/or shape of the virtual cut surface.

Figure 10G:
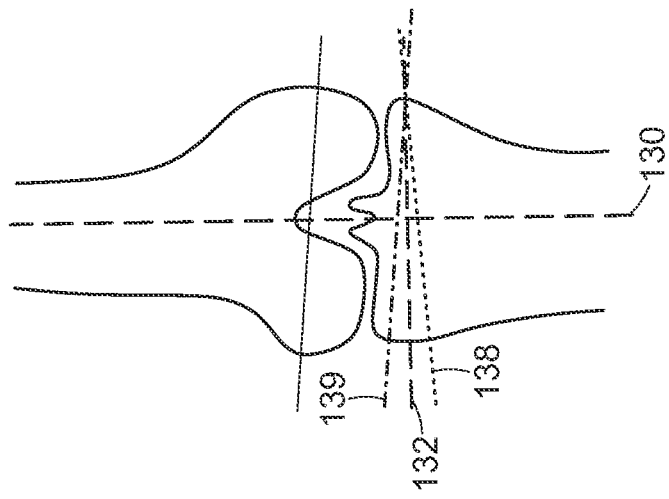
Figure 10E:
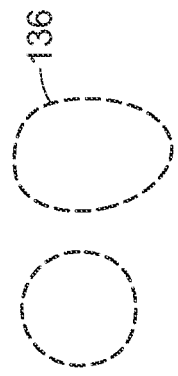

In FIG. 10E, once the perimeter and/or cross-section and/or surface area and/or shape of the physical cut distal femur has been detected, for example using an image and/or video capture system integrated into, attached to or separate from the OHMD or using a laser scanner and/or 3D scanner or using a mechanical or optical probe, for example using RF, optical, navigation and other markers, a corresponding perimeter and/or cross-section and/or surface area and/or shape of the physical cut distal femur can be identified in the virtual data of the patient 136, for example using image processing algorithms known in the art.

Figure 10F:
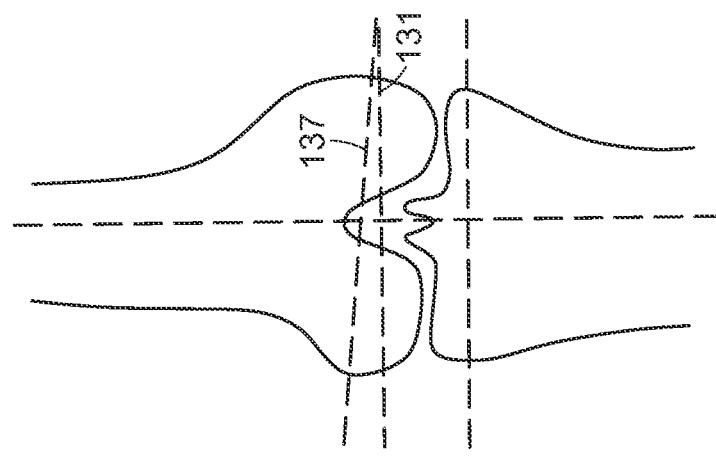

In FIG. 10F, once the corresponding perimeter and/or cross-section and/or surface area and/or shape has been identified in the virtual data of the patient (FIG. 10E), a virtual femur cut 137 which approximates the physical femoral cut can be identified in the virtual data of the patient. The difference in position, location, orientation, coronal, sagittal, axial angle/angulation between the originally planned or predetermined virtual femoral bone cut 131 and the new virtual femoral bone cut and the physical bone cut can be determined. Depending on the severity and/or clinical significance of the difference between them, the surgeon can then decide or chose between or combine any of the preceding Options A-E, e.g. modify the last surgical step (e.g. recut the femur), modify the next surgical step(s) (e.g. cut the tibia at a different coronal angulation than originally planned to account for the femoral mis-cut and, optionally, to achieve a composite alignment that is, for example, still within normal (180 degrees) mechanical axis alignment), modify the virtual surgical plan of the patient, modify the registration of the virtual data of the patient in relationship to the live data of the patient, and/or apply registration correction or combinations thereof.

In FIG. 10G, the surgeon can elect to modify the next surgical step and, in this example, modify the proximal tibial cut as shown in the two examples, one with a straight broken dotted line 139 and the other with a straight dotted line 138. In some embodiments, the surgeon can cut the tibia at a different coronal angulation than originally planned to account for the femoral mis-cut and, optionally, to achieve a composite alignment that is, for example, still within normal (180 degrees) mechanical axis alignment.

In another example, an OHMD can be used for guiding the placement of femoral pins or drills, which can be utilized for setting femoral component rotation, as is commonly done in total knee replacement procedures. Such femoral pins or drills can, for example, be placed through openings in a femoral cut block or a pin or drill block. In this example, the OHMD can guide the placement of the physical femoral cut block or pin or drill block by projecting a virtual femoral cut block or pin or drill block with which the surgeon can align the physical femoral cut block or drill or pin block, followed by the placement of the physical pins or drills. Alternatively, the OHMD can guide the placement of the physical pins or drills by projecting the virtual pins or drills or by projecting virtual pin or drill paths, followed by the placement of the physical pins or drills.

An image and/or video capture system integrated into, attached to or separate from the OHMD, or an optical or mechanical probe, optionally with attached optical markers, LEDs, navigation markers including, but not limited to, infrared markers, retroreflective markers, RF markers, and/or IMUs, optical markers, LEDs, navigation markers including, but not limited to, infrared markers, retroreflective markers, RF markers, and/or IMUs attached to the drills or pins can be used for assessing the position and/or orientation and/or alignment of the one or more physical pins or drills or resultant physical pin or drill holes and to compare them to the position and/or orientation and/or alignment of the one or more virtual pins or drills or virtual pin or drill holes, e.g. in the patient's virtual surgical plan using, for example, the existing registration or a new registration of the live and virtual data using the surgically altered or modified surface. If a difference in position and/or orientation and/or alignment between the physical and the virtual pins or drills or pin holes or drill holes is detected and found to be clinically significant, the surgeon can then decide or chose between or combine any of the preceding options A-E, e.g. modify the last surgical step (e.g. repeat/revise one or more pin placements), modify the next surgical step(s) (e.g. change femoral rotation to be different than indicated by the one or more pins or drills or pin holes or drill holes), modify the virtual surgical plan of the patient, modify the registration of the virtual data of the patient in relationship to the live data of the patient, and/or apply registration correction or combinations thereof.

In another example, an OHMD can be used for guiding the placement of tibial pins or drills, which can be utilized for setting tibial component rotation, as is commonly done in total knee replacement procedures. Such tibial pins or drills can, for example, be placed through openings in a tibial cut block or a pin or drill block. In this example, the OHMD can guide the placement of the physical tibial cut block or pin or drill block by projecting a virtual tibial cut block or pin or drill block with which the surgeon can align the physical tibial cut block or drill or pin block, followed by the placement of the physical pins or drills. Alternatively, the OHMD can guide the placement of the physical pins or drills by projecting the virtual pins or drills or by projecting virtual pin or drill paths, followed by the placement of the physical pins or drills.

An image and/or video capture system integrated into, attached to or separate from the OHMD, or an optical or mechanical probe, optionally with attached RF markers, optical markers, LEDs, navigation markers including, but not limited to, infrared markers, retroreflective markers, RF markers, and/or IMUs, or optical markers, LEDs navigation markers including, but not limited to, infrared markers, retroreflective markers, RF markers, and/or IMUs attached to the drills or pins can be used for assessing the position and/or orientation and/or alignment of the one or more physical pins or drills or resultant physical pin or drill holes and to compare them to the position and/or orientation and/or alignment of the one or more virtual pins or drills or virtual pin or drill holes, e.g. in the patient's virtual surgical plan using, for example, the existing registration or a new registration of the live and virtual data using the surgically altered or modified surface. If a difference in position and/or orientation and/or alignment between the physical and the virtual pins or drills or pin holes or drill holes is detected and found to be clinically significant, the surgeon can then decide or chose between or combine any of the preceding options A-E, e.g. modify the last surgical step (e.g. repeat/revise one or more pin placements), modify the next surgical step(s) (e.g. change tibial rotation to be different than indicated by the one or more pins or drills or pin holes or drill holes), modify the virtual surgical plan of the patient, modify the registration of the virtual data of the patient in relationship to the live data of the patient, and/or apply registration correction or combinations thereof.

Similarly, if the surgeon mis-cut, e.g. overcut the tibia, the OHMD can project optional modifications to the femoral cut, e.g. moving the virtual femoral cut and resultant physical femoral cut more distal to account for a tibial over-resection.

The preceding examples are in no way meant to be limiting of the invention, but are only exemplary of the invention. Someone skilled in the art can readily recognize how they can be applied to other types of surgery, e.g. ankle replacement, shoulder replacement, elbow replacement, ligament repair and/or reconstruction or replacement, spinal procedures, e.g. vertebroplasty, kyphoplasty, spinal fusion and/or pedicle screw and rod placement.

Pin Based Registration, Registration after Bone Cuts, Reaming, Milling, Etc.

If the tissue is being drilled or a pin or drill is placed in the tissue, for example for placement of a pedicle screw with pin placement or drilling through portions or all of the pedicle or for placement of a cut block in partial or total knee replacement or for planning a femoral cut or acetabular reaming for hip arthroplasty or for shoulder arthroplasty or for various types of surgery, e.g. cranial/brain surgery, the registration procedure can be repeated after the pin or drill has been placed or after the drilling has occurred. For example, an initial registration can be performed using an intraoperative x-ray, e.g. of a spine, or a knee, or a hip, e.g. with the patient in a prone position or supine position. The intraoperative x-ray can include one or more of an AP projection, PA projection, lateral projection, e.g. from left and/or from right side, oblique views, CT view using rotational x-ray acquisition, e.g. on rotating C-arm system. One or more of the intra-operative x-ray projections can be matched with pre-operative imaging data of the patient or virtual data of the patient including, optionally, a virtual surgical plan, using, for example, pattern recognition algorithms, image processing algorithms, or manual/visual matching by the surgeon or operator, optionally with magnification adjustment for a given film/detector focus distance, with magnification or de-magnification of either the intraoperative x-ray data, the pre-operative data, the virtual data of the patient, including, optionally, the virtual surgical plan, with the aim that all data used have similar or the same magnification.

In the example of spinal surgery, once the initial registration has been performed, a pin or drill can be placed in a first pedicle, e.g. in a cervical, thoracic or lumbar spine. Then a second pin or drill and/or additional pins or drills can be placed in a second pedicle, optionally at the same or different spinal levels, optionally on the same side of the spine (e.g. left or right) or alternatingly left and right from spinal level to spinal level. Similarly, pins or drills can be placed and registered for various aspects of knee replacement surgery, hip replacement surgery, shoulder replacement surgery, ACL repair or reconstruction and/or various sports related surgeries and/or cranial/brain surgery.

The position of the one or more pins or drills can be registered, for example using an image and/or video capture system integrated into, attached to or separate from the OHMD or using a laser scanner and/or 3D scanner that detects the one or more pins or drills. The position of the one or more pins or drills can be registered using attached or integrated optical markers or navigation markers including, but not limited to infrared markers, retroreflective markers, RF markers, e.g. with an optionally used navigation system, or IMUs. The position of the drill(s) or pin(s) can be detected using a touch probe, wherein the touch probe can include attached or integrated IMUs, optical markers, navigation markers including, but not limited to, infrared markers, retroreflective markers, RF markers and the like, using for example an image and/or video capture system or a navigation system. If more than one marker is placed along the trajectory of the pin or drill or if image capture is used, the two or more markers or the trajectory of the visualized portions of the pin(s) or drill(s) using image capture can be used to estimate the trajectory of the pin(s) or drill(s) and to estimate a projected path as the pin(s) or drill(s) are advanced. If the length and the thickness of the pins are known, not only the endpoint outside the patient's tissue can be determined, but also the location of the tip can be estimated even though it can be seated deep inside the patient's tissue in spinal surgery, knee replacement, hip replacement, shoulder replacement, brain surgery and various types of other surgery.

The position of the pins or drills can be registered in relationship to the patient and/or the OHMD using any of the techniques described in the specification. The one or more optical markers can be retroreflective or can include LEDs. Combinations of optical and RF markers can be used.

In some embodiments of the invention, a first drill or pin is registered, optionally followed by registration of a second or more pin and drills. The position and/or orientation of the one or more pins or drills can be used to maintain registration during the surgery, e.g. placement of pedicle screws and related devices, e.g. rods, or knee replacement with placement of one or more pins or drills in the femur and/or the tibia or hip replacement with placement of one or more pins or drills in the acetabulum or proximal femur. Since the one or more pins or drills are fixed to the bone, accurate registration can be maintained even if there is patient movement after the initial registration, if the pin or drill(s) are used for registration after the initial registration. Optionally, both the initial registration and the subsequent registration to the altered surgical surface/site after the placement of the pin or drill with registration to the pin or drill(s) can be used together. In this case, statistical techniques can be applied to reconcile small differences between the initial registration and the registration to the altered surgical surface or site including the one or more pins or drills. For example, the mean or the median of the different registrations can be used for any subsequent surgical steps.

In some embodiments of the invention, an initial registration can be performed between virtual data of the patient, e.g. pre-operative imaging, including optionally a virtual surgical plan for the patient, and live data of the patient during surgery. The initial registration can, for example, be performed using intra-operative imaging, which can be referenced to and registered with the live data of the patient. Any other technique of registration described in the specification or known in the art can be used for the initial registration. A first pin or drill or a first set of pins or drills can be placed using the initial registration of virtual data of the patient and live data of the patient.

Following the placement of a first pin or drill or a first set of pins or drills, intra-operative imaging can be repeated. In some embodiments of the invention, intra-operative imaging is used for the initial registration and the same intraoperative imaging modality and technique or similar intra-operative imaging modality or technique is used after placing the first pin or drill or the first set of pins or drills. Alternatively, a different intra-operative imaging modality is used after placing the first pin or drill or the first set of pins or drills. Intra-operative imaging modalities can include, for example, x-rays, e.g. AP, PA, lateral and oblique views, C-arm acquisition, optionally with CT capability, CT scan or ultrasound scan or MRI scan or any other imaging technique known in the art.

In some embodiments of the invention, after a first pin or drill or a first set of pins or drills is placed, the accuracy of the placement can be assessed. The accuracy of the placement can be assessed using, for example, any of the following:

Intraoperative imaging, e.g. also if the initial registration was performed without use of intraoperative imaging Intraoperative imaging using the same or a different imaging modality used for an initial registration (if applicable)

Image capture of the visible portions of the pin(s) or drill(s), with optional projection/estimation of the location and/or orientation of any non-visualized portions inside the patient's tissue Optical markers, navigation markers including, but not limited to, infrared markers, retroreflective markers, RF markers, IMUs, and any other electronic or optical or magnetic marker known in the art, with optional projection/estimation of the location and/or orientation of any non-visualized portions inside the patient's tissue Any deviations in the physical placement including the physical position and/or the physical orientation of the pin(s) or drill(s) compared to the intended position and/or intended orientation of the pin(s) or drill(s) in the virtual surgical plan can be measured in this manner. If one or more of the pins show a deviation in physical vs. intended virtual position and/or orientation, the difference in coordinates can be determined and a coordinate transfer or coordinate correction can be applied for any subsequent registration that uses one or more of the pins or drills placed inside the patient's tissue. A coordinate transfer or coordinate correction can be applied globally, e.g. to all pins or drills placed using the same values. Alternatively, a coordinate transfer or coordinate correction can be applied individually to each pin or drill accounting for their specific deviation from physical vs. intended virtual placement/position/and/or orientation. The former approach can be more time efficient. The latter approach can be more accurate for any subsequent registrations. A coordinate transfer or coordinate correction applied to each pin or drill individually using data on the amount of deviation/difference in coordinates between physical placement/position/and/or orientation compared to intended virtual placement/position/and/or orientation based on the virtual surgical plan can be particularly helpful in spinal surgery, when one or more spinal segment can move in relationship to each other during the surgery, e.g. if the surgeon has to adjust the position of the patient on the table. In this case, one or more pins or drills can optionally be placed at more than one spinal level, for example all spinal levels involved in the surgery, after the initial registration and the accuracy of the placement can be assessed using the foregoing techniques. A coordinate transfer or coordinate correction can then optionally be applied for more than one spinal level, e.g. all spinal levels involved in the surgery, wherein the difference in physical vs. intended virtual placement/position/and/or orientation of the pins or drills can be used to improve the accuracy of any subsequent registration using the one or more pins or drills for subsequent surgical steps for each spinal level for which the coordinate transfer or coordinate correction has been applied.

In the example of spinal surgery, one or more pedicle screws can be placed, at the same spinal level or different spinal levels. Optionally, the accuracy of the physical placement/position and/or orientation of each pedicle screw can be assessed compared to the intended virtual placement/position/and/or orientation in the virtual surgical plan using any of the foregoing techniques. Optionally a coordinate transfer or coordinate correction can be determined based on any deviations between physical and intended virtual placement of the pedicle screw and the pedicle screw can be used for registration of the patient, the spine, and/or the OHMD during any subsequent surgical steps, e.g. placement of additional pedicle screws, e.g. at the same or other spinal levels, or placement of one or more connectors or rods and the like.

During the placement of the pedicle screw, registration can be maintained by referencing one or more of the pins or drills or pedicle screws placed in the pedicles at the same or adjacent spinal levels.

Similarly, in other surgical procedures, e.g. knee replacement, hip replacement, shoulder replacement, ACL repair and reconstruction, cranial, maxillofacial and brain surgery, the physical position of any drill, pin, instrument, implant, device or device component can be determined using any of the techniques described in the specification and any deviations or differences between the physical and the intended virtual placement/position/and/or orientation can be determined. The differences measured can be used to determine a coordinate transfer or coordinate correction for any subsequent registrations for subsequent surgical steps using now the one or more drill, pin, instrument, implant, device or device component as the registration reference or marker.

By referencing a pin or drill that is fixed inside the bone or a hard tissue (following the first surgical alteration), it is possible to maintain accurate registration, e.g. during pedicle screw placement, knee replacement, hip replacement, ACL repair and/or reconstruction, maxillofacial surgery, cranial and/or brain surgery.

In this case, the pinned or drilled tissue of the live patient or portions thereof can be matched to or superimposed and/or registered with the corresponding pinned or drilled tissue in the virtual surgical plan. Once an adequate match of the live and virtual cut pinned or drilled area has been obtained, registration can optionally be repeated. In some embodiments of the invention, the bone void or hole created by any pinning or drilling can be used for any subsequent registrations. Optionally, a pin or drill can be temporarily placed back into the bone void or hole for any subsequent registration and subsequent surgical steps. If other surgical instruments are used, e.g. other than a drill or pin, such as a burr or a blade, other resultant bone voids can optionally also be used for any subsequent registrations.

Optionally, the position, location, and/or orientation and/or size and/or shape of any bone void or hole created by any surgical instrument can be assessed, e.g. using intraoperative imaging such as x-rays or ultrasound, and the difference between the physical and the intended virtual position, location, and/or orientation and/or size and/or shape of any bone void or hole can be assessed. The difference or deviation between the physical and the intended virtual position, location, and/or orientation and/or size and/or shape of the bone void or hole can be used to determine a coordinate difference or coordinate transfer or coordinate correction so that the bone void or hole can be used for any subsequent registration and subsequent surgical steps. Any subsequent registration can be performed by optionally introducing a partial or complete bone void filler (e.g. a pin or a drill) and registering the bone void filler. Any subsequent registration can also be performed by registering the bone void or hole directly, e.g. with intraoperative imaging. Any subsequent registration can also be performed by placing one or more IMUs, optical markers, and/or navigation markers including, but not limited to, infrared markers, retroreflective markers, RF markers inside or adjacent to the bone void and registered one or more of the IMUs, optical markers, LEDs and/or navigation markers including, but not limited to, infrared markers, retroreflective markers, RF markers using any of the techniques described in the specification. Moreover, any subsequent registration can also be performed by marking portions or all of the bone void or hole with a color, e.g. toluidine blue, and by registering the marked and/or stained portions of the bone void or hole, e.g. using an image and/or video capture system integrated into, attached to, or separate from the OHMD.

If a tissue cut is performed, for example with a scalpel or a saw, the registration procedure can be repeated after the tissue cut has been placed. In this case, the cut tissue surface of the live patient or portions thereof or the perimeter of the cut tissue surface of the live patient or portions thereof or the surface area of the cut tissue surface of the live patient or portions thereof or the volume of the removed tissue of the live patient or portions thereof can be matched to or superimposed and/or registered with the corresponding cut tissue surface of the virtual data or portions thereof or the perimeter of the cut tissue surface of the virtual data or portions thereof or the surface area of the cut tissue surface of the virtual data or portions thereof or the volume of the removed tissue of the virtual data or portions thereof in the virtual surgical plan. Once an adequate match of the live and virtual cut surfaces has been obtained, registration can optionally be repeated.

If a tissue cut is performed, the registration procedure can be repeated after the tissue cut has been completed. In this case, the cut tissue surface of the live patient or portions thereof or the perimeter of the cut tissue surface of the live patient or portions thereof can be matched to or superimposed onto and/or registered with the corresponding cut tissue surface or portions thereof in the virtual surgical plan or the perimeter of the cut tissue surface in the virtual surgical plan or portions thereof. Once an adequate match of the live and virtual cut surfaces has been obtained, registration can optionally be repeated.

If a bone cut is performed, for example with a saw, the registration procedure can be repeated after the bone cut has been placed. In this case, the cut bone surface of the live patient or portions thereof or the perimeter of the cut bone surface of the live patient or portions thereof or the surface area of the cut bone surface of the live patient or portions thereof or the volume of the removed bone of the live patient or portions thereof can be matched to or superimposed onto and/or registered with the corresponding cut bone surface of the virtual data or portions thereof or the perimeter of the cut bone surface of the virtual data or portions thereof or the surface area of the cut bone surface of the virtual data or portions thereof or the volume of the removed bone of the virtual data or portions thereof in the virtual surgical plan. Once an adequate match of the live and virtual cut surfaces has been obtained, registration can optionally be repeated.

If a milling, reaming or impacting procedure is performed, for example with a reamer, a mill or an impactor, the registration procedure can be repeated after the milling, reaming or impacting has been performed. In this case, the milled, reamed or impacted bone surface of the live patient or portions thereof or the perimeter of the milled, reamed or impacted bone surface of the live patient or portions thereof or the surface area of the milled, reamed or impacted bone surface of the live patient or portions thereof or the volume of the removed bone of the live patient or portions thereof can be matched to or superimposed onto and/or registered with the corresponding milled, reamed or impacted bone surface of the virtual data or portions thereof or the perimeter of the milled, reamed or impacted bone surface of the virtual data or portions thereof or the surface area of the milled, reamed or impacted bone surface of the virtual data or portions thereof or the volume of the removed bone of the virtual data or portions thereof in the virtual surgical plan.

Once an adequate match of the live and virtual cut surfaces has been obtained, registration can optionally be repeated.

If a drilling procedure is performed, for example with a drill or a pin or a K-wire, the registration procedure can be repeated after the drill or pin or K-wire has been placed. In this case, the drilled surface of the live patient or portions thereof or the perimeter of the drilled surface of the live patient or portions thereof or the surface area of the drilled surface of the live patient or portions thereof or the volume of the removed bone of the live patient or portions thereof or the location of the drill hole or the orientation of the drill hole or the size of the drill hole or a marker such as a drill, a pin or a K-wire or an ink inserted into the drill hole can be matched to or superimposed onto and/or registered with the corresponding drilled surface in the virtual data or portions thereof or the perimeter of the drilled surface in the virtual data or portions thereof or the surface area of the drilled surface in the virtual data or portions thereof or the volume of the removed bone in the virtual data or portions thereof or the location of the drill hole in the virtual data or the orientation of the drill hole in the virtual data or the size of the drill hole in the virtual data or a marker such as a drill, a pin or a K-wire or an ink inserted into the drill hole in the virtual data, optionally in the virtual surgical plan. Once an adequate match of the live and virtual cut surfaces has been obtained, registration can optionally be repeated.

If a drilling procedure is performed, the drill holes can optionally be marked with india ink or another color in the live patient. The color marking can be recognized with use of an image and/or video capture system integrated into, attached to or separate from the OHMD. The color markings in the live patient can then optionally be used to re-register the live data of the patient with the virtual data after one or more surgical alterations of the tissue has/have been performed. The color markings can be used with an image and/or video capture system to detect them in the live patient data and to register them with the virtual patient data. Alternatively, the color markings can be used by the surgeon to identify the previously placed drill holes visually, for example after one or more surgical alterations or surgical steps have been performed. A drill, a pin, a K-wire, a screw, or another surgical instrument can then optionally be placed inside the drill hole and the registration of the live data and the virtual data can be performed by matching, superimposing and/or registering the live drill, pin, K-wire, screw, or other surgical instrument with a corresponding virtual drill, pin, K-wire, screw, or other surgical instrument or a corresponding drill hole in the virtual surgical plan.

For example, in a knee replacement procedure, a drill guide can be applied to the distal femur and/or the distal femoral condyles before the distal femoral cut and bone removal is performed. The drill guide can be integrated into the distal femoral cut block. Typically, two or more drill holes can be placed, for example with one or more drill holes located in the medial femoral condyle or in the medial femur and one or more drill holes located in the lateral femoral condyle or in the lateral femur. The location of the medial and lateral drill holes and the intersect between the two drill holes can be used to define the rotation axis of the femoral component.

The OHMD can display the desired location of the distal femoral cut block for achieving the desired mechanical axis correction and the desired location of the drill holes for setting the desired rotation axis of the femoral implant component. The drill holes can be drilled prior to performing the cut and can be optionally marked with ink prior to performing the distal femoral cut. The distal femoral cut can then be performed. The ink in the drill holes can then be identified on the cut surface. The ink seen in the live patient data can be registered using an image and/or video capture system integrated into, attached to or separate from the OHMD and can be registered in relationship to the virtual drill holes as defined in the virtual surgical plan. Alternatively, the surgeon can elect to insert a drill, pin, K-wire, screw, or other surgical instrument into the drill holes in the live patient data and the location of the drill, pin, K-wire, screw, or other surgical instrument can be registered using an image and/or video capture system integrated into, attached to or separate from the OHMD and can be registered in relationship to a virtual drill, pin, K-wire, screw or other surgical instrument optionally introduced into the virtual surgical plan.

In this manner, live patient data and virtual patient data can be re-registered after the distal femoral bone cut has been performed. The surgeon can also use the re-registration to check the accuracy of the initial registration and perform adjustments to the physical surgical plan or the virtual surgical plan depending on any discrepancies detected.

The foregoing embodiment can be applied to any type of joint replacement or joint sparing procedure including arthroscopy.

If a radiofrequency ablation, heat ablation, cryoablation, or cauterization is performed, the registration procedure can be repeated after the radiofrequency ablation, heat ablation, cryoablation, or cauterization has been performed. In this case, the ablated or cauterized tissue surface of the live patient or portions thereof or the perimeter of the ablated or cauterized tissue surface of the live patient or portions thereof or the surface area of the ablated or cauterized tissue surface of the live patient or portions thereof or the volume of the removed tissue of the live patient or portions thereof can be matched to or superimposed and/or registered with the corresponding ablated or cauterized tissue surface of the virtual data or portions thereof or the perimeter of the ablated or cauterized tissue surface of the virtual data or portions thereof or the surface area of the ablated or cauterized tissue surface of the virtual data or portions thereof or the volume of the removed tissue of the virtual data or portions thereof in the virtual surgical plan. Once an adequate match of the live and virtual ablated or cauterized surfaces has been obtained, registration can optionally be repeated.

If a placement of a medical implant component, a trial implant, a tissue graft, a tissue matrix, a transplant, a catheter, a surgical instrument or an injection of cells or a drug is performed, the registration procedure can be repeated after the surgical step or surgical alteration has been performed. In this case, the altered tissue of the live patient or portions thereof, the altered tissue surface of the live patient or portions thereof, or the perimeter of the altered tissue surface of the live patient or portions thereof, or the surface area of the altered tissue surface of the live patient or portions thereof, or the volume of the removed tissue of the live patient or portions thereof can be matched to or superimposed and/or registered with the corresponding altered tissue of the virtual data or portions thereof, altered tissue surface of the virtual data or portions thereof, or the perimeter of the altered tissue surface of the virtual data or portions thereof, or the surface area of the altered tissue surface of the virtual data or portions thereof, or the volume of the removed tissue of the virtual data or portions thereof in the virtual surgical plan. Once an adequate match of the live and virtual altered tissue has been obtained, registration can optionally be repeated.

Libraries of Surgical Instruments

In some aspects, the system includes libraries of surgical instruments for different surgical procedures. The concept of a virtual library of surgical instruments used in a virtual surgical plan and optionally displayed by an OHMD during the live surgery, e.g. superimposed onto the physical surgical instruments to provide positional, orientation or directional guidance of the physical surgical instrument according to the virtual and/or intended surgical plan, is applicable to any surgical procedure, e.g. cardiovascular procedures, thoracic or pulmonary procedures, neurological procedures, urological procedures, gynecological procedures, hepatic or other inner organ procedures, intestinal procedures and/or musculoskeletal procedures. Virtual and physical surgical instruments and implant components can be registered in a common coordinate system, for example with one or more OHMDs and live data of the patient; the OHMD can project or display a virtual representation of the virtual surgical instrument.

In some embodiments, a virtual library of surgical instruments can correspond to a physical library of surgical instruments during surgery. Optionally, only a few, select surgical instruments can be included in the virtual library of surgical instruments. These few select surgical instruments can, for example, be the ones used for the principal, key surgical steps, or select sub-steps. Alternatively, all surgical instruments used during the live surgery can be included in a virtual library of virtual surgical instruments.

The virtual library of virtual surgical instruments can include these instruments in various file formats. In some embodiments, CAD file formats can be used. In general, any type of surface representation, 2D or 3D shape representation 3D volume representation, 3D display and different file formats can be used in a virtual surgical plan, followed by optional display by the OHMD during surgery.

Examples of libraries of surgical instruments that can be used in pedicle screw placement or spinal rod placement, artificial disk replacement, hip replacement and knee replacement are provided below. Any other surgical instruments used in any other surgical procedure can be utilized in a virtual surgical plan and/or can be displayed by the OHMD.

Pedicle Screw & Spinal Rod Placement

A virtual and/or physical library of surgical instruments for pedicle screw instrumentation and/or spinal rod placement can for example include:

For Pedicle Preparation:
Awl, e.g. round awl
Single ended feeler probe
Dual ended feeler probe
Sounding/feeler probe
Thoracic ball handle probe
Lumbar ball handle probe
Straight probe, e.g. lumbar, thoracic, cervical
Curved probe, e.g. lumbar, thoracic, cervical
Ratcheting handle
Taps of different diameter/dimensions
For Screw Insertion:
Screw driver, e.g.
　Multi-axial screw driver
　Self-retaining screw driver
Rod template
Rod inserter
Rod gripper
Bender, e.g. French bender
Single ended plug starter
Dual ended plug starter
Provisional driver
For Rod Reduction:
Compressor, e.g. parallel compressor
Distractor, e.g. parallel distractor
For Tightening:
Break-off driver, e.g. self-retaining
Obturator
Counter torque
Other Instruments:
Plug starter, e.g. non-break-off
Quick connector
Torque limiting driver
Tissue retractors
Frame to hold tissue retractors
Clamps
Plate Instruments:
Implant positioners
Screw driver, e.g. torque limiting or non-torque limiting
Measuring caliper
Measuring credit card
Counter torque
Plate holder, e.g. in line
Plate bender(s)
Forceps plate holder
Removal driver, e.g. hex head shaft style The foregoing list of surgical instruments for pedicle screw instrumentation and/or spinal rod placement is only an example. It is by no means meant to be limiting of the invention. Any current and future surgical instrument for pedicle screw instrumentation and/or spinal rod placement can be used in a virtual surgical plan and live surgical plan for pedicle screw instrumentation and/or spinal rod placement.

All of the above surgical instruments can be provided in different sizes and/or diameters and/or widths and/or lengths and/or shapes and/or dimensions, for example based on the size or dimensions of the physical implant, implant component and/or medical device used.

Libraries of Medical Devices, Implants, Implant Components

Pedicle Screw & Spinal Rod Placement

A library of virtual and physical implants, implant components and/or medical devices for pedicle screw instrumentation and/or spinal rod placement can, for example, include screws including, but not limited to, screw heads, screw thread portion, multi-axial screws, single-axial screws, set screws, all of the foregoing in different sizes and/or diameters (optionally color coded during the display in the OHMD); plates including, but not limited to, fixed plates, cross-link plates, multi-span plates, all of the foregoing in different sizes and/or diameters (optionally color coded during the display in the OHMD); rods including, but not limited to, straight rods, contoured rods, all of the foregoing in different sizes and/or diameters (optionally color coded during the display in the OHMD). All of the foregoing device, device components, implants and implant components can be provided in different diameters, widths, lengths, dimensions, shapes, or sizes.

Knee Replacement

A library of virtual and physical implants, implant components and/or medical devices for partial and total knee replacement can, for example, include left and right femoral components of different sizes, e.g. size 1, 2, 3, 4, . . . , 17, 18, 19, 20, and shapes, e.g. without or with distal medial-lateral femoral offset, e.g. 1, 2, 3, 4, 5, 6, 7, 8 or more mm, without or with posterior medial-lateral femoral condyle offset, e.g. 1, 2, 3, 4, 5, 6, 7, 8 or more mm; left and right tibial components of different sizes, metal-backed or all polyethylene, e.g. size 1, 2, 3, 4, . . . , 17, 18, 19, 20, and shapes, e.g. symmetric, asymmetric, optionally with different degrees of asymmetry; left and right tibial inserts of different sizes, e.g. size 1, 2, 3, 4, . . . , 17, 18, 19, 20, and shapes, e.g. symmetric, asymmetric, optionally with different degrees of asymmetry; left and right patellar components of different of different sizes, e.g. size 1, 2, 3, 4, . . . , 17, 18, 19, 20, and shapes, e.g. symmetric, asymmetric.

Hip Replacement

A library of virtual and physical implants, implant components and/or medical devices for hip replacement can, for example, include left and right standard offset, high offset, coxa vara offset femoral components, with collar or collarless, cemented or non-cemented, with different porous ingrowth options, with different sizes, stem lengths, offsets, neck lengths, neck shaft angles; ceramic or metal femoral heads of different sizes, plus and minus heads; acetabular cups of different sizes, cemented or non-cemented with different porous ingrowth options; different acetabular liners including lipped and asymmetric liners, of different sizes.

The foregoing lists are only of illustrative and exemplary nature and should not be construed as limiting the invention. Any implant component known in the art can be included in one or more libraries of virtual and physical implants.

Virtually Aligning Implant Components

An optical head mounted display can display or project digital holograms of one or more virtual implants, virtual implant components and/or virtual medical devices and virtual instruments without the use of pre-operative or intra-operative imaging. In some embodiments of the invention, the OHMD can display an arbitrary virtual implant component over the surgical field. The arbitrary virtual implant component can, for example, be an implant component selected from the middle of a size range or a shape range. The arbitrary virtual implant component can be selected based on surgeon preferences. The arbitrary virtual implant component can be the most common size used in a particular patient population. The arbitrary virtual implant component can be moveable using a virtual or other interface. For example, the virtual representation of the arbitrary virtual implant component can include a "touch area", wherein gesture recognition software, for example the one provided by Microsoft with the Microsoft Hololens including, for example, the integrated virtual "drag function" for holograms can be used to move the arbitrary virtual implant component. For example, one or more cameras integrated or attached to the OHMD can capture the movement of the surgeon's finger(s) in relationship to the touch area; using gesture tracking software, the arbitrary virtual implant component can then be moved by advancing the finger towards the touch area in a desired direction. A surgeon can, for example, also "hold" the arbitrary virtual implant component by closing two fingers, e.g. thumb and index finger, over the touch area and then moving the fingers in the desired direction, thereby moving the arbitrary virtual implant component into the desired position and/or orientation on the patient's joint.

The OHMD can display the virtual implant component in any location initially, e.g. projected onto or outside the surgical field, e.g. a hip joint, knee joint, shoulder joint, ankle joint, or a spine. The OHMD can optionally display the virtual implant component at a defined angle, e.g. orthogonal or parallel, relative to a fixed structure in the operating room, which can, for example, be recognized using one or more cameras, image capture or video capture systems integrated into the OHMD and spatial recognition software such as the one provided by Microsoft with the Microsoft Hololens or which can be recognized using one or more attached optical markers or navigation markers including, but not limited to, infrared or RF markers. For example, one or more optical markers can be attached to an extension of the operating table. The OHMD can detect these one or more optical markers and determine their coordinates and, with that, the horizontal plane of the operating room table. The virtual implant component can then be displayed perpendicular or at another angle relative to the operating room table. The virtual implant component can be displayed at a defined angle to one or more anatomic or biomechanical axes, e.g. a mechanical axis when a knee replacement is contemplated. The virtual implant component can be displayed or projected tangent with one or more anatomic landmarks. The virtual implant component can be displayed intersecting one or more anatomic landmarks.

The surgeon can move the virtual implant component to align it in the desired location and/or orientation over the implantation site. The surgeon can then evaluate the size of the virtual implant component and the fit of the virtual implant component by evaluating the size and fit of the virtual representation of the implant component superimposed onto the intended implantation site. The surgeon can move and align the virtual implant component so that, for example, its external surface co-locates, e.g. has similar or substantially the same coordinates, as the external surface of the intended implantation site. The OHMD can display the other portions of the virtual implant component which project underneath the external surface of the implantation site. If the virtual implant component is too large for an implantation site, the surgeon can cancel the virtual display of the particular size of virtual implant component displayed and the surgeon can select a smaller virtual implant component from the library of virtual and physical implant components. If the virtual implant component is too small for an implantation site, the surgeon can cancel the virtual display of the particular size of virtual implant component displayed and the surgeon can select a larger virtual implant component from the library of virtual and physical implant components. In this manner, the surgeon can optimize the implant size and fit in three-dimensions in the actual surgical site, rather than reverting to pre-operative sizing and fitting using, for example, 2D xrays or 3D imaging studies, e.g. CT and MRI. If an implantation site is characterized by one or more asymmetries, e.g. in a knee joint or a tumor or an internal organ, the surgeon can optionally size and fit one or more asymmetric implant components, optionally with different asymmetries and geometries, for the implantation site.

The surgeon can move the virtual implant component to place it and/or align and/it or orient in a desired position, location, and/or orientation over the implantation site for a given patient. Since the moving and aligning is performed over the live implantation site of the patient, the surgeon can optimize the implant position, location, and/or orientation. The surgeon can further modify and/or optimize the position, location, and/or orientation of the virtual implant component and, with that, the physical implant component for a desired function in an implantation site, e.g. a desired flexion angle, rotation angle, range of motion, ligamentous laxity, desired movement. The surgeon can align at least a portion of the external surface of the virtual implant component with at least a portion of the external surface of the implantation site. After the surgeon has placed, aligned and/or oriented the virtual implant component superimposed in the desired position and/or orientation over or aligned with the live implantation site, the coordinates of the virtual implant component can be saved, e.g. in a common coordinate system in which the OHMD and the implantation site can also be registered. The saved coordinates of the virtual implant component can, optionally be incorporated in a virtual surgical plan, which can optionally also be registered in the common coordinate system. The OHMD can subsequently display one or more digital holograms of one or more virtual surgical instruments and/or virtual implant components wherein the position, location, and/or orientation of the one or more digital holograms of the one or more virtual surgical instruments and/or virtual implant components are derived from or take into consideration the saved coordinates of the virtual implant component.

For example, in a hip replacement, a virtual acetabular cup can be displayed near the surgical site including the exposed acetabulum of a patient. The surgeon can move the virtual acetabular cup using a virtual or other interface and superimpose it onto the patient's exposed acetabulum. The surgeon can evaluate the size and fit of the virtual acetabular cup. The surgeon can upsize or downsize the virtual acetabular cup by selecting smaller or larger virtual acetabular cups until the surgeon is satisfied with the fit of the virtual representation of the acetabular cup and the patient's exposed acetabulum. The surgeon can optionally center the virtual acetabular cup over the center of the patient's exposed acetabulum, matching the outer rim of the virtual acetabular cup to co-incide with or be equidistant superiorly, inferiorly, medially and laterally to the acetabular rim of the patient's exposed acetabulum. The coordinates of the virtual acetabular cup can then be saved, e.g. in the same coordinate system in which the surgical site, e.g. the acetabulum and/or the proximal femur, and the OHMD are registered. The coordinates of the virtual acetabular cup identified in this manner can be used to set a desired acetabular anteversion, e.g. during a reaming or impacting of the acetabular cup. Optionally, the virtual representation of the virtual acetabular cup fitted and placed by the surgeon can be displayed by the OHMD prior to impacting the physical acetabular cup. The surgeon can then align the physical acetabular cup with the virtual projection of the acetabular cup; once the desired alignment has been achieved, the surgeon can start impact the physical acetabular cup, while optionally intermittently comparing its position and/or orientation including offset and anteversion with the virtual display of the virtual acetabular cup.

In some embodiments, in a hip replacement, a virtual femoral component, optionally including a head component, can be displayed near the surgical site including the exposed proximal femur of a patient. The surgeon can move the virtual femoral component, optionally including a head component, using a virtual or other interface and superimpose it onto the patient's exposed proximal femur, optionally before and/or after the femoral neck cut. The surgeon can evaluate the size and fit of the virtual femoral component, optionally including a head component; optionally, the OHMD can display one or more pre-operative or intraoperative x-ray images or other imaging study, e.g. CT or MRI, of the patient registered in a common coordinate system with the surgical site; the imaging study can be superimposed onto the corresponding portions of the proximal femur, e.g. greater trochanter of live patient with greater trochanter on x-ray or imaging study, lesser trochanter of live patient with lesser trochanter on x-ray or image study etc. The surgeon can upsize or downsize the virtual femoral component by selecting smaller or larger virtual femoral components until the surgeon is satisfied with the fit of the virtual representation of the acetabular cup and the patient's exposed proximal femur or with the fit of the virtual representation of the femoral component and/or femoral head and the patient's projected or displayed x-ray or imaging study, including marrow cavity and/or endosteal interface. The surgeon can optionally center the virtual femoral component over the exposed proximal femur, optionally before and/or after the femoral neck cut, centering also over the cut femoral neck surface, aligning the virtual femoral component and/or head with the corresponding anatomy or imaging data of the patient. The coordinates of the virtual femoral component and/or head can then be saved, e.g. in the same coordinate system in which the surgical site, e.g. the acetabulum and/or the proximal femur, and the OHMD are registered. The coordinates of the virtual femoral component and/or head identified in this manner can be used to set a desired femoral anteversion and/or offset, e.g. during a reaming or broaching of the femoral component. Optionally, the virtual representation of the virtual femoral component and/or head fitted and placed by the surgeon can be displayed by the OHMD prior to impacting the physical femoral component. The surgeon can then align the physical virtual femoral component and/or head with the virtual projection of the femoral component and/or head; once the desired alignment has been achieved, the surgeon can start impact the physical femoral component, while optionally intermittently comparing its position and/or orientation including offset and anteversion with the virtual display of the virtual femoral component.

In some embodiments, in a knee replacement, a virtual femoral component can be displayed near the surgical site including the exposed distal femur of a patient. The surgeon can move the virtual femoral component, using a virtual or other interface, e.g. a "touch zone" on the virtual representation of the virtual femoral component with image or video capture of the surgeon's hand and/or fingers and/or gesture tracking, and superimpose it onto the patient's exposed distal femur, optionally before and/or after any bone cuts. The surgeon can evaluate the size and fit of the virtual femoral component. The surgeon can evaluate the fit in three dimensions, anteriorly, posteriorly, at the medial aspect of the medial condyle, at the lateral aspect of the medial condyle, at the medial aspect of the lateral condyle, at the lateral aspect of the lateral condyle, in the intercondylar notch, in the medial and lateral trochlear region. The surgeon can evaluate the size and fit of the virtual femoral component for different degrees of femoral component flexion and/or extension relative to the physical distal femur of the patient and different degrees of femoral component rotation, e.g. external rotation. The surgeon can upsize or downsize the virtual femoral component by selecting smaller or larger virtual femoral components from the virtual library until the surgeon is satisfied with the fit of the virtual representation of the femoral component and the patient's exposed distal femur. If the virtual femoral implant component is too large for an implantation site, the surgeon can cancel the virtual display of the particular size of virtual femoral component displayed and the surgeon can select a smaller virtual femoral component from the library of virtual and physical femoral components. If the femoral implant component is too small for an implantation site, the surgeon can cancel the virtual display of the particular size of virtual femoral component displayed and the surgeon can select a larger virtual femoral component from the library of virtual and physical femoral components. The surgeon can also evaluate the position and/or orientation of the virtual femoral component for possible notching relative to the physical anterior cortex of the distal femur of the patient.

The surgeon can evaluate the shape of the virtual femoral component and compare it with the shape of the patient's distal femur. The surgeon can optionally align at least portions of the external surface of the virtual femoral component with at least portions of the patient's articular surface, e.g. on the medial femoral condyle, the lateral femoral condyle and/or the trochlear articular surface. The surgeon can select different shapes of virtual femoral components from the virtual library of implants, e.g. femoral components with one or more offsets between the medial distal femoral condyle and the lateral distal femoral condyle and/or one or more offsets, the same or different, between the medial posterior femoral condyle and the lateral posterior femoral condyle. The offset can be a reflection of different radii of the medial distal and/or posterior and the lateral distal and/or posterior femoral condyle. For example, the surgeon can align at least portions of the external surface or projection of the medial condyle of the virtual femoral component with at least portions of the external surface of the physical medial condyle of the patient; if the external surface or projection of the lateral condyle of the virtual femoral component is proud relative to the external surface of the physical lateral condyle of the patient, i.e. extends beyond the external surface of the physical lateral condyle of the patient, the surgeon can discard the digital hologram of the virtual femoral component and select a different virtual femoral component from the virtual library; for example, the surgeon can select a virtual femoral component with a smaller lateral condyle radius than medial condyle radius and/or with a distal and/or posterior offset of the lateral condyle compared to the medial condyle. The surgeon can project, move, align, e.g. with the external surface of the medial and/or the lateral femoral condyle, multiple different virtual femoral component shapes, e.g. with multiple different offsets, until the surgeon has identified a virtual femoral component that yields the desired shape. If a virtual femoral component is chosen with an offset between the medial and the lateral femoral component, a matching offset can optionally be selected for the tibial polyethylene, wherein the lateral portion of the tibial insert can be 1, 2, 3, 4, 5, 6, 7, 8 or more mm thicker than the medial portion of the tibial insert, corresponding to the smaller radius of the lateral femoral condyle of the virtual femoral component. The coordinates of the final position of the virtual femoral component can be saved and can, optionally, be incorporated into a virtual surgical plan. If the virtual surgical plan indicates a variation in position, orientation, alignment, implant flexion of the virtual femoral component relative to the virtual surgical plan, the surgeon can adjust the position of the virtual femoral component to come closer to the intended position, orientation, alignment, implant flexion of the virtual surgical plan or to replicate it. Alternatively, the virtual surgical plan can be modified based on the position, orientation, alignment, implant flexion of the virtual femoral component.

In some embodiments, in a knee replacement, a virtual tibial component can be displayed near the surgical site including the exposed proximal tibia of a patient. The surgeon can move the virtual tibial component, using a virtual or other interface, e.g. a "touch zone" on the virtual representation of the virtual tibial component with image or video capture of the surgeon's hand and/or fingers and/or gesture tracking, and superimpose it onto the patient's exposed proximal tibia, optionally before and/or after any bone cuts. The surgeon can evaluate the size and fit of the virtual tibial component. The surgeon can evaluate the fit in three dimensions, anteriorly, posteriorly, at the medial aspect of the medial tibial plateau, at the lateral aspect of the lateral tibial plateau. The surgeon can evaluate the size and fit of the virtual tibial component for different levels of tibial resection and different tibial slopes and different degrees of tibial component rotation, e.g. external rotation. The surgeon can upsize or downsize the virtual tibial component by selecting smaller or larger virtual tibial components from the virtual library until the surgeon is satisfied with the fit of the virtual representation of the tibial component and the patient's exposed proximal tibia. If the virtual tibial implant component is too large for an implantation site, the surgeon can cancel the virtual display of the particular size of virtual tibial component displayed and the surgeon can select a smaller virtual tibial component from the library of virtual and physical tibial components. If the tibial implant component is too small for an implantation site, the surgeon can cancel the virtual display of the particular size of virtual tibial component displayed and the surgeon can select a larger virtual tibial component from the library of virtual and physical tibial components. The surgeon can also evaluate the position and/or orientation of the virtual tibial component for possible PCL impingement with cruciate retaining implants or patellar tendon impingement.

The surgeon can evaluate the shape of the virtual tibial component and compare it with the shape of the patient's proximal tibia. The surgeon can optionally select asymmetric virtual tibial components from an optional variety of different asymmetric tibial shapes from the virtual library of tibial components.

The surgeon can optionally align at least portions of the external surface of the virtual tibial component, e.g. the superior surface of one or more polyethylene inserts with at least portions of the patient's tibial articular surface, e.g. on the medial tibial plateau, the lateral tibial plateau. By aligning at least portions of the external surface of the virtual tibial component, e.g. the superior surface of one or more polyethylene inserts with at least portions of the patient's tibial articular surface, e.g. on the medial tibial plateau, the lateral tibial plateau, the surgeon can determine the desired slope of the tibial resection, for example if the surgeon intends to cut the tibia and install the tibial component with a slope similar to the patient's native slope. By aligning at least portions of the external surface of the virtual tibial component, e.g. the superior surface of one or more polyethylene inserts with at least portions of the patient's tibial articular surface, e.g. on the medial tibial plateau, the lateral tibial plateau, the surgeon can determine any desired medial to lateral offsets for the tibial polyethylene.

For example, the surgeon can align at least portions of the external, superior surface or projection of the medial portion of the virtual tibial component including the medial polyethylene with at least portions of the external surface of the physical medial tibial plateau of the patient; if the external surface or projection of the external, superior surface of the lateral portion of the tibial polyethylene of the virtual tibial component is subjacent, inferior relative to the external surface of the physical lateral tibial plateau of the patient, i.e. remains below the external surface of the physical lateral tibial plateau of the patient, the surgeon can discard the digital hologram of the virtual tibial component and select a different virtual tibial component from the virtual library; for example, the surgeon can select a virtual tibial component including a polyethylene with a thicker lateral insert portion than medial insert portion. The surgeon can repeat this process until a desired alignment, match or fit is achieved. The aligning of the external contour, shape or surface of the digital hologram of the virtual tibial component medially and/or laterally with the tibial plateau of the patient can take any desired varus or valgus correction and/or slope into account, for example by adjusting a selected medial or lateral polyethylene thickness or shape based on the desired varus or valgus correction and/or slope. The coordinates of the final position of the virtual tibial component can be saved and can, optionally, be incorporated into a virtual surgical plan. If the virtual surgical plan indicates a variation in position, orientation, alignment, or slope of the virtual tibial component relative to the virtual surgical plan, the surgeon can adjust the position of the virtual tibial component to come closer to the intended position, orientation, alignment, and/or slope of the virtual surgical plan or to replicate it. Alternatively, the virtual surgical plan can be modified based on the position, orientation, alignment, and/or slope of the virtual tibial component.

Alignment criteria can be displayed by the OHMD while the surgeon is moving, orienting or aligning a virtual femoral component, a virtual tibial component and/or a virtual patellar component. The resultant varus/valgus, external/internal rotation, flexion of a femoral component and/or slope of a tibial component, Q-angle and axes can be numerically or graphically displayed and, optionally, compared, for example, with the desired varus/valgus, external/internal rotation, flexion of a femoral component and/or slope of a tibial component based on a virtual surgical plan. The surgeon can elect to apply different alignment criteria, for example anatomic alignment wherein the surgeon can, for example, more closely match one or more virtual and physical implant surfaces with one or more articular surfaces of the patient, e.g. on one or two femoral condyles, on a medial and/or lateral tibial plateau, on a trochlea and/or a patella.

Someone skilled in the art can recognize that the foregoing embodiments can be modified and applied to patellar replacement, patellar resurfacing, shoulder replacement, and/or ankle replacement.

In some embodiments of the invention, an intra-operative 2D or 3D imaging study can be performed, e.g. one or more x-rays or a CT scan, for example using an O-arm system in spinal surgery. The intra-operative imaging study can be registered in a common coordinate system with the surgical site, e.g. a spine, and one or more OHMDs, for example worn by a first surgeon, a surgical resident and a physician assistant or a nurse. The OHMD can display one or more digital holograms of subsurface anatomy of the patient, hidden or obscured by overlying skin, soft-tissue and/or bone. The OHMD can display an arbitrary virtual pedicle screw over the surgical field. The arbitrary virtual pedicle screw can, for example, be pedicle screw selected from the middle of a size range or a shape range. The arbitrary virtual pedicle screw can be selected based on surgeon preferences. The arbitrary virtual pedicle screw can be the most common size used in a particular patient population. The arbitrary virtual pedicle screw can be moveable using a virtual or other interface. For example, the virtual representation of the arbitrary virtual pedicle screw can include a "touch area", wherein gesture recognition software, for example the one provided by Microsoft with the Microsoft Hololens including, for example, the integrated virtual "drag function" for holograms can be used to move the arbitrary virtual pedicle screw. For example, one or more cameras integrated or attached to the OHMD can capture the movement of the surgeon's finger(s) in relationship to the touch area; using gesture tracking software, the arbitrary virtual pedicle screw can then be moved by advancing the finger towards the touch area in a desired direction. A surgeon can, for example, also "hold" the arbitrary virtual pedicle screw by closing two fingers, e.g. thumb and index finger, over the touch area and then moving the fingers in the desired direction, thereby moving the arbitrary virtual pedicle screw into the desired position and/or orientation in the patient's spine, e.g. centered in the target pedicle, towards the medial pedicle wall, towards the lateral pedicle wall, towards the superior pedicle wall and/or towards the inferior pedicle wall, forward and, optionally, backward. As an alternative to virtually moving or aligning a virtual pedicle screw, a virtual predetermined path for a pedicle screw or for a vertebroplasty or kyphoplasty needle can also be virtually moved or aligned, e.g. using a virtual interface or other interface.

The OHMD can display the virtual pedicle screw in any location initially, e.g. projected onto or outside the surgical field, e.g. a lumbar, thoracic or cervical spine. The OHMD can optionally display the virtual pedicle screw at a defined angle, e.g. orthogonal or parallel, relative to a fixed structure in the operating room, which can, for example, be recognized using one or more cameras, image capture or video capture systems integrated into the OHMD and spatial recognition software such as the one provided by Microsoft with the Microsoft Hololens or which can be recognized using one or more attached optical markers or navigation markers including infrared or RF markers. The virtual pedicle screw can then displayed perpendicular or at another angle relative to the operating room table. The virtual pedicle screw can be displayed at a defined angle to one or more anatomic or biomechanical axes.

The surgeon can move the virtual pedicle screw to align it in the desired location and/or orientation in the pedicle and/or vertebral body. The surgeon can then evaluate the size of the virtual pedicle screw and the fit of the virtual pedicle screw by evaluating the size and fit of the virtual representation of the virtual pedicle screw superimposed onto the intended implantation site in the pedicle and vertebral body. The surgeon can move and align the virtual pedicle screw. If the virtual pedicle screw is too large for the patient's pedicle, the surgeon can cancel the virtual display of the particular size of virtual pedicle screw displayed and the surgeon can select a smaller virtual pedicle screw from the library of virtual and physical pedicle screws. If the virtual pedicle screw is too small for a patient's pedicle, the surgeon can cancel the virtual display of the particular size of virtual pedicle screw displayed and the surgeon can select a larger virtual pedicle screw from the library of virtual and physical pedicle screws. In this manner, the surgeon can optimize the pedicle screw size and fit in three-dimensions in the actual surgical site, level by level.

Virtual Surgical Plans

Virtual and physical surgical instruments and implant components can be registered in a common coordinate system, for example with one or more OHMDs and live data of the patient. When pre-operative imaging studies, intra-operative imaging studies or intra-operative measurements are registered in a common coordinate system with one or more OHMDs using, for example, anatomic features, anatomic landmarks, implantable and attachable markers, calibration and registration phantoms including optical markers, LEDs with image capture, navigation markers, infrared markers, RF markers, IMUs, or spatial anchors and spatial recognition, one or more of an instrument or implant position, orientation, alignment can be predetermined using the information from the pre- and intra-operative imaging studies and/or the intra-operative measurements.

In some embodiments of the invention, a surgeon or an operator can develop a virtual surgical plan. The virtual surgical plan can include the virtual removal of select tissues, e.g. bone or cartilage or soft-tissue, e.g. for installing or implanting a medical device. The virtual surgical plan can include removal of a tumor or other tissues. The virtual surgical plan can include placing a graft or a transplant. Any surgical procedure known in the art can be simulated in a virtual surgical plan, for example spinal fusion including anterior and posterior, spinal disk replacement using motion preservation approaches, hip replacement, knee replacement, ankle replacement, shoulder replacement, ACL repair or reconstruction, ligament reconstruction.

A virtual surgical plan can be developed using intra-operative data or measurements, including measurements obtained using one or more optical markers which can, for example, be detected using one or more cameras, an image capture system, a video capture system integrated into, attached to or separate from an OHMD. The one or more cameras, an image capture system, a video capture system integrated into, attached to or separate from an OHMD can, for example, detect the coordinates of one or more optical markers attached to the surgical site, e.g. a bone or cartilage, an altered surgical site, e.g. a bone cut, the operating room table, an extension of the operating room table, and/or fixture structures in the operating room, e.g. walls. The one or more cameras, an image capture system, a video capture system integrated into, attached to or separate from an OHMD can detect the one or more optical markers in static positions and/or dynamic, moving positions. The coordinates (x, y, z) of the optical markers can be measured in static and dynamic conditions.

Any other sensor described in the specification, e.g. IMUs, navigation markers, e.g. infrared markers and/or RF markers, LEDs, can be used for obtaining intraoperative measurements and can be combined, for example with optical marker measurements, for deriving intra-operative measurements and for generating and/or developing a virtual surgical plan.

Intra-operative measurements using one or more cameras, an image capture system, a video capture system integrated into or attached to an OHMD can be beneficial when measurements are desired to be obtained from the view angle of the surgeon or, when multiple OHMDs are used, from the view angle of a surgical assistant or second surgeon. Intra-operative measurements using one or more cameras, an image capture system, a video capture separate from an OHMD can be advantageous when measurements are desired to be obtained from a view angle other than the surgeon or, when multiple OHMDs are used, from a view angle other than of a surgical assistant or second surgeon.

Pre-operative data, e.g. pre-operative imaging studies or kinematic studies of a patient, e.g. with the joint or the spine measured or imaged in motion, can also be incorporated into a virtual surgical plan. Pre-operative data alone can be used to develop a virtual surgical plan.

The virtual surgical plan can be developed with use of a computer or computer workstation as well as a local or remote computer or computer network. The computer or computer workstation can include one or more displays, keyboard, mouse, trackball, mousepad, joystick, human input devices, processor, graphics processors, memory chips, storage media, disks, and software, for example for 3D reconstruction, surface displays, volume displays or CAD design and display, as well as optional CAM output. The software can include one or more interfaces for CAD design, for displaying the patient's anatomy, for displaying virtual surgical instruments and for displaying virtual implants, implant components, medical devices and/or medical device components.

The different anatomic and pathologic structures as well as the different virtual instruments, e.g. virtual surgical guides including drill guides or cut blocks, virtual implants, implant components, medical devices and/or medical device components can optionally be displayed simultaneously on the same screen or screen section or non-simultaneously, e.g. on different screens, on the same screen at different times, or no different screen sections. The different anatomic and pathologic structures including hidden and/or obscured or partially hidden and/or obscured anatomic and pathologic structures as well as the different virtual instruments, e.g. virtual surgical guides including drill guides or cut blocks, virtual implants, implant components, medical devices and/or medical device components can optionally be displayed using different colors or different shading. Some of the different anatomic and pathologic structures as well as the different virtual instruments, e.g. virtual surgical guides including drill guides or cut blocks, virtual implants, implant components, medical devices and/or medical device components can optionally be displayed in a form of outline mode or pattern mode, where only the outline or select features or patterns of the anatomic and pathologic structures as well as the virtual instruments, e.g. virtual surgical guides including drill guides or cut blocks, different virtual implants, implant components, medical devices and/or medical device components are being displayed, for example with solid, dotted or stippled lines or geometric patterns.

Figure 11:
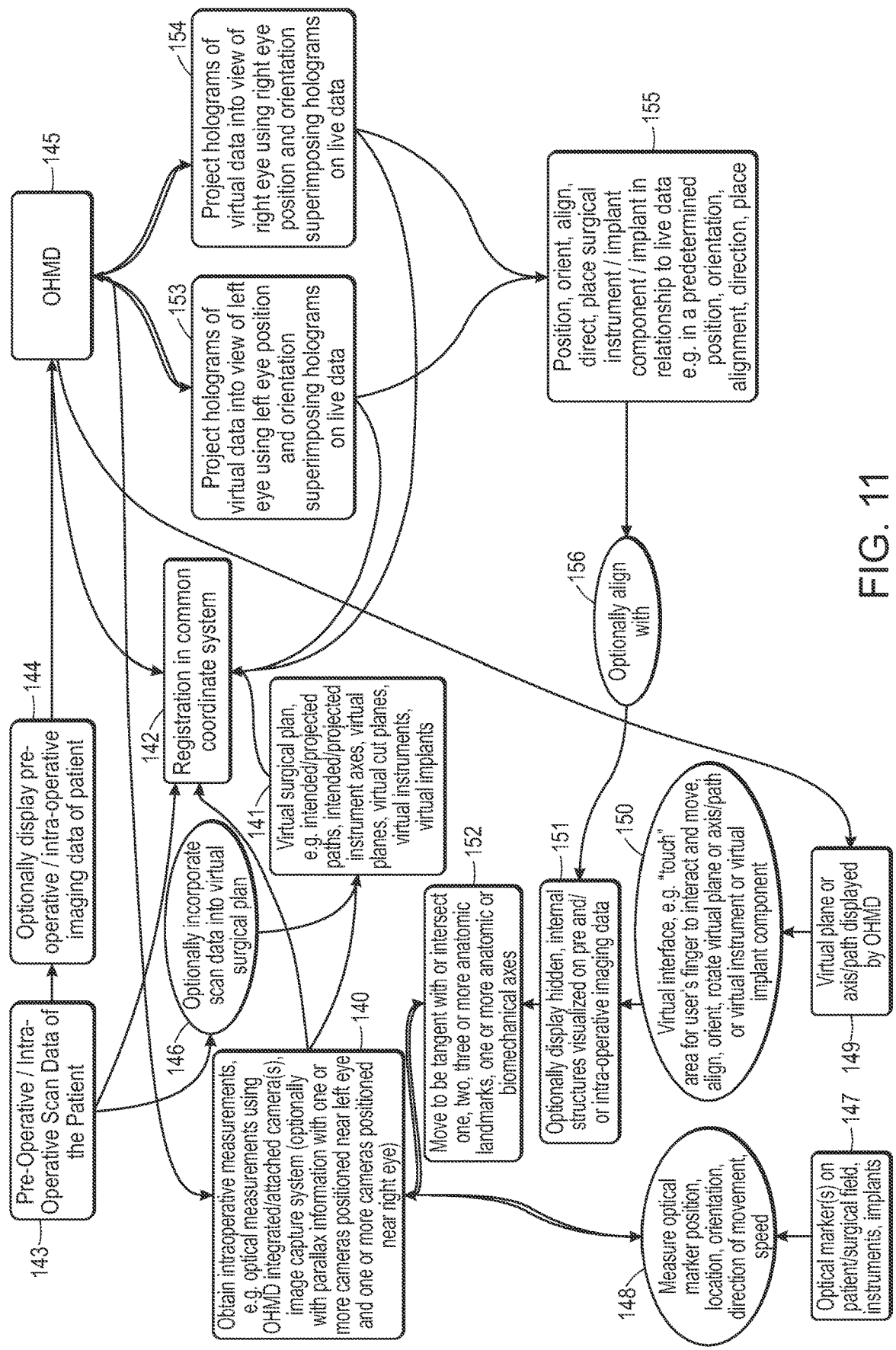
FIG. 11 is an illustrative example how a virtual surgical plan can be generated using intraoperative data, e.g. intraoperative measurements, for example measurements obtained with one or more cameras, an image capture system or a video capture system integrated into, attached to or separate from an optical head mount display according to some embodiments of the present disclosure.

FIG. 11 shows how a virtual surgical plan 141 can be generated using intraoperative data, e.g. intra-operative measurements 140, for example measurements obtained with one or more cameras, an image capture system or a video capture system integrated into, attached to or separate from an optical head mount display. Intraoperative measurements 140 can be utilized to generate a virtual surgical plan 141 which can be registered in a common coordinate system 142. The intraoperative measurements 140 can also be directly registered in the common coordinate system 142. Preoperative and/or intraoperative scan data 143 can be generated and can be optionally displayed 144 in two or three dimensions in an OHMD 145. Preoperative and/or intraoperative scan data 143 can optionally be incorporated 146 in the virtual surgical plan 141. Optical markers 147 can be present on the patient, the surgical field, surgical instruments or implants and can be measured with regard to their position, location, orientation, direction of movement and/or speed 148. A virtual plane or path or axis 149 can be displayed by the OHMD 145 and, using a virtual interface 150, the plane or path or axis, as well as optionally virtual implants or instruments, can be moved by the surgeon. Optionally, the OHMD 145 can display hidden or internal structures 151, e.g. visualized on preoperative or intraoperative imaging studies or combinations of both, and the surgeon or the software can align the planes, axis or path, as well as optionally virtual implants or instruments, relative to the hidden or internal structures 149. The plane, axis or path or virtual surgical instruments or virtual implants can be moved to be tangent with or intersect anatomic landmarks, and/or anatomical axes and/or biomechanical axes 152, for example for alignment purposes or to achieve a predetermined position and/or orientation of an instrument or an implant. The OHMD can project stereoscopic views for the left eye and right eye by displaying electronic holograms with virtual data superimposing the virtual data using the left eye position and orientation on the live data for the left eye 153 and superimposing the virtual data using the right eye position and orientation on the live data for the right eye 154. The projected virtual data in 153 and 154 can be used to position, orient, align, direct or place one or more of a surgical instrument, an implant component and an implant in relationship to the live data of the patient, e.g. in a predetermined position, orientation, alignment direction or place 155. The position, orientation, alignment direction or place of the one or more of a surgical instrument, an implant component and an implant can optionally be aligned with hidden anatomy or internal structures 151, optionally using a virtual interface 150. Someone skilled in the art can recognize that multiple coordinate systems can be used instead of a common coordinate system. In this case, coordinate transfers can be applied from one coordinate system to another coordinate system, for example for registering the OHMD, live data of the patient including the surgical site, virtual instruments and/or virtual implants and physical instruments and physical implants.

Figure 12:
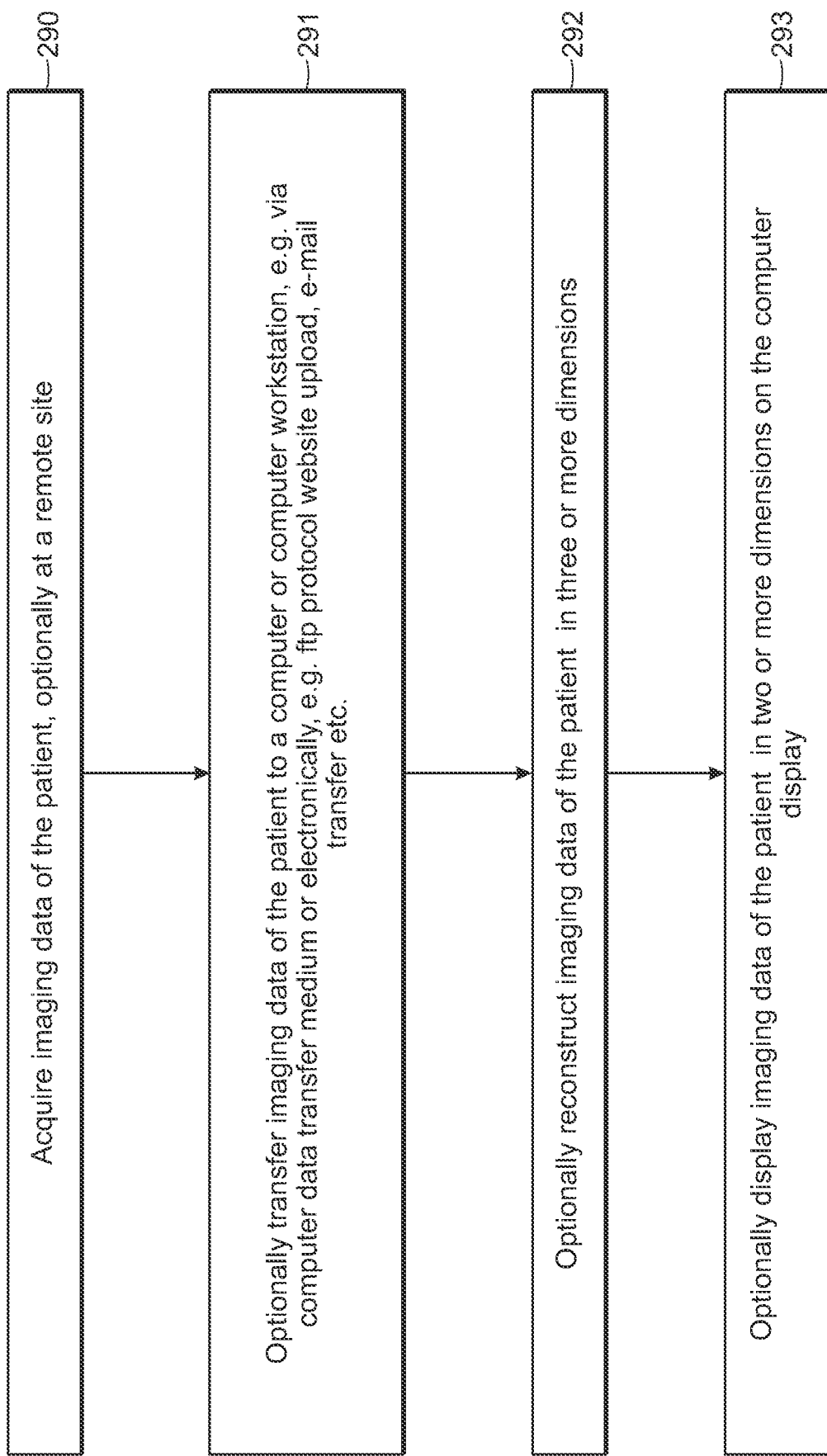
FIG. 12 is an exemplary workflow for generating a virtual surgical plan according to some embodiments of the present disclosure.

FIG. 12 is another exemplary workflow for generating a virtual surgical plan. Imaging data of a patient are acquired, e.g. at a site remote from the operating room 290. The imaging data can be transferred to a computer or workstation, e.g. via electronic data transfer routines such as ftp or internet 291. The imaging data of the patient can be reconstructed in three dimensions 292. The imaging data can be displayed in two or three dimensions on a computer display 293 or OHMD.

Figure 13:
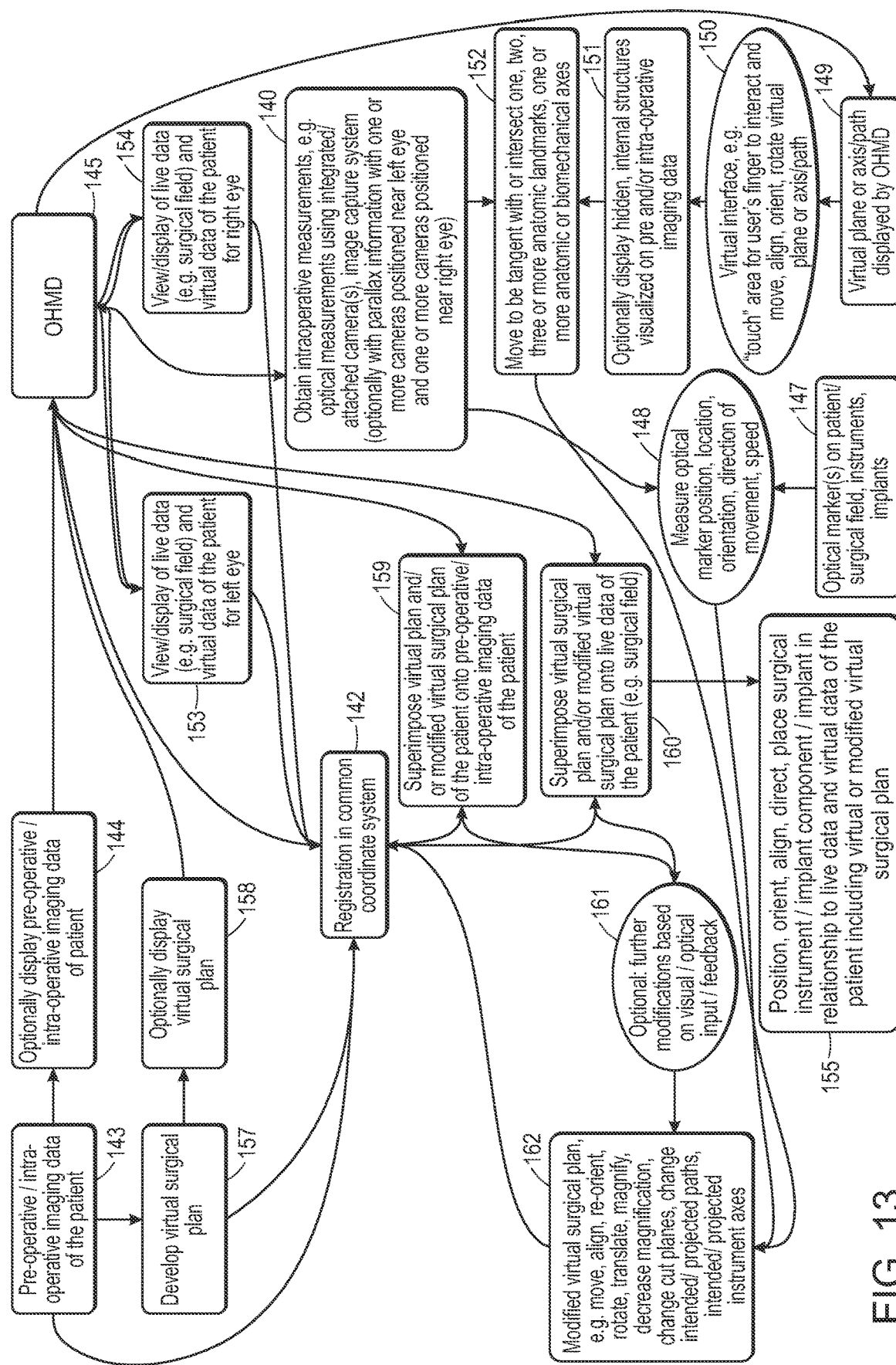
FIG. 13 shows an example how a virtual surgical plan can be modified using intraoperative data, e.g. intraoperative measurements according to some embodiments of the present disclosure.

FIG. 13 shows an example how a virtual surgical plan 157 can be modified using intraoperative data, e.g. intraoperative measurements 140. The virtual surgical plan 157 can be developed using pre-operative and intra-operative imaging data of the patient 143. The virtual surgical plan 157 can be registered in a common coordinate system 142. Preoperative and/or intraoperative scan data 143 can be generated and can be optionally displayed 144 in two or three dimensions in an OHMD 145. Preoperative and/or intraoperative scan data 143 can be used to develop the virtual surgical plan 157 which can be optionally displayed 158 by the OHMD 145. Optical markers 147 can be present on the patient, the surgical field, surgical instruments or implants and can be measured with regard to their position, location, orientation, direction of movement and/or speed 148. A virtual plane or path or axis 149 can be displayed by the OHMD 145 and, using a virtual interface 150, the plane or path or axis, as well as optionally virtual implants or instruments, can be moved by the surgeon. Optionally, the OHMD 145 can display hidden or internal structures 151, e.g. visualized on preoperative or intraoperative imaging studies or combinations of both, and the surgeon can align the planes, axis or path, as well as optionally virtual implants or instruments, relative to the hidden or internal structures 149. The plane, axis or path or virtual surgical instruments or virtual implants can be moved to be tangent with or intersect anatomic landmarks, and/or anatomical axes and/or biomechanical axes 152, for example for alignment purposes or to achieve a predetermined position and/or orientation of an instrument or an implant. The OHMD can project stereoscopic views for the left eye and right eye by displaying virtual data superimposing the virtual data using the left eye position and orientation on the live data for the left eye 153 and superimposing the virtual data using the right eye position and orientation on the live data for the right eye 154. The projected virtual data in 153 and 154 can be used to position, orient, align, direct or place one or more of a surgical instrument, an implant component and an implant in relationship to the live data of the patient, e.g. in a predetermined position, orientation, alignment direction or place 155. The position, orientation, alignment direction or place of the one or more of a surgical instrument, an implant component and an implant can optionally be aligned with hidden anatomy or internal structures 151, optionally using a virtual interface 150. Intraoperative measurements 140 can be utilized to generate or modify a virtual surgical plan 157. The virtual surgical plan 157 and/or a modified virtual surgical plan 162 can optionally be superimposed on preoperative and intraoperative imaging data of the patient 159. The virtual surgical plan 157 and/or a modified virtual surgical plan 162 can optionally be superimposed on preoperative and intraoperative imaging data of the patient 159. The modified virtual surgical plan 162 can be further modified based on visual or optical feedback or input 161 and it can be used to position, orient, align, direct, place one or more virtual or physical instruments, implant components and/or implants in a predetermined position 155. Someone skilled in the art can recognize that multiple coordinate systems can be used instead of a common coordinate system. In this case, coordinate transfers can be applied from one coordinate system to another coordinate system, for example for registering the OHMD, live data of the patient including the surgical site, virtual instruments and/or virtual implants and physical instruments and physical implants.

In some embodiments of the invention, one or more of a virtual surgical tool, virtual surgical instrument including a virtual surgical guide or cut block, virtual trial implant, virtual implant component, virtual implant or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be moved, re-oriented and/or re-aligned by the surgeon using a virtual or other interface. For example, the virtual representation of the one or more of a virtual surgical tool, virtual surgical instrument including a virtual surgical guide or cut block, virtual trial implant, virtual implant component, virtual implant or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can include a "touch area", wherein an image or video capture system and gesture recognition software, for example the one provided by Microsoft with the Microsoft Hololens including, for example, the integrated virtual "drag function" for holograms can be used to move the virtual data. For example, one or more cameras integrated or attached to the OHMD can capture the movement of the surgeon's finger(s) in relationship to the touch area; using gesture tracking software, the hologram(s) can then be moved by advancing the finger towards the touch area in a desired direction. A surgeon can, for example, also "hold" the hologram(s) by closing two fingers, e.g. thumb and index finger, over the touch area and then moving the fingers in the desired direction.

Placement Rules, Selection Rules, Design Rules

A virtual surgical plan can optionally include placement rules for surgical instruments and/or medical devices, implants or implant components. These placement rules can be based on standard rules of surgery or on standard surgical techniques, e.g. placement rules of knee arthroplasty, hip arthroplasty or for pedicle screws. Placement rules or selection rules or design rules for a virtual surgical plan can be based on the patient's anatomy, desired implant, component or medical device position, location, orientation, rotation or alignment, one or more anatomical axes, one or more biomechanical axes, a mechanical axis of the knee or lower extremity, one or more rotational axes, a desired function of an implant, implant component or medical device. Placement rules or selection rules or design rules for a surgical plan can be used, for example, to select an implant. Placement rules or selection rules or design rules can include implant, implant component, or medical device dimensions or shape. Placement rules or selection rules or design rules can include avoidance of certain soft-tissues, vessels or neural structures as well as other sensitive tissues or structures, e.g. ligaments intended to be preserved. For example, in unicompartmental arthroplasty, a placement rule can include that a vertical tibial cut spares the medial tibial spine. In cruciate retaining total knee arthroplasty, a placement rule can include to spare the posterior cruciate ligament during the tibial resection, for example by designing a bone cut in a manner to avoid the posterior cruciate ligament. Placement rules, selection rules or design rules of a virtual surgical plan can include demographic information of the patient, e.g. weight, height, age, gender, other information such as bone mineral density or structure, clinical history, history of prior fractures, or functional information, e.g. on motion of a joint, or metabolic information, e.g. for certain organs or pathologic tissues. Automatic placement of a virtual medical device, device component or implant is possible, for example based on anatomic criteria, pathologic criteria, or functional criteria using placement rules, selection rules or design rules for virtual surgical plans. Placement of a virtual medical device using placement rules, selection rules or design rules can be manual, semi-automatic or automatic. Manual, semi-automatic or automatic placement rules will typically require a software and a user interface.

For example, in spinal surgery the placement of a pedicle screw in the virtual surgical plan can be based on Distance between pedicle screw or related bone void to accept the pedicle screw to the medial, lateral, superior, and/or inferior endosteal surface or cortical surface in portions or all of the pedicle.

Area or volume between pedicle screw or related bone void to accept the pedicle screw to the medial, lateral, superior, and/or inferior endosteal surface or cortical surface in portions or all of the pedicle.

The foregoing information on distance or area can also be used for selecting a size, width, diameter or length of a pedicle screw.

In spinal surgery the placement of a pedicle screw in the virtual surgical plan can also be based on:

Location of the pedicle screw including its tip in the vertebral body.

Location of the pedicle screw including its tip in relationship to a spinal/vertebral body fracture.

Location of the pedicle screw including its tip in relationship to a superior endplate.

Location of the pedicle screw including its tip in relationship to an inferior endplate.

Location of the pedicle screw including its tip in relationship to an anterior vertebral cortex.

Location of the pedicle screw including its tip in relationship to a vessel.

Location of the pedicle screw including its tip in relationship to the aorta.

Location of the pedicle screw including its tip in relationship to the inferior vena cava.

Location of the pedicle screw including its tip in relationship to neural structures, the thecal sac, nerve roots and/or the spinal cord.

Distance, area or volume between the pedicle screw including its tip to a spinal/vertebral body fracture.

Distance, area or volume between the pedicle screw including its tip to a superior endplate.

Distance, area or volume between of the pedicle screw including its tip to an inferior endplate.

Distance, area or volume between the pedicle screw including its tip to an anterior vertebral cortex.

Distance, area or volume between the pedicle screw including its tip to a vessel.

Distance, area or volume between the pedicle screw including its tip to the aorta.

Distance, area or volume between the pedicle screw including its tip to the inferior vena cava.

Distance, area or volume between the pedicle screw including its tip to neural structures, the thecal sac, nerve roots and/or the spinal cord.

The foregoing information on location or distance or area or volume can also be used for selecting a size, width, diameter or length of a pedicle screw.

The placement and the selection of a pedicle screw in spinal surgery can be based on any of the foregoing including any combinations thereof.

The surgeon can receive 2D or 3D or multi-dimensional information of the patient. The information can be displayed, for example using a display screen, e.g. a computer screen separate from the OHMD or the OHMD. The surgeon can mark anatomic structures or pathologic structures on the computer screen using the 2D or 3D or multi-dimensional information of the patient. The information can optionally be segmented or can be modified, for example using image processing techniques known in the art. The marking can be performed using the display of the OHMD unit, e.g. using a virtual user interface.

The surgeon can also mark sensitive tissue, e.g. nerves, brain structure, vessels etc., that the surgeon wants to preserve or protect during the surgery. Such sensitive structure(s) can be highlighted, for example using different colors, when the virtual surgical plan and the related anatomic data or pathologic tissue information is being transmitted to or displayed by the OHMD. The surgical plan can be designed, adapted or modified so that sensitive structures are avoided or only minimally perturbed. For example, if a virtual surgical plan would result in an interference between a surgical instrument, e.g. a scalpel, a saw, a drill or a bur and a sensitive structure such as a vessel or a nerve, the virtual surgical plan can be adapted or modified by moving the position, location, orientation and/or direction of the virtual surgical instrument in order to avoid any interference or contact of the sensitive structure(s) with the surgical instrument. The marking can be performed using the display of the OHMD unit, e.g. using a virtual user interface. For example, the surgeon can optionally point at or circle with his or her finger sensitive structure on the live surgical site including by optionally touching the sensitive tissue. One or more cameras, an image or video capture system integrated into, attached to or separate from the OHMD can detect the finger movement and can highlight the sensitive areas pointed out or circled by the surgeon's finger.

In some embodiments of the invention, if an interference or contact between the surgical instrument and one or more sensitive structures cannot be avoided (in the virtual data and/or the live or physical surgery), the virtual surgical plan can be adapted or modified to move, typically at least partially, the sensitive structure(s), for example using tissue retractors, in order to minimize or reduce any interference or contact of the surgical instrument with the sensitive structure(s).

In some embodiments of the invention, if an interference or contact between the surgical instrument and one or more sensitive structures cannot be avoided (in the virtual data and/or the live or physical surgery), the virtual surgical plan can be adapted or modified to protect, at least partially, the sensitive structure(s), for example using a virtual and in the live patient physical metal or plastic shield which can optionally be interposed between the sensitive structure(s) and the surgical instrument in order to minimize or reduce any interference or contact of the surgical instrument with the sensitive structure(s).

The surgeon can mark the desired location, position, orientation, and or alignment of a graft, transplant or an implant or components thereof. Implant materials can include organic and inorganic matter. Implant materials can include biologic and non-biologic matter.

In a hip replacement procedure, for example, the surgeon can indicate the desired location, position, orientation, alignment, anteversion or offset of an acetabular component or a femoral component. With the femoral component, the surgeon can also indicate the desired femoral neck resection level and the desired position of the component in the femoral canal including the desired entry point into the cut femoral neck, e.g. medially, laterally, anteriorly or posteriorly as well as the desired entry angle. With the acetabular component, the surgeon can also indicate the desired reaming depth and any desired medialization or lateralization.

With the implantation of any medical device, the surgeon can indicate the desired location, position, orientation, alignment of the medical device. Thus, the virtual surgical plan can show the desired location, position, orientation, or alignment of a medical device. The virtual surgical plan can also show the desired location, position, orientation, or alignment of a medical device relative to neighboring tissue. Neighboring tissue can be the tissue of the same organ or joint. Neighboring tissue can also be the tissue of adjacent sensitive structures, e.g. vessel, nerves, other organs and the like.

The surgeon can optionally simulate different locations, positions, orientations or alignments of a medical device. The simulation of different locations, positions, orientations or alignments of a medical device can be particularly helpful when the medical device entails more than one component as can be the case, for example, with Pedicle screws, connectors and spinal rods Artificial intervertebral disks, e.g. metallic endplates and ultra-high molecular weight polyethylene mobile sliding core Knee replacement components, including tibial tray, polyethylene inserts, femoral components, mobile bearings Hip replacement components, including acetabular cup, acetabular liner, femoral head, optionally modular femoral neck, femoral stem or mono-block femoral neck and stem With these multicomponent devices, the surgeon can plan the placement of individual components in the virtual surgical plan and the surgeon can optionally evaluate their location, position, orientation or alignment relative to each other. The surgeon can then make adjustments to the placement, e.g. the position, location, orientation, rotation or alignment of one or more of the components in the virtual plan and, optionally later, in the live surgery. Optionally, the surgeon can also test the function of these components in relationship to each other. For example, in a surgical plan for an artificial intervertebral disk, the software can allow the surgeon to virtually simulate spinal flexion or extension or lateral bending to the left and right with one or more of the medical device components included in the virtual surgical plan or the motion simulation. The surgeon can repeat the virtual surgical plan or the simulation with different degrees of flexion or extension or lateral bending to the left and the right and/or with differently sized or shaped medical devices or medical device components. If there is interchangeability of parts or components between different sizes and shapes or a medical device, the surgeon can optionally repeat the virtual surgical plan or the simulation using such different size components, e.g. a large size polyethylene insert or spacer with a medium size metal backing components or vice versa.

The surgeon can optionally superimpose medical device components with different size and/or shapes on the information and select the device component(s) that best fit the patient or that best match the patient.

In some embodiments of the invention, when, for example, a virtual surgical plan is developed using pre-operative data, e.g. pre-operative imaging data, the information is sent from the surgeon's or operator's office, e.g. a radiology office, to a central site, e.g. for image processing or for generating an initial draft surgical plan resulting in processed data or information. The processed information can be transmitted back to the surgeon or the operator. The surgeon or the operator can review the draft surgical plan. The surgeon or the operator can accept the draft surgical plan. The surgeon or the operator can optionally modify the draft surgical plan. The accepted or modified draft surgical plan can optionally be transmitted back to the central site. The central site can, for example, generate instructions to ship certain medical device components that the surgeon has accepted or selected with the accepted or modified surgical plan.

When intra-operative data are used for developing the virtual surgical plan, the surgeon can develop portions or the entire virtual surgical plan on his or her own, for example using a computer, standard hardware components, display and software in his or her office, a computer, standard hardware components, display and software in the operating room, or the optical head mount display, e.g. using a virtual interface, or combinations thereof. Different computers including the OHMD can be connected via a network, e.g. a WiFi or LiFi network.

The surgeon can optionally incorporate pre-operative data into the virtual surgical plan. For example, in knee replacement, the surgeon can perform intra-operative measurements using, for example, optical markers to determine the mechanical axis of the leg and to define femoral and/or tibial and/or patellar landmarks and register them in the common coordinate system and can be used for the virtual surgical plan which can also be registered in the common coordinate system. The surgeon can then incorporate or import data from one or more pre-operative and/or intra-operative knee x-rays, for example femoral, tibial or patellar component size and/or desired varus or valgus correction and/or desired femoral and/or tibial component rotation and/or desired femoral component flexion and/or desired tibial slope, and/or desired femoral, tibial and/or patellar component position and/or orientation and/or alignment into the virtual surgical plan. Standard data, e.g. a fixed tibial slope, e.g. 0 degrees, 3 degrees or 5 degrees can also be incorporated into the virtual surgical plan. Any of the foregoing can be registered in the common coordinate system and optionally virtually displayed by the OHMD.

In hip replacement, the surgeon can perform intra-operative measurements using, for example, optical markers to determine the location of the center of rotation of the hip joint, to define femoral and acetabular landmarks, e.g. the top of the greater trochanter, the sulcus point, e.g. the lowest point between the greater trochanter and the femoral neck, and the lesser trochanter, the acetabular rim and/or the center of the acetabulum, e.g. by pointing at them using a pointer with one or more attached optical markers; these and other intra-operative measurements can be registered in the common coordinate system and can be used for the virtual surgical plan which can also be registered in the common coordinate system. The surgeon can then incorporate or import data from one or more pre-operative and/or intra-operative hip x-rays and/or pelvic x-rays, for example femoral and acetabular component size, desired liner including lipped and offset liners, desired femoral head size including plus and minus head sizes, and/or desired leg length, and/or desired center of rotation, and/or desired femoral neck length, and/or desired femoral neck angle, and/or desired femoral and/or acetabular component anteversion and/or offset, including combined anteversion. Standard data, e.g. a fixed femoral, acetabular or combined anteversion, a fixed femoral neck angle, a range of angles for an acetabular safe zone can also be incorporated into the virtual surgical plan. Any of the foregoing can be registered in the common coordinate system and optionally virtually displayed by the OHMD.

In some embodiments of the invention, aspects of the surgical plan, e.g. the intended location of a medical device that the surgeon is planning to implant can be displayed by the OHMD superimposed onto the live data. The intended location can be indicated, for example, by a virtual medical device component that is a representation of the medical device component selected for implantation. The virtual medical device component displayed by the OHMD in superimposition with the live data can be displayed, for example, in its final desired position. The surgeon can then intraoperatively place or insert the medical device component aligning the physical device with the virtual device component.

In some embodiments, the intended location of a graft, transplant, medical device or other implantable can be indicated using virtual markers or targets displayed by the OHMD simultaneous with the live data of the patient. The surgeon can then align the graft, transplant, medical device or other implantable with the virtual markers or targets or the surgeon can direct the graft, transplant, medical device or other implantable towards the virtual markers or targets.

A visual or acoustic or other warning signal can be emitted or provided if the surgeon/operator deviates from the surgical plan. The visual warning signal can be provided by the OHMD, e.g. a red background flashing in the display of the virtual data or a color change, e.g. to red, of the virtual data.

In some embodiments of the invention, the virtual surgical plan can start by selecting or designing a desired implant or implant component or medical device size and/or dimension and/or shape based on the patient's anatomy, surgical site, pathologic conditions, deformity and other information including but not limited to a desired location, position, orientation, rotation or alignment in relationship to one or more anatomic or rotational or biomechanical axes. The selection or design of the desired size and/or dimension and/or shape can be followed by the placement of the implant, implant component or medical device in the desired location, position, orientation, rotation or alignment in relationship to one or more anatomic or biomechanical axes, the patient's anatomy surgical site, pathologic conditions or deformity. The process can be iterative. For example, the implant or implant component or medical device selection or design can be followed by a desired placement, which can be followed by changes in the selection or design of the implant or implant component or medical device selection, which can be followed by adjustments in placement and so forth. The iterative process can be automatic or semiautomatic.

Once the final implant selection or design and placement have been determined in the virtual surgical plan, the preceding surgical steps can be designed or selected in the virtual surgical plan in relationship to the patient's anatomy, the surgical site, the pathologic condition, one or more anatomic or biomechanical axes, functional information, information on sensitive tissues and other tissues. The preceding surgical steps can be designed or selected in reverse order starting with the final implant or implant component or medical device placement, in consecutive order or in random order or any combinations thereof. Surgical steps can be optionally repeated to optimize any tissue alterations and/or implant placement and/or implant selection and/or implant design. If a virtual surgical plan indicates the potential for complications during the surgery, e.g. placement too close to a vessel or neural structure or other sensitive structure, the surgical plan, portions of the surgical plan, the sequence of the surgical plan and the implant, implant component or medical device selection or design can be modified in order to avoid such potential complications. Thus, the entire process between selection and placement of the implant and surgical steps including display of surgical instruments can be iterative in the virtual surgical plan.

In some embodiments of the invention, the virtual surgical plan can start by placing a virtual implant or implant component or medical device in a desired location, position, orientation, rotation or alignment in relationship to one or more anatomic or biomechanical axes, the patient's anatomy surgical site, pathologic conditions or deformity. The implant used for this initial or final placement can be an implant selected from an average, a minimum or a maximum size, dimension or shape or combinations thereof. The placing of the implant or implant component or medical device can then be followed by the selection or design of a desired implant or implant component or medical device size and/or dimension and/or shape. The process can be iterative. For example, placement of the implant or implant component or medical device can be followed by a selection or design of the desired the implant or implant component or medical device size, dimension or shape, which can be followed by changes in the placement of the implant or implant component or medical device, which can be followed by changes in the selection or design of size, dimension or shape and so forth. The iterative process can be automatic or semiautomatic.

Once the final implant placement and selection or design have been determined in the virtual surgical plan, the preceding surgical steps can be designed or selected in the virtual surgical plan in relationship to the patient's anatomy, the surgical site, the pathologic condition, one or more anatomic or biomechanical axes, functional information, information on sensitive tissues and other tissues. The preceding surgical steps can be designed or selected in reverse order starting with the final implant or implant component or medical device placement, in consecutive order or in random order or any combinations thereof. Surgical steps can be optionally repeated to optimize any tissue alterations and/or implant placement and/or implant selection and/or implant design. If a virtual surgical plan indicates the potential for complications during the surgery, e.g. placement too close to a vessel or neural structure or other sensitive structure, the surgical plan, portions of the surgical plan, the sequence of the surgical plan and the implant, implant component or medical device selection or design can be modified in order to avoid such potential complications. Thus, the entire process between selection and placement of the implant and surgical steps including display of surgical instruments can be iterative in the virtual surgical plan.

In some embodiments of the invention, the virtual surgical plan can start out with the initial surgical step as defined, for example, in the surgical technique. This can be followed optionally by each or some of the subsequent surgical steps, for example only the major steps. The virtual surgical plan can then continue up to the selection and/or design and placement of the implant in the virtual data of the patient. If the resultant selection and/or design and/or placement of the implant, implant component or medical device differs from the desired result, for example as defined in the surgical plan or as desired by the surgeon, any of the foregoing surgical steps, the placement and/or the selection or the design of the implant, implant component or medical device can be modified. This process can be iterative, manual, semi-automatic or automatic until the desired virtual surgical plan, implant, implant component or medical device selection and/or design or placement are achieved.

Figure 14:
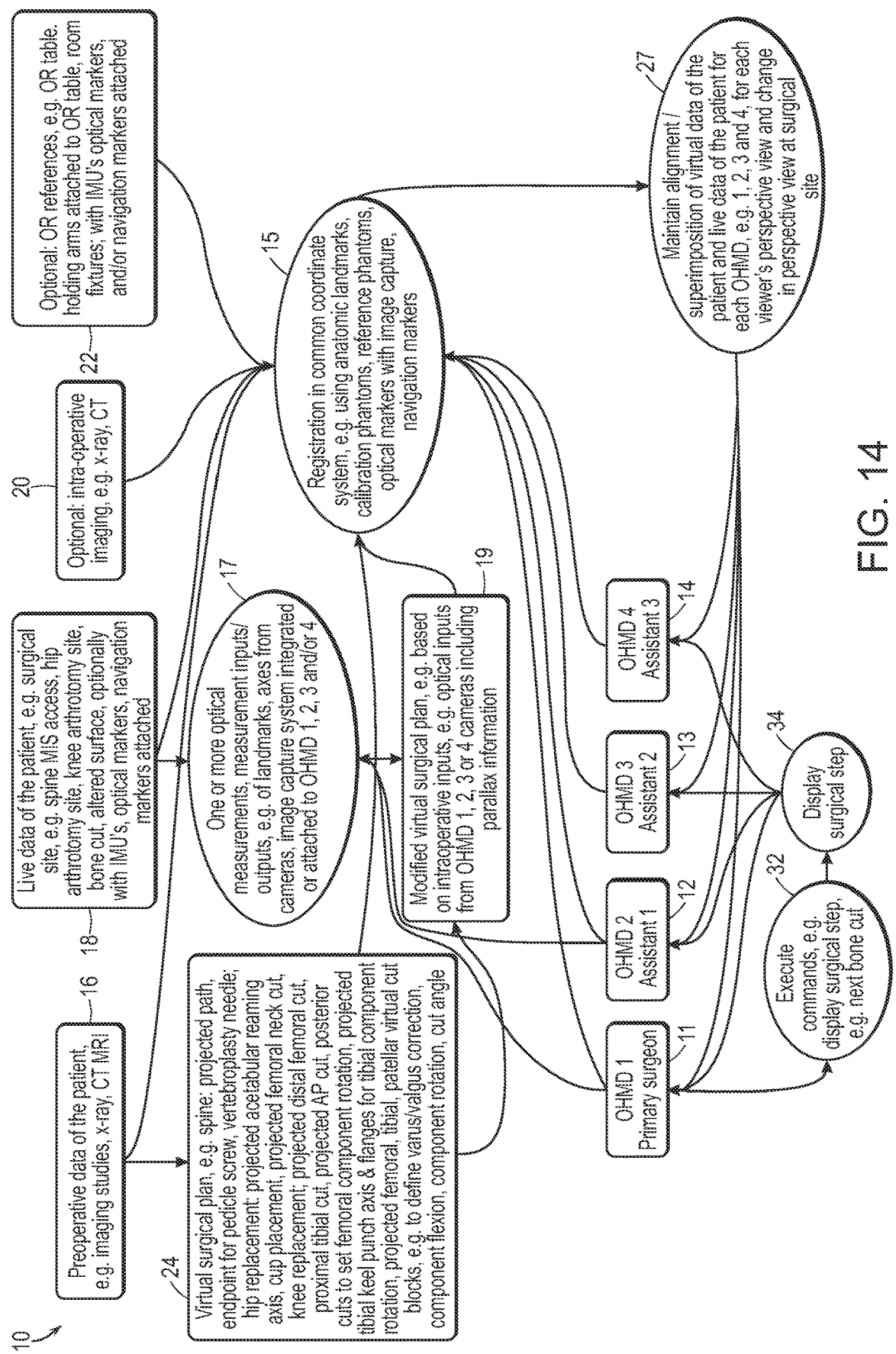
FIG. 14 shows an illustrative example how multiple OHMDs can be used during a surgery, for example by a first surgeon, a second surgeon, a surgical assistant and/or one or more nurses and how a surgical plan can be modified and displayed during the procedure by multiple OHMDs while preserving the correct perspective view of virtual data and corresponding live data for each individual operator according to some embodiments of the present disclosure.

FIG. 14 shows an illustrative example how multiple OHMDs can be used during a surgery, for example by a first surgeon, a second surgeon, a surgical assistant and/or one or more nurses and how a surgical plan can be modified and displayed during the procedure by multiple OHMDs while preserving the correct perspective view of virtual data and corresponding live data for each individual operator. A system 10 for using multiple OHMDs 11, 12, 13, 14 for multiple viewer's, e.g. a primary surgeon, second surgeon, surgical assistant(s) and/or nurses(s) is shown. The multiple OHMDs can be registered in a common coordinate system 15 using anatomic structures, anatomic landmarks, calibration phantoms, reference phantoms, optical markers, navigation markers, and/or spatial anchors, for example like the spatial anchors used by the Microsoft Hololens. Pre-operative data 16 of the patient can also be registered in the common coordinate system 15. Live data 18 of the patient, for example from the surgical site, e.g. a spine, optionally with minimally invasive access, a hip arthrotomy site, a knee arthrotomy site, a bone cut, an altered surface can be measured, for example using one or more IMUs, optical markers, navigation markers, image or video capture systems and/or spatial anchors. The live data 18 of the patient can be registered in the common coordinate system 15. Intra-operative imaging studies 20 can be registered in the common coordinate system 15. OR references, e.g. an OR table or room fixtures can be registered in the common coordinate system 15 using, for example, optical markers IMUs, navigation markers or spatial mapping 22. The pre-operative data 16 or live data 18 including intra-operative measurements or combinations thereof can be used to develop, generate or modify a virtual surgical plan 24. The virtual surgical plan 24 can be registered in the common coordinate system 15. The OHMDs 11, 12, 13, 14 can maintain alignment and superimposition of virtual data of the patient and live data of the patient for each OHMD 11, 12, 13, 14 for each viewer's perspective view and position and head position and orientation 27. Using a virtual or other interface, the surgeon wearing OHMD 1 11 can execute commands 32, e.g. to display the next predetermined bone cut, e.g. from a virtual surgical plan or an imaging study or intra-operative measurements, which can trigger the OHMDs 11, 12, 13, 14 to project virtual data of the next surgical step 34 superimposed onto and aligned with the surgical site in a predetermined position and/or orientation. Any of the OHMDs 11, 12, 13, 14 can acquire one or more optical measurements or measurement inputs, e.g. of anatomic landmarks, axes from cameras, anatomic axes, biomechanical axes, a mechanical axis of a leg 17, using for example an integrated or attached camera, image capture or video system. By using multiple OHMDs 11, 12, 13, 14 from different view angles with multiple cameras, image capture or video systems, the accuracy of the measurements can optionally be improved. Optionally, parallax measurements can be performed using the multiple OHMDs 11, 12, 13, 14 from different view angles with multiple cameras, image capture or video systems. The one or more optical measurements can be used to modify the virtual surgical plan 19, optionally using the information from multiple OHMDs 11, 12, 13, 14. Someone skilled in the art can recognize that multiple coordinate systems can be used instead of a common coordinate system. In this case, coordinate transfers can be applied from one coordinate system to another coordinate system, for example for registering the OHMD, live data of the patient including the surgical site, virtual instruments and/or virtual implants and physical instruments and physical implants.

Tissue Morphing Including Bone Morphing, Cartilage Morphing

In some embodiments of the invention, the shape of one or more of the patient's tissues, such as a bone, a cartilage, a joint or an organ, can be estimated or morphed in three dimensions intra-operatively, e.g. during the surgery. The estimating or morphing of the patient's tissue shape, e.g. bone shape, cartilage shape, joint shape or organ shape, can help reduce or obviate the need for pre-operative imaging and, in select embodiments, intra-operative imaging.

In some embodiments of the invention, 2D preoperative data can be used and the shape of one or more of the patient's tissues, such as a bone, a cartilage, a joint or an organ, can be estimated or morphed in three dimensions pre-operatively, e.g. prior to surgery.

Bone Morphing and/or Cartilage and/or Tissue Morphing Using Pre-Operative Imaging or Intra-Operative Imaging In some embodiments of the invention, one or more two-dimensional images of the patient can be obtained. These images can, for example, include one or more x-rays of the patient. X-rays can be obtained using digital acquisition techniques. X-rays can also be obtained using conventional film based technique, in which case the x-rays can be subsequently digitized using a scanner.

Exemplary x-ray images can include:
Spine: AP, PA, lateral, oblique views, and/or angled views, flexion, extension views, lateral bending views; upright, supine or prone
Hip: AP, PA, lateral, oblique views, angled views, and/or frogleg view; standing or lying, weight-bearing or non-weight-bearing
Knee: AP, PA, lateral, oblique views, angled views, and/or Merchant view, sunrise view and the like; standing or lying, weight-bearing or non-weight-bearing
Full leg x-rays films; standing or lying, weight-bearing or non-weight-bearing
Selective leg x-rays films, e.g. hip, knee, ankle; standing or lying, weight-bearing or non-weight-bearing X-rays can be obtained with the patient in upright, supine and/or prone position. X-rays can be obtained with the patient in weight-bearing and in non-weight-bearing position. In some embodiments of the invention, x-rays are obtained intra-operatively, for example with the patient already positioned and placed for the intended surgical procedure.

The x-ray data of the patient can be transferred into a computer. Optionally, image processing can be applied to segment select patient tissues, such as a bone or vertebra or vertebral structure, subchondral bone, cortical bone, osteophytes. Image processing can, for example, also be applied to determine the edge of select patient tissues, such as a bone or vertebra or vertebral structure, subchondral bone, cortical bone, osteophytes. When subchondral bone has been identified and/or derived from the images, including a subchondral bone curvature and/or geometry and/or shape, a cartilage shape, curvature or geometry can be superimposed or added to the subchondral bone shape. The cartilage shape, curvature or geometry can assume a standard cartilage thickness for a given joint and/or a given patient, e.g. 1.0 mm, 1.5 mm, 2.0 mm, 2.5 mm, 3.0 mm, 3.5 mm. The cartilage geometry can also assume a variable cartilage thickness, e.g. depending on the location of the cartilage in the joint and/or on the articular surface and/or based on the patient's age, gender, race, body weight, and/or BMI, as well as underlying deformity, e.g. varus or valgus deformity.

In some embodiments of the invention, the 2D x-rays images can be used to derive information about the dimensions and shape of the anatomic structure(s) included in the x-ray. Some of this information can be, for example:
Anatomic landmark(s)
Distances and/or dimensions between two or more known landmarks/structures
Angles between landmarks
Anatomic axes
Biomechanical axes
Curvature information
Surface information
Edge information
Curvature information
Shape information, e.g. when information from multiple x-rays images obtained with different projection or beam angles is combined or aggregated
Length information, e.g. in AP, ML, SI direction, AP, ML, SI plane, oblique planes
Width information, e.g. in AP, ML, SI direction, AP, ML, SI plane, oblique planes
Depth information, e.g. in AP, ML, SI direction, AP, ML, SI plane, oblique planes Examples of landmarks, distances, dimensions, surfaces, edges, angles, axes, curvatures, shapes, lengths, widths, depths and/or other features for the spine, the hip, the knee and the shoulder joint that can be used for bone morphing and 3D model selection, development, derivations, and deformations in any surgeries of these or to these areas are provided below. These examples are in no way meant to be limiting of the invention, but are only exemplary in nature. Someone skilled in the art will readily recognize other landmarks, distances, dimensions, surfaces, edges, angles, axes, curvatures, shapes, lengths, widths, depths and/or other features for these joints as well as any other joint in the human body.

Spine
Cortical bone of a pedicle
Endosteal bone of a pedicle
Posterior cortical bone of a vertebral body
Anterior cortical bone of a vertebral body
Lateral cortical bone of a vertebral body
Superior endplate
Inferior endplate
Intervertebral disk
Vertebral body
Trabecular bone of the vertebral body
Superior facet
Inferior facet
Spinous process
Any fracture components or fragments, e.g. involving a pedicle, a facet joint or a vertebral body
Endplate shape, e.g. sagittal plane
Endplate shape, e.g. coronal plane
Schmorl's node(s)
Interpedicular distance
Intervertebral height or disk height
AP length of vertebral body, e.g. at level of inferior endplate, superior endplate, mid-portion
ML width of vertebral body, e.g. at level of inferior endplate, superior endplate, mid-portion
Oblique width vertebral body, e.g. at level of inferior endplate, superior endplate, mid-portion
Vertebral body height, e.g. anterior, mid-portion, posterior
Pedicle length
Pedicle width
Pedicle height Pedicle angle
Spinous process SI thickness, e.g. anterior, mid-portion, tip
Spinous process width, e.g. anterior, mid-portion, tip
Spinous process inferior angle from origin
Facet dimensions, AP, ML, SI
Facet angle, e.g. angle of joint formed between inferior facet of superior vertebra and superior facet of inferior vertebra
Lamina SI height
Lamina AP width
Lamina ML radius, diameter
Spinal canal AP diameter, ML diameter
Lordosis
Kyphosis
Scoliosis
Side bending, e.g. left lateral, right lateral
Cobb angle
Lumbosacral angle
Hip
Lateral acetabular point or edge
Medial acetabular point or edge
Superior acetabular point or edge
Anterior acetabular point or edge
Posterior acetabular point or edge
Triradiate cartilage and region
Acetabular labrum, medial, lateral, anterior, posterior (e.g. when x-ray contrast has been injected into the joint)
Fovea capitis
Femoral head subchondral bone, contour, outline
Femoral head neck/junction, curvature, convex, concave
Greater trochanter, e.g. lateral cortex, superior cortex, anterior cortex, posterior cortex
Sulcus point (lowest point between greater trochanter and femoral neck)
Sulcus curvature
Greater trochanter/sulcus transition, curvature, convex, concave
Lesser trochanter
Lesser trochanter/femoral neck transition, curvature
Lesser trochanter/femoral shaft transition
Femoral shaft, anterior cortex, posterior cortex, medial cortex, lateral cortex
Anterior cortex, posterior cortex, medial cortex, lateral cortex for any of the foregoing structures as applicable
Endosteal bone, anterior, posterior, medial, lateral for any of the foregoing structures as applicable
Femoral neck angle
Femoral shaft angle
Acetabular angle
Acetabular anteversion
Femoral anteversion
Femoral shaft angle
Pelvic tilt
Femoral offset
Shenton's line
Hilgenreiner line
Perkin line
Acetabular index
Knee
Medial wall of the femoral notch
Lateral wall of the femoral notch
Roof of the femoral notch
Medial wall of the medial condyle
Lateral wall of the lateral condyle
Medial epicondylar eminence
Lateral epicondylar eminence
Medial femoral condyle shape, e.g. radii, convexities, concavities
Lateral femoral condyle shape, e.g. radii, convexities, concavities
Intercondylar notch shape
Intercondylar notch surface features
Medial tibial spine
Lateral tibial spine
Anteromedial tibial rim
Anterolateral tibial rim
Medial tibial rim
Lateral tibial rim
Lowest point of the medial plateau
Lowest point of the lateral plateau
Highest point of the medial plateau
Highest point of the lateral plateau
Medial tibial plateau shape
Lateral tibial plateau shape
Medial tibial plateau sagittal curvature
Lateral tibial plateau sagittal curvature
Medial tibial plateau coronal curvature
Lateral tibial plateau coronal curvature
Medial tibial plateau surface features, e.g. radii, convexities, concavities
Lateral tibial plateau surface features, e.g. radii, convexities, concavities
Femoral osteophytes
Tibial osteophytes
Patellar osteophytes
Femoral subchondral cysts
Tibial subchondral cysts
Patellar osteophytes
Patellar subchondral cysts
Trochlea osteophytes
Trochlea subchondral cysts
Patellar sagittal curvature
Patellar coronal curvature
Patellar axial curvature
Patellar surface features, e.g. radii, convexities, concavities
Patellar surface features, e.g. radii, convexities, concavities
Patellar circumference shape
Patellar rise
Patellar thickness
Trochlear depth
Trochlear sagittal curvature
Trochlear axial curvature
Trochlear coronal curvature
Trochlea sagittal shape
Trochlea axial shape
Trochlea coronal shape
Trochlear angle
Epicondylar axis
Posterior femoral axis
Trochlear rotation axis
Mechanical axis
Q-angle
Shoulder
Clavicle
AC joint
Acromion
Glenoid
Scapula
Coracoid
Humeral head Humeral neck
Humeral shaft
Glenoid osteophytes
Humeral osteophytes
AC joint osteophytes
Glenoid subchondral cysts
Humeral subchondral cysts
AC joint subchondral cysts
Acromio-humeral distance
Acromio-humeral space
Deepest point of glenoid
Most anterior point or edge of glenoid
Most posterior point or edge of glenoid
Most superior point or edge of glenoid
Most inferior point or edge of glenoid
Glenoid shape
Humeral head shape
Glenoid sagittal curvature, e.g. radii, convexities, concavities
Glenoid axial curvature, e.g. radii, convexities, concavities
Glenoid coronal curvature, e.g. radii, convexities, concavities
Humeral head sagittal curvature, e.g. radii, convexities, concavities
Humeral head axial curvature, e.g. radii, convexities, concavities
Humeral head coronal curvature, e.g. radii, convexities, concavities
Mechanical axis
Anatomical axis
Angle of inclination
Axis of head and neck
Axis through epicondyles
Angle of retroversion By measuring any of the foregoing landmarks, distances, dimensions, surfaces, edges, angles, axes, curvatures, shapes, lengths, widths, depths and/or other features, it is possible to estimate a 3D shape, volume or surface(s) of a bone, e.g. a proximal femur, a distal femur, a proximal tibia, an acetabulum, a vertebral body and spinal elements and a glenoid and/or a proximal humerus. The more landmarks, distances, dimensions, surfaces, edges, angles, axes, curvatures, shapes, lengths, widths, depths and/or other features are being measured, the more accurate can the estimation of the 3D shape, volume or surface(s) of the bone be. In addition, the more 2D images are being taken or acquired from different view angles, projection angles, beam angles, optionally with the same magnification or different magnifications, the more accurate can the estimation of the 3D shape, volume or surface(s) of the bone be.

The 3D shape, volume or surface of the bone can, for example, be estimated by filling in the information, e.g. intermediate or connecting landmarks, distances, dimensions, surfaces, edges, angles, axes, curvatures, shapes, lengths, widths, depths and/or other features between known landmarks, distances, dimensions, surfaces, edges, angles, axes, curvatures, shapes, lengths, widths, depths and/or other features derived from the one, two, three or more x-ray images. In some embodiments of the invention, a standard model of the bone can be used and can be deformed using one or more of the known landmarks, distances, dimensions, surfaces, edges, angles, axes, curvatures, shapes, lengths, widths, depths and/or other features derived from the one, two, three or more x-ray images. Such deformations can be performed using various statistical models known in the art.

In some embodiments of the invention, a database or library of bone models and tissue models can be used. The one or more of these anatomic landmarks, distances, dimensions, surfaces, edges, angles, axes, curvatures, shapes, lengths, widths, depths and/or other features can be used to identify a standard bone shape and/or a standard cartilage shape by comparing the one or more landmarks, distances, dimensions, surfaces, edges, angles, axes, curvatures, shapes, lengths, widths, depths and/or other features with data in a reference database of reference patients and/or reference bone and/or cartilage shapes and by selecting a 3D model that most closely matches the selected landmarks, distances, dimensions, surfaces, edges, angles, axes, curvatures, shapes, lengths, widths, depths and/or other features. In this manner, the 3D shape of the patient's bones and/or cartilage, e.g. the distal femur and/or the proximal tibia and/or the acetabulum and/or the proximal femur, and/or the vertebral body and/or the spinal elements and/or the glenoid and/or the proximal humerus, can be estimated without the need acquire 3D data or without the need of segmentation of the 3D data or limiting the amount of segmentation needed from available 3D data, e.g. a CT scan or an MRI scan of the patient. The reference database can be, for example, an anatomic reference database from cadaver data. The reference database can also be, for example, scan data, e.g. acquired in the NIH Osteoarthritis Initiative or acquired from imaging data to generate patient specific instruments for knee replacement. Such scan data can be used to generate a database of 3D shapes of patients with different age, gender, ethnic background, race, weight, height and/or BMI.

Of note, the use 2D imaging data or 3D imaging data, e.g. x-ray, ultrasound, CT or MRI, in combination with one or more reference databases of 3D shape(s) of select anatomic structures, such as a bone, a cartilage, an organ for reducing or limiting or obviating the need for acquiring 3D data or for segmenting 2D or 3D data is applicable to any embodiment of the invention throughout the specification including for all other clinical applications, e.g. hip replacement, knee replacement, spinal surgery, spinal fusion, vertebroplasty, kyphoplasty, fracture fixation, brain surgery, liver surgery, cancer surgery etc.

In some embodiments of the invention, a standard model, optionally already deformed using the patient's landmarks, distances, dimensions, surfaces, edges, angles, axes, curvatures, shapes, lengths, widths, depths and/or other features, can be combined or fused with a model selected from a database using the patient's landmarks, distances, dimensions, surfaces, edges, angles, axes, curvatures, shapes, lengths, widths, depths and/or other features. In some embodiments, the model selected from the database can be deformed and/or adapted using the patient's landmarks, distances, dimensions, surfaces, edges, angles, axes, curvatures, shapes, lengths, widths, depths and/or other features. Such deformations can be performed using various statistical models known in the art.

If one or more x-rays are used, they can, for example, be obtained in an AP projection of the knee (or PA), and a lateral projection of the knee. Other views are possible, as known in the art, e.g. a tunnel view, Merchant view, patellar view, oblique views, standing views, supine views, prone views. Optionally, the medial and lateral femoral condyles can be identified on the AP/PA and/or lateral and/or oblique views; optionally, the medial and lateral tibial plateau can be identified on the AP/PA and/or lateral and/or oblique views. Other landmarks, distances, dimensions, surfaces, edges, angles, axes, curvatures, shapes, lengths, widths, depths and/or other features can be identified.

A lateral knee x-ray can, for example, be used to derive curvature information about the medial and the lateral condyle. Two distinct curves can be seen on a lateral knee radiograph, one representing the medial condyle and the other representing the lateral condyle. In most instances, the lateral condyle has a smaller radius than the medial condyle, for example in the central weight-bearing zone. Software can identify and/or segment each curve using, for example, some of the software packages described in Data Segmentation. This can be followed by a curvature analysis assessing the radii of each curve. In some embodiments of the invention, the curve with the smaller radii, e.g. in the central weight bearing area, can be assigned as the lateral condyle. Other combinations are possible.

The foregoing description of techniques to estimate or morph the three-dimensional shape of a patient's bone is only exemplary in nature and is in no way meant to be limiting of the invention. Someone skilled in the art will readily recognize other means to estimate the shape of the patient's bone in three dimensions. Any technique known in the art for determining or estimating the three-dimensional shape of a bone from two-dimensional data can be used. Any technique known in the art for modeling and displaying the three-dimensional shape of a bone from two-dimensional data can be used.

Bone and/or Tissue Morphing Using Mechanical Probes and/or Opto-Electronic and/or RF Probes In some embodiments of the invention, a mechanical probe can be used to determine the three-dimensional shape of a patient's tissue, e.g. cartilage or bone or organ tissue, intra-operatively. The tissue probe can be attached to a stand or holder. The tissue probe can also be handheld.

The tissue probe can be configured similar to a mechanical detection device known in the art and used, for example, for industrial shape inspection purposes, e.g. coordinate measuring machines (CMM) known in the art, such as, for example, the Faro arm system.

In some embodiments of the invention, a mechanical probe can be used that has at least one of an optical marker, navigation marker, including infrared markers, retroreflective markers, RF markers, LED and/or IMU attached. The position and/or orientation and/or alignment and/or direction of movement of the probe can be determined then, for example, using a navigation system and/or an image and/or video capture system integrated into, attached to or separate from the OHMD.

By moving the mechanical probe along the bone, cartilage, tissue and/or organ surface, the position of the tip of the probe can, for example, be registered and, for example, a point cloud can be generated which can be used to generate a 3D surface. Standard techniques known in the art, e.g. tessellation, can be used for this purpose.

Bone and/or Tissue Morphing Using Optical Probes and/or 3D Scanners and/or Image Capture Systems In some embodiments of the invention, an image and/or video capture system integrated into, attached to or separate from the OHMD can be used to image the patient's bone and/or cartilage and/or tissue and/or ligaments and/or menisci and/or organ surface. With the position, orientation, alignment and/or direction of movement of the image and/or video capture system(s) known, for example using optical markers, navigation markers including infrared markers, retroreflective markers, RF markers, LEDs and/or IMUs, images of the patient's bone and/or cartilage and/or tissue and/or ligaments and/or menisci and/or organ surface can be acquired from multiple viewpoints or continuously and, using software and image processing as described in Data Segmentation or spatial mapping techniques as described in Spatial Mapping, images can be used to derive one or more 3D volumes, 3D surfaces and/or 3D shapes of the patient's bone and/or cartilage and/or tissue and/or ligaments and/or menisci and/or organ. The accuracy of such image acquisitions and reconstruction of 3D volumes, 3D surfaces and/or 3D shapes can optionally be enhanced with image and/or video capture systems that use two or more cameras, which can be used to generated parallax information and/or stereoscopic information of the same structures, wherein, for example, the parallax and/or stereoscopic information can be used to enhance the accuracy of the reconstructions. Alternatively, the information from two or more cameras can be merged by averaging the 3D coordinates or detected surface points or other geometric structures such as planes or curved surfaces.

In some embodiments of the invention, 3D laser scanners or depth sensors known in the art, such as, for example, the Structure laser scanner provided by Occipital Inc., can be used to image the surface of the patient's bone and/or cartilage and/or tissue and/or ligaments and/or menisci and/or organ. Other 3D scanners known in the art can be used. Any laser scanning, optical or light scanning technique known in the art for determining, estimating or deriving the 3D volume, 3D surface or 3D shape of a structure known in the art can be used.

In some embodiments of the invention, the 3D scanner or image and/or video capture system can be attached to an arm or tripod. Images of the patient's bone and/or cartilage and/or tissue and/or ligaments and/or menisci and/or organ can be acquired at a constant distance. Images of the patient's bone and/or cartilage and/or tissue and/or ligaments and/or menisci and/or organ can be acquired at a variable distance. The laser or optical scanner can optionally be used to measure the distance to the patient's bone and/or cartilage and/or tissue and/or ligaments and/or menisci and/or organ during the image acquisition. Using the laser's starting position or the starting position of the image and/or video capture system and/or at least one of an optical marker, navigation marker including infrared markers, retroreflective markers, RF markers, LED and/or IMU, the position, orientation, alignment and/or direction of movement of the image and/or video capture system and/or 3D scanner can be known throughout the acquisition allowing for magnification correction and optional view angle adjustments and/or projection and/or surface generation calculation and/or adjustments and/or corrections.

Combining Pre-Operative and Intra-Operative Data

In some embodiments of the invention, 2D or 3D data obtained intra-operatively with a mechanical probe, opto-electronic probe, RF probe, optical probe, image and/or video capture system, laser scanner and/or 3D scanner can be combined with pre-operative data, e.g. pre-operative imaging data and/or a virtual surgical plan.

The 2D or 3D information obtained pre-operatively can, for example, include mechanical axis information, e.g. of the knee and/or lower extremity (e.g. obtained using a standing x-ray), rotation axis information, e.g. of a hip or a knee, e.g. using epicondylar axis information, posterior condylar axis information, tibial tubercle information, one or more AP dimensions of a joint, one or more ML dimensions of a joint, one or more SI dimensions of a joint, a medial condyle curvature and/or a lateral condyle curvature, e.g. as seen on a lateral and/or an AP radiograph, a medial tibial curvature and/or a lateral tibial curvature, e.g. as seen on a lateral and/or an AP radiograph, joint line information, e.g. the location of a medial and/or a lateral joint line in a knee, offset information, e.g. an offset in a hip or an offset between a medial and/or a lateral condyle.

The 2D or 3D data obtained intra-operatively can, for example, include dimensional information, geometric information, curvature information, volume information, shape information, and/or surface information of the tissue, organ, e.g. cartilage and/or bone. The 2D or 3D data obtained intra-operatively can, for example, include information about joint line location, e.g. medial and/or lateral, femoral offsets and/or tibial offsets, measured based on cartilage and/or subchondral bone.

Optionally, adjustments or corrections can be applied to data obtained pre-operatively and/or intra-operatively. For example, osteophytes and/or subchondral cysts can be virtually removed from the pre-operative and/or intra-operative 2D or 3D data. Flattening of a joint surface seen on any of the data can be optionally corrected, e.g. by applying a corrected shape, e.g. using spline surfaces or smoothing functions or averaging functions.

In some embodiments of the invention, 2D or 3D pre-operative data can be combined with 2D or 3D intra-operative data. For example, mechanical axis information obtained from a pre-operative standing x-ray can be combined with an intra-operative 3D scan of a joint, e.g. a knee joint or a hip joint. A virtual surgical plan can be developed or derived based on the combined data, for example with resections that are planned to maintain or restore normal mechanical axis alignment or any other alignment desired by the surgeon, e.g. 5% or less of varus or valgus alignment of a joint. If a virtual surgical plan has already been developed pre-operatively, the virtual surgical plan can be modified intra-operatively using intra-operative 3D scan information of one or more joints, for example using more accurate intra-operative surface information of the joint or organ.

In some embodiments of the invention, 3D surfaces morphed from 2D pre-operative data, e.g. using one or more pre-operative x-rays, can be combined with 3D surfaces derived intra-operatively, e.g. derived using an intra-operative mechanical and/or opto-electronic and/or laser and/or 3D scanner. For example, the pre-operative morphed surfaces of a femoral head can be matched, aligned, superimposed or merged in this manner with the intra-operative surfaces. Or the pre-operative morphed surfaces of one or both femoral condyles and/or tibial plateaus can be matched, aligned superimposed or merged in this manner with their corresponding intra-operative surfaces. By matching, aligning, superimposing or merging surfaces derived from pre-operative and intra-operative data, axis information obtained on pre-operative data, e.g. standing x-rays can be readily superimposed or merged with intra-operative data. The resultant model can be used to develop, derive and/or modify a virtual surgical plan, for example with subsequent display of one or more cut planes or tissue resections or axes by an OHMD.

2D data obtained pre-operatively and/or intra-operatively using 2D to 3D tissue morphing, e.g. bone morphing, for example as described in the specification, and morphed into a 3D model can be displayed stereoscopically and/or non-stereoscopically using one or more OHMD displays. In addition, any of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be displayed by the OHMD concurrent with the 2D to 3D morphed 3D model, e.g. bone model, stereoscopically or non-stereoscopically. The one or more of a virtual surgical tool, virtual surgical instrument including a virtual surgical guide or cut block, virtual trial implant, virtual implant component, virtual implant or virtual device, predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be planned using the 2D to 3D morphed 3D model, for example using a virtual surgical plan.

In some embodiments of the invention, at least one or more of the same landmarks, distances, dimensions, surfaces, edges, angles, axes, curvatures, shapes, lengths, widths, depths and/or other features used for 2D to 3D tissue morphing, e.g. bone morphing, can be used for intra-operative registration of live data and virtual data, e.g. pre-operative data, of the patient by identifying the at least one or more of the corresponding landmarks, distances, dimensions, surfaces, edges, angles, axes, curvatures, shapes, lengths, widths, depths and/or other features in the live data, using, for example, some of the techniques described in the specification.

Figure 15:
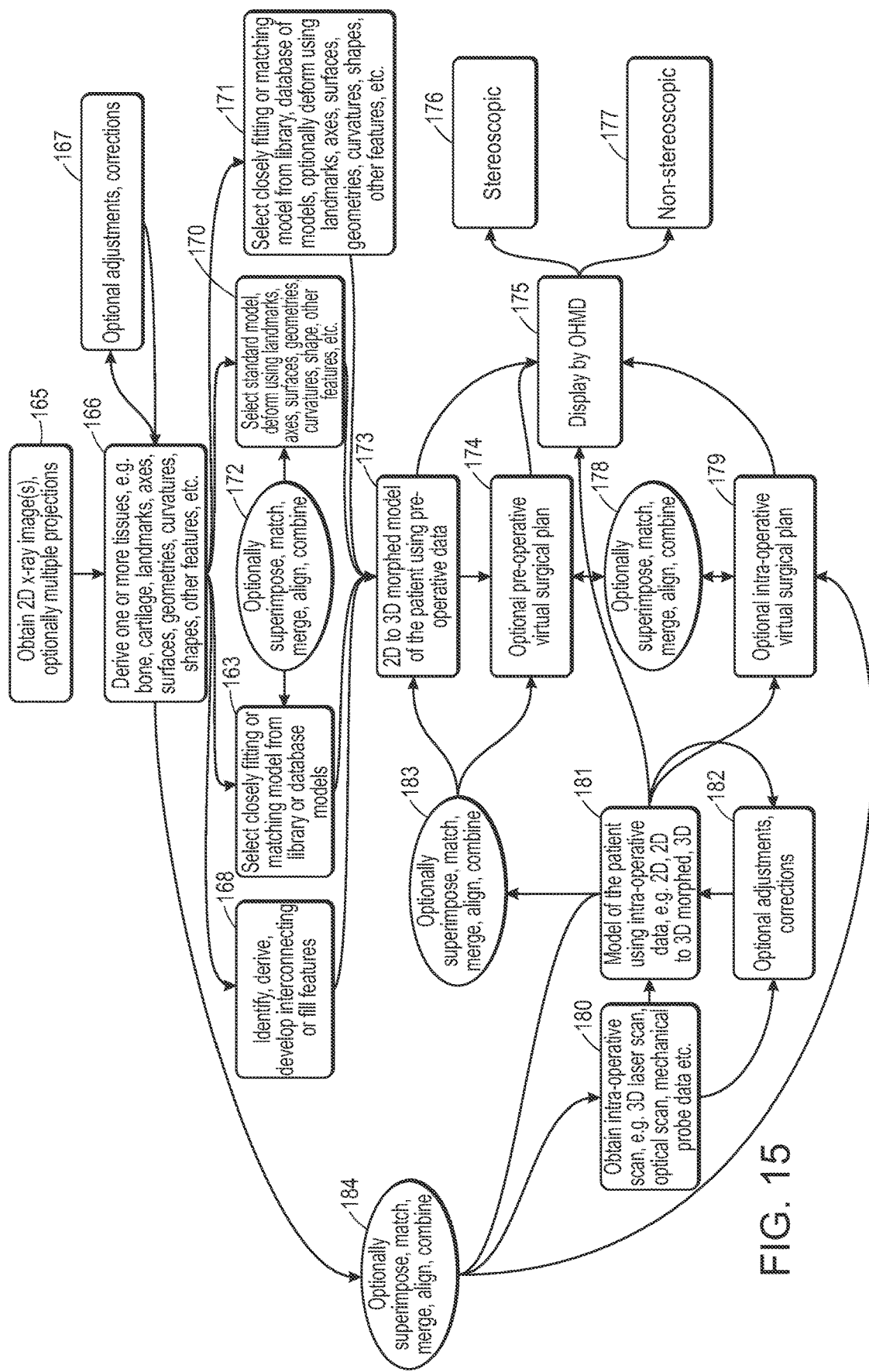
FIG. 15 is an example how 2D to 3D morphed data can be used or applied.

FIG. 15 is an example how 2D to 3D morphed data can be used or applied. The example is in no way meant to be limiting of the invention. In this example, 2D x-ray images can be obtained, optionally with multiple projections 165. One or more tissues, e.g. bone, cartilage, their landmarks, shapes and or geometries or other features can be derived 166 and can be optionally adjusted 167. Interconnecting or fill features can be determined 168, a closely fitting or matching model can be selected from a library or database of models 169, a standard model can be selected and optionally be deformed 170 using the shapes, geometries or features 166, a closely fitting or matching model can be selected from a library or database of models 171 and deformed using the information in 166. Steps and processes in 168, 169, 170, and 171 can optionally be combined 172. Steps and processes 168, 169, 170, 171, and 172 can be used to generate a 2D to 3D morphed model 173, which can be used to generate pre-operative virtual surgical plan 174. The morphed model 173 and the pre-operative virtual surgical plan 174 can be displayed by one or more OHMDs 175, optionally stereoscopic 176 or non-stereoscopic 177. An intra-operative virtual surgical plan 179 can optionally be superimposed, merged, matched or aligned with the pre-operative virtual surgical plan 174. An intra-operative scan or probe data 180 can be used to generate a model of the patient using intra-operative data, e.g. 2D, 2D to 3D morphed, 3D 181, which can optionally be superimposed, matched, merged or aligned 173 with the morphed model of the patient using pre-operative data 173 or the pre-operative virtual surgical plan 174. Optional adjustments to the model of the patient using intra-operative data 181 can be made 182.

Virtual Data and Live Data Seen Through One or More OHMDs

A virtual surgical plan using, for example, virtual data of the patient, can be used to develop or determine any of the following for placing or directing a surgical tool, a surgical instrument, a trial implant component, a trial implant, an implant component, an implant, a device including any type of biological treatment or implant or matrix known in the art:
  Predetermined start point
  Predetermined start position
  Predetermined start orientation/alignment
  Predetermined intermediate point(s)
  Predetermined intermediate position(s)
  Predetermined intermediate orientation/alignment
  Predetermined end point
  Predetermined end position
  Predetermined intermediate orientation/alignment
  Predetermined path
  Predetermined plane (e.g. for placing or orienting a surgical instrument or an implant component)
  Predetermined cut plane (e.g. for directing a saw or other surgical instruments (e.g. drills, pins, cutters, reamers, rasps, impactors, osteotomes) and/or for placing or orienting an implant component or a trial implant component)
  Projected contour/outline/cross-section/surface features/shape/projection
  Predetermined depth marker or depth gauge, optionally corresponding to a physical depth marker or depth gauge on the physical surgical tool, surgical instrument, trial implant, implant component, implant or device
  Predetermined angle/orientation/rotation marker, optionally corresponding to a physical angle/orientation/rotation marker on the physical surgical tool, surgical instrument, trial implant, implant component, implant or device
  Predetermined axis, e.g. rotation axis, flexion axis, extension axis
  Predetermined axis of the physical surgical tool, surgical instrument, trial implant, implant component, implant or device, e.g. a long axis, a horizontal axis, an orthogonal axis, a drilling axis, a pinning axis, a cutting axis (move this to ensuing examples)
  Estimated/projected non-visualized portions of device/implant/implant component/surgical instrument/surgical tool, e.g. using image capture or markers attached to device/implant/implant component/surgical instrument/surgical tool with known geometry
  Predetermined virtual tissue change/alteration.

Any of the foregoing, e.g. a cut plane or an outline, e.g. an outline of an implant or a surgical instrument, can be displayed in 2D and/or in 3D, optionally alternatingly. For example, a 2D visualization, e.g. a line, of a cut plane can be used when a surgeon looks substantially on end on a bone, e.g. a distal femur, for orienting and/or directing a cutting instrument, e.g. a saw or a saw blade. When the surgeon looks from the side, e.g. at an angle, the visualization can optionally switch to a 3D display to show the desired angular orientation of the cut and/or the blade in relationship to the bone. The display can also remain in 2D mode. The switching between 2D and 3D display can be manual, e.g. through a voice command or a command on a virtually projected keyboard or a virtually projected user interface, or automatic, e.g. based on the position and/or orientation of the operator's head and/or the OHMD in relationship to the surgical site (e.g. operator head/OHMD in frontal orientation relative to surgical site, or close to including 90 degree side (near orthogonal) orientation, or angular, non-90 degree side orientation, e.g. 30, 40, 50, 60, 70 degree angles). A 2D or 3D display of a cut plane can help determine/display the desired angular orientation of the intended cut. The angular orientation can, for example, be a reflection of a planned/intended mechanical axis correction in a knee replacement, a planned/intended femoral component flexion or extension in a knee replacement, a planned/intended tibial slope in a knee replacement or a planned/intended femoral neck resection for a planned/intended leg length in a hip replacement.

A 2D or 3D display can also include multiple cut planes, e.g. two or more femoral neck cuts in a hip replacement procedure, as can be used in hip replacement procedures involving, for example, an anterior approach and using a "napkin ring" like dual cut through the femoral neck. In this example, the 3D cut plane can include the distal cut plane at its inferior pointing surface and the proximal cut plane at its superior surface. These "napkin ring" inferior, distal facing, and superior, proximal facing cuts can be parallel or non-parallel, e.g. for easier extraction of the femoral head. Any cut planes visualized in 2D or 3D using the OHMD display can be parallel or non-parallel, using stereoscopic or non-stereoscopic display.

If the surgeon elects to change or adjust any of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration used in the one or more virtual surgical plans using, for example, a virtual interface displayed by the OHMD display, e.g. a finger slider or finger tab to move and/or rotate a virtual cut plane by virtually touching it, or any other interface, including, for example, a finger command or a voice command, the virtual representation of the virtual data can move accordingly and the virtual data displayed in the OHMD can be updated accordingly in the surgeon's display. The change in position and/or orientation of the virtual representation of the virtual data can also be seen in other OHMDs, e.g. worn by a second surgeon, a resident, a scrub nurse or a PA, and the projection of the virtual data can also be updated accordingly in a second, third or any additional OHMD units used, for example, by a second surgeon, a resident, a scrub nurse or a PA during the surgery. Optionally, the virtual interface or any other interface to change or adjust one or more of the virtual data can only be available for the surgeon's OHMD unit, i.e. the lead OHMD unit, while the other OHMD units can operate as slave units that simply follow the display of the lead OHMD unit. In this manner, potential intraoperative errors, for example with a non-surgeon modifying virtual data or aspects of the virtual surgical plan, can be avoided. Optionally, the lead can be passed over to any of the other units, in which case the surgeon's OHMD unit can operate as a slave unit. This can be beneficial when complex changes are required to the virtual surgical plan and/or the virtual data of the patient, which may require a separate person to implement such changes, while the surgeon is managing the physical operation in the live patient.

In some embodiments of the invention, the OHMD unit of the surgeon can capture the live data of the patient using one or more image and/or video capture systems integrated into or attached to the OHMD. The captured live data of the patient can then be transmitted in electronic, digital form as live stream to slave OHMD units, optionally together with the virtual data of the patient, e.g. superimposed onto or co-displayed with the virtual data of the patient. Alternatively, the slave units in this example can be non-see through virtual reality (VR) systems such as the Google Daydream system or the Zeiss VR One system and others known in the art. Any intended cut plane displayed by the OHMD can optionally include or account for the thickness of the saw blade to reflect bone last during the sawing step. Any intended path for a drill or pin or other surgical instrument can include or account for the thickness of the surgical instrument to reflect bone lost during the surgical step. In addition, any bone lost due to movement of a surgical instrument, e.g. movement not in the primary direction of the surgical step such as saw blade flutter or saw vibration or a slightly eccentric drill or drill vibration can be included in the virtual surgical plan, for example through estimations of saw blade flutter or saw vibrations in addition to a known saw blade thickness, and can be accounted for in the virtual resection planning and in the resultant display of one or more 2D or 3D cut planes by the OHMD.

Someone skilled in the art can readily recognize that accounting for the thickness of a saw blade or dimensions of other bone removing instruments as well as related instrument or device movement or vibration induced bone loss can be accounted for in one, two, three or more bone removing steps, if a surgical procedure involves multiple bone removing steps, such as the femoral preparation of a partial or total knee replacement, which can include two, three or more bone cuts.

When the OHMD is used to display the estimated/projected non-visualized portions of a device, an implant, an implant component, a surgical instrument and/or a surgical tool, the display of the non-visualized portion of the device, implant, implant component, surgical instrument and/or surgical tool can also account for any bone loss that may have been or will be induced by the device, implant, implant component, surgical instrument and/or surgical tool. By accounting for the bone loss induced by the device, implant, implant component, surgical instrument and/or surgical tool, the virtual surgical plan and the display of any surgical steps including subsequent surgical steps by the OHMD can be more accurate.

A virtual surgical plan can be used to define a predetermined start point for a surgical tool, a surgical instrument, a trial implant component, a trial implant, an implant component, an implant, a device. A start point can be, for example, the entry at the patient's skin. If pre-operative imaging, e.g. ultrasound, CT and/or MRI, is used for developing the surgical plan, the skin can be located in the imaging data and the start point can be defined at an area typically near the intended surgical site. A start point can also be defined at a select soft-tissue depth, e.g. 5, 8 or 10 cm into the soft-tissue, e.g. subcutaneous tissue or muscle or other tissues or organ tissue. A start point can be defined at the surface of an organ, e.g. a liver or a spleen or a kidney or a bladder or a brain. A start point can be defined at an anatomic landmark or in relationship to an anatomic landmark of an organ, e.g. a rim of a liver, a liver portal, an entry of an inferior vena cava into the liver, an entry of a portal vein into the liver, a superior or inferior pole of a kidney, a renal hilum. A start point can be defined at a bone surface or bony landmark The one or more of a virtual surgical tool, virtual surgical instrument including a virtual surgical guide or cut block, virtual trial implant, virtual implant component, virtual implant or virtual device, one or more a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration used in the one or more virtual surgical plans can be highlighted in the one or more OHMD displays using various techniques known in the art, including but not limited to:

Colored display
    Grey scale display
    Shaded display
    Patterned display, e.g. squares, lines, bars
    Line display, e.g. solid, stippled, dotted
    Arrow display
    Target like display
    Intermittent display, e.g. blinking or flashing
    Appearing or disappearing display
    Magnified display
    Minified display For example, a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration is displayed by the OHMD multiple colors can be chosen.

For example, a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be highlighted using an arrow display. The arrows can be aligned with the direction of the one or more surgical tools, surgical instruments, implant components, implants or devices. The arrows can also not be aligned with the direction of the one or more surgical tools, surgical instruments, implant components, implants or devices. The arrows can be orthogonal to the direction of the one or more surgical tools, surgical instruments, implant components, implants or devices. The arrows can be aligned with the one or more surgical tools, surgical instruments, implant components, implants or devices. The arrows cannot be orthogonal with the one or more surgical tools, surgical instruments, implant components, implants or devices.

One or more arrows can directly point at the one or more of a virtual surgical tool, virtual surgical instrument including a virtual surgical guide or cut block, virtual trial implant, virtual implant component, virtual implant or virtual device, one or more a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. The one or more arrows can optionally be magnified or minified. The one or more arrows can optionally be displayed intermittently, e.g. blinking or flashing. The one or more arrows can optionally be appearing or disappearing. For example, the one or more arrows can disappear when the predetermined end point is reached by the physical surgical tool, surgical instrument, implant component, implant or device.

The one or more of a virtual surgical tool, virtual surgical instrument including a virtual surgical guide or cut block, virtual trial implant, virtual implant component, virtual implant or virtual device, one or more predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration can be highlighted using a target like display. More than one target-like display can be used.

The target-like display can, for example, be positioned over a starting point, one or more intermediate points, an end point, a starting position, one or more intermediate positions, an end position, a intended path, predetermined plane, predetermined cut plane, a predetermined axis of the physical surgical tool, surgical instrument, trial implant, implant component, implant or device. A line or an axis oriented in orthogonal fashion through the target and passing through the center of one or more targets can optionally be aligned with a predetermined path, predetermined plane, predetermined cut plane, or predetermined axis of the physical surgical tool, surgical instrument, trial implant, implant component, implant or device, and/or one or more of a predetermined tissue change/alteration.

An intermittent, e.g. blinking or flashing display can be used to show one or more of a virtual surgical tool, virtual surgical instrument including a virtual surgical guide or cut block, virtual trial implant, virtual implant component, virtual implant or virtual device, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. An intermittent display can, for example, highlight if and when one or more of the surgical tool, surgical instrument, trial implant, implant component, implant or device are not aligned with one or more of the virtual surgical tool, virtual surgical instrument including a virtual surgical guide or cut block, virtual trial implant, virtual implant component, virtual implant or virtual device, one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration. An intermittent display can, for example, highlight if and when one or more of the surgical tool, surgical instrument, trial implant, implant component, implant or device are aligned with one or more of the one or more of a virtual surgical tool, virtual surgical instrument including a virtual surgical guide or cut block, virtual trial implant, virtual implant component, virtual implant or virtual device, a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

An intermittent display can optionally change colors or have intermittent, varying color schemes. For example, a blinking or flashing red color can turn into solid, not intermittent green color when one or more of the physical surgical tool, surgical instrument, trial implant, implant component, implant and/or devices are aligned with one or more of a virtual surgical tool, virtual surgical instrument including a virtual surgical guide or cut block, virtual trial implant, virtual implant component, virtual implant or virtual device, or one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration.

An intermittent display can, for example, highlight if and when one or more of the surgical tool, surgical instrument, trial implant, implant component, implant or device are not aligned with one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration in the OHMD can turn from a solid color, e.g. green or blue, to a blinking or flashing red color. Different colors can be chosen for intermediate versus final, end positions, e.g. blue for intermediate and green for final/end.

An appearing or disappearing display can be used to show one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device inside the OHMD. An appearing or disappearing display can, for example, highlight if and when one or more of the surgical tool, surgical instrument, trial implant, implant component, implant or device are not aligned with one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. In this example, the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device can appear in the OHMD display when the physical surgical tool, surgical instrument, trial implant, implant component, implant, and/or device are not aligned, e.g. with the surgical plan or the one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. The one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can disappear in the OHMD display when alignment is achieved again. The reverse can be possible, e.g. with the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device disappearing when alignment is not achieved and appearing when alignment is achieved.

A magnified or minified display can be used to show one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. The OHMD can also, optionally, provide or superimpose a magnified or minified display of the virtual anatomy or virtual data of the patient, for example after registration with the live anatomy/live data of the patient. The unmagnified, magnified or minified virtual anatomy or virtual data of the patient can be displayed by the OHMD simultaneously, e.g. with use of different colors, grey scale or patterns, or alternatingly with the unmagnified, magnified or minified display by the OHMD of the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. In some embodiments of the invention, the magnification (including no magnification) or minification of the display of the virtual anatomy or virtual data of the patient can be the same as the magnification (including no magnification) or minification of the one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. Virtual anatomy or virtual data of the patient as used in the foregoing includes all virtual data of the patient, including, for example, data from vascular flow studies, metabolic imaging, kinematic data and the like.

A magnified or minified display by the OHMD can, for example, highlight if and when one or more of the surgical tool, surgical instrument, trial implant, implant component, implant or device are not aligned with one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. In this example, the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be magnified or minified in the OHMD display when the physical surgical tool, surgical instrument, trial implant, implant component, implant, and/or device are not aligned, e.g. with the surgical plan or the one or more of the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device. The one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be set to zero magnification or minification or can go from magnified to minified or from minified to magnified in the OHMD display when alignment is achieved again.

If more than one a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device are displayed by the OHMD, any combination of display styles or techniques, e.g. multi-colored, grey scale, shaded, patterned, line, arrow, target, intermittent, appearing, disappearing, magnified, minified is possible. In some embodiments, different display styles or techniques can be chosen for different predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device.

Two-Dimensional and Three-Dimensional Displays

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the OHMD in two dimensions.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the OHMD in three dimensions.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the OHMD in two dimensions and/or three dimensions, for example alternatingly or as triggered by voice commands or other commands. Simultaneous display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device in three dimensions can be possible.

Stereoscopic and Non-Stereoscopic Displays

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the OHMD in a non-stereoscopic manner in three dimensions, with similar view angle of the virtual data of the patient seen by the surgeon's eyes through the display of the OHMD unit and the live data of the patient seen by the surgeon's eyes through the OHMD unit.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the OHMD in a stereoscopic manner in three dimensions.

One or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be displayed by the OHMD in a stereoscopic and/or a non-stereoscopic display, for example alternatingly or as triggered by voice commands or other commands. Simultaneous display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device in a non-stereoscopic manner with display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device in a stereoscopic manner can be possible.

In some embodiments of the invention, one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be located in a spine, more specifically a vertebral body, a pedicle, a vertebral fracture, a posterior element, a facet joint depending on the virtual surgical plan and the anatomy and clinical condition of the patient. The predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can be located in the posterior elements of a spine, a pedicle and a vertebral body, for example, if spinal fusion with pedicle screws or vertebroplasty of kyphoplasty are contemplated.

If spinal fusion with pedicle screws is planned, the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can coincide with, be parallel with, or be aligned and/or superimposed with the long axis of the pedicle screw in its intended virtual placement position from the virtual surgical plan, optionally using placement criteria, e.g. distance from cortex, as used in the virtual surgical plan.

If vertebroplasty or kyphoplasty or spinal biopsy is planned, the predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device can coincide with, be parallel with, or be aligned and/or superimposed with the long axis of the vertebroplasty, kyphoplasty or biopsy needle or needle set in its intended virtual placement position from the virtual surgical plan, optionally using placement criteria, e.g. distance from cortex, as used in the virtual surgical plan.

When stereoscopic projection is used by the OHMD, the display for the left eye and the right eye can be adjusted for the surgeon's or operator's inter-ocular distance, including, for example, the inter-pupillary distance. For example, the distance between the left pupil and the right pupil can be measured prior to operating the OHMD. Such measurements can be performed using an image and/or video capture system integrated into, attached to or separate from the OHMD. Such measurements can also be performed using any other technique known in the art, including, for example, mechanical rulers, optical measurement tools and standard tools used by optometrists.

Adjusting the OHMD Unit Including the Display

In some embodiments, once the inter-ocular, e.g. the inter-pupillary distance, of the surgeon or operator is known, it can be entered into the display system interface and/or software and the 3D projection of the left and the right eye can be adjusted for the user. For example, with a narrow inter-ocular or inter-pupillary distance, the projection for the left eye and the right eye can be moved closer to the nose so that the center of the left and the right projections will be aligned with the center of the left eye/pupil and the right eye/pupil. With a wide inter-ocular or inter-pupillary distance, the projection for the left eye and the right eye can be moved further away from the nose so that the center of the left and the right projections will be aligned with the center of the left eye/pupil and the right eye/pupil. Different user settings can be stored in the system, e.g. by user name. In this manner, when a different user is placing the OHMD on his or her head, the user or the system can call up their preferred user settings, including their respective inter-ocular or inter-pupillary distance. User settings can be called up, for example, using a visual or optical keyboard interface, projected by the OHMD, where the operator can select virtual buttons. User settings can also be called up using voice commands, keyboards and any other known technique or technique for executing user commands.

Refresh Rates, Addressing Image Flicker

In many embodiments of the invention, a fast refresh rate can be desirable, e.g. 15 Hz, 20 Hz, 25 Hz, or 30 Hz, 50 Hz, 70 Hz, 80 Hz, 100 Hz, 120 Hz, 150 Hz, 175 Hz, 200 Hz or greater. When higher refresh rates are used, the spatial resolution of the display of the virtual data can optionally be reduced if bandwidth and transmission speed and/or display speed reach their limits. Alternatively, there can be an alternating of a high resolution display, e.g. 1920×1080 pixel resolution, and lower resolution, e.g. 1024×768 pixel resolution. The ratio of high to lower resolution images can be 1:1, 2:1, 3:1, 1:2, 1:3, with any other combination possible.

Some users physicalize no flicker with refresh rates of 30 Hz, sometimes less. Other users can feel or experience flicker with refresh rates of 70 Hz or faster. If a user is experiencing flicker effects or a flicker feeling with the display of virtual data, the user can have the option of increasing the refresh rate and, optionally, decreasing the display resolution if necessary, for example for reasons of bandwidth or transmission speed. The user can also select alternating resolutions, e.g. 1920×1080 pixel resolution intermixed with 1024×768 pixel resolution; any other pixel resolution and combination of pixel resolutions is possible. In this manner, the user can select the setting that will yield a pleasant, substantially flicker free display while at the same time maintaining sufficient spatial and/or temporal resolution to enable an accurate physical/virtual work environment.

In some embodiments of the invention, the display will automatically turn of and, optionally, turn on depending where the user and/or operator and/or surgeon directs the view.

Automated Turning Off and/or Turning On

In select circumstances, the user and/or operator and/or surgeon may elect to turn off the OHMD display or to turn it back on. The turning off and/or on can be executed via voice commands. It can also be executed via gesture commands, eye commands, digital/finger commands on a physical or virtual keypad or keyboard, e.g. projected by the OHMD.

In some embodiments, the OHMD display can turn off and/or on automatically. The turning off and/or on can be triggered by any number of initiating events or movements, which can optionally be defined by the user. Events or movements triggering an automatic turning off and/or turning on can be different between different users and can be stored as user preferences.

Automatic turning off and/or turning on can, for example, also help reduce the times the OHMD display is on or active, which can be desirable when users experience a flicker like feeling or encounter a flicker experience with the OHMD display or other feelings of discomfort. In this way, the periods of potential flicker exposure or other feelings of discomfort can be reduced to the key parts or portions or sections when the user requires the OHMD to execute an activity, e.g. a physical surgical step optionally defined in a virtual surgical plan with display of one or more of a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device.

In some embodiments of the invention, the OHMD display can optionally automatically turn on when the user looks at the target area of activity, e.g. a surgical field or an organ or a tissue located within the coordinates of a live surgical field or area and/or a virtual surgical field or area. In some embodiments of the invention, the OHMD display can optionally automatically turn off when the user looks away from the target area of activity, e.g. a surgical field or area or an organ or a tissue located within the coordinates of a live and/or virtual surgical field or area. In some embodiments, the OHMD display can optionally automatically turn on when the user looks at the target area of activity, e.g. a surgical field or an organ or a tissue located within the coordinates of a live surgical field or area and/or a virtual surgical field or area, and one or more optical markers are detected in the surgical field or an organ or a tissue located within the coordinates of the live surgical field or area and/or a virtual surgical field or area by a camera, image or video capture system integrated into, attached to or separate from the OHMD. In some embodiments of the invention, the OHMD display can optionally automatically turn off when the user looks away from the target area of activity, e.g. a surgical field or area or an organ or a tissue located within the coordinates of a live and/or virtual surgical field or area, and one or more optical markers are absent from the surgeon's view and/or the view of a camera, an image or video capture system integrated into, attached to or separate from the OHMD.

The target area of activity, e.g. a surgical field and/or a target tissue can be defined and/or identified using different means, e.g. image capture, optical markers, navigation markers including infrared markers, retroreflective markers, RF markers, surgical navigation, LEDs, reference phantoms, calibration phantoms, marks drawn on the target area, e.g. on the skin or a surgical drape. If surgery is contemplated, any of the foregoing active and/or passive markers can be placed on the patient, e.g. underneath a surgical drape, or within the visible sterile, exposed area of the patient on which the surgery will be performed. Alternatively, any active or passive markers can also be placed on top of the sterile drape or on the patient's skin, e.g. surrounding the surgical area or surgical field. A target area can also be identified with use of one or more anatomic landmarks, e.g. in a hip a most inferior point, e.g. sulcus point, between the greater trochanter and the femoral neck, a most superior point on the greater trochanter, a most superior point on a lesser trochanter, an acetabular rim, an acetabular center or in a knee a most medial point on a medial condyle, a most lateral point on a lateral condyle, a center of a trochlear notch, a tibial spine, a most anterior point of a tibia, a central point of a patella. One or more of the same landmarks that have been/are being used for registration of virtual data and live data of the patient can be used for defining or identifying a target area of activity. The landmarks can be identified using, for example, an image and/or video capture system integrated into, attached to or separate from an OHMD. The landmarks can be identified by attaching optionally one or more optical markers, navigation markers including infrared markers, retroreflective markers, RF markers, surgical navigation, LEDs, reference phantoms, calibration phantoms, or marks. A target area can be enclosed by landmarks, e.g. by three or more landmarks. A target area can extend beyond one or more landmarks, e.g. by 2, 4, 5, 6, 8, 10 cm or more or any other distance or radius, e.g. selected by the surgeon or operator.

If image capture is used to define an area of intended activity, e.g. a surgical field, the user and/or the surgeon can optionally look at the area of intended activity, e.g. the intended field. Optionally, identify the center area of the area of activity and/or the surgical field can be defined by the user, e.g. by pointing at it with a finger or a pointing device or an RF marker, an optical marker, a navigation marker including infrared markers, retroreflective markers, RF markers, an LED and/or a calibration phantom or a reference phantom. Once the user's and/or the surgeon's view is focused on the intended area of activity and/or the intended surgical field, the user and/or surgeon can execute a command, e.g. a voice command or a finger command, to identify the intended area of activity and/or the surgical field and to store it in the image and/or video capture system. The identified intended area of activity and/or the surgical field is in this manner memorized in the image and/or video capture system. Using standard image processing techniques, the image and/or video capture system can subsequently identify if 20%, 30%, 40%, 50%, 60%, 70%, 80%, 90% or 100% of the intended area of activity and/or the surgical field are included in the field of view of the user and/or the operator and/or the surgeon. Once a certain percentage, e.g. 50% or 60% or 70% or 80% or 90% of the area of intended activity and/or the surgical field is included in the field of view of the surgeon, the OHMD can automatically turn on the OHMD display. Optionally, as the user, operator and/or surgeon turns away his or her view, the OHMD display can automatically turn off, e.g. when less than 90%, 80%, 70%, 60% or 50% of the intended area of activity and/or surgical field area included in the field of view.

The area or percentage used for turning on the OHMD and for turning off the OHMD can be different. The percentage can be selected and, optionally, stored as a user preference.

The field of view can be defined in various different ways, optionally as a user preference. For example, the field of view can be the area covered by the OHMD display when the user is looking through the OHMD. The field of view can be the entire visual field available to the user and/or operator and/or surgeon. The field of view can be a subsection of the visual field of the user, operator and/or surgeon.

Rather than using a percentage of area of the intended area of activity and/or surgical field included, other triggers can be used using, for example, anatomic landmarks, image capture or optical markers, a navigation marker including infrared markers, retroreflective markers, RF markers, an LED and/or a calibration phantom or a reference phantom. For example, the OHMD display can automatically turn on when the user, operator and/or surgeon starts looking at the intended area of activity and/or the surgical field when an anatomic landmark, an optical marker, a navigation marker including infrared markers, retroreflective markers, RF markers, an LED or a calibration phantom or reference phantom (e.g. as seen through an image and/or video capture system integrated into, attached to or separate from the OHMD) is located in the outer one third, central one third or inner one third or the inner half or other landmark or demarcation/separation of the field of view.

Alternatively, the OHMD display can also automatically turn on when the field of view reaches within a certain centimeter range of one or more of an anatomic landmark, an optical marker, a navigation marker including infrared markers, retroreflective markers, RF markers, an LED or a calibration phantom or reference phantom or IMU, e.g. within 15 cm, 10 cm, 5 cm etc. The OHMD display can also automatically turn on when the field of view reaches within a certain centimeter range of one or more of a marker of an area of intended activity and/or a surgical field, e.g. a pin or a screw, e.g. within 15 cm, 10 cm, 5 cm etc.

The OHMD display can optionally also automatically turn off when the intended area of activity or the surgical field or area decreases below a certain threshold percentage (optionally set by the user) of the field of view, e.g. 90%, 80%, 70%, 60%, 50%, 40%, 30%, 20%, 10%, etc. In some embodiments, the OHMD display can automatically turn off when the user, operator and/or surgeon starts looking away from the intended area of activity and/or the surgical field when an anatomic landmark, an optical marker, a navigation marker including infrared markers, retroreflective markers, RF markers, an LED or a calibration phantom or reference phantom (e.g. as seen through an image and/or video capture system integrated into, attached to or separate from the OHMD) is located outside the outer one third, central one third or inner one third or the inner half or other landmark or demarcation/separation of the field of view. Alternatively, the OHMD display can also automatically turn off when the field of view reaches outside a certain centimeter range of one or more of an anatomic landmark, an optical marker, a navigation marker including infrared markers, retroreflective markers, RF markers, an LED or a calibration phantom or reference phantom or IMU, e.g. outside 5 cm, 10 cm, 15 cm or more. The OHMD display can also automatically turn off when the field of view reaches outside a certain centimeter range of one or more of a marker of an area of intended activity and/or a surgical field, e.g. a pin or a screw, e.g. within 5 cm, 10 cm, 15 cm or more.

In some embodiments of the invention, the OHMD display can automatically turn on when a select surgical instrument, e.g. an awl or a pin driver or a reamer or a saw, or a select medical device component, or multiple thereof (either simultaneously or sequentially) appear in the field of view. Optionally, the OHMD display can automatically turn off when a select surgical instrument, e.g. an awl or a pin driver or a reamer or a saw, or a select medical device component, or multiple thereof (either simultaneously or sequentially) disappear from the field of view. The appearing or disappearing of the one or more surgical instruments or medical device components can be caused by the user/surgeon moving the head away from the intended area of activity and/or the surgical field; it can also be caused by the user/surgeon moving the surgical instrument and/or medical device component outside the field of view or away from the area of intended activity and/or surgical field while continuing to look at the area of intended activity and/or the surgical field.

In some embodiments of the invention, the OHMD display can automatically turn off when the user/operator/surgeon looks at a display monitor other than the OHMD. Such a display monitor can be a video screen or a TV screen or a computer monitor, or a PACS monitor or other display monitor, e.g. located in an operating room or in a factory. In some embodiments of the invention, the monitor can be recognized, e.g. based on its square or rectangular outline/shape using image capture combined with standard image processing techniques. In some embodiments of the invention, a video screen or a TV screen or a computer monitor, or a PACS monitor or other display monitor can be identified for example with optical markers, navigation markers including infrared markers, retroreflective markers, RF markers, LEDs and other markers placed on, surrounding or nearby the monitor.

Optionally, the OHMD can automatically turn back on when the user/operator/surgeon looks away from the monitor. The turning on and turning off of the OHMD display can be triggered, for example, when the monitor occupies 25%, 50% or 75% or more of the field of view. The turning on and turning off of the OHMD display can be triggered, for example, when the field of view, e.g. through the OHMD display, reaches the central area of the point of the monitor, or within 5 cm, 10 cm, 15 cm or more of the central area or point of the monitor, or within a certain distance or area from an optical marker, navigation marker including infrared markers, retroreflective markers, RF markers, LED and/or other markers placed on, surrounding or nearby the monitor.

In select embodiments, it can be preferable that the OHMD display turns on when the user looks at the monitor and it turns off when the user looks away from the monitor. It can then optionally turn back on when the user looks at the intended area of activity, e.g. a surgical field or area.

In some embodiments of the invention, when flicker or the feeling of experiencing flicker with the OHMD display is a concern for a user, the OHMD can turn on an off on an intermittent basis, e.g. it can display the virtual data for 1, 2, 3, 4 or more seconds and then turn off for a break, e.g. 1, 2, 3, 4 or more seconds. The periods of display on and display off can be defined by the user based on user preferences. The periods of display on and off can be combined with various triggers of automatic turning on and off of the OHMD display, as outlined, for example in the foregoing.

The foregoing embodiments and examples describing non-automated and automated or automatic techniques for turning on an OHMD display and turning off an OHMD display are only exemplary in nature and are in no way meant to be limiting of the invention. Someone skilled in the art can recognize many different triggers for turning on and off an OHMD display automatically. The automatic turning on and off of an OHMD display can also be a useful feature for preserving battery life, e.g. disposable or rechargeable.

Managing Display, Hardware, Software or Bandwidth Limitations

In some embodiments of the invention, the display of the OHMD unit can display a subset of the data and/or images representing a smaller portion of the field of view visible through the OHMD or displayable by the display of the OHMD unit, using, for example, only a portion of the available display. If data from a pre-operative or intra-operative imaging study, e.g. x-rays, a CT scan, an MRI scan, are displayed, the data or images displayed by the OHMD can also be targeted to a volume smaller than the original scan volume or area covered by the imaging study in order to decrease the amount of data displayed. In addition, the data or images displayed by the OHMD can also be targeted to a volume or area smaller than the volume or area to be operated or smaller than the volume or area of the surgical site. This embodiment can, for example, be useful, when the software environment limits the amount of surface points or nodes displayed or limits the size or amount of the data displayed by the OHMD. This embodiment can also be useful when a WiFi or Bluetooth or other wireless connection is used with the OHMD with limitations in bandwidth and/or data transmission, thereby limiting the amount of data being transmitted to the OHMD and, ultimately, displayed, in particular when this limitation implies a limitation in the amount of data available for the display of the data and/or images by the OHMD.

This smaller portion of the field of view visible through the OHMD or displayable by the display of the OHMD unit, smaller, targeted volume from an imaging study, or the volume or area smaller that the volume or area of the surgical site can be targeted to portions of the surgical site or to anatomic landmarks. For example, in a knee replacement, this smaller portion of the field of view can be targeted to the distal femur or portions of the distal femur while the surgeon is contemplating surgical steps on the femur, e.g. a distal femoral cut or an anterior or posterior cut or chamfer cuts; it can be targeted to the proximal tibia or portions thereof while the surgeon is contemplating surgical steps on the tibia, e.g. a proximal tibial cut or a tibial keel preparation and punch; it can be targeted to the patella, while the surgeon is contemplating surgical steps on the patella, e.g. a milling or cutting of the patella. In a hip replacement, the smaller portion of the field of view can be targeted to the proximal femur or portions thereof, while the surgeon is contemplating steps on the proximal femur, e.g. a femoral neck cut; it can be targeted to the acetabulum, while the surgeon is contemplating surgical steps on the acetabulum, e.g. an acetabular reaming or an impaction of an acetabular cup; it can be re-focused or re-targeted on the proximal femur when the surgeon contemplates femoral broaching or reaming, optionally followed by femoral component impaction. In a pedicle screw placement or a vertebroplasty or kyphoplasty, the smaller portion of the field of view can be targeted to the level and/or the side where the surgeon contemplates the next surgical step, e.g. an insertion of an awl, a pedicle screw, a needle, a vertebra- or kyphoplasty needle.

A targeted area or smaller portion of the field of view visible through the OHMD or displayable by the display of the OHMD, a smaller, targeted volume from an imaging study, or a volume or area smaller that the volume or area of the surgical site can also be defined with use of one or more anatomic landmarks, e.g. in a hip a most inferior point, e.g. sulcus point, between the greater trochanter and the femoral neck, a most superior point on the greater trochanter, a most superior point on a lesser trochanter, an acetabular rim or portions thereof, an acetabular center, or in a knee, a most medial point on a medial condyle, a most lateral point on a lateral condyle, a center of a trochlear notch, a tibial spine, a most anterior point of a tibia, a central point of a patella. One or more of the same landmarks that have been/are being used for registration of virtual data and live data of the patient can be used for defining or identifying a target area or a smaller portion of the field of view visible through the OHMD or displayable by the display of the OHMD. The landmarks can be identified using, for example, an image and/or video capture system integrated into, attached to or separate from an OHMD. The landmarks can be identified by attaching optionally one or more optical markers, navigation markers including infrared markers, retroreflective markers, RF markers, surgical navigation, LEDs, reference phantoms, calibration phantoms, or marks. A target area can be enclosed by landmarks, e.g. by three or more landmarks. A target area can extend beyond one or more landmarks, e.g. by 2, 4, 5, 6, 8, 10 cm or more or any other distance or radius, e.g. selected by the surgeon or operator.

By limiting the display to such a smaller portion of the field of view visible through the OHMD or displayable by the display of the OHMD or target area, a smaller, targeted volume from an imaging study, or a volume or area smaller that the volume or area of the surgical site the amount of data displayed can be reduced. In addition, the amount of data transmitted, e.g. using a Wifi, Bluetooth or LiF network can also be reduced.

Viewing 2D Computer Monitors Through an OHMD Unit

In some embodiments of the invention, the OHMD system can detect, e.g. automatically, if the surgeon or operator is looking at a computer or display monitor separate from the OHMD, for example, with use of an image and/or video capture system integrated into, attached to or separate from the OHMD. The standalone or separate computer or display monitor can be used, for example, to display image data, e.g. of a patient, or to concurrently display virtual data displayed by the OHMD. The image and/or video capture system can, for example, capture the outline of the computer or display monitor, e.g. round, square or rectangular, and the software can, optionally, automatically match, superimpose or align the items or structures displayed by the OHMD with the items or structures displayed by the standalone or separate computer or display monitor. Alternatively, the user, operator and/or surgeon can execute a command, e.g. a voice command or a command using a virtual finger/keyboard interface, indicating that he or she is looking at the standalone or separate computer or display monitor and the software can then match, superimpose or align the items or structures displayed by the OHMD with the items or structures displayed by the standalone or separate computer or display monitor. The OHMD system can match, superimpose, or align all of the structures displayed by the standalone or separate computer monitor. The OHMD system can match, superimpose or align a portion of the structures displayed by the standalone or separate computer monitor.

The OHMD can display the structures displayed by the standalone or separate computer monitor using the same color. The OHMD can display the structures displayed by the standalone or separate computer monitor using the different colors. The OHMD can display structures not displayed by the standalone or separate computer monitor using a different color or greyscale or contrast than that used by the standalone or separate computer monitor. The OHMD can display the structures displayed by the standalone or separate computer monitor using the same greyscale and/or contrast used by the standalone or separate computer monitor. The OHMD can display the structures displayed by the standalone or separate computer monitor using a different greyscale and/or contrast used by the standalone or separate computer monitor.

The OHMD can display the structures displayed by the standalone or separate computer monitor using the same image intensity used by the standalone or separate computer monitor. The OHMD can display the structures displayed by the standalone or separate computer monitor using a different image intensity used by the standalone or separate computer monitor, e.g. brighter or less bright.

In some embodiments of the invention, a standalone or separate computer or display monitor located in a user area, e.g. an operating room or a surgical suite, can be used as a calibration or reference or registration phantom for the OHMD unit including the frame and display position, orientation and/or alignment and/or direction of movement. The monitor can have a round, rectangular or square shape of known dimensions. An image and/or video capture system integrated into, attached to or separate from the OHMD can be used to capture one or more images of the monitor. Since the dimensions of the monitor are known, the size, shape or dimensions, for example along its edges, or the area of the monitor on the captured image(s) can be used to determine the distance of the OHMD to the monitor; the shape of the circle, oval, rectangle or square can be used to determine the angle of the OHMD relative to the monitor. If the image and/or video capture system integrated into or attached to the OHMD uses two or more cameras, the difference in shape of the circle, oval, rectangle or square detected between a first, second and any additional cameras can be used to increase the accuracy of any estimates of the angular orientation of the OHMD to the display monitor, e.g. by calibrating the measurement of a first camera against a second camera against a third camera and so forth. If two or more cameras are used integrated into or attached to different portions of the OHMD frame, e.g. the left side of the frame and the right side of the frame, the difference in projection of the monitor circle, oval, rectangle or square between the two cameras can also be used to estimate the user's head position and/or orientation and/or alignment and/or the position and/or orientation and/or alignment of the OHMD frame in relationship to the user's head and/or face.

In some embodiments of the invention, the user and/or surgeon can optionally look at the display monitor through the OHMD while maintaining his or her head in a neutral position, e.g. with no neck abduction, adduction, flexion, extension or rotation. This head position can be used to calibrate the position of the OHMD display in relationship to the target area and/or the patient and/or the surgical site, e.g. during an initial registration or a subsequent registration. This head position can also be used to calibrate the position of the OHMD unit/frame in relationship to the user's and/or the surgeon's head and face. Optionally, the user and/or surgeon can place his or her head on a chin stand or head holder for purposes of this calibration or registration. This process of using an external computer or display monitor as a reference for calibration and/or registration purposes can be performed at the beginning of an activity and/or a surgical procedure, e.g. as part of an initial registration process. This process of using an external display monitor as a reference for calibration and/or registration purposes can also be performed during an activity or after an activity and/or surgical procedure, for example when there is concern that the OHMD unit may have moved relative to the user's and/or surgeon's face.

In some embodiments of the invention, the position, location, orientation, and/or alignment of the outline of the standalone or separate computer or display monitor can be monitored, for example using an image and/or video capture system integrated into, attached to or separate from the OHMD. Optionally, the position, location, orientation and/or alignment of the outline of the standalone or separate computer or display monitor can be monitored using attached optical markers, navigation markers including infrared markers, retroreflective markers, RF markers, LEDs and/or IMUs as well as any other techniques described in the specification or known in the art for determining and/or tracking the position, location, orientation and/or alignment of an object. With the position, location, orientation and/or alignment of the standalone or external computer or display monitor known, the position, location, orientation, alignment and/or direction of movement of the OHMD unit can be tracked in relationship to it, e.g. via an image and/or video capture system integrated into or attached to the OHMD or optical markers, navigation markers including infrared markers, retroreflective markers, RF markers, LEDs and/or IMUs integrated into it or attached to it. As the position, location, orientation, alignment and/or direction of movement of the OHMD unit can be tracked, the display of the OHMD unit can at all times or, if preferred, intermittently, display the same structures, or at least a portion or subset thereof, displayed by the standalone or separate computer or display monitor, spatially matched. If the standalone or separate computer or display monitor occupies only a portion of the visual field covered by the OHMD display, the OHMD display can match the displayed structures with the structures displayed by the standalone or separate computer or display monitor only for the portion of the visual field occupied by the standalone or separate computer or display monitor. Optionally, the OHMD display can display structures extending beyond the portion of the visual field occupied by the standalone or separate computer or display monitor. The structures extending beyond the portion of the visual field occupied by the standalone or separate computer or display monitor can be continuous with the structures displayed by the standalone or separate computer or display monitor. The structures outside the portion of the visual field occupied by the standalone or separate computer or display monitor can be separate and/or from the structures displayed by the standalone or separate computer or display monitor. For example, in addition to displaying one or more structures matching or corresponding to what is displayed by the standalone or separate computer or display monitor, the OHMD display can display items such as vital signs or patient demographics, or pre-operative imaging studies in those portions of the visual field that do not include the standalone or separate computer or display monitor. This can be useful when the user, operator and/or surgeon is not looking at the patient.

In some embodiments of the invention, the OHMD can display surgical field related information, e.g. details or aspects of a virtual surgical plan, e.g. intended/projected cut planes, or anatomic information of the patient, e.g. from a pre-operative imaging study, when the user or surgeon is looking at the surgical field; the OHMD can display portions of information or all of the information displayed by a standalone or separate computer or display monitor, for example in 3D while the standalone or separate computer or display monitor display can be in 2D, when the user or surgeon is looking at the standalone or separate computer or display monitor; the OHMD can display non-surgical field related information and non-standalone or separate computer or display monitor related or displayed information when the user or surgeon is neither looking at the surgical field nor at the standalone or separate computer or display monitor or when the surgical field and/or the standalone or separate computer or display monitor occupy only a portion of the visual field covered by the OHMD display. The switching or toggling between surgical field related information, standalone or separate computer or display monitor information and other information by the OHMD display can be automatic, for example via image capture and related image processing and recognition which area the user or surgeon is currently looking at (optionally demarcated by optical markers, navigation markers including infrared markers, retroreflective markers, RF markers, and/or LEDs, or it can be via commands executed by the user or surgeon, e.g. voice commands or finger/keyboard commands, for example using a virtual keyboard displayed by the OHMD display.

The OHMD can display information related to the information displayed on the standalone or separate computer display or monitor in two dimensions or three dimensions, the latter stereoscopically or non-stereoscopically. Any number of combinations of displays can be applied between the display by the OHMD display and the display by the standalone or separate computer or monitor display. For example, when the computer or monitor displays shows a pre-operative or intra-operative imaging study of the patient, these can be displayed in 2D (e.g. cross-sectional) or 3D using pseudo-3D display techniques, for example with surface reconstruction and shading. Overlaying or superimposing, for example, a true 3D, e.g. stereoscopic 3D, view of the anatomy from the pre- or intra-operative imaging study and/or virtual surgical plan of the patient using the OHMD display onto the same anatomic structures and/or virtual surgical plan displayed in 2D or pseudo 3D by the standalone or separate computer or display monitor can be beneficial for the surgeon as he or she executes surgical plans or plans next surgical plans during a procedure.

In some embodiments, the display of the OHMD unit or the standalone or separate computer or display monitor can display functional and/or time studies of the patient, e.g. the surgeon moving a leg or an arm of the patient using physical-time fluoroscopic imaging, while the other of the two display modalities can simultaneously display and/or superimpose static images. For example, the standalone or separate computer or display monitor can display 2D or 3D function and/or time studies, e.g. of knee motion captured using physical-time 2D single or biplane fluoroscopy or captured using 3D CT fluoroscopy, while the display of the OHMD unit can superimpose 2D or 3D non-stereoscopic or 3D stereoscopic images of the corresponding anatomy.

The following is an exemplary list of select possible combinations of 2D, 3D non-stereoscopic and stereoscopic displays by the OHMD and 2D and pseudo 3D displays of the standalone or separate computer or display monitor. The list in Table 8 is in no way meant to be limiting of the invention.

The standalone or separate computer or display monitor can optionally display some virtual data, e.g. pre-operative images and/or image reconstructions, of the patient in 2D, while it can display other virtual data, e.g. aspects or components of the virtual plan, e.g. intended cut planes, in pseudo 3D, e.g. with perspective views and shading. Similarly, the standalone or separate computer or display monitor can optionally display some virtual data, e.g. pre-operative images and/or image reconstructions, of the patient in 3D, while it can display other virtual data, e.g. aspects or components of the virtual plan, e.g. intended pin or drill placement, in 2D, e.g. as a line.

Aspects or components of the virtual surgical plan can, for example, include one or more of the following: a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical

TABLE 8

Examples of possible combinations of display modes or types by the display of the OHMD unit and the display of the standalone or separate computer or display monitor.

| OHMD Display | | | | | Standalone or Separate Computer or Display Monitor | | | |
|---|---|---|---|---|---|---|---|---|
| 2D | 3D Non-Stereoscopic | 3D Stereoscopic | 3D Non-Stereoscopic with Function/Time | 3D Stereoscopic with Function/Time | 2D | Pseudo 3D | 2D with Function/Time | Pseudo 3D with Function/Time |
| X | | | | | X | | | |
| X | | | | | | X | | |
| X | | | | | | | X | |
| X | | | | | | | | X |
| | X | | | | X | | | |
| | X | | | | | X | | |
| | X | | | | | | X | |
| | X | | | | | | | X |
| | | X | | | X | | | |
| | | X | | | | X | | |
| | | X | | | | | X | |
| | | X | | | | | | X |
| | | | X | | X | | | |
| | | | X | | | X | | |
| | | | X | | | | X | |
| | | | X | | | | | X |

X denotes type of display mode used

The OHMD display can optionally display some virtual data, e.g. pre-operative images and/or image reconstructions, of the patient in 2D, while it can display other virtual data, e.g. aspects or components of the virtual plan, e.g. intended cut planes, in 3D. Similarly, the OHMD display can optionally display some virtual data, e.g. pre-operative images and/or image reconstructions, of the patient in 3D, while it can display other virtual data, e.g. aspects or components of the virtual plan, e.g. intended pin or drill placement, in 2D, e.g. as a line.

tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device.

In an additional embodiment, the OHMD display can optionally display some of the aspects or components of the virtual surgical plan in 2D and other aspects and components in 3D, stereoscopic or non-stereoscopic. For example, the OHMD display can display a intended cut plane in 3D stereoscopic or non-stereoscopic, while it can display a virtual cut block as an outline in 2D, for example projected with a stereoscopic 3D view of the underlying tissue to be cut, e.g. a femoral neck for a hip replacement. The OHMD display can display a virtual surgical instrument, e.g. a reamer in 3D, e.g. stereoscopic or non-stereoscopic, and it can project the intended reaming axis in 2D or in 3D.

The standalone or separate computer or display monitor can optionally co-display some of the aspects or components of the virtual surgical plan in 2D and other aspects and components in pseudo 3D, optionally with different colors. For example, the standalone or separate computer or display monitor can display a intended cut plane in pseudo 3D, while it can display a virtual cut block as an outline in 2D, for example projected on a pseudo 3D view of the underlying tissue to be cut, e.g. a distal femur for a knee replacement. The standalone or separate computer or display monitor can display a virtual implant or trial implant in pseudo 3D, and it can project its intended central axis, e.g. a femoral shaft axis for a femoral component of a hip replacement, in 2D.

The different 2D and 3D displays by the OHMD display and the standalone or separate computer or display monitor can be displayed and viewed simultaneously, in many embodiments substantially or partially superimposed. Since the user or surgeon can view the standalone or separate computer or display monitor through the OHMD display, the user or surgeon can experience a combination of 2D and 3D display information, e.g. of virtual anatomy of the patient and/or aspects of the virtual surgical plan, not previously achievable.

TABLE 9

Further examples of possible combinations for simultaneous viewing of display modes or types by the display of the OHMD unit and the display of the standalone or separate computer or display monitor for virtual data of the patient including anatomy, e.g. pre-operative imaging, and/or aspects and/or components of a virtual surgical plan, and/or virtual surgical instruments and/or virtual implants or implant components and/or intra-operative imaging of the patient.

| | Standalone or Separate Computer or Display Monitor | | | | | | | | | | | |
|---|---|---|---|---|---|---|---|---|---|---|---|---|
| | Virtual Anatomic Data of the Patient | | | | Components of Virtual Surgical Plan of the Patient | | | | Virtual Surgical Instruments | | | |
| OHMD Display | 2D | Pseudo 3D | 2D with Function/ Time | Pseudo 3D with Function/ Time | 2D | Pseudo 3D | 2D with Function/ Time | Pseudo 3D with Function/ Time | 2D | Pseudo 3D | 2D with Function/ Time | Pseudo 3D with Function/ Time |
| Virtual Anatomic Data of the Patient | | | | | | | | | | | | |
| 2D | X | X | X | X | X | X | X | X | X | X | X | X |
| 3D Non-Stereoscopic | X | X | X | X | X | X | X | X | X | X | X | X |
| 3D Stereoscopic | X | X | X | X | X | X | X | X | X | X | X | X |
| 3D Non-Stereoscopic with Function/Time | X | X | X | X | X | X | X | X | X | X | X | X |
| 3D Stereoscopic with Function/Time | X | X | X | X | X | X | X | X | X | X | X | X |
| Components of Virtual Surgical Plan of the Patient | | | | | | | | | | | | |
| 2D | X | X | X | X | X | X | X | X | X | X | X | X |
| 3D Non-Stereoscopic | X | X | X | X | X | X | X | X | X | X | X | X |
| 3D Stereo scopic | X | X | X | X | X | X | X | X | X | X | X | X |
| 3D Non-Stereoscopic with Function/Time | X | X | X | X | X | X | X | X | X | X | X | X |
| 3D Stereoscopic with Function/Time | X | X | X | X | X | X | X | X | X | X | X | X |
| Virtual Surgical Instruments | | | | | | | | | | | | |
| 2D | X | X | X | X | X | X | X | X | X | X | X | X |
| 3D Non-Stereoscopic | X | X | X | X | X | X | X | X | X | X | X | X |
| 3D Stereoscopic | X | X | X | X | X | X | X | X | X | X | X | X |
| 3D Non-Stereoscopic with Function/Time | X | X | X | X | X | X | X | X | X | X | X | X |
| 3D Stereoscopic with Function/ Time | X | X | X | X | X | X | X | X | X | X | X | X |
| Virtual Implant or Trial Implant Components | | | | | | | | | | | | |
| 2D | X | X | X | X | X | X | X | X | X | X | X | X |
| 3D Non-Stereoscopic | X | X | X | X | X | X | X | X | X | X | X | X |

TABLE 9-continued

Further examples of possible combinations for simultaneous viewing of display modes or types by the display of the OHMD unit and the display of the standalone or separate computer or display monitor for virtual data of the patient including anatomy, e.g. pre-operative imaging, and/or aspects and/or components of a virtual surgical plan, and/or virtual surgical instruments and/or virtual implants or implant components and/or intra-operative imaging of the patient.

| | | | | | | | | | | | | |
|---|---|---|---|---|---|---|---|---|---|---|---|---|
| 3D Stereoscopic | X | X | X | X | X | X | X | X | X | X | X | X |
| 3D Non-Stereoscopic with Function/Time | X | X | X | X | X | X | X | X | X | X | X | X |
| 3D Stereoscopic with Function/Time Intra-Operative Imaging of the Patient | X | X | X | X | X | X | X | X | X | X | X | X |
| 2D | X | X | X | X | X | X | X | X | X | X | X | X |
| 3D Non-Stereoscopic | X | X | X | X | X | X | X | X | X | X | X | X |
| 3D Stereoscopic | X | X | X | X | X | X | X | X | X | X | X | X |
| 3D Non-Stereoscopic with Function/Time | X | X | X | X | X | X | X | X | X | X | X | X |
| 3D Stereoscopic with Function/Time | X | X | X | X | X | X | X | X | X | X | X | X |

| | Standalone or Separate Computer or Display Monitor | | | | | | | |
|---|---|---|---|---|---|---|---|---|
| | Virtual Implant or Trial Implant Components | | | | Intra-Operative Imaging of the Patient | | | |
| OHMD Display | 2D | Pseudo 3D | 2D with Function/ Time | Pseudo 3D with Function/ Time | 2D | Pseudo 3D | 2D with Function/ Time | Pseudo 3D with Function/ Time |
| Virtual Anatomic Data of the Patient | | | | | | | | |
| 2D | X | X | X | X | X | X | X | X |
| 3D Non-Stereoscopic | X | X | X | X | X | X | X | X |
| 3D Stereoscopic | X | X | X | X | X | X | X | X |
| 3D Non-Stereoscopic with Function/Time | X | X | X | X | X | X | X | X |
| 3D Stereoscopic with Function/Time | X | X | X | X | X | X | X | X |
| Components of Virtual Surgical Plan of the Patient | | | | | | | | |
| 2D | X | X | X | X | X | X | X | X |
| 3D Non-Stereoscopic | X | X | X | X | X | X | X | X |
| 3D Stereo scopic | X | X | X | X | X | X | X | X |
| 3D Non-Stereoscopic with Function/Time | X | X | X | X | X | X | X | X |
| 3D Stereoscopic with Function/Time | X | X | X | X | X | X | X | X |
| Virtual Surgical Instruments | | | | | | | | |
| 2D | X | X | X | X | X | X | X | X |
| 3D Non-Stereoscopic | X | X | X | X | X | X | X | X |
| 3D Stereoscopic | X | X | X | X | X | X | X | X |
| 3D Non-Stereoscopic with Function/Time | X | X | X | X | X | X | X | X |
| 3D Stereoscopic with Function/ Time | X | X | X | X | X | X | X | X |
| Virtual Implant or Trial Implant Components | | | | | | | | |
| 2D | X | X | X | X | X | X | X | X |
| 3D Non-Stereoscopic | X | X | X | X | X | X | X | X |
| 3D Stereoscopic | X | X | X | X | X | X | X | X |
| 3D Non-Stereoscopic with Function/Time | X | X | X | X | X | X | X | X |

TABLE 9-continued

Further examples of possible combinations for simultaneous viewing of display modes or types by the display of the OHMD unit and the display of the standalone or separate computer or display monitor for virtual data of the patient including anatomy, e.g. pre-operative imaging, and/or aspects and/or components of a virtual surgical plan, and/or virtual surgical instruments and/or virtual implants or implant components and/or intra-operative imaging of the patient.

| | | | | | | | | |
|---|---|---|---|---|---|---|---|---|
| 3D Stereoscopic with Function/Time Intra-Operative Imaging of the Patient | X | X | X | X | X | X | X | X |
| 2D | X | X | X | X | X | X | X | X |
| 3D Non-Stereoscopic | X | X | X | X | X | X | X | X |
| 3D Stereoscopic | X | X | X | X | X | X | X | X |
| 3D Non-Stereoscopic with Function/Time | X | X | X | X | X | X | X | X |
| 3D Stereoscopic with Function/Time | X | X | X | X | X | X | X | X |

X denotes type of display mode combinations used or possible

Virtual data of the patient including anatomy, e.g. pre-operative imaging, and/or aspects and/or components of a virtual surgical plan, and/or virtual surgical instruments and/or virtual implants or implant components and/or intra-operative imaging of the patient can be displayed using different colors, greyscale values and image intensities by the display of the OHMD unit and the display of the standalone or separate computer or display monitor.

Intra-operative imaging of the patient can include, for example, x-ray imaging, laser scanning, 3D scanning or mechanical probe scanning of a joint, e.g. hip joint, knee joint, shoulder joint, or a spine. Intra-operative X-ray images, laser scans, 3D scans, mechanical probe scans, pre-operative imaging data of the patient including 2D and 3D reconstructions, aspects or components of a virtual surgical plan, virtual surgical instruments, and/or virtual implants and implant components can be displayed simultaneously and, optionally, superimposed by the display of the OHMD unit and the display of the standalone or separate computer or display monitor. If two or more imaging modalities or pre-operative and intra-operative imaging studies are co-displayed, they can optionally be anatomically matched and they can optionally be displayed using the same projection plane or, optionally, different projection planes.

If 2D views are co-displayed with 3D views or pseudo 3D views by the OHMD display alone, by the standalone or separate computer or display monitor alone, or the two together and partially or completely superimposed, the 2D views can optionally be displayed using certain standard projections, e.g. AP, lateral, oblique; the standard projection, e.g. AP, lateral and oblique, can optionally be referenced to the live data of the patient, e.g. the corresponding planes with the patient positioned on the OR table, or to the data of the patient displayed on the standalone or separate computer or display monitor. Standard projections or standard views can also include view angles from the patient's side, front, top, bottom, or oblique views.

Dynamic views or functional views, for example with two or three spatial dimensions and a time dimension can be displayed by the display of the OHMD unit and/or the display of the standalone or separate computer or display monitor, optionally superimposed onto or co-displayed with static images, e.g. 2D or 3D, by the second display unit, e.g. the display of the OHMD unit or the display of the standalone or separate computer or display monitor. Such dynamic views or functional views can include kinematic studies of a joint, e.g. obtained with an intraoperative laser or 3D scanner, which can be used by a surgeon to obtain scans of the knee, hip, shoulder an any other joint at different flexion angles, extensions angles, rotation angles, abduction angles, adduction angles, e.g. 0, 10, 15, 20, 30, 40, 45, 50, 60, 70, 80, 90, 100, 110, 120, 130, 140, 150 degrees etc. Any other type of dynamic scan, which can include a time element or time dimension or a functional element or functional dimension can be displayed by the display of the OHMD unit and/or the display of the standalone or separate computer or display monitor.

In some embodiments of the invention, the display of the OHMD unit can be used for displaying lower resolution data and/or images, while the display of the display of the standalone or separate computer or display monitor can be used for displaying corresponding or matching or overlapping higher resolution data and/or images. This embodiment can be particularly useful when, for example, the maximum available display resolution of the OHMD is lower than desirable for a particular application or surgical procedure. This embodiment can also be useful, when the software environment limits, for example, the amount of surface points or nodes displayed or limits the available resolution. This embodiment can also be useful when a WiFi or Bluetooth or other wireless connection is used with the OHMD with limitations in bandwidth and/or data transmission, thereby limiting the amount of data being transmitted to the OHMD and, ultimately, displayed, in particular when this limitation implies a limitation in available spatial resolution for the display of the data and/or images by the OHMD. By viewing the lower resolution data and/or images through the OHMD, the user can have, for example, the benefit of stereoscopic visualization or the benefit of viewing components or aspects of the surgical plan, e.g. a virtual resection line, a virtual cut plane, a virtual instrument and/or a virtual implant, while by viewing simultaneously and/or with partial or complete superimposition the higher resolution data and/or images on the display of the standalone or separate computer or display monitor the viewer can have the concurrent benefit of viewing the data and/or images in high resolution.

In some embodiments of the invention, the display of the OHMD unit can be used for displaying static data and/or images, while the display of the standalone or separate computer or display monitor can be used for displaying corresponding or matching or overlapping dynamic data and/or images, e.g. images demonstrating a function, e.g. kinematic movement of a joint, and/or a time element or dimension including a change in condition or function monitored over a time period. This embodiment can be particularly useful when, for example, the refresh rate of the OHMD display is lower than desirable for a particular application or surgical procedure. This embodiment can also be useful, when the software environment limits, for example, the amount of data and/or images displayed. This embodiment can also be useful when a WiFi or Bluetooth or other wireless connection is used for connecting the OHMD with limitations in bandwidth and/or data transmission, thereby limiting the amount of data being transmitted to the OHMD and, ultimately, displayed, in particular when this limitation implies a limitation in available temporal and/or spatial resolution for the display of the data and/or images by the OHMD. By viewing the static data and/or images through the OHMD, the user can have, for example, the benefit of stereoscopic visualization or the benefit of viewing components or aspects of the surgical plan, e.g. a virtual resection line, a virtual cut plane, a virtual instrument and/or a virtual implant, while by viewing simultaneously and/or with partial or complete superimposition the dynamic data and/or images on the display of the standalone or separate computer or display monitor the viewer can have the concurrent benefit of viewing the dynamic data and/or images, optionally in high resolution.

In some embodiments of the invention, the display of the OHMD unit can be used for displaying a subset of the data and/or images representing a smaller portion of the field of view displayed by the standalone or separate computer or display monitor, while the display of the display of the standalone or separate computer or display monitor can be used for displaying corresponding or matching or overlapping higher data and/or images using the full intended field of view of patient data. This embodiment can, for example, be useful, when the software environment limits the amount of surface points or nodes displayed or limits the size of the data displayed by the OHMD. This embodiment can also be useful when a WiFi or Bluetooth or other wireless connection is used with the OHMD with limitations in bandwidth and/or data transmission, thereby limiting the amount of data being transmitted to the OHMD and, ultimately, displayed, in particular when this limitation implies a limitation in the amount of data available for the display of the data and/or images by the OHMD. By viewing data and/or images with a smaller, more narrow field of view through the OHMD, the user can have, for example, the benefit of stereoscopic visualization or the benefit of viewing components or aspects of the surgical plan, e.g. a virtual resection line, a virtual cut plane, a virtual instrument and/or a virtual implant, while by viewing simultaneously and/or with partial or complete superimposition the data and/or images with the full field of view on the display of the standalone or separate computer or display monitor the viewer can have the concurrent benefit of viewing the data and/or images using the full intended field of view of patient data. When 3D views are superimposed onto or co-displayed with 2D views by the display of the OHMD unit and the display of the standalone or separate computer or display monitor or when multiple 2D views are superimposed or co-displayed by the display of the OHMD unit and the display of the standalone or separate computer or display monitor, they can be anatomically matched, for example using corresponding landmarks and/or using common coordinates. They can also have different view angles, e.g. a view angle as the patient is positioned on the OR table, a view angle from the side, front, top, bottom, or oblique views. Thus, the OHMD display can, for example, show a stereoscopic 3D view of the patient's virtual anatomy, e.g. from a pre-operative imaging study, while the standalone or separate computer or display monitor can show a matching AP or lateral intraoperative radiographic view or a matching pseudo 3D laser view of the patient.

The matching of data displayed by the display of the OHMD unit and the display of the standalone or separate computer or display monitor can be achieved in different ways, e.g. using Matching of data and/or image using coordinates Matching of data and/or image using content Combinations of matching of data and/or image coordinates and data and/or image content In some embodiments of the invention, data and/or images displayed by the OHMD and data and/or images displayed by the standalone or separate computer or display monitor can be matched using known image coordinates and can then optionally be partially or completely superimposed, e.g. as the user and/or surgeon moves his or her head and/or body while looking at the standalone or separate computer or display monitor. For example, if the OHMD is registered in space, e.g. with regard to the patient and/or the surgical site and/or the standalone computer or display monitor, data and/or images displayed by the OHMD and/or displayed by the standalone computer or display monitor can be in the same or a common coordinate system, which can allow the matching or superimposition of the display by the OHMD with the display by the standalone or separate computer or display monitor, when portions or all of the separate computer or display monitor are included in the field of view of the user or surgeon through the OHMD.

In some embodiments of the invention, when both the display of the OHMD and the display of the separate computer or display monitor are registered in the same coordinate system, the OHMD can display then a set of data and/or images at least partially matching the coordinates of the data and/or images of the separate computer or display monitor. For example, the OHMD can display stereoscopic 3D views that share common coordinates with a pseudo 3D visualization displayed by the standalone or separate computer or display monitor. Such common coordinates can, for example, be corner points or edges or select geometric features and/or locations which can be superimposed then in the resultant composite OHMD/standalone monitor view that the user or surgeon sees. The OHMD can also, for example, display a stereoscopic 3D view of live data of the patient or virtual data of the patient or both, while the standalone or separate computer or display monitor displays a 2D view, e.g. a pre-operative imaging study, of the patient. The 2D plane or view display by the standalone or separate computer or display monitor can have the same or common coordinates with the corresponding 2D plane embedded in or contained in the 3D data and/or images displayed by the OHMD which can be matched or superimposed then in the resultant composite OHMD/standalone monitor view that the user or surgeon sees. Alternatively, in a similar example, if the OHMD provides only a surface display, for example, the periphery or outline or select peripheral points of the 2D plane displayed by the standalone or separate computer or display monitor can have the same or common coordinates with corresponding surface points in the location corresponding to the 2D plane in the 3D data and/or images displayed by the OHMD.

The data and/or images displayed by the OHMD can be matched to the data displayed by the standalone or separate computer or display monitor, e.g. by identifying common coordinates and superimposing them and/or by defining a common coordinate system. Alternatively, the data and/or images displayed by the standalone or separate computer or display monitor can be matched to the data displayed by the OHMD, e.g. by identifying common coordinates and superimposing them and/or by defining a common coordinate system. When the data and/or images displayed by the OHMD are superimposed with the data and/or images displayed by the standalone or separate display monitor, the data and/or images displayed by the OHMD and the data and/or images displayed by the standalone or separate display monitor can be displayed with the same magnification in order to optimize the superimposition or matching.

In some embodiments of the invention, the surgical table can be moved. The movement of the surgical table can translate into a comparable movement of the patient and/or the surgical site in x, y, and/or z direction. When the magnitude and direction of the table movement is known, it can be used to move the common coordinate system by a corresponding amount or direction for matching or superimposing the data and/or images displayed by the OHMD and the data and/or images displayed by the standalone or separate display monitor. For example, if the OHMD displays live data of the patient, e.g. captured through an image and/or video capture system integrated into, attached to or separate from the OHMD, and/or virtual data of the patient and/or virtual data of the patient superimposed onto live data of the patient and the standalone or separate computer or display monitor displays a pre-operative imaging study of the patient, the surgical table and the patient can be moved and the display of the live or virtual data by the OHMD can be moved by a corresponding amount, thereby maintaining registration including registration to the data displayed on the standalone or separate computer or display monitor.

In some embodiments of the invention, the data and/or images displayed by the OHMD and the data and/or images displayed by the standalone or separate computer or display monitor can be cross-registered and, for example, moved into a shared or common coordinate system with use of an image and/or video capture system integrated into, attached to, or separate from the OHMD, capturing the data displayed by the standalone or separate computer or display monitor. For example, the standalone or separate computer or display monitor can display data from a physical-time intra-operative imaging study of the patient, including, for example, imaging during movement of the patient or surgical table or both. Standard image processing techniques can, for example, recognize anatomic landmarks or features on the data or images displayed on the standalone or separate computer or display monitor and match these with the corresponding anatomic landmarks or features in the data and/or images available for display by the OHMD. The OHMD can then display the corresponding data and/or images, optionally superimposing the data based on landmark matching. The landmark matching can, for example, occur by moving and/or translating the data or images available for display by the OHMD by an amount that will superimpose or match in a common coordinate system corresponding anatomic landmarks and/or features.

In some embodiments, the same process can be applied without using the image and/or video capture system by directly comparing images acquired with the physical-time intra-operative imaging system with data and/or images available for display by the OHMD. Standard image processing techniques can, for example, recognize anatomic landmarks or features on the data or images acquired by the physical-time imaging system and match these with the corresponding anatomic landmarks or features in the data and/or images available for display by the OHMD. The OHMD can then display the corresponding data and/or images, optionally superimposing the data based on landmark matching. The landmark matching can, for example, occur by moving and/or translating the data or images available for display by the OHMD by an amount that will superimpose or match in a common coordinate system corresponding anatomic landmarks and/or features.

In the foregoing embodiments, the data and/or images displayed by the OHMD can be matched to the data displayed by the standalone or separate computer or display monitor, e.g. by identifying common coordinates and superimposing them and/or by defining a common coordinate system. Alternatively, the data and/or images displayed by the standalone or separate computer or display monitor can be matched to the data displayed by the OHMD, e.g. by identifying common coordinates and superimposing them and/or by defining a common coordinate system. When the data and/or images displayed by the OHMD are superimposed with the data and/or images displayed by the standalone or separate display monitor, the data and/or images displayed by the OHMD and the data and/or images displayed by the standalone or separate display monitor can be displayed with the same magnification in order to optimize the superimposition or matching.

Matching of images displayed by the OHMD and a standalone or separate computer or display monitor can also be performed by combining coordinate based matching, e.g. using the same coordinate system for both displays, and landmark based matching using any of the foregoing techniques. Someone skilled in the art will readily recognize other means of coordinate matching and landmark matching.

In some embodiments of the invention, the magnification of the items displayed by the OHMD can be adjusted so that it is reflective of, corresponds to, is smaller or larger than the magnification used by the standalone or separate computer or display monitor. Alternatively, the standalone or separate computer or display monitor can have one or more markers, e.g. one or more LEDs, that an image and/or video capture system, e.g. integrated into, attached to or separate from the OHMD, can detect which, in turn, can then trigger the adjustment of the magnification of the items displayed by the OHMD. In some embodiments, an image and/or video capture system integrated into, attached to or separate from the OHMD can visualize the size and shape (round, oval, ellipsoid, rectangular, square) of the standalone or separate computer or display monitor; using standard image processing techniques and geometry, the size and shape can then be used to derive the distance and angle of the OHMD relative to the standalone or separate computer or display monitor. If more than one camera is used, additional parallax information (difference in size and/or shape of the standalone or separate computer or display monitor) can be used to further estimate or improve the estimation of the distance or angle of the OHMD to the standalone or separate computer or display monitor. The resultant estimation of the distance and/or angle of the OHMD display to the standalone or separate computer or display monitor can then optionally be used to match the magnification of the data displayed by the standalone or separate computer or display monitor or to display at a higher or lower magnification than the data display by the standalone or separate computer or display monitor.

Similarly, the OHMD can detect, e.g. automatically, if the surgeon or operator is not looking at the standalone or separate computer or display monitor, for example, with use of an image and/or video capture system integrated into, attached to or separate from the OHMD. The image and/or video capture system can, for example, detect that the outline of the standalone or separate computer or display monitor (e.g. round, square, rectangular) is not present in the captured image data and the software can the automatically adjust the magnification of the items displayed by the OHMD so that it is reflective of or corresponds to the distance of the OHMD or the surgeon's eyes to the patient's surgical site, or is smaller or larger than that. Alternatively, a standalone or separate computer or display monitor can have one or more markers, e.g. one or more LEDs or optical markers, that the image and/or video capture system can detect; in this case, when the image captures system notices that the one or more LEDs or optical markers are not included in the image capture data, the software can then automatically adjust the magnification of the items displayed by the OHMD so that it is reflective of or corresponds to the distance of the OHMD or the surgeon's eyes to the patient's surgical site, or is smaller or larger than that. Similarly, markers or LEDs placed on the patient's surgical site can be detected by the OHMD including an image and/or video capture system integrated into, attached to or separate from the OHMD thereby triggering an adjustment in magnification so that it is reflective of, corresponds to the distance of the OHMD or the surgeon's eyes to the patient's surgical site, or is smaller or larger than that when the surgeon or operator is looking at the patient's surgical site.

In some embodiments of the invention, the OHMD can be used to display data and/or images instead of a standalone or separate computer or display monitor. Optionally, the OHMD can replace the standalone or separate computer or display monitor. In some embodiments, the OHMD can display the live data from the patient's surgical site and project them for the surgeon and superimpose them with virtual data. The OHMD can also display one or more aspects or components of the virtual surgical plan, e.g. projected paths for one or more surgical instruments, or it can display one or more virtual implants or implant components. In this embodiment, the OHMD can optionally match the magnification of the one or more projected paths, and/or one or more surgical instruments and/or one or more virtual implants or implant components relative to the magnification of the live data from the patient. The OHMD can also apply a larger or smaller magnification and/or size than the magnification of the live data from the patient for the one or more projected paths and/or virtual surgical instruments, and/or one or more virtual implants or implant components. The live data of the patient can be seen through the transparent display of the OHMD. Alternatively, the display can be partially or completely opaque and the live data can be capture through an image and/or video capture system integrated into, attached to or separate from the OHMD and then subsequently be displayed by the OHMD display.

In some embodiments of the invention, for example when the OHMD is the primary display unit, the OHMD can be non-transparent to light or minimally transparent to light reflected from the patient's surgical field and can display, for example, live (electronic) images collected by the image and/or video capture system and, optionally, it can display, in addition, aspects or components of the virtual surgical plan, e.g. one or more projected paths for one or more physical surgical instruments, probes, pointers, and/or one or more virtual instruments and/or one or more virtual implants or implant components (optionally with various chosen matching or non-matching magnifications). In this setting, the OHMD can also display electronic images of the physical surgical instruments and or devices and their respective movements, for example captured with an image and/or video capture system integrated into, attached to, or separate from the OHMD (with various chosen matching or non-matching magnifications).

The OHMD can be permanently non-transparent to light or minimally transparent to light reflected from the patient's surgical field. Alternatively, the degree of transparency can be variable, for example with use of one or more optical filters, e.g. polarizing light filters, in front of or integrated into the OHMD or electronic, e.g. LCD, or optical filters in front or integrated into the OHMD, or via intensity adjustments. The OR theater can optionally use light sources, e.g. polarized or filtered light that will support modulation or aid with adjustments of the transparency of the OHMD to light reflected from the patient's surgical field.

Magnified Displays

Magnified displays of the following structures and/or devices can be shown with an OHMD for example for one or more of the following, simultaneously or non-simultaneously:
Physical anatomy (e.g. using intra-operative imaging with optional magnification or demagnification)
Static
Dynamic, e.g. with functional or time element or dimension
Virtual anatomy, e.g. from pre-operative imaging study
Aspects or components of a virtual surgical plan, e.g. a predetermined start point, predetermined start position, predetermined start orientation or alignment, predetermined intermediate point(s), predetermined intermediate position(s), predetermined intermediate orientation or alignment, predetermined end point, predetermined end position, predetermined end orientation or alignment, predetermined path, predetermined plane, predetermined cut plane, predetermined contour or outline or cross-section or surface features or shape or projection, predetermined depth marker or depth gauge, predetermined angle or orientation or rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, non-visualized portions for one or more devices or implants or implant components or surgical instruments or surgical tools, and/or one or more of a predetermined tissue change or alteration and/or one or more of a predetermined position and/or orientation of the virtual surgical tool, virtual surgical instrument including virtual surgical guide or cut block, virtual trial implant, virtual implant component, implant or device
Virtual surgical instrument(s)
Virtual implant(s) or implant component(s)

In some embodiments of the invention, the OHMD display can display live data of the patient captured through an image and/or video capture system integrated into, attached to or separate from the OHMD with higher magnification than the live data seen through transparent portions of the OHMD by the user's or surgeon's eye. Thus, the live data of the patient captured through an image and/or video capture system integrated into, attached to or separate from the OHMD can be displayed in a magnified manner for a given distance of the OHMD display to the surgical field. This has the benefit that select structures can be seen with greater detail, for example offering a low power microscopic, magnified view of portions or all of the surgical field. The distance of the OHMD to the surgical field can be determined using techniques described in the specification, e.g. optical markers, navigation markers including infrared markers, retroreflective markers, RF markers, IMUs, LEDs and any other technique known in the art.

The magnified display of live data can be performed while partially or completely blending out live data seen through the OHMD, e.g. with the OHMD turned partially or completely opaque to light emitted from the surgical field and primarily or only data displayed captured through the image and/or video capture system. The magnified display of live data captured through the image and/or video capture system can be superimposed on live data seen through one or more partially or completely transparent portions of the OHMD. In this example, the magnified display of the live data can be a portion of the surgical field seen through the OHMD.

Optionally, a declining gradient of magnification can be applied to the live data so that the magnified live data can blend in seamlessly or near seamlessly with the non-magnified live data, e.g. the live data seen through one or more partially or completely transparent portions of the OHMD.

The magnification of a portion or all of the live data captured through an image and/or video capture system can be at preset levels, e.g. 1.5×, 2.0×, 3.0×, 4.0×, or 5.0× or any The magnified display of virtual data can be performed while partially or completely blending out live data seen through the OHMD, e.g. with the OHMD turned partially or completely opaque to light emitted from the surgical field and primarily or only virtual data displayed. The magnified display of virtual data captured through the image and/or video capture system can be superimposed on live data seen through one or more partially or completely transparent portions of the OHMD. In this example, the magnified display of the virtual data can be a portion of the surgical field seen through the OHMD.

Optionally, a declining gradient of magnification can be applied to the virtual data so that the magnified virtual data can blend in seamlessly or near seamlessly with the non-magnified live data, e.g. the live data seen through one or more partially or completely transparent portions of the OHMD.

The magnification of a portion or all of the virtual data can be at preset levels, e.g. 1.5×, 2.0×, 3.0×, 4.0×, or 5.0× or any other magnification level. The magnification can be continuous, e.g. on a sliding scale. The magnification can be selected by the user and/or surgeon, for example using voice commands, eye commands or using a virtual keyboard interface displayed by the OHMD.

Both portions or all of live data and virtual data can be displayed using magnification or no magnification. Non-limiting examples of possible magnification combinations between live data and virtual data are provided below.

TABLE 10

Exemplary, non-limiting combinations of magnifications of live data and/or virtual data.

| | Live data, e.g. as captured by image capture system and displayed by OHMD | | | | |
|---|---|---|---|---|---|
| Virtual data | Original size | Portions magnified | All magnified | Portions minified | All minified |
| Original size | X | X | X | X | X |
| Portions magnified | X | X | X | X | X |
| All magnified | X | X | X | X | X |
| Portions minified | X | X | X | X | X |
| All minified | X | X | X | X | X |

X denotes type of magnification mode combinations used or possible other magnification level. The magnification can be continuous, e.g. on a sliding scale. The magnification can be selected by the user and/or surgeon, for example using voice commands, eye commands or using a virtual keyboard interface displayed by the OHMD.

Virtual data can optionally be displayed with the same magnification as the live data. Optionally, virtual data can be displayed with no magnification or lesser or greater magnification than live data.

In some embodiments of the invention, the OHMD display can display virtual data of the patient with higher magnification than the live data seen through transparent portions of the OHMD by the user's or surgeon's eye. Thus, the virtual data of the patient can be displayed in a magnified manner for a given distance of the OHMD display to the surgical field. This has the benefit that select structures or aspects of components of a virtual surgical plan can be seen with greater detail, for example offering a low power microscopic, magnified view of portions or all of the virtual data. The distance of the OHMD to the surgical field can be determined using techniques described in the specification, e.g. optical markers, navigation markers including infrared markers, retroreflective markers, RF markers, IMUs, LEDs and any other technique known in the art.

The magnification of live data and virtual data can be the same. The magnification of live data and virtual data can be different. Virtual data can be partially, e.g. affecting only part of the displayed virtual data, or all magnified. Live data can be partially, e.g. affecting only part of the displayed live data, or all magnified. Virtual data can be magnified while live data are not magnified. Live data can be magnified while virtual data are not magnified. Any combination is possible.

The term magnification includes also displays wherein the live data or the virtual data are displayed in a format or with a magnification that is smaller than live data seen through transparent portions of the OHMD for a given distance.

The magnification can be applied around a central point, e.g. an anchor point, an anatomic landmark, a pin entry into a bone, a screw head, or central axis of the field of view of the OHMD, a pin axis or a screw axis. When a central point is used, the coordinates of the central point in the live data of the patient as seen by the surgeon's right eye through the OHMD unit will be the same as the view coordinates of the central point in the virtual data of the patient seen by the surgeon's right eye projected by the display of the OHMD unit; the coordinates of the central point in the live data of the patient as seen by the surgeon's left eye through the OHMD unit will be the same as the view coordinates of the central point in the virtual data of the patient seen by the surgeon's left eye projected by the display of the OHMD unit. When a central axis is used, the coordinates of the central axis in the live data of the patient as seen by the surgeon's right eye through the OHMD unit will be the same as the view coordinates of the central axis in the virtual data of the patient seen by the surgeon's right eye projected by the display of the OHMD unit; the coordinates of the central axis in the live data of the patient as seen by the surgeon's left eye through the OHMD unit will be the same as the view coordinates of the central axis in the virtual data of the patient seen by the surgeon's left eye projected by the display of the OHMD unit. When stereoscopic projection is used with the left and right displays of the OHMD unit, the view coordinates for the left display and the right display of the OHMD unit will be different for the left eye and the right eye; the difference in view coordinates is a reflection of the parallax. For example, when the user or surgeon elects to turn on magnification of live and/or virtual data, the magnification can be applied around the central point of the last unmagnified field of view. The system including its software can optionally apply the magnification automatically around the central point of the last field of view. Alternatively, the user and/or surgeon can use a different central point or central axis as the center around which the live and/or virtual data are being magnified. The central point or central axis can, for example, coincide with the center of a pedicle, when spinal surgery is contemplated. The central axis can coincide with an acetabular or femoral axis, e.g. an anteversion axis. The central axis can, for example, be a predetermined path. The central point, can, for example, be an endpoint. The central point or central axis can, for example, be the center of an acetabulum when hip replacement or other hip surgery is contemplated. The central point or central axis can, for example, be the center of a glenoid when shoulder surgery is contemplated. The central point or central axis for magnification can be pre-selected for various anatomic sites or surgical fields or surgeries contemplated, e.g. hip replacement, knee replacement surgery, knee arthroscopy or spinal fusion. Using, for example, one or more image and/or video capture systems integrated into, attached to or separate from the OHMD, or using intra-operative imaging, one or more anatomic structures can optionally be identified using standard image processing techniques (e.g. the acetabulum and its center) and the central point or central axis for any magnified views can optionally be set or defined automatically.

View Patient/View Computer Monitor/Screen

In some embodiments, the magnification of the OHMD display can be matched with the magnification of a computer monitor, e.g. in the OR, so that corresponding tissues shown by the OHMD and/or the computer monitor are displayed using the same magnification and can, for example, be substantially aligned or superimposed between the OHMD and the computer monitor display.

Displaying Surgical Instruments and/or Medical Devices/Implantables

In some embodiments of the invention, surgical instruments or medical devices or implantables can be displayed virtually with the live data of the patient. The virtual data surgical instrument or virtual implantable can be shown by the OHMD superimposed onto the live data of the patient including the live data surgical instrument.

The OHMD can show the virtual surgical instrument or the virtual implantable indicating the desired orientation or direction or placement of the virtual surgical instrument or the virtual implantable, for example using a virtual surgical plan. Optionally, the OHMD can display directional markers such as an intended path derived from a surgical plan to help guide the surgeon direct the physical surgical instrument or the physical implantable.

The physical surgical instrument or physical implantable can be scanned preoperatively to derive its shape and/or dimensions for subsequent display of a derived shape or dimension of a virtual representation of the surgical instrument or the implantable by the OHMD. Alternatively, a CAD file or 3D file of the surgical instrument or the implantable can be used. Preoperative scanning of the surgical instrument or the implantable can be performed using any technique known in the art. Scanning of the surgical instrument or the implantable can be performed by the OHMD, for example using a built in image capture device. Scanning of the surgical instrument or the implantable can be performed by a separate image capture device.

In some embodiments, scanning of the surgical instrument or the implantable can occur in two or more dimensions. The more dimensions are used typically the more accurate the resultant virtual representation of the surgical instrument or the implantable.

If an image capture device is used, e.g. one attached to or integrated into the OHMD or coupled to or separate from the OHMD, the surgical instrument or the implantable can be scanned in one, two or more projections, positions or orientation, e.g. by moving the OHMD or the surgical instrument or implantable into different positions or orientations. In some embodiments, the surgical instrument or the implantable can be placed on a tray or fixture for this purpose, which allows to move the surgical instrument or the implantable into different positions and, optionally, to rotate the surgical instrument or the implantable. In some embodiments, the distance between the surgical instrument or the implantable and the image capture device, including an image capture device attached to or integrated into the OHMD or coupled to or separate from the OHMD, is fixed, while the surgical instrument or the implantable are being scanned.

Scans of the physical surgical instrument or implantable can then be used to derive a virtual 2D or 3D representation of the surgical instrument or the implantable.

By scanning the surgical instrument or the implantable intraoperatively, the surgeon has great flexibility in using different surgical instruments or implantables which he can change and modify and, optionally, integrate into his physical or virtual surgical plan.

The surgeon can optionally store each surgical instrument or implantable that has been scanned in this manner in a virtual library of surgical instruments or implantables. The virtual surgical instruments or implantables stored in this manner can be named and stored for future use in subsequent surgical procedures in other patients. By storing the virtual surgical instruments or implantables the need for repeat scans of the same surgical instrument or same type or shape of implantable is obviated.

In some embodiments of the invention, the surgeon can use the virtual data of the surgical instrument or implantables that were previously generated in a new surgical plan for another, new patient. The surgeon can select a desired virtual surgical instrument or implantable from the virtual library and use the virtual surgical instrument or the virtual implantable in his or her virtual surgical plan.

When the surgeon performs the physical surgery and the OHMD displays optionally the virtual surgical instrument or implantable, optionally superimposed onto or displayed near the physical surgical instrument or implantable, the software can optionally compare the size and shape of the physical surgical instrument or implantable with that of the previously selected virtual surgical instrument or implantable. Alternatively, the surgeon can visually compare the size and/or shape of the virtual and the physical surgical instrument or implantable.

If a size and/or shape mismatch is detected, the software can send an alert or alarm to the surgeon, e.g. visual or audible, that indicates a mismatch. A mismatch can indicate to the surgeon that the accuracy of registration of virtual data and live data has been compromised and that re-registration may be required. A mismatch can also indicate to the surgeon that the wrong physical surgical instrument or implantable has been selected in comparison to the previously identified virtual surgical instrument or implantable. In this case, the surgeon can check the virtual surgical plan or the physical surgical plan and modify either or both, for example by selecting a different size or shape virtual or live surgical instrument or implantable.

Stereoscopic and Non-Stereoscopic 3D Display of Virtual Data of the Patient with Superimposition on Live Data of the Patient In some embodiments of the invention, the OHMD can display a virtual 2D or 3D image of the patient's normal or diseased tissue or an organ or a surgical site or target tissue with a view angle or a perspective or projection that is different for the display for the left eye compared to the display for the right eye resulting in a stereoscopic projection of the anatomy or the pathologic tissue. The virtual data of the patient is thus superimposed on the live data of the patient, e.g. the surgical site, for the left and right eye of the surgeon, respectively, using both the left and the right view angle for the surgeon. This means that two separate views are rendered from the virtual 2D or 3D data sets, one for the left eye and one for the right eye. Multidimensional views exceeding three dimensions generated for the left eye and the right eye are possible. For example, in addition to the virtual anatomy of the patient vascular flow or joint motion can be displayed separately for the left eye and the right eye. The difference in perspective between the left eye and the right eye projection of virtual data or parallax can be selected or programmed so that it will change, for example, with the distance of the OHMD, the surgeon's head or the surgeon's eye in relationship to the target site, surgical site or target tissue. The distance between the surgeon's or operator's eyes can also be taken into account. In some embodiments, the difference in perspective or parallax will be selected or programmed so that a 3D effect is generated in a stereoscopic 3D manner or effect. The difference in perspective or parallax can change depending on any changes in the distance of the OHMD, the surgeon's or operator's head or the surgeon's or operator's eye in relationship to the target site, surgical site or target tissue. For example, as the surgeon or operator moves away from the target site, surgical site or target tissue, the difference in perspective or parallax can decrease. As the surgeon or operator moves towards the target site, surgical site or target tissue, the difference in perspective or parallax can increase. The decrease or increase can be linear, non-linear, exponential or algorithmic. Any other mathematical function is possible. In some embodiments, the difference in perspective or parallax will change similar to the change experienced by the human eye as the surgeon or operator moves towards or away from a target.

The distance of the OHMD, the surgeon's or operator's head or the surgeon's or operator's eye in relationship to the target site, surgical site or target tissue can be measured via image capture, anatomic landmark embodiments, image capture used in conjunction with calibration or registration phantoms, surgical navigation or any of the other embodiments described in this specification and or spatial mapping. The distance and any changes in distance of the OHMD, the surgeon's or operator's head or the surgeon's or operator's eye in relationship to the target site, surgical site or target tissue can be used to change the difference in perspective views or parallax in views for the left eye and the right eye.

FIGS. 16A and 16B are flow charts summarizing model generation, registration and view projection for one or more OHMDs, e.g. by a primary surgeon, second surgeon, surgical assistant nurse, or others. Pre-operative, intra-operative or post-operative images of the patient can be acquired 240. The image data can optionally be segmented 241. 3D reconstructions of the patient's anatomy or pathology including multiple different tissues, e.g. using different colors or shading, can be generated 242. Virtual 3D models of surgical instruments and devices components can be generated which can include their predetermined position, location, rotation, orientation, alignment and/or direction 243. The virtual 3D models can be registered, for example in relationship to the OHMD and the patient 244. The virtual 3D models can be registered relative to the live patient data 245. Optionally, adjustments can be made for different view perspectives, parallax, skin, skin movement and other tissue specific issues 246. Different perspective views can be generated for the user's left eye and right eye to facilitate a stereoscopic viewing experience, e.g. like an electronic hologram, of the virtual models of subsurface or hidden anatomic or pathologic tissues 247 and the virtual 3D models of tools, instruments, implants and devices 248. Virtual patient data 249 and virtual 3D models of tools, instruments, implants and devices 250 can be displayed in the OHMD, optionally with different view perspectives adjusted for the left and the right eye of the user 251 and 252. Left eye and right eye offsets or parallax can optionally be adjusted based on the distance from the OHMD, surgeon head or surgeon eyes to the surgical site using, for example, depth sensors or spatial mapping or other registration techniques and also based on interocular distance 253. Polarization or color techniques for stereoscopic views 254 can be combined with electronic holograms such as those provided by the Microsoft Hololens.

In an alternative description in FIG. 16B, multiple 3D models 260, 261, 262 can be generated, e.g. one for subsurface anatomic or pathologic structures of the patient, one for virtual surgical tools or instruments and one for virtual surgical implant components. These can be registered, e.g. in a common coordinate system or multiple coordinate systems using coordinate transfers, also with the OHMD 263. Using shared coordinates for the different virtual 3D models 260, 261, 262 multiple viewers using multiple OHMDs can share a 3D World 264 with projection or display of one or more of the models onto the live data of the patient 265. The display can be generated separately for the left eye of each user using the user's left eye coordinates 266 and the right eye of each user using the user's right eye coordinates 267.

Stereoscopic views or different perspective views or views with a parallax for the left eye and the right eye can be generated for multiple virtual data sets or data volumes of the patient. Any of the dimensions listed in Table 4 or virtual structures, tissues or data mentioned in the application can be displayed separately for the left eye and the right eye using stereoscopic views or different perspective views or views with a parallax, simultaneously, non-simultaneously, or sequentially. In addition, any of the virtual data in Table 11 can be displayed using stereoscopic views or different perspective views or views with a parallax for the left eye and the right eye. Multiple of the data listed in Table 11 can be displayed simultaneously, non-simultaneously or sequentially, for example also with the live data or images of the patient seen through the OHMD, stereoscopically or non-stereoscopically:

TABLE 11: Exemplary, non-limiting list of virtual data of the patient, surgical sites and alterations to surgical sites, surgical instruments and surgical steps or procedures, and medical devices that can be displayed, optionally simultaneously, using stereoscopic views or different perspective views or views with a parallax for the left eye and the right eye or non-stereoscopically. Virtual data are typically displayed in conjunction with viewing or displaying live data of the patient. Virtual data can be displayed stereoscopically or non-stereoscopically or combinations thereof if multiple virtual data sets are displayed in the OHMD.

TABLE 11A: Exemplary virtual data of the patient that can be displayed stereoscopically or non-stereoscopically
    Native anatomy, e.g.
        Gyri of the brain
        Venous sinus of the brain
        Arterial structures of the brain
        Brain lesion
        Brain tumor
        Features of the face
        Features of an ear
        Liver margin
        Liver lobes
        Spleen margin
        Kidney, renal outline
        One or more osteophytes
        Bone spurs
        Bony anatomy
        Bony deformity
        Acetabular rim of a hip
        Tri-radiate cartilage region
        Fovea capitis
        Anterior superior iliac spine
        Anterior inferior iliac spine
        Symphysis pubis
        Femoral head of a hip
        Femoral neck
        Greater trochanter
        Lesser trochanter
        Condyles of a knee
        Trochlea of a knee
        Patella of a knee
        Tibial plateau of a knee
        Medial tibial plateau of a knee
        Lateral tibial plateau of a knee
        Anterior cruciate ligament of a knee
        Posterior cruciate ligament of a knee
        Distal tibia of an ankle joint
        Distal fibula of an ankle joint
        Talus of an ankle joint
        Any ligament or ligamentous structure of a patient
        Glenoid rim of a shoulder
        Glenoid of a shoulder
        Humeral head or neck of a shoulder
        Facet joint of a spine
        Spinous process
        Pedicle of a spine
        Vertebral endplate
        Intervertebral disk
        Herniated disk
        Any tumor affecting the human body TABLE 11B: Exemplary virtual surgical sites and alterations to a surgical site that can be displayed stereoscopically or non-stereoscopically
    Alterations planned to surgical site, e.g.
        Tissue removal
        Removal of normal tissue
        Removal of diseased tissue
        Removal of neoplastic tissue
        Bone cuts
        Reaming (e.g. in proximal femur)
        Broaching (e.g. in proximal femur)
        Impacting (e.g. in a femur or a tibia)
        Milling
        Drilling
        Tissue transplants
        Organ transplants
        Partial or complete resections, e.g. of organs
        Placement of a medical device
        Placement of a stent TABLE 11C: Exemplary virtual surgical instruments and surgical steps or procedures that can be displayed stereoscopically or non-stereoscopically
    Tissue cutters,
        e.g. scalpels, blades, drills, saws, burrs, reamers, broaches
    Tissue ablation devices
        e.g. heat or cryotherapy
    Robotic arms
    Instruments attached to robotic arms
    Endoscopy devices
    Endoscopic cameras
    Endoscopic cutting devices
    Endoscopic ablation devices
    A predetermined surgical path or predetermined placement or position, location, rotation, orientation, alignment, or direction of one surgical instrument
    A predetermined surgical path or predetermined placement or position, location, rotation, orientation, alignment, or direction of more than one surgical instrument
    A predetermined surgical path or predetermined placement or position, location, rotation, orientation, alignment, or direction of more than one surgical instrument used simultaneously
    A predetermined surgical path or predetermined placement or position, location, rotation, orientation, alignment, or direction of more than one surgical instrument used non-simultaneously
    A predetermined surgical path or predetermined placement or position, location, rotation, orientation, alignment, or direction of more than one surgical instrument used in succession
    A predetermined surgical path or predetermined placement or position, location, rotation, orientation, alignment, or direction of more than one surgical instrument not used in succession
    A predetermined surgical path or predetermined placement or position, location, rotation, orientation, alignment, or direction of more than one surgical instrument used on the same side of a joint A predetermined surgical path or predetermined placement or position, location, rotation, orientation, alignment, or direction of more than one surgical instrument used on one or more opposing sides of a joint A predetermined surgical path or predetermined placement or position, location, rotation, orientation, alignment, or direction of more than one surgical instrument used on the same vertebral levels A predetermined surgical path or predetermined placement or position, location, rotation, orientation, alignment, or direction of more than one surgical instrument used on adjacent vertebral levels A predetermined surgical path or predetermined placement or position, location, rotation, orientation, alignment, or direction of more than one surgical instrument used on non-adjacent vertebral levels A predetermined surgical path or predetermined placement or position, location, rotation, orientation, alignment, or direction of one surgical instrument used on a vertebral endplate A predetermined surgical path or predetermined placement or position, location, rotation, orientation, alignment, or direction of more than one surgical instrument used on a superior vertebral endplate and on an adjacent, inferior vertebral endplate A predetermined surgical path or predetermined placement or position, location, rotation, orientation, alignment, or direction of an instrument used for disk removal TABLE 11D: Exemplary virtual medical devices and implants that can be displayed stereoscopically or non-stereoscopically Hip replacement components
  Acetabular cup including predetermined placement or position, location, rotation, orientation, alignment, anteversion, retroversion, inclination, offset, location in relationship to the safe zone
  Acetabular liner including predetermined placement or position, location, rotation, orientation, alignment, anteversion, retroversion, inclination, offset, location in relationship to the safe zone
  Femoral head including predetermined placement or position, location, rotation, orientation, alignment, anteversion, retroversion, inclination, offset, location in relationship to the safe zone
  Femoral neck including predetermined placement or position, location, rotation, orientation, alignment, anteversion, retroversion, inclination, offset, location in relationship to the safe zone (optionally with modular necks)
  Femoral stem including predetermined placement or position, location, rotation, orientation, alignment, anteversion, retroversion, inclination, offset, location in relationship to the femoral neck cut, the calcar, the greater or the lesser trochanter, the acetabulum Knee replacement components
  Femoral component including predetermined placement or position, location, internal or external rotation, orientation, alignment, flexion, extension, position in relationship to anterior cortex, or mechanical axis or other axis alignment, all optionally through the range of motion
  Tibial component including predetermined placement or position, location, internal or external rotation, orientation, alignment, flexion, extension, slope, position in relationship to cortical rim, or mechanical axis or other axis alignment, all optionally through the range of motion
  Polyethylene or other inserts including predetermined placement or position, location, internal or external rotation, orientation, alignment, flexion, extension, slope, position in relationship to cortical rim, or mechanical axis or other axis alignment, all optionally through the range of motion
  Patellar component including predetermined placement or position, location, internal or external rotation, orientation, alignment, position in relationship to patellar cortical rim, position in relationship to trochlea, optionally in flexion and/or extension and/or through the range of motion, position in relationship to mechanical axis, trochlear axis, trochlear groove, epicondylar axis or other axis alignment
  Trial femoral component including predetermined placement or position, location, internal or external rotation, orientation, alignment, flexion, extension, position in relationship to anterior cortex, or mechanical axis or other axis alignment, all optionally through the range of motion
  Trial tibial component including predetermined placement or position, location, internal or external rotation, orientation, alignment, flexion, extension, slope, position in relationship to cortical rim, or mechanical axis or other axis alignment, all optionally through the range of motion
  Trial inserts including predetermined placement or position, location, internal or external rotation, orientation, alignment, flexion, extension, slope, position in relationship to cortical rim, or mechanical axis or other axis alignment, all optionally through the range of motion
  Trial patellar component including predetermined placement or position, location, internal or external rotation, orientation, alignment, position in relationship to patellar cortical rim, position in relationship to trochlea, optionally in flexion and/or extension and/or through the range of motion, position in relationship to mechanical axis, trochlear axis, trochlear groove, epicondylar axis or other axis alignment Spinal screws including predetermined placement or position, location, rotation, orientation, alignment, location in relationship to the pedicle, the cortical bone of the pedicle, the endosteal bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, the trabecular bone of the vertebral body, any fracture components or fragments, e.g. involving a pedicle, a facet joint or a vertebral body Pedicle screws including predetermined placement or position, location, rotation, orientation, alignment, location in relationship to the pedicle, the cortical bone of the pedicle, the endosteal bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, the trabecular bone of the vertebral body, any fracture components or fragments, e.g. involving a pedicle, a facet joint or a vertebral body Spinal rods including predetermined placement or position, location, rotation, orientation, alignment, location in relationship to one or more pedicles, the cortical bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, any fracture components or fragments, e.g. involving a pedicle, a facet joint or a vertebral body, a scoliotic deformity, and predetermined correction for a scoliotic deformity Artificial spinal disks including predetermined placement or position, location, rotation, orientation, alignment, location in relationship to one or more pedicles, the cortical bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, any fracture components or fragments, e.g. involving a pedicle, a facet joint or a vertebral body, a scoliotic deformity, and predetermined correction for a scoliotic deformity Metal screws, pins, plates, rods for trauma including predetermined placement or position, location, rotation, orientation, alignment, location in relationship to one or more pedicles, the cortical bone of the pedicle, the posterior cortical bone of the vertebral body, the anterior cortical bone of the vertebral body, the lateral cortical bone of the vertebral body, the superior endplate, the inferior endplate, the intervertebral disk, the vertebral body, any fracture components or fragments, e.g. involving a pedicle, a facet joint or a vertebral body, a long bone, a joint, an articular surface, and any predetermined correction fora fracture or fracture deformity Intramedullary nails including predetermined placement or position, location, rotation, orientation, alignment, location in relationship to one or more fracture components or fragments, e.g. a long bone, a joint, an articular surface, and any predetermined correction for a fracture or fracture deformity Vascular stents
  Coronary stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
  Carotid stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
  Aortic stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves
  Femoral stents including predetermined placement or position, location, rotation, orientation, alignment, for example in relationship to an area of stenosis, an area of vascular occlusion, a thrombus, a clot, a plaque, an ostium, two or more ostia, an aneurysm, a dissection, an intimal flap, adjacent vessels, adjacent nerves Cochlear implants including predetermined placement or position, location, rotation, orientation, alignment, for example in relationship to osseous structures, neural structures, auditory structures, the labyrinth Retinal implants including predetermined placement or position, location, rotation, orientation, alignment, for example in relationship to osseous structures, neural structures, vascular structures Neural implants including predetermined placement or position, location, rotation, orientation, alignment, for example in relationship to neural structures, vascular structures, osseous structures Neuroprosthetics including predetermined placement or position, location, rotation, orientation, alignment, for example in relationship to neural structures, vascular structures, osseous structures Implants for deep brain stimulation, e.g. for treatment of Parkinson's disease including predetermined placement or position, location, rotation, orientation, alignment, for example in relationship to neural structures, vascular structures, osseous structures The list in Table 11 is only exemplary and is not meant to be limiting of the invention. Any of the exemplary virtual data of the patient listed in Table 11A, exemplary virtual surgical sites and alterations to a surgical site listed in Table 11B, exemplary virtual surgical instruments and surgical steps or procedures listed in Table 11C, and exemplary virtual medical devices and implants listed in Table 11D can be displayed by the OHMD in two, three or more dimensions (e.g. as described also in Table 4), using stereoscopic as well as non-stereoscopic projections or view. Thus, the invention is not limited to stereoscopic displays and/or 2D displays and/or 3D displays. Any combination of virtual displays is possible, e.g. 3D stereoscopic patient anatomy or surgical site with 2D surgical instrument displays and/or 2D medical device displays, or 3D patient anatomy, with 3D non-stereoscopic surgical instrument display and/or 3D stereoscopic medical device display.

Aligning or Superimposing Physical Surgical Instruments with Virtual Surgical Instruments With virtual displays of the surgical instruments in the OHMD, the surgical instruments displayed in the virtual data can be representative of the physical surgical instruments used in the live patient and can have the same projected dimensions and shape as the physical surgical instruments. As indicated in Table 11, the virtual view of the virtual surgical instrument or instruments can, for example, indicate the predetermined position, location, rotation, orientation, alignment, direction of a surgical instrument. When the physical surgical instrument is aligned with and/or superimposed onto the virtual representation of the virtual surgical instrument, the surgical step can optionally be executed or the surgeon can elect to make adjustments to the position, location, rotation, orientation, alignment, direction of a physical surgical instrument relative to the virtual surgical instrument, for example on the basis of a ligament tension or ligament balance, e.g. in flexion or extension. The resultant alteration of the live surgical site induced by the surgical step in the live patient is typically consistent with the virtual surgical plan, when the virtual and physical surgical instruments are superimposed in their respective position, location, rotation, orientation, alignment, or direction.

More than one surgical step can be executed in this manner, e.g. by aligning the physical surgical instruments with the corresponding virtual surgical instruments using stereoscopic or non-stereoscopic displays of virtual surgical instruments. The aligning can be performed in two dimensions, three dimensions, and more than three dimensions. The aligning can be performed with stereoscopic and non-stereoscopic displays. More than one virtual surgical step can be planned utilizing the virtual surgical plan. Two or more virtual surgical steps can be planned. The virtual surgical steps can include the major surgical steps of the intended procedure, they can include optionally sub-steps, or, optionally, the entire procedure. When the physical surgical steps are executed after aligning one or more physical instruments with the virtual instruments in the corresponding surgical steps, each surgical step using the physical instruments is effectively image guided using, optionally, the virtual surgical plan with the operator or the surgeon using the image guidance information, for example from a preoperative scan or imaging study obtained at a time different from the surgical procedure, typically preceding the surgical procedure, and typically with the surgical site in a different object coordinate system at the time of the preoperative imaging when compared to the time of the surgical procedure. The display of the virtual surgical instruments can be stereoscopic or non-stereoscopic.

Thus, by aligning physical surgical instruments seen through the OHMD or displayed by the OHMD with virtual surgical instruments using stereoscopic or non-stereoscopic displays of virtual surgical instruments in the OHMD, it is possible to execute accurately on a surgical plan in the live patient using pre-existing image information and image guidance information, as defined, for example, in a virtual surgical plan. In addition, by aligning physical surgical instruments seen through the OHMD or displayed by the OHMD with virtual surgical instruments using stereoscopic or non-stereoscopic displays of virtual surgical instruments in the OHMD, it is possible to achieve an predetermined position, location, rotation, orientation, alignment, direction of a medical implant including, but not limited to, for example the implants listed in Table 11D.

The OHMD can show the one or more virtual surgical instruments with a continuous surface view, for example, using one color or multiple colors for different features of the instrument. The continuous surface display can include shading based on light sources used in the operating room and/or over the surgical field. The directional orientation of the OR light sources can, for example, be measured using image capture, optionally integrated into, attached to or separate from the OHMD.

The OHMD can show the one or more virtual surgical instruments with an outline view which can be in 2D or in 3D. The outline view can include an outline of the entire virtual surgical instrument, for example in a particular plane or cross-sectional plane. The outline view can optionally only highlight select features of the virtual surgical instrument, e.g. a bone cutting surface or feature or a grip feature or combinations thereof. The OHMD can show two or more outline views, for example extending through or along the surface or the periphery of the virtual surgical instrument along different planes. These planes can be chosen to be different than at a 0 or 180 degree angles to each other. In some embodiments of the invention, the outline views can be orthogonal to each other. In this manner, even though the two or more outline views can be two-dimensional, the OHMD can still provide information to the surgeon or the operator on the intended orientation, position and/or direction of the surgical instrument in three-dimensions by providing two or more outline views with different angular orientations and by providing information on the x, y and z-axis alignment or position or orientation or direction of the surgical instrument. Outline views can help limiting the amount of information displayed by the OHMD, which can help the surgeon maintaining his or her focus on the surgical site, with full visibility of the surgical site. Outline view can help decrease the risk of obscuring important live information from the patient, e.g. a bleeding vessel, by inadvertently superimposing virtual data, e.g. 3D surface data, and obscuring portions of the live anatomy.

By aligning physical surgical instruments seen through the OHMD or displayed by the OHMD with virtual surgical instruments using stereoscopic or non-stereoscopic displays of virtual surgical instruments in the OHMD, it is possible to achieve certain alterations of a surgical site or certain implant placement or implant component placement in live patients that can, for example, determine at least one of a Surgical instrument position
Surgical instrument location
Surgical instrument orientation
Surgical instrument rotation
Surgical instrument alignment
Surgical instrument direction
Depth of advancement of a surgical instrument, e.g. for acetabular or glenoid reaming
Implant position
Implant location
Implant orientation
Implant rotation
Implant alignment
Implant position of two or more implant components in relationship to each other and/or in relationship to the patient
Implant location of two or more implant components in relationship to each other and/or in relationship to the patient
Implant orientation of two or more implant components in relationship to each other and/or in relationship to the patient
Implant rotation of two or more implant components in relationship to each other and/or in relationship to the patient
Implant alignment of two or more implant components in relationship to each other and/or in relationship to the patient
Anatomic or pathologic structures and/or tissue including but not limited to one or more osteophytes or bone spurs or other bony anatomy or deformity or soft-tissue or neoplastic tissue or abnormality can be used for referencing the patient both in the virtual and in the live data and for determining or cross-referencing to the other anatomy the desired instrument or implant component position, location, orientation, rotation or alignment.

Aligning or Superimposing Physical Surgical Instruments or Physical Medical Devices with Virtual Alterations to a Surgical Site The OHMD can display virtual alterations to a surgical site superimposed onto the live surgical site prior to the physical alteration of the live surgical site. The virtual alterations to a surgical can be simulated using a virtual surgical plan. The virtual surgical alterations and/or the virtual surgical plan can be executed or displayed in two, three or more dimensions, optionally with a stereoscopic or non-stereoscopic display.

In some embodiments of the invention, the OHMD can display a virtual alteration to a surgical site. The operator or the surgeon can then align the physical surgical instrument selected to perform the intended alteration to the physical surgical site and align the physical surgical instrument with the virtual alteration of the surgical site. The virtual alteration can, for example, be the removal or shape modification of one or more osteophytes or bone spurs or other bony anatomy or deformity or soft-tissue or neoplastic tissue or abnormality. The operator or surgeon can then advance or move the physical surgical instrument into the direction of or into the physical surgical site, optionally while maintaining alignment of the physical instrument with the virtual alteration of the surgical site. In this manner, the operator or the surgeon can effect the desired change or alteration to the surgical site in the live patient, and the change or alteration achieved in the surgical site of the live patient is typically similar to or aligned with or consistent with the intended virtual change or alteration to the surgical site and, if applicable, the virtual surgical plan.

For example, a surgeon can plan to make a bone cut to a distal femur of a patient. The OHMD can display the virtual bone cut superimposed onto the uncut bone of the live patient. The virtual bone cut and the intended physical bone cut can, for example, remove or correct one or more osteophytes or bone spurs or other bony anatomy or deformity or soft-tissue. The surgeon can then align the saw blade of the physical bone saw with the planar surface of the intended bone cut in the virtual alteration of the bone surface displayed by the OHMD. By advancing the saw blade in the direction of the cut while maintaining alignment between the physical saw blade, e.g. the flat surface of the physical saw blade, and the planar surface of the virtual bone cut, the surgeon can achieve an accurate physical bone cut in the live patient. Alternatively, the surgeon can align a cutting tool or cut block or cut guide to guide a bone saw with the planar surface of the intended bone cut in the virtual alteration of the bone surface displayed by the OHMD; the cutting tool or cut block or cut guide can then optionally be affixed to the tissue and/or bone, for example using one or more pins or screws and the cut can be performed using the cutting tool, cut block or cut guide.

In another example, a surgeon can plan to make a bone cut to a proximal femur of a patient, e.g. for partial or total hip arthroplasty, or to a distal femur or proximal tibia, e.g. for partial or total knee replacement, or to a proximal humerus, e.g. for partial or total shoulder arthroplasty. The OHMD can display the virtual bone cut superimposed onto the uncut bone of the live patient. The surgeon can then align the saw blade of the physical bone saw with the planar surface of the intended bone cut in the virtual alteration of the bone displayed by the OHMD. By advancing the saw blade in the direction of the cut while maintaining alignment between the physical saw blade and the planar surface of the virtual bone cut, the surgeon can achieve an accurate physical bone cut in the live patient. The bone cut can be oriented to achieve a desired component rotation and/or component flexion or extension. The bone cut can be oriented to achieve a desired slope. The same result can be achieved by aligning a cutting tool, cut block, or cut guide with the planar surface of the virtual bone cut, optionally affixing it to the tissue and/or bone, and performing the cut with the bone saw.

In another example, a surgeon can plan to ream or broach a bone, e.g. a proximal femur or a proximal humerus. The OHMD can display the bone after the virtual reaming or broaching procedure showing the intended virtual alteration of the inner bone surface after the reaming or broaching procedure; the display can optionally be superimposed onto the live image of the unaltered physical bone. The surgeon can then align the physical reamer or broach onto the intended virtual alteration and shape change of the bone after the reaming or broaching procedure displayed by the OHMD. By advancing the reamer or broach in the direction of the virtually reamed or broached bone surface while maintaining alignment between the physical reamer or broach and the virtually reamed or broached bone surface, the surgeon can achieve an accurate physical reaming or broaching of the bone in the live patient.

In another example, a surgeon can plan to place a pedicle screw in a pedicle of a patient, e.g. for spinal fusion. The OHMD can display the virtual bone void or space created by a virtual pedicle screw, optionally superimposed onto the unaltered pedicle of the live patient. The surgeon can then align a physical drill or a physical pedicle screw with the virtual bone void or space for the pedicle screw in the virtual alteration of the pedicle displayed by the OHMD. By advancing the physical drill or pedicle screw in the direction of the virtual bone void or space in the pedicle while maintaining alignment between the physical drill or pedicle screw and the virtual bone void or space in the pedicle, the surgeon can achieve accurate placement of the physical drill or pedicle screw in the live patient. The bone void in the pedicle or the position of the pedicle screw can be chosen in the virtual surgical plan so that there is one or more desired minimum distance or a minimum area or volume of bone between the bone void or the pedicle screw and the endosteal bone surface or cortical bone surface of the pedicle, medially, laterally, superiorly, and/or inferiorly.

In another example, a surgeon can plan to place an intervertebral disk replacement in an intervertebral disk space of a patient, e.g. for motion preserving disk replacement. The OHMD can display the virtual alteration required for the placement of the disk replacement, for example with virtual alterations to the superior and/or inferior endplates of the two adjacent vertebral bodies, optionally superimposed onto the endplates of the live patient. The virtual and intended physical alterations can include, for example, the removal of one or more osteophytes or bone spurs or other bony anatomy or deformity or the resection of portions of or all of the endplate(s). The surgeon can then align physical instruments used for altering the vertebral endplates to accept the intervertebral disk replacement with the virtual alteration of the endplates displayed by the OHMD. By advancing the physical surgical instruments in the direction of the virtual alteration of the endplates while optionally maintaining alignment between the physical surgical instrument and the virtual alteration of the endplates, the surgeon can achieve accurate placement of the physical surgical instruments and the physical disk replacement in the live patient.

Thus, by aligning with or directing physical surgical instruments or medical devices towards a display of virtual alterations to a surgical site in the OHMD it is possible to achieve certain alterations of a surgical site or certain implant placement or implant component placement in live patient that can, for example, determine at least one of a Surgical instrument position
Surgical instrument location
Surgical instrument orientation
Surgical instrument rotation
Surgical instrument alignment
Surgical instrument direction
Depth of advancement of a surgical instrument, e.g. for acetabular reaming Implant position Implant location Implant orientation, e.g. anteversion, retroversion, offset (e.g. in a hip replacement acetabular cup or femoral component), abduction, adduction, internal rotation, external rotation, flexion, extension (e.g. in a knee replacement femoral component or tibial component)

Implant rotation

Implant alignment

Implant position of two or more implant components in relationship to each other and/or in relationship to the patient Implant location of two or more implant components in relationship to each other and/or in relationship to the patient Implant orientation of two or more implant components in relationship to each other and/or in relationship to the patient Implant rotation of two or more implant components in relationship to each other and/or in relationship to the patient Implant alignment of two or more implant components in relationship to each other and/or in relationship to the patient Optionally, the surgeon can toggle the display of the virtual data between a display of the surgical site prior to the alteration and/or after the alteration. Optionally, the surgeon can advance the display of the virtual data several surgical steps so that, for example, not the next but one or more subsequent virtual alterations to the surgical site be displayed.

Optionally, the surgeon can use displays with different colors for simultaneously or non-simultaneously viewing the physical, live surgical site and the virtual surgical site before and after one or more consecutive or non-consecutive virtual alterations intended or planned for the surgical site, optionally superimposed onto the live or virtual surgical site before the one or more alterations are made.

Optionally, the virtual display of the planned alteration can be superimposed onto the physical surgical site after the surgical alteration has been made to check for the accuracy of the physical alteration in the live patient. If the surgeon notices a discrepancy between the planned virtual alteration and the physical alteration, the surgeon can modify the physical alteration. For example, if the surgeon has executed a bone cut, for example in a proximal femur for a hip replacement or in a distal femur or proximal tibia for a knee replacement, the surgeon can use the OHMD to superimpose the planned, intended virtual bone cut onto the physical bone cut after the bone cut was made. If the surgeon notices that the physical bone cut took less bone than intended when compared to the planned, intended virtual bone cut, the surgeon can recut the bone to more closely match the physical bone cut with the intended virtual bone cut and, optionally the virtual surgical plan.

If the surgeon notices a discrepancy between the planned virtual alteration and the physical physical alteration, the surgeon can optionally also modify the virtual alteration to match the physical alteration induced by the patient. The virtual surgical plan can then be modified, for example for one or more of the subsequent surgical steps or procedures so that the virtual surgical plan will continue to work with the physical surgical alterations achieved with or induced in the live patient. The modification of the virtual surgical plan can be performed manually by the operator or surgeon, semi automatically or automatically using the input from the physical surgical alteration induced in the patient.

For example, if the surgeon has executed a bone cut, e.g. in a proximal femur for a hip replacement or in a distal femur or proximal tibia for a knee replacement, the surgeon can use the OHMD to superimpose the planned, intended virtual bone cut onto the physical bone cut after the bone cut was made. If the surgeon notices that the physical bone cut took more bone than intended when compared to the planned, intended virtual bone cut, the surgeon can modify the virtual surgical plan. The modified surgical plan can then, for example, included that a subsequent bone cut or reaming step on the opposite articular surface will take less bone, typically the same amount less bone on the opposite articular surface than was removed too much during the prior physical bone cut in the live patient. Alternatively, the modified surgical plan can include that one or more components of the medical device be thicker to compensate for the larger bone cut. In a knee replacement, for example, a thicker tibial insert can optionally be used. In a hip replacement, for example, a thicker acetabular liner or an offset liner can optionally be used.

Aligning Physical Medical Devices and Implants with Virtual Medical Devices and Implants By aligning with or directing physical medical devices or medical device components towards a display of virtually implanted medical devices or medical device components, for example in their intended final virtual position, location, orientation, rotation or alignment, in the OHMD, it is possible to achieve predetermined implant placement or implant component placement in the live patient that can, for example, determine at least one of a physical, final Implant position Implant location Implant orientation, e.g. anteversion, retroversion, offset (e.g. in a hip replacement acetabular cup or femoral component), internal rotation, external rotation, flexion, extension (e.g. in a knee replacement femoral component or tibial component)

Implant rotation

Implant alignment

Implant position of two or more implant components in relationship to each other and/or in relationship to the patient Implant location of two or more implant components in relationship to each other and/or in relationship to the patient Implant orientation of two or more implant components in relationship to each other and/or in relationship to the patient Implant rotation of two or more implant components in relationship to each other and/or in relationship to the patient Implant alignment of two or more implant components in relationship to each other and/or in relationship to the patient The OHMD can show the one or more virtual and, optionally, virtually implanted medical devices or medical device components with a continuous surface view, for example, using one color or with multiple colors for different features of the device or for different device components. The continuous surface display can include shading based on light sources used in the operating room and/or over the surgical field. The directional orientation of the OR light sources can, for example, be measured using image capture, optionally integrated into, attached to or separate from the OHMD.

The OHMD can show the one or more virtual and, optionally, virtually implanted medical devices or medical device components with an outline view which can be in 2D or in 3D. The outline view can include an outline of the entire virtual medical device or virtual medical device component, for example in a particular plane or cross-sectional plane. The outline view can optionally only highlight select features of the virtual medical device or virtual medical device component, e.g. a bone facing surface or a surface between two or more components facing each other, or a linking portion of the device or component or combinations thereof. The OHMD can show two or more outline views, for example extending through or along the surface or the periphery of the virtual medical device or virtual medical device component along different planes. These planes can be chosen to be different than at a 0 or 180 degree angle to each other. In some embodiments of the invention, the outline views can be orthogonal to each other. In this manner, even though the two or more outline views can be two-dimensional, the OHMD can still provide information to the surgeon or the operator on the intended orientation, position and/or direction of the device or device component in three-dimensions by providing two or more outline views with different angular orientations and by providing information on the x, y and z-axis alignment or position or orientation of the device or device component. Outline views can help limiting the amount of information displayed by the OHMD, which can help the surgeon maintaining his or her focus on the surgical site, with full visibility of the surgical site. Outline view can help decrease the risk of obscuring important live information from the patient, e.g. an exposed nerve root, by superimposing virtual data in a reduced format.

Optionally, the surgeon can toggle the display of the virtual data between a display of one or more of the virtual medical device components and, optionally, the live medical device components.

Optionally, the surgeon can use displays with different colors for simultaneously or non-simultaneously viewing the two or more virtual medical device components, optionally superimposed onto or displayed with the physical medical device.

Optionally, the virtual display of the medical device or medical device component after virtual implantation can be superimposed onto the physical medical device or medical device component after the physical implantation or placement to check for the accuracy of the physical implantation or placement in the live patient. If the surgeon notices a discrepancy between the planned virtual position, location, orientation, rotation, alignment of the medical device or medical device components and the physical position, location, orientation, rotation, alignment of the physical medical device or medical device components, the surgeon can modify the physical device placement or the surgeon can utilize different device components, e.g. in a knee replacement use a thicker or a thinner or a differently shaped tibial polyethylene insert or in a hip replacement use a different polyethylene liner, e.g. thicker, thinner or with offsets.

Visors

In some embodiments of the invention, a visor or splash shield can be integrated into the OHMD to protect the surgeon including his or her eyes from bodily fluids, e.g. blood. In some embodiments of the invention, a visor or splash shield can be attached to the OHMD to protect the surgeon including his or her eyes from bodily fluids, e.g. blood. In some embodiments of the invention, a visor or splash shield can be placed in front of the OHMD to protect the surgeon including his or her eyes from bodily fluids, e.g. blood.

Color Coding

Optionally, the different surgical instruments, devices or device components can be color coded during the display in the OHMD. For example, the color coding in the OHMD display will correspond to the color coding of the physical surgical instruments, devices or device components, if applicable. An exemplary color coding chart is provided below:
Physical Device:
4.0 mm screw—grey
4.5 mm screw—pink
5.0 mm screw—brown
5.5 mm screw—blue
6.0 mm screw—orange
6.5 mm screw—yellow
7.0 mm screw—no color
7.5 mm screw—green
8.5 mm screw—black
Virtual Device Display:
4.0 mm screw—grey
4.5 mm screw—pink
5.0 mm screw—brown
5.5 mm screw—blue
6.0 mm screw—orange
6.5 mm screw—yellow
7.0 mm screw—no color
7.5 mm screw—green
8.5 mm screw—black
Such screws can, for example, be used with pedicle screws or glenoid components or acetabular components. The foregoing color coding is only exemplary. Any colors, combination of colors, stripes, patterns can be used for identifying different sizes, dimensions, shapes, diameters, widths or lengths. Any instrument or implant can be color coded.

Color coding is applicable to any surgical instrument, medical device or medical device component, e.g. also with vascular stents, cardiac implants, cardiac defibrillators, hip replacement components, knee replacement components etc.

Optionally, in addition to the color coding or as an alternative to color coding, the OHMD can display one or more numerical values next to the virtual surgical instrument or medical device, e.g. a thickness or diameter or a size from a sizing chart.

In some embodiments of the invention, the OHMD can recognize if there is a discrepancy in diameter, width, length, dimension, shape, or size of an physical surgical instrument or device and a virtual device chosen in a surgical plan. For example, an image and/or video capture system integrated into, attached to or connected to the OHMD or separate from the OHMD can be used to image a surgical instrument, medical device or medical device component, optionally correct its diameter, width, length, dimension, shape, or size based on the distance of the surgical instrument or device from the image and/or video capture system (e.g. using parallax based measurements or registration or calibration phantoms) and then determine if the physical medical device or medical device component chosen by the operator or surgeon matches that selected in the virtual surgical plan. If the physical surgical instrument or medical device or medical device component is mismatched, for example with regard to diameter, width, length, dimension, shape, or size relative to the virtual instrument or component, the system can provide a warning signal, such as an acoustic alert or a visual warning sign (e.g. a red exclamation mark displayed by the OHMD).

Partially Visible or Partially Obscured Instruments, Tools, Devices, Implants, Implant Components In certain situations during surgery or in certain surgical sites, one or more physical surgical instruments or tools or one or more physical devices, implants, implant components and systems for implantation may only be partially visible during aspects or a period of the surgery. This is particular the case with surgeries involving deep seated organs, e.g. a liver or a kidney, a brain, or deep seated, obscured or hidden body structures, e.g. a hip joint or aspects of a spine, where important parts of one or more physical surgical instruments or tools or one or more physical devices, implants, implant components and systems for implantation may be at least partially obscured from view. This may be aggravated if the portion that is obscured from view is a portion that is inducing one or more alteration to a tissue surface, for example by electro-cautery, ablation, cutting or reaming or impacting. This reduction or limitation in visualization of the one or more physical surgical instruments or tools or one or more physical devices, implants, implant components and systems for implantation can result in a decreased accuracy of the surgical technique and, for example, placement errors of a device, implant, implant component or system for implantation or potential complications. In an embodiment of the invention, one or more of the physical surgical instruments or tools and/or one or more of the physical devices, implants, implant components and systems for implantation can include certain standardized geometric features, e.g. rectangles, triangles, circles and the like, that can be readily recognized by an image and/or video capture system integrated into or attached to or coupled to or separate from the OHMD. Alternatively, the image and/or video capture system may simply recognize the visible geometric shapes, surfaces, features or portions of the one or more of the physical surgical instruments or tools and/or one or more of the physical devices, implants, implant components and systems for implantation. The information can then be used to compute the shape, geometry, outline, surface or other features of the non-visualized, non-visible portions of the one or more of the physical surgical instruments or tools and/or one or more of the physical devices, implants, implant components and systems for implantation. With any of the foregoing techniques, the position, location, orientation, alignment, motional direction, and/or trajectory of the one or more of the surgical instruments or tools and/or one or more of the devices, implants, implant components and systems for implantation can be determined even though the one or more of the surgical instruments or tools and/or one or more of the devices, implants, implant components and systems for implantation is only partially or incompletely visualized or visible in the surgical site.

The non-visualized or non-visible portions of the one or more of the physical surgical instruments or tools and/or one or more of the physical devices, implants, implant components and systems for implantation can then optionally be displayed by the OHMD and projected onto the view of the surgical site. Optionally, the non-visualized or non-visible portions of the one or more of the physical surgical instruments or tools and/or one or more of the physical devices, implants, implant components and systems for implantation can be displayed by the OHMD simultaneous with the one or more of the corresponding virtual surgical instruments or tools and/or one or more of the corresponding virtual devices, implants, implant components and systems for implantation. Different colors or display patterns can optionally be used to display and differentiate the virtual from the physical of the one or more of the surgical instruments or tools and/or one or more of the devices, implants, implant components and systems for implantation in the OHMD display.

In alternative embodiments, one or more of the physical surgical instruments or tools and/or one or more of the physical devices, implants, implant components and systems for implantation can include one or more IMUs, including, for example, with accelerometers, magnetometers, and gyroscopes, similar, for example, to the OHMD. In some embodiments, one or more of the physical surgical instruments or tools and/or one or more of the physical devices, implants, implant components and systems for implantation can include one or more radiofrequency tags or markers or retroreflective markers and the like and its/their position, location and/or orientation can be captured by a surgical navigation system. Optionally, the OHMD may also include one or more radiofrequency tags or markers or retroreflective markers and the like and its position, location and/or orientation can also be captured by the surgical navigation system and cross-referenced to the one or more of the physical surgical instruments or tools and/or one or more of the physical devices, implants, implant components and systems for implantation. One or more of the physical surgical instruments or tools and/or one or more of the physical devices, implants, implant components and systems for implantation can also include light sources, such as lasers or LEDs. A laser can be projected, for example, on a wall or a ceiling and the OHMD and the patient can be referenced in relationship to that. An LED attached to or integrated into the one or more of the physical surgical instruments or tools and/or one or more of the physical devices, implants, implant components and systems for implantation can be recognized, for example, by an image and/or video capture system integrated into or attached to or coupled to or separate from the OHMD.

With any of the foregoing techniques, the position, location, orientation, alignment, motional direction, and/or trajectory of the one or more of the physical surgical instruments or tools and/or one or more of the physical devices, implants, implant components and systems for implantation can be determined even though the one or more of the physical surgical instruments or tools and/or one or more of the physical devices, implants, implant components and systems for implantation is only partially or incompletely visualized or visible in the surgical site. A computer program or software can then optionally compute the shape, geometry, outline, surface of other features of the non-visualized, non-visible portions of the one or more of the physical surgical instruments or tools and/or one or more of the physical devices, implants, implant components and systems for implantation. The non-visualized or non-visible portions of the one or more of the physical surgical instruments or tools and/or one or more of the physical devices, implants, implant components and systems for implantation can then optionally be displayed by the OHMD and projected onto the view of the surgical site.

Optionally, the non-visualized or non-visible portions of the one or more of the physical surgical instruments or tools and/or one or more of the physical devices, implants, implant components and systems for implantation can be displayed by the OHMD simultaneous with the one or more of the corresponding virtual surgical instruments or tools and/or one or more of the corresponding virtual devices, implants, implant components and systems for implantation.

Different colors or display patterns can optionally be used to display and differentiate the virtual from the physical of the one or more of the surgical instruments or tools and/or one or more of the devices, implants, implant components and systems for implantation in the OHMD display.

Difficult Lighting and Tissue Contrast Conditions

In certain situations during surgery or in certain surgical sites, the lighting conditions and tissue contrast may be such that any virtual anatomic data or structures, virtual surgical plans, virtual tool or instrument or device paths, virtual surgical instruments or tools and/or any virtual devices, implants, implant components and systems for implantation may be difficult to see in the OHMD display by the human operator. In any of these circumstances, the system can optionally allow the operator or the surgeon to change the display mode or it can actively change the display mode of one or more the virtual anatomic data or structures, virtual surgical plans, virtual tool or instrument or device paths, virtual surgical instruments or tools and/or the virtual devices, implants, implant components and systems for implantation, for example by changing the color, brightness, intensity, and/or contrast of one or more of the virtual anatomic data or structures, virtual surgical plans, virtual tool or instrument or device paths, virtual surgical instruments or tools and/or the virtual devices, implants, implant components and systems for implantation. Different changes in color, brightness, intensity, and/or contrast can be applied to different virtual data, e.g. virtual anatomic data or structures, virtual surgical plans, virtual tool or instrument or device paths, virtual surgical instruments or tools and/or the virtual devices, implants, implant components and systems for implantation.

The surgeon or operator or the software or the system may change the color of one or more of the virtual anatomic data or structures, virtual surgical plans, virtual tool or instrument or device paths, virtual surgical instruments or tools and/or the virtual devices, implants, implant components and systems for implantation. The surgeon or operator or the software or the system may change the brightness of one or more of the virtual anatomic data or structures, virtual surgical plans, virtual tool or instrument or device paths, virtual surgical instruments or tools and/or the virtual devices, implants, implant components and systems for implantation. The surgeon or operator or the software or the system may change the intensity of one or more of the virtual anatomic data or structures, virtual surgical plans, virtual tool or instrument or device paths, virtual surgical instruments or tools and/or the virtual devices, implants, implant components and systems for implantation. The surgeon or operator or the software or the system may change the contrast of one or more of the virtual anatomic data or structures, virtual surgical plans, virtual tool or instrument or device paths, virtual surgical instruments or tools and/or the virtual devices, implants, implant components and systems for implantation. The surgeon or the operator or the software or the system may change the display pattern of the one or more of the virtual anatomic data or structures, virtual surgical plans, virtual tool or instrument or device paths, virtual surgical instruments or tools and/or the virtual devices, implants, implant components and systems for implantation. For example, one or more of the virtual anatomic data or structures, virtual surgical plans, virtual tool or instrument or device paths, virtual surgical instruments or tools and/or the virtual devices, implants, implant components and systems for implantation may be displayed with a raster pattern or a line pattern or a point pattern or any other display pattern known in the art. Alternatively, one or more of the virtual anatomic data or structures, virtual surgical plans, virtual tool or instrument or device paths, virtual surgical instruments or tools and/or the virtual devices, implants, implant components and systems for implantation may be displayed with a temporally changing display pattern, including, but not limited to a blinking pattern or a flashing pattern, e.g. with only intermittent display of the virtual information. Alternatively, one or more of the virtual anatomic data or structures, virtual surgical plans, virtual tool or instrument or device paths, virtual surgical instruments or tools and/or the virtual devices, implants, implant components and systems for implantation may be displayed with a "skeletonization pattern", wherein, for example, only key features or key outlines of one or more of the virtual anatomic data or structures, virtual surgical plans, virtual tool or instrument or device paths, virtual surgical instruments or tools and/or the virtual devices, implants, implant components and systems for implantation can be displayed. Alternatively, one or more of the virtual anatomic data or structures, virtual surgical plans, virtual tool or instrument or device paths, virtual surgical instruments or tools and/or the virtual devices, implants, implant components and systems for implantation may be displayed with a "highlighting pattern" or mode, wherein, for example, key features or key outlines of one or more of the virtual anatomic data or structures, virtual surgical plans, virtual tool or instrument or device paths, virtual surgical instruments or tools and/or the virtual devices, implants, implant components and systems for implantation may be displayed using an enlargement of the feature or outline or a color or brightness or contrast or other display enhancement of the feature or outline. Optionally, less important features or outline components or portions may be reduced in display intensity or removed from the display. The foregoing display adjustments can be performed via operator controlled commands, e.g. manual or voice or other commands. Alternatively, these adjustments can be semi-automatic with operator input or automatic using, for example, information about brightness, contrast and/or color of the virtual and/or the live data of the patient as well as ambient light conditions, e.g. OR light intensity, light reflections, etc. For semi-automatic or automated adjustment of the display of select, one or more virtual data, e.g. virtual anatomic data or structures, virtual surgical plans, virtual tool or instrument or device paths, virtual surgical instruments or tools and/or the virtual devices, implants, implant components and systems for implantation, light intensity and contrast sensors can be employed which can optionally be integrated into, attached to or separate from one or more OHMDs. Alternatively, the information about color, brightness, intensity, contrast of the live data seen through the OHMD and/or ambient lighting conditions can be obtained through one or more image and/or video capture systems integrated into, attached to or separate from the OHMD.

Any of the foregoing changes to the display of virtual anatomic data or structures, virtual surgical plans, virtual tool or instrument or device paths, surgical instruments or tools and/or the devices, implants, implant components and systems for implantation can also be applied to any partially obscured or non-visible portions of the physical surgical instruments or tools and/or the physical devices, implants, implant components and systems for implantation.

Any of the virtual anatomic data or structures, virtual surgical plans, virtual tool or instrument or device paths, surgical instruments or tools and/or the devices, implants, implant components and systems for implantation described anywhere in the invention can be modified in the display using one or more of these techniques or any other technique of display modification known in the art.

In certain situations during surgery or in certain surgical sites, the lighting conditions and tissue contrast may be such that any obscured portions of the anatomy or obscured pathology or obscured target tissue(s) or deep seated, obscured or hidden portions of the anatomy or target tissue(s) or intended alterations to deep seated tissue(s) may be difficult to see in the OHMD display by the human operator. This includes also normal tissue and normal anatomic structures, hidden or obscured or deep seated. In any of these circumstances, the system can optionally allow the operator or the surgeon to change the display mode or the system can actively change the display mode of the anatomy or deep seated portions of the anatomy or target tissue(s) or intended alterations to deep seated, obscured or hidden tissue(s). For example, the surgeon or operator may change the color of the anatomy or deep seated, obscured or hidden portions of the anatomy or target tissue(s) or intended alterations to deep seated, obscured or hidden tissue(s). Alternatively, the surgeon or the operator may change the display pattern of the anatomy or deep seated, obscured or hidden portions of the anatomy or target tissue(s) or intended alterations to deep seated, obscured or hidden tissue(s). For example, the anatomy or deep seated, obscured or hidden portions of the anatomy or target tissue(s) or intended alterations to deep seated, obscured or hidden tissue(s) may be displayed with a raster pattern or a line pattern or a point pattern or any other display pattern known in the art. Alternatively, the anatomy or deep seated, obscured or hidden portions of the anatomy or target tissue(s) or intended alterations to deep seated, obscured or hidden tissue(s) may be displayed with a temporally changing display pattern, including, but not limited to a blinking pattern or a flashing pattern, e.g. with only intermittent display of the information. Alternatively, the anatomy or deep seated, obscured or hidden portions of the anatomy or target tissue(s) or intended alterations to deep seated, obscured or hidden tissue(s) may be displayed with a "skeletonization pattern", wherein, for example, only key features or key outlines of the anatomy or deep seated, obscured or hidden portions of the anatomy or target tissue(s) or intended alterations to deep seated, obscured or hidden tissue(s) may be displayed. Alternatively, the anatomy or deep seated, obscured or hidden portions of the anatomy or target tissue(s) or intended alterations to deep seated, obscured or hidden tissue(s) may be displayed with a "highlighting pattern" or mode, wherein, for example, key features or key outlines of the anatomy or deep seated, obscured or hidden portions of the anatomy or target tissue(s) or intended alterations to deep seated, obscured or hidden tissue(s) may be displayed using an enlargement of the feature or outline or a color or brightness or contrast or other display enhancement of the feature or outline. Optionally, less important features or outline components or portions may be reduced in display intensity or removed from the display. Any of the tissues described anywhere in the invention, such as by way of example, a cerebral cortex, gyri, a pedicle, vertebral endplates, an anterior vertebral wall, a posterior vertebral wall, an acetabulum, vessels, nerves, tumors, can be modified in the display using one or more of these techniques or any other method of display modification known in the art.

Any of the foregoing adjustments in color, brightness, intensity, and/or contrast can be applied to 2D or 3D, stereoscopic and non-stereoscopic displays of one or more of the virtual anatomic data or structures, virtual surgical plans, virtual tool or instrument or device paths, virtual surgical instruments or tools and/or the virtual devices, implants, implant components and systems for implantation. If live data of the patient are not directly seen through the OHMD, but are captured through an image and/or video capture system integrated into, attached to or separate from the OHMD and then displayed by the OHMD, optionally in combination with virtual anatomic data or structures, virtual surgical plans, virtual tool or instrument or device paths, virtual surgical instruments or tools and/or the virtual devices, implants, implant components and systems for implantation, the same or similar adjustments can be applied to one or more of the live data of the patient, e.g. select anatomic structures, or all of the live data of the patient.

In some aspects, the invention provides a method for preparing a joint for a prosthesis in a patient. In some embodiments, the method comprises registering the patient's joint and one or more optical head mounted displays worn by a surgeon or surgical assistant in a coordinate system, obtaining one or more intra-operative measurements, registering the one or more intra-operative measurements in the coordinate system, developing a virtual surgical plan based on the one or more intra-operative measurements, and displaying or projecting aspects of the virtual surgical plan superimposed onto the corresponding portions of the patient's joint with the optical head mounted display. In some embodiments, the one or more optical head mounted displays are registered in the same coordinate system. In some embodiments, the one or more intra-operative measurements are morphological measurements, optical measurements or combinations thereof. In some embodiments, the one or more intra-operative measurements are not pressure measurements.

In some aspects, the invention provides a method for preparing an orthopedic procedure in a patient. In some embodiments, the method comprises registering the patient's surgical site and one or more optical head mounted display worn by a surgeon or surgical assistant in a common coordinate system, obtaining one or more intra-operative optical measurements using one or more optical markers, registering the one or more intra-operative optical measurements using one or more optical markers in the common coordinate system, developing a virtual surgical plan based on the one or more intra-operative optical measurements, and displaying or projecting aspects of the virtual surgical plan superimposed onto the corresponding portions of the patient's physical joint with the optical head mounted display. The virtual surgical plan can be displayed or projected onto the patient's physical joint based at least in part on coordinates of the predetermined position of the virtual surgical plan.

In some embodiments, the virtual surgical plan incorporates data from a pre-operative scan. In some embodiments, the virtual surgical plan incorporates data from an intra-operative scan. In some embodiments, the virtual surgical plan incorporates data from a pre-operative scan and an intra-operative scan. The scan includes one or more x-rays, a CT scan, an MRI scan, an ultrasound or combinations thereof.

In some embodiments, the scan data are registered in the common coordinate system. In some embodiments, the registered scan data are displayed superimposed onto the surgical site by the optical head mounted display. In some embodiments, the scan data include a three-dimensional display of the surgical site.

In some embodiments, the registering step includes identifying one or more landmarks in the live surgical site. In some embodiments, one or more corresponding anatomic landmarks are identified in the patient's scan data.

In some embodiments, the registering step includes identifying one or more anatomic axes or biomechanical axes in the live surgical site. In some embodiments, the one or more corresponding anatomic axes or biomechanical axes are identified in the patient's scan data.

In some embodiments, the live surgical site includes one or more of a bone, a cartilage, a joint, a joint surface, an opposing joint surface, a ligament, a meniscus, a labrum, an intra-articular structure, a spinous process, a pedicle, a facet joint, a superior or inferior process or a vertebral body.

In some embodiments, the registering step includes detecting one or more optical markers attached to one or more structures in the live surgical site. In some embodiments, the registering step includes detecting one or more optical markers attached to the OR table. In some embodiments, the detecting of the one or more optical markers includes determining one or more of a position, orientation, alignment, direction of movement or speed of movement of the one or more optical markers.

The optical marker can include a geometric pattern, a QR code, a barcode or combinations thereof. The QR code or barcode can be included in or integrated into or attached to the geometric pattern.

In some embodiments, the optical head mounted display includes one or more cameras or image capture or video capture systems. The one or more cameras or image capture or video capture systems can detect the one or more optical markers including their coordinates (x, y, z). In some embodiments, the optical marker includes information about implant inventory management. For example, the QR code can include information about implant inventory management.

In some embodiments, the one or more cameras or image capture or video capture systems included in the optical head mounted display reads the inventory management in the QR and transmits it to another computer.

In some embodiments, the intraoperative measurement includes identifying coordinates (x, y, z) of a live anatomic landmark in the patient's joint using one or more optical markers. In some embodiments, the intraoperative measurement includes identifying coordinates (x, y, z) of an anatomic landmark in the intra-operative scan data.

In some embodiments, the one or more optical markers are radiopaque and their coordinates (x, y, z) can be detected in the intra-operative scan data.

In some embodiments, the optical markers are detected using the one or more cameras or image capture or video capture systems included in the optical head mounted display and detected in the intra-operative scan data are registered in the common coordinate system.

In some embodiments, the intraoperative measurement includes identifying an anatomic axis or a biomechanical axis of the patient. The biomechanical axis can be a mechanical axis of the leg. In some embodiments, the intraoperative measurement includes obtaining information from a surgically altered surface.

In some embodiments, the intraoperative measurement includes identifying a center of rotation of a joint of the patient. The joint can be the joint being operated on, or the joint can be a joint different than the joint being operated on.

In some embodiments, the intraoperative measurement includes identifying an anatomic plane. The anatomic plane can be tangent with one or more anatomic landmarks. The anatomic plane can intersect one or more anatomic landmarks. In some embodiments, the anatomic plane can be found by placing a virtual plane to be tangent with or intersect with one or more anatomic landmarks. The virtual plane can be placed using a virtual interface.

In some embodiments, the virtual surgical plan includes predetermined path for a surgical instrument. In some embodiments, the virtual surgical plan includes a projected or intended cut plane. In some embodiments, the virtual surgical plan includes a virtual cut block projected in a desired or intended position, orientation and/or alignment. In some embodiments, the virtual surgical plan includes a projected or intended reaming, milling or impacting axis. In some embodiments, the virtual surgical plan includes a virtual surgical instrument displayed or projected in a desired or predetermined position, orientation, alignment and/or direction of movement. In some embodiments, the virtual surgical plan includes a virtual surgical implant component displayed or projected in a desired or predetermined position, orientation and/or alignment.

In some aspects, the method of preparing a joint for a prosthesis in a patient comprises obtaining scan data associated with the joint of the patient; preparing a virtual surgical plan for the patient's joint based on the scan data; registering the patient's physical joint, the virtual surgical plan, and one or more optical head mounted displays worn by a surgeon or surgical assistant in a common coordinate system, obtaining one or more intra-operative measurements, adjusting or modifying the virtual surgical plan based on the one or more intra-operative measurements, and displaying or projecting aspects of the adjusted or modified surgical plan superimposed onto corresponding portions of the patient's physical joint with the optical head mounted display. In some embodiments, the one or more intra-operative measurements are morphological measurements, optical measurements or combinations thereof.

In some aspects, the method of preparing an orthopedic procedure in a patient comprises obtaining scan data associated with the surgical site of the patient; preparing a virtual surgical plan for the patient based on the scan data; registering the patient's live surgical site, the virtual surgical plan, and one or more optical head mounted displays worn by a surgeon or surgical assistant in a common coordinate system, obtaining one or more intra-operative measurements; adjusting or modifying the virtual surgical plan based on the one or more intra-operative measurements, and displaying or projecting aspects of the adjusted or modified surgical plan superimposed onto corresponding portions of the patient's live surgical site with the optical head mounted display.

In some embodiments, the one or more intra-operative measurements include one or more optical markers.

In some embodiments, the scan data is obtained pre-operatively and/or intra-operatively. In some embodiments, the scan data include pre-operative and intra-operative scan data. In some embodiments, the scan data include one or more x-rays, a CT scan, an MRI scan, an ultrasound or combinations of the foregoing.

In some embodiments, the scan data are registered in the common coordinate system. In some embodiments, the registered scan data are displayed superimposed onto the surgical site by the optical head mounted display.

In some embodiments, the scan data include a three-dimensional display of the surgical site.

In some embodiments, the registering includes identifying one or more anatomic landmarks in the patient's scan data. In some embodiments, the registering includes identifying one or more corresponding landmarks in the live surgical site. In some embodiments, the registering includes identifying one or more anatomic axes or biomechanical axes in the patient's scan data. In some embodiments, the registering includes identifying one or more corresponding anatomic axes or biomechanical axes in the live surgical site.

In some embodiments, the live surgical site includes one or more of a bone, a cartilage, a joint, a joint surface, an opposing joint surface, a ligament, a meniscus, a labrum, an intra-articular structure, a spinous process, a pedicle, a facet joint, a superior or inferior process or a vertebral body.

In some embodiments, the registering includes detecting one or more optical markers attached to one or more structures in the live surgical site. In some embodiments, the registering includes detecting one or more optical markers attached to the OR table. In some embodiments, the detecting of the one or more optical markers includes determining one or more of a position, orientation, alignment, direction of movement or speed of movement of the one or more optical markers.

The optical marker can include a geometric pattern, a QR code, a barcode or combinations thereof. The QR code or barcode can be included in or integrated into or attached to the geometric pattern.

In some embodiments, the optical head mounted display includes one or more cameras or image capture or video capture systems. The one or more cameras or image capture or video capture systems can detect the one or more optical markers including their coordinates (x, y, z). In some embodiments, the optical marker includes information about implant inventory management. For example, the QR code can include information about implant inventory management.

In some embodiments, the QR code includes information about implant inventory management. In some embodiments, the one or more cameras or image capture or video capture systems included in the optical head mounted display reads the inventory management in the QR and transmits it to another computer.

In some embodiments, the intraoperative measurement includes identifying coordinates (x, y, z) of a live anatomic landmark in the patient's joint using one or more optical markers. In some embodiments, the intraoperative measurement includes identifying coordinates (x, y, z) of an anatomic landmark in the intra-operative scan data.

In some embodiments, the one or more optical markers are radiopaque and their coordinates (x, y, z) can be detected in the intra-operative scan data.

In some embodiments, the optical markers are detected using the one or more cameras or image capture or video capture systems included in the optical head mounted display and detected in the intra-operative scan data are registered in the common coordinate system.

In some embodiments, the intraoperative measurement includes identifying an anatomic axis or a biomechanical axis of the patient. For example, the biomechanical axis can be a mechanical axis of the leg.

In some embodiments, the intraoperative measurement includes identifying a center of rotation of a joint of the patient. The joint can be the joint being operated on or a joint different than the joint being operated on.

In some embodiments, the intraoperative measurement includes identifying an anatomic plane. The anatomic plane can be tangent with one or more anatomic landmarks. The anatomic plane can intersect one or more anatomic landmarks. In some embodiments, the anatomic plane is found by placing a virtual plane to be tangent with or intersect with one or more anatomic landmarks. The virtual plane can be placed using a virtual interface.

In some embodiments, the intraoperative measurement includes obtaining information from a surgically altered surface.

In some embodiments, the adjusting or modifying the virtual surgical plan includes placing or moving a predetermined path for a surgical instrument. In some embodiments, the adjusting or modifying the virtual surgical plan includes the placing or moving of a virtual cut plane. In some embodiments, the adjusting or modifying the virtual surgical plan includes the placing or moving of a virtual cut block. In some embodiments, the adjusting or modifying the virtual surgical plan includes the placing or moving of a virtual reaming, milling or impacting axis. In some embodiments, the adjusting or modifying the virtual surgical plan includes the placing or moving of a virtual surgical instrument. In some embodiments, the adjusting or modifying the virtual surgical plan includes the placing or moving of a virtual surgical implant component. According to some aspects of the invention, the method of preparing a joint for a prosthesis in a patient comprises registering the patient's live surgical site and one or more optical head mounted displays worn by a surgeon or surgical assistant in a common coordinate system, obtaining one or more intra-operative measurements, registering the one or more intra-operative measurements in the common coordinate system, developing a virtual surgical plan based on the one or more intra-operative measurements, the virtual surgical plan including at least one virtual cut plane, and displaying or projecting the one or more virtual cut planes superimposed onto the corresponding portions of the patient's live surgical site with the optical head mounted display.

According to some aspects of the invention, the method of preparing a joint for a prosthesis in a patient comprises registering the patient's live surgical site and an optical head mounted display worn by a surgeon or surgical assistant in a common coordinate system, developing a virtual surgical plan, registering the virtual surgical plan in the common coordinate system, the virtual surgical plan including at least one virtual cut plane, and displaying or projecting the at least one virtual cut planes superimposed onto the corresponding portions of the patient's live surgical site with the optical head mounted display. In some embodiments, the method further comprises obtaining one or more intra-operative measurements. In some embodiments, the method further comprises registering the one or more intra-operative measurements in the common coordinate system. In some embodiments, the one or more intra-operative measurements comprise intra-operative morphological and optical measurements.

In some embodiments, the prosthesis is a knee replacement and the virtual cut plane defines a tibial slope after implantation of the tibial implant component(s). In some embodiments, the prosthesis is a knee replacement and the virtual cut plane defines an angle of varus or valgus correction in relationship to the patient's mechanical axis of the leg for a tibial component and related bone cuts. In some embodiments, the prosthesis is a knee replacement and the virtual cut plane defines an angle of varus or valgus correction in relationship to the patient's mechanical axis of the leg for a femoral component and related bone cuts. In some embodiments, the prosthesis is a knee replacement and the virtual cut planes define an angle of varus or valgus correction in relationship to the patient's mechanical axis of the leg for a femoral component and a tibial component and related bone cuts including a combined correction. In some embodiments, the prosthesis is a knee replacement and the virtual cut plane corresponds to a distal femoral cut and defines a femoral component flexion. In some embodiments, the prosthesis is a knee replacement and the virtual cut plane corresponds to an anterior femoral cut and defines a femoral component rotation. In some embodiments, the prosthesis is a knee replacement and the virtual cut plane corresponds to a posterior femoral cut and defines a femoral component rotation. In some embodiments, the prosthesis is a knee replacement and the virtual cut plane corresponds to chamfer cut and defines a femoral component rotation. In some embodiments, the prosthesis is a hip replacement and wherein the virtual cut plane defines a leg length after implantation.

According to some aspects of the invention, the method for preparing a joint for a prosthesis in a patient comprises registering the patient's live surgical site and one or more optical head mounted displays worn by a surgeon or surgical assistant in a common coordinate system, developing a virtual surgical plan, registering the virtual surgical plan in the common coordinate system, the virtual surgical plan including at least two or more projected or intended pin or drill paths, and displaying or projecting the two or more projected or intended pin or drill paths superimposed onto the corresponding portions of the patient's bone or cartilage in the live surgical site with the optical head mounted display.

In some embodiments, a first physical pin or drill is aligned with the first virtual pin or drill path and the pinning or drilling is executed while maintaining the alignment. In some embodiments, a second physical pin or drill is aligned with the second virtual pin or drill path and the pinning or drilling is executed while maintaining the alignment. In some embodiments, the first and second pins or drills are used to fixate or reference a surgical guide or cut block. In some embodiments, the drill holes created by the physical first and second pins or drills are used to fixate or reference a surgical guide or cut block.

In some embodiments, the surgical guide or cut block is used to execute a bone cut. The bone cut can define a leg length based on the virtual surgical plan. The bone cut can define a varus or valgus correction based on the virtual surgical plan. The bone cut can define a femoral component flexion based on the virtual surgical plan. The bone cut can define a femoral component rotation based on the virtual surgical plan. The bone cut can determine a tibial slope based on the virtual surgical plan. In some embodiments, the bone cut is a keel punch and determines a tibial component rotation based on the virtual surgical plan.

According to some aspects, the method for preparing a joint for a prosthesis in a patient comprises registering the patient's joint and one or more optical head mounted displays worn by a surgeon or surgical assistant in a common coordinate system, obtaining one or more intra-operative measurements, registering the one or more intra-operative measurements in the common coordinate system, developing a virtual surgical plan based on the one or more intra-operative [morphological or optical] measurements, the virtual surgical plan including a virtual surgical drill guide, and displaying or projecting the virtual drill guide superimposed onto the corresponding portions of the patient's live surgical site intended for the drilling with the optical head mounted display. In some embodiments, the one or more intra-operative measurements are morphological and/or optical measurements. In some embodiments, the physical drill corresponding to the virtual drill guide includes at least two openings to accommodate two or more drills. In some embodiments the virtual drill guide corresponds to a physical drill guide and has at least one or more dimensions similar to the physical drill guide. According to some aspects, the method for preparing a joint for a prosthesis in a patient comprises registering the patient's joint and one or more optical head mounted displays worn by a surgeon or surgical assistant in a common coordinate system, obtaining one or more intra-operative measurements, registering the one or more intra-operative measurements in the common coordinate system, developing a virtual surgical plan based on the one or more intra-operative measurements, the virtual surgical plan including at least one virtual axis for a reamer, a mill or an impactor, and displaying or projecting the at least one virtual axis for a reamer, a mill or an impactor superimposed onto the corresponding portions of the patient's live surgical site with the optical head mounted display.

According to some aspects, the method for preparing a joint for a prosthesis in a patient comprises registering the patient's joint and an optical head mounted display worn by a surgeon or surgical assistant in a common coordinate system, developing a virtual surgical plan, registering the virtual surgical plan in the common coordinate system, the virtual surgical plan including at least one virtual axis for a reamer, a mill or an impactor, and displaying or projecting the at least one virtual axis for a reamer, a mill or an impactor superimposed onto the corresponding portions of the patient's live surgical site with the optical head mounted display. In some embodiments, the method further comprises obtaining one or more intra-operative measurements. In some embodiments, the method further comprises registering the one or more intra-operative measurements in the common coordinate system.

In some embodiments, the prosthesis is a hip replacement and the virtual axis defines an acetabular anteversion after implantation of the acetabular component(s) based on the virtual surgical plan. In some embodiments, the prosthesis is a hip replacement and the virtual axis defines an acetabular offset after implantation of the acetabular component(s) based on the virtual surgical plan. In some embodiments, the prosthesis is a hip replacement and the virtual axis defines a combined acetabular and femoral component anteversion. A physical reamer, mill or impactor can be aligned with the virtual axis for the reamer, mill or impactor and the reaming, milling or impacting can be executed while maintaining the alignment.

According to some aspects, the method for preparing a joint for a prosthesis in a patient comprises registering the patient's live surgical site and one or more optical head mounted displays worn by a surgeon or surgical assistant in a common coordinate system, obtaining one or more intra-operative measurements, registering the one or more intra-operative measurements in the common coordinate system, developing a virtual surgical plan based on the one or more intra-operative measurements, the virtual surgical plan including a virtual tibial template, and displaying or projecting the virtual tibial template superimposed onto the cut tibia with the optical head mounted display.

In some embodiments, the physical tibial template is aligned with the virtual cut tibial template, a tibial keel punch is inserted, and the proximal tibia is punched to accommodate the tibial keel and fins.

In some embodiments, the virtual and the physical tibial template determine the alignment and rotation of the tibial implant component.

According to some aspects, the method for preparing an orthopedic procedure in a patient comprises registering the patient's surgical site and one or more] optical head mounted displays worn by a surgeon or surgical assistant in a common coordinate system, wherein the registration of the patient's surgical site in the common coordinate system is performed using one or more optical markers attached to the patient in or around the surgical site, wherein the optical marker includes one or more geometric patterns, wherein the optical markers are detected with a camera, an image capture or video system integrated into, attached to or separate from the optical head mounted display. In some embodiments, the optical marker includes at least one portion that is radiopaque. In some embodiments, internal structures of the patient or the surgical site are visualized using an imaging test with ionizing radiation. For example, the imaging test can be one or more x-rays and/or a CT scan.

In some embodiments, the radiopaque portions of the optical marker are detected on the imaging test using image processing software. In some embodiments, the radiopaque portions of the optical marker detected on the imaging test are cross-referenced with the visible portions of the optical marker detected with the camera, image capture or video system and wherein the information is used to register the internal structures of the patient or the surgical site in the common coordinate system.

In some embodiments, the optical head mounted display displays the internal structures of the patient or the surgical site superimposed onto the corresponding external surfaces of the patient or the surgical site. In some embodiments, the optical head mounted display superimposes a virtual surgical plan onto the corresponding external and internal structures. The virtual surgical plan can be a predetermined path for a surgical device.

Examples

The following examples show representative applications of various embodiments of the invention. The examples are not meant to be limiting. Someone skilled in the art will recognize other applications or modifications of the methods, techniques, devices and systems described. Any embodiment described for one joint or anatomic region, e.g. a spine or pedicle, can be applied to other joints or other regions, e.g. a hip, hip replacement, knee, knee replacement, vascular imaging study, angiography etc.

In some embodiments, when a physical guide, tool, instrument or implant is aligned with or superimposed onto a virtual surgical guide, tool, instrument or implant displayed or projected by the OHMD, the aligning or superimposing can be performed with a location accuracy of about 10 mm, about 9 mm, about 8 mm, about 7 mm, about 6 mm, about 5 mm, about 4 mm, about 3 mm, about 2 mm, about 1 mm, about 0.5 mm, about 0.25 mm, or less, 0.25 mm to 0.5 mm, 0.25 mm to 1 mm, 0.25 mm to 2 mm, 0.25 mm to 3 mm, 0.25 mm to 4 mm, 0.25 mm to 5 mm, 0.25 mm to 6 mm, 0.25 mm to 7 mm, 1 mm to 2 mm, 1 mm to 3 mm, 1 mm to 4 mm, 1 mm to 5 mm, 1 mm to 6 mm, 1 mm to 7 mm, 2 mm to 3 mm, 2 mm to 4 mm, 2 mm to 5 mm, 2 mm to 6 mm, 2 mm to 7 mm, 3 mm to 4 mm, 3 mm to 5 mm, 3 mm to 6 mm, 3 mm to 7 mm, 4 mm to 5 mm, 4 mm to 6 mm, 4 mm to 7 mm, 5 mm to 6 mm, 5 mm to 7 mm, 6 mm to 7 mm or as needed depending on the clinical application, in one, two or three directions, x, y, z. When the physical guide, tool, instrument or implant is aligned with or superimposed onto the virtual surgical guide, tool, instrument or implant displayed or projected by the OHMD, the aligning or superimposing can be performed with an orientation or angle accuracy of about 10°, about 9°, about 8°, about 7°, about 6°, about 5°, about 4°, about 3°, about 2°, about 1°, about 0.5°, about 0.25° or less, 0.25-10°, 0.25 to 9°, 0.25-8°, 0.25-7°, 0.25-6°, 0.25-5°, 0.25-4°, 0.25-3°, 0.25-2°, 0.25-1°, 0.25-0.5°, 0.5 to 9°, 0.5-8°, 0.5-7°, 0.5-6°, 0.5-5°, 0.5-4°, 0.5-3°, 0.5-2°, 0.5-1°, 1 to 9°, 1-8°, 1-7°, 1-6°, 1-5°, 1-4°, 1-3°, 1-2°, 2-9°, 2-8°, 2-7°, 2-6°, 2-5°, 2-4°, 2-3°, 3-9°, 3-8°, 3-7°, 3-6°, 3-5°, 3-4°, 4-9°, 4-8°, 4-7°, 4-6°, 4-5°, 5-9°, 5-8°, 5-7°, 5-6°, 6-9°, 6-8°, 6-7°, 7-9°, 7-8°, 8-9° or as needed depending on the clinical application, in one, two or three directions, x, y, z.

The mechanical axis of the lower extremity is determined by drawing a line from the center of the femoral head to the center of the ankle joint, which corresponds typically to an approximately 3° slope compared with that of the vertical axis. This can be subdivided into the femoral mechanical axis, which runs from the head of the femur to the intercondylar notch of the distal femur, and the tibial mechanical axis, which extends from the center of the proximal tibia to the center of the ankle. The medial angle formed between the mechanical axis of the femur and the mechanical axis of the tibia is called the hip-knee-ankle angle, which represented the overall alignment of the lower extremity and is usually about or slightly less than 180° in normal knees, also called normal mechanical axis alignment. The position of the mechanical axis causes it to usually pass just medial to the tibial spine, but this can vary widely based on the patient height and pelvic width.

Pedicle Screw, Spinal Rod Placement for Example for Correction of Spinal Deformities, Scoliosis and/or Fracture Treatment Pedicle screw and rod placement is one of the most common spinal procedures. It can be performed for a number of different conditions, including, for example, spinal instability, correction of spinal deformities, e.g. scoliosis, kyphosis and combinations thereof, as well as congenital spinal defects. Pedicle screw and rod placement can be combined with bone graft, e.g. allograft or autograft. Sometimes, infusable or injectable bone morphogenic protein can be used during the procedure to facilitate healing and stabilization of bone graft.

Preoperatively, patients will commonly undergo x-ray imaging, for example in anteroposterior, lateral and oblique views. Special views of select regions, e.g. the sacrum or the occipito-atlantic junction can be obtained. X-rays can be obtained in standing and lying position. X-rays can also be obtained in prone or supine position. X-rays may be obtained with the patient erect, spinal flexion and spinal extension. X-rays may also be obtained with the patient bending to the left side or to the right side.

Patients may optionally undergo CT scanning or MRI scanning. CT scanning and MRI scanning have the added advantage of providing a 3D dataset of the patient's anatomy. Moreover, the thecal sac and the nerve roots can be visualized. With MRI, the spinal cord can also be visualized.

Virtual Surgical Plan

The surgeon can develop a virtual surgical plan for the pedicle screw and rod placement which can optionally incorporate any desired deformity correction. Typical criteria for placement of pedicle screws can include the following:

The entry point of the pedicle screw and any awl, probe, tap, k-wire, y-wire, other wires, and other surgical instruments can be chosen, for example, to be at the lateral border of the superior articular process with the intersect to a horizontal line bisecting the transverse processes on the left and right side.

In the lumbar spine, the trajectory of the pedicles will typically converge 5-10 degrees in the upper lumbar spine, 10-15 degrees in the lower lumbar spine. Typically no cephalad or caudad tilt of the trajectory is needed in the lumbar spine.

In the thoracic spine, the entry point can be just below the rim of the upper facet joint, and approximately 3 mm lateral to the center of the joint near the base of the transverse process. In the thoracic spine, the pedicles and with that the screws can converge to the midline at approximately 7-10 degrees; in the sagittal plane, they can be oriented 10-20 degrees caudally. In accessing T12, the virtual surgical plan can include removal of transverse process to open the marrow space. The angulation can be medial and caudal angulation.

Surgeon can generally use between a lateral intersection method for pedicle screw placement, with the lateral border of the superior articular processes forming an intersect to a horizontal line bisecting the transverse processes on the left and right side. A more medial entry point can be chosen, in which case a rangeur may be required to remove the base of the articular process. This can be included in the virtual surgical plan.

For S1, the entry point can be chosen at the intersect of a vertical line tangential to the S1 articular process and a horizontal line tangential to its inferior border. Typically, at S1, pedicle screws converge, but an overhanging pelvis may limit this in vivo. The screws will typically aim at the superior border of sacral promontory. The instrument placement and the pedicle screw placement in the virtual surgical plan will be selected or defined in a manner where the pedicle screw and/or the instruments will avoid the S1 foramen and any nerve roots. If bicortical screws are used, the screw position will be selected or oriented in order to avoid any injury to the L5 nerve roots; any imaging test such as a CT scan or an MRI scan can be used to identify the L5 nerve root and to place the pedicle screw(s) in the virtual surgical plan, with optional display of the CT or MRI scan and the nerve root, so that its tip and body have a safety margin relative to the nerve root.

The virtual surgical plan can comprise a 2D or 3D display of the spinal structures. The 2D display can be a multiplanar display, for example showing the spine in axial, oblique axial, sagittal, oblique or curved sagittal, coronal, oblique or curved coronal projections. A 3D display can show the spine, for example, from a posterior projection, an anterior projection, a lateral projection, a projection from the top or the bottom, or a projection along a nerve root or the thecal sac or the cord. Representative bony structures that can be displayed in this manner include, for example, the spinous processes, the lamina, the facet joints, the pedicles and the vertebral bodies including the endplates, anterior, posterior, medial and lateral cortex. In some embodiments of the invention, the view perspective will be the perspective that the surgeon's head and the OHMD have relative to the surgical field and the patient. The perspective can be different for the left eye display and the right eye display, in particular when stereoscopic display technique is used, with substantially identical view angles of the virtual data of the patient seen by the surgeon's left eye through the display of the OHMD unit and the live data of the patient seen by the surgeon's left eye through the OHMD unit and substantially identical view angles of the virtual data of the patient seen by the surgeon's right eye through the display of the OHMD unit and the live data of the patient seen by the surgeon's right eye through the OHMD unit.

In some embodiments, the thecal sac, neural structures and nerve roots, e.g. L4, L5, and S1 are highlighted in the surgical plan in addition to the bony structures. The nerve roots can be highlighted using segmentation techniques known in the art, e.g. automatic or semi-automatic or manual segmentation. Alternatively, an operator or a surgeon can click on the nerve root in the vicinity of a pedicle or intended pedicle screw placement. The location of the click can be stored in the image data volume and can be highlighted with a different color. The area or volume that includes the click can be registered as a safety zone which the pedicle screw and any instruments used for the placement should not enter. A safety margin, e.g. of 2, 3, 4, 5, 7 or 10 mm can be added to the safety zone. The surgical plan and the placement or position or orientation of any pedicle screw and related instrumentation will be modified or adapted during the virtual planning to ensure that no nerve damage or impingement will be caused by the surgical procedure.

In some embodiments, vascular structures can be highlighted using automated, semi-automated, or manual segmentation techniques or simple clicks or image markings performed by a surgeon or operator. Such vascular structures can, for example, include the aorta, the inferior vena cava, any branches of the aorta or the inferior vena cava, intercostal arteries, the innominate artery. A safe zone and/or a safety margin of 2, 3, 4, 5, 7 or 10 mm or more mm can be defined around these vascular structures. The surgical plan and the placement or position or orientation of any pedicle screw and related instrumentation will be modified or adapted during the virtual planning to ensure that no vascular damage will be caused in the surgical procedure.

The virtual surgical plan can include
Identifying the desired pedicle screw position and/or location and/or orientation
Identifying the desired position and/or location and/or orientation and/or trajectory of any surgical instrument used for placing the pedicle screw, e.g. an awl, a probe, a wire, a tab, a screw driver and the like, including the pedicle screw itself.
Identifying the desired rod position and/or location and/or orientation
Identifying the desired spinal deformity correction if applicable, e.g. correction of kyphosis, lordosis, scoliosis, sagittal deformity, coronal deformity, rotational deformity, facture deformity
Identifying sensitive structures, e.g. neural structures, nerve roots, vascular structures
Defining safe zone, e.g. for cortical penetration, e.g. in a pedicle, neural structures, nerve roots and/or vascular structures The virtual surgical plan can include, optionally predefined, criteria to automated or semi-automated virtual placement of a pedicle screw in the patient's data. Such criteria can include the distance between the pedicle screw or related bone void to accept the pedicle screw to the medial, lateral, superior, and/or inferior endosteal surface or cortical surface in portions or all of the pedicle or the area or volume between pedicle screw or related bone void to accept the pedicle screw to the medial, lateral, superior, and/or inferior endosteal surface or cortical surface in portions or all of the pedicle. If the surgeon manually, visually places the virtual pedicle screw on the 2D or 3D display, the same or similar criteria can be applied by the software to highlight potential areas that may result in clinical problems, e.g. a cortical breach or a nerve root injury. For example, if a virtual pedicle screw comes within 1, 2, or 3 mm of the medial cortex of a pedicle, the software, using image processing and segmentation of the bone, endosteal bone or cortical bone, can highlight such proximity and potential risk. The highlighting can occur, for example, by color coding areas of proximity to a cortex or to a neural or vascular structure or by other visual cues and acoustic warning signals. Such highlighted areas can optionally also be displayed by the OHMD during the surgical procedure, stereoscopically or non-stereoscopically. Optionally, highlighted areas can be displayed in outline format.

The selection of a size, width, diameter or length of a pedicle screw can also be performed in a manual, semi-automatic or automatic matter using criteria such as the distance between the pedicle screw or related bone void to accept the pedicle screw to the medial, lateral, superior, and/or inferior endosteal surface or cortical surface in portions or all of the pedicle or the area or volume between pedicle screw or related bone void to accept the pedicle screw to the medial, lateral, superior, and/or inferior endosteal surface or cortical surface in portions or all of the pedicle.

The surgeon can place the digital hologram of the virtual pedicle screw manually, for example using a virtual interface, on the virtual display of the patient's hidden subsurface anatomy using criteria such as location of the pedicle screw including its tip in the vertebral body, location of the pedicle screw including its tip in relationship to a spinal/vertebral body fracture, location of the pedicle screw including its tip in relationship to a superior endplate, location of the pedicle screw including its tip in relationship to an inferior endplate, location of the pedicle screw including its tip in relationship to an anterior vertebral cortex and/or a posterior vertebral cortex, location of the pedicle screw including its tip in relationship to a vessel, location of the pedicle screw including its tip in relationship to the aorta, location of the pedicle screw including its tip in relationship to the inferior vena cava, location of the pedicle screw including its tip in relationship to neural structures, the thecal sac, nerve roots and/or the spinal cord, distance, area or volume between the pedicle screw including its tip to a spinal/vertebral body fracture, distance, area or volume between the pedicle screw including its tip to a superior endplate, distance, area or volume between of the pedicle screw including its tip to an inferior endplate, distance, area or volume between the pedicle screw including its tip to the an anterior and/or posterior vertebral cortex, distance, area or volume between the pedicle screw including its tip to a vessel, distance, area or volume between the pedicle screw including its tip to the aorta, distance, area or volume between the pedicle screw including its tip to the inferior vena cava, distance, area or volume between the pedicle screw including its tip to neural structures, the thecal sac, nerve roots and/or the spinal cord. The surgeon can use this information on location or distance or area or volume also to select the size, width, diameter or length of the pedicle screw in the virtual surgical plan or using the virtual representations of the pedicle screw(s) and the patient's anatomy. Safe zone criteria can be defined for the foregoing criteria, for example 1, 2 or 3 or 5 or more mm from a cortex or a neural structure. If the surgeon places the pedicle screw or any related surgical instruments for the placement of the pedicle screw too close to the safe zone or within the safe zone, the area can be highlighted or another visual or acoustic alert can be triggered by the software.

Alternatively, the software can place the pedicle screw automatically or semiautomatically on the virtual display of the patient using criteria such as location of the pedicle screw including its tip in the vertebral body, location of the pedicle screw including its tip in relationship to a spinal/vertebral body fracture, location of the pedicle screw including its tip in relationship to a superior endplate, location of the pedicle screw including its tip in relationship to an inferior endplate, location of the pedicle screw including its tip in relationship to the an anterior and/or posterior vertebral cortex, location of the pedicle screw including its tip in relationship to a vessel, location of the pedicle screw including its tip in relationship to the aorta, location of the pedicle screw including its tip in relationship to the inferior vena cava, location of the pedicle screw including its tip in relationship to neural structures, the thecal sac, nerve roots and/or the spinal cord, distance, area or volume between the pedicle screw including its tip to a spinal/vertebral body fracture, distance, area or volume between the pedicle screw including its tip to a superior endplate, distance, area or volume between of the pedicle screw including its tip to an inferior endplate, distance, area or volume between the pedicle screw including its tip to the an anterior and/or posterior vertebral cortex, distance, area or volume between the pedicle screw including its tip to a vessel, distance, area or volume between the pedicle screw including its tip to the aorta, distance, area or volume between the pedicle screw including its tip to the inferior vena cava, distance, area or volume between the pedicle screw including its tip to neural structures, the thecal sac, nerve roots and/or the spinal cord. The software can use the information on location or distance or area or volume can also to select the size, width, diameter or length of the pedicle screw in the virtual surgical plan. Safe zone criteria can be defined for the foregoing criteria, for example 1, 2 or 3 or more mm from a cortex or a neural structure. If the software cannot place the pedicle screw or any related surgical instruments for the placement of the pedicle screw without violating one of the safe zones or places it too close to the safe zone, the area can be highlighted or another visual or acoustic alert can be triggered by the software. The surgeon can then manually adjust the virtual position of the pedicle screw or any related surgical instruments for the placement of the pedicle screw such as an awl, a probe, a needle, a wire, a tap and the like.

The virtual surgical plan can only simulate the final desired placement of the pedicle screw(s) and any related rods. The desired trajectory of any surgical instruments used for placing the pedicle screw such as an awl, a probe, a needle, a wire, a tap and the like can then be projected during the surgery based on the virtual surgical plan and the final desired placement position of the pedicle screw(s) and any related rods.

In some embodiments of the invention, each instrument or, for example, the principal instruments used for the placement of the pedicle screw(s) and/or the rods can be displayed during the surgery in the virtual display. The physical instruments seen through the OHMD can be aligned with the corresponding virtual instruments displayed by the OHMD, optionally in 3D, stereoscopic or non-stereoscopic, thereby achieving the desired surgical alterations, for example according to the virtual surgical plan.

Figure 17A:
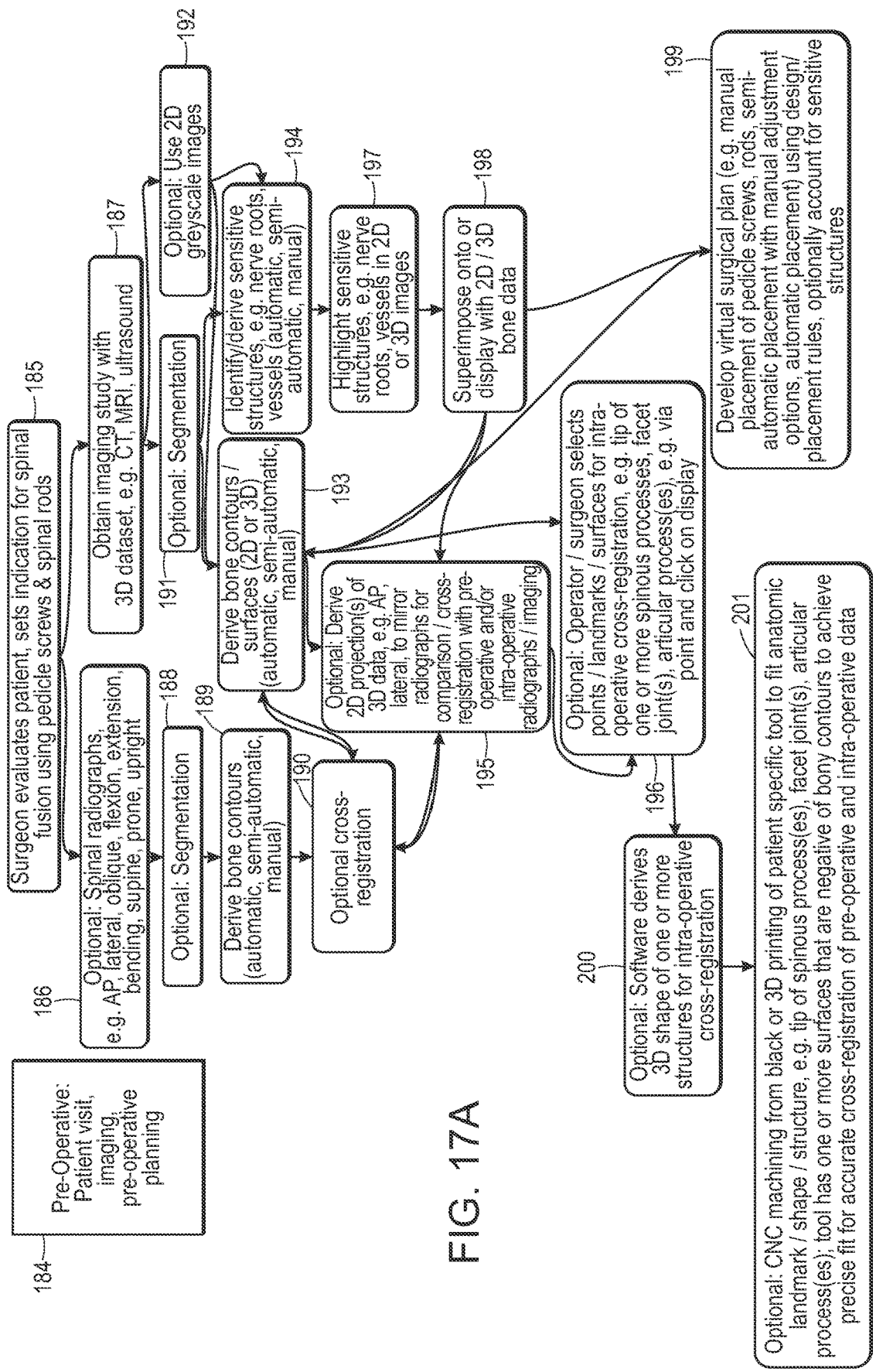
FIGS. 17A-17D are illustrative flow charts of select options and approaches for performing spine surgery in a mixed reality environment according to some embodiments of the present disclosure.

FIGS. 17A-17D are illustrative flow charts of select options and approaches for performing spine surgery in a mixed reality environment. In FIG. 17A, pre-operative patient visit, imaging, pre-operative planning 184, a surgeon evaluates a patient and sets the indication for spinal fusion using pedicle screws and spinal rods 185. Optionally spinal radiographs 186 and/or 3D imaging, e.g. CT or MRI 187, can be obtained. Optionally the data can be segmented 188 and 191. Optionally 2D data can be used 192. Bone contours can be derived automatically, semi-automatically or manually 189 from the radiographs 189 or CT or MRI 193. Optionally, sensitive structures such as nerve roots and vessels can be determined 194 and superimposed on the display of the 2D or 3D bone data 198. Bone contours from radiographs and other imaging studies such as CT or MRI can optionally be cross-registered, e.g. using coordinate transfer or using registration in a common coordinate system 190. Optionally, 2D projections of 3D data can be generated, for example to generate matching projections that can align with and/or be superimposed with intra-operative radiographs 195. Optionally, a surgeon or operator can select points or landmarks or surfaces for intra-operative registration 196. Bone contours 189 and/or 193 and other data, e.g. 198, 197, 196 can be used to develop a virtual surgical plan for placement of the pedicle screw(s) and rod(s) 199. Optionally, the shape of one or more structures used for intra-operative registration can be derived 200 using software as described for example in Data Segmentation. Optionally, a patient specific template can be generated for the spine 201, as described, for example in WO9325157A1.

Figure 17B:
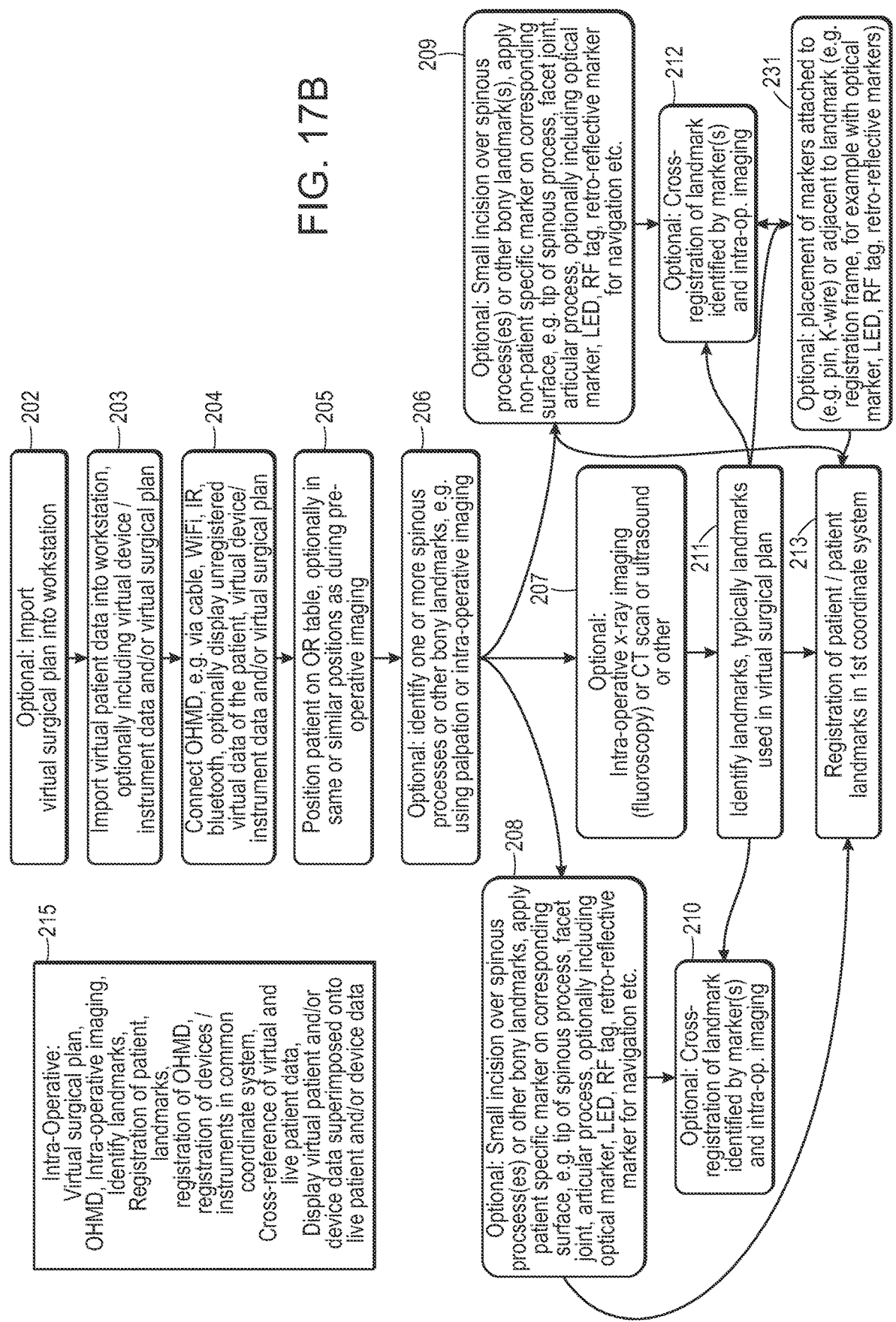

In FIG. 17B, intra-operative virtual surgical plan, imaging, landmarks, registration, cross-reference of virtual and live patient data 215, the data from FIG. 17A, e.g. 189, 193, 194, 195, 199, 200, can be imported into a workstation 202. The virtual data of the patient can also be imported, optionally including virtual instrument data, virtual device data and/or the virtual surgical plan 203. The OHMD can be connected to the workstation 204 and can, optionally, display unregistered virtual data 204. The patient can be positioned on the OR table, optionally in the same position as that used for pre-operative imaging 205. Step 205 can optionally be performed before 202, 203 and 204. Optionally, one or more spinous processes or other bone landmarks or skin references can be identified 206. Optionally, intra-operative imaging can be performed 207 using, for example, x-rays or CT/O-arm imaging 207. Optionally, an incision can be performed over a spinous process and a patient specific marker or template, an optical marker or other markers can be applied for registration 208 and 209. Landmarks, e.g. ones used in the virtual surgical plan 199, can be identified 211, and can optionally be cross-referenced or registered with landmarks identified by intra-operative imaging or patient specific markers or optical markers or other markers 210 and 212, for example in a common coordinate system, e.g. with the OHMD, or in different coordinate systems using coordinate transfers. The patient can then be registered in a common, e.g. first, coordinate system 213. Optionally, markers can be attached to rigid structures fixed to the spine and/or landmarks 231.

Figure 17C:
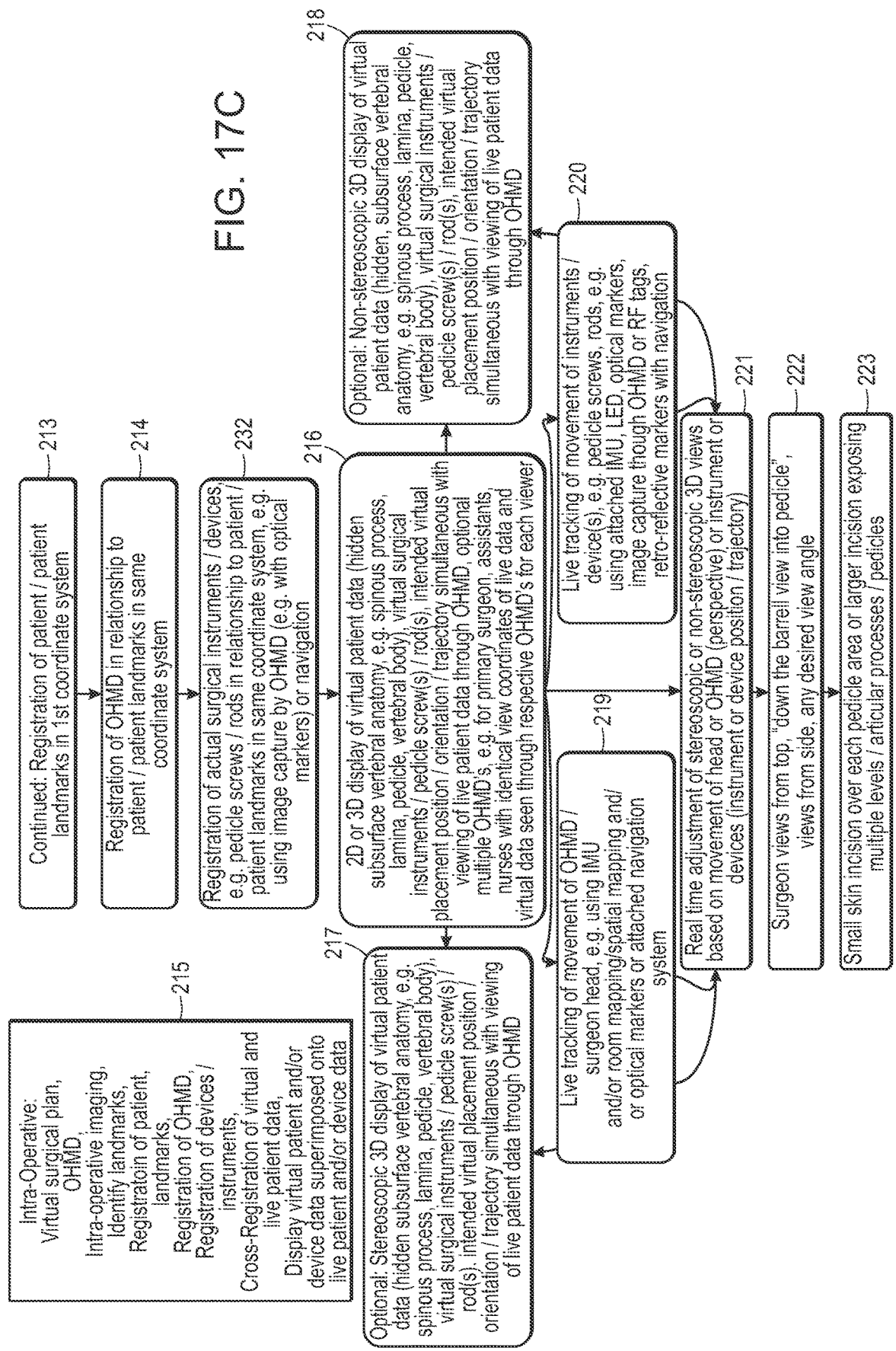

In FIG. 17C, continuation of intra-operative virtual surgical plan, imaging, landmarks, registration, cross-reference of virtual and live patient data 215, after the registration of patient landmarks 213 one or more OHMD/s can be registered in relationship to the patient or patient landmarks 214, e.g. using spatial mapping or optical markers or navigation markers or combinations thereof or any other registration technique described in the application. Actual surgical instruments such as awls and pins and implants such as pedicle screws and rods can also be registered 232. A 2D or 3D display can be generated, which can include hidden subsurface anatomy, e.g. of a vertebral body, pedicle, facet joints, virtual surgical instruments and virtual implants 216. These can be superimposed with and aligned with the corresponding live data of the patient, e.g. the center of a pedicle in which an awl or a screw can be placed in a predetermined position 216. Stereoscopic 217 and non-stereoscopic 218 displays can be generated. Multiple viewers can see the virtual data and the live data superimposed using multiple OHMDs each displaying the virtual data with the view perspective matching the view perspective of the live data for the individual viewer 216, 217, 218. The viewer(s) can move their head freely and the OHMD worn by each viewer can remain registered with the live data using, for example, one or more of IMUs attached to the OHMD, room mapping, spatial mapping, e.g. of the surgical site or the patient or both, optical markers or navigation markers 219. Instruments or implants, e.g. pedicle screws or rods, can also be tracked using, for example, IMUs, LEDs, optical markers, or navigation markers 220. The display of the OHMD can be adjusted in real time, e.g. 30 frames per second or more, based on head movement or instrument or device movement or combinations thereof 221. The surgeon can obtain a down the barrel view of a pedicle for placing tools, such as pins, or screws, for example in real time 222. A skin incision can be performed over select pedicle or multiple spine levels 223.

Figure 17D:
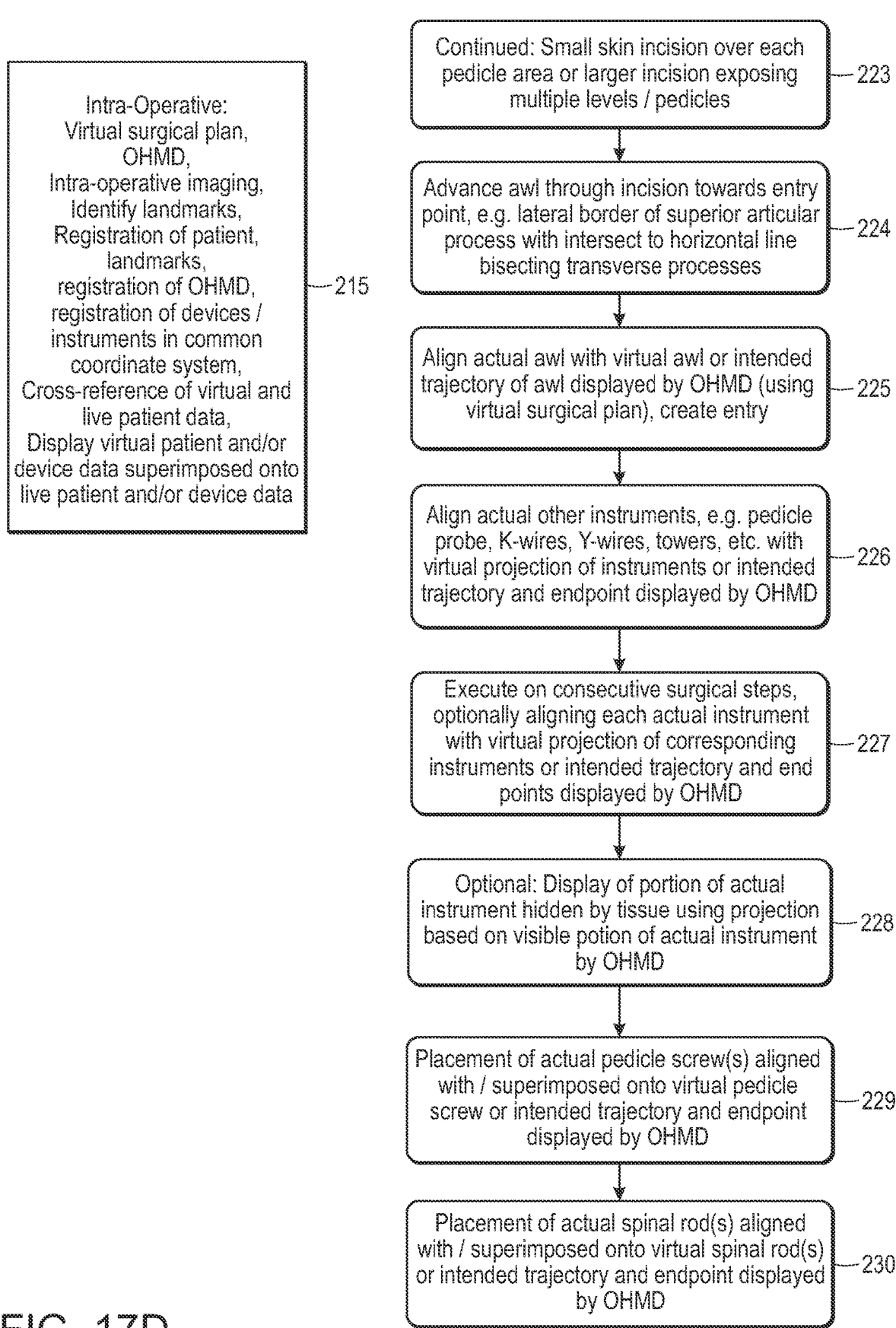

In FIG. 17D, continuation of intra-operative virtual surgical plan, imaging, landmarks, registration, cross-reference of virtual and live patient data 215, the surgeon can, for example, advance an awl towards the entry point for a pedicle screw 224. The actual or physical awl can be aligned with a virtual awl 225. Other physical instruments can be aligned with their corresponding virtual instrument or, for example, an intended path or endpoint 226. Consecutive surgical steps can be executed aligning physical with virtual tools, instruments or implants 227. Optionally, portions of the physical instrument that are hidden inside or by the tissue can be displayed in the virtual display in the augmented reality system using, for example, the alignment information from the visible portions of the instrument 228. For this purpose, optical markers or navigation markers can, for example, be attached to the instrument to register it and compute its hidden portions. The physical or actual pedicle screw can be placed aligned with or superimposed with the hidden subsurface anatomy, e.g. the pedicle, or a virtual pedicle screw, or an intended path or endpoint or combinations thereof 229. The physical spinal rod can be placed aligned with or superimposed onto a virtual spinal rod 230; optionally, the spinal rod can be placed aiming at virtual representations of the rod receptacle or receiving or holding or attachment mechanisms of the pedicle screw(s). The rod receptacle or receiving or holding or attachment mechanisms can be magnified by the OHMD for this purpose, for example around a central axis or central point, to facilitate aiming of the physical rod. The hidden portions of the physical rod can be virtually displayed by the OHMD, optionally also magnified, and aimed at the rod receptacle or receiving or holding or attachment mechanisms.

Any of the registration techniques and/or techniques described in the embodiments including implantable and attachable markers, calibration and registration phantoms including optical markers, navigation markers, infrared markers, RF markers, LEDs with image capture and IMUs can be applied for spinal surgery and procedures. For example, in a spinal surgery or procedure, one or more patient specific markers or templates can be applied to one or more spinous processes or articular processes or transverse processes or other spinal structures, for example through a small incision. By applying the patient specific markers or templates to the corresponding structure(s) on the patient, reliable identification of spinal levels is possible, optionally without intraoperative imaging. Moreover, pedicle screws and related instruments or vertebroplasty or kyphoplasty needles and trocars and related instruments can be placed reliably following a trajectory or desired position of the pedicle screws and related instruments or vertebroplasty or kyphoplasty needles and trocars projected by the OHMD using an optional virtual surgical plan. Of note, reliable identification of spinal levels and reliable placement of pedicle screws, rods, and related instruments and or vertebroplasty or kyphoplasty needles and trocars is also possible using the OHMD with the other registration and cross-referencing techniques described in the invention or known in the art.

The same steps and OHMD guided spinal procedures are also possible using the OHMD with the other registration and cross-referencing techniques described in the invention or known in the art, such as, for example, registration using anatomic landmarks or registration or calibration phantoms including optical markers or image capture, optionally using optical markers, or surgical navigation.

In some embodiments of the invention, the registration of virtual patient data and live patient data using the techniques described herein can be repeated after one or more surgical steps have been performed in an OHMD guided spinal procedure. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the digital holograms of the patient's tissue and/or surgical site including hidden and/or obscured parts after the surgical tissue alteration can be performed using the same techniques described in the foregoing or any of the other registration techniques described in the specification or any other registration technique known in the art.

Hip Replacement

Any of the registration techniques and/or techniques described in the embodiments can be applied for hip replacement surgery, including resurfacing, partial and total hip replacement including implantable and attachable markers, calibration and registration phantoms including optical markers, navigation markers, infrared markers, RF markers, patient specific markers, LEDs with image capture and IMUs. For example, one or more patient specific markers or templates or optical markers can be applied to the edge of the acetabulum, the inside of the acetabulum or a pelvic wall. Similarly, one or more patient specific markers or templates or optical markers can be applied to a greater trochanter, a lesser trochanter, a femoral shaft or a femoral neck. By applying the one or more patient specific markers or templates and/or optical markers to the corresponding structures on the patient, virtual data and live data can be effectively cross-referenced and/or registered in a common coordinate system, for example with one or more OHMDs. By registering the patient specific marker or template and/or optical marker in relationship to the OHMD also or by using any of the other registration techniques or techniques described herein or known in the art, the OHMD can display or superimpose the desired position, location, orientation, alignment and/or trajectory of any surgical instrument used during hip replacement. For example, an acetabular reamer can be applied at a predetermined angle, with the long axis of the reamer typically matching the desired acetabular cup angle, offset, medial or lateral position and/or anteversion and/or inclination, e.g. from a virtual surgical plan for the patient.

Figure 18A:
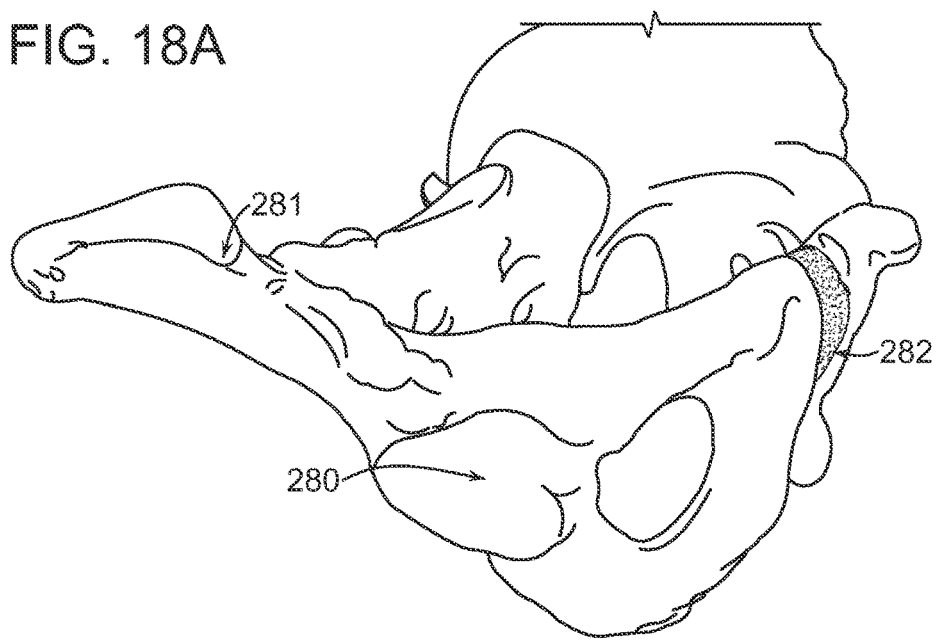
FIGS. 18A-18F are illustrative examples of displaying a virtual acetabular reaming axis using one or more OHMDs and aligning a physical acetabular reamer with the virtual reaming axis for placing an acetabular cup with a predetermined cup angle, offset, medial or lateral position and/or anteversion according to some embodiments of the present disclosure.
Figure 18B:
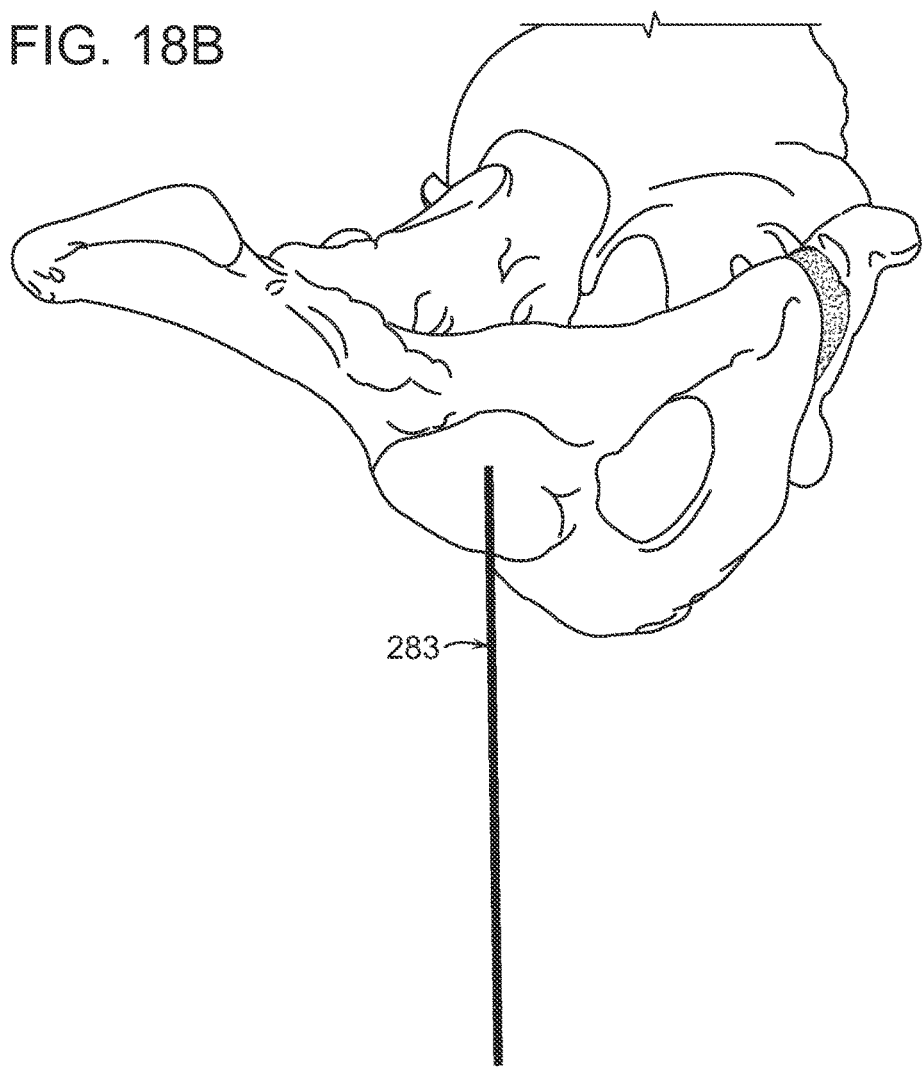
Figure 18C:
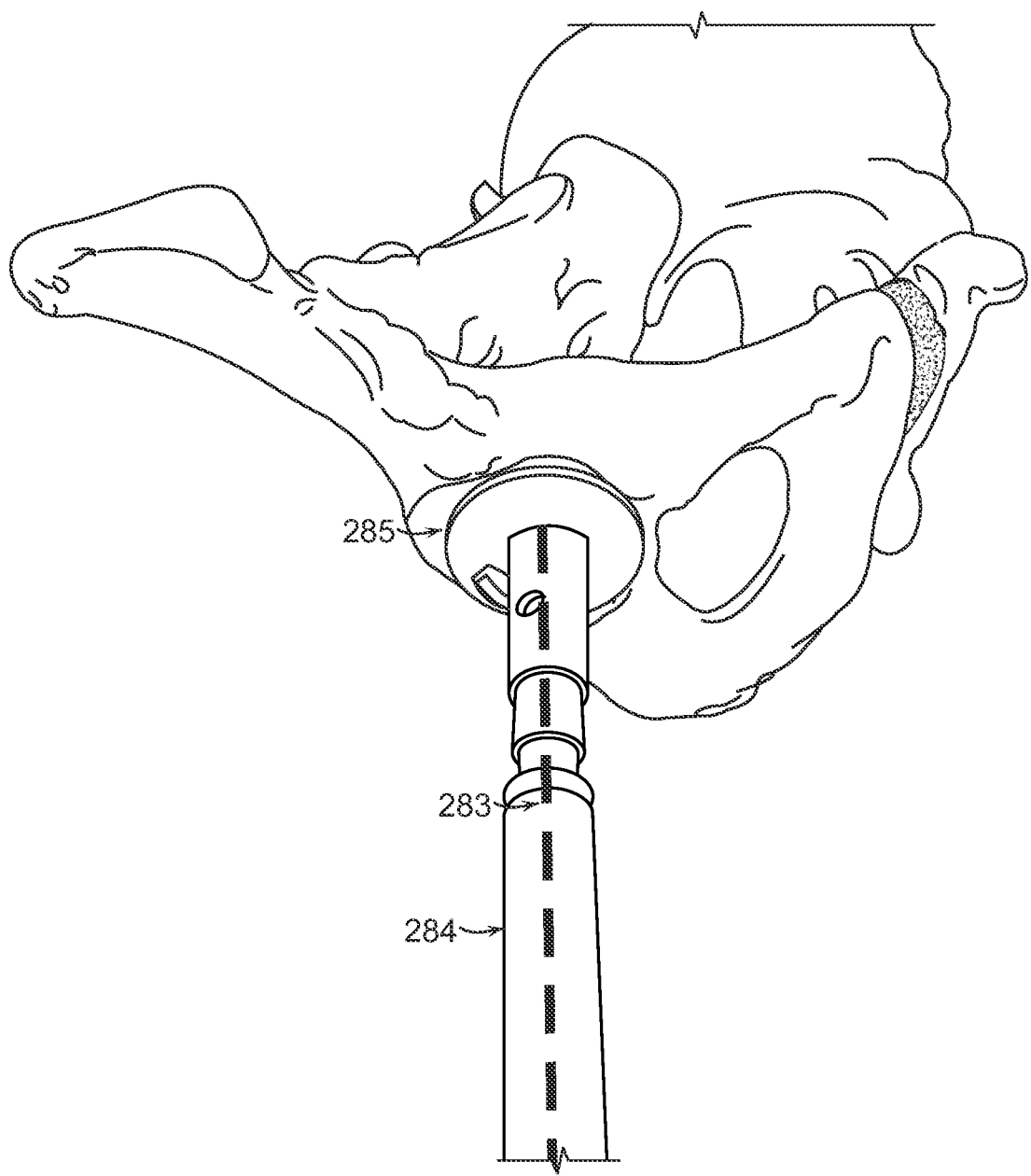

FIGS. 18A-18F are illustrative examples of displaying a virtual acetabular reaming axis using one or more OHMDs and aligning a physical acetabular reamer with the virtual reaming axis for placing an acetabular cup with a predetermined cup angle, offset, medial or lateral position and/or anteversion and/or inclination. FIG. 18A shows a first surgeon's view, e.g. through an OHMD, onto the patient's exposed acetabulum 280. Note also the anterior superior iliac spine 281 and the symphysis pubis 282, which can optionally be used for registration purposes, for example using attached optical markers or navigation markers. In FIG. 18B, the first surgeon can see a virtual acetabular reaming axis 283 through the OHMD, which can be oriented in a predetermined manner to achieve a predetermined acetabular cup angle, offset, medial or lateral position and/or anteversion and/or inclination, e.g. from a virtual surgical plan for the patient. In FIG. 18C, the first surgeon aligns the physical acetabular reamer shaft 284 so that its central axis is aligned or superimposed with the virtual acetabular reaming axis thereby placing the reamer head 285 in the acetabulum in a predetermined position and orientation for a predetermined acetabular cup angle, offset, medial or lateral position and/or anteversion and/or inclination.

Figure 18D:
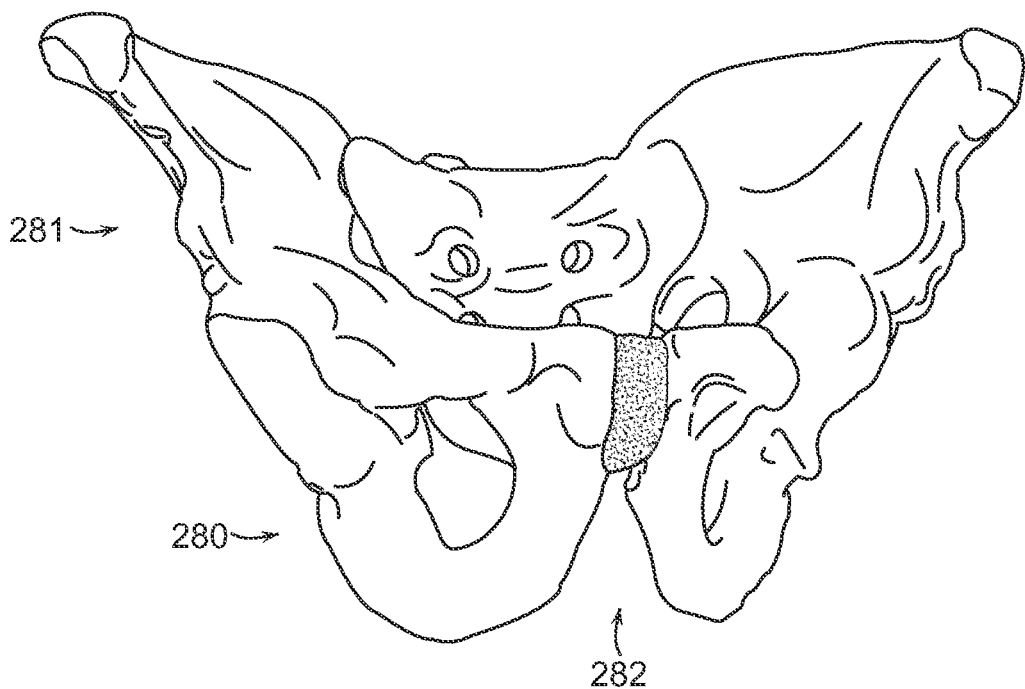
Figure 18E:
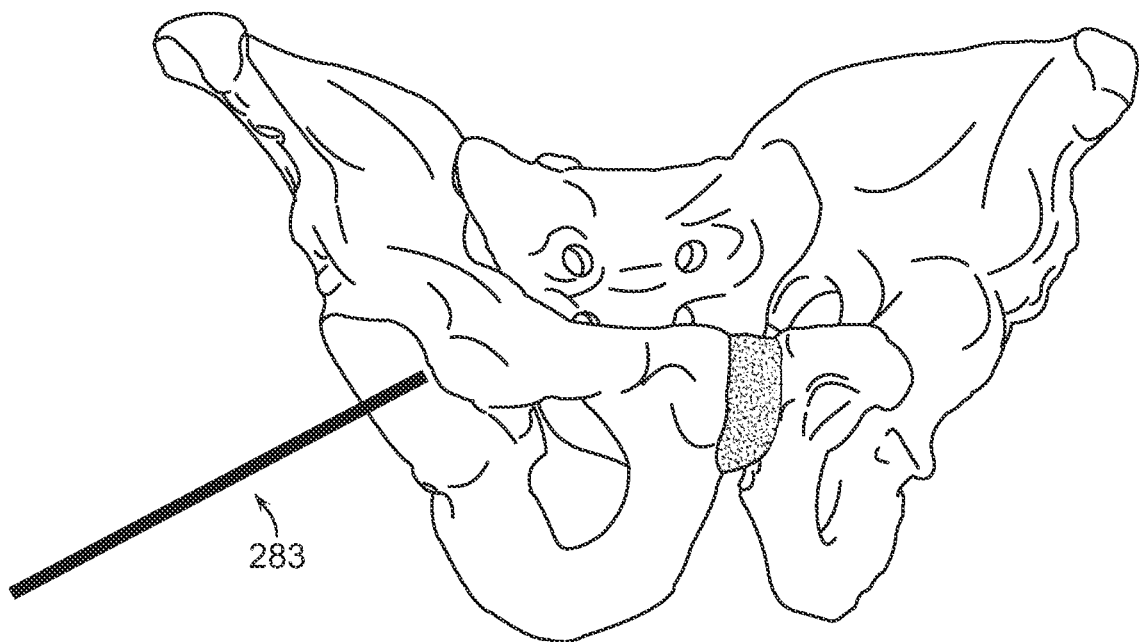
Figure 18F:
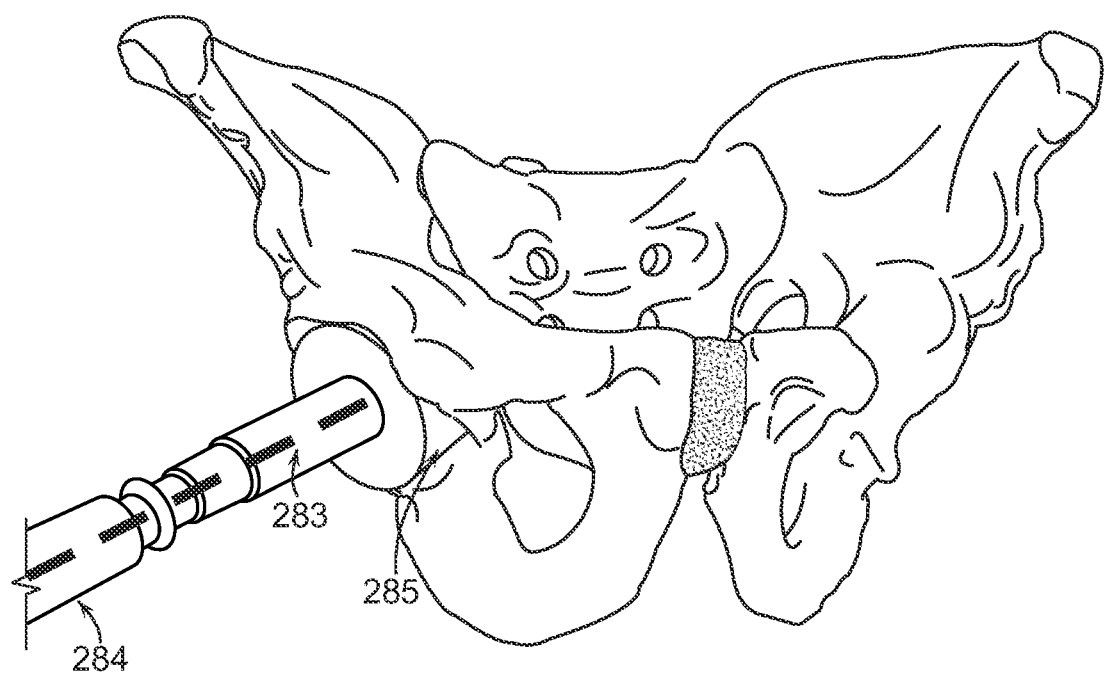

FIG. 18D shows a second surgeon's view with his or her respective view perspective of live data and virtual data through the OHMD onto the patient's exposed acetabulum 280. Note also the anterior superior iliac spine 281 and the symphysis pubis 282, which can optionally be used for registration purposes, for example using attached optical markers or navigation markers. In FIG. 18E, the second surgeon can see the virtual acetabular reaming axis 283 through the OHMD, which can be oriented in a predetermined manner to achieve a predetermined acetabular cup angle, offset, medial or lateral position and/or anteversion and/or inclination, e.g. from a virtual surgical plan for the patient. The virtual acetabular reaming axis is projected with a view angle or view perspective matching the view angle or view perspective of the live data of the patient seen by the second surgeon. In FIG. 18F, the second surgeon can see how the physical acetabular reamer shaft 284 is aligned by the first surgeon so that its central axis is aligned or superimposed with the virtual acetabular reaming axis thereby placing the reamer head 285 in the acetabulum in a predetermined position and orientation for a predetermined acetabular cup angle, offset, medial or lateral position and/or anteversion and/or inclination.

Thus, the surgeon can hold the physical acetabular reamer seeing the live data through the OHMD; at the same time, the OHMD can display or project a digital hologram of the corresponding virtual acetabular reamer with the virtual acetabular reamer aligned and oriented to achieve a desired acetabular cup position, e.g. anteversion, inclination, as optionally defined in a virtual surgical plan. Alternatively, the OHMD can display a partial (e.g. broken or dotted) or complete 2D or 3D outline of the virtual acetabular reamer or one or more placement indicators, e.g. lines indicating the predetermined placement position and orientation of the acetabular reamer, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position and/or or virtual predetermined rim position and/or a virtual predetermined central axis orientation or position and/or a virtual predetermined anteversion.

The surgeon can now align the physical acetabular reamer with the virtual acetabular reamer or its 2D or 3D outline or placement indicator or predetermined or virtual reaming axis displayed by the OHMD so that the physical acetabular reamer is substantially superimposed or aligned with or oriented along the virtual acetabular reamer or its 2D or 3D outline or placement indicator or virtual reaming axis. The OHMD can also indicate the desired reaming depth as optionally defined in a virtual surgical plan. The desired reaming depth can be displayed by the OHMD, e.g. as a virtual red border to which the physical reamer can be advanced. If the reaming surface of the physical reamer is not visible since it is hidden by tissue, e.g. soft-tissue or bone, it can be estimated based on the visible portions of the physical reamer and it can be optionally displayed by the OHMD, e.g. using a different color than the display of the virtual reamer or the virtual "red border" for the reaming depth. The physical reaming depth of the physical reamer can also be measured, for example via image capture or mechanical data capture of a numeric scale on the physical reamer which indicates reaming depth, or by attaching IMUs or one or more optical markers, RF tags or retro-reflective markers for navigation to the reamer and by comparing physical measured reaming depth to the virtual surgical plan. The OHMD can indicate when the desired reaming depth has been achieved, for example with a visual or acoustic signal. One or more optical markers can also be attached to the shaft of the acetabular reamer. By measuring the position of the one or more optical markers, e.g. two optical markers in two different locations along the shaft of the reamer, the long axis of the physical acetabular reamer can be determined using image or video capture and can be compared to the predetermined virtual reaming axis to achieve a desired cup placement, including a desired offset and/or cup angle and/or anteversion.

The physical acetabular cup can be placed by obtaining substantial or near substantial superimposition with the virtual acetabular cup or its 2D or 3D outline or placement indicator(s) projected by the OHMD using, for example, the virtual surgical plan for the patient, whereby the virtual acetabular cup or its 2D or 3D outline or placement indicator(s) show the desired anteversion and inclination. Depending on the surgical approach, e.g. anterior, posterior or posterolateral, only those portions of the virtual acetabular cup can be displayed that correspond to the portions of the physical acetabular cup which would be visible for the surgical approach or surgical site. Optionally, the physical values of anteversion and inclination can be numerically displayed, e.g. by the OHMD, showing, for example, the desired values for the patient from the virtual surgical plan and the physical values based on the physical cup or trial cup position, location, orientation, and/or alignment. If there is a visual discrepancy, i.e. incomplete superimposition between virtual cup displayed by the OHMD and the physical or trial cup, or a numeric discrepancy, e.g. in virtual cup anteversion and/or inclination from the virtual surgical plan versus physical cup anteversion and/or inclination, the surgeon can correct the position, location, orientation, and/or alignment of the physical cup prior to impaction.

By utilizing the 3D anatomic information of the patient from the pre-operative data or by using intra-operative measurements, for example optical markers for determining a center of rotation of a hip joint or for determining a desired anteversion, the surgeon can work more accurately in this manner, thereby reducing, for example, the need for offset or asymmetric liners.

Of note, the same steps and OHMD guided acetabular procedures are also possible using the OHMD with any of the registration and cross-referencing techniques described in the invention and known in the art, such as, for example, registration using anatomic landmarks or registration or calibration phantoms including optical markers or image capture, optionally using optical markers, or surgical navigation or patient specific markers or intra-operative imaging.

Any of the registration techniques or techniques described herein including implantable and attachable markers, calibration and registration phantoms including optical markers, navigation markers, infrared markers, RF markers, patient specific markers, LEDs with image capture and IMUs can be applied for registering the patient's proximal femur in relationship to, for example, one or more OHMDs worn by the surgeon and/or is assistants, and/or in relationship to one or more surgical instruments, pins, drills, saws, reamers, impactors, broaches and the like and/or in relationship to one or more femoral or acetabular implants, including metal and/or polyethylene components. For example, by applying one or more optical markers and/or patient specific markers or templates to a greater trochanter, a lesser trochanter, a femoral shaft or a femoral neck, virtual and physical live patient data can be cross-referenced on the femoral side. Optionally, a pin or a screw can be inserted into the proximal femur, e.g. in a greater trochanter, which can be used as a reference for registration, for example if an optical marker or patient specific marker moves. Optical markers can be optionally attached to the pin or screw. Multiple pins or screws can be used in this manner. The virtual surgical plan can include a desired neck cut location for a particular femoral component. The neck cut can be designed or selected to avoid any offset issues and to maintain the patient's leg length in the virtual surgical plan. By registering the optical marker and/or patient specific marker or template in relationship to the OHMD also, e.g. in a common coordinate system with the OHMD, the surgical site, the proximal femur, the OHMD can display or superimpose and/or project digital holograms showing the desired or predetermined position, location, orientation, alignment and/or trajectory or predetermined plane of any surgical instrument including a saw for performing the femoral neck cut. After successful registration of virtual and live data of the patient using any of the techniques or techniques described herein, the OHMD can show the desired 3D trajectory including the desired location, entry point and angles in x, y and z direction for the femoral neck cut or the OHMD can display one or more digital holograms of a virtual cut plane and/or a virtual saw or saw blade in the position, location, angular orientation, and trajectory (e.g. as a dotted line or arrow) defined in the surgical plan which the surgeon can then match with the physical saw, i.e. the surgeon can orient and align the physical saw so that it will be aligned with or substantially superimposed onto the virtual saw (see also FIGS. 4A-4C). Alternatively, the OHMD can show a digital hologram of a partial (e.g. broken or dotted) or complete 2D or 3D outline of the virtual saw or placement indicators, e.g. lines indicating the predetermined placement position and orientation of the saw, e.g. a virtual predetermined medial placement or position, a virtual predetermined lateral placement or position, a virtual predetermined anterior placement or position, a virtual predetermined posterior placement or position, a virtual predetermined superior placement or position and/or a virtual predetermined inferior placement or position. Alternatively, the OHMD can show a digital hologram of a virtual femoral neck cut plane.

Optionally, for example once the entry point on the femoral neck has been defined or the desired location, orientation and/or direction of the saw has been determined with assistance from the OHMD, the surgeon can apply a standard saw guide to the femoral neck to facilitate the neck cut. Alternatively, the OHMD can display a digital hologram of a virtual femoral neck saw guide or its corresponding 2D or 3D outline or placement indicators in its desired position or location on the femoral neck. The physical saw guide can then be aligned with the corresponding virtual saw guide or its corresponding 2D or 3D outline or placement indicators placed in the desired position, orientation and angulation based on the virtual surgical plan of the patient. The virtual saw guide can have the same or similar shape and/or one or more dimensions or planes as the physical saw guide. Once the physical saw guide is substantially superimposed in position with the virtual saw guide or its corresponding 2D or 3D outline or placement indicators displayed by the OHMD, the surgeon can optionally pin the physical saw guide in place and perform the neck cut. By executing the neck cut using one of these approaches which utilize accurate 3D anatomic information of the patient from the pre-operative scan and/or intra-operative measurements including registration, e.g. using optical markers, leg length and offset can be more accurately preserved or addressed.

Similarly, the OHMD can project the desired position, location, orientation and trajectory of any virtual femoral reamers and impactors. Alternatively, the OHMD can only show a partial (e.g. broken or dotted) or complete 2D or 3D outline of the virtual femoral reamers or impactors or placement indicators, e.g. lines indicating the predetermined placement position and orientation of the reamers or impactors, e.g. a virtual predetermined medial placement or position, a virtual predetermined lateral placement or position, a virtual predetermined anterior placement or position, a virtual predetermined posterior placement or position, a virtual predetermined superior placement or position or a virtual predetermined inferior placement or position or a virtual reaming axis, e.g. a central axis through the reamer shaft. The OHMD can also display a digital hologram of a predetermined virtual reaming and/or broaching axis, which can provide a desired femoral component position including one or more of an offset and/or anteversion including, for example, composite anteversion for both femoral and acetabular components. The virtual femoral reamers and impactors can have the same or similar shape and dimensions as the physical femoral reamers and impactors. The surgeon can then match the position, location, orientation and trajectory (e.g. indicated by a dotted line or an arrow in the virtual data) of the physical femoral reamers and impactors with the virtual reamers and impactors or their corresponding 2D or 3D outlines or placement indicators or a virtual reaming or broaching axis, thereby reducing the possibility of mal-seating of the femoral stem and possibly incorrect femoral anteversion, incorrect femoral offset or femoral component angulation or leg length discrepancy. In some embodiments of the invention, the surgeon can align the OHMD so that the view angle is perpendicular to the femoral shaft axis or, alternatively, the femoral neck axis. The OHMD can then display a bulls-eye or target like structure whereby the surgeon will aim the femoral reamers, impactors, femoral trials and the physical femoral component to be located in the center of the bulls-eye or target. The OHMD can display the desired entry point, e.g. with regard to medial or lateral, anterior or posterior location on the cut femoral neck, and/or entry angle based on the virtual surgical plan including, for example, the virtual femoral component placement. The OHMD can also display the desired femoral version, for example via a solid or dotted line or arrows on the cut femoral neck surface or in relationship to the cut femoral neck surface. The desired femoral version can also be displayed by the OHMD by displaying one or more digital holograms of the femoral reamers, impactors, femoral trials and the final femoral component or their respective 2D or 3D outlines or placement indicators in the desired virtual location and orientation including femoral version based on the virtual surgical plan. In this manner, the surgeon can align the physical femoral reamers, physical impactors, physical femoral trials and the physical final femoral component to be substantially aligned or superimposed with the digital holograms of the one or more virtual femoral reamers, virtual impactors, virtual femoral trials and virtual final femoral component thereby achieving a result near the desired femoral version and, optionally, leg length based on the virtual surgical plan.

All of the foregoing steps and OHMD guided femoral procedures are also possible using the OHMD with any of the other registration and cross-referencing techniques described in the invention or known in the art, such as, for example, registration using anatomic landmarks or implantable and attachable markers, calibration and registration phantoms including optical markers, navigation markers, infrared markers, RF markers, patient specific markers, LEDs with image capture and IMUs.

In some embodiments of the invention, an ultrasound scan can be used to derive the shape information used for designing and producing the patient specific template, e.g. for use on the acetabular side or the femoral side. Optionally, the ultrasound scan can be obtained in supine and/or upright position. By obtaining the ultrasound scan in upright position, information about femoro-acetabular alignment and orientation can be obtained under weight-bearing positions including, for example, femoral or acetabular anteversion, femoral/acetabular/hip flexion, extension, abduction, adduction and/or rotation. By obtaining the ultrasound scan in supine position, information about femoro-acetabular alignment and orientation can be obtained under non-weight-bearing positions including, for example, femoral or acetabular anteversion, femoral/acetabular/hip flexion, extension, abduction, adduction and/or rotation. By comparing data from one or more upright and one or more supine ultrasound scans, e.g. by comparing the relative movement of corresponding anatomic landmarks, information can be obtained about pelvic tilt. The information from the upright and/or supine scan can be used for selecting the desired femoral and acetabular components including, for example, the shape and length of the femoral neck, the offsets, the femoral head component, as well as the shape of the acetabular component, including, for example, offset, mesialized, lateralized, or rimmed acetabular components. The information from the upright and/or supine scan can be used for developing or adjusting the virtual surgical plan, for example by changing the predetermined cup position based on the upright scan information or based on information on pelvic tilt. Similar information can be obtained using supine and upright x-rays studies.

Optionally, the information from the upright and/or supine imaging data can be used to assess information on pelvic tilt, which in turn can be introduced into the surgical plan and component selection in order to avoid or minimize the risk of postoperative complications such as component dislocation.

Thus, by performing hip replacement using the different embodiments of the invention, it is possible for the surgeon to conduct the surgery with high accuracy thereby reducing the possibility of common complications in hip replacement such as offset error or wrong acetabular or femoral anteversion leading to hip dislocation or leg length discrepancy. Optionally, the OHMD can also display sensitive vascular or neural structures, thereby reducing the possibility of vascular injury or, for example, sciatic nerve injury.

In some embodiments of the invention, the registration of virtual patient data and live patient data using the techniques described herein can be repeated after one or more surgical steps have been performed in an OHMD guided hip replacement procedure. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art. For example, the re-registration can be performed using a cut bone surface, e.g. a cut femoral neck using the surface shape, surface area or perimeter or other feature, optionally measured with image capture or mechanical or physical probes, to match, superimpose and/ or register the live patient data and the virtual patient data prior to performing subsequent surgical steps, e.g. a reaming, milling or impacting of the femoral canal for placement of a femoral component. For example, the re-registration can be performed using a milled bone surface, e.g. a milled acetabulum using the surface shape, surface area or perimeter or other feature, optionally measured with image capture or mechanical or physical probes, to match, superimpose and/or register the live patient data and the virtual patient data prior to performing subsequent surgical steps, e.g. a placement of an acetabular component including trial components.

Knee Replacement, Partial or Total

With knee replacement general alignment and orientation recommendations exist, some of which have been summarized in a review (Gromov et al. Acta Orthop 2014, 85, 5, 480-487): Neutral overall coronal alignment is currently the gold standard, and a neutral mechanical axis of the leg or 2-7° valgus anatomical tibial femoral axis can be targeted. The femoral component can be placed in 2-8° coronal valgus with respect to the femoral anatomic axis (e.g., 2°, 3°, 4°, 5°, 6°, 7°, 8°, 2-3°, 2-4°, 2-5°, 2-6°, 2-7°, 2-8°, 3-4°, 3-5°, 3-6°, 3-7°, 3-8°, 4-5°, 5-6°, 5- 7°, 5-8°, 6-7°, 6-8°, 7-8°) and >3 mm of implant component overhang over the bone should be avoided. The tibial component can be placed in neutral coronal alignment (90°) with maximum bone coverage and minimal, if any, implant component overhang. In the sagittal plane, the femoral component can be placed with 0-3° of flexion (e.g. 0°, 1°, 2°, 3°, 0-1°, 0-2°, 0-3°, 1-2°, 1-3°, 2-3°), and the tibial slope can be 0-7° (e.g. 0°, 1°, 2°, 3°, 4°, 5°, 6°, 7°, 0-1°, 0-2°, 0-3°, 0-4°, 0-5°, 0-6°, 0-7°, 1-2°, 1-3°, 1-4°, 1-5°, 1-6°, 1-7°, 2-3°, 2-4°, 2-5°, 2-6°, 2-7°, 3-4°, 3-5°, 3-6°, 3-7°, 4-5°, 4-6°, 4-7°, 5-6°, 5-7°, 6-7°). Internal rotation of the femoral component should be avoided, as the femoral component should be placed in 2-5° of external rotation in relation to surgical transepicondylar axis (e.g., 2°, 3°, 4°, 5°, 2-3°, 2-4°, 2-5°, 3-4°, 3-5°, 4-5°). Excessive tibial rotation with respect to neutral transverse axis of the tibia, tibial tubercle axis and also combined internal tibiofemoral rotation should also be avoided.

Any of the registration techniques and/or techniques described in the embodiments can be applied for knee replacement, e.g. resurfacing, partial and total knee replacement procedures, including implantable and attachable markers, calibration and registration phantoms including optical markers, navigation markers, infrared markers, RF markers, patient specific markers, LEDs with image capture and IMUs. For example, one or more optical marker and/or patient specific markers or templates can be applied to the distal femur, for example the distal anterior cortex and/or the superior trochlea, optionally along with any osteophytes when present. Similarly, one or more optical markers and/or patient specific markers or templates can be applied to the proximal tibia, e.g. the anterior tibial cortex, for example in the tibial plateau area, optionally along with any osteophytes when present, or a tibial spine. By applying the one or more optical markers and/or patient specific markers or templates or any of the other registration techniques including implantable and attachable markers, calibration and registration phantoms, navigation markers, infrared markers, RF markers, LEDs with image capture and IMUs to the corresponding structures on the patient, virtual data, e.g. derived from pre-operative imaging, and live data can be effectively cross-referenced for knee replacement surgery and can be, for example registered in a common coordinate system, e.g. with one or more OHMDs worn by the surgeon and his or her surgical assistants and nurses. By registering optical marker and/or the patient specific marker or template in relationship to the OHMD also, the OHMD can display or superimpose the desired position, location, orientation, alignment and/or axes and/or trajectory of any surgical instrument used during knee replacement.

In some embodiments of the invention, an ultrasound scan can be used to obtain the shape information of the distal femur and/or the proximal tibia and/or the patella, for example for designing, selecting or manufacturing a patient specific marker or template. For example, a handheld ultrasound or an ultrasound probe attached to a holding device, stand, tripod or the like can be used to image the distal anterior cortex and the superior trochlea of the femur, optionally along with any osteophytes when present. The ultrasound device can then be used to optionally image the proximal tibia, e.g. the anterior tibial cortex, for example in the tibial plateau area, optionally along with any osteophytes when present. The ultrasound device can then be used to optionally image the patella, e.g. the patellar surface, the whole patella or portions of the patella, for example the superior pole or inferior pole, medial or lateral edge, optionally along with any osteophytes when present. The ultrasound data can optionally be segmented. For example, bone shape and/or cartilage shape as well as, optionally, meniscal shape, when present, can be derived. Moreover, information about ligament location and/or morphometry, including, but not limited to, the origin, insertion, location, length, movement with flexion, extension, rotation of the knee, of the medial collateral ligament, lateral collateral ligament, anterior cruciate ligament, posterior cruciate ligament, patellofemoral ligament or tendon and quadriceps insertion can optionally also be captured with ultrasound.

In some embodiments, the shape information derived from the ultrasound data can optionally be used to design, select and/or manufacture a patient specific marker or template, for example one that fits on the distal anterior cortex and the superior trochlea of the femur of the patient, optionally along with any osteophytes when present; or one that fits on the proximal tibia of the patient, e.g. the anterior tibial cortex, for example in the tibial plateau area, optionally along with any osteophytes when present; or one or more that fits on the patella of the patient, e.g. the patellar surface, the whole patella or portions of the patella, for example the superior pole or inferior pole, medial or lateral edge, optionally along with any osteophytes when present.

Optionally, the ultrasound probe can also be used to image portions of the patient's hip joint, for example, to identify the center of the hip joint. Optionally, the ultrasound probe can also be used to image portions of the patient's ankle joint, for example to identify the ankle mortise or the center of the ankle joint or the ⅓ or ⅔ equidistant distance of the ankle joint in the coronal plane or select radii or distance from the medial or lateral ankle mortise.

Optionally, the ultrasound scan(s) of the knee, optionally the hip and optionally the ankle can be obtained in supine or in upright position. By obtaining the ultrasound scan or scans in upright position, optionally more accurate information on mechanical axis alignment, in particular during weight-bearing, can be obtained. For example, varus or valgus deformity of the knee can be more pronounced under weight-bearing conditions. Correction of varus or valgus deformity using mechanical axis information under weight-bearing conditions can be more accurate than correction of varus or valgus deformity based on non-weight-bearing information. This information can be beneficial when planning any desired mechanical axis corrections.

Optionally, the location of the ultrasound probe can be captured while performing the hip scan and/or the ankle scan and, optionally, the knee scan, for example using optical markers with image capture or video capture, retro-reflective markers, infrared markers or RF markers or other tracking means used in conjunction with a surgical navigation system or, for example, using image capture, e.g. integrated into, attached to, coupled to or separate from an OHMD, or using one or more IMUs. By imaging the hip joint and the ankle joint, and, optionally, the knee joint in this manner and by capturing information of the ultrasound probe location and orientation using one or more attached markers during the ultrasound scan, it is possible to derive information on the mechanical axis and/or the anatomic axis of the patient's leg and knee joint.

In some embodiments, information from an ultrasound, e.g. of the distal femur, proximal tibia, and/or patella, can be combined or fused with information from another imaging modality, e.g. an MRI, CT or x-ray. X-rays can include x-rays in prone, supine, non-weight-bearing position or in standing, weight-bearing position. X-rays can be limited to the knee only. X-rays can be obtained in different poses of the knee, e.g. in extension and at different flexion angles, weight-bearing or non-weight-bearing. Flexion/extension x-rays can, for example, be used to derive information about the rotational axes of the knee, e.g. an epicondylar or trochlear axis. X-rays can also include other portions of the lower extremity or the entire lower extremity, such as a standing full length x-ray of the leg in weight-bearing position. A standing full length x-ray of the leg in weight-bearing position can be used to identify the center of the hip joint as well as the ankle mortise, for example to estimate or derive a mechanical axis and/or an anatomic axis of the knee. In some embodiments of the invention, mechanical axis and/or anatomic axis and/or rotational axis information of the knee obtained from x-rays can be included in a patient specific marker or template derived from ultrasound. For example, a patient specific, ultrasound derived surface of the patient-specific marker can fit to a select anatomic region of the patient, e.g. a distal femur including portions of the superior trochlea or an anterior tibial cortex, for example in the tibial plateau area. One or more external facing surfaces of the patient specific marker or template can have a standard shape and can, optionally, include markers or indicators to show an anatomic axis of the knee of the patient, a mechanical axis of the knee of the patient, a desired new mechanical axis of the knee of the patient after the surgery is performed, e.g. as defined in an optional virtual surgical plan, and/or a rotational axis of the knee of the patient and/or a desired new rotational axis of the knee of the patient after the surgery is performed, e.g. as defined in an optional virtual surgical plan. These external markers or indicators including optical markers can then optionally be used during the surgery to confirm, for example, a desired mechanical axis correction or rotational axis correction or combinations thereof. An image and/or video capture system attached to, integrated with, coupled to or separate from an OHMD can optionally be used to identify such corrections using, for example, one or more of the optical markers or indicators on the patient specific marker or template and, optionally to compare them to a virtual surgical plan. Any deviations or differences from the virtual surgical plan can be identified and the surgeon or operator can optionally perform modifications to the surgical technique, e.g. using additional ligament releases, bone cuts or different implant components including, for example, different medial, lateral or combined insert heights, insert shapes, spacers, and augments.

In some embodiments of the invention, the accuracy of the placement of an optical marker or a patient specific marker can be checked during the surgery. For example, in a knee replacement, the optical marker or patient specific marker can be placed on a distal femur or a proximal tibial or combinations thereof. A visual or an optical marker, e.g. an LED or a laser light, can indicate a mechanical axis of the patient, e.g. by projecting an arrow or a beam towards the center of the hip and/or the ankle. Alternatively, a mechanical marker, e.g. a femoral alignment rod pointing towards the hip or a tibial alignment rod pointing towards the ankle, can be used to indicate the mechanical axis of the patient as determined using the optical marker or patient specific marker. The femoral and/or tibial alignment rod can be integral, attachable or physically or visually linkable to the optical marker or patient specific marker. One or more optical markers can be integrated into or attached to a femoral and/or tibial alignment rod.

An intraoperative x-ray or an intra-operative ultrasound or an intra-operative CT can then be used to determine the physical center of the hip and/or the physical center of the ankle in the live patient on the OR table and, optionally, the patient's physical mechanical axis prior to any corrections. If the projected mechanical axis from optical marker or the patient specific marker coincides with the physical center of the hip and/or the physical center of the ankle, the placement or the information from the optical marker or patient specific marker is accurate. If the projected mechanical axis from the optical marker and/or patient specific marker does not coincide with the physical center of the hip and/or the physical center of the ankle, the placement of the optical marker and/or patient specific marker is not accurately placed and can be repositioned. The degree or amount of difference between the physical and the projected center of the hip and/or the ankle can be used to determine the amount of correction of placement needed. Alternatively, the optical marker and/or patient specific marker can remain in place; however, a correction can be applied to any subsequent registration, wherein the correction is based on the degree or amount of difference between the physical (from the intra-operative imaging study) and the projected center of the hip and/or the ankle (from the optical marker(s) and/or patient specific marker(s)). Someone skilled in the art can recognize that these types of corrections in placement or corrections can be applied to other measurements, e.g. rotational axes, and other joints.

Once any correction of placement inaccuracies of the optical markers and/or patient specific markers has been performed, if applicable, the intended axis correction, e.g. a correction of the patient's abnormal mechanical or rotational axis or both, can be executed on.

Femur

In some embodiments of the invention, once the femur is registered using any of the techniques described in the invention and/or any of the other registration techniques described in the invention or known in the art, including implantable and attachable markers, calibration and registration phantoms including optical markers, navigation markers, infrared markers, RF markers, patient specific markers, LEDs with image capture and IMUs, the OHMD can display a virtual distal femoral cut block for performing the distal femoral cut.

Figure 19A:
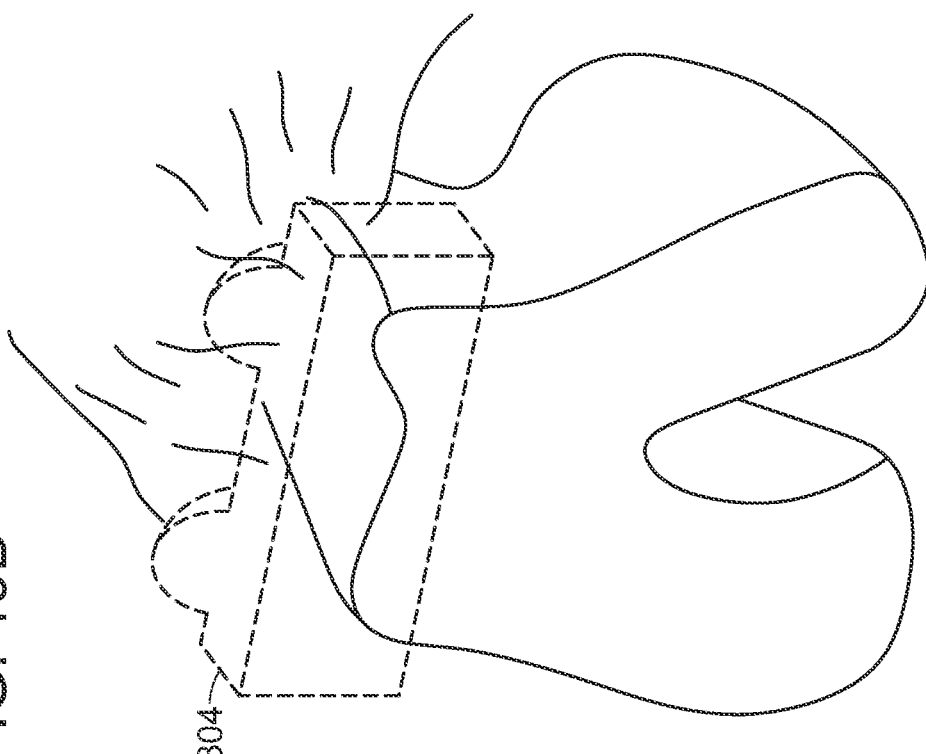
FIGS. 19A-19D provide an illustrative, non-limiting example of the use of virtual surgical guides such as a distal femoral cut block displayed by an OHMD and physical surgical guides such as physical distal femoral cut blocks for knee replacement according to some embodiments of the present disclosure.
Figure 19B:
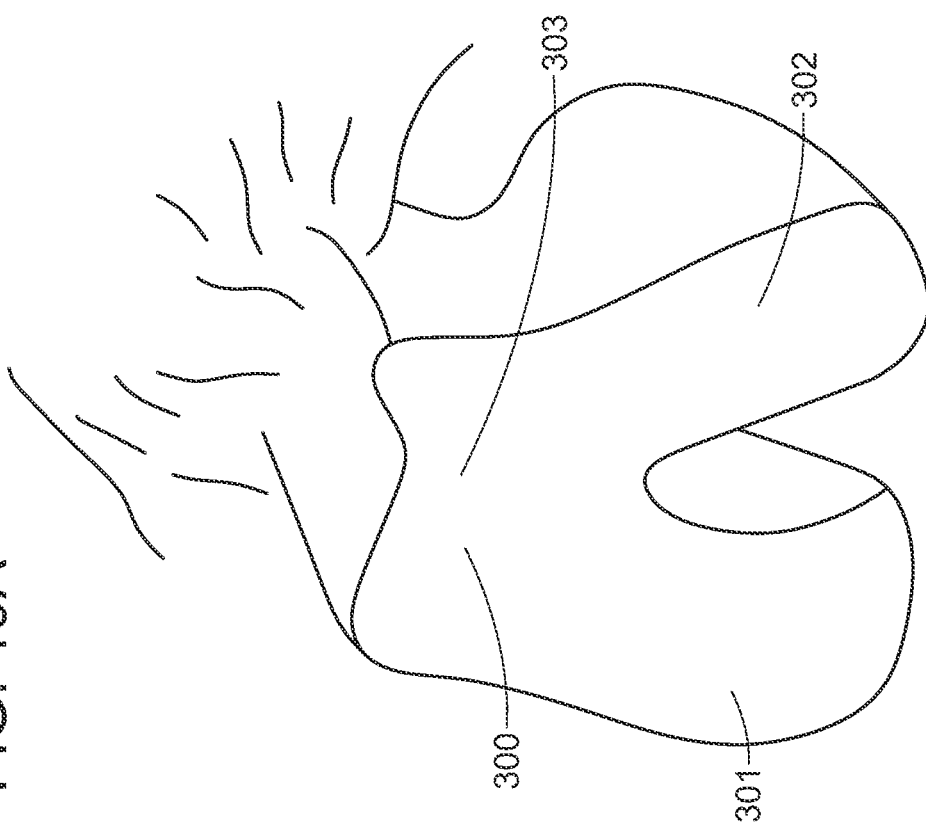
Figure 19D:
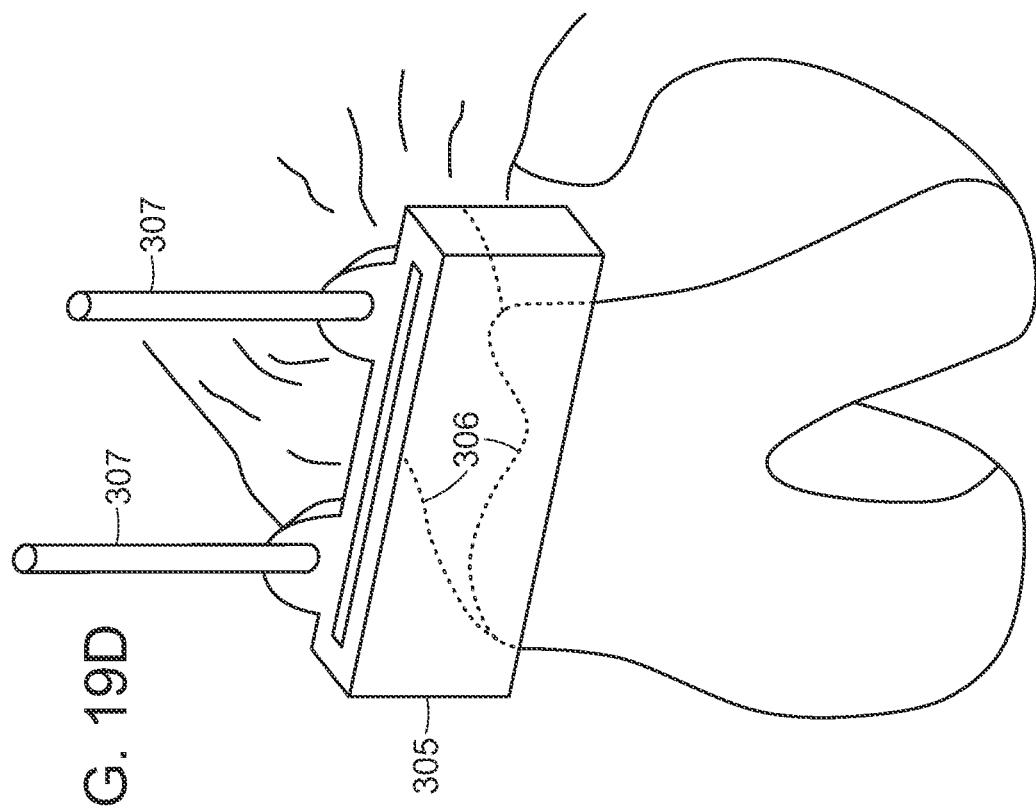
Figure 19C:
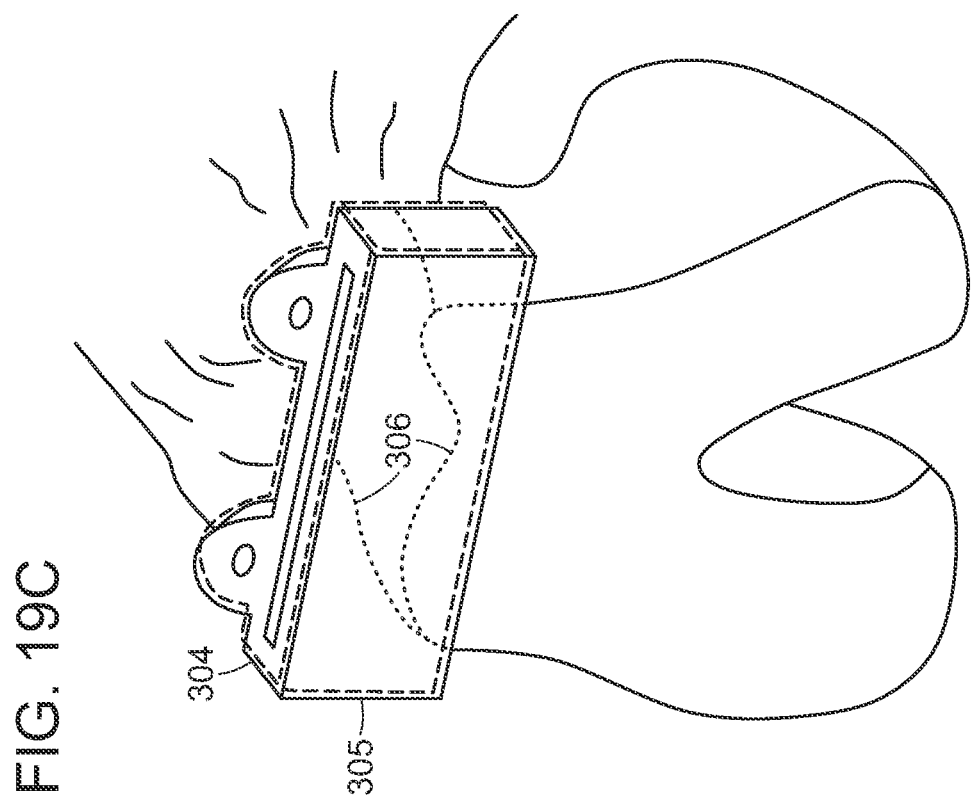

FIGS. 19A-19D provide an illustrative, non-limiting example of the use of virtual surgical guides such as a distal femoral cut block displayed by an OHMD and physical surgical guides such as physical distal femoral cut blocks. FIG. 19A shows live data of a patient with a distal femur 300 exposed during knee replacement surgery, a medial condyle 301, a lateral condyle 302 and a trochlea 303. In FIG. 19B, one or more OHMDs can display a virtual distal femoral cut block, e.g. in a stereoscopic manner for the left eye and the right eye of the surgeon(s) creating a form of electronic hologram of the virtual surgical guide, i.e. the virtual distal cut block. The virtual distal femoral cut block 304 in this example is an outline of the physical distal femoral cut block with substantially similar dimensions as those of the physical distal femoral cut block. The virtual distal femoral cut block 304 is aligned based at least in part on coordinates of a predetermined position for guiding the distal femoral cut, for example for achieving a predetermined varus or valgus correction and/or a predetermined femoral component flexion relative to the distal femur and, for example, its anatomic or biomechanical axes. In FIG. 19C, the physical surgical guide 305, i.e. the physical distal femoral cut block 305 (solid line) in this example, can be moved and aligned to be substantially superimposed with or aligned with the virtual surgical guide 304, i.e. the virtual distal femoral cut block 304 (broken line) in this example. The hidden areas of the knee joint 306, obscured or hidden by the physical distal femoral cut block 305, can optionally also be displayed by the OHMD. In FIG. 19 D, the physical distal femoral cut block 305 can be attached to the distal femoral bone using two pins 307. These pins 307 can be used for subsequent surgical steps, for example for referencing a flexion gap or an extension gap or for ligament balancing. The OHMD can stop display the virtual surgical guide, i.e. the virtual distal femoral cut block in this example, but can optionally continue display the hidden anatomy 306.

The virtual distal femoral cut block can have the same or similar shape and one or more dimensions and one or more planes as the physical distal femoral cut block. Alternatively, the OHMD can only show a partial (e.g. broken or dotted) or complete 2D or 3D outline of the virtual distal femoral cut block or placement indicators, e.g. lines or planes indicating the predetermined placement position and orientation of the distal femoral cut block, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. In the virtual surgical plan, the distal femoral cut will typically be perpendicular to the mechanical axis of the femur in order to restore mechanical axis alignment, unless the surgeon desires to preserve a mild varus deformity, for example, as can be the case with partial or some total knee replacements, or unless the surgeon uses a different alignment approach, e.g. kinematic alignment, or unless the surgeon desires to maintain a certain amount of pre-existing varus or valgus alignment in a patient. The surgeon can then take the physical distal femoral cut block and substantially align or superimpose the physical distal femoral cut block with the virtual distal femoral cut block or its 2D or 3D outline or its placement indicators displayed by the OHMD. Once adequate alignment or superimposition of the physical distal femoral cut block with the virtual distal femoral cut block or its 2D or 3D outline or its placement indicators displayed by the OHMD based on the patient's virtual surgical plan is achieved, the surgeon can pin or attach the physical distal femoral cut block to the bone and perform the cut. By utilizing preoperative 3D data information or intra-operative measurements of combinations of both for the alignment of the physical distal femoral cut block with the assistance of the OHMD, the surgeon can perform the distal femoral cut in an accurate manner, without the need for intramedullary rods or patient specific instrumentation for performing the cut. Alternatively, the OHMD can display a digital hologram of a virtual cut plane corresponding to the distal femoral cut and the surgeon can align the saw blade with the digital hologram of the virtual distal femoral cut plane.

Optionally, the OHMD can display a digital hologram of a virtual femoral alignment rod, which can extend from the distal femur to the hip joint. The surgeon can compare the alignment of the virtual femoral alignment rod with the physical femoral alignment rod in the live patient and assess if both align with the center of the hip joint of the live patient. If the virtual and the physical femoral alignment rod are not aligned with each other and/or the center of the hip joint, the surgeon can check the accuracy of alignment of the physical alignment rod in the live patient, the accuracy of registration of live data of the patient and virtual data of the patient and/or the accuracy of the virtual surgical plan. The surgeon can then optionally make adjustments to the alignment of the physical alignment rod in the live patient, the registration or the virtual surgical plan.

The surgeon can then, for example, select to display or project a digital hologram of the virtual femoral AP cut block in the OHMD. The virtual femoral AP cut block can have the same or similar shape and dimensions as the physical femoral AP cut block. The OHMD can display the virtual femoral AP cut block or a partial (e.g. broken or dotted) or complete 2D or 3D outline of the virtual distal femoral cut block or placement indicators, e.g. planes or lines indicating the predetermined placement position and orientation of the AP femoral cut block, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. The virtual surgical plan can include the predetermined position and rotation for the virtual femoral AP cut block. The rotation of the femoral AP cut block can determine the rotation of the resultant anterior and posterior femoral cuts in relationship to the femoral axis and, with that, can determine the femoral component implant rotation. The OHMD can display the virtual femoral AP cut block or its 2D or 3D outline or one or more placement indicators.

Figure 20B:
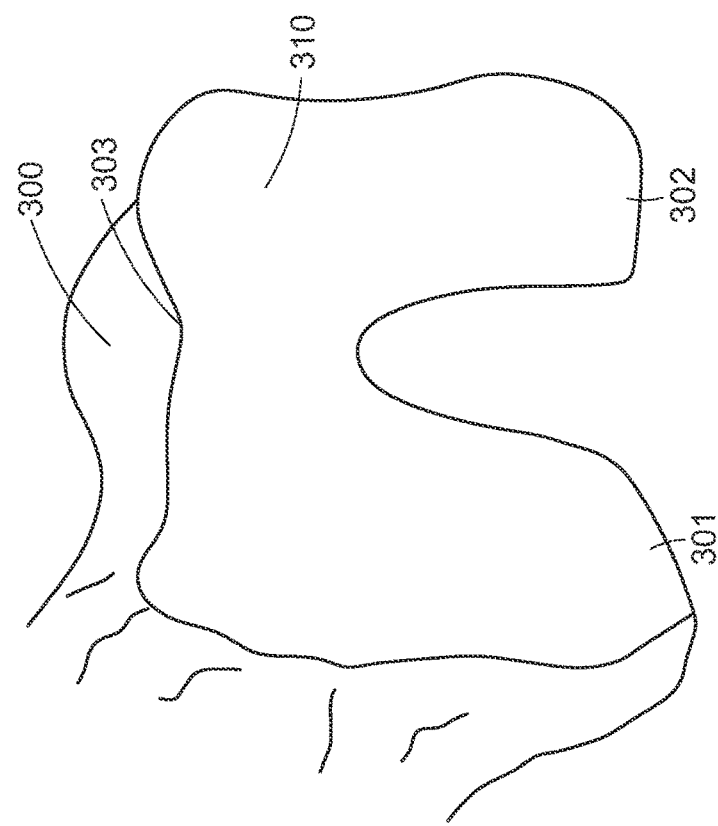
FIGS. 20A-20C provide an illustrative, non-limiting example of the use of virtual surgical guides such as an AP femoral cut block displayed by an OHMD and physical surgical guides such as physical AP cut blocks for knee replacement according to some embodiments of the present disclosure.
Figure 20A:
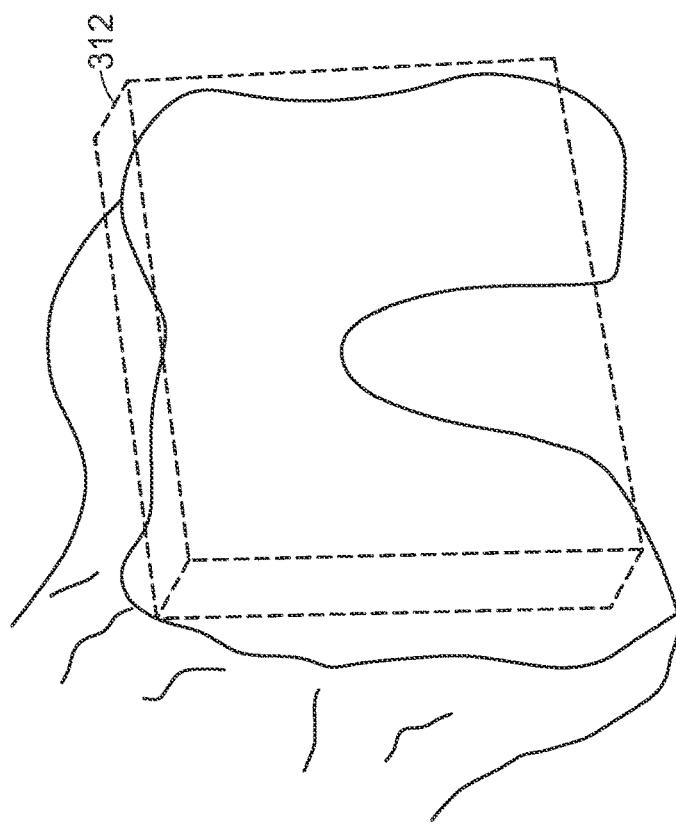
Figure 20C:
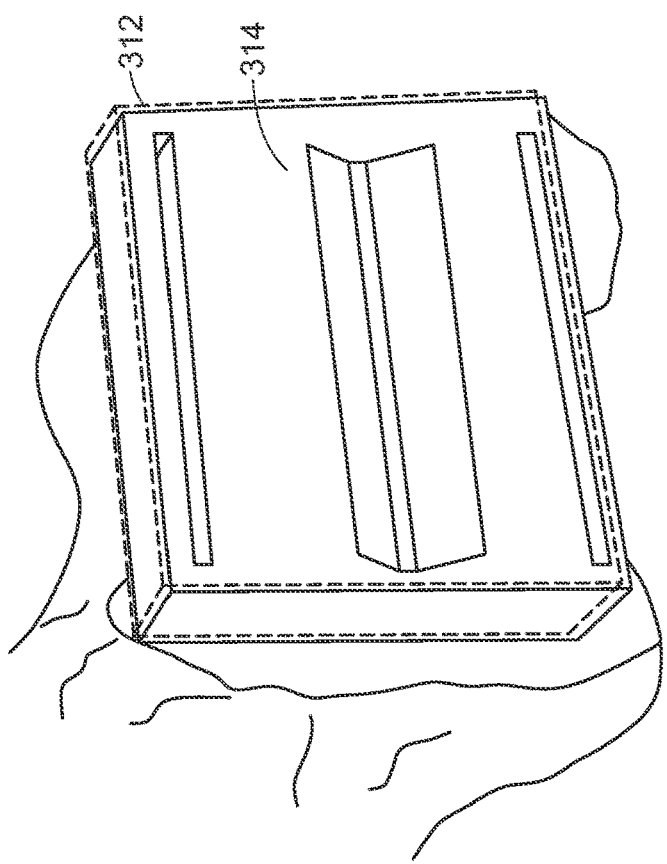

FIGS. 20A-20C provide an illustrative, non-limiting example of the use of virtual surgical guides such as an AP femoral cut block displayed by an OHMD and physical surgical guides such as physical AP cut blocks for knee replacement. FIG. 20A shows live data of a patient with a distal femur 300 exposed during knee replacement surgery after a distal femoral cut creating a planar distal surface 310, a medial condyle 301, a lateral condyle 302 and a trochlea 303. In FIG. 20B, one or more OHMDs can display a virtual femoral AP cut block 312, e.g. in a stereoscopic manner for the left eye and the right eye of the surgeon(s) creating a form of electronic or digital hologram of the virtual surgical guide, i.e. the virtual femoral AP cut block 312. The virtual femoral AP cut block 312 in this example is an outline of the physical femoral AP cut block with similar dimensions, edges, or planes as those of the physical femoral AP cut block. The virtual femoral AP cut block 312 is aligned based at least in part on coordinates of a predetermined position for guiding the different bone cuts, e.g. an anterior cut, posterior cut and/or chamfer cuts depending on the configuration of the physical femoral AP cut block, for example for achieving a predetermined femoral component rotation. In FIG. 20C, the physical surgical guide 314, i.e. the physical femoral AP cut block 314 (solid line) in this example, can be moved and aligned to be substantially superimposed with or aligned with the virtual surgical guide 312, i.e. the virtual femoral AP cut block 312 (broken line) in this example. The physical femoral AP cut block can be attached to the distal femoral bone using pins (not shown) and the cuts can be performed. Subsequent surgical steps can optionally be referenced based on one or more of the cuts executed using the physical femoral AP cut block.

The surgeon can align or substantially superimpose the physical femoral AP cut block with the digital hologram of the virtual femoral AP cut block or its 2D or 3D outline or one or more placement indicators projected by the OHMD. Once adequate alignment or superimposition of the physical AP cut block with the virtual AP cut block or its 2D or 3D outline or one or more placement indicators displayed by the OHMD has been achieved, the surgeon can pin the physical AP cut block and perform the cuts. By utilizing preoperative 3D data information or intra-operative information, e.g. from optical marker and image or video capture measurements, for the position, alignment and rotation of the physical femoral AP cut block with the assistance of the OHMD, the surgeon can perform the anterior and posterior femoral cuts in a highly accurate manner, thereby achieving accurate rotational alignment of the femoral component. The same approaches and display options, e.g. virtual cut blocks, 2D or 3D outline or one or more placement indicators, can be applied to all subsequent femoral preparation steps including chamfer cuts and chamfer cut blocks.

Of note, similar steps and OHMD guided femoral procedures are also possible using the OHMD with any of the other registration and cross-referencing techniques described in the invention or known in the art, for example intraoperative image guidance.

Tibia

In some embodiments of the invention, once the tibia is registered using any of the techniques described in the invention or known in the art, including, for example, implantable and attachable markers, calibration and registration phantoms including optical markers, navigation markers, infrared markers, RF markers, patient specific markers, LEDs with image capture and IMUs, the OHMD can display a virtual proximal tibial cut block for performing the proximal tibial cut. Alternatively, the OHMD can only show a partial (e.g. broken or dotted) or complete 2D or 3D outline of the virtual proximal tibial cut block or placement indicators, e.g. planes or lines indicating the predetermined placement position and orientation of the proximal tibial cut block, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. The virtual proximal tibial cut block can have the same or similar shape and dimensions as the physical proximal tibial cut block or it can have at least one or more dimensions or planes that are identical to the physical proximal tibial cut block or guide.

Figure 21A:
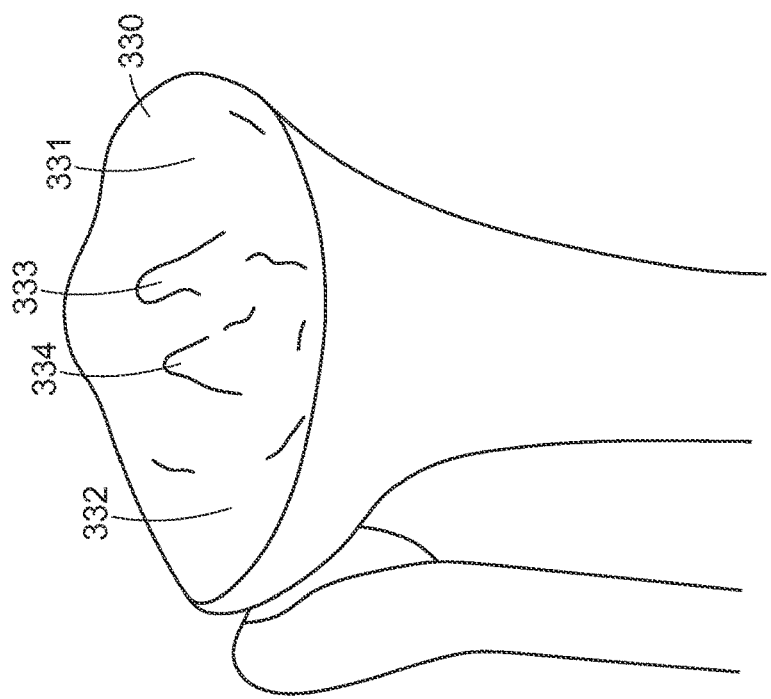
FIGS. 21A-21F provide an illustrative, non-limiting example of the use of virtual surgical guides such as a virtual proximal tibial cut guide displayed by an OHMD and physical surgical guides such as physical proximal tibial cut guide according to some embodiments of the present disclosure.
Figure 21B:
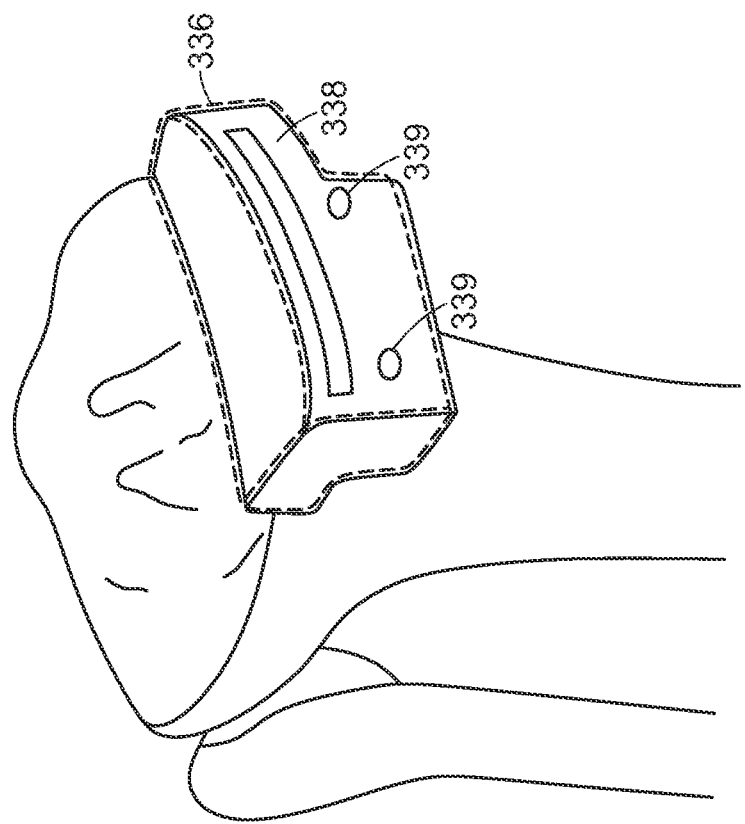
Figure 21C:
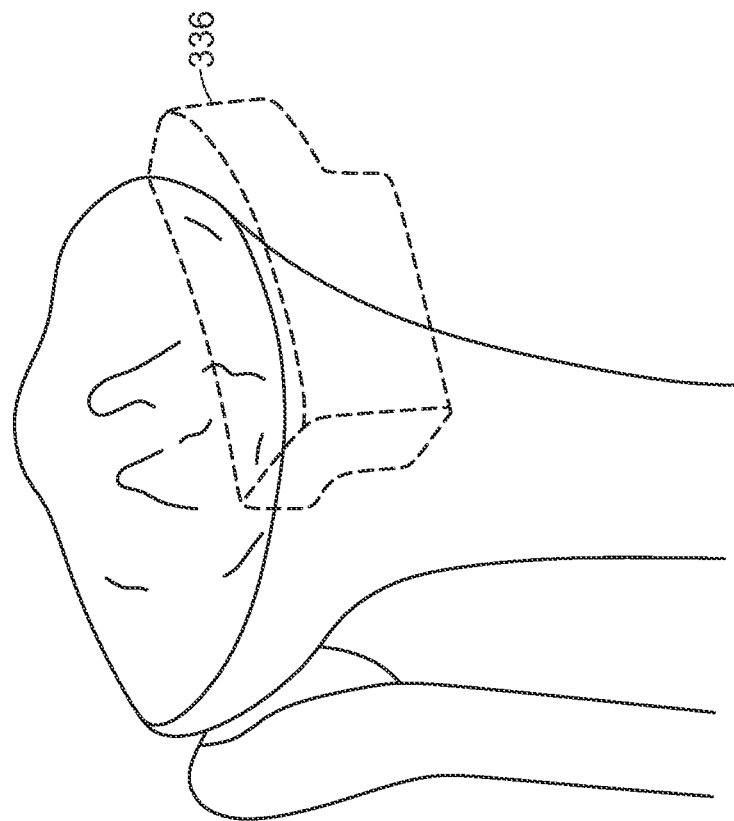
Figure 21E:
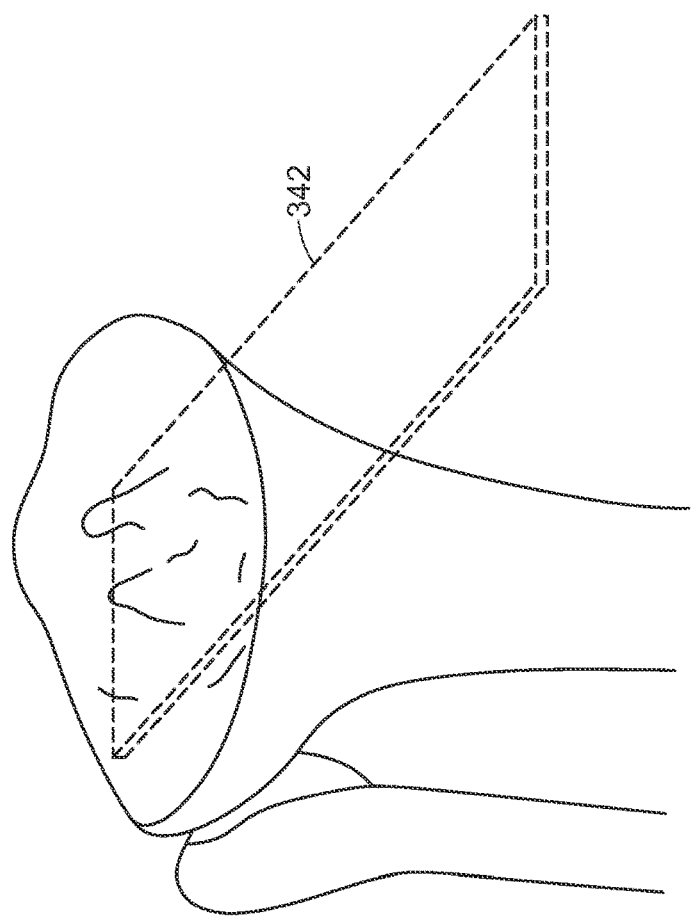
Figure 21D:
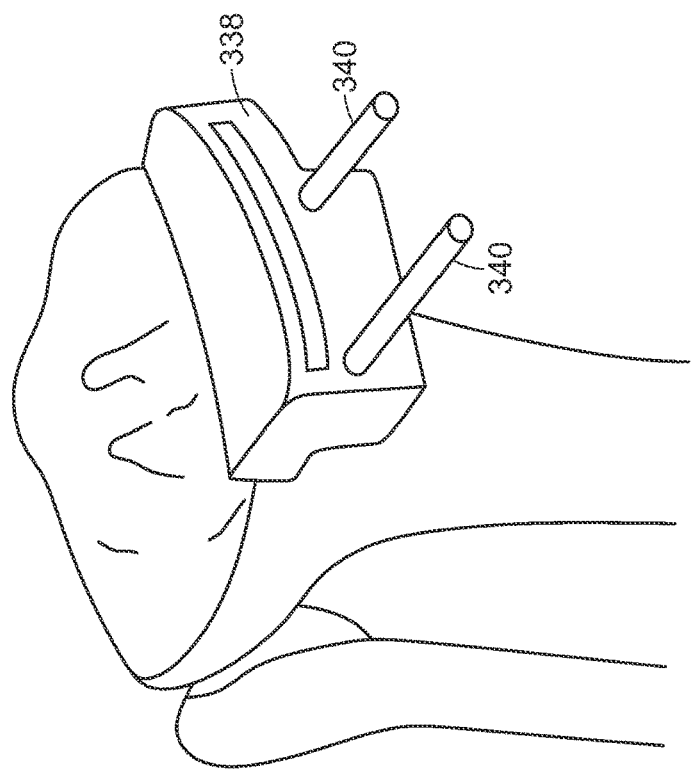
Figure 21F:
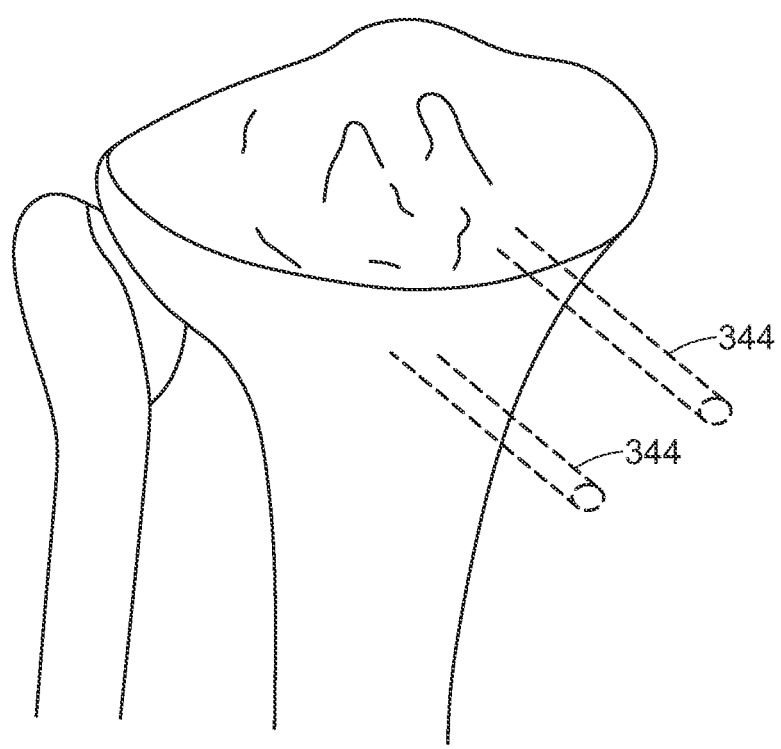

FIGS. 21A-21F provide an illustrative, non-limiting example of the use of virtual surgical guides such as a virtual proximal tibial cut guide displayed by an OHMD and physical surgical guides such as physical proximal tibial cut guide. FIG. 21A shows live data of a patient with a proximal tibia 330 exposed during knee replacement surgery, a medial tibial plateau 331, a lateral tibial plateau 332 and a medial tibial spine 333 and a lateral tibial spine 334. In FIG. 21B, one or more OHMDs can display a virtual proximal tibial cut guide, e.g. in a stereoscopic manner for the left eye and the right eye of the surgeon(s), creating a form of electronic hologram of the virtual surgical guide, i.e. the virtual proximal tibial cut guide. The virtual proximal tibial cut guide 336 in this example can be an outline of the physical proximal tibial cut guide with substantially similar dimensions as those of the physical proximal tibial cut guide. The virtual proximal tibial cut guide 336 is aligned based at least in part on coordinates of a predetermined position for guiding the proximal tibial cut, for example for achieving a predetermined varus or valgus correction and/or a predetermined slope relative to the proximal tibia and, for example, its anatomic or biomechanical axes. In FIG. 21C, the physical surgical guide 338, i.e. the physical proximal tibial cut guide 338 (solid line) in this example, can be moved and aligned to be substantially superimposed with or aligned with the virtual surgical guide 336, i.e. the virtual proximal tibial cut guide 336 (broken line) in this example. Note two pin holes 339 in the physical proximal tibial cut guide 338. In FIG. 21D, the physical proximal tibial cut guide 338 can be attached to the proximal tibia bone using two pins 340. These pins 307 can be used for subsequent surgical steps, for example for referencing a flexion gap or an extension gap or for ligament balancing. In FIG. 21E, an alternative embodiment is shown to FIG. 21B. One or more OHMDs can display a virtual proximal tibial cut plane 342, e.g. in a stereoscopic manner for the left eye and the right eye of the surgeon(s), creating a form of electronic hologram of the virtual tibial cut plane. The virtual proximal tibial cut plane 342 in this example is parallel with and substantially aligned and superimposed with the predetermined cut plane for the physical proximal tibial cut guide. The virtual proximal tibial cut plane 342 is aligned based at least in part on coordinates of a predetermined position for guiding the proximal tibial cut, for example for achieving a predetermined varus or valgus correction and/or a predetermined slope relative to the proximal tibia and, for example, its anatomic or biomechanical axes. A physical saw blade or a slot for aligning the physical saw blade in a physical proximal tibial cut guide or an open guide area for accommodating the saw blade in a physical proximal tibial cut guide can then be aligned and at least partially superimposed with the virtual proximal tibial cut plane 342. In FIG. 21F, an alternative embodiment is shown to FIG. 21B. One or more OHMDs can display two or more virtual drills or pins 344 for placement in the proximal tibia, e.g. in a stereoscopic manner for the left eye and the right eye of the surgeon(s), creating a form of electronic hologram of the virtual tibial pins or drills. The virtual drills or pins 344 in this example can be an outline or a projected path of the physical pins or drills that can be used to fixate a physical proximal tibial cut guide to the proximal tibia. The virtual drills or pins 344 are aligned based at least in part on coordinates of a predetermined position for guiding the proximal tibial cut, for example for achieving a predetermined varus or valgus correction and/or a predetermined slope relative to the proximal tibia and, for example, its anatomic or biomechanical axes. The physical drills or pins (not shown) can then be aligned and superimposed with the virtual drills or pins 344 and placed in the proximal tibia. A physical proximal tibial cut guide can then be attached to the physical pins and the proximal tibial cut can be executed.

In some embodiments of the invention, a physical and a corresponding virtual proximal tibial guide or a physical and a corresponding virtual distal femoral guide can also be pin guides, wherein the physical guide can be used to place two or more pins in the bone for attaching physical cut guides for subsequent surgical steps. The embodiments for aligning physical with virtual guides, as shown for example in FIGS. 19B and 19C, 20B and 20C, and 21B and 21C, can also be applied to pin guides.

Someone skilled in the art can recognize that the use of virtual and physical surgical guides, including cut guides and pin guides, can be applied to any joint of the human body and the spine.

In the virtual surgical plan, the proximal tibial cut can be perpendicular to the mechanical axis of the tibia in order to restore neutral mechanical axis alignment, unless the surgeon desires to preserve a mild varus deformity, for example, as can be the case with partial or some total knee replacements, or unless the surgeon uses a different alignment approach, e.g. kinematic alignment, or unless the surgeon desires to maintain a certain amount of pre-existing varus or valgus alignment in a patient. The surgeon can then take the physical proximal tibial cut block and substantially align or superimpose the physical proximal tibial cut block with the virtual proximal tibial cut block or its 2D or 3D outline or its placement indicators displayed by the OHMD. The virtual surgical plan and/or the intraoperative measurements can optionally determine not only the alignment of the proximal tibial cut in relationship to the mechanical axis of the leg, but can also determine the anterior-posterior slope with which the proximal tibia is cut in sagittal direction. In some embodiments, the surgeon, the operator or semi-automatic or automatic software may elect to cut the proximal tibia with a fixed sagittal slope, e.g. 5 degrees or 7 degrees or 3 degrees, for example with a Cruciate Retaining (CR) knee replacement system. Or the surgeon, the operator or semi-automatic or automatic software may elect to cut the proximal tibia with a fixed sagittal slope, e.g. 0 degrees or 2 degrees or 3 degrees, for example with a Posterior Substituting (PS) knee replacement system. Or the surgeon, the operator or semi-automatic or automatic software may elect to cut the proximal tibia with a patient specific slopes, which can be identical to or derived from the medial slope of the native, un-operated medial tibial plateau, the lateral slope of the native, un-operated lateral tibial plateau, or combinations or averages thereof. Once adequate alignment or superimposition of the physical proximal tibial cut block with the virtual representation of the virtual proximal tibial cut block or its 2D or 3D outline or its placement indicators displayed by the OHMD based on the patient's virtual surgical plan and/or intra-operative measurements is achieved, the surgeon can pin the physical proximal tibial cut block and perform the cut, which can then reflect an alignment with the desired mechanical axis correction and the desired tibial slope. By utilizing preoperative 3D data information and/or intraoperative measurements and/or information for the alignment of the physical proximal tibial cut block with the assistance of the OHMD, the surgeon can perform the proximal tibial cut in an accurate manner, without the need for intramedullary rods or patient specific instrumentation for performing the cut. At the same time, the surgeon retains the ability to perform intraoperative adjustments, which can be as simple as manually moving the distal or other femoral cut blocks or moving the proximal tibial cut block or other tibial cut blocks, for example also with use of a stylus like device, e.g. for checking and measuring slope. Any such adjustment can be checked against the virtual surgical plan and/or the intraoperative measurements, by displaying in the OHMD, for example, the final desired implant position or the predetermined position of the corresponding virtual surgical instruments for which the adjustment is contemplated in the physical surgical instrument. Any difference in alignment between any virtual surgical instrument and any physical surgical instrument can be indicated in numeric values by the OHMD, e.g. distance in millimeters or angles in degrees, e.g. difference in external rotation of the femoral component. Any subsequent steps in the virtual surgical plan can be modified in the event the surgeon or operator elected to perform an adjustment, e.g. of tibial slope or femoral or tibial resection levels.

Of note, the same steps and OHMD guided tibial procedures are also possible using the OHMD with any of the other registration and cross-referencing techniques described in the invention or known in the art, for example using intraoperative image guidance and implantable and attachable markers, calibration and registration phantoms including optical markers, navigation markers, infrared markers, RF markers, patient specific markers, LEDs with image capture and IMUs.

A tibial template or tibial base trial can be used to prepare the proximal tibia for accepting the tibial implant component. A drill can be used to remove the bone in the center of the proximal tibia to accept the central bore of the keel of the tibial component. A keel punch can be used to punch out the space to accept the keel wings of the tibial component. The final seating and orientation of the tibial keel and keel wings can determine tibial implant rotation. Accurate tibial rotation, for example aligned with the rotation axis of the native knee, is an important objective for avoiding postoperative pain.

In some embodiments of the invention, the OHMD can display a digital hologram of a virtual tibial template or virtual tibial base trial as well as virtual tibial drill towers and virtual keel punches. Other virtual tibial preparation instruments can be displayed depending on the configuration and surgical technique of the knee replacement system used. Alternatively, the OHMD can only show a partial (e.g. broken or dotted) or complete 2D or 3D outline of the virtual tibial template or virtual tibial base trial as well as virtual tibial drill towers and virtual keel punches or other virtual tibial preparation instruments or placement indicators, e.g. planes or lines indicating the predetermined placement position and orientation of the tibial template or tibial base trial as well as tibial drill towers and keel punches or other tibial preparation instruments, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. The virtual tibial template or tibial base trial as well as virtual tibial drill towers and virtual keel punches and other virtual tibial preparation instruments can have the same or similar shape and dimensions as the physical tibial template or physical tibial base trial as well as physical tibial drill towers and physical keel punches and physical tibial preparation instruments. In the virtual surgical plan, the virtual tibial template or tibial base trial as well as virtual tibial drill towers and virtual keel punches and virtual tibial preparation instruments can be aligned in a manner to achieve close to zero tibial rotation error of the final, physical tibial tray implanted in relationship to the native rotation axis of the tibia of the un-operated knee, if intended. The surgeon or operator has the option to deviate from zero rotation and can add optionally 1, 2, 3 or more degrees of internal or external tibial component rotation to the virtual surgical plan and/or the intra-operative measurements.

For each step of the tibial preparation, the OHMD can display digital holograms of the virtual tibial instrument(s) used or its (their) 2D or 3D outline or its (their) placement indicators along with its (their) desired alignment and rotation based on the virtual surgical plan. The surgeon can then align or superimpose the corresponding physical tibial instrument with the virtual tibial instrument(s) or its (their) 2D or 3D outline or its (their) placement indicators thereby achieving the desired alignment and/or rotation of the physical tibial instrument in relationship to the virtual surgical plan and/or the intraoperative measurements. All virtual tibial preparation tools and instruments including virtual tibial templates or virtual tibial base trials as well as virtual tibial drills, drill towers or saws and keel punches can be displayed using digital holograms by the OHMD if desired. Alternatively, the OHMD can display digital holograms of a 3D contour or placement indicators of the virtual tibial instruments. Optionally, the OHMD can only display the key instruments used for setting tibial component alignment and rotation. By utilizing preoperative 3D data information and/or intra-operative measurements and/or information for the position, alignment and rotation of the virtual tibial preparation instruments, the tibial trials and final tibial components or their respective 2D or 3D outlines or placement indicators displayed with the assistance of the OHMD, the surgeon can perform the physical tibial preparation in an accurate manner by matching physical instruments and components with the alignment and rotation of the virtual instruments and components or their respective 2D or 3D outlines or placement indicators, thereby achieving accurate rotational alignment of the tibial component.

Optionally, the OHMD can display a digital hologram of a virtual tibial alignment rod, which can extend from the proximal tibia to the ankle joint. The surgeon can compare the alignment of the virtual tibial alignment rod with the physical tibial alignment rod in the live patient and assess if both align with the desired location in the ankle joint of the live patient. If the virtual and the physical tibial alignment rod are not aligned with each other and/or the desired location in the ankle joint, the surgeon can check the accuracy of alignment of the physical alignment rod in the live patient, the accuracy of registration of live data of the patient and virtual data of the patient and/or the accuracy of the virtual surgical plan and/or the intra-operative measurements. The surgeon can then optionally make adjustments to the alignment of the physical alignment rod in the live patient, the registration or the virtual surgical plan.

Of note, the same steps and OHMD guided tibial procedures are also possible using the OHMD with the other registration and cross-referencing techniques described in the invention or known in the art including implantable and attachable markers, calibration and registration phantoms including optical markers, navigation markers, infrared markers, RF markers, patient specific markers, LEDs with image capture and IMUs.

Patella

In some embodiments of the invention, one or more optical markers and/or patient specific markers or templates or combinations thereof can be applied to the patella or patellar surface or portions of the patella, for example the superior pole or inferior pole, medial or lateral edge, optionally along with any osteophytes when present. By applying the one or more optical markers and/or patient specific markers or templates to the corresponding structures on the patient or using any of the other techniques and techniques for registration described in the invention or known in the art, e.g. implantable and attachable markers, calibration and registration phantoms, navigation markers, infrared markers, RF markers, LEDs with image capture and IMUs, virtual data and live data can be effectively cross-referenced for patellar replacement or partial or complete resurfacing. By registering the optical marker and/or patient specific marker or template in relationship to the OHMD, e.g. in a common coordinate system with the OHMD and the femur, tibia and patella, or by registering the OHMD in relationship to the live data and virtual data of the patient using any of the registration techniques described in the invention, the OHMD can display or superimpose digital holograms indicating the desired position, location, orientation, alignment and/or trajectory of any surgical instrument used during patellar replacement or partial or complete resurfacing, including with a virtual display of the patellar preparation instrument, a 2D or 3D outline of the patellar preparation instrument or a virtual display of predetermined placement indicators.

In some embodiments of the invention, once the patella is registered using any of the techniques described in the invention, including, for example, implantable and attachable markers, calibration and registration phantoms including optical markers, navigation markers, infrared markers, RF markers, patient specific markers, LEDs with image capture and IMUs, the OHMD can display or project a digital hologram of a virtual patellar clamp, patellar tool, patellar cutting device, patellar milling device, predetermined milling axis and/or patellar cut block or other patellar preparation instrument for performing the patellar cut or patellar preparation. Alternatively, the OHMD can only show a partial (e.g. broken or dotted) or complete 2D or 3D outline of the virtual patellar clamp, patellar tool, patellar cutting device, patellar milling device, and/or patellar cut block or other patellar preparation instrument or placement indicators, e.g. lines indicating the predetermined placement position and orientation of the virtual patellar clamp, patellar tool, patellar cutting device, patellar milling device, and/or patellar cut block or other patellar preparation instrument, e.g. a virtual predetermined medial border or placement or position, a virtual predetermined lateral border or placement or position, a virtual predetermined anterior border or placement or position, a virtual predetermined posterior border or placement or position, a virtual predetermined superior border or placement or position and/or a virtual predetermined inferior border or placement or position. The digital holograms of the virtual patellar clamp, patellar tool, patellar cutting device, patellar milling device, and/or patellar cut and/or other patellar preparation instrument block can have the same or similar shape and at least one or more dimensions or planes that are identical to those of the corresponding physical patellar clamp, patellar tool, patellar cutting device, patellar milling device, and/or patellar cut block and/or other patellar preparation instrument. In the virtual surgical plan, the patellar cut or milling can be planned, for example at a desired resection depth or angle selected for a particular patellar implant or replacement and/or a particular patient anatomy, and/or based on patellar shape, patellar tracking, patellofemoral kinematics or knee rotation axes. The surgeon can then take the physical patellar clamp, patellar tool, patellar cutting device, patellar milling device, and/or patellar cut block and/or other patellar preparation instrument and substantially align or superimpose the physical patellar clamp, patellar tool, patellar cutting device, patellar milling device, and/or patellar cut block and/or other patellar preparation instrument with the corresponding virtual patellar clamp, patellar tool, patellar cutting device, patellar milling device, and/or patellar cut block and/or other patellar preparation instrument or its respective virtual contour or placement indicators displayed by the OHMD. Once adequate alignment or superimposition of the physical patellar clamp, patellar tool, patellar cutting device, patellar milling device, and/or patellar cut block and/or other patellar preparation instrument with the digital holograms of the virtual patellar clamp, patellar tool, patellar cutting device, patellar milling device, and/or patellar cut block and/or other patellar preparation instrument or its respective contour or placement indicators displayed by the OHMD based on the patient's virtual surgical plan and/or intra-operative measurements is achieved, the surgeon can optionally pin or fixate the physical virtual patellar clamp, patellar tool, patellar cutting device, patellar milling device, and/or patellar cut block and/or other patellar preparation instrument and perform the cut or milling. By utilizing preoperative 3D data information or intraoperative data and/or measurements or combinations thereof for the alignment of the physical virtual patellar clamp, patellar tool, patellar cutting device, patellar milling device, and/or patellar cut block and/or other patellar preparation instrument with the assistance of the OHMD, the surgeon can perform the patellar cut or milling in a highly accurate manner.

The patellar procedures described in the invention can also be implemented using any of the other registration techniques described in the invention or known in the art including implantable and attachable markers, calibration and registration phantoms including optical markers, navigation markers, infrared markers, RF markers, patient specific markers, LEDs with image capture and IMUs. For example, using an image and/or video capture system integrated into, attached to, coupled to or separate from the OHMD, it is possible to image the patellar shape or surface or contour. The information can be compared to pre-operative imaging information about patellar shape or surface or contour and a match can optionally be performed for purposes of registration. Any of the other registration techniques described in the invention or known in the art including, but not limited to, surgical navigation can be used.

Optionally, an IMU including, for example, pyrometers, magnetometers and accelerometers can be applied to the patella during the surgery or pre-operatively.

In some embodiments of the invention, the registration of virtual patient data and live patient data using the techniques described herein can be repeated after one or more surgical steps have been performed in an OHMD guided knee replacement procedure. In this case, the surgically altered tissue or tissue surface or tissue contour or tissue perimeter or tissue volume or other tissue features in the live patient can be matched to, superimposed onto and/or registered with the surgically altered tissue or tissue surface or tissue contour or tissue perimeter or tissue volume or other tissue features in the virtual data of the patient, e.g. in a virtual surgical plan developed for the patient. The matching, superimposing and/or registering of the live data of the patient and the virtual data of the patient after the surgical tissue alteration can be performed using the same techniques described in the foregoing or any of the other registration techniques described in the specification or any other registration technique known in the art including implantable and attachable markers, calibration and registration phantoms including optical markers, navigation markers, infrared markers, RF markers, patient specific markers, LEDs with image capture and IMUs. For example, the re-registration can be performed using a cut bone surface, e.g. a cut distal femur using the surface shape, surface area or perimeter or other feature to match, superimpose and/or register the live patient data and the virtual patient data prior to performing subsequent surgical steps.

Someone skilled in the art that the same concepts and embodiments described for spinal surgery, knee replacement and hip replacement can be applied to other surgeries of the human body, e.g. repair or reconstruction of the anterior cruciate ligament, posterior cruciate ligament, other ligaments, shoulder replacement, ankle replacement, and/or wrist replacement. For example, an OHMD can display or project digital holograms of one or more surgical instruments, trial implants or implant components or one or more outlines or axes of the surgical instruments, trial implants, or implant components or digital holograms of predetermined start point, predetermined start position, predetermined start orientation/alignment, predetermined intermediate point(s), predetermined intermediate position(s), predetermined intermediate orientation/alignment, predetermined end point, predetermined end position, predetermined end orientation/alignment, predetermined path, predetermined plane, predetermined cut plane, projected contour/outline/cross-section/surface features/shape/projection, predetermined depth marker or depth gauge, predetermined angle/ orientation/rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated/ projected non-visualized portions for one or more devices/ implants/implant components/surgical instruments/surgical tools, and/or one or more of a predetermined tissue change/ alteration for a shoulder replacement, wherein the one or more digital holograms can be used to determine a humeral resection, arm length, glenoid component version, orientation and/or position, humeral component version, orientation and/or position.

An OHMD can display or project digital holograms of one or more surgical instruments, trial implants or implant components or one or more outlines or axes of the surgical instruments, trial implants, or implant components or digital holograms of a predetermined start point, predetermined start position, predetermined start orientation/alignment, predetermined intermediate point(s), predetermined intermediate position(s), predetermined intermediate orientation/ alignment, predetermined end point, predetermined end position, predetermined end orientation/alignment, predetermined path, predetermined plane, predetermined cut plane, projected contour/outline/cross-section/surface features/ shape/projection, predetermined depth marker or depth gauge, predetermined angle/orientation/rotation marker, predetermined axis, e.g. rotation axis, flexion axis, extension axis, predetermined axis of the virtual surgical tool, virtual surgical instrument including virtual surgical guide or cut block, virtual trial implant, virtual implant component, implant or device, estimated/projected non-visualized portions for one or more devices/implants/implant components/ surgical instruments/surgical tools, and/or one or more of a predetermined tissue change/alteration for an ankle replacement, wherein the one or more digital holograms can be used to display or project an predetermined tibial resection and/or talar resection with desired coordinates, angles, orientation and/or alignment to achieve a desired ankle alignment including at least one of a coronal plane implant component alignment, sagittal plane implant component alignment including flexion and axial plane component alignment or rotation Repair and/or Reconstruction of the Anterior Cruciate Ligament The following embodiments and description on performing an ACL repair using aspects of the invention are only meant to be exemplary and are not meant to be limiting of the invention. Any of the methods described in the specification can be applied or used. Any of the imaging techniques, patient positioning techniques, registration techniques, methods for developing surgical plans including at different flexion and extension or rotation angles, displaying virtual and live patient data can be applied to any of the other embodiments in this specification, including, for example, knee replacement, hip replacement, pedicle screw placement and spinal fusion, and vertebroplasty or kyphoplasty.

Tears of the anterior cruciate ligament (ACL) represent one of the most common injuries of the human knee. They can result in knee instability, for example with flexing or bending the knee. Surgical treatment of an ACL tear can include the placement of an autograft or an allograft or another graft material. ACL repair can be performed using the so-called single bundle technique or double bundle technique.

The objective of ACL repair or reconstruction is the restoration of normal knee kinematics in patients with unstable or ACL deficient knees. Anatomical reconstruction of the ACL may help restore normal knee kinematics and reduce the possibility of developing osteoarthritis of the knee after ACL injury. Anatomically, two different portions or bundles of the ACL have been described, an antero-medial bundle and a postero-lateral bundle.

ACL reconstruction can be performed using a so-called single bundle technique or a double bundle technique. One of the objectives of the surgical ACL reconstruction includes placing the graft tissue in an isometric position to restore knee function and to reduce the possibility of postoperative graft complications and graft failure. Placement of the graft near or at the location of the native, torn ACL has the benefit that the ACL graft is placed in a location that ensure primarily isometric ligament function which can help the long-term survival of the graft. The surgeon will typically try to place the ACL graft in the location and/or orientation of the native, torn ACL. A femoral and a tibial bone tunnel need to be placed in order to accommodate the graft. The femoral tunnel extends from the posterior femoral cortex into the area of the femoral notch, typically where the origin of the native ACL was located. The tibial canal extends typically from the medial tibial spine, the attachment of the native, torn ACL, to the anteromedial tibial cortex. An anchor can typically be placed in the area where the graft enters the femoral bone and/or exits the tibial bone.

Tunnel positions can be chosen in a predetermined position and/or orientation to achieve such an isometric function. Tunnel positions can be placed in a predetermined position and/or orientation so that the femoral tunnel will exit the distal femur near the origin of the ACL. The tibial tunnel can be placed in a predetermined position and/or orientation so that it enters the proximal tibia near the insertion of the ACL on the medial tibial spine. The angle and/or orientation of the femoral and/or tibial tunnel can be placed in a predetermined position and/or orientation so that it is similar to the natural angle and/or orientation of the native ACL or, optionally, different from the natural orientation of the native ACL of the patient. If a single bundle technique is used, the angle and/or orientation of the femoral and/or tibial tunnel including their entry and exit areas can be directed in predetermined positions and/or orientations so that the location and/or orientation of the graft is a compromise between the location and/or orientation of the antero-medial bundle of the ACL and the postero-lateral bundle of the ACL. A trans-tibial technique can be used as a method for tunnel placement, wherein the femoral tunnel can be drilled in a predetermined position and/or orientation through the tibial tunnel. This has the benefit that both tunnels can be linked. Alternatively, the tibial tunnel can be drilled first in a predetermined position and/or orientation, for example through a small incision in the skin of the anterior tibia, followed by drilling of the femoral tunnel, for example through a small incision and portal into the knee joint. Optionally, the tunnel location can be placed in a predetermined position and/or orientation with arthroscopic visualization, for example by evaluating the location of residual ACL fibers on the femur and/or on the tibia. Placement of the graft outside the intended location and/or orientation can be caused by incorrect placement of the femoral and/or tibial tunnel. Incorrect placement of one or both tunnels and incorrect placement of the graft can lead to limitations in knee function and early wear and tear of the graft.

Figure 22A:
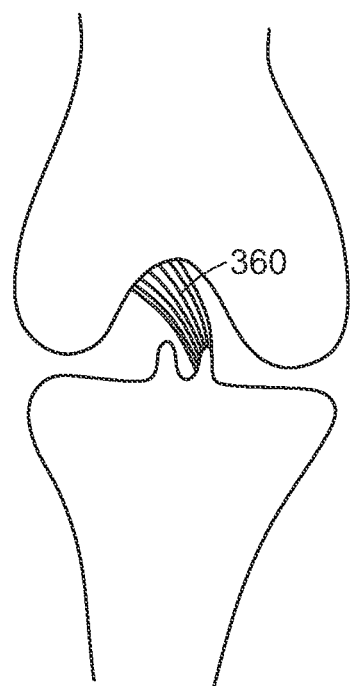
FIGS. 22A and 22B show AP and lateral views demonstrating exemplary normal ACL including antero-medial and postero-lateral fibers.
Figure 22B:
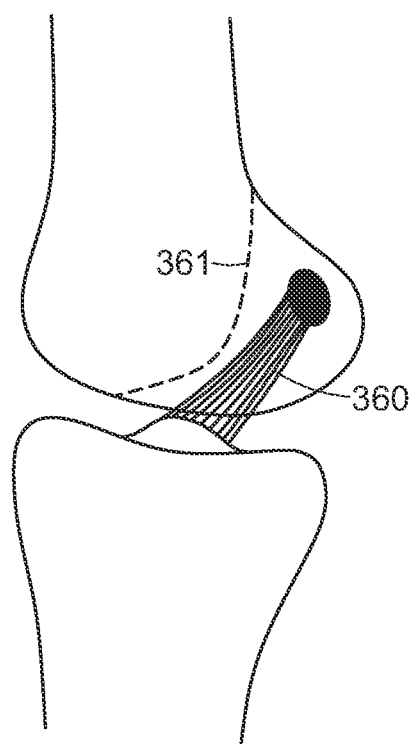

FIGS. 22A AP and 22B lateral views demonstrating exemplary normal ACL 360 including antero-medial and postero-lateral fibers. Curved broken line on femoral side indicates intercondylar notch area/roof 361.

Figure 22C:
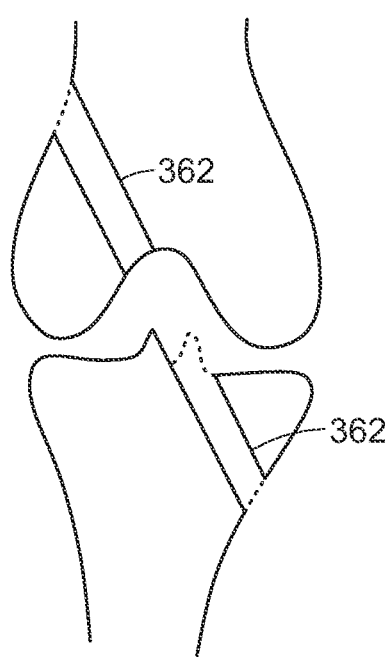
FIGS. 22C and 22D show AP and lateral views demonstrating exemplary ACL tunnels (solid straight lines) on femoral side and tibial side.
Figure 22D:
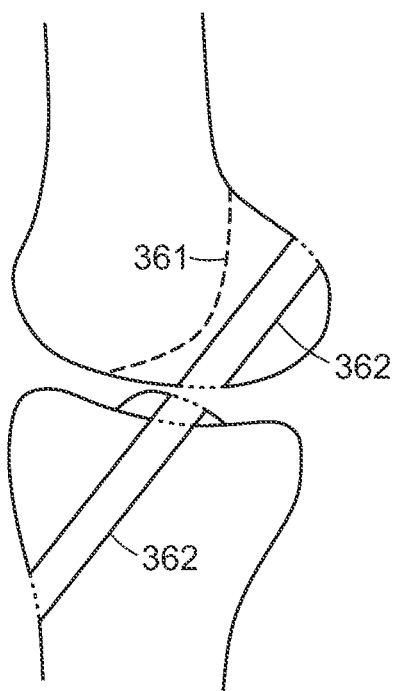

FIGS. 22C AP and 22D lateral views demonstrating exemplary ACL tunnels 362 (solid straight lines) on femoral side and tibial side. Curved broken line on femoral side indicates intercondylar notch area/roof 361.

Imaging

In some embodiments of the invention, the patient can undergo a pre-operative or intra-operative scan, e.g. a CT scan, an MRI scan or an ultrasound scan. Optionally, the femoral and tibial bones can be segmented and displayed in two or three dimensions. In some embodiments, the origin and the insertion of the native, torn ACL can be identified. Alternatively or in addition, one or more portions of the torn native ACL can be identified. The information can be used to develop a virtual surgical plan for placement of the femoral and/or the tibial tunnel or the graft using OHMD guidance, e.g. by displaying one or more virtual femoral or tibial tunnels or one or more virtual grafts.

For example, if an MRI scan is used, the MRI data can be imported into a software program to segment the femoral and/or tibial bones. For this purpose, a T1-weighted MRI sequence can be chosen without fat suppression. On the T1-weighted sequence without fat suppression, the marrow space can display intermediate to high signal intensity. The marrow space is bounded by low signal intensity cortical bone. The high intensity marrow space can be segmented, for example using a thresholding algorithm or a seed growing algorithm or an active contour or level set technique or any other algorithm or technique known in the art. A two or three millimeter or other thickness cortical bone and subchondral bone envelope can be added. The thickness envelope can be applied using a reference database, e.g. for bones of known size or dimensions. The cortical bone or subchondral bone envelope can vary in thickness depending on the location on the tibia or the femur. The thickness can be derived based on anatomic reference data. Alternatively, the cortical bone and subchondral bone can be segmented using any method and/or algorithm known in the art. Optionally, a 3D display of the data can be generated. Alternatively, the original 2D data can be displayed. The surgeon can use a pointer or marking tool to mark the original of the torn ACL and the insertion of the torn ACL. The location of the origin and insertion of the antero-medial bundle and the postero-lateral can be marked separately. Any ACL remnants or portions thereof can be marked by the surgeon or operator.

If a CT scan is used, the CT data can be imported into a software program to segment the femoral and/or tibial bones using, for instance a thresholding or isosurface algorithm. Optionally, an algorithm can be applied that detects surface roughness and based on this information identified the femoral original of the ACL. Alternatively, the femoral surface in the posterolateral femoral notch can be visually inspected on the 2D or 3D images to identify the origin of the ACL. The medial tibial spine can be identified to mark the insertion of the ACL.

If an ultrasound is used, the femoral and tibial bones can be visualized in 2D. The ultrasound data can optionally be imported into a software program to segment the femoral and/or tibial bones. The residual femoral fibers of the ACL can optionally be identified to determine the location of the native ACL origin. Or the femoral surface roughness in the location of the ACL origin can be used for this purpose. The medial tibial spine can be identified to mark the insertion of the ACL. Any other imaging test known in the art can be used.

Optionally, the medial and lateral femoral condyles can be identified on the ultrasound images or ultrasound data; optionally, the medial and lateral tibial plateau can be identified on the ultrasound images or ultrasound data. Other anatomic landmarks, surfaces and features (for example as provided in the Table below entitled "Exemplary anatomic landmarks, surfaces and features in the knee for registration of virtual and live data including, optionally, pre-operative and intraoperative imaging data, for ACL Repair/Reconstruction" can be identified. Optionally, one or more of these anatomic landmarks, surfaces and features of the distal femur and/or the proximal tibial can be used to identify a standard femoral shape or a standard tibial shape by comparing the one or more anatomic landmarks, surfaces and features with data in a reference database of reference patients and/or reference femoral shapes and/or reference tibial shapes and by selecting a 3D model of the distal femur and/or proximal tibial that most closely matches the selected anatomic landmarks, surfaces or features. In this manner, the 3D shape of the patient's bones, e.g. the distal femur and/or the distal tibia, can be estimated without the need acquire 3D data or without the need of segmentation of the 3D data or limiting the amount of segmentation needed. The reference database can be, for example, an anatomic reference database from cadaver data. The reference database can also be, for example, scan data, e.g. acquired in the NIH Osteoarthritis Initiative or acquired from imaging data to generate patient specific instruments for knee replacement.

If one or more x-rays are used, they can, for example, be obtained in an AP projection of the knee (or PA), and a lateral projection of the knee. Other views are possible, as known in the art, e.g. a tunnel view, Merchant view, patellar view, oblique views, standing views, supine views, prone views. Optionally, the medial and lateral femoral condyles can be identified on the AP/PA and/or lateral and/or oblique views; optionally, the medial and lateral tibial plateau can be identified on the AP/PA and/or lateral and/or oblique views. Other anatomic landmarks, surfaces and features (for example as provided in Table 12 can be identified. Optionally, one or more of these anatomic landmarks, surfaces and features of the distal femur and/or the proximal tibial can be used to identify a standard femoral shape or a standard tibial shape by comparing the one or more anatomic landmarks, surfaces and features with data in a reference database of reference patients and/or reference femoral shapes and/or reference tibial shapes and by selecting a 3D model of the distal femur and/or proximal tibial that most closely matches the selected anatomic landmarks, surfaces or features. In this manner, the 3D shape of the patient's bones, e.g. the distal femur and/or the distal tibia, can be estimated without the need acquire 3D data or without the need of segmentation of the 3D data or limiting the amount of segmentation needed. The reference database can be, for example, an anatomic reference database from cadaver data. The reference database can also be, for example, scan data, e.g. acquired in the NIH Osteoarthritis Initiative or acquired from imaging data to generate patient specific instruments for knee replacement.

Of note, the use 2D imaging data or 3D imaging data, e.g. x-ray, ultrasound, CT or MRI, in combination with one or more reference databases of 3D shape(s) of select anatomic structures, such as a bone, a cartilage, an organ for reducing or limiting or obviating the need for acquiring 3D data or for segmenting 2D or 3D data is applicable to any embodiment of the invention throughout the specification including for all other clinical applications, e.g. hip replacement, knee replacement, spinal surgery, spinal fusion, vertebroplasty, kyphoplasty, fracture fixation, brain surgery, liver surgery, cancer surgery etc.

Virtual Surgical Plans

With the location of the origin and the insertion or the remnants of the patient's native ACL identified using any of the foregoing methods or any other method known in the art, the surgeon or the software can develop/generate a virtual surgical plan using the 2D or 3D imaging data or, optionally, kinematic data, e.g. data simulating knee flexion and/or extension and/or rotation. For example, software can display the virtual data, e.g. imaging data, of the patient. The surgeon or the software can optionally select a desired size or diameter femoral tunnel and/or tibial tunnel for a given patient. The diameter and size of the tunnel can be chosen, for example, based on the size of the patient's bone, the size of the patient's tendon, e.g. if a tendon autograft is contemplated, the size of the patient's patellar tendon, e.g. if a patellar autograft is contemplated, the size of the patient's semitendinosus tendon, e.g. if a semitendinosus autograft is contemplated, or the expected size of an allograft or an artificial graft or the expected biomechanical loads or stresses applied to the graft; the same or similar or other parameters can also be used in choosing a femoral and/or a tibial anchor for the graft, which can include one or more interference screws or other types of anchors including button type anchors. The surgeon or the software can optionally select a predetermined femoral or tibial tunnel location and/or orientation, for example using the femoral origin of the native, torn ACL as an entry point in the femur and the medial tibial spine as an entry point into the tibia. Note, the term entry and exit point can be used interchangeably in the specification.

The surgeon or the software can optionally select a desired size and length graft, e.g. an allograft or an autograft, for a given patient. The diameter and size of the graft can be chosen, for example, based on the size of the patient's bone, the size of the patient's tendon, e.g. if a tendon autograft is contemplated, the size of the allograft tendon, e.g. if an allograft is contemplated, or the expected size of an artificial graft or the expected biomechanical loads or stresses applied to the graft; the same or other parameters can also be used in choosing a femoral and/or a tibial anchor for the graft, which can include one or more interference screws or other types of anchors including button type anchors. The surgeon or the software can optionally select a predetermined femoral or tibial tunnel location and/or orientation, for example using the femoral origin of the native, torn ACL as an entry point in the femur and the medial tibial spine as an entry point into the tibia. Note, the term entry and exit point can be used interchangeably in the specification.

The projected femoral and/or tibial tunnel location and/or orientation can be the extension of a line created by connecting the femoral origin and tibial insertion of the native ACL, optionally the antero-medial bundle or the posterolateral bundle or intermediate positions between the two, for example in extension or 15 degrees flexion. The projected femoral and/or tibial tunnel location and/or orientation and/or the projected graft position, location and/or orientation can be determined for different flexion and extension and/or rotation angles. If the location and/or orientation of the projected femoral and/or tibial tunnel and/or the projected graft varies depending on the degree of flexion, extension and/or rotation, a statistical average can be chosen for select values or other statistical measures or methods can be applied to determine the location, position and/or orientation of the projected femoral and/or tibial tunnel and/or the projected graft.

A graphical user interface, for example implemented on a standard PC or Apple computer, can be utilized for displaying the 2D and/or 3D data of the patient and for identifying the ACL origin and/or insertion and/or the ACL remnants as well as any other bony landmarks, features, surfaces, and/or shapes that can be of interest for developing the surgical plan. The surgeon or the operator can optionally execute the virtual surgical plan on the graphical user interface. The surgeon or the operator can place virtual femoral and/or tibial tunnels, e.g. for single and for double bundle technique, on the graphical user interface and the associated display of the data. The surgeon or the operator can place virtual grafts, e.g. for single and for double bundle technique, on the graphical user interface and the associated display of the data. The surgeon or the operator can place both virtual tunnels and virtual grafts on the graphical user interface and the associated display of the data. The software can optionally display the tunnels and/or the graft in one or more degrees of knee flexion and/or extension and/or rotation. The software and/or the operator can virtually assess the tunnel and/or graft position, location, and/or orientation for one or more flexion, extension, and/or rotation angles and can perform a virtual assessment of graft performance for these one or more different angles. The software and/or the operator/surgeon can optionally make adjustments to the tunnel and/or graft position, location, and/or orientation based on the information obtained in this manner from the one or more flexion, extension, and/or rotation angles.

Optionally, the graphical user interface can provide or display an assessment of the mechanical forces applied to the graft and/or the anchor as well as the surrounding bone. Software can be used for the purpose of assessing the mechanical forces which can, for example, include finite element modeling. In addition, software can be used for assessing the kinematics of the knee for different tunnel and/or graft positions, locations and/or orientations. Such software can, for example, include Anybody or other kinematic modeling software.

Figure 22E:
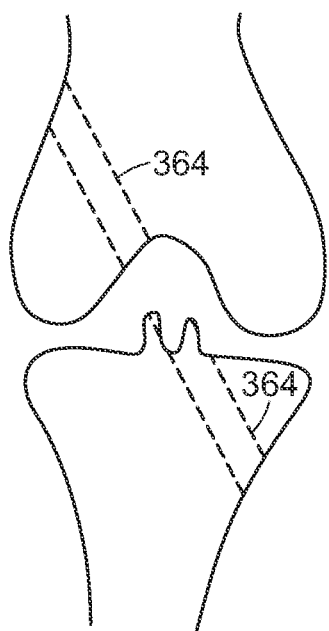
FIGS. 22E and 22F show AP and lateral views demonstrating exemplary virtual ACL tunnels on femoral side and tibial side (straight broken lines) according to some embodiments of the present disclosure.
Figure 22F:
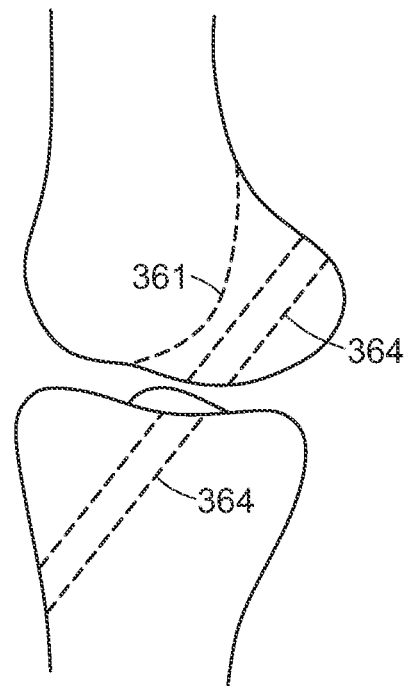

FIGS. 22E AP and F lateral views demonstrating exemplary virtual ACL tunnels 364 on femoral side and tibial side (straight broken lines). Curved broken line on femoral side indicates intercondylar notch area/roof.

Figure 22G:
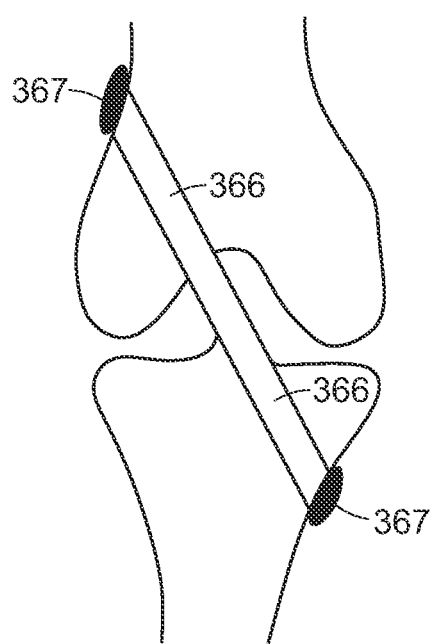
FIGS. 22G and 22H show AP and lateral views demonstrating exemplary virtual ACL graft on femoral side and tibial side extending through intra-articular space between femur and tibia (straight solid lines) according to some embodiments of the present disclosure.
Figure 22H:
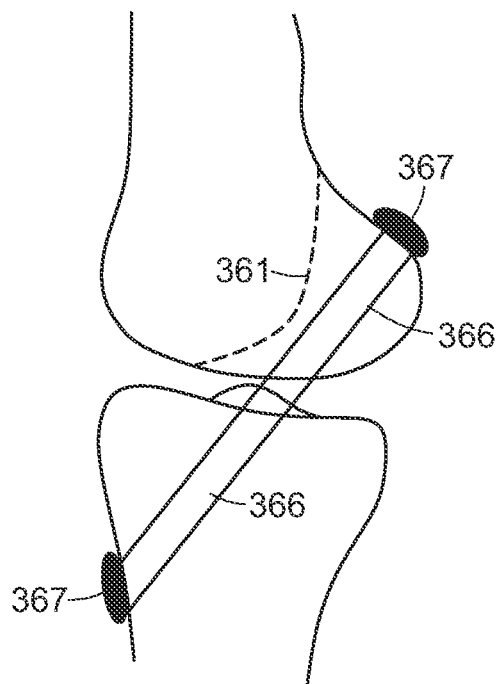

FIGS. 22G AP and 22H lateral views demonstrating exemplary virtual ACL graft 366 on femoral side and tibial side extending through intra-articular space between femur and tibia (straight solid lines). Virtual anchors are also shown on femoral and tibial side (solid black oval structures) 367. Note, instead of virtual anchors, virtual interference screws could be used on the femoral and/or the tibial side or any other means of fixation. Curved broken line on femoral side indicates intercondylar notch area/roof.

Figure 23:
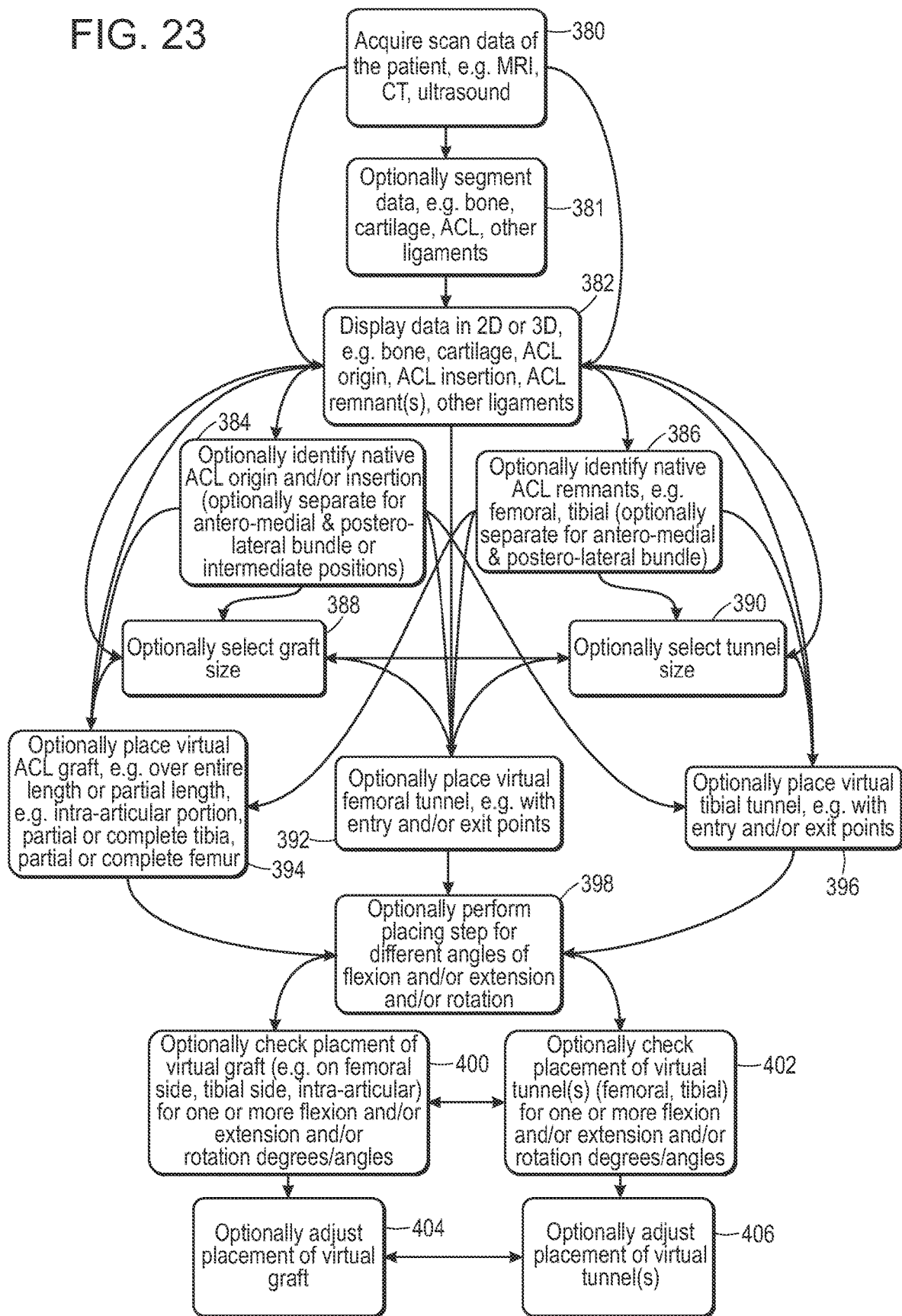
FIG. 23 is an illustrative non-limiting flow chart describing different approaches to planning the location, position, orientation, alignment and/or direction of one or more femoral or tibial tunnels (e.g. for single or double bundle technique) or for placing an ACL graft according to some embodiments of the present disclosure.

FIG. 23 is an illustrative non-limiting flow chart describing different approaches to planning the location, position, orientation, alignment and/or direction of one or more femoral or tibial tunnels (e.g. for single or double bundle technique) or for placing an ACL graft. Scan data can be acquired initially, e.g. ultrasound, CT, MRI 380. The scan data can optionally be segmented 381, e.g. for bone, cartilage, ACL tissue or structures. The segmented 381 or unsegmented 380 scan data can be displayed in 2D or 3D 382. Optionally, the native ACL origin and insertion, optionally separate for anteromedial and posterolateral bundle, can be identified 384. Optionally, the native ACL remnants can be identified, also for anteromedial and posterolateral bundle 386. Optionally, using the information from 384 and/or 386, a graft size 388 or tunnel size 390 or both can be selected. Optionally, the virtual femoral 392 and tibial 396 tunnels can be projected by the OHMD in their respective predetermined position and orientation; alternatively, their central axis can be projected by the OHMD in its predetermined position and orientation, all optionally with entry and exit points displayed. Optionally, a virtual ACL graft can be displayed by the OHMD 394 in its predetermined position. Optionally, steps 392, 394 and/or 396 can be performed or repeated for different degrees of knee flexion or extension and/or rotation including instability testing 398. Optionally, the predetermined position and orientation of the virtual femoral tunnel 392, virtual tibial tunnel 396 and/or virtual ACL graft can be checked in steps 400 and/or 402. Optionally, the predetermined position and orientation of the virtual femoral tunnel 392, virtual tibial tunnel 396 and/or virtual ACL graft can be adjusted or modified in steps 404 and/or 406.

Optionally, the software can simulate different degrees of femoral and tibial flexion and/or rotation during the range of motion or portions of the range of motion.

Registration of Virtual Data and Live Data of the Patient for ACL Repair or Reconstruction In some embodiments of the invention, the pre-operative imaging or scan data or virtual data of the patient, e.g. from an MRI scan, CT scan, ultrasound scan (2D or 3D), x-ray imaging, or x-ray imaging, ultrasound, CT or MRI with selection of a 3D femoral and/or tibial model of the patient from a reference database, can be displayed on a computer screen and an operator, e.g. a surgeon or a radiologist, can manually or semi-automatically identify one or more of the following: lateral femoral notch wall, ACL origin, proximal ACL remnant(s) on the femoral side, including, for example, antero-medial or postero-lateral bundle portions or intermediate portions, medial tibial spine, distal ACL remnant(s) on the tibial side, including, for example, antero-medial or postero-lateral bundle portions or intermediate portions, ACL insertion or any other anatomic structure of the knee. The operator, surgeon or radiologist can, for example, click or circle on one more of these structures to identify them. Optionally, the operator, surgeon or radiologist can assign a label designating the name of the anatomic structure that has been identified with the click or circle, e.g. lateral femoral notch wall, ACL origin, proximal ACL remnant(s) on the femoral side, including, for example, antero-medial or postero-lateral bundle portions or intermediate portions, medial tibial spine, distal ACL remnant(s) on the tibial side, including, for example, antero-medial or postero-lateral bundle portions or intermediate portions, ACL insertion or any other anatomic structure of the knee.

Intra-operatively, the surgeon can then, for example, use a pointer or pointing device to touch the corresponding structures in the live data of the patient. The pointer or pointing device can be registered in relationship to an OHMD or a navigation system and/or the patient and/or the patient's knee, for example with use of one or more IMUs or one or more optical or navigation markers including infrared markers, retroreflective markers, RF markers, or an image and/or video capture system integrated into, attached to or separate from the OHMD so that the position of the pointer and the location, position, orientation and direction of the tip of the pointer is captured in a 3D object coordinate system. The surgeon can then optionally touch the structures corresponding to what was clicked or circled in the pre-operative imaging/virtual data of the patient in the live data of the patient, i.e. the patient's live knee, as seen, for example, through the arthroscope or with an intraoperative ultrasound probe and scan with a pointer. Such structure can, for example, be one or more of a lateral femoral notch wall, ACL origin, proximal ACL remnant(s) on the femoral side, including, for example, antero-medial or postero-lateral bundle portions or intermediate portions, medial tibial spine, distal ACL remnant(s) on the tibial side, including, for example, antero-medial or postero-lateral bundle portions or intermediate portions, ACL insertion or any other anatomic structure of the knee. In this manner, virtual data and live data can be registered in space.

The foregoing anatomic landmarks, surfaces and features are only exemplary and are not meant to be limiting. Someone skilled in the art can readily identify other anatomic landmarks, surfaces or features that can be used for purposes of registration of virtual data and live data of the patient or other data of the patient and/or surgical instruments, for example some of the landmarks in Table 12.

Any of the registration techniques described in the specification can be used for registering virtual data of the patient and live data of the patient for ACL repair or reconstruction. For example, a pre-operative imaging test such as an ultrasound scan, CT scan or MRI scan or one or more x-ray images can be used to produce a patient specific marker. The patient specific marker can be designed to have at least one patient specific surface that can mate with the patient's anatomy, e.g. a femoral surface or a tibial surface. The patient specific marker can be applied to the patient's femur or tibia. Optionally, the patient specific marker can be designed so that it can be passed through a small incision or a small portal inside the knee joint in intra-articular location. For this purpose, the patient specific markers can consist of multiple parts, which can, optionally, be assembled inside the joint. The sub-parts or components of the patient specific marker can have engage-able connectors. Once the patient specific marker has been applied to the corresponding patient surface(s) and is properly seated in a mating position, it can optionally be affixed to the underlying bone or cartilage or ligament structure. The patient specific surface on the physical patient specific marker which mates with the live patient surface corresponds to the virtual patient surface in the virtual patient data. Once the patient specific marker is located in the predetermined position and orientation on the mating surface in the live patient, registration between the virtual data and the live data of the patient can be performed, e.g. using any of the means described in the specification.

The position of the patient specific marker can optionally be captured optically through the arthroscope, for example using an image and/or video capture system integrated into or attached to the arthroscope system and associated display system. The arthroscope or any related instruments or pointers can be registered in relationship to an OHMD or a navigation system and/or the patient and/or the patient's knee, for example with use of one or more IMUs or one or more optical or navigation markers including infrared markers, retroreflective markers, RF markers, or an image and/or video capture system integrated into, attached to or separate from the OHMD so that the position of the arthroscope, instrument and/or pointer and the location, position, orientation and direction of the tip of the arthroscope, instrument and/or pointer is captured in a 3D object coordinate system that can be cross-referenced and registered in relationship to the patient's knee, for example by registering it in relationship to the patient specific marker and/or in relationship to the OHMD or any other reference coordinate system used in the operating room.

The patient specific marker can have a known geometric shape, e.g. a square or a triangle. As the projected shape of the known geometric shape changes in the projection of the arthroscope, the information about the change in shape and size of the projected shape of the known geometric shape can be used, for example with an image and/or video capture system, to compute or estimate the position of the arthroscope in relationship to the patient specific marker and/or the live data, e.g. the live arthroscopic images obtained from inside the patient's joint, during the procedure. Instead of a known geometric shape, the patient specific marker can include other markers, e.g. one, two, three or more LEDs. The change in position of the one, two, three or more LEDs projected by the arthroscope from within the patient's joint can be used to compute or estimate the position of the arthroscope in relationship to the patient specific marker and/or the live data, e.g. the live arthroscopic images obtained from inside the patient's joint, during the procedure. The patient specific marker can also include physical reference areas or points, e.g. a groove or a recess that can accommodate the tip of a pointer. In this manner, the tip of the pointer can be placed in the groove or recess. The pointer can have one or more IMUs or one or more optical or navigation markers including infrared markers, retroreflective markers, RF markers attached to it which can be detected by the OHMD or a navigation system. The position of the can also be detected with used of an image and/or video capture system, for example integrated into, attached to or separate from the OHMD.

In some embodiments of the invention, the patient's knee can be imaged intra-operatively, for example using an x-ray or multiple x-ray images or a CT or an ultrasound scan. Anatomic landmarks can be identified on the scan, which can, for example, include:

TABLE 12: Exemplary anatomic landmarks, surfaces and features in the knee for registration of virtual and live data including, optionally, pre-operative and intraoperative imaging data, for ACL Repair/Reconstruction Medial wall of the femoral notch
Lateral wall of the femoral notch
Roof of the femoral notch
Residual ACL origin
Residual ACL insertion
Medial wall of the medial condyle
Lateral wall of the lateral condyle
Medial epicondylar eminence
Lateral epicondylar eminence
Medial femoral condyle shape, e.g. radii, convexities, concavities
Lateral femoral condyle shape, e.g. radii, convexities, concavities
Intercondylar notch shape
Intercondylar notch surface features
Medial tibial spine
Lateral tibial spine
Anteromedial tibial rim
Anterolateral tibial rim
Medial tibial rim
Lateral tibial rim
Lowest point of the medial plateau
Lowest point of the lateral plateau
Highest point of the medial plateau
Highest point of the lateral plateau
Medial tibial plateau shape
Lateral tibial plateau shape
Medial tibial plateau surface features, e.g. radii, convexities, concavities
Lateral tibial plateau surface features, e.g. radii, convexities, concavities The foregoing anatomic landmarks, surfaces and features are only exemplary and are not meant to be limiting. Someone skilled in the art can readily identify other anatomic landmarks, surfaces or features that can be used for purposes of registration of virtual data and live data of the patient or other data of the patient and/or surgical instruments.

The anatomic landmarks, surfaces and features can be used for registering one or more of the following: pre-operative data, e.g. pre-operative kinematic data, pre-operative imaging data; intra-operative data, e.g. intra-operative kinematic data, intra-operative imaging data; virtual data of the patient, e.g. virtual kinematic data, virtual imaging data, virtual anatomic data, virtual instrument data, virtual device data, virtual surgical plan of the patient, live data of the patient including physical surgical instruments and arthroscope, for example as seen through the OHMD or as captured by an image and/or video capture system integrated into, attached to or separate from the OHMD, or as seen through the arthroscope. The anatomic landmarks, surfaces and features can, for example, be clicked on or circled or can be identified automatically on one or more of the virtual data of the patient, and/or on one or more of the intraoperative imaging data of the patient, e.g. intraoperatively obtained x-rays or ultrasound, and the corresponding anatomic landmarks, surfaces and features in the live patient/knee can, for example, be touched with a pointer or probe by the surgeon. The pointer or probe can be registered in relationship to an OHMD or a navigation system and/or the patient and/or the patient's knee, for example with use of one or more IMUs or one or more optical or navigation markers including infrared markers, retroreflective markers, RF markers or an image and/or video capture system integrated into, attached to or separate from the OHMD so that the position of the pointer and the location, position, orientation and direction of the tip of the pointer is captured in a 3D object coordinate system which can be cross-referenced to the intra-operative data.

The intra-operative data, e.g. intra-operative imaging data, can be manually or semi-automatically or automatically (e.g. through image processing and/or pattern recognition techniques) cross-referenced and registered to the virtual data of the patient, virtual surgical plan and/or the live data of the patient. Virtual data, virtual surgical plan, intra-operative data, e.g. intra-operative imaging, and live data of the patient can be registered in the same coordinate system, optionally through various coordinate transfers. The surgeon can optionally touch the structures corresponding to what was clicked or circled in the pre-operative imaging/virtual data and/or the intra-operative data, e.g. intra-operative imaging data, of the patient in the live data of the patient, i.e. the patient's live knee, as seen, for example, through the arthroscope with a pointer which can include or carry one or more IMUs or one or more optical or navigation markers including infrared markers, retroreflective markers, RF markers or which can be registered with use of an image and/or video capture system integrated into, attached to or separate from the OHMD. Optionally, an ultrasound probe can be introduced through one or more of the portals and the ultrasound probe can be used for intra-operative imaging, e.g. in addition to x-ray imaging. The ultrasound probe can be used to identify, for example, the ACL origin, ACL insertion and/or any proximal or distal ACL remnants. The ultrasound probe can include or carry one or more IMUs or one or more optical or navigation markers including infrared markers, retroreflective markers, RF markers which can be registered with use of an image and/or video capture system integrated into, attached to or separate from the OHMD. Alternatively, an optical pointer, e.g. a laser can be used to point at one or more of the anatomic landmarks, surfaces and features in the live patient, corresponding to the anatomic landmarks, surfaces and features that had been marked in the virtual data of the patient and/or the intra-operative data of the patient. The optical pointer can include or carry one or more IMUs or one or more optical or navigation markers including infrared markers, retroreflective markers, RF markers which can be registered with use of an image and/or video capture system integrated into, attached to or separate from the OHMD or a navigation system. Whenever the optical pointer highlights one or more of the anatomic landmarks, surfaces and features in the live patient, the area can be captured through the imaging system of the arthroscope or through an an image and/or video capture system integrated into, attached to or separate from the OHMD. In this manner, corresponding anatomic landmarks, surfaces and features can be identified in the live data of the patient and can be cross-referenced to and registered with the virtual data of the patient and/or the intra-operative data of the patient.

The arthroscope, surgical instruments, probes, pointers ACL grafts, femoral and/or tibial anchors and other devices can also be registered in relationship to any of the anatomic landmarks, surfaces or features used for registration in the virtual, intra-operative, live or other data of the patient. For this purpose, the physical and, optionally, the virtual arthroscope, surgical instruments, probes, pointers, ACL grafts, femoral and/or tibial anchors and other virtual devices and/or virtual femoral and/or tibial tunnels can be registered in relationship to an OHMD or a navigation system and/or the patient and/or the patient's knee, for example with use of one or more IMUs or one or more optical or navigation markers including infrared markers, retroreflective markers, RF markers or an image and/or video capture system integrated into, attached to or separate from the OHMD so that the position of the arthroscope, surgical instruments, probes, pointers ACL grafts, femoral and/or tibial anchors and other devices and the location, position, orientation and direction of the arthroscope, surgical instruments, probes, pointers ACL grafts, femoral and/or tibial anchors and other devices is captured in a 3D object coordinate system.

Optionally, one or more anatomic landmarks identified on the intraoperative scan can be cross-referenced to the virtual data of the patient obtained prior to the surgical procedure, e.g. pre-operative x-rays, a CT scan, an MRI scan, or an ultrasound scan, for example used in developing the virtual surgical plan. The imaging modality used during the surgery, e.g. ultrasound, can be different from the imaging modality used to generate the virtual data of the patient and, optionally, the virtual surgical plan, e.g. an MRI.

Optionally, the arthroscope and/or one or more instruments introduced through any of the portals can carry one, two, three or more IMUs, optical, light or other markers, navigation markers including infrared markers, retroreflective markers, RF markers, image capture markers (e.g. LEDs) and the like. Only one or more instruments can be registered in relationship to the virtual data of the patient or the intra-operative data of the patient, while the scope cannot be registered. Only the scope can be registered in relationship to the virtual data of the patient or the intra-operative data of the patient, while the one or more instruments cannot be registered. Any marker described in the specification or known in the art can be used. The position and/or orientation of the scope and/or the one or more instruments can be registered, for example in relationship to one or more anatomic landmarks identified on the intra-operative imaging data or in relationship to the virtual data of the patient, e.g. a pre-operative x-ray, CT, MRI or ultrasound, or in relationship to the virtual surgical plan.

Other markers that can be used for any of the foregoing embodiments for ACL repair and/or ACL reconstruction include, but are not limited to, skin markers, intra-articular markers, RF markers, optical markers, arthroscopic anchors, arthroscopic tags, pins and/or screws.

In some embodiments of the invention, the surgeon can obtain an image of the origin and/or the insertion of the ACL or an image of a proximal and/or a distal remnant of the ACL or a combination of both through the arthroscope or through use of an intraoperative imaging technology such as an ultrasound, e.g. inserted through one of the portals. A comparable projection can then be obtained on a computer monitor or in the projection of the OHMD, wherein the view angle and the magnification of the virtual data and the live data of the patient can be substantially similar and can be superimposed, e.g. visually in the OHMD. Once substantial similarity for a view angle and magnification of the live data and the virtual data of the patient has been obtained, the data can be registered, e.g. in the same coordinate system or in separate coordinate systems with a known coordinate transfer. The arthroscope, surgical instruments, probes, pointers, ACL grafts, femoral and/or tibial anchors and other devices can include or can have attached one or more IMUs or one or more optical or navigation markers including infrared markers, retroreflective markers, RF markers or an image and/or video capture system can be used that can be integrated into, attached to or separate from the OHMD so that the arthroscope, surgical instruments, probes, pointers, ACL grafts, femoral and/or tibial anchors and other devices can remain registered as they are being moved, for example after the initial registration using the substantially similar projections of the physical and the virtual data of the patient.

In some embodiments, the landmarks of the distal femur can be registered, optionally in relationship to the tibia. The tibia can optionally be in a fixed position, e.g. with use of a leg holder in relationship to the femur. Optionally, pins can be placed, e.g. in the bone, e.g. at or near the position of the predetermined femoral tunnel. The position of the one or more pins can be registered, for example with use of an image and/or video capture system or one or more attached IMUs or optical markers or navigation markers including infrared markers, retroreflective markers, RF markers. In this manner, by keeping the pin and/or one or more IMUs, optical markers or navigation markers in place or by using an image and/or video capture system integrated into, attached to or separate from the OHMD, the femoral and/or tibial registration can be maintained even as the knee is moved into different positions, e.g. different flexion, extension, rotation, abduction, adduction angles.

In some embodiments, the landmarks of the proximal tibia can be registered, optionally in relationship to the femur. The femur can optionally be in a fixed position, e.g. with use of a leg holder in relationship to the tibia. Optionally, pins can be placed, e.g. in the bone, e.g. at or near the position of the predetermined tibial tunnel. The position of the one or more pins can be registered, for example with use of an image and/or video capture system or one or more attached IMUs or optical markers or navigation markers. In this manner, by keeping the pin and/or one or more IMUs or optical markers or navigation markers in place or by using an image and/or video capture system integrated into, attached to or separate from the OHMD, the tibial and/or femoral registration can be maintained even as the knee is moved into different positions, e.g. different flexion, extension, rotation, abduction, adduction angles.

The following data can be registered in relationship to each other using one or more of the methods described herein:

Virtual data of the patient, e.g. pre-operative imaging data, pre-operative kinematic data Virtual surgical plan Intraoperative imaging data, e.g. select landmarks, surfaces or features of the patient visualized using an intraoperative scan (see for example foregoing list), e.g. one or more x-rays, CT, MRI, ultrasound Intraoperative image capture data, e.g. select landmarks, surfaces or features of the patient's knee (see for example foregoing list) or the patient's joint One or more patient specific markers applied to the joint, e.g. applied to one or more articular surfaces or osteophytes, optionally visualized using an image and/or video capture system integrated into, attached to or separate from the arthroscopy system or optionally visualized through the arthroscopy system Scope position, location, orientation, alignment and direction, for example measured via attached IMUs, optical markers, navigation markers including infrared markers, retroreflective markers, RF markers, or an image and/or video capture system integrated into, attached to or separate from the OHMD Instrument, probe, graft, anchor or other device position, location, orientation, alignment and direction, for example measured via attached IMUs, optical markers, navigation markers including infrared markers, retroreflective markers, RF markers, or an image and/or video capture system integrated into, attached to or separate from the OHMD Projected Path of the Physical Instruments, Devices or Grafts and Virtual Path of Virtual Instruments, Devices, Grafts or Tunnels Registration can be effected or achieved using any of the techniques described in the specification. For example, the position, location, orientation, direction of any of the IMUs or optical markers or navigation markers including infrared markers, retroreflective markers, RF markers, integrated into or attached to any of the arthroscope, surgical instruments, probes, pointers, ACL grafts, femoral and/or tibial anchors and other devices can be captured using the OHMD or navigation system or the position, location, orientation, direction of the arthroscope, surgical instruments, probes, pointers, ACL grafts, femoral and/or tibial anchors and other devices can be captured using an image and/or video capture system, e.g. integrated into, attached to or separate from the OHMD, and, for example, a projected path for an physical surgical instrument, e.g. a probe or a drill, can be computed and/or displayed by the OHMD and/or the display monitor(s) of the arthroscopy system once registration has been completed. The projected path of an physical surgical instrument can, for example, be parallel to, coinciding with, superimposed onto, or orthogonal to or at a defined angle to the predetermined position and/or orientation of one or more of the predetermined femoral tunnel, tibial tunnel, ACL graft or anchor(s) or interference screws. The projected path can change as the position, location, orientation, direction of the physical arthroscope, surgical instruments, probes, pointers, ACL grafts, femoral and/or tibial anchors and other devices changes. The projected path can be an extension of the long or other axis or the direction of travel of the one or more of the physical arthroscope, surgical instruments, probes, pointers, ACL grafts, femoral and/or tibial anchors and other devices. The projected path can be displayed by the OHMD, in 3D stereoscopic or 3D non-stereoscopic or 2D form, optionally with different colors or patterns. The projected path can be displayed by the display monitor of the arthroscopy system and/or both.

If the display is through the OHMD, the magnification can be adjusted if the operator looks at the patient or the patient's knee, which can require, for example, no magnification, or if the operator looks at the display of the arthroscopic images obtained through the scope and, optionally, displayed by the monitor system of the arthroscopy unit. Since images of the patient's knee and internal structures obtained through the arthroscope and optionally displayed by the arthroscopy system display monitor are typically magnified, the display of the projected path can be magnified as well, for example matching the magnification factor of the arthroscopy display or system. The display of the projected path and/or any virtual instruments or virtual displays of any non-visualized portions of physical instruments can be matched in magnification to the magnification of the arthroscopic images or the inherent magnification of the arthroscopy system or, optionally, it can be slightly less or more in magnification than the magnification of the arthroscope or the arthroscopy monitor display unit.

In some embodiments of the invention, a virtual path for one or more the arthroscope, surgical instruments, probes, pointers, ACL grafts, femoral and/or tibial anchors and other devices can be displayed by the OHMD and/or the arthroscopy system display monitor(s). The virtual path can coincide or be substantially aligned with or parallel with or be identical with the predetermined path of the surgical instrument. The virtual path can, for example, be parallel to, coinciding with, superimposed onto, or orthogonal to or at a defined angle to the predetermined position and/or orientation of one or more of the predetermined femoral tunnel, tibial tunnel, ACL graft or anchor(s) or interference screws. The virtual path can be projected through the OHMD, optionally in 3D stereoscopic or 3D non-stereoscopic or 2D form, optionally with different colors or patterns. The virtual path can be projected by the display monitor of the arthroscopy system. Virtual instruments and or devices such as virtual arthroscope, surgical instruments, probes, pointers, ACL grafts, femoral and/or tibial anchors and other virtual devices can also be displayed by the OHMD and/or the arthroscopy system display monitor(s).

If the display is through the OHMD, the magnification can be adjusted if the operator looks at the patient or the patient's knee, which can require, for example, no magnification, or if the operator looks at the display of the arthroscopic images obtained through the scope and, optionally, displayed by the display monitor system of the arthroscopy unit. Since images of the patient's knee and internal structures obtained through the arthroscope and optionally displayed by the arthroscopy system display monitor are typically magnified, the display of the virtual path or any virtual instruments or devices such as the arthroscope, surgical instruments, probes, pointers, ACL grafts, femoral and/or tibial anchors and other virtual devices can be magnified as well, for example matching the magnification factor of the arthroscopy display or system. The display of the virtual path and/or any virtual instruments or devices can be matched in magnification to the magnification of the arthroscopic images or the inherent magnification of the arthroscopy system or, optionally, it can be slightly less or more in magnification than the magnification of the arthroscope or the arthroscopy monitor display unit. The display of the virtual path and/or any virtual instruments or devices can be using different colors or patterns, for example different than the live data of the patient, including the arthroscopic images of the internal structures of the knee.

In some embodiments of the invention, the extremity, in the case of shoulder surgery or elbow surgery the arm, in the case of knee or hip surgery, including ACL repair or reconstruction, is held or positioned in the same position, e.g. the same degrees of flexion, extension, abduction, adduction, internal or external rotation, for the acquisition of data that will be used for purposes of registration of pre-operative data, e.g. pre-operative imaging data and/or kinematic data, intra-operative data, e.g. intra-operative imaging data and/or kinematic data, and/or live data of the patient, e.g. data observed through the OHMD such as live patient data of the knee joint or data observed through the OHMD or the display monitor unit of the arthroscopy system, e.g. live patient data of the internal structures of the patient's knee. By acquiring these pre-operative, intra-operative and live patient data in the same position of the extremity or the target tissue or the joint, less variability in positioning can be encountered which can help facilitate registration using any of the methods described in the specification. For example, an upper arm holder or a leg holder can be used for obtaining pre-operative imaging data, e.g. x-ray images, ultrasound data, CT or MRI data of the extremity or target joint or target tissue; the upper arm or leg holder can fixate the extremity or target joint or target tissue in one or more positions. The same or a similar upper arm holder or a leg holder can be used for obtaining intra-operative imaging data, e.g. x-ray images, ultrasound data, CT or MRI data of the extremity or target joint or target tissue; the upper arm or leg holder can fixate the extremity or target joint or target tissue in one or more positions for the intra-operative data acquisition. The live patient data including arthroscopic data obtained from inside the patient's joint can be obtained with the extremity, the target joint or the target tissue in a similar position than that used when the pre-operative or intra-operative data were obtained. Registration of two or more of pre-operative data of the patient, intra-operative data of the patient, virtual data of the patient, virtual surgical plan of the patient or live data of the patient, including arthroscopic image or other data obtained from within the patient's joint can be facilitated in this manner.

Any of the foregoing embodiments, e.g. those related to virtual surgical plans, registration, and extremity or target joint or tissue positioning are applicable to other surgical procedures, e.g. knee replacement, hip replacement, spinal surgery, spinal fusion, vertebroplasty, kyphoplasty, brain surgery, other organ surgery, e.g. liver, renal, spleen, intestinal surgery as well as removal of any kind of neoplasms.

OHMD

The OHMD can optionally display the one or more virtual tunnels or the virtual graft or the virtual graft position. The OHMD can also display a projected path of one or more physical surgical instruments or devices, e.g. an arthroscope, surgical instruments, probes, pointers, ACL grafts, femoral and/or tibial anchors and other devices. The OHMD can also display the virtual path of one or more physical surgical instruments or devices, e.g. an arthroscope, surgical instruments, probes, pointers, ACL grafts, femoral and/or tibial anchors and other devices. The virtual path can be the predetermined path from the virtual surgical plan.

Optionally, one or more physical surgical instrument(s) or devices, e.g. an arthroscope, probes, pointers, ACL grafts, femoral and/or tibial anchors and other devices, and/or their projected path can be aligned with the display of the virtual tunnel(s), virtual graft or virtual graft position. Alternatively, the OHMD can display the virtual position of the corresponding virtual surgical instrument(s) or devices, e.g. an arthroscope, surgical instruments, probes, pointers, ACL grafts, femoral and/or tibial anchors and other devices, and the operator can optionally align the one or more physical surgical instruments or devices with the virtual surgical instruments or devices. Alternatively, the OHMD can display the position and/or orientation and/or alignment or direction of travel of the virtual surgical instruments or devices as well as one or more of the virtual tunnel(s), virtual graft or virtual graft position and the physical surgical instruments or devices, e.g. a probe or drill, and/or their projected path can be aligned with combinations of both of the virtual surgical instruments or devices and or the virtual tunnel(s), virtual graft or virtual graft.

The projected path, virtual path, predetermined path, virtual surgical instruments and/or devices, the arthroscope, surgical instruments, probes, pointers, ACL grafts, femoral and/or tibial anchors and other virtual devices, virtual tunnel(s), and/or virtual graft can be displayed by the OHMD and/or the display unit of the arthroscopy system using different patterns and colors, e.g. solid lines, broken lines, dotted lines, different colors, e.g. green, red, blue, orange, different thickness, different opacity or transparency.

In some embodiments, one or more IMUs and/or optical markers, LEDs, navigation markers including infrared markers, retroreflective markers, RF markers, calibration phantoms can be applied to the arthroscope, surgical instruments, probes, pointers, ACL grafts, femoral and/or tibial anchors and other devices. The arthroscope, surgical instruments, probes, pointers, ACL grafts, femoral and/or tibial anchors and other devices can be registered, e.g. in relationship to the virtual data of the patient. The arthroscope or one or more arthroscope instruments, e.g. probes or pointers, can be applied to various landmarks inside the knee joint, visualized through the arthroscope, and registered with the patient's virtual data, e.g. preo-operative scan data, and/or intra-operative scan data.

Once virtual data and live data of the patient are registered, the physical drill or instrument used for preparing the tunnel can be aligned with the axis, position and/or orientation of the virtual drill or virtual tunnel displayed by the OHMD and/or the display unit of the arthroscopy system, both on the femoral and on the tibial side. Alternatively, a virtual path can be displayed by the OHMD and/or the display unit of the arthroscopy system, and the physical drill, e.g. the long axis of the physical drill, and the entry point of the physical drill can be aligned with the virtual path. This can be performed with single and double bundle technique. This can also be performed separately for the femoral and/or the tibial tunnel and the femoral and/or the tibial side of the graft. If a transtibial technique is used, the femoral and the tibial tunnels can be linked for a given angle of knee flexion (and/or rotation) in the virtual surgical plan and the virtual display by the OHMD or the display unit of the arthroscopy system so that the virtual surgical plan is consistent with the intended transtibial technique of the surgeon.

In some embodiments of the invention, the scope can optionally have one or more IMUs or optical markers or navigation markers including infrared markers, retroreflective markers, RF markers attached and the scope can be registered in its location in relationship to the OHMD. The position and/or orientation of the scope can also be captured with an image and/or video capture system integrated into, attached to or separate from the OHMD. The surgeon can move the arthroscope back and forth over a target area of the distal femur or the proximal tibia, e.g. the area(s) of the approximate tunnel placement or the area(s) of the ACL origin and/or insertion. By moving the scope back and forth over the target area, a visual perception of the surface topography and/or shape can be obtained. In addition, since the scope can be registered in a coordinate system with use of the one or more IMUs, optical markers, navigation markers including infrared markers, retroreflective markers, RF markers and/or the image and/or video capture system, the surface topography and/or shape of the target area can also be captured and registered in relationship to the scope and/or the OHMD and their respective object coordinate systems. As the scope is moved back and forth over the target area, multiple projections of the target area can be obtained by the scope at different angular orientations of the scope. Optionally, these multiple angular projections of the target area can be used to reconstruct a 3D surface of the target area or estimate a target area surface or topography or shape from the scope image data. The surface topography and/or the shape can be compared to the surface topography and/or shape of the target area in the virtual data of the patient or, optionally, the intra-operative data of the patient. Using standard image processing techniques known in the art and feature comparisons, substantially similar surface topographies and/or shapes can be identified in the scope image data and the virtual data of the patient and registration of the scope image data and with that live data of the patient, virtual data of the patient, and/or OHMD can be performed. Any object coordinate transfers can now be known for purposes of the registration.

If the virtual surgical instruments, devices, grafts or tunnels and/or the virtual surgical plan are displayed by the OHMD and/or the display unit of the arthroscopy system, the surgeon can move the arthroscope back and forth or, for example, in a circular fashion to obtain a depth perspective or pseudo 3D effect of the intra-articular structures including, for example, the visual representation by the arthroscopy unit of the respective tunnel entry areas; while the surgeon is moving the arthroscope in this manner, the arthroscope motion including the change in angular orientation or direction can be monitored using one or more IMUs or optical markers and/or navigation markers including infrared markers, retroreflective markers, RF markers attached to the arthroscope or it can be monitored by an image and/or video capture system integrated into, attached to or separate from the OHMD. The software can maintain the registration of the arthroscopy system in relationship to the virtual data of the patient and the live data of the patient through the change in angular orientation and or direction and the display of the virtual surgical instruments, devices, grafts or tunnels and/or the virtual surgical plan will remain steady in the OHMD.

The following is an exemplary list of physical and virtual instruments that can be used during the ACL reconstruction. The OHMD can display one or more or all of these instruments in virtual form during the course of the surgical procedure following the virtual surgical plan. For example, each virtual instrument can be displayed with the predetermined position, location, orientation and/or direction to execute on the virtual surgical plan so that the surgeon can align the physical instruments used for the ACL reconstruction with the virtual instruments displayed by the OHMD or the virtual tunnels on the femoral or tibial side or a central tunnel axis on the femoral or the tibial side or a virtual ACL graft. The OHMD can also display a virtual path of the virtual surgical instruments, wherein the virtually path can be the predetermined path from the virtual surgical plan. The OHMD can also display the projected path of the physical surgical instruments used in the live data of the patient.

TABLE 13: Exemplary list of physical surgical instruments and virtual surgical instruments displayed by the OHMD for ACL reconstruction (multiple of each can be used, e.g. with different dimensions, lengths, shapes):

Arthroscope
Power instrument
Power tool
Arthroscopy portal
Arthroscopy sheath
Obturator
Grasper, e.g. alligator grasper, bulldog grasper
Duckster
Upbiter
Punch, e.g. wishbone punch
Burr
Shaver
Suture cutter
Scissors
Drill, various kinds, different diameters, solid, cannulated
Drill guide
Offset drill guide
Offset drill guide screw or pin
Drill sleeve(s), various kinds, e.g. stepped drill sleeve, straight drill sleeve
Chuck key
Hook probe
Parallel guide
Parallel guide sleeve
Tendon stripper, e.g. semitendinosus tendon stripper, hamstring tendon stripper
Rasp, e.g. notchplasty rasp
Reamer
Reamer handle
Pin puller
Tunnel plug
Tunnel notcher
Retractor, e.g. graft harvesting retractor
Hook, e.g. femoral or tibial ACL marking hook
ACL guide, e.g. femoral or tibial, left, right
Screwdriver, e.g. retro-screwdriver, interference screw driver
Screwdriver shaft, cannulated or non-cannulated
ACL guides, e.g. transportal ACL guide
ACL drill guide, e.g. transtibial ACL drill guide
Tibial or femoral tunnel guides, e.g. with single point elbow slide, single point forked slide, dual point forked slide
Femoral aimer
Tibial aimer
Osteotome
Handle
Cannula, e.g. tibial tunnel cannula, optionally with one or more obturators
Cut guides, e.g. for graft harvesting
Graft sizing tool
Graft knife
Graft knife holder/handle
Interference screw, resorbable, non-resorbable The OHMD can display the complete femoral and/or tibial tunnel, it can display only a central line or axis, or it can display a directional arrow for the tunnel(s). The OHMD can display the complete femoral and/or intra-articular and/or tibial graft portions, it can display only a central line or axis in the femoral, intra-articular or tibial area, or it can display a directional arrow for the graft(s).

Optionally, if the surgeon elects to change the physical surgical plan, the virtual surgical plan can be adapted accordingly, for example via a computer interface, and the sequence of steps and virtual instruments displayed in the OHMD can be changed by changing the virtual surgical plan. Changes to the virtual surgical plan can include a change in sequence of surgical steps, a change in surgical approach, e.g. femur first, tibia first, transtibial, omitting select surgical steps, adding surgical steps, re-orienting virtual surgical tunnel(s), re-orienting virtual surgical graft etc.

If the surgeon elects to adjust the position, location and/or orientation of the femoral or the tibial tunnel, the software can adjust the position of the tunnel on the opposing side in the virtual surgical plan. Such adjustments can be automatic, e.g. if a transtibial technique is used, the femoral tunnel can be an extension of an adjusted tibial tunnel. The adjustments in the virtual surgical plan of the opposing tunnel can also be manual, e.g. by the surgeon, for example after the surgeon has adjusted the first physical tunnel and altered its position in relationship to the virtual surgical plan. The software can optionally re-compute the location of the opposing tibial tunnel for different angles of extension, flexion and rotation after the position and/or orientation of the first tunnel has been changed, either in the virtual surgical plan or in the physical surgery.

Any surgical technique or approach known in the art for ACL reconstruction and also for ACL repair can be used. Accordingly, virtual surgical plans can be used for any surgical technique or approach known in the art for ACL reconstruction and also for ACL repair and can be displayed by the OHMD. Such surgical techniques or approaches can include, but are not limited to, open surgical ACL reconstruction or repair, arthroscopic surgical ACL reconstruction or repair, all inside ACL reconstruction or repair, trans-tibial ACL reconstruction, femur first techniques, tibia first techniques, use of interference screws or other types of anchors, single and double bundle techniques, patellar autograft techniques, semitendinosus tendon techniques, other types of tendon graft techniques, allograft techniques.

In some embodiments of the invention, the OHMD can optionally display any non-visualized portions of one or more of the physical arthroscope, surgical instruments, probes, pointers, ACL grafts, femoral and/or tibial tunnels, femoral and/or tibial anchors and other devices. Since the geometries, shapes and dimensions of the physical arthroscope, surgical instruments, probes, pointers, ACL grafts, femoral and/or tibial anchors and other devices are known, optionally an image and/or video capture system can be used to capture the visualized portions of the one or more arthroscope, surgical instruments, probes, pointers, ACL grafts, femoral and/or tibial anchors and other devices. Optional markers, e.g. cm or mm marks, can be used to identify which portions of the physical arthroscope, surgical instruments, probes, pointers, ACL grafts, femoral and/or tibial anchors and other devices are visualized and which ones are not visualized. The software can then identify which portions of the arthroscope, surgical instruments, probes, pointers, ACL grafts, femoral and/or tibial tunnels, femoral and/or tibial anchors and other devices are not included in the image capture data or are not visualized and the software can compute the position, location, orientation and size/magnification (if applicable) of the non-visualized portions of the arthroscope, surgical instruments, probes, pointers, ACL grafts, femoral and/or tibial tunnels, femoral and/or tibial anchors and other devices, which can then optionally be displayed by the OHMD, e.g. as an extension of the visualized portions of the physical arthroscope, surgical instruments, probes, pointers, ACL grafts, femoral and/or tibial tunnels, femoral and/or tibial anchors and other devices. Other means described in the specification for displaying the non-visualized portions of the physical arthroscope, surgical instruments, probes, pointers, ACL grafts, femoral and/or tibial tunnels, femoral and/or tibial anchors and other devices can be used. The non-visualized portions of the physical arthroscope, surgical instruments, probes, pointers, ACL grafts, femoral and/or tibial tunnels, femoral and/or tibial anchors and other devices can be displayed by the OHMD, the display unit of the arthroscopy system or both.

In some embodiments of the invention, the OHMD can display one or more projected paths for one or more physical arthroscope, surgical instruments, probes, pointers, ACL grafts, femoral and/or tibial tunnels, femoral and/or tibial anchors and other devices and/or it can display one or more virtual arthroscope, surgical instruments, probes, pointers, ACL grafts, femoral and/or tibial tunnels, femoral and/or tibial anchors and other devices and/or one or more virtual paths and/or virtual surgical plans for the one or more virtual arthroscope, surgical instruments, probes, pointers, ACL grafts, femoral and/or tibial tunnels, femoral and/or tibial anchors and other devices. In some embodiments, the display unit of the arthroscopy system, e.g. one or more electronic monitors used, can display one or more projected paths for one or more physical arthroscope, surgical instruments, probes, pointers, ACL grafts, femoral and/or tibial tunnels, femoral and/or tibial anchors and other devices and/or it can display one or more virtual arthroscope, surgical instruments, probes, pointers, ACL grafts, femoral and/or tibial tunnels, femoral and/or tibial anchors and other devices and/or one or more virtual paths and/or virtual surgical plans for the one or more virtual arthroscope, surgical instruments, probes, pointers, ACL grafts, femoral and/or tibial tunnels, femoral and/or tibial anchors and other devices. In some embodiments s of the invention, both the OHMD and the display unit of the arthroscopy system, e.g. one or more electronic monitors used, can display one or more projected paths for one or more physical arthroscope, surgical instruments, probes, pointers, ACL grafts, femoral and/or tibial tunnels, femoral and/or tibial anchors and other devices and/or it can display one or more virtual arthroscope, surgical instruments, probes, pointers, ACL grafts, femoral and/or tibial tunnels, femoral and/or tibial anchors and other devices and/or one or more virtual paths and/or virtual surgical plans for the one or more virtual arthroscope, surgical instruments, probes, pointers, ACL grafts, femoral and/or tibial tunnels, femoral and/or tibial anchors and other devices.

The OHMD can display the one or more projected paths for one or more physical arthroscope, surgical instruments, probes, pointers, ACL grafts, femoral and/or tibial tunnels, femoral and/or tibial anchors and other devices and/or it can display the one or more virtual arthroscope, surgical instruments, probes, pointers, ACL grafts, femoral and/or tibial tunnels, femoral and/or tibial anchors and other devices and/or one or more virtual paths and/or virtual surgical plans for the one or more virtual arthroscope, surgical instruments, probes, pointers, ACL grafts, femoral and/or tibial tunnels, femoral and/or tibial anchors and other devices using a magnification or size that is reflective of or corresponds to the distance of the OHMD or the surgeon's or operator's eyes to the patient's knee joint when the surgeon looks at the knee joint. The display unit, e.g. one or more electronic monitors, of the arthroscopy system can display the one or more projected paths for one or more physical arthroscope, surgical instruments, probes, pointers, ACL grafts, femoral and/or tibial tunnels, femoral and/or tibial anchors and other devices and/or it can display the one or more virtual arthroscope, surgical instruments, probes, pointers, ACL grafts, femoral and/or tibial tunnels, femoral and/or tibial anchors and other devices and/or one or more virtual paths and/or virtual surgical plans for the one or more virtual arthroscope, surgical instruments, probes, pointers, ACL grafts, femoral and/or tibial tunnels, femoral and/or tibial anchors and other devices using a magnification or size that is reflective of or corresponds to the magnification of the display unit of the arthroscopy system for the display of the live data of the patient from inside the patient's knee joint so that the size and/or magnification of the one or more projected paths for one or more physical arthroscope, surgical instruments, probes, pointers, ACL grafts, femoral and/or tibial tunnels, femoral and/or tibial anchors and other devices and/or the one or more virtual arthroscope, surgical instruments, probes, pointers, ACL grafts, femoral and/or tibial tunnels, femoral and/or tibial anchors and other devices and/or one or more virtual paths and/or virtual surgical plans for the one or more virtual arthroscope, surgical instruments, probes, pointers, ACL grafts, femoral and/or tibial tunnels, femoral and/or tibial anchors and other devices is matched to the live display of the intra-articular structures of the patient's knee joint visualized by the arthroscopy system. In this manner, the surgeon can work in a seamless manner between live intra-articular image data of the patient and projected data and virtual data of the patient since they can have matching size and/or magnification.

The magnification used by the OHMD for displaying the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices can change as the surgeon moves closer to or further away from the patient's knee. The magnification of the display unit of the arthroscopy system can change; for example, it can be increased or decreased, and the magnification for displaying the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices can be adjusted correspondingly.

The OHMD can optionally display the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices when the surgeon looks at the display unit of the arthroscopy system through the OHMD using a magnification or size that is reflective of or corresponds to or is larger or smaller than the magnification used by the display unit of the arthroscopy system for the display of the live data from inside the patient's knee joint.

The magnification used by the OHMD for the display of the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices can switch back to be reflective of or correspond to the distance of the OHMD or the surgeon's eyes to the patient's knee or it can be smaller or larger when the surgeon looks at the patient's knee again, rather than the display unit of the arthroscopy system.

In some embodiments, the display unit of the arthroscopy system can display the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices. The display unit of the arthroscopy system, e.g. one or two electronic monitors, can display the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices at a magnification that is reflective of or corresponds to the magnification of the live data of the structures projected from inside the patient's knee seen through the arthroscope and displayed by the display unit of the arthroscopy unit, or at a magnification that is smaller or larger than that.

When the surgeon looks through the OHMD at the display unit of the arthroscopy system, e.g. one or two electronic monitors, the OHMD can optionally turn of the display of the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices. The turning off or turning on of the display of the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices can be performed via manual commands, voice commands, various commands from various input systems, or automatically. An automatic turning on or off can be achieved, for example, with use of an image and/or video capture system integrated into, attached to or separate from the OHMD. The image and/or video capture system can, for example, capture the outline of the display unit of the arthroscopy system and the software can the automatically turn off the OHMD display or aspects of the OHMD display. Alternatively, the display unit of the arthroscopy system can have one or more markers, e.g. one or more LEDs, that the image and/or video capture system can detect which, in turn, can then trigger the turning on or off of the OHMD display.

In some embodiments, the OHMD can detect, e.g. automatically, if the surgeon or operator is looking at the display unit of the arthroscopy system, for example, with use of an image and/or video capture system integrated into, attached to or separate from the OHMD. The image and/or video capture system can, for example, capture the outline of the display unit of the arthroscopy system and the software can the automatically adjust the magnification of the items displayed by the OHMD so that it is reflective of, corresponds to, is smaller or larger than the magnification used by the display unit of the arthroscopy system for the live data/images from inside the patient's knee. Alternatively, the display unit of the arthroscopy system can have one or more markers, e.g. one or more LEDs, that the image and/or video capture system can detect which, in turn, can then trigger the adjustment of the magnification of the items displayed by the OHMD.

Similarly, the OHMD can detect, e.g. automatically, if the surgeon or operator is not looking at the display unit of the arthroscopy system, for example, with use of an image and/or video capture system integrated into, attached to or separate from the OHMD. The image and/or video capture system can, for example, detect that the outline of the display unit of the arthroscopy system is not present in the captured image data and the software can the automatically adjust the magnification of the items displayed by the OHMD so that it is reflective of or corresponds to the distance of the OHMD or the surgeon's eyes to the patient's knee, or is smaller or larger than that. Alternatively, the display unit of the arthroscopy system can have one or more markers, e.g. one or more LEDs, that the image and/or video capture system can detect; in this case, when the image captures system notices that the one or more LEDs are not included in the image capture data, the software can the automatically adjust the magnification of the items displayed by the OHMD so that it is reflective of or corresponds to the distance of the OHMD or the surgeon's eyes to the patient's knee, or is smaller or larger than that. Similarly, markers or LEDs placed on the patient's knee can be detected by the OHMD including an image and/or video capture system integrated into, attached to or separate from the OHMD thereby triggering an adjustment in magnification so that it is reflective of, corresponds to the distance of the OHMD or the surgeon's eyes to the patient's knee, or is smaller or larger than that when the surgeon or operator is looking at the patient's knee.

In some embodiments of the invention, the OHMD can be used to display the live data collected by the arthroscope from inside the patient's knee, for example instead of the display unit of the arthroscopy system or in addition to the display unit of the arthroscopy system. Optionally, the OHMD can replace the display unit of the arthroscopy system or it can be the display unit of the arthroscopy system. In this example, the OHMD can display the live data from inside the patient's knee collected by the arthroscope and project them for the surgeon. The OHMD can also display one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices in addition to the live images from inside the patient's knee. In this embodiment, the OHMD can optionally match the magnification of the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices relative to the magnification of the live data from inside the patient's knee collected by the arthroscope. The OHMD can also can apply a larger or smaller magnification and or size than the magnification of the live data from inside the patient's knee collected by the arthroscope for the one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices.

In some embodiments of the invention, for example when the OHMD is the primary display unit of the arthroscopy system, the OHMD can be non-transparent to light or minimally transparent to light reflected from the patient's knee or surgical theatre and can display, for example, live (electronic) images collected by the arthroscope from within the patient's knee and, optionally, it can display, in addition, one or more projected paths for one or more physical arthroscope, surgical instruments, probes, pointers, ACL grafts, femoral and/or tibial tunnels, femoral and/or tibial anchors and other devices and/or one or more virtual arthroscope, surgical instruments, probes, pointers, ACL grafts, femoral and/or tibial tunnels, femoral and/or tibial anchors and other devices and/or one or more virtual paths and/or virtual surgical plans for one or more virtual arthroscope, surgical instruments, probes, pointers, ACL grafts, femoral and/or tibial tunnels, femoral and/or tibial anchors and other devices (with various chosen matching or non-matching magnifications). In this setting, the OHMD can also display electronic images of the physical arthroscope, surgical instruments, probes, pointers, ACL grafts, femoral and/or tibial tunnels, femoral and/or tibial anchors and other devices and their respective movements, for example captured with an image and/or video capture system integrated into, attached to, or separate from the OHMD (with various chosen matching or non-matching magnifications).

The OHMD can be permanently non-transparent to light or minimally transparent to light reflected from the patient's knee or surgical theatre. Alternatively, the degree of transparency can be variable, for example with use of one or more optical filters, e.g. polarizing light filters, in front of or integrated into the OHMD or electronic, e.g. LCD, or optical filters in front or integrated into the OHMD. The OR theater can optionally use light sources, e.g. polarized or filtered light that will support modulation or aid with adjustments of the transparency of the OHMD to light reflected from the patient's knee or surgical theatre.

Someone skilled in the art will readily recognize that all examples and embodiments provided in the foregoing for ACL repair and ACL reconstruction are applicable to all other arthroscopic procedures such as arthroscopy of the shoulder, hip and ankle and can be applied to many endoscopic procedures as well as to other embodiments and hip replacement, knee replacement, spinal surgery, spinal fusion, pedicle screw fixation, vertebroplasty and/or kyphoplasty and many others.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

The invention claimed is:

1. A system for preparing a physical joint in a patient, the system comprising:
    at least one processor,
    a see through optical head mounted display,
    a user interface,
    wherein the system is configured to display, by the see through optical head mounted display, at least a portion of a virtual implant component onto a surface of the physical joint visible directly through the see through optical head mounted display, so as to superimpose the at least portion of the virtual implant component onto the surface of the physical joint,
    wherein the at least portion of the virtual implant component is a three-dimensional digital representation corresponding to at least a portion of a physical implant component, a placement indicator of the physical implant component, or a combination thereof,
    wherein the system is configured to superimpose and align the at least portion of the virtual implant component with at least one anatomic structure of the physical joint, and
    wherein the user interface is configured to adjust the position, orientation or position and orientation of the at least portion of the virtual implant component in relationship to the at least one anatomic structure of the physical joint.

2. The system of claim 1, wherein the system is configured to track the see through optical head mounted display, the virtual implant component, the physical implant component, the physical joint, the at least one anatomic structure, a physical tool, a physical instrument, a robotic arm or a combination thereof in a coordinate system.

3. The system of claim 1, wherein the system is configured to maintain the display of the at least portion of the virtual implant component in relationship to the at least one anatomic structure.

4. The system of claim 3, wherein the system is configured to maintain the display of the at least portion of the virtual implant component in relationship to the at least one anatomic structure when the joint is moved through a range of motion or when the joint is moved into different positions corresponding to a flexion, extension, rotation, abduction, adduction or combinations thereof.

5. The system of claim 1, wherein the user interface comprises at least one of a graphical user interface, a voice recognition, a gesture recognition, a virtual interface displayed by the see through optical head mounted display, a virtual keyboard displayed by the see through optical head mounted display, a physical keyboard, a physical computer mouse, or a physical track pad.

6. The system of claim 1, wherein the system is for preparing the physical joint of the patient for the physical implant component, wherein the physical implant component is a knee implant component, a hip implant component, a shoulder joint implant component, or an ankle joint implant component.

7. The system of claim 1, wherein the user interface is configured to select the virtual implant component from a library of virtual implant components, wherein the library of virtual implant components is composed of two or more virtual implant components of different sizes, different shapes, or different sizes and different shapes, and wherein each virtual implant component of the library is a three-dimensional digital representation corresponding to at least a portion of a corresponding physical implant component, a placement indicator of a corresponding physical implant component, or a combination thereof.

8. The system of claim 7, wherein the user interface is configured to select the virtual implant component based on a size, a shape or a size and a shape of the virtual implant component, or wherein the user interface is configured to select the virtual implant component based on a size, a shape or a size and a shape of the virtual implant component in relationship to the physical joint of the patient.

9. The system of claim 1, wherein the user interface is configured to adjust a color, brightness, intensity, contrast, transparency or combination thereof of the display of the at least portion of the virtual implant component by the see through optical head mounted display, and wherein at least a portion of the physical joint is visible through the superimposed virtual implant component.

10. The system of claim 7, wherein the system is configured to display two or more virtual implant components.

11. The system of claim 10, wherein the system is configured to display the two or more virtual implant components with a different color, a different degree of transparency or a combination thereof.

12. The system of claim 1, wherein the user interface is configured to move the virtual implant component in relationship to the physical joint of the patient, in relationship to the at least one anatomic structure or a combination thereof.

13. The system of claim 1, wherein the user interface is configured to align the display of the virtual implant component in relationship to the physical joint of the patient, in relationship to the at least one anatomic structure or a combination thereof.

14. The system of claim 1, wherein the system is configured to display, by the see through optical head mounted display, the virtual implant component onto the surface of the physical joint at a predetermined position, predetermined orientation, predetermined rotation, predetermined resection level, predetermined alignment or combination thereof.

15. The system of claim 1, wherein the system is configured to align the virtual implant component relative to a predetermined rotation axis, a predetermined flexion axis, a predetermined extension axis, a predetermined slope, a predetermined anteversion, a predetermined inclination or a combination thereof.

16. The system of claim 14, wherein the user interface is configured to modify the predetermined position, predetermined orientation, predetermined rotation, predetermined resection level, predetermined alignment or combination thereof of the virtual implant component to adjust for ligamentous laxity or tightness.

17. The system of claim 14, wherein the predetermined position, predetermined orientation, predetermined rotation, predetermined resection level, predetermined alignment or combination thereof of the virtual implant component is based on at least one of a predetermined varus correction, a predetermined valgus correction, a predetermined femoral component flexion, a predetermined femoral component extension, a predetermined femoral component rotation, a predetermined femoral component position relative to an anterior cortex, a predetermined tibial component slope, a predetermined tibial component rotation, or a predetermined tibial component position relative to a tibial cortical rim in a knee replacement, or is based on at least one of a predetermined femoral neck resection for a femoral component, a predetermined leg length, a predetermined femoral component anteversion, a predetermined femoral component offset, a predetermined acetabular component anteversion, or a predetermined acetabular component inclination in a hip replacement.

18. The system of claim 1, wherein the system is configured to display the virtual implant component at a predetermined position, a predetermined orientation, a predetermined rotation, a predetermined alignment or a combination thereof relative to an anatomic axis, a biomechanical axis, a deformity or a combination thereof.

19. The system of claim 1, wherein the system is configured to display the virtual implant component, by the see through optical head mounted display, in relationship to the physical joint of the patient with a predetermined resection level, a predetermined varus angle, a predetermined valgus angle, a predetermined rotation, a predetermined flexion, a predetermined slope or a combination thereof.

20. The system of claim 19, wherein the user interface is configured to modify the position, orientation or position and orientation of the display of the virtual implant component relative to the predetermined resection level, predetermined varus angle, predetermined valgus angle, predetermined rotation, predetermined flexion, predetermined slope or combination thereof.

21. The system of claim 1, wherein the at least one anatomic structure comprises at least one anatomic landmark, anatomic plane, articular surface, cartilage surface, subchondral bone surface, cortical bone surface, cut bone surface, reamed bone surface, milled bone surface, impacted bone surface, tissue resection, tissue surface, or a combination thereof.

22. The system of claim 1, wherein the at least one anatomic structure comprises information about an anatomic axis, a biomechanical axis, a mechanical axis, a distance between two or more anatomic landmarks, a dimensions between two or more anatomic landmarks, a dimension between an anterior and a posterior anatomic structure, a dimension between a medial and a lateral anatomic structure, a dimension between a superior and an inferior anatomic structure, a curvature, a surface, an edge, a shape, a length, a width, a depth, or a combination thereof.

23. The system of claim 21, wherein the at least one anatomic landmark comprises at least a portion of or an entire acetabulum, a portion of or an entire edge of an acetabulum, multiple portions of an edge of an acetabulum, a portion of an iliac wall, a portion of a pubic bone, a portion of an ischial bone, an anterior superior iliac spine, an anterior inferior iliac spine, a symphysis pubis, a portion of or an entire greater trochanter, a portion of or an entire lesser trochanter, a center of the femoral head, a portion of or an entire femoral shaft, a portion of or an entire femoral neck, a portion of or an entire femoral head, a fovea capitis, a transverse acetabular ligament, a pulvinar, a ligamentum teres, a labrum, one or more femoral osteophytes, one or more acetabular osteophytes, a portion of or an entire medial femoral condyle, a portion of or an entire lateral femoral condyle, a portion of or an entire femoral notch, a portion of or an entire trochlea, a portion of an anterior cortex of the femur, a portion of an anterior cortex of the femur with adjacent portions of the trochlea, a portion of an anterior cortex of the femur with adjacent portions of the trochlea and osteophytes, one or more femoral osteophytes, one or more tibial osteophytes, an epicondylar eminence, a medial epicondylar eminence, a lateral epicondylar eminence, a portion of or an entire medial tibial plateau, a portion of or an entire lateral tibial plateau, a portion of or an entire medial tibial spine, a portion of or an entire lateral tibial spine, a portion of an anterior cortex of the tibia, a portion of an anterior cortex of the tibia and a portion of a tibial plateau, a portion of or an entire patella, a medial edge of a patella, a lateral edge of a patella, a superior pole of a patella, an inferior pole of a patella, a patellar osteophyte, a medial wall of the femoral notch, a lateral wall of the femoral notch, a roof of the femoral notch, an anterior cruciate ligament origin, an anterior cruciate ligament insertion, a medial wall of the medial condyle, a lateral wall of the lateral condyle, a medial femoral condyle shape, a medial femoral condyle radius, a medial femoral condyle convexity, a medial femoral condyle concavity, a lateral femoral condyle shape, a lateral femoral condyle radius, a lateral femoral condyle convexity, a lateral femoral condyle concavity, an intercondylar notch shape, an intercondylar notch surface feature, a medial tibial spine, a lateral tibial spine, an anteromedial tibial rim, an anterolateral tibial rim, a medial tibial rim, a lateral tibial rim, a lowest point of the medial plateau, a lowest point of the lateral plateau, a highest point of the medial plateau, a highest point of the lateral plateau, a medial tibial plateau shape, a lateral tibial plateau shape, a medial tibial plateau surface, a medial tibial plateau surface feature, a medial tibial plateau radius, a medial tibial plateau convexity, a medial tibial plateau concavity, a lateral tibial plateau shape, a lateral tibial plateau surface, a lateral tibial plateau surface feature, a lateral tibial plateau radius, a lateral tibial plateau convexity, a lateral tibial plateau concavity, a portion of or an entire glenoid, a portion of or an entire coracoid process, a portion of or an entire acromion, a portion of a clavicle, a portion of or an entire humeral head, a portion of or an entire humeral neck, a portion of a humeral shaft, one or more humeral osteophytes, one or more glenoid osteophytes, a portion of or an entire glenoid labrum, a portion of or an entire shoulder ligament, a portion of or an entire coracoacromial ligament, or a portion of or an entire glenohumeral ligament.

24. The system of claim 1, wherein the virtual implant component is a virtual trial femoral component, a virtual trial tibial component, a virtual trial tibial insert, a virtual trial patellar component, a virtual trial acetabular component, a virtual trial glenoid component, or a virtual trial humeral component.

25. The system of claim 1, wherein the joint is a knee and wherein the system is configured to display at least a portion of a virtual femoral implant component superimposed onto at least a portion of the femoral articular surface of the physical joint and to display at least a portion of a virtual tibial implant component superimposed onto at least a portion of the tibial articular surface of the physical joint, wherein the system is configured to maintain the display of the at least portion of the virtual femoral implant component in relationship to the at least portion of the femoral articular surface and to maintain the display of the at least portion of the virtual tibial implant component in relationship to the at least portion of the tibial articular surface when the knee is moved through a range of motion or when the knee is moved into different positions of flexion, extension, rotation, abduction, adduction or combinations thereof, or wherein the joint is a hip and wherein the system is configured to display at least a portion of a virtual femoral implant component superimposed onto at least a portion of the proximal femur of the physical joint and to display at least a portion of a virtual acetabular implant component superimposed onto at least a portion of the acetabular articular surface of the physical joint, wherein the system is configured to maintain the display of the at least portion of the virtual femoral implant component in relationship to the at least portion of the proximal femur and to maintain the display of the at least portion of the virtual acetabular implant component in relationship to the at least portion of the acetabular articular surface when the hip is moved through a range of motion or when the hip is moved into different positions of flexion, extension, rotation, abduction, adduction or combinations thereof, or wherein the joint is a shoulder and wherein the system is configured to display at least a portion of a virtual humeral implant component superimposed onto at least a portion of the proximal humerus of the physical joint and to display at least a portion of a virtual glenoid implant component superimposed onto at least a portion of the glenoid articular surface of the physical joint, wherein the system is configured to maintain the display of the at least portion of the virtual humeral implant component in relationship to the at least portion of the proximal humerus and to maintain the display of the at least portion of the virtual glenoid implant component in relationship to the at least portion of the glenoid articular surface when the shoulder is moved through a range of motion or when the shoulder is moved into different positions of flexion, extension, rotation, abduction, adduction or combinations thereof.

26. The system of claim 1, wherein at least one portion of the virtual implant component is tangent or intersecting with the at least one anatomic structure.

27. The system of claim 1, wherein the at least one processor is integrated into the see through optical head mounted display.

28. The system of claim 1, wherein the at least one processor is separate from the see through optical head mounted display.

29. The system of claim 1, wherein the system is configured to use the position, orientation or position and orientation of the virtual implant component in relationship to the at least one anatomic structure of the physical joint for determining the position, orientation or position and orientation of at least one bone resection, wherein the at least one bone resection comprises at least a bone cut, a drilling, a pinning, a burring, a milling, a reaming, a broaching, an impacting of the physical joint or a combination thereof.

30. The system of claim 29, wherein the system further comprises a robot for the bone resection.

\* \* \* \* \*